US009891239B2

(12) United States Patent
Desai et al.

(10) Patent No.: US 9,891,239 B2
(45) Date of Patent: *Feb. 13, 2018

(54) MODULATORS OF PHARMACOKINETIC PROPERTIES OF THERAPEUTICS

(75) Inventors: Manoj C. Desai, Pleasant Hill, CA (US); Hongtao Liu, Cupertino, CA (US); Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 1997 days.

This patent is subject to a terminal disclaimer.

(21) Appl. No.: 12/528,185

(22) PCT Filed: Feb. 22, 2008

(86) PCT No.: PCT/US2008/054788
§ 371 (c)(1),
(2), (4) Date: Apr. 7, 2010

(87) PCT Pub. No.: WO2008/103949
PCT Pub. Date: Aug. 28, 2008

(65) Prior Publication Data
US 2010/0189687 A1 Jul. 29, 2010

Related U.S. Application Data

(60) Provisional application No. 60/903,228, filed on Feb. 23, 2007, provisional application No. 60/958,716, filed on Jul. 6, 2007.

(51) Int. Cl.
| | | |
|---|---|---|
| G01N 33/94 | (2006.01) |
| A61K 31/427 | (2006.01) |
| A61K 31/496 | (2006.01) |
| A61K 31/5377 | (2006.01) |
| A61K 45/06 | (2006.01) |
| C07D 277/28 | (2006.01) |
| C07D 277/30 | (2006.01) |
| C07D 417/14 | (2006.01) |
| G01N 33/58 | (2006.01) |

(52) U.S. Cl.
CPC ........... *G01N 33/94* (2013.01); *A61K 31/427* (2013.01); *A61K 31/496* (2013.01); *A61K 31/5377* (2013.01); *A61K 45/06* (2013.01); *C07D 277/28* (2013.01); *C07D 277/30* (2013.01); *C07D 417/14* (2013.01); *G01N 33/58* (2013.01)

(58) Field of Classification Search
CPC .. C07D 277/28; C07D 277/30; C07D 417/14; A61K 31/5377; A61K 31/496; A61K 31/427
USPC ..................................................... 514/236.8
See application file for complete search history.

(56) References Cited

U.S. PATENT DOCUMENTS

| | | |
|---|---|---|
| 3,400,197 A | 9/1968 | Lippman et al. |
| 3,786,058 A | 1/1974 | Edwards |
| 3,882,114 A | 5/1975 | Kalopissis et al. |
| 3,907,782 A | 9/1975 | Edwards |
| 3,957,774 A | 5/1976 | Kalopissis et al. |
| 4,254,099 A | 3/1981 | Asmussen et al. |
| 4,603,143 A | 7/1986 | Schmidt |
| 4,739,081 A | 4/1988 | Toke et al. |
| 5,142,056 A | 8/1992 | Kempe et al. |
| 5,354,866 A | 10/1994 | Kempf et al. |
| 5,362,912 A | 11/1994 | Sowin et al. |
| 5,539,122 A | 7/1996 | Kempf et al. |
| 5,541,206 A | 7/1996 | Kempf et al. |
| 5,552,558 A | 9/1996 | Kempf et al. |
| 5,565,418 A | 10/1996 | Kempf et al. |
| 5,567,823 A | 10/1996 | Tien et al. |
| 5,580,984 A | 12/1996 | Kempf et al. |
| 5,583,232 A | 12/1996 | Kempf et al. |
| 5,583,233 A | 12/1996 | Kempf et al. |
| 5,591,451 A | 1/1997 | Gupta et al. |
| 5,591,860 A | 1/1997 | Kempf et al. |
| 5,597,926 A | 1/1997 | Kempf et al. |
| 5,597,927 A | 1/1997 | Kempf et al. |
| 5,597,928 A | 1/1997 | Kempf et al. |
| 5,608,072 A | 3/1997 | Kempf et al. |
| 5,616,720 A | 4/1997 | Kempf et al. |
| 5,625,072 A | 4/1997 | Kempf et al. |
| 5,635,523 A | 6/1997 | Kempf et al. |
| 5,648,497 A | 7/1997 | Kempf et al. |
| 5,659,044 A | 8/1997 | Kempf et al. |
| 5,659,045 A | 8/1997 | Kempf et al. |

(Continued)

FOREIGN PATENT DOCUMENTS

| | | |
|---|---|---|
| EP | 0163178 | 12/1985 |
| EP | 0345109 | 12/1989 |
| EP | 0428849 | 5/1991 |
| EP | 0486948 | 5/1992 |
| EP | 0674513 | 10/1995 |
| EP | 0783889 | 7/1997 |
| EP | 1004296 | 5/2000 |
| EP | 1090914 | 4/2001 |
| EP | 1183026 | 3/2002 |
| EP | 1287823 | 3/2003 |
| EP | 1302468 | 4/2003 |
| EP | 1800681 | 6/2007 |

(Continued)

OTHER PUBLICATIONS

"Human Immunodeficiency Virus Type 2." Published by the CDC, Oct. 1998.*

(Continued)

*Primary Examiner* — Rebecca L Anderson
(74) *Attorney, Agent, or Firm* — Fish & Richardson P.C.

(57) ABSTRACT

The present application provides for a compound of Formula IV, or a pharmaceutically acceptable salt, solvate, and/or ester thereof, compositions containing such compounds, therapeutic methods that include the administration of such compounds, and therapeutic methods and include the administration of such compounds with at least one additional therapeutic agent.

4 Claims, No Drawings

(56) References Cited

U.S. PATENT DOCUMENTS

| | | | |
|---|---|---|---|
| 5,674,882 A | 10/1997 | Kempf et al. |
| 5,679,797 A | 10/1997 | Kempf et al. |
| 5,696,270 A | 12/1997 | Kempf et al. |
| 5,763,464 A | 6/1998 | Randad et al. |
| 5,814,639 A | 9/1998 | Liotta et al. |
| 5,888,548 A | 3/1999 | Wongsuragrai et al. |
| 5,892,052 A | 4/1999 | Kempf et al. |
| 5,914,331 A | 6/1999 | Liotta et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,004,927 A | 12/1999 | Benet et al. |
| 6,028,054 A | 2/2000 | Benet et al. |
| 6,030,645 A | 2/2000 | Tritsch et al. |
| 6,037,157 A | 3/2000 | Norbeck et al. |
| 6,043,230 A | 3/2000 | Arimilli et al. |
| 6,342,249 B1 | 1/2002 | Wong et al. |
| 6,448,245 B1 | 9/2002 | DePetrillo et al. |
| 6,524,615 B2 | 2/2003 | Gutierrez-Rocca et al. |
| 6,642,245 B1 | 11/2003 | Liotta et al. |
| 6,703,396 B1 | 3/2004 | Liotta et al. |
| 6,703,403 B2 | 3/2004 | Norbeck et al. |
| 6,946,449 B2 | 9/2005 | Elzein et al. |
| 6,960,251 B2 | 11/2005 | Uhrlandt et al. |
| 7,176,220 B2 | 2/2007 | Satoh et al. |
| 7,217,431 B2 | 5/2007 | Holm et al. |
| 7,279,487 B2 | 10/2007 | Egbertson et al. |
| 7,285,566 B2 | 10/2007 | Erickson et al. |
| 7,348,345 B2 | 3/2008 | Dunn et al. |
| 7,635,704 B2 | 12/2009 | Satoh et al. |
| 7,749,537 B2 | 7/2010 | Hite et al. |
| 7,786,153 B2 | 8/2010 | Kempf et al. |
| 7,834,043 B2 | 11/2010 | Degoey |
| 8,067,449 B2 | 11/2011 | Desai et al. |
| 8,148,374 B2 | 4/2012 | Desai et al. |
| 8,486,942 B2 | 7/2013 | Desai et al. |
| 8,633,219 B2 | 1/2014 | Matsuzaki et al. |
| 8,981,103 B2 | 3/2015 | Ando et al. |
| 2002/0015715 A1 | 2/2002 | Beaurline et al. |
| 2002/0091159 A1 | 7/2002 | Spireas |
| 2002/0115665 A1 | 8/2002 | DePetrillo et al. |
| 2002/0127274 A1 | 9/2002 | Kushla et al. |
| 2002/0197311 A1 | 12/2002 | Hasenzahl et al. |
| 2003/0004182 A1 | 1/2003 | Gierer |
| 2003/0035834 A1 | 2/2003 | Pawan |
| 2003/0068368 A1 | 4/2003 | Kushla et al. |
| 2003/0158263 A1 | 8/2003 | Radhakrishnan et al. |
| 2003/0191319 A1 | 10/2003 | Vazquez et al. |
| 2004/0022844 A1 | 2/2004 | Hasenzahl et al. |
| 2004/0022848 A1 | 2/2004 | Kikuchi et al. |
| 2004/0057992 A1 | 3/2004 | Gierer |
| 2004/0101555 A1 | 5/2004 | Clouatre et al. |
| 2004/0127689 A1 | 7/2004 | Sigler et al. |
| 2004/0254210 A1 | 12/2004 | Haeberlin et al. |
| 2005/0084529 A1 | 4/2005 | Rosenberg et al. |
| 2005/0095287 A1 | 5/2005 | Matharu et al. |
| 2005/0096390 A1 | 5/2005 | Holm et al. |
| 2005/0238675 A1 | 10/2005 | Li et al. |
| 2006/0084628 A1 | 4/2006 | Pottage |
| 2006/0115524 A1 | 6/2006 | Eliasen |
| 2006/0182691 A1 | 8/2006 | Besse et al. |
| 2006/0199851 A1 | 9/2006 | Kempf et al. |
| 2006/0229210 A1 | 10/2006 | Neugebauer et al. |
| 2006/0292192 A1 | 12/2006 | Hasenzahl et al. |
| 2007/0014854 A1 | 1/2007 | Zalit et al. |
| 2007/0077295 A1 | 4/2007 | Dahl et al. |
| 2007/0099902 A1 | 5/2007 | Dahl et al. |
| 2007/0122482 A1 | 5/2007 | Holm et al. |
| 2007/0219243 A1 | 9/2007 | Kearney et al. |
| 2007/0298108 A1 | 12/2007 | Svete et al. |
| 2008/0108617 A1 | 5/2008 | Desai et al. |
| 2008/0207620 A1* | 8/2008 | Desai et al. ............ 514/238.2 |
| 2009/0093467 A1* | 4/2009 | Kearney et al. ............ 514/221 |
| 2009/0093482 A1* | 4/2009 | Kearney et al. ............ 514/236.8 |
| 2009/0143314 A1 | 6/2009 | Dahl et al. |
| 2009/0181902 A1 | 7/2009 | Desai et al. |
| 2009/0233964 A1 | 9/2009 | Kearney et al. |
| 2009/0324729 A1* | 12/2009 | Koziara et al. ............ 424/490 |
| 2010/0016448 A1 | 1/2010 | Kothari et al. |
| 2010/0215753 A1 | 8/2010 | Sherwood et al. |
| 2010/0285122 A1* | 11/2010 | Oliyai et al. ............ 424/464 |
| 2010/0285157 A1 | 11/2010 | Hirai et al. |
| 2010/0331331 A1* | 12/2010 | Kearney et al. ............ 514/236.8 |
| 2011/0009411 A1* | 1/2011 | Kearney et al. ............ 514/236.8 |
| 2012/0237478 A1 | 9/2012 | Desai et al. |
| 2014/0017199 A1 | 1/2014 | Desai et al. |
| 2014/0343062 A1 | 11/2014 | Kearney et al. |
| 2014/0343063 A1 | 11/2014 | Kearney et al. |
| 2015/0105350 A1 | 4/2015 | Ramanathan |
| 2015/0139948 A1 | 5/2015 | Desai et al. |
| 2015/0150810 A1 | 6/2015 | Oliyai et al. |
| 2016/0069915 A1 | 3/2016 | Desai et al. |
| 2017/0136001 A1 | 5/2017 | Kearney et al. |
| 2017/0158647 A1 | 6/2017 | Desai et al. |

FOREIGN PATENT DOCUMENTS

| | | |
|---|---|---|
| FR | 2767071 | 2/1999 |
| FR | 2773994 | 7/1999 |
| GB | 1241024 | 7/1971 |
| GB | 1317400 | 5/1973 |
| GB | 1422974 | 1/1976 |
| JP | 6127981 A | 5/1994 |
| JP | 2004-184681 A | 7/2004 |
| JP | 2005-075826 | 3/2005 |
| JP | 2005-091988 A | 4/2005 |
| JP | 2006-003701 A | 1/2006 |
| JP | 4018664 | 12/2007 |
| JP | 2009-528378 A | 8/2009 |
| JP | 2011-231132 A | 11/2011 |
| WO | WO 94/14436 | 7/1994 |
| WO | WO 97/01349 | 1/1997 |
| WO | WO-99/33792 A2 | 7/1999 |
| WO | WO-99/33792 A3 | 7/1999 |
| WO | WO-00/74677 A2 | 12/2000 |
| WO | WO-00/74677 A3 | 12/2000 |
| WO | WO 01/25240 | 4/2001 |
| WO | WO2003/047551 | 6/2003 |
| WO | WO2005/087199 | 9/2005 |
| WO | WO 2005/111006 | 11/2005 |
| WO | WO2006/000229 | 1/2006 |
| WO | WO-2006/014282 A2 | 2/2006 |
| WO | WO-2006/014282 A3 | 2/2006 |
| WO | WO2007/074472 | 7/2007 |
| WO | WO2007/076874 | 7/2007 |
| WO | WO-2007/103670 A2 | 9/2007 |
| WO | WO-2007/103670 A3 | 9/2007 |
| WO | WO2007/111866 | 10/2007 |
| WO | WO 2008/010921 | 1/2008 |
| WO | WO2008/017867 | 2/2008 |
| WO | WO-2008/027932 A2 | 3/2008 |
| WO | WO-2008/027932 A3 | 3/2008 |
| WO | WO2008/029417 | 3/2008 |
| WO | WO-2008/103949 A1 | 8/2008 |
| WO | WO-2009/086356 A2 | 7/2009 |
| WO | WO2010/115886 | 10/2010 |

OTHER PUBLICATIONS

Kashman et al. J. Med. Chem. 1992, 35, pp. 2735-2743.*
Marcus et al., PubMed Abstract (Intervirology 45(4-6):260-6) 2002.*
Miles, Medline Abstract (Community Pract, vol. 78, Issue 8, pp. 292-294) Aug. 2005.*
Clercq, Biochemica et Biophysica Acta 1587 (2002) 258-275.*
Savarino, Retrovirology (2007) 4:21, pp. 1-15.*
Andretta, K. et al. (2012) "HIV-2 Antiviral Potency and Selection of Drug Resistance Mutations by the Integrase Strand Transfer Inhibitor Elvitegravir and NRTIs Entricitabine and Tenofovir in vitro", *Poster No. 694, Presented at 19th Conference on Retroviruses and Opportunistic Infections (CROI)*, Mar. 5-8, 2012, Seattle, Washington.

(56) References Cited

OTHER PUBLICATIONS

Bai, J. et al. "Use of Classification Regression Tree in Predicting Oral Absorption in Humans," *J. Chem Inf. Comput. Sci* 44, 2061-2069, 2004.

Balzarini, J. et al. "Pronounced in vitro and in vivo antiretroviral activity of 5-substituted 2,4-dimino-6-[2-(phosphonomethoxy)ethoxy]pyrimidines" *Journal of Antimicrobial Chemotherapy*, vol. 59, pp. 80-86, 2007.

Barral, K. et al. "Acyclic nucleoside thiophsphonates as potent inhibitors of HIV and HBV replication", *European Journal of Medicinal Chemistry*, vol. 46, pp. 4281-4288, 2011.

Brenner, B. et al. "HIV-1 subtype C viruses rapidly develop K65R resistance to tenofovir in cell culture", *AIDS*, vol. 20, pp. F9-F13, 2006.

Callebaut, C. et al. (2010) "Biological profiling of GS-9350, a Novel Pharmacoenhancer that Lacks Anti-HIV Activity and Exhibits Low Potential for Metabolic Adverse Effects In Vitro", Poster No. 55, 23rd *International Conference on Antiviral Research*, Apr. 25-28, 2010, San Francisco, CA.

Damond, F. et al. "Selection of K65R mutation in HIV-2infected patients receiving tenofovir-containing regimen", Antiviral Therapy, vol. 9, pp. 635-636, 2004.

Francisci, D. et al. "HIV-2 Infection, End-Stage Renal Disease and Protease Inhibitor Intolerance", *Clinical Drug Invest*, vol. 31(5), pp. 345-349, 2011.

Frecer, V. et al. "Structure Based Design of Inhibitors of Aspartic Protease of HIV-1," *Letters in Drug Design & Discovery* 2, 638-646, 2005.

Gurjar et al. "Synthesis of Novel C2-symmetric and Pseudo C2-symmetric Based Diols. Epoxides and Dideoxy Derivatives of HIV Protease Inhibitors," *Tetrahedron* 53(13), 4769-4778, 1997.

Kempf et al. "Discovery of Ritonavir, Patent Inhibitor of HIV Protease with High Oral Bioavailability and Clinical Efficacy," *J. Med. Chem* 41:602-617, 1998.

Kempf, et al. "Lack of Stereospecificity in the Binding of the P2 Amino Acid of Ritonavir to HIV Protease," *Bioorganic & Medicinal Chemistry Letters* 7(6), 699-704, 1997.

Mekapati, S.B. et al. "Quantitative Structure-Activity Relationship of some HIV-1 Protease Inhibitors: A Fujita-Ban Type Analysis," *J. Enzyme Inhibition* 16, 185-197, 2001.

Merriam-Webster Online Dictionary. "Analogue." 2012. Merriam-Webster Online. Accessed Apr. 12, 2012. <http://merriam-webster.com/dictionary/analogue.

Merriam-Webster Online Dictionary. "Derivative." 2012. Merriam-Webster Online. Accessed Apr. 12, 2012. http://merriam-webster.com/dictionary/derivative.

Molla et al. "Ordered Accumulation of Mutations in HIV Protease Confers Resistance to Ritonavir," *Nature Medicine* 2:(7), 760-766, 1996.

Munoz, R. et al. "Tenofovir disoproxil fumarate-emtricitabine coformulation for once-daily dual NRTI backbone", Expert Rev. *Anti Infect. Ther* vol. 4(4), pp. 523-535, 2006.

Nair, A. et al. "A Computational Study of the Resistance of HIV-1 Aspartic Protease to the Inhibitors ABT-538 and VX-478 and Design of New Analogues," *Biochemical and Biophysical Research Communications* 242, 545-551, 1998.

Ntemgwa, M. et al. "Nucleoside and Nucleotide Analogs Select in Culture for Different Patterns of Drug Resistance in Human Immunodeficiency Virus Types 1 and 2", *Antimicrobial Agents and Chemotherapy*, vol. 53(2), pp. 708-715, 2009.

Office Action from European Patent Application No. 08743531.9, dated May 3, 2010.

Otten, R. et al. "Efficacy of Postexposure Prophylaxis after Intravaginal Exposure of Pig-Tailed Macaques to a Human-Derived Retrovirus", *Journal of Virology*, vol. 74(20), pp. 9771-9775, 2000.

Roquebert, B. et al. "HIV-2 integrase gene polymorphism and phenotypic susceptibility of HIV-2 clinical isolates to the integrase inhibitors raltegravir and elvitegravir in vitro", *Journal of Antimicrobial Chemotherapy* vol. 62, pp. 914-920, 2008.

Roquebert, B. et al. "Polymorphism of HIV-2 integrase gene and in vitro phenotypic susceptibility of HIV-2 clinical isolates to integrase inhibitors: raltegravir and elvitegravir", Poster No. EN11293, *XVI International HIV Drug Resistance Workshop*; Jun. 12-17, 2007.

Schinazi, R. et al. "Selective Inhibition of Human Immunodeficiency Viruses by Racemates and Enantiomers of cis-5-Fluoro-1[2(Hydroxymethyl)-1,3-Okathiolan-5-yl]Cytosine", *Antimicrobial Agents and Chemotherapy*, vol. 36(11), pp. 2423-2431, 1992.

Shimura et al. "Broad Antiretroviral Activity and Resistance Profile of the Novel Human Immunodeficiency Virus Integrase Inhibitor Elvitegravir (JTK-303/GS-9137)", *Journal of Virology*, vol. 82(2), pp. 764-774, 2008.

Smith R. et al. "Human Immunodeficiency Virus Types 1 and 2 Exhibit Comparable Sensitivities to Zidovudine and Other Nucleoside Analog Inhibitors In Vitro", *Antimicrobial Agents and Chemotherapy*, vol. 52(1), pp. 329-332, 2008.

Smith R. et al. "Antiretroviral Drug Resistance in HIV-2:Three Amino Acid Changes Are Sufficient for Classwide Nucleoside Analogue Resistance", *The Journal of Infectious Diseases*, 199(9), pp. 1323-1326, 2009.

Truvada® label revision approved on Jul. 8, 2011, NDA No. 021752, p. 23.

Witvrouw, M. et al. "Susceptibility of HIV-2, SIV and SHIV to various anti-HIV-1 compounds: implications for treatment and postexposure prophylaxis", *Antiviral Therapy*, vol. 9 pp. 57-65, 2004.

Xu, L et al. "Discovery of GS-9350: A Novel Pharmacoenhancer without Anti-HIV Activity," Poster No. H-934, *49th Interscience Conference on Antimicrobial Agents and Chemotherapy (ICAAC)*, Sep. 12-15, 2009 San Francisco, CA USA.

Xu, L. et al. "Genetic Diversity of Integrase (IN) Sequences in Antiretroviral Treatment-Naïve and Treatment-Experienced HIV Type 2 Patients", *AIDS Res Human Retroviruses*, vol. 24(7), pp. 1003-1007, 2009.

AIDS Healthcare Foundation, Inc. Complaint for Declaratory Judgment of Patent Invalidity and Violation of the Sherman Act, 15 U.S.C. §§ 1 and 2 against Gilead Sciences, Inc., Japan Tobacco, Inc., Japan Tobacco International U.S.A., Inc., and Emory University dated Jan. 26, 2016 for Case No. 3:16-cv-00443, thirty-three pages.

Becker, "The Role of Pharmacological Enhancement in Protease Inhibitor-Based Highly Active Antiretroviral Therapy", Expert Opin. Investig. Drugs 12(3), pp. 401-412 (2003).

Babine & Bender (1997),"Molecular Recognition of Protein-Ligand Complexes: Applications to Drug Design" Chem. Rev. 97, pp. 1359-1472.

Byoung, J. et al. (2008). "Synthesis of a Novel Bezyl-Octahydropyrazino[1,2-α]Pyrimidin-6-One Derivative as a Convenient Internal Bicyclic Peptidomimetic," Tetrahedron Letters 49:2316-2319.

Correia & Ortiz de Montellano, "Inhibition of Cytochrome P450 Enzymes" in Cytochrome P450: Structure, Mechanism, and Biochemistry (Kluwer Academic/Plenum Publisher 3rd Ed. 2005), pp. 247-322.

Dejesus, E., M.D., et al., (Sep. 2006), "Antiviral Activity, Pharmacokinetics, and Dose Response of the HIV-1 Integrase Inhibitor GS-9137 (JTK-303) in Treatment-Naive and Treatment-Experienced Patients" *J Acquir Immune Defic Syndr*, 43(1):1-5.

Giron, D. (2002). "Applications of Thermal Analysis and Coupled Techniques in Pharmaceutical Industry," Journal of Thermal Analysis and Calorimetry 68:335-357.

Giron, D. (2001). "Investigations of Polymorphism and Pseudo-Polymorphism in Pharmaceuticals by Combined Thermoanalytical Techniques," Journal of Thremal Analysis and Calorimetry 64:37-60.

Johnston, T.P. et al. (Nov. 1963). "The Synthesis of Antineoplastic Agents. XXXII. N-Nitrosoureas," Journal of Medicinal Chem. 6(6):669-681.

Kempf, D.J. et al., (1995), "ABT-538 Is a Potent Inhibitor of Human Immunodeficiency Virus Protease and Has High Oral Bioavailability in Humans", Proc. Natl. Acad. Sci. USA 92, pp. 2484-2488.

(56) References Cited

OTHER PUBLICATIONS

Kobori, A. et al. (2004). "2-Ureidoquinoline: A Useful Molecular Element for Stabilizing Single Cytosine and Thymine Bulges," Bioorganic & Medicinal Chemistry Letters 14(13):3431-3433.
Kurita, K. et al. (1979). "Synthesis and Properties of Polyurethanes Derived from Bis-N-Hydroxyimides and Diisocynates," Journal of Polymer Science 17:1619-1629.
Merriam-Webster Online Dictionary (2010), Definition of "Analogue," Merriam-Webster Online, located at http://merriam-webster.com/dictionary/analogue>, last visited on May 3, 2010, 2 pages.
Merriam-Webster Online Dictionary (2010), Definition of "Derivative," Merriam-Webster Online, located at http://merriam-webster.com/dictionary/derivative>, last visited on Apr. 20, 2010, 2 pages.
Morissette, S.L. et al. (2004). "High-Throughput Crystallization: Polymorphs, Salts, Co-Crystals and Solvates of Pharmaceutical Solids," Advanced Drug Delivery Reviews 56:275-300.
Nair, V. (2002). "HIV Integrase as a Target for Antiviral Chemotherapy," Rev. Med. Virol. 12:179-193.
Rodriguez-Spong, B. et al. (Feb. 23, 2004). "General Principles of Pharmaceutical Solid Polymorphism: a Supramolecular Perspective," *Advanced Drug Delivery Reviews* 56(3):241-274.
Savarino, A., (Mar. 2007), In-Silico docking of HIV-1 integrase inhibitors reveals a novel drug type acting on an enzyme/DNA reaction intermediate, *Retrovirology*, 4(21):1-15.
Souillac, P. et al. (1999). "Characterization of Delivery Systems, Differential Scanning Calorimetry," in Encyclopedia of Controlled Drug Delivery, pp. 212-227, John Wiley & Sons.
Weiss, T. (May 1, 1997). "High-Resolution Reversed-Phase High-Performance Liquid Chromatography Analysis of Polyamines and Their Monoacetyl Conjugates by Fluorescence Detection after Derivatization with N-Hydroxysuccinimidyl 6-Quinolinyl Carbamate," Analytical Biochemistry 247(2):294-304.
Wermuth, "Preparation of Water-Soluble Compounds by Covalent Attachment of Solubilizing Moieties," in The Practice of Medicinal Chemistry (Academic Press 2nd Ed.2003), pp. 617-630 (2003).
Xu et al., Cobicistat (GS-9350): A Potent and Selective Inhibitor of Human CYP3A as a Novel Pharmacoenhancer, ACS Med. Chem. Lett. 1, pp. 209-213 (2010).
Yano et al., The Structure of Human Microsomal Cytochrome P450 3A4 determined by X-ray Crystallography to 2.05-A Resolution: J. Biol. Chem. 279(37), pp. 38091-38094 (2004).
Advisory Action mailed on Dec. 15, 2011 for U.S. Appl. No. 12/340,419, filed Dec. 19, 2008, 3 pages.
Non-Final Office Action mailed on Mar. 2, 2015, for U.S. Appl. No. 14/532,868, filed Nov. 4, 2014, 16 pages.
Non-Final Office Action mailed on Jun. 5, 2014, for U.S. Appl. No. 13/935,117, filed Jul. 3, 2013, 22 pages.
Non-Final Office Action mailed on Nov. 25, 2011, for U.S. Appl. No. 12/434,513, filed May 1, 2009, 22 pages.
Final Office Action mailed on Aug. 30, 2011, for U.S. Appl. No. 12/340,419, filed Dec. 19, 2008, 13 pages.
Non-Final Office Action mailed on Aug. 24, 2011, for U.S. Appl. No. 13/103,970, filed May 9, 2011, 8 pages.
Non-Final Office Action mailed on May 13, 2010, for U.S. Appl. No. 12/036,124, filed Feb. 22, 2008, 14 pages.
International Preliminary Report on Patentability mailed on Jul. 6, 2010, for PCT Patent Application No. PCT/US2008/087821, filed on Dec. 19, 2008, seven pages.
International Preliminary Report on Patentability mailed on Sep. 3, 2009 for PCT Patent Application No. PCT/US2008/054788, filed on Feb. 22, 2008, seven pages.
International Search Report mailed on Mar. 31, 2009, for PCT Patent Application No. PCT/US2008/087821, filed on Dec. 19, 2008, three pages.
International Search Report mailed on Oct. 8, 2008, for PCT Patent Application No. PCT/US2008/008231, filed on Jul. 3, 2008, two pages.
International Preliminary Report on Patentability mailed on Sep. 24, 2008, for PCT Patent Application No. PCT/US2007/015604, filed on Jul. 6, 2007, seven pages.
International Search Report mailed on Jul. 24, 2008, for PCT Patent Application No. PCT/US2008/054788, filed on Feb. 22, 2008, two pages.
International Search Report mailed on May 14, 2008 for PCT Patent Application No. PCT/US2007/015604 filed on Jul. 6, 2007, two pages.
Written Opinion of the International Searching Authority mailed on Mar. 31, 2009, for PCT Patent Application No. PCT/US2008/087821, filed on Dec. 19, 2008, six pages.
Response to Written Opinion dated Dec. 23, 2008 for PCT Patent Application No. PCT/US2008/054788, filed on Feb. 22, 2008, four pages.
Written Opinion of the International Searching Authority mailed on Oct. 8, 2008, for PCT Patent Application No. PCT/US2008/008231, filed on Jul. 3, 2008, seven pages.
Response to Written Opinion dated Aug. 22, 2008 for PCT Patent Application No. PCT/US2007/015604, filed on Jul. 6, 2007, four pages.
Written Opinion of the International Searching Authority mailed on Jul. 24, 2008, for PCT Patent Application No. PCT/US2008/054788, filed on Feb. 22, 2008, six pages.
Written Opinion of the International Searching Authority mailed on May 14, 2008, for PCT Patent Application No. PCT/US2007/015604, filed on Jul. 6, 2007, seven pages.
African Regional (ARIPO) Office Action mailed on Jan. 8, 2015, for African Regional (ARIPO) Patent Application No. AP/P/2013/007042, filed on Feb. 22, 2008, 6 pages.
Australian Office Action mailed on Feb. 25, 2016 for Australian Patent Application No. 2015204378, filed on Feb. 22, 2008, three pages.
Australian Office Action mailed on Apr. 1, 2014 for Australian Patent Application No. 2013204815, filed on Apr. 12, 2013, three pages.
Australian Office Action mailed on Mar. 18, 2014 for Australian Patent Application No. 2013204817 filed on Feb. 22, 2008, three pages.
Australian Notice of Allowance mailed on Jan. 14, 2014 for Patent Application No. 2008218186, filed on Feb. 22, 2008, two pages.
Chinese Office Action mailed on Aug. 12, 2014, for Chinese Patent Application No. 201310326757.5, filed on Feb. 22, 2008.
Chinese Office Action mailed on Jun. 8, 2011 for Chinese Patent Application No. 200880105422.8, seven pages.
Chinese Office Action mailed on Jan. 26, 2011, for Chinese Patent Application No. 200780025607.3, five pages.
Eurasian Office Action mailed on Aug. 24, 2011, for Eurasian Patent Application No. 200901155, filed on Feb. 22, 2008, one page.
Eurasian Office Action mailed on May 3, 2011, for Eurasian Patent Application No. 200901155, filed on Feb. 22, 2008, two pages.
European Communication, Expert Declaration, mailed on Apr. 13, 2016 for European Patent Application No. EP 12167589.6, filed on May 11, 2012, twelve pages.
European Communication, Third Party Opposition against EP 2049506, mailed on Apr. 13, 2016 for European Patent Application No. EP 12167589.6, filed on May 11, 2012, twenty-five pages.
European Communication, Third Party Opposition, mailed on Apr. 13, 2016 for European Patent Application No. EP 12167589.6, filed on May 11, 2012, five pages.
European Communication, Third Party Opposition, mailed on Apr. 13, 2016 for European Patent Application No. EP 12167591.2, filed on May 11, 2012, five pages.
European Communication, Third Party Opposition, mailed on Apr. 13, 2016 for European Patent Application No. EP 12167590.4, filed on May 11, 2012, five pages.
European Communication, Third Party Opposition, mailed on Apr. 13, 2016 for European Patent Application No. EP 12167596.1, filed on May 11, 2012, five pages.
European Office Action mailed on Mar. 12, 2015, for European Patent Application No. 12167590.4, filed on May 11, 2012, three pages.
European Office Action mailed on Mar. 11, 2015, for European Patent Application No. 12167589.6, filed on May 11, 2012, four pages.

(56) References Cited

OTHER PUBLICATIONS

European Office Action mailed on Mar. 11, 2015, for European Patent Application No. 12167591.2, filed on May 11, 2012, three pages.
European Office Action mailed on Mar. 12, 2015, for European Patent Application No. 12167593.8, filed on May 11, 2012, three pages.
European Office Action mailed on Mar. 11, 2015, for European Patent Application No. 12167599.5, filed on May 11, 2012, three pages.
European Office Action mailed on Mar. 11, 2015, for European Patent Application No. 12167596.1, filed on May 11, 2012, three pages.
European Office Action mailed on Mar. 12, 2015, for European Patent Application No. 12167597.9, filed on May 11, 2012, three pages.
European Communication mailed on Jan. 28, 2013, for European Patent Application No. 08743531.9, filed on Feb. 22, 2008, three pages.
European Communication mailed on Jan. 31, 2012, for European Patent Application No. 08743531.9, filed on Feb. 22, 2008, three pages.
European Communication mailed on Jul. 29, 2011, for European Patent Application No. 08743531.9 filed on Feb. 22, 2008, nine pages.
European Communication mailed on Jul. 29, 2011, for European Patent Application No. 07836007.0, filed on Jul. 6, 2007.
European Communication mailed on Jul. 29, 2011 for European Patent Application No. 08826245.6, three pages.
European Communication mailed on Jun. 24, 2011, for European Patent Application No. 08869426.0, nineteen pages.
European Communication mailed on May 3, 2010, for European Patent Application No. 07836007.0, filed on Jul. 6, 2007, five pages.
European Communication mailed on May 3, 2010 for European Patent Application No. 08826245.6, five pages.
Extended European Search Report mailed on Jun. 29, 2012, for European Patent Application No. 12167589.6, filed on May 11, 2012, five pages.
Extended European Search Report mailed on Jun. 29, 2012 for European Patent Application No. 12167590.4 filed on May 11, 2012, six pages.
Extended European Search Report mailed on Jun. 29, 2012 for European Patent Application No. 12167591.2 filed on May 11, 2012, six pages.
Extended European Search Report mailed on Jul. 3, 2012 for European Patent Application No. 12167593.8 filed on May 11, 2012, six pages.
Extended European Search Report mailed on Jun. 29, 2012 for European Patent Application No. 12167599.5 filed on May 11, 2012, six pages.
Extended European Search Report mailed on Jun. 29, 2012 for European Patent Application No. 12167596.1 filed on May 11, 2012, six pages.
Extended European Search Report mailed on Jun. 29, 2012 for European Patent Application No. 12167597.9, filed on May 11, 2012, six pages.
Indian Office Action mailed on Dec. 31, 2015, for Indian Patent Application No. 5324/DELNP/2009, filed on Feb. 22, 2008, two pages.
Indonesian Office Action mailed in Jun. 2014 for Indonesian Patent Application No. W00200902299, filed on Feb. 22, 2008, one page.
Japanese Office Action mailed on Apr. 4, 2013 for Japanese Patent Application No. JP-2011-181974, filed on Feb. 22, 2008, five pages.
Japanese Office Action mailed on Oct. 26, 2011, for Japanese Patent Application No. JP-2009518393, filed Jul. 6, 2007, two pages.
Japanese Office Action mailed on Feb. 28, 2011, for Japanese Patent Application No. 2009518393, filed on Jul. 6, 2007, ten pages.
Japanese Office Action mailed on Feb. 24, 2011, for Japanese Patent Application No. JP-2009551 044, filed on Feb. 22, 2008, six pages.
Korean Office Action mailed on Mar. 2, 2015, for Korean Patent Application No. 10-2009-7019921, filed on Feb. 22, 2008, two pages.
New Zealand Office Action mailed on Apr. 16, 2015, for New Zealand Patent Application No. 612093, filed on Feb. 22, 2008, three pages.
New Zealand Office Action mailed on Jan. 16, 2015, for New Zealand Patent Application No. 612093, filed on Feb. 22, 2008, three pages.
New Zealand Office Action mailed on Nov. 5, 2010 for New Zealand Patent Application No. 582092, two pages.
New Zealand Office Action mailed on Sep. 22, 2010, for New Zealand Patent Application No. 579802, filed on Feb. 22, 2008, two pages.
New Zealand Office Action mailed on Jul. 16, 2010, for New Zealand Patent Application No. 573060, filed on Jul. 6, 2007, two pages.
Singapore Office Action mailed on Aug. 25, 2011, for Singapore Patent Application No. 2009054750, filed on Feb. 22, 2008, six pages.
Singapore Office Action mailed on Apr. 8, 2011, for Singapore Patent Application No. 200808926-0, filed on Jul. 6, 2007, twenty-six pages.
Singapore Written Opinion and Search Report mailed on Nov. 18, 2010, for Singapore Patent Application No. 200905475-0, filed on Feb. 22, 2008, thirteen pages.
Vietnamese Office Action mailed on Nov. 30, 2015, for Vietnamese Patent Application No. 12012-02698, filed on Feb. 23, 2007, two pages.
Vietnamese Office Action mailed on Nov. 30, 2015, for Vietnamese Patent Application No. 12012-02700, filed on Feb. 23, 2007, two pages.
Vietnamese Office Action mailed on Nov. 30, 2015, for Vietnamese Patent Application No. 12012-02699, filed on Feb. 23, 2007, two pages.
Vietnamese Office Action mailed on Oct. 30, 2015, for Vietnamese Patent Application No. 1-201202696, filed on Feb. 23, 2007, two pages.
Vietnamese Office Action mailed on Oct. 30, 2015, for Vietnamese Patent Application No. 1-201202697, filed on Feb. 23, 2007, two pages.
Vietnamese Office Action mailed on Oct. 30, 2015, for Vietnamese Patent Application No. 1-201202695, filed on Feb. 23, 2007, two pages.
Notice of Allowance mailed on Sep. 9, 2016, for U.S. Appl. No. 14/817,068, filed Aug. 3, 2015, 7 pages.
Notice of Allowance dated Jan. 14, 2014 for Australian Patent Application No. 2008218186, filed Feb. 22, 2008, two pages.
Blachez et al., "Development of tablets with self-micro-emulsifying drug delivery system (SMEDDS)," AAPS Annual Meeting and Exposition Abstract, W 5114, 2005.
CAS entry for ritonavir. Accessed at http://scifinder.cas.org on Aug. 15, 2012.
Degussa, "Product Information, AEROPERL® 300 Pharma, Colloidal Silicon Dioxide," www.aerosil.com, 2006, 2 pages.
EMEA (European Medical Agency). ATRIPLA monograph, Scientific Discussion (2007).
Evonik Industries, "Specification, AEROPEL® 300 Pharma," SZO_SPEZ/DEG/17.06.2010/16:32/P04ASS25/001, JQP001, 2010, 2 pages.
Evonik: AEROPERL product data sheet, Nov. 13, 2011, retrieved from http://www.aerosil.com/product/aerosil/en/products/granulated-products/pages/default.aspx, _pages.
German et al., "Pharmacokinetics and Bioavailability of an Integrase and Novel Pharmacoenhancer-Containing Single-Tablet Fixed-Dose Combination Regimen for the Treatment of HIV," J. Acquired Immune Deficiency Syndromes, 2010, 55(3):323-329.
Goncalves et al., "Solid Micromulsions prepared by Adsorption of Micromulsion Preconcentrates onto Silica," AAPS Annual Meeting and Exposition, Abstract, T3112, 2006.
Gunsel et al., "Chapter 5: Compression-coated an layer tablets," Pharmaceutical Dosage Forms: Tablets, 1989, 1(2E):274-284.

(56) References Cited

OTHER PUBLICATIONS

Hammer et al., "Antiretroviral Treatment of Adult HIV Infection," J. American Medical Assoc., 2008, 300(5):555-570.
Hirsch et al., "Antiretroviral Drug Resistance Testing in Adult HIV-1 Infection: 2008 Recommendations of an International AIDS Society—USA Panel," Clinical Infectious Diseases, 2008, 47:266-285.
International Search Report and Written Opinion in International Appln. No. PCT/US2009/042607, dated Apr. 4, 2011, 10 pages.
International Search Report and Written Opinion in International Application No. PCT/US2010/023226, dated Apr. 8, 2011, 12 pages.
J.M. Huber Corporation, "North America Silica Specifications, Zeofree® 5161 Product Specifications," Huber Engineered Materials, 2009, 1 page.
J.M. Huber Corporation, "Product Dossier, synthetic Amorphous Silica," Huber Engineered Materials, www.hubermaterials.com, 2010, 14 pages.
Martinez-Cajas et al., "Antiretroviral Therapy," Drugs, 2008, 68(1):43-72.
Phillips et al., "Risk of extensive virological failure to the three original antiretroviral drug classes over long-term follow-up from the start of therapy in patients with HIV infection: an observational cohort study," The Lancet, 2007, 370(9603):1923-1928.
Rowe et al., Alcohol (ethanol), Handbook of Pharmaceutical Excipients 5E, 2006, 18-20.
Szczech, "Tenofovir Nephrotoxicity: Focusing Research Questions and Putting Them into Clinical Context," J. Infectious Diseases, 2008, 197(1): 7-9.
Von Wyl et al., "Emergence of HIV-1 Drug Resistance in Previously Untreated Patients Initiating Combination Antiretroviral Treatment," Archives of Internal Medicine, 2007, 167(16):1782-1790.
Argentinian Office Action in Argentinian Application No. P080100737, dated Mar. 15, 2017, 10 pages (with English abstract).
Ukrainian Office Action in Ukrainian Application No. 201210749, dated May 19, 2017, 8 pages (with English translation).
*Gilead Sciences, Inc.* v. *Mylan Pharmaceuticals Inc.*, "Complaint for Patent Infringement," Civil Action No. 1:17-cv-00036-IMK (N.D.W. Va. Mar. 3, 2017) 12 pages.
*Gilead Sciences, Inc.* v. *Mylan Pharmaceuticals Inc.*, "Mylan Pharmaceuticals Inc .'s Answer to Plaintiffs Complaint for Patent Infringement," Civil Action No. 1:17-cv-00036-IMK (N.D.W. Va. Mar. 3, 2017) 18 pages.
*Gilead Sciences, Inc.* v. *Mylan Pharmaceutical Inc.*, "Complaint for Patent Infringement," Civil Action No. 1:16-cv-00053-IMK (N.D. W. Va. Mar. 30, 2016) 11 pages.
*Gilead Sciences, Inc.* v. *Mylan Pharmaceuticals Inc.*, "Mylan Pharmaceuticals Inc.'s Answer to Plaintiffs Complaint for Patent Infringement," Civil Action No. 1:16-cv-00053-IMK (N.D.W. Va. Mar. 30, 2016) 17 pages.
*Gilead Sciences, Inc.* v. *Mylan Pharmaceuticals Inc.*, "Complaint for Patent Infringement," Civil Action Nos. 1:16-cv-00192-RGA (D. Del. Mar. 15, 2016) and 1:17-cv-00187-RGA, (D. Del. Feb. 22, 2017), consolidated, 200 pages.
*Gilead Sciences, Inc.* v. *Mylan Pharmaceuticals Inc.*, "Mylan Pharmaceuticals Inc.'s Answer to Plaintiffs Complaint for Patent Infringement" Civil Action Nos. 1:16-cv-00192-RGA (D. Del. Mar. 15, 2016) and 1:17-cv-00187-RGA (D. Del. Feb. 22, 2017), consolidated, 21 pages.
Defendant's Final Invalidity Contentions C.A. No. 16-192 (RGA) (Consolidated) 110 pages, 2017.
Abdel-Rahman, H.M., et al., "HIV Protease Inhibitors: Peptidomimetic Drugs And Future Perspectives," Current Medicinal Chemistry, 2002, 9, 1905-1922.

Barker, A.J, et al., "Studies Leading to the Identification of ZD1839 (IressaTM): An Orally Active, Selective Epidermal Growth Factor Receptor Tyrosine Kinase Inhibitor Targeted to the Treatment of Cancer," Bioorganic & Med. Chem. Letters, 2001, 11, 1911-1914.
Berge, S.M., et al, "Pharmaceutical Salts," J. Pharm. Sci., vol. 66(1), 1:1-19, 1977.
Erickson, J. et al., "Design, Activity, and 2.8 Å Crystal Structure of a C2 Symmetric Inhibitor Complexed to HIV-1 Protease," Science, vol. 249, pp. 527-533 (Aug. 3, 1990).
Ernest, C.S., et al., "Mechanism-Based Inactivation of CYP3A by HIV Protease Inhibitors," J. of Pharmacology And Experimental Therapeutics, 2005, 312, 583-591.
Gallant, J.E. "Protease-Inhibitor Boosting in the Treatment-Experienced Patient," AIDS Reviews, 2004, 6, 226-233.
Gutsche, C.D. and Pastoet al., Fundamentals of Organic Chemistry, Chapter 10, pp. 251-281 (1975).
Israel Office Action dated Apr. 18, 2012 for Israel Patent Application No. 200550, filed Feb. 22, 2008 (English Translation) 3 pages.
Kempf, D.J. et al., "Antiviral and Pharmacokinetic Properties of C2 Symmetric Inhibitors of the Human Immunodeficiency Virus Type 1 Protease," Antimicrobial Agents and Chemotherapy, 1991, 35(11), 2209-2214.
Kempf, D.J. et al., "Pharmacokinetic Enhancement of Inhibitors of the Human Immunodeficiency Virus Protease by Coadministration with Ritonavir," Antimicrobial Agents and Chemotherapy, 1997, 41(3), 654-660.
Kempf, D.J. et al., "Structure-Based, C2 Symmetric Inhibitors of HIV Protease," J. Med. Chem. 1990, 33(10), 2687-2689.
Koudriakova, T. et al. "Metabolism of the Human Immunodeficiency Virus Protease Inhibitors Indinavir And Ritonavir by Human Intestinal Microsomes And Expressed Cytochrome P4503A4/3A5: Mechanism Based Inactivation of Cytochrome P4503A by Ritonavir," Drug Metabolism And Disposition, 1998, 26(6):552-61.
Lin, J.H., "Human Inmunodeficiency Virus Protease Inhibitors from Drug Design to Clinical Studies," Advanced Drug Delivery Reviews, 1997, 27, 215-213.
Meunier, B. et at., "Mechanism of Oxidation Reaction Catalyzed by Cytochrome P450 Enzymes," Chem. Rev. 2004, 104, 3947-3980.
Morissette, S.L., et al., "Elucidation of Crystal Form Diversity of the HIV Protease Inhibitor Ritonavir by High-Throughput Crystallization," Proc. Natl. Acad. Sci. USA, 2003, 100(5), 2180-2184.
Prescribing information for Aptivus® (Capsules, 250 mg) (2005).
Prescribing information for Invirase® (Capsules) (Dec. 24, 2003).
Prescribing information for Kaletra® (2000).
Prescribing information for Norvir® (2001).
Prescribing information for Prezista® (2001).
Prescribing information for Reyataz® (2004).
Product Information for Morpholine, Huntsman brochure (2005).
Protein Data Bank, Crystal Structure of Human Microsomal P450 3A4 (1TQN) Structure (http://www.rcsb.org/pdb/explore/explore.do?structureId=1TQN) dated Nov. 1, 2017.
Protein Data Bank, HIV-1 Protease Dimer Complexed with A-84538, (1HXW) Structure (http://www.resb.org/pdb/explore/explore.do?structureID=1HXW) dated Nov. 1, 2017.
United Nations Environment Programme International Labor Organisation World Health Organization, IPCS International Programme on Chemical Safety Health And Safety Guide on Morpholine, Health And Safety Guide No. 92, Geneva (1995).
Vacca, J.P., et al., "L-735,524: An Orally Bioavailable Human Immunodeficiency Virus Type 1 Protease Inhibitor," Proc. Natl. Acad. Sci. USA, 1994, 91, 4096-4100.
Williams, D.A., et al. and Lemke, Foye's Principles of Medicinal Chemistry, 5th ed. Ch. 2 (2002), pp. 37-67.
Williams, D.A., and Lemkeet al., Foye's Principles of Medicinal Chemistry, 5th ed. Ch. 8 (2002), pp. 174-233.

\* cited by examiner

US 9,891,239 B2

MODULATORS OF PHARMACOKINETIC PROPERTIES OF THERAPEUTICS

CROSS-REFERENCE TO RELATED APPLICATIONS

This application claims priority to U.S. Provisional Application Ser. No. 60/903,228, entitled "Modulators of Pharmacokinetic Properties of Therapeutics", filed Feb. 23, 2007, and U.S. Provisional Application Ser. No. 60/958,716, entitled "Modulators of Pharmacokinetic Properties of Therapeutics", filed Jul. 6, 2007. The contents of these provisional applications are herein incorporated by reference in their entirety for all purposes.

FIELD OF THE INVENTION

This application relates generally to compounds and pharmaceutical compositions which modify, e.g., improve, the pharmacokinetics of a co-administered drug, and methods of modifying, e.g., improving, the pharmacokinetics of a drug by co-administration of the compounds with the drug.

BACKGROUND OF THE INVENTION

Oxidative metabolism by cytochrome P450 enzymes is one of the primary mechanisms of drug metabolism. It can be difficult to maintain therapeutically effective blood plasma levels of drugs which are rapidly metabolized by cytochrome P450 enzymes. Accordingly, the blood plasma levels of drugs which are susceptible to cytochrome P450 enzyme degradation can be maintained or enhanced by co-administration of cytochrome P450 inhibitors, thereby improving the pharmacokinetics of the drug.

While certain drugs are known to inhibit cytochrome P450 enzymes, more and/or improved inhibitors for cytochrome P450 monooxygenase are desirable. Particularly, it would be desirable to have cytochrome P450 monooxygenase inhibitors which do not have appreciable biological activity other than cytochrome P450 inhibition. Such inhibitors can be useful for minimizing undesirable biological activity, e.g., side effects. In addition, it would be desirable to have P450 monooxygenase inhibitors that lack significant or have a reduced level of protease inhibitor activity. Such inhibitors could be useful for enhancing the effectiveness of antiretroviral drugs, while minimizing the possibility of eliciting viral resistance, especially against protease inhibitors.

SUMMARY OF THE INVENTION

One aspect of the present application is directed to compounds and pharmaceutical compositions which modify, e.g., improve, the pharmacokinetics of a co-administered drug, e.g., by inhibiting cytochrome P450 monooxygenase.

In one embodiment, the present application provides for compounds having a structure according to Formula IV, Formula IV

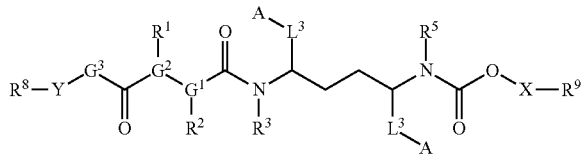

or a pharmaceutically acceptable salt, solvate, and/or ester thereof, wherein,
each $L^3$ is independently an alkylene or substituted alkylene;
each A is independently an aryl or substituted aryl;
X is heterocyclylalkyl;
Y is heterocyclylalkyl or alkyl;
$G^1$ and $G^2$ are independently CH or N, with the proviso that $G^1$ and $G^2$ are different;
$G^3$ is —$NR^7$— or —O—;
$R^1$, $R^3$, $R^5$, and $R^7$ are each independently selected from the group consisting of H, alkyl, substituted alkyl, arylalkyl, and substituted arylalkyl;
$R^2$ is independently selected from the group consisting of substituted alkyl, alkoxyalkyl, hydroxyalkyl, trialkylsiloxyalkyl, heterocyclylalkyl, substituted heterocyclylalkyl, aminoalkyl, substituted aminoalkyl, -alkylene-N($R^a$)—C(O)-alkyl, -alkylene-N$R^a$—C(O)—N($R^a$)$_2$, -alkylene-N$R^a$—C(=N—$R^b$)—N($R^a$)$_2$, -alkylene-C(=N—$R^b$)—N($R^a$)$_2$, -alkylene-C(O)—OH, -alkylene-C(O)—Oalkyl, and -alkylene-C(O)—N($R^c$)$_2$;
$R^8$ and $R^9$ are each one or more substituents independently selected from the group consisting of H, alkyl, substituted alkyl, halogen, and —CN;
each $R^a$ is independently selected from the group consisting of H, alkyl, and substituted alkyl;
$R^b$ is selected from the group consisting of H, alkyl, substituted alkyl, CN, and —S(O$_2$)-alkyl; and
each $R^c$ is independently selected from the group consisting of H, alkyl, substituted alkyl, heterocyclyl, substituted heterocyclyl, —S(O$_2$)-alkyl, —S(O$_2$)-aryl, and substituted —S(O$_2$)-aryl.

In another embodiment, the present application provides for a pharmaceutical composition comprising a compound of Formula I, and a pharmaceutically acceptable carrier or excipient.

In another embodiment, the present application provides for a pharmaceutical composition comprising a compound of Formula I, at least one additional therapeutic agent, and a pharmaceutically acceptable carrier or excipient.

In another embodiment, the present application provides for a method for improving the pharmacokinetics of a drug, comprising administering to a patient treated with said drug, a therapeutically effective amount of a compound of Formula I, or a pharmaceutically acceptable salt, solvate, and/or ester thereof.

In another embodiment, the present application provides for a method for inhibiting cytochrome P450 monooxygenase in a patient comprising administering to a patient in need thereof an amount of a compound of Formula I, or a pharmaceutically acceptable salt, solvate, and/or ester thereof, effective to inhibit cytochrome P450 monooxygenase.

In another embodiment, the present application provides for a method for treating a viral infection, e.g., HIV, comprising administering to a patient in need thereof a therapeutically effective amount of a compound of Formula I, or a pharmaceutically acceptable salt, solvate, and/or ester thereof, in combination with a therapeutically effective amount of one or more additional therapeutic agents which are metabolized by cytochrome P450 monooxygenase, and are suitable for treating a viral infection, e.g., HIV.

In another embodiment, the present application provides for a combination pharmaceutical agent comprising:
a) a first pharmaceutical composition comprising a compound of Formula I, or a pharmaceutically acceptable salt, solvate, and/or ester thereof; and b) a second pharmaceutical composition comprising at least one additional active agent which is metabolized by cytochrome P450 monooxygenase.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

All documents cited herein are each incorporated by reference in their entirety for all purposes.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of formula (I)" means a compound of formula (I) or a pharmaceutically acceptable salt, solvate, ester or stereoisomer thereof, or a physiologically functional derivative thereof. Similarly, with respect to isolatable intermediates, the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)$ $CH_2CH_3$), 2-methyl-2-propyl (t-Bu, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or -OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡CH—).

"Amino" means an $NH_2$ or a —$NR_2$ group in which the "R" groups are independently H, alkyl, haloalkyl, hydroxylalkyl, carbocyclyl (substituted or unsubstituted, including saturated or partially unsaturated cycloalkyl and aryl groups), heterocyclyl (substituted or unsubstituted, including saturated or unsaturated heterocycloalkyl and heteroaryl groups), arylalkyl (substituted or unsubstituted) or arylalkyl (substituted or unsubstituted) groups. Non-limiting examples of amino groups include —NH$_2$, —NH(alkyl), NH(haloalkyl), —NH(carbocyclyl), —NH(heterocyclyl), —N(alkyl)$_2$, —N(carbocyclyl)$_2$, —N(heterocyclyl)$_2$, —N(alkyl)(carbocyclyl), —N(alkyl)(hetero cyclyl), —N(carbocyclyl)(heterocyclyl), etc., wherein alkyl, carbocyclyl, and heterocyclyl can be substituted or unsubstituted and as defined and described herein. "Substituted" or "protected" amino means an aminoalkyl as described and defined herein in which a H of the amino group is replaced with e.g., acyl groups, for example conventional amine protecting groups such as 9-Fluorenylmethyl carbamate ("Fmoc"), t-Butyl carbamate ("Boc"), Benzyl carbamate ("Cbz"), acetyl, trifluoracetyl, —C(O)-amino, phthalimidyl, triphenylmethyl, p-Toluenesulfonyl ("Tosyl"), methylsulfonyl ("mesyl"), etc.

"Aminoalkyl" means an acyclic alkyl radical in which one of the hydrogen atoms bonded to a carbon atom, typically a terminal or sp$^3$ carbon atom, is replaced with an amino radical as defined and described herein. Non-limiting examples of aminoalkyl include —CH$_2$—NH$_2$, —CH$_2$CH$_2$—NH$_2$, —CH$_2$CH$_2$CH$_2$—NH$_2$, —CH$_2$CH$_2$CH$_2$CH$_2$—NH$_2$, —CH$_2$CH(CH$_3$)—NH$_2$, —CH$_2$CH$_2$CH(CH$_3$)—NH$_2$, NH(CH$_3$), —CH$_2$CH$_2$—NH (CH$_3$), —CH$_2$CH$_2$CH$_2$—NH(CH$_3$), —CH$_2$CH$_2$CH$_2$CH$_2$—NH(CH$_3$), —CH$_2$CH(CH$_3$)—NH(CH$_3$), —CH$_2$CH$_2$CH (CH$_3$)—NH(CH$_3$), —CH$_2$—N(CH$_3$)$_2$, —CH$_2$CH$_2$—N (CH$_3$)$_2$, —CH$_2$CH$_2$CH$_2$—N(CH$_3$)$_2$, —CH$_2$CH$_2$CH$_2$CH$_2$—N(CH$_3$)$_2$, —CH$_2$CH(CH$_3$)—N(CH$_3$)$_2$, —CH$_2$CH$_2$CH (CH$_3$)—N(CH$_3$)$_2$, —CH$_2$—NH(CH$_2$CH$_3$), —CH$_2$CH$_2$—NH(CH$_2$CH$_3$), —CH$_2$CH$_2$CH$_2$—NH(CH$_2$CH$_3$), —CH$_2$CH$_2$CH$_2$CH$_2$—NH(CH$_2$CH$_3$), —CH$_2$CH(CH$_3$)—NH(CH$_2$CH$_3$), —CH$_2$CH$_2$CH(CH$_3$)—NH(CH$_2$CH$_3$), —CH$_2$—N(CH$_2$CH$_3$)$_2$, —CH$_2$CH$_2$—N(CH$_2$CH$_3$)$_2$, —CH$_2$CH$_2$CH$_2$—N(CH$_2$CH$_3$)$_2$, —CH$_2$CH$_2$CH$_2$CH$_2$—N (CH$_2$CH$_3$)$_2$, —CH$_2$CH(CH$_3$)—N(CH$_2$CH$_3$)$_2$, —CH$_2$CH$_2$CH(CH$_3$)—N(CH$_2$CH$_3$)$_2$, etc. "Substituted" or "protected" aminoalkyl means an aminoalkyl as described and defined herein in which the H of the amino group is replaced with e.g., acyl groups, for example conventional amine protecting groups such as 9-Fluorenylmethyl carbamate ("Fmoc"), t-Butyl carbamate ("Boc"), Benzyl carbamate ("Cbz"), acetyl, —C(O)-amino, trifluoracetyl, phthalimidyl, triphenylmethyl, p-Toluenesulfonyl ("Tosyl"), methylsulfonyl ("mesyl"), etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —NCS, —NO, —NO$_2$, =NO$_2$, —N$_3$, —NHC(=O)R, —NHS(=O)$_2$R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O) (OR)$_2$, —P(=O)(OR)$_2$, —P(=O)(O$^-$)$_2$, —P(=O)(OH)$_2$, —P(O)(OR)(O$^-$), —C(=O)R, —C(=O)OR, —C(=O)X, —C(S)R, —C(O)OR, —C(O)O$^-$, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted. When the number of carbon atoms is designated for a substituted group, the number of carbon atoms refers to the group, not the substituent (unless otherwise indicated). For example, a C$_{1-4}$ substituted alkyl refers to a C$_{1-4}$ alkyl, which can be substituted with groups having more the, e.g., 4 carbon atoms.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or 5). The terms "heterocycle" or "heterocyclyl" includes saturated rings (i.e., heterocycloalkyls), partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

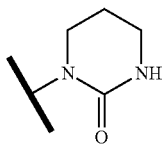

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, thiadiazinyl, 2H,6H-1,5,2-dithiazinyl, thienyl, thianthrenyl, pyranyl, isobenzofuranyl, chromanyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

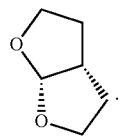

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or spa carbon atom, is replaced with a heterocyclyl radical (i.e., a heterocyclyl-alkylene-moiety). Typical heterocyclyl alkyl groups include, but are not limited to heterocyclyl-CH$_2$—, heterocyclyl-CH(CH$_3$)—, heterocyclyl-CH$_2$CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms, e.g., the alkyl portion of the heterocyclylalkyl group is 1 to 6 carbon atoms and the heterocyclyl moiety is 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or sp$^3$ carbon atom, but also a sp$^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclylalkenyl group comprises 3 to 20 carbon atoms, e.g., the alkenyl portion of the heterocyclyl alkenyl group is 2 to 6 carbon atoms and the heterocyclyl moiety is 1 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclylalkynyl group comprises 3 to 20 carbon atoms, e.g., the alkynyl portion of the heterocyclylalkynyl group is 2 to 6 carbon atoms and the heterocyclyl moiety is 1 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-5-aryl, -alkylene-5-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothio phenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I (e.g., an optionally substituted aryl group) refers to a moiety having 0, 1, 2, or more substituents.

"Ac" means acetyl (—C(O)CH$_3$).
"Ac$_2$O" means acetic anhydride.
"DCM" means dichloromethane (CH$_2$Cl$_2$).
"DIBAL" means diisobutylaluminum hydride.
"DMAP" means dimethylaminopyridine.
"EDC" means 1-(3-Dimethylaminopropyl)-3-ethylcarbodiimide.
"Et" means ethyl.
"EtOAc" means ethylacetate.
"HOBt" means N-hydroxybenzotriazole.
"Me" means methyl (—CH$_3$).
"MeOH" means methanol.
"MeCN" means acetonitrile.
"Pr" means propyl.
"i-Pr" means isopropyl (—CH(CH$_3$)$_2$).
"i-PrOH" means isopropanol.
"rt" means room temperature.
"TFA" means trifluoroacetic acid.
"THE" means tetrahydrofuran.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of*

Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in Protective Groups in Organic Synthesis, Theodora W. Greene and Peter G. M. Wuts (John Wiley & Sons, Inc., New York, 1999, ISBN 0-471-16019-9) ("Greene"). See also Kocienski, Philip J.; Protecting Groups (Georg Thieme Verlag Stuttgart, N.Y., 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I

In one embodiment, the present application provides compounds according to Formula I,

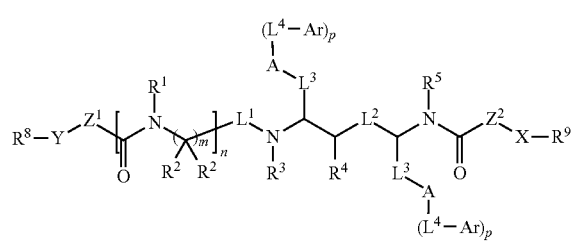

Formula I or a pharmaceutically acceptable salt, solvate, and/or ester thereof, wherein, $L^1$ is selected from the group consisting of —C($R^6$)$_2$—, —C(O)—, —S(O$_2$)—, —N($R^7$)—C(O)—, and —O—C(O)—;

$L^2$ is a covalent bond, —C($R^6$)$_2$— or —C(O)—;

each $L^3$ is independently a covalent bond, an alkylene, or substituted alkylene;

each $L^4$ is independently selected from the group consisting of a covalent bond, alkylene, substituted alkylene, —O—, —CH$_2$—O—, and —NH—;

each A is independently selected from the group consisting of H, alkyl, substituted alkyl, aryl, substituted aryl, heterocyclyl, and substituted heterocyclyl,
with the proviso that when A is H, p is 0;
$Z^1$ and $Z^2$ are each independently —O— or —N($R^7$)—;
Y and X are independently selected from the group consisting of heterocyclyl and heterocyclylalkyl;
each Ar is independently selected from the group consisting of aryl, substituted aryl, heteroaryl, and substituted heteroaryl;
$R^1$, $R^3$, and $R^5$ are each independently selected from the group consisting of H, alkyl, substituted alkyl, arylalkyl, and substituted arylalkyl;
each $R^2$ is independently selected from the group consisting of H, alkyl, substituted alkyl, alkoxyalkyl, hydroxyalkyl, arylheteroalkyl, substituted arylheteroalkyl, arylalkyl, substituted arylalkyl, heterocyclylalkyl, substituted heterocyclylalkyl, aminoalkyl, substituted aminoalkyl, -alkylene-C(O)—OH, -alkylene-C(O)—Oalkyl, -alkylene-C(O)amino, -alkylene-C(O)-alkyl;
$R^4$ and $R^6$ are independently selected from the group consisting of H, alkyl, substituted alkyl, and heteroalkyl;
each $R^7$ is independently selected from the group consisting of H, alkyl, substituted alkyl, heteroalkyl, carbocyclyl, substituted carbocyclyl, heterocyclyl, and substituted heterocyclyl;
$R^8$ and $R^9$ are each one or more substituents independently selected from the group consisting of H, alkyl, substituted alkyl, halogen, aryl, substituted aryl, heterocyclyl, substituted heterocyclyl, and —CN;
m is 1 or 2;
n is 0 or 1; and
each p is independently 0 or 1.

In another embodiment of the compounds of Formula I, n is 1.

In another embodiment of the compounds of Formula I, n is 0.

In another embodiment of the compounds of Formula I, n is 1 and $L^2$ is —CH($R^6$—, wherein $R^6$ is selected from the group consisting of H, alkyl, substituted alkyl, and heteroalkyl.

In another embodiment of the compounds of Formula I, n is 1 and $L^1$ is —$CH_2$—.

In another embodiment of the compounds of Formula I, n is 1 and $L^2$ is —C(O)—.

In another embodiment of the compounds of Formula I, n is 1 and Y is heterocyclylalkyl.

In another embodiment of the compounds of Formula I, n is 1 and Y—$R^8$ is —$CH_2$-(substituted heteroaryl).

In another embodiment of the compounds of Formula I, n is 1 and Y—$R^8$ is

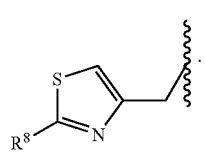

In another embodiment of the compounds of Formula I, n is 1 and Y—$R^8$ is

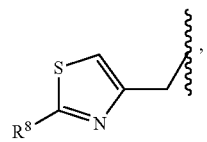

wherein $R^8$ is alkyl, for example 2-propyl.

In another embodiment of the compounds of Formula I, n is 1 and X is heterocyclylalkyl.

In another embodiment of the compounds of Formula I, n is 1 and X is —$CH_2$-heteroaryl.

In another embodiment of the compounds of Formula I, n is 1 and X—$R^9$ is

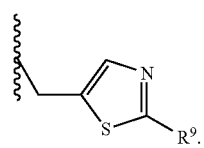

In another embodiment of the compounds of Formula I, n is 1 and X—$R^9$ is

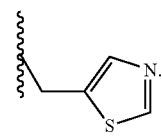

In another embodiment of the compounds of Formula I, n is 1 and $Z^1$ is —N($R^7$)—.

In another embodiment of the compounds of Formula I, n is 1 and $Z^1$ is —N(alkyl)- or —N(carbocyclyl)-.

In another embodiment of the compounds of Formula I, n is 1 and $Z^1$ is —N($CH_3$)— or —N(cyclopropyl)-.

In another embodiment of the compounds of Formula I, n is 1 and $Z^1$ is —NH—.

In another embodiment of the compounds of Formula I, n is 1 and each A is independently aryl or substituted aryl.

In another embodiment of the compounds of Formula I, n is 1 and each A is phenyl.

In another embodiment of the compounds of Formula I, n is 1 and each A is phenyl and each p is 0.

In another embodiment of the compounds of Formula I, n is 1 and $R^2$ is H, alkyl, substituted alkyl, or heteroalkyl.

In another embodiment of the compounds of Formula I, n is 1 and $R^2$ is 2-propyl, methyl, —$CH_2$—O-benzyl, —CH($CH_3$)(O-t-Bu), or —CH($CH_3$)(OH).

In another embodiment of the compounds of Formula I, $L^1$ is —C(O)—;
each A is independently aryl, substituted aryl, alkyl, or substituted alkyl;
$R^1$ is H or alkyl;
each $R^2$ is independently H, alkyl, substituted alkyl, or heteroalkyl;
$R^3$, $R^4$, $R^5$, and $R^6$ are each H;
each $R^7$ is independently H, alkyl, or carbocyclyl;
$R^8$ is H or alkyl;

R⁹ is H;
X and Y are both heterocyclylalkyl;
Z² is —O—; and
p is 0.
In another embodiment of the compounds of Formula I, each A is phenyl;
R¹ is H or —CH₃;
each R² is H, methyl, ethyl, 2-propyl, —CH₂—O-benzyl, —CH(CH₃)—OH,
or —CH(CH₃)(O-t-Bu);
each R⁷ is H, methyl or cyclopropyl;
R⁸ is H or 2-propyl;
X is

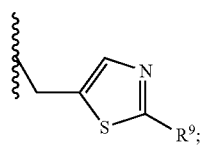

and
Y is

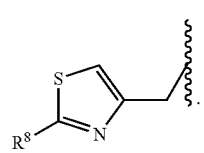

In another embodiment, the compounds of Formula I have the following general Formula IA:

In another embodiment of the compounds of Formula IA, L² is —C(R⁶)₂—, wherein each R⁶ is H.

In another embodiment of the compounds of Formula IA, L² is —C(R⁶)₂—, wherein each R⁶ is independently H or alkyl, and said alkyl includes any alkyl disclosed herein.

In another embodiment of the compounds of Formula IA, L² is —C(R⁶)₂—, wherein one R⁶ is H and the other R⁶ is alkyl, wherein said alkyl includes any alkyl disclosed herein.

In another embodiment of the compounds of Formula IA, m is 1 and R² is H.

In another embodiment of the compounds of Formula IA, m is 1 and R² is alkyl, wherein said alkyl includes any alkyl disclosed herein.

In another embodiment of the compounds of Formula IA, m is 1 and R² is i-propyl.

In another embodiment of the compounds of Formula IA, m is 1 and R² is i-butyl.

In another embodiment of the compounds of Formula IA, m is 1 and R² is ethyl.

In another embodiment of the compounds of Formula IA, m is 1 and R² is methyl.

In another embodiment of the compounds of Formula IA, m is 2 and each R² is independently selected from H and alkyl.

In another embodiment of the compounds of Formula IA, m is 2 and each R² is H.

In another embodiment, the compounds of Formula I have the following general Formula IB:

Formula IA

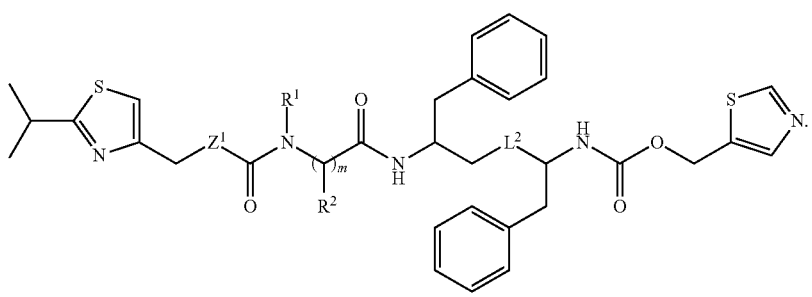

In another embodiment of the compounds of Formula IA, Z¹ is —N(R⁷)—. In a particular embodiment, R⁷ is H. In another particular embodiment, R⁷ is alkyl, for example any of the alkyl groups disclosed herein. In another particular embodiment, R⁷ is heteroalkyl, for example any of the heteroalkyl groups disclosed herein. In another particular embodiment, R⁷ is substituted or unsubstituted carbocyclyl, wherein for example, said carbocyclyl is any of the carbocyclyl groups disclosed herein. In another particular embodiment, R⁷ is substituted or unsubstituted heterocyclyl, wherein for example, said heterocyclyl is any of the heterocyclyl groups disclosed herein.

In another embodiment of the compounds of Formula IA, Z¹ is —O—.

Formula IB

In another embodiment of the compounds of Formula IB, Z¹ is —NTT. In a particular embodiment, R⁷ is H. In another particular embodiment, R⁷ is alkyl, for example any of the alkyl groups disclosed herein. In another particular embodiment, $R^7$ is heteroalkyl, for example any of the heteroalkyl groups disclosed herein. In another particular embodiment, $R^7$ is substituted or unsubstituted carbocyclyl, wherein for example, said carbocyclyl is any of the carbocyclyl groups disclosed herein. In another particular embodiment, $R^7$ is substituted or unsubstituted heterocyclyl, wherein for example, said heterocyclyl is any of the heterocyclyl groups disclosed herein.

In another embodiment of the compounds of Formula IB, $Z^1$ is —O—.

In another embodiment of the compounds of Formula IB, $L^2$ is —C($R^6$)$_2$—, wherein each $R^6$ is H.

In another embodiment of the compounds of Formula IB, $L^2$ is —C($R^6$)$_2$—, wherein each $R^6$ is independently H or alkyl, and said alkyl includes any alkyl disclosed herein.

In another embodiment of the compounds of Formula IB, $L^2$ is —C($R^6$)$_2$—, wherein one $R^6$ is H and the other $R^6$ is alkyl, wherein said alkyl includes any alkyl disclosed herein.

In another embodiment of the compounds of Formula IB, $R^8$ and $R^9$ are both H.

In another embodiment of the compounds of Formula IB, W and $R^9$ are independently selected from H and alkyl, wherein said alkyl includes any alkyl disclosed herein.

In another embodiment, the compounds of Formula I have one of the following structures:

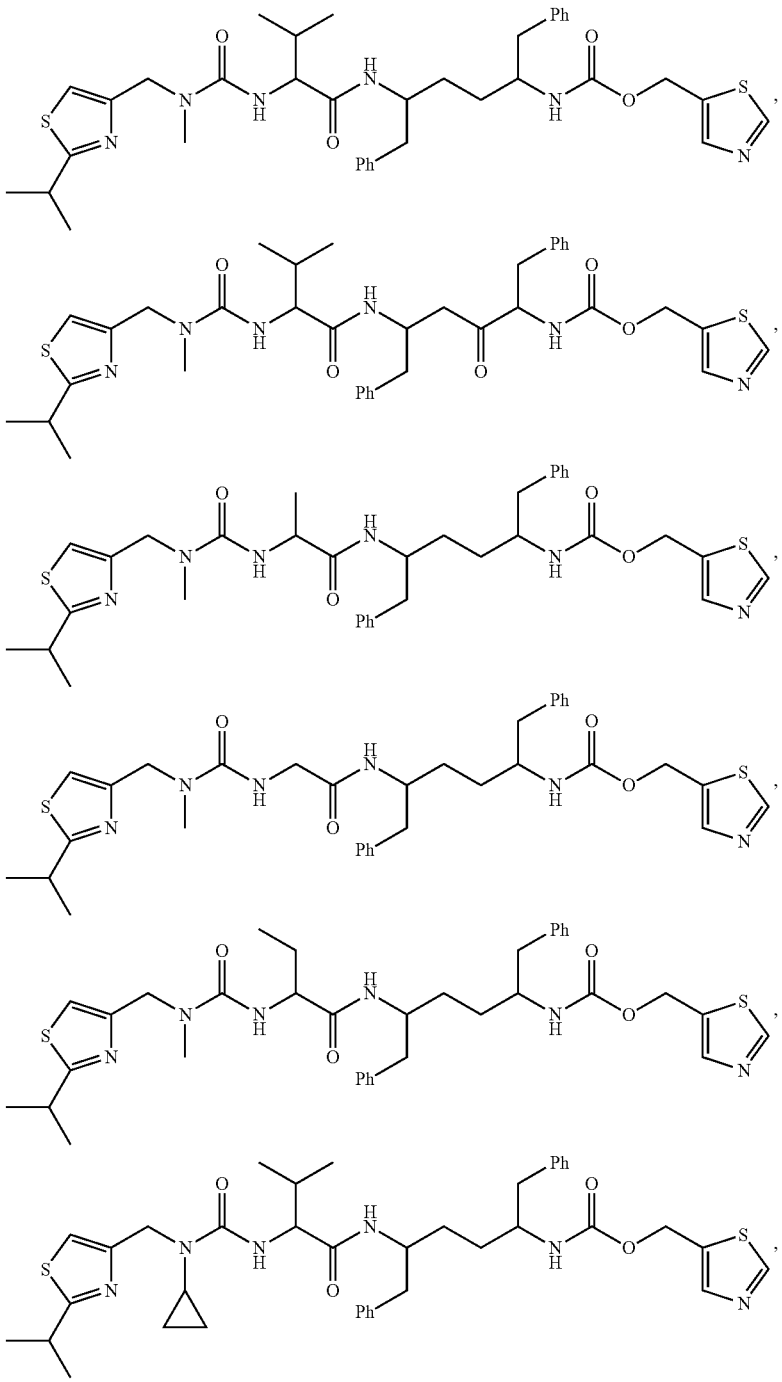

-continued
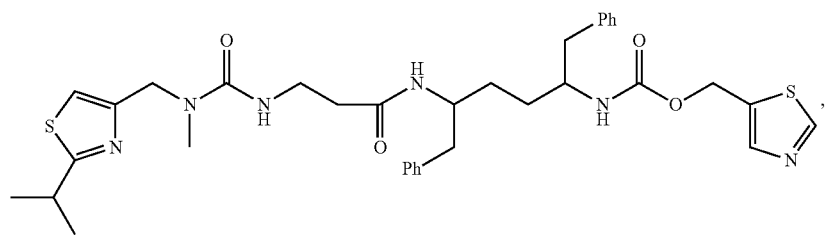,
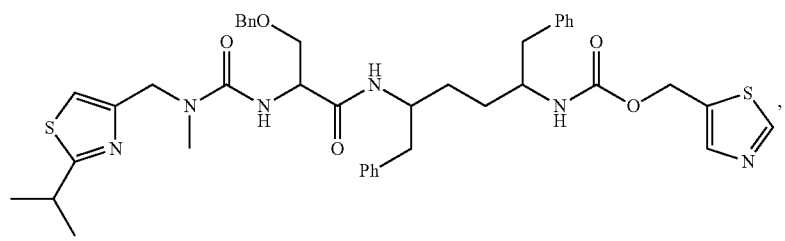,
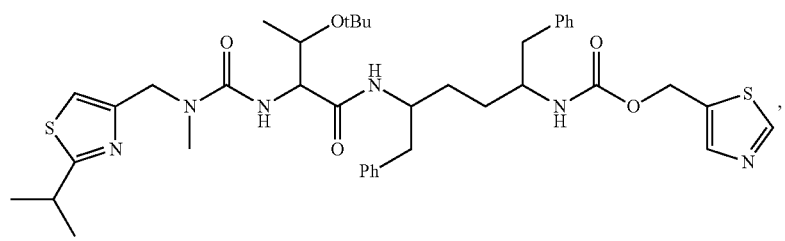,
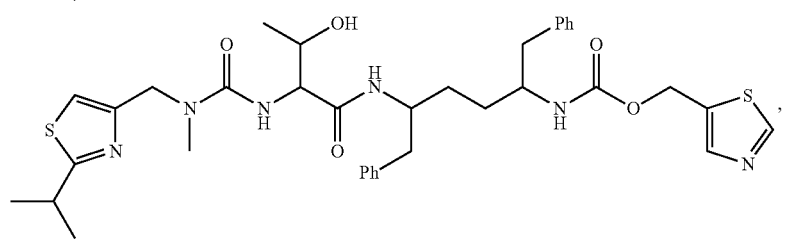,
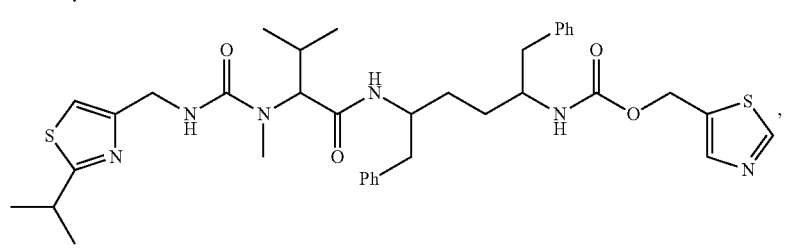,
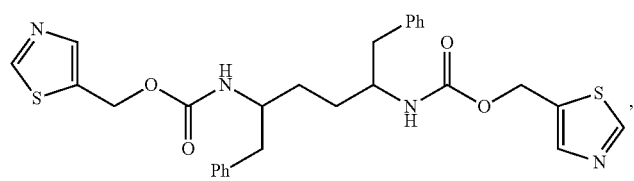,
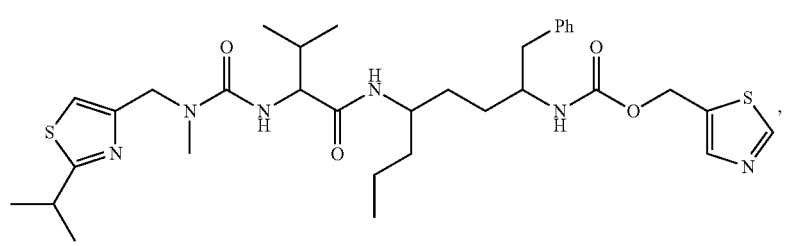,

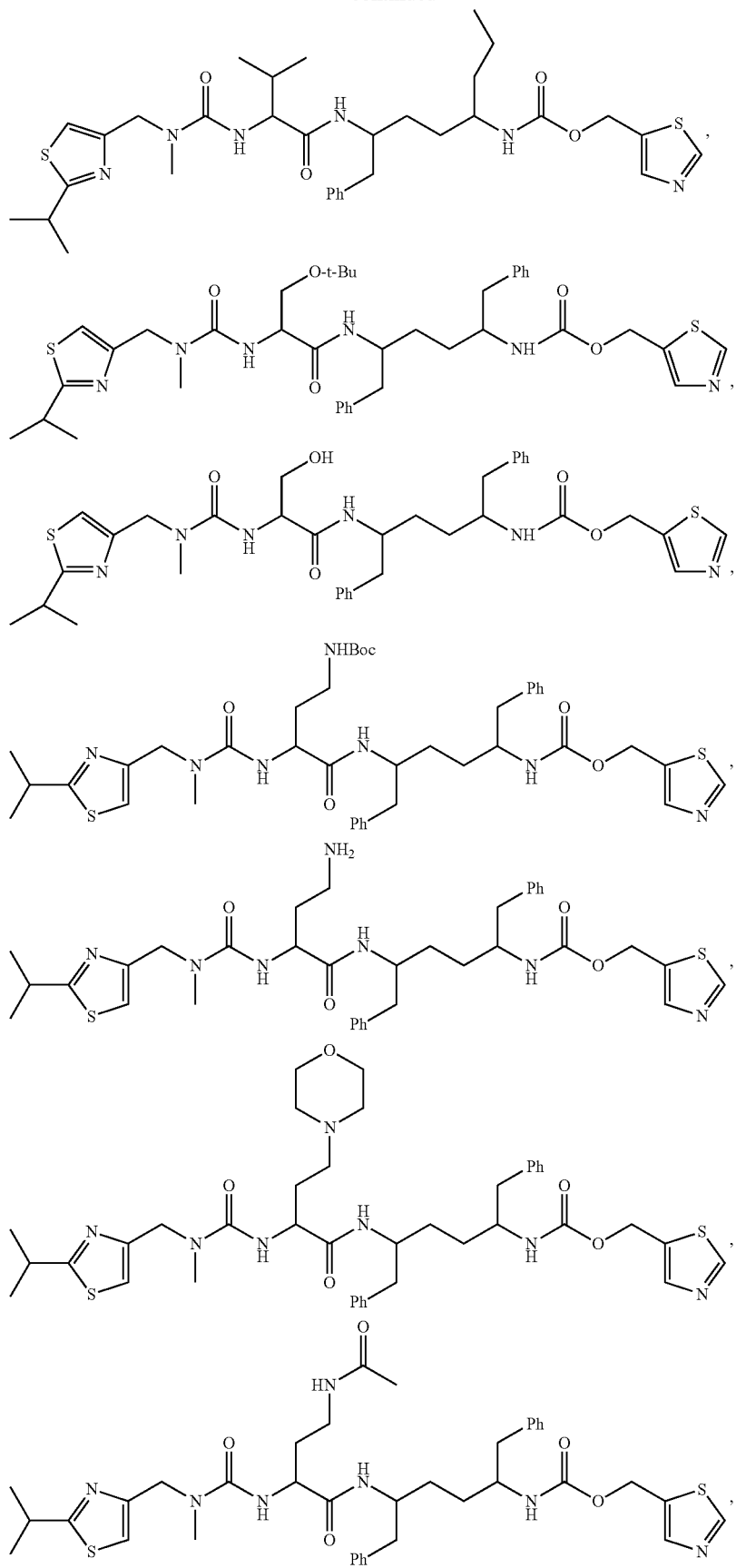

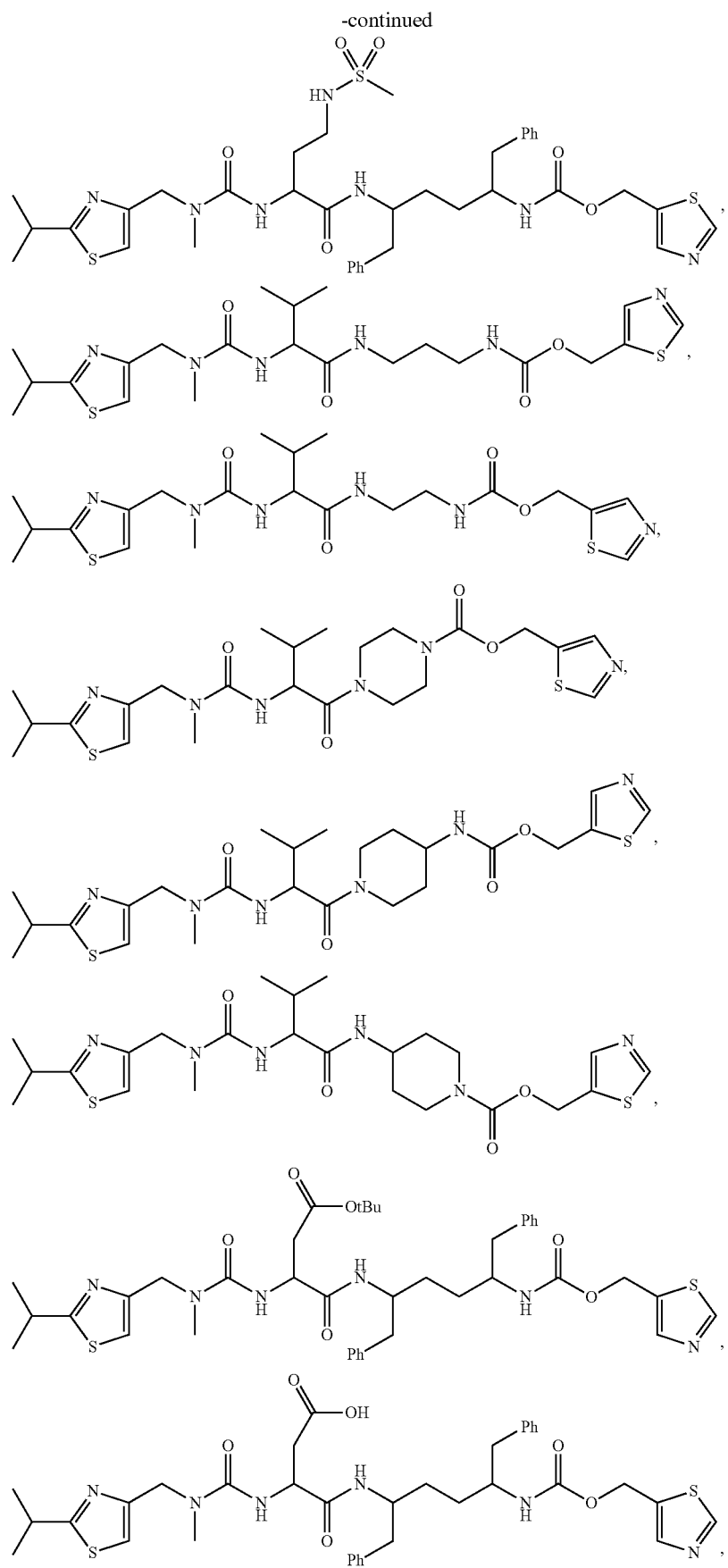

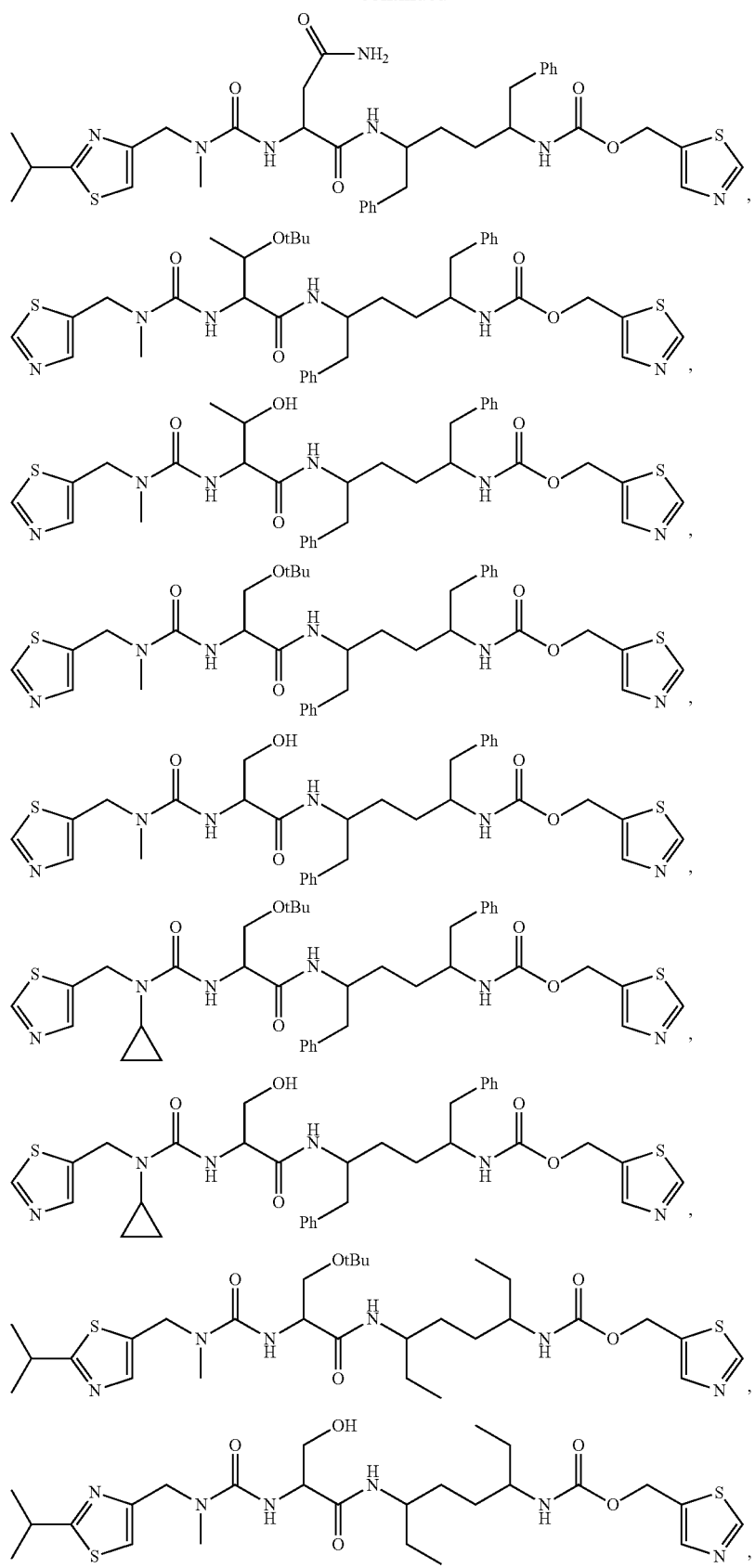

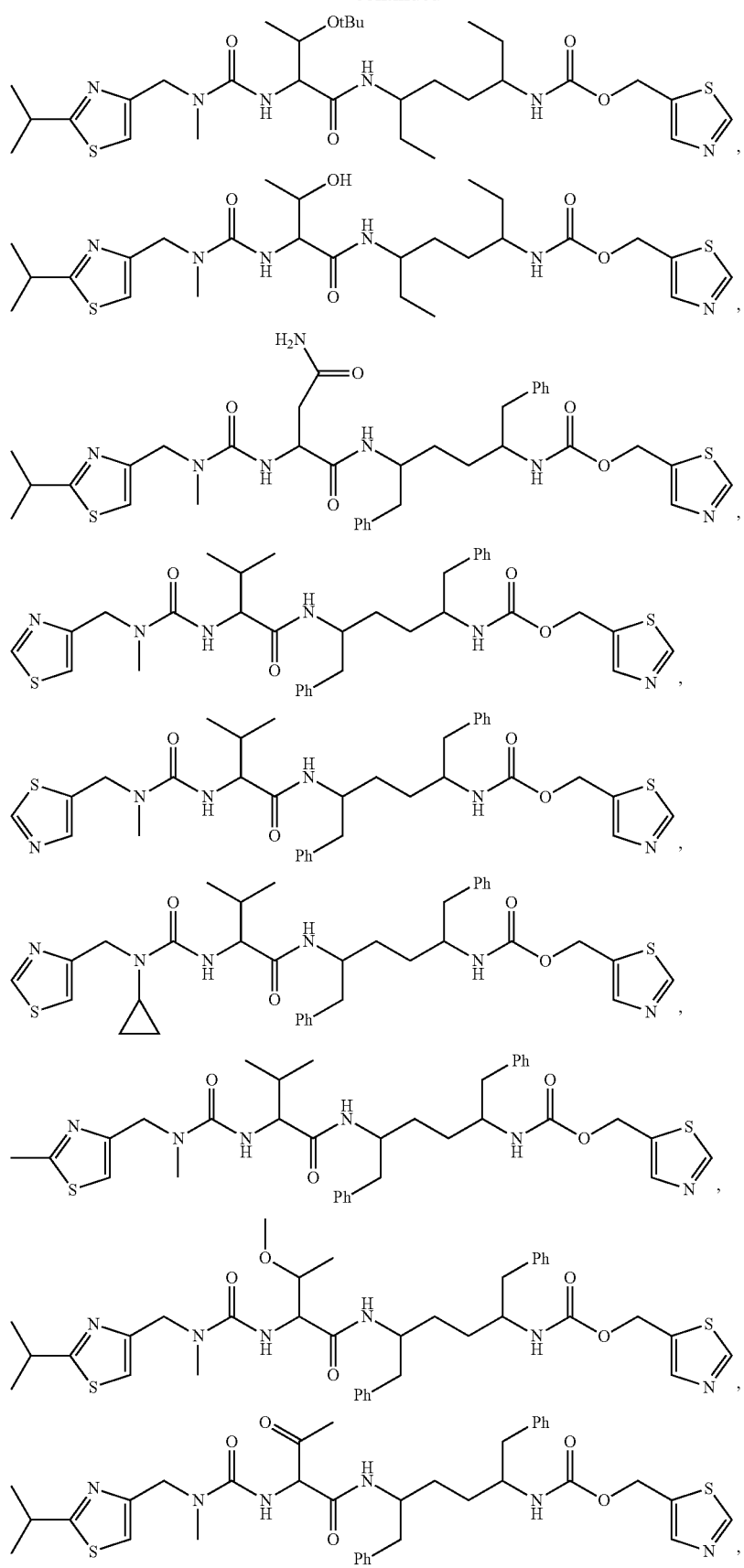

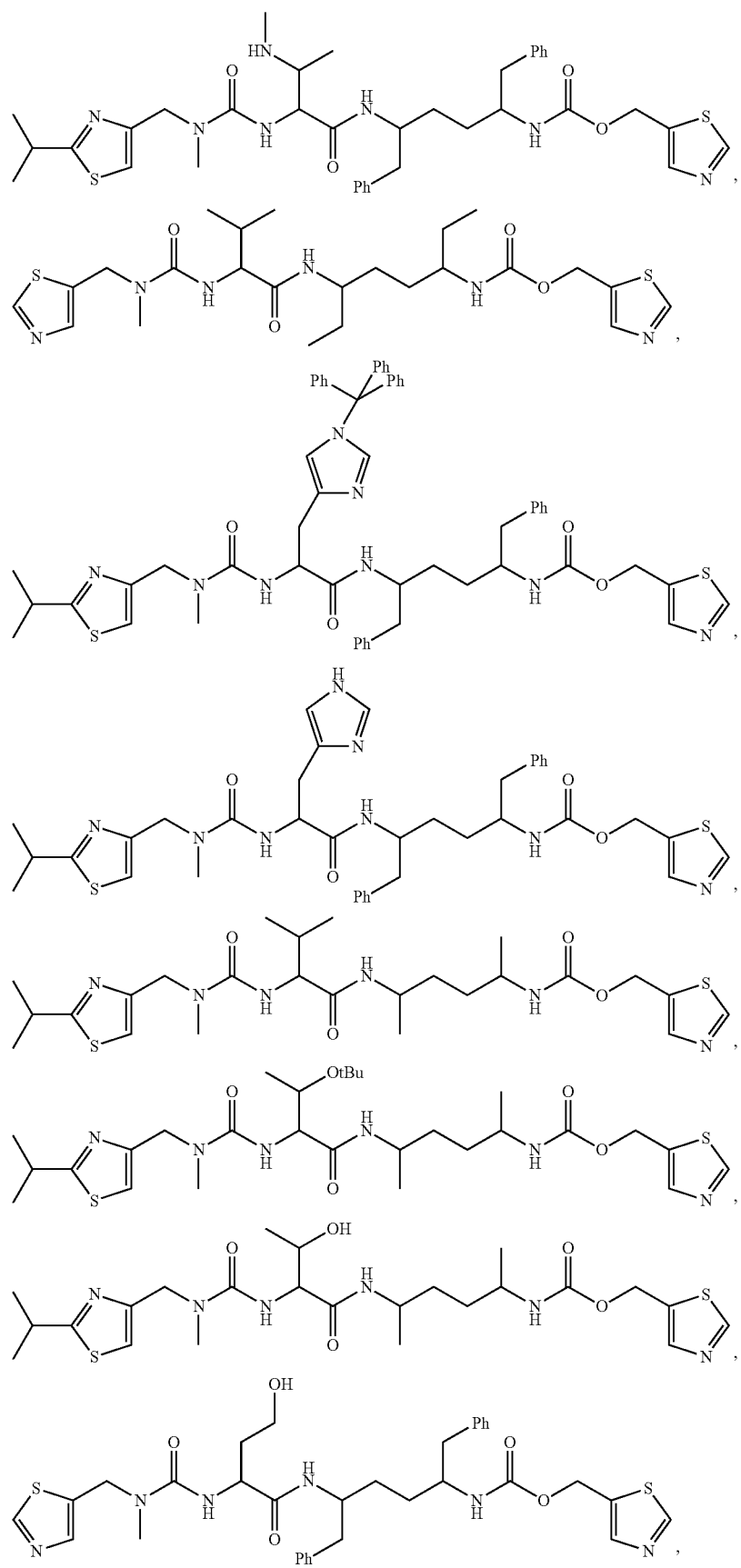

-continued
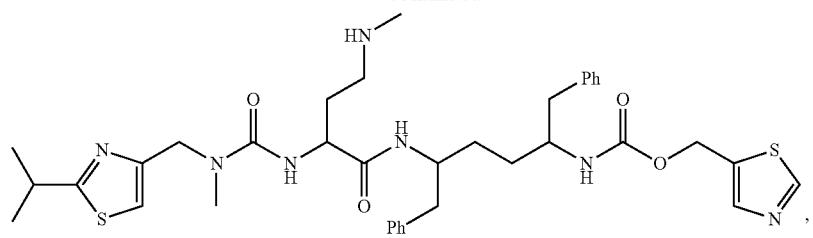
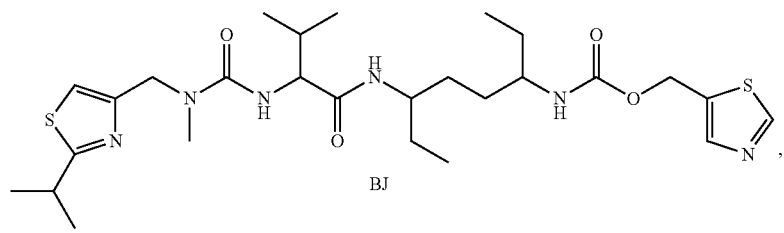
BJ
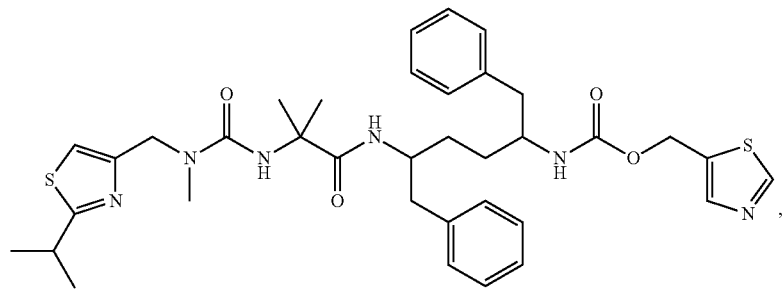
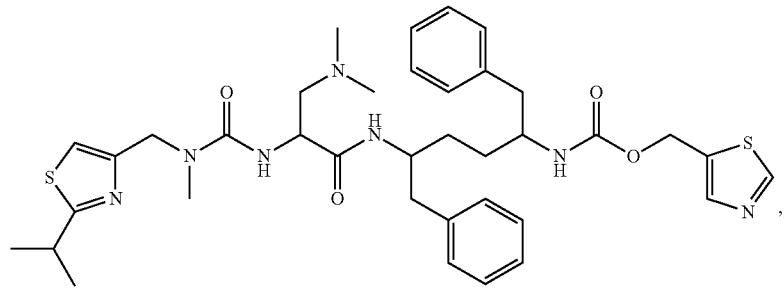
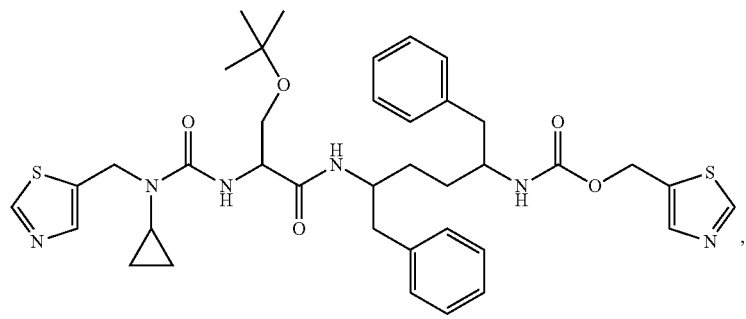
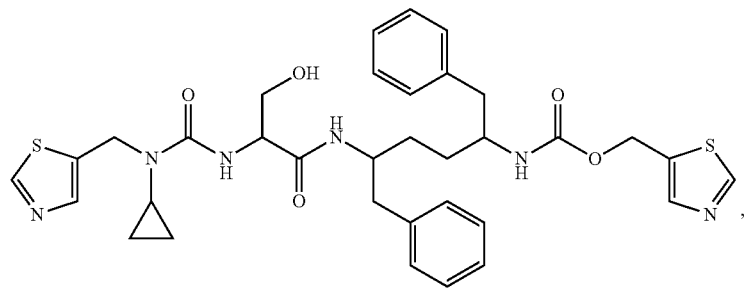

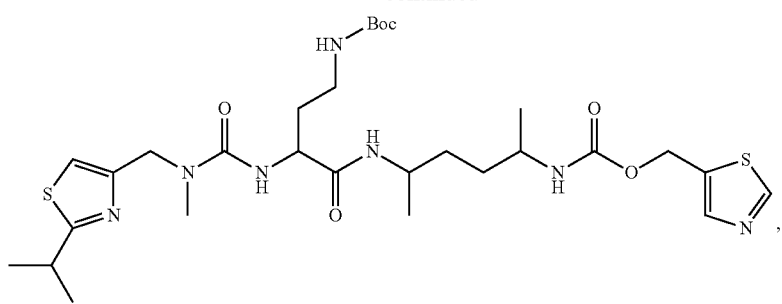
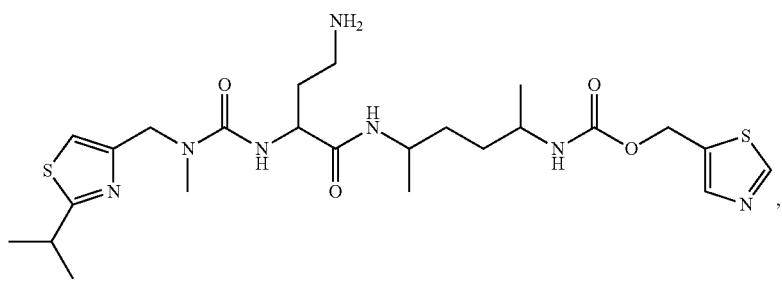
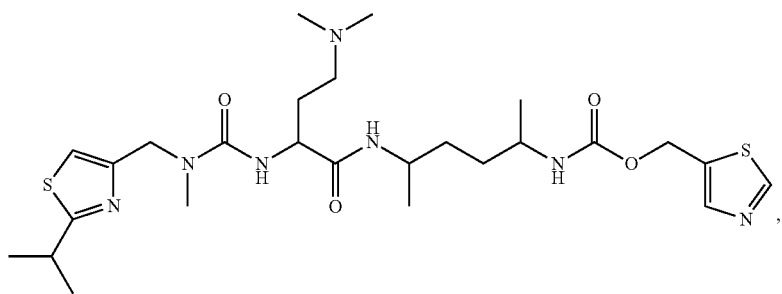
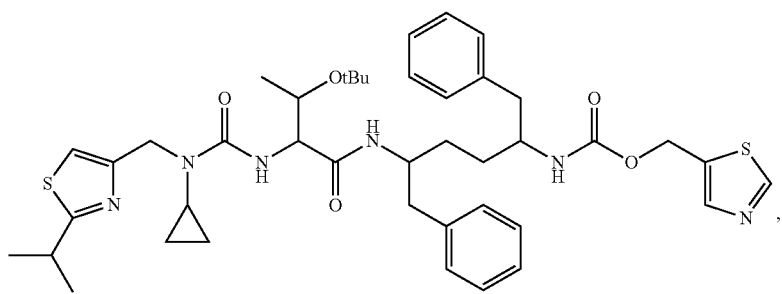
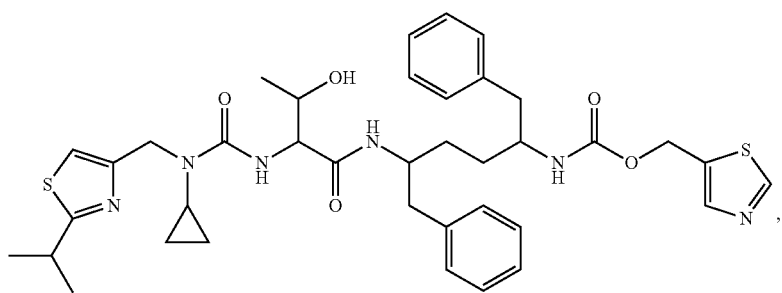

-continued
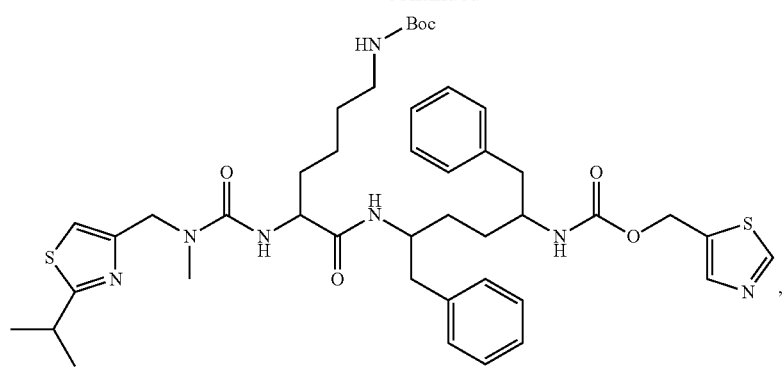
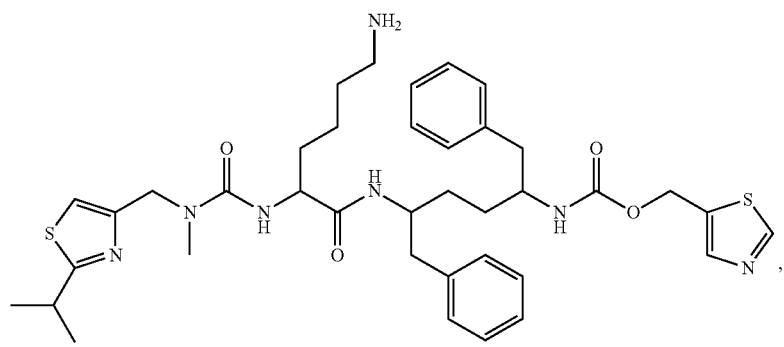
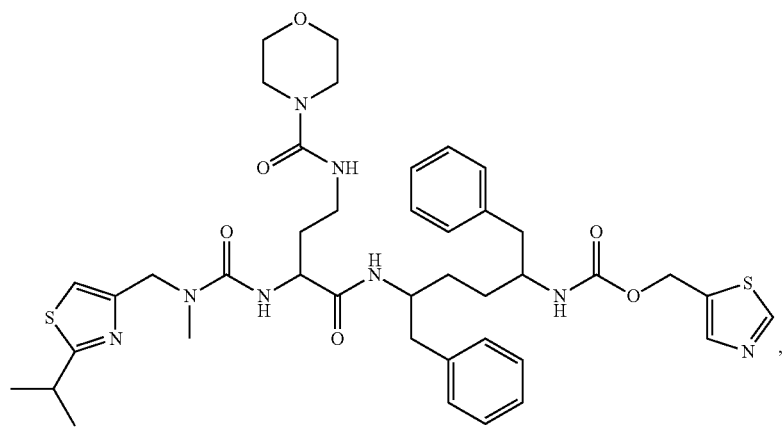
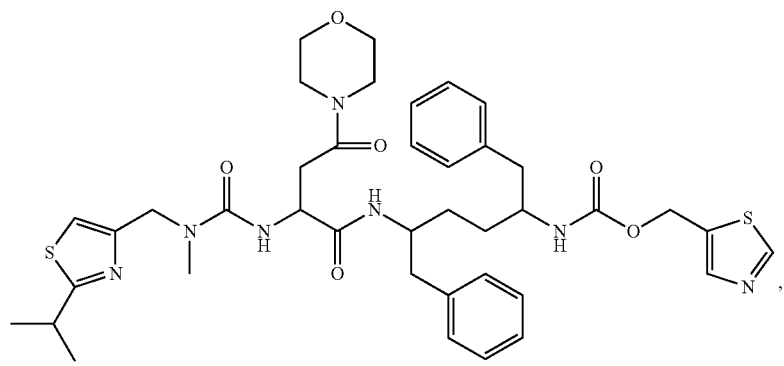

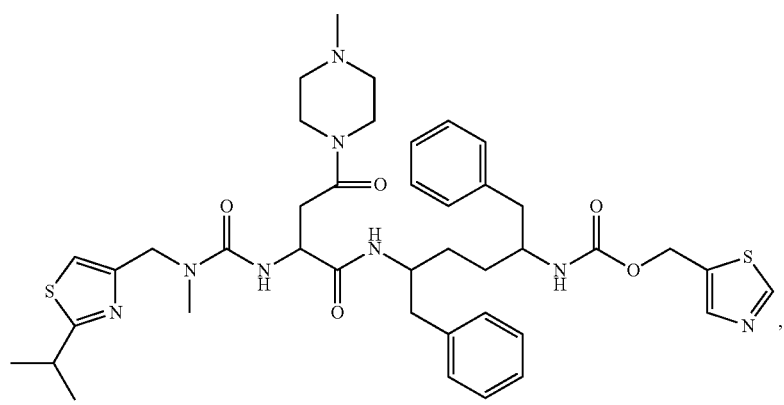
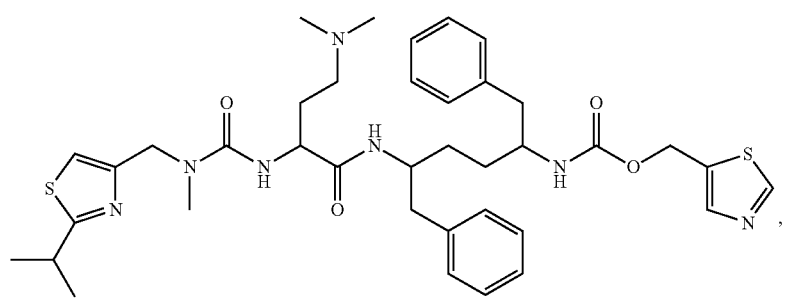
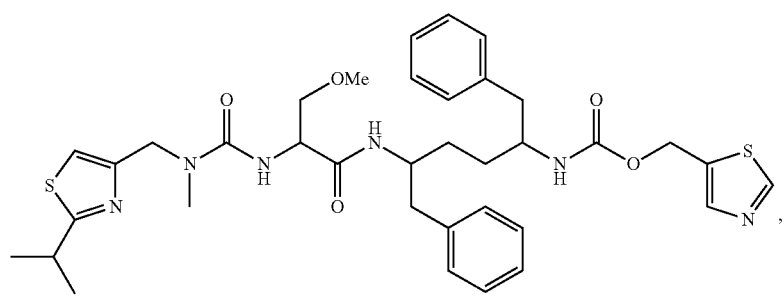
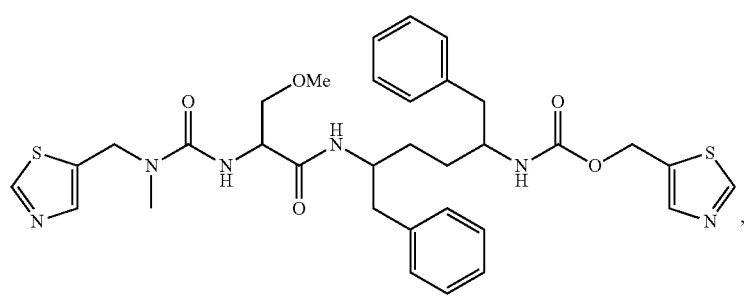
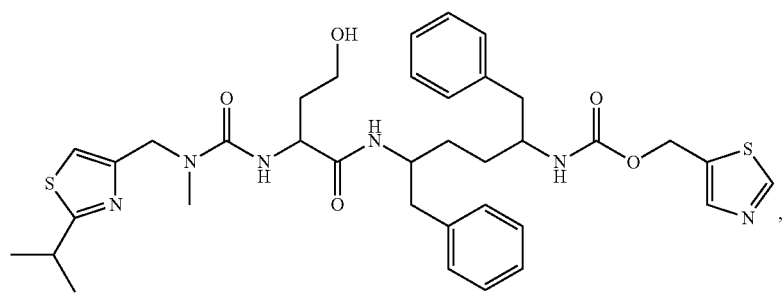

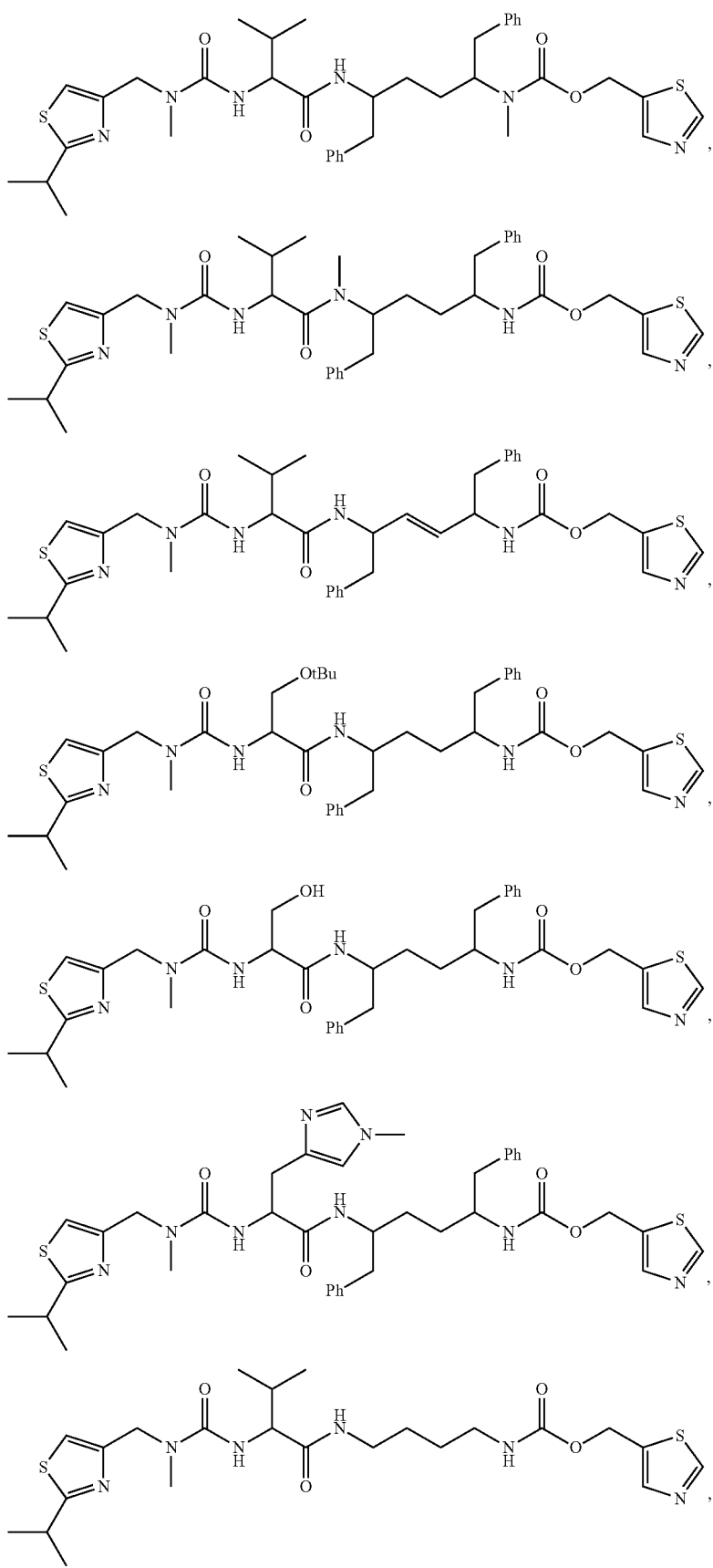

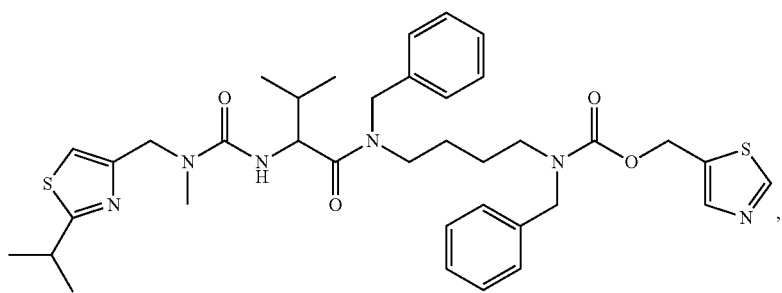
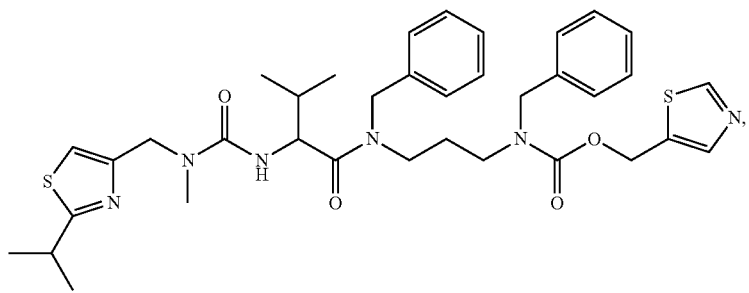
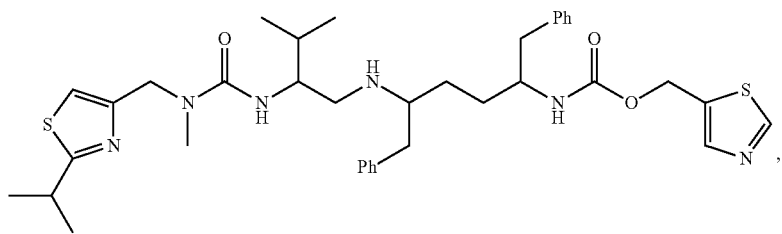
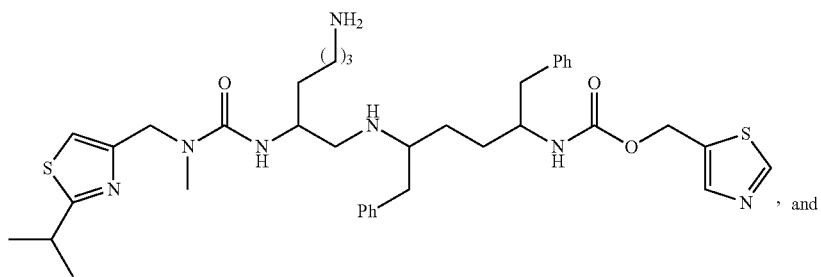, and
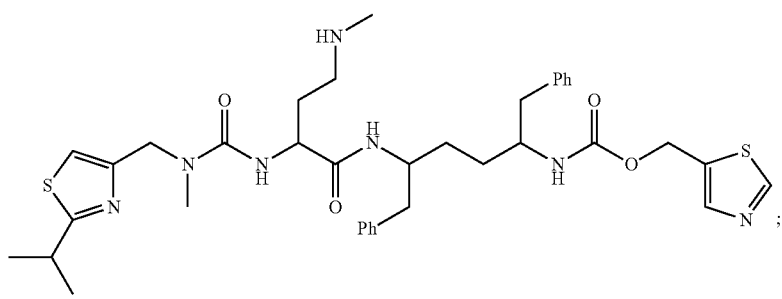 [SMILES: CNCCC(NC(=O)N(C)Cc1csc(C(C)C)n1)C(=O)NC(CCC(Cc1ccccc1)NC(=O)OCc1cncs1)Cc1ccccc1 ; ";"];

including stereoisomers or mixtures of stereoisomers thereof. One skilled in the art will recognize that stereoisomers or mixtures of stereoisomers of the compounds of the present application include enantiomers, diastereomers, and other stereoisomers. For example, for:

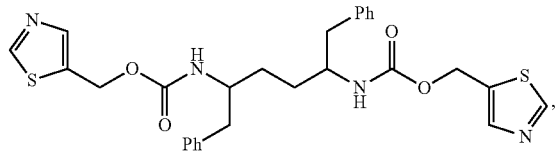 [SMILES: O=C(NC(CCC(Cc1ccccc1)NC(=O)OCc1cncs1)Cc1ccccc1)OCc1cncs1]

contemplated stereoisomers include at least:

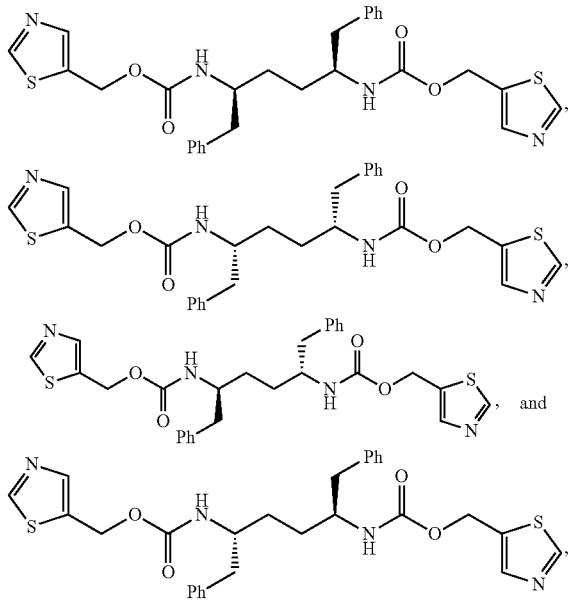

as well as mixtures of two or more of these stereoisomers.

In still another embodiment of the compounds of Formula I, $L^1$ is —$C(R^6)_2$—, —C(O)—, —$S(O_2)$—, —$N(R^7)$—C(O)—, or —O—C(O)—. When $L^1$ is —$C(R^6)_2$—, each $R^6$ is independently selected from the group consisting of H, alkyl, substituted alkyl, and heteroalkyl, wherein alkyl, substituted alkyl, and heteroalkyl are as defined and exemplified herein. Non-limiting examples of —$C(R^6)_2$— include —$CH_2$—, —CH(alkyl)-, —CH(substituted alkyl)-, —CH(heteroalkyl)-, —C(alkyl)$_2$-, —C(substituted alkyl)$_2$-, —C(heteroalkyl)$_2$-, —C(alkyl)(substituted alkyl)-, —C(heteroalkyl)(substituted alkyl)-, and —C(alkyl)(heteroalkyl)-, wherein alkyl, substituted alkyl, and heteroalkyl are as defined and exemplified herein. When $L^1$ is —$N(R^7)$—C(O)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are as defined and exemplified herein.

In still another embodiment of the compounds of Formula I, $L^2$ is —$C(R^6)_2$— or —C(O)—. When $L^2$ is —$C(R^6)_2$—, each $R^6$ is independently selected from H, alkyl, substituted alkyl or heteroalkyl, where each alkyl, substituted alkyl, or heteroalkyl can include any of the alkyl, substituted alkyl, or heteroalkyl groups defined or disclosed herein. Non-limiting examples of —$C(R^6)_2$— include —$CH_2$—, —$CH(CH_3)$—, —$CH(—CH_2CH_3)$—, —$CH(—CH_2CH_2CH_3)$—, —$CH(—CH(CH_3)_2)$—, —$CH(—CH_2CH_2CH_2CH_3)$—, —$CH(—CH_2CH(CH_3)_2)$—, —$CH(—CH(CH_3)CH_2CH_3)$—, —$CH(—C(CH_3)_3)$—, —$C(CH_3)_2$—, —$CH(OCH_3)$—, —$CH(CH_2OH)$—, —$CH(CH_2CH_2OH)$—, etc.

In still another embodiment of the compounds of Formula I, each $L^3$ is independently a covalent bond, an alkylene or substituted alkylene. When any $L^3$ is an alkylene, non-limiting examples of alkylene includes any of the alkylenes defined or disclosed herein. When any $L^3$ is a substituted alkylene, non-limiting examples of substituted alkylene includes any of the substituted alkylenes defined or disclosed herein. For example, substituted alkylenes include alkylenes substituted with one or more —OH group, alkylenes substituted with one or more ether group, e.g., a —O-Bn group, alkylenes substituted with one or more halogen, or alkylenes substituted with combinations of two or more substituents (e.g., —OH and halogen, halogen and ether, etc.).

In still another embodiment of the compounds of Formula I, each $L^3$ is the same, i.e., each $L^3$ is the same alkylene or substituted alkylene group.

In still another embodiment of the compounds of Formula I, each $L^3$ is different, i.e., one $L^3$ is an alkylene and the other $L^3$ is a substituted alkylene, one $L^3$ is an alkylene and the other $L^3$ is a different alkylene, or one $L^3$ is a substituted alkylene, and the other $L^3$ is a different substituted alkylene.

In still another embodiment of the compounds of Formula I, each $L^4$ is independently selected from the group consisting of a covalent bond, alkylene, substituted alkylene, —O—, —$CH_2$—O—, and —NH—. When $L^4$ is alkylene, said alkylene includes any alkylene defined or exemplified herein. When $L^4$ is substituted alkylene, said substituent includes any alkylene defined or exemplified herein, substituted by one or more substituents as defined herein.

In still another embodiment of the compounds of Formula I, both $L^4$ groups are the same, i.e. both $L^4$ groups are a covalent bond, both are —O—, both are —$CH_2$—O—, (wherein the $CH_2$ group is attached to either the "A" moiety or the "Ar" moiety of Formula I), both are a substituted or unsubstituted alkylene, or both are —NH—.

In still another embodiment of the compounds of Formula I, each $L^4$ is different. For example, one $L^4$ is a covalent bond and the other $L^4$ is —O—, one $L^4$ is a covalent bond and the other $L^4$ is —$CH_2$—O— (wherein the $CH_2$ group is attached to either the "A" moiety or the "Ar" moiety of Formula I), one $L^4$ is a covalent bond and the other $L^4$ is —NH—, one $L^4$ is a —O— and the other $L^4$ is —$CH_2$—O— (wherein the $CH_2$ group is attached to either the "A" moiety or the "Ar" moiety of Formula I), one $L^4$ is —O— and the other $L^4$ is —NH—, one $L^4$ is —$CH_2$—O— (wherein the $CH_2$ group is attached to either the "A" moiety or the "Ar" moiety of Formula I) and the other $L^4$ is —NH—, one $L^4$ is a covalent bond and the other $L^4$ is a substituted or unsubstituted alkylene, one $L^4$ is a substituted alkylene and the other $L^4$ is a unsubstituted alkylene, one $L^4$ is a substituted or unsubstituted alkene and the other $L^4$ is —O—, one $L^4$ is a substituted or unsubstituted alkylene and the other $L^4$ is —$CH_2$—O— (wherein the $CH_2$ group is attached to either the "A" moiety or the "Ar" moiety of Formula I), or one $L^4$ is substituted or unsubstituted alkylene and the other $L^4$ is —NH—.

In still another embodiment of the compounds of Formula I, each A is independently H, alkyl, substituted alkyl, aryl, substituted aryl, heterocyclyl, or substituted heterocyclyl, with the proviso that when A is H, p is 0. When any A is alkyl, said alkyl includes any alkyl defined or exemplified herein. When any A is substituted alkyl, said alkyl includes any alkyl defined or exemplified herein substituted with one or more of any substituent defined or exemplified herein. When any A is aryl, said aryl includes any aryl defined or exemplified herein. When any A is substituted aryl, said aryl includes any aryl defined or exemplified herein substituted with one or more of any substituent defined or exemplified herein. When any A is heterocyclyl, said heterocyclyl includes any heterocyclyl defined or exemplified herein. When any A is substituted heterocyclyl, said heterocyclyl is any heterocyclyl defined or exemplified herein substituted with one or more of any substituent defined or exemplified herein.

In still another embodiment of the compounds of Formula I, each A is H and each p is 0.

In still another embodiment of the compounds of Formula I, each A is substituted or unsubstituted alkyl, wherein alkyl is any alkyl defined or exemplified herein, and, when present, the substituents on said alkyl include one or more of any substituents defined or exemplified herein.

In still another embodiment of the compounds of Formula I, each A is substituted or unsubstituted aryl, wherein aryl is any aryl defined or exemplified herein, and, when present, the substituents on said aryl include one or more of any substituents defined or exemplified herein. In a particular embodiment, A is phenyl.

In still another embodiment of the compounds of Formula I, each A is substituted or unsubstituted heterocyclyl, wherein heterocyclyl is any heterocyclyl defined or exemplified herein, and, when present, the substituents on said heterocyclyl include one or more of any substituents defined or exemplified herein.

In still another embodiment of the compounds of Formula I, one A is H and the other A is substituted or unsubstituted alkyl, wherein alkyl is any alkyl defined or exemplified herein, and, when present, the substituent on said alkyl includes one or more of any substituent defined or exemplified herein.

In still another embodiment of the compounds of Formula I, one A is H and the other A is substituted or unsubstituted aryl, wherein aryl is any aryl defined or exemplified herein, and the substituents on said aryl are any substituents defined and exemplified herein. In a particular embodiment, one A is phenyl.

In still another embodiment of the compounds of Formula I, one A is H and the other A is substituted or unsubstituted heterocyclyl, wherein heterocyclyl is any heterocyclyl defined or exemplified herein, and, when present, the substituents on said heterocyclyl include one or more of any substituent defined or exemplified herein.

In still another embodiment of the compounds of Formula I, one A is substituted or unsubstituted alkyl, and the other A is substituted or unsubstituted aryl, wherein alkyl and aryl are any alkyl or aryl defined or exemplified herein, and, when present, the substituents on said alkyl or aryl include one or more of any substituents defined or exemplified herein.

In still another embodiment of the compounds of Formula I, one A is substituted or unsubstituted alkyl, and the other A is substituted or unsubstituted heterocyclyl, wherein alkyl and heterocyclyl are any alkyl or heterocyclyl defined or exemplified herein, and, when present, the substituents on said alkyl or heterocyclyl include one or more of any substituents defined or exemplified herein.

In still another embodiment of the compounds of Formula I, one A is substituted or unsubstituted aryl, and the other A is substituted or unsubstituted heterocyclyl, wherein aryl and heterocyclyl are any aryl or heterocyclyl defined or exemplified herein, and, when present, the substituents on said aryl or heterocyclyl include one or more of any substituents defined or exemplified herein.

In still another embodiment of the compounds of Formula I, $Z^1$ is —O— or —N($R^7$)—. When $Z^1$ is —N($R^7$)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, $Z^2$ is —O— or —N($R^7$)—. When $Z^2$ is —N($R^7$)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, $Z^1$ and $Z^2$ are the same, e.g., $Z^1$ and $Z^2$ are both —O—, or $Z^1$ and $Z^2$ are both —N($R^7$)—, where $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, $Z^1$ and $Z^2$ are different, e.g. $Z^1$ is —O— and $Z^2$ is —N($R^7$)—, $Z^1$ is —N($R^7$)— and $Z^2$ is —O—, or $Z^1$ and $Z^2$ are both —N($R^7$)— but in $Z^1$ the $R^7$ is different from the $R^7$ in $Z^2$. When either $Z^1$ of $Z^2$ is —N($R^7$)—, $R^7$ is H, alkyl, substituted alkyl, heteroalkyl, carbocyclyl, substituted carbocyclyl, heterocyclyl, or substituted heterocyclyl, wherein alkyl, substituted alkyl, heteroalkyl, carbocyclyl, substituted carbocyclyl, heterocyclyl, or substituted heterocyclyl are any alkyl, substituted alkyl, heteroalkyl, carbocyclyl, substituted carbocyclyl, heterocyclyl, or substituted heterocyclyl defined or exemplified herein.

In still another embodiment of the compounds of Formula I, Y is heterocyclyl or heterocyclylalkyl, wherein heterocyclyl and heterocyclylalkyl are any heterocyclyl or heterocyclylalkyl defined or exemplified herein. In a particular embodiment, Y is heterocyclylalkyl, e.g. thiazolylmethyl (—$CH_2$-thiazolyl).

In still another embodiment of the compounds of Formula I, X is heterocyclyl or heterocyclylalkyl, wherein heterocyclyl and heterocyclylalkyl are any heterocyclyl or heterocyclylalkyl defined or exemplified herein. In a particular embodiment, X is heterocyclylalkyl, e.g. thiazolylmethyl.

In still another embodiment of the compounds of Formula I, X and Y are different, e.g., X and Y are different heterocyclyls, X and Y are different heterocyclylalkyls, X is heterocyclyl and Y is heterocyclylalkyl, or X is heterocyclylalkyl and Y is heterocyclyl, wherein heterocyclyl and heterocyclylalkyl are any heterocyclyl or heterocyclylalkyl defined or exemplified herein.

In still another embodiment of the compounds of Formula I, X and Y are the same. In a particular embodiment both X and Y are heterocyclylalkyls, e.g. thiazolylmethyl.

In still another embodiment of the compounds of Formula I, each Ar is aryl, substituted aryl, heteroaryl, or substituted heteroaryl, wherein the aryl or heteroaryl are any aryl or heteroaryl defined or exemplified herein, and, when present, the substituents on the aryl or heteroaryl include one or more of any substituents defined or exemplified herein.

In still another embodiment of the compounds of Formula I, each Ar is the same, e.g., each Ar is an aryl such as phenyl.

In still another embodiment of the compounds of Formula I, each Ar is different, e.g. one Ar is a substituted or unsubstituted aryl and the other Ar is a substituted or unsubstituted heteroaryl, each Ar is a different substituted or unsubstituted aryl, or each Ar is a different substituted or unsubstituted heteroaryl, wherein aryl and heteroaryl are any aryl or heteroaryl defined or exemplified herein, and, when present, the substituents on the aryl or heteroaryl include one or more of any substituents defined or exemplified herein.

In still another embodiment of the compounds of Formula I, $R^1$, $R^3$, and $R^5$ are each independently H, alkyl, or substituted alkyl, wherein alkyl and substituted alkyl include any of the alkyl or substituted alkyls defined or disclosed herein.

In still another embodiment of the compounds of Formula I, $R^1$, $R^3$, and $R^5$ are each the same. In a particular embodiment $R^1$, $R^3$, and $R^5$ are each H. in another particular embodiment $R^1$, $R^3$, and $R^5$ are each alkyl, e.g. one of the alkyl groups defined or disclosed herein.

In still another embodiment of the compounds of Formula I, $R^1$, $R^3$, and $R^5$ are each different.

In still another embodiment of the compounds of Formula I, one of IV, $R^3$, and $R^5$ is different from the other two groups.

In still another embodiment of the compounds of Formula I, n and m are both 1, and each $R^2$ is independently H, alkyl, substituted alkyl, arylheteroalkyl, arylalkyl, or heterocyclylalkyl, wherein alkyl, substituted alkyl, arylheteroalkyl, aryl alkyl, or heterocyclylalkyl is any alkyl, substituted alkyl, arylheteroalkyl, aryl alkyl, or heterocyclylalkyl defined or disclosed herein.

In still another embodiment of the compounds of Formula I, n and m are both 1, and $R^2$ is H.

In still another embodiment of the compounds of Formula I, n is 1, m is 2, and $R^2$ is H.

In still another embodiment of the compounds of Formula I, n and m are both 1, and at least one $R^2$ is alkyl. In a particular embodiment at least one $R^2$ is methyl. In another particular embodiment at least one $R^2$ is ethyl. In another particular embodiment at least one $R^2$ is i-propyl. In another particular embodiment at least one $R^2$ is t-butyl. In another particular embodiment, one $R^2$ is H, and the other $R^2$ is methyl. In another particular embodiment, one $R^2$ is H, and the other $R^2$ is ethyl. In another particular embodiment, one $R^2$ is H, and the other $R^2$ is i-propyl. In another particular embodiment, one $R^2$ is H, and the other $R^2$ is t-butyl.

In still another embodiment of the compounds of Formula I, n and m are both 1, and $R^2$ is substituted alkyl. In a particular embodiment at least one $R^2$ is —CH(CH$_3$)OH or —CH(CH$_3$)O(t-Bu)

In still another embodiment of the compounds of Formula I, n and m are both 1, and at least one $R^2$ is arylheteroalkyl. In particular embodiment n and m are both 1, and at least one $R^2$ is selected from the group consisting of H, methyl, ethyl, benzyl-O—CH$_2$—, i-propyl, —CH(CH$_3$)OBn, —CH$_2$CH(CH$_3$)—O-tBu, —CH(CH$_3$)OH, —CH$_2$OH, —CH$_2$OtBu, —CH$_2$CH$_2$NH$_2$, —CH$_2$CH$_2$NH—P (where P is a protecting group such as Boc, Ac, methanesulfonyl, etc.), —CH$_2$CH$_2$-morpholine, —CH$_2$C(O)OH, —CH$_2$C(O)OtBu, and —CH$_2$C(O)—NH$_2$.

In still another embodiment of the compounds of Formula I, n and m are both 1, and at least one $R^2$ is arylheteroalkyl. In particular embodiment n and m are both 1, one $R^2$ is H and one $R^2$ is selected from the group consisting of H, methyl, ethyl, benzyl-O—CH$_2$—, i-propyl, —CH(CH$_3$)OBn, —CH$_2$CH(CH$_3$)—O-tBu, —CH(CH$_3$)OH, —CH$_2$OH, —CH$_2$OtBu, —CH$_2$CH$_2$NH$_2$, —CH$_2$CH$_2$NH—P (where P is a protecting group such as Boc, Ac, methanesulfonyl, etc.), —CH$_2$CH$_2$-morpholine, —CH$_2$C(O)OH, —CH$_2$C(O)OtBu, and —CH$_2$C(O)—NH$_2$.

In still another embodiment of the compounds of Formula I, $R^4$ is H, alkyl, substituted alkyl, and heteroalkyl, wherein alkyl, substituted alkyl, and heteroalkyl are any alkyl, substituted alkyl, or heteroalkyl defined or disclosed herein. A particular embodiment, $R^4$ is H.

In still another embodiment of the compounds of Formula I, $R^6$ is H, alkyl, substituted alkyl, and heteroalkyl, wherein alkyl, substituted alkyl, and heteroalkyl are any alkyl, substituted alkyl, or heteroalkyl defined or disclosed herein. A particular embodiment, $R^6$ is H.

In still another embodiment of the compounds of Formula I, $R^5$ and $R^9$ are each one or more substituents independently selected from the group consisting of H, alkyl, substituted alkyl, halogen, aryl, substituted aryl, heterocyclyl, substituted heterocyclyl, and —CN, wherein when $R^5$ or $R^9$ are alkyl, substituted alkyl, halogen, aryl, substituted aryl, heterocyclyl, or substituted heterocyclyl, said alkyl, substituted alkyl, halogen, aryl, substituted aryl, heterocyclyl, or substituted heterocyclyl are any such groups defined or disclosed herein.

In still another embodiment of the compounds of Formula I, $R^8$ and $R^9$ are the same. In a particular embodiment $R^5$ and $R^9$ are both H.

In still another embodiment of the compounds of Formula I, $R^8$ and $R^9$ are different. In a particular embodiment $R^8$ is alkyl and $R^9$ is H. in another particular embodiment, $R^5$ is i-propyl and $R^9$ is H.

In yet another embodiment of the compounds of Formula I, at least one of the -L$^3$-A-(L$^4$-Ar)$_p$ moieties is an -alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -L$^3$-A-(L$^4$-Ar)$_p$ moieties is an -alkylene-aryl-alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -L$^3$-A-(L$^4$-Ar)$_p$ moieties is an -alkylene-aryl-alkylene-heteroaryl group, wherein said alkylene, aryl, and heteroaryl moieties are any alkylene, aryl, and heteroaryl moieties defined or exemplified herein, optionally substituted on the alkylene and/or aryl, and/or heteroaryl with one or more of any substituents defined or exemplified herein.

In yet another embodiment of the compounds of Formula I, at least one of the -L$^3$-A-(L$^4$-Ar)$_p$ moieties is an -alkylene-heteroaryl-alkylene-heteroaryl group, wherein said alkylene and heteroaryl moieties are any alkylene and heteroaryl moieties defined or exemplified herein, optionally substituted on the alkylene and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-alkylene-aryl group, wherein said alkylene, aryl, and heteroaryl moieties are any alkylene, aryl, and heteroaryl moieties defined or exemplified herein, optionally substituted on the alkylene and/or aryl, and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-O-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-$CH_2$—O-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-$OCH_2$-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-NH-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, at least one of the -$L^3$-A-($L^4$-Ar)$_p$ moieties is an -alkylene-aryl-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-$CH_2$—O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-$OCH_2$-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-NH-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-O-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-$CH_2$—O-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-$OCH_2$-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-NH-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-CH$_2$—O-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-OCH$_2$-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-heterocyclyl-NH-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, at least one of the -$L^3$-A-($L^4$-Ar)$_p$ moieties is an -alkylene-aryl-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-CH$_2$—O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-OCH$_2$-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-aryl-NH-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-O-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-CH$_2$—O-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-OCH$_2$-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-NH-aryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heterocyclyl-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heterocyclyl-O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heterocyclyl-CH$_2$—O-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-OCH$_2$-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an -alkylene-heteroaryl-NH-heteroaryl group, wherein said alkylene, aryl, and heteroaryl moieties are any alkylene, aryl, and heteroaryl moieties defined or exemplified herein, optionally substituted on the alkylene and/or aryl and/or heteroaryl with one or more of any substituents defined or exemplified herein.

In yet another embodiment of the compounds of Formula I, at least one of the -$L^3$-A-($L^4$-Ar)$_p$ moieties is an alkyl group.

In yet another embodiment of the compounds of Formula I, both of the -$L^3$-A-($L^4$-Ar)$_p$ moieties are alkyl groups, wherein the alkyl groups are the same or different.

In yet another embodiment of the compounds of Formula I, both -$L^3$-A-($L^4$-Ar)$_p$ moieties are —$CH_2$-phenyl and X and Y are both —$CH_2$-heterocyclyl.

In yet another embodiment of the compounds of Formula I, both -$L^3$-A-($L^4$-Ar)$_p$ moieties are —$CH_2$-phenyl and Y is —$CH_2$-heterocyclyl.

In yet another embodiment of the compounds of Formula I, both -$L^3$-A-($L^4$-Ar)$_p$ moieties are —$CH_2$-phenyl and X is —$CH_2$-heterocyclyl.

In yet another embodiment of the compounds of Formula I, both -$L^3$-A-($L^4$-Ar)$_p$ moieties are —$CH_2$-phenyl and Y is —$CH_2$-thiazolyl.

In yet another embodiment of the compounds of Formula I, both -$L^3$-A-($L^4$-Ar)$_p$ moieties are —$CH_2$-phenyl and X is —$CH_2$-thiazolyl.

In yet another embodiment of the compounds of Formula I, both -$L^3$-A-($L^4$-Ar)$_p$ moieties are —$CH_2$-phenyl and X and Y are both —$CH_2$-thiazolyl.

In yet another embodiment of the compounds of Formula I, both -$L^3$-A-($L^4$-Ar)$_p$ moieties are —$CH_2$-phenyl, X and Y are both —$CH_2$-thiazolyl, and n and m are both 1.

In yet another embodiment of the compounds of Formula I, both -$L^3$-A-($L^4$-Ar)$_p$ moieties are —$CH_2$-phenyl, X and Y are both —$CH_2$-thiazolyl, n and m are both 1, and at least one $R^2$ is a $C_1$-$C_6$ alkyl.

In yet another embodiment of the compounds of Formula I, both -$L^3$-A-($L^4$-Ar)$_p$ moieties are —CH-phenyl, X and Y are both —$CH_2$-thiazolyl, n and m are both 1, and at least one $R^2$ is a $C_1$-$C_6$ hydroxyalkyl.

In yet another embodiment of the compounds of Formula I, both -$L^3$-A-($L^4$-Ar)$_p$ moieties are —$CH_2$-phenyl, X and Y are both —$CH_2$-thiazolyl, n and m are both 1, and at least one $R^2$ is a $C_2$-$C_{10}$ alkoxyalkyl.

In yet another embodiment of the compounds of Formula I, both -$L^3$-A-($L^4$-Ar)$_p$ moieties are —$CH_2$-phenyl, X and Y are both —$CH_2$-thiazolyl, n and m are both 1, and at least one $R^2$ is a $C_7$-$C_{14}$ arylalkyloxyalkyl.

In yet another embodiment of the compounds of Formula I, both -$L^3$-A-($L^4$-Ar)$_p$ moieties are —$CH_2$-phenyl, X and Y are both —$CH_2$-thiazolyl, n and m are both 1, and at least one $R^2$ is a $C_1$-$C_6$ aminoalkyl.

In yet another embodiment of the compounds of Formula I, both -$L^3$-A-($L^4$-Ar)$_p$ moieties are —$CH_2$-phenyl, X and Y are both —$CH_2$-thiazolyl, n and m are both 1, and at least one $R^2$ is a $C_1$-$C_6$ aminoalkyl substituted on the nitrogen with an amine protecting group selected from acyl, alkylsulfonyl, arylsulfonyl, heterocyclylacyl, and benzyl.

In yet another embodiment of the compounds of Formula I, both -$L^3$-A-($L^4$-Ar)$_p$ moieties are —CH-phenyl, X and Y are both —$CH_2$-thiazolyl, n and m are both 1, and at least one $R^2$ is a substituted or unsubstituted heterocyclylalkyl.

In yet another embodiment of the compounds of Formula I, both -$L^3$-A-($L^4$-Ar)$_p$ moieties are —$CH_2$-phenyl, X and Y are both —$CH_2$-thiazolyl, n and m are both 1, and $L^2$ is —$CH_2$—.

In yet another embodiment of the compounds of Formula I, at least one -$L^3$-A-($L^4$-Ar)$_p$ moiety is —$CH_2$-phenyl-$CH_2$-phenyl.

In yet another embodiment of the compounds of Formula I, at least one -$L^3$-A-($L^4$-Ar)$_p$ moiety is —$CH_2$— heteroaryl-$CH_2$-phenyl.

In yet another embodiment of the compounds of Formula I, at least one -$L^3$-A-($L^4$-Ar)$_p$ moiety is —$CH_2$-phenyl-$CH_2$-heteroaryl.

In yet another embodiment of the compounds of Formula I, at least one -$L^3$-A-($L^4$-Ar)$_p$ moiety is —$CH_2$— heteroaryl-$CH_2$-heteroaryl.

In yet another embodiment of the compounds of Formula I, X and Y are both heterocyclylalkyl.

In yet another embodiment of the compounds of Formula I, X and Y are both heteroarylalkyl.

In another embodiment of the compounds of Formula I, $L^1$ is —C(O)—, $R^4$ is H, and both -$L^3$-A-($L^4$-Ar)$_p$ groups are substituted or unsubstituted benzyl.

In another embodiment of the compounds of Formula I, $L^1$ is —C(O)—, $R^4$ is H, both -$L^3$-A-($L^4$-Ar)$_p$ groups are substituted or unsubstituted benzyl, and $L^2$ is —$CH_2$—.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, and m and n are both 1.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, and $R^1$ is H.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, and $Z^1$ is —N(alkyl)-.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, and $Z^1$ is —N($CH_3$)—.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, is —N(alkyl)-, and $Z^2$ is —O—.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, is —N($CH_3$)—, and $Z^2$ is —O—.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(alkyl)-, $Z^2$ is —O—, and Y is substituted or unsubstituted —$CH_2$-4-thiazole.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(alkyl)-, $Z^2$ is —O—, and $R^8$—Y is —$CH_2$-(2-alkyl-4-thiazole).

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —$CH_2$—, m and n are both 1, $R^1$ is H, $Z^1$ is —N(H)—, $Z^2$ is —O—, and $R^8$—Y is —$CH_2$-(2-iPr-4-thiazole).

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(alkyl)-, $Z^2$ is —O—, Y is substituted or unsubstituted —CH$_2$-4-thiazole, and X is substituted or unsubstituted —CH$_2$-5-thiazole.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(alkyl)-, $Z^2$ is —O—, Y is substituted or unsubstituted —CH$_2$-4-thiazole, and X is unsubstituted —CH$_2$-5-thiazole.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), and X is unsubstituted —CH$_2$-5-thiazole.

In another embodiment of the compounds of Formula I, each $R^2$ is independently H or hydroxyalkyl.

In another embodiment of the compounds of Formula I, each $R^2$ is independently H or heterocyclylalkyl.

In another embodiment of the compounds of Formula I, each $R^2$ is independently H or —CH$_2$-heterocyclyl, wherein said heterocyclyl is a 5- or 6-membered ring having at least one ring nitrogen atom.

In another embodiment of the compounds of Formula I, each $R^2$ is independently H or —CH$_2$-heterocyclyl, wherein said heterocyclyl is a 6-membered ring having at least one ring nitrogen atom.

In another embodiment of the compounds of Formula I, each $R^2$ is independently H or —CH$_2$-heterocyclyl, wherein said heterocyclyl is a 6-membered ring having at least one ring nitrogen atom, where the —CH$_2$— moiety thereof is bonded to the ring nitrogen atom.

In another embodiment of the compounds of Formula I, each $R^2$ is independently H or —CH$_2$-heterocyclyl, wherein said heterocyclyl is selected from the group consisting of piperadyl, piperazyl, and morpholinyl.

In another embodiment of the compounds of Formula I, each $R^2$ is independently H or —CH$_2$-heterocyclyl, wherein said heterocyclyl is selected from the group consisting of piperadyl, piperazyl, and morpholinyl, and the —CH$_2$- moiety thereof is bonded to a ring nitrogen atom of the heterocyclyl.

In another embodiment of the compounds of Formula I, each $R^2$ is independently H or aminoalkyl.

In another embodiment of the compounds of Formula I, each $R^2$ is independently H or aminoalkyl substituted with an amine protecting group selected from the group consisting of acetyl, alkylsulfonyl, Boc, Cbz, and Fmoc.

In another embodiment of the compounds of Formula I, each $R^2$ is independently H or ethylacetamide (—CH$_2$CH$_2$NHC(O)CH$_3$).

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and $R^2$ is independently H or hydroxyalkyl.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and one $R^2$ is H and the other $R^2$ is hydroxymethyl.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and each $R^2$ is independently H or —CH$_2$-heterocyclyl, wherein said heterocyclyl is a 5- or 6-membered ring having at least one ring nitrogen atom.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and each $R^2$ is independently H or —CH$_2$-heterocyclyl, wherein said heterocyclyl is selected from the group consisting of piperadyl, piperazyl, and morpholinyl, and the —CH$_2$— moiety thereof is bonded to a ring nitrogen atom of the heterocyclyl In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and one $R^2$ is H and the other $R^2$ is —CH$_2$-heterocyclyl, wherein said heterocyclyl is selected from the group consisting of piperadyl, piperazyl, and morpholinyl, and the —CH$_2$— moiety thereof is bonded to a ring nitrogen atom of the heterocyclyl In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and each $R^2$ is independently H or aminoalkyl substituted with an amine protecting group selected from the group consisting of acetyl, alkylsulfonyl, Boc, Cbz, and Fmoc.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, is —N(H)—, $Z^2$ is —O—, $R^8$—Y is —CH$_2$-(2-iPr-4-thiazole), X is unsubstituted —CH$_2$-5-thiazole, and one $R^2$ is H and the other $R^2$ is aminoalkyl substituted with an amine protecting group selected from the group consisting of acetyl, alkylsulfonyl, Boc, Cbz, and Fmoc.

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(H)—, $Z^2$ is —O—, $R^8$—Y is —CH$_2$-(2-iPr-4-thiazole), X is unsubstituted —CH$_2$-5-thiazole, and one $R^2$ is H and the other $R^2$ is ethylacetamide (—CH$_2$CH$_2$NHC(O)CH$_3$).

In another embodiment of the compounds of Formula I, $L^1$ is —C(O)—, $R^4$ is H, both -$L^3$-A-($L^4$-Ar)$_p$ groups are substituted or unsubstituted benzyl, $L^2$ is —CH$_2$—, m and n are both 1, $R^1$ is H, $Z^1$ is —N(alkyl)-, $Z^2$ is —O—, and Y is substituted or unsubstituted —CH$_2$-thiazole.

In still another embodiment, the compounds of Formula I, or pharmaceutically acceptable salts, solvates, esters, or stereoisomers thereof, have the structure shown in Formula IIA:

Formula IIA

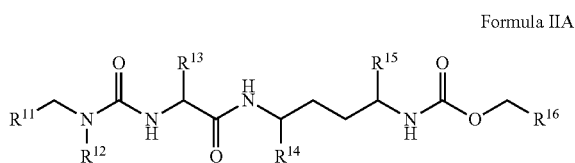

wherein $R^{11}$ and $R^{16}$ are each independently heterocyclyl or substituted heterocyclyl; and $R^{12}$, $R^{13}$, $R^{14}$, and $R^{15}$ are each independently H, —$C_{1-4}$ alkyl or —$C_{1-4}$ substituted alkyl.

In still another embodiment of the compounds of Formula IIA, $R^{13}$ is H, —$C_{1-4}$ alkyl, —$(CH_2)_{0-1}CR^{17}R^{18}OR^{19}$, —$(CH_2)_{0-3}CR^{17}R^{18}NR^{20}R^{21}$, —$(CH_2)_{0-3}CR^{17}R^{18}NR^{17}C(O)$—$NR^{20}R^{21}$, —$(CH_2)_{1-3}C(O)R^{22}$, —$(CH_2)_{1-3}S(O)_2R^{22}$ or —$(CH_2)_{1-3}$—$R^{23}$; $R^{14}$ and $R^{15}$ are each independently H, —$C_{1-4}$ alkyl or arylalkyl; $R^{17}$ and $R^{18}$ are each independently H or $C_{1-3}$ alkyl; $R^{19}$ is H, —$C_{1-4}$ alkyl or arylalkyl; $R^{20}$ and $R^{21}$ are each independently H, —$C_{1-3}$ alkyl, —$C(O)R^{17}$ or —$S(O)_2R^{17}$; or $R^{20}$ and $R^{21}$, taken together with the nitrogen atom to which they are attached, form an unsubstituted or substituted 5-6 membered heterocyclyl ring containing 1-2 heteroatoms selected from the group consisting of N and O; $R^{22}$ is H, —$C_{1-3}$ alkyl, —$OR^{19}$ or —$NR^{20}R^{21}$; and $R^{23}$ is an unsubstituted or substituted 5-6 membered heterocyclyl ring containing 1-2 heteroatoms selected from the group consisting of N and O.

In still another embodiment of the compounds of Formula IIA, $R^{13}$ is —$(CH_2)_{0-3}CR^{17}R^{18}NR^{20}R^{21}$, —$(CH_2)_{0-3}CR^{17}R^{18}NR^{17}C(O)$—$NR^{20}R^{21}$, or —$(CH_2)_{1-3}$—$R^{23}$ wherein $R^{20}$ and $R^{21}$ form a 5-6 membered heterocyclyl ring containing 1-2 heteroatoms selected from the group consisting of N and O or $R^{23}$ is an unsubstituted or substituted 5-6 membered heterocyclyl ring containing 1-2 heteroatoms selected from the group consisting of N and O, and the 5-6 membered heterocyclyl ring is optionally substituted with a $C_{1-2}$ alkyl.

In still another embodiment of the compounds of Formula IIA, $R^{13}$ is —$(CH_2)_{0-1}CR^{17}R^{18}OR^{19}$. In a particular embodiment, $R^{13}$ is a $C_{1-2}$ hydroxyalkyl or a $C_{1-6}$ alkoxyalkyl group.

In still another embodiment of the compounds of Formula IIA, $R^{13}$ is —$(CH_2)_{0-3}CR^{17}R^{18}NR^{20}R^{21}$. In a particular embodiment, $R^{13}$ is a $C_{1-4}$alkylene-$NH_2$ group, $C_{1-4}$alkylene-NHP (wherein P is a protecting group such as Boc, Fmoc, Cbz, Ac, trifluoroacetyl, toluenesulfony group, benzyl, etc.), or $C_{1-4}$alkylene-N(alkyl)$_2$ group.

In still another embodiment of the compounds of Formula IIA, $R^{13}$ is —$(CH_2)_{0-3}CR^{17}R^{18}NR^{17}C(O)$—$NR^{20}R^{21}$. In a particular embodiment, $R^{13}$ is a $C_{1-4}$alkylene-$C(O)NH_2$ group or $C_{1-4}$-alkylene-$C(O)N(alkyl)_2$ group.

In still another embodiment of the compounds of Formula IIA, $R^{11}$, $R^{12}$, $R^{13}$, $R^{14}$, $R^{15}$, and $R^{16}$ are each independently selected from the groups shown in the Table, below:

In still another embodiment of the compounds of Formula IIA, $R^{11}$ is substituted or unsubstituted heterocyclyl, $R^{12}$ is alkyl, $R^{13}$ is substituted or unsubstituted heterocyclylalkyl, $R^{14}$ and $R^{15}$ are each independently substituted or unsubstituted arylalkyl, and $R^{16}$ is substituted or unsubstituted heterocyclyl.

In still another embodiment of the compounds of Formula IIA, $R^{11}$ is substituted heterocyclyl, $R^{12}$ is alkyl, $R^{13}$ is unsubstituted heterocyclylalkyl, $R^{14}$ and $R^{15}$ are both unsubstituted arylalkyl, and $R^{16}$ is unsubstituted heterocyclyl.

In still another embodiment of the compounds of Formula IIA, $R^{11}$ is substituted or unsubstituted heterocyclyl, $R^2$ is alkyl, $R^{13}$ is hydroxyalkyl, $R^{14}$ and $R^{15}$ are each independently substituted or unsubstituted arylalkyl, and $R^{16}$ is substituted or unsubstituted heterocyclyl.

In still another embodiment of the compounds of Formula IIA, $R^{11}$ is substituted heterocyclyl, $R^{12}$ is alkyl, $R^{13}$ is hydroxyalkyl, $R^{14}$ and $R^{15}$ are both unsubstituted arylalkyl, and $R^{16}$ is unsubstituted heterocyclyl.

In still another embodiment of the compounds of Formula IIA, $R^{11}$ is substituted or unsubstituted heterocyclyl, $R^{12}$ is alkyl, $R^{13}$ is protected or unprotected aminoalkyl, $R^{14}$ and $R^{15}$ are each independently substituted or unsubstituted arylalkyl, and $R^{16}$ is substituted or unsubstituted heterocyclyl.

In still another embodiment of the compounds of Formula IIA, $R^{11}$ is substituted heterocyclyl, $R^{12}$ is alkyl, $R^{13}$ is protected aminoalkyl, $R^{14}$ and $R^{15}$ are both unsubstituted arylalkyl, and $R^{16}$ is unsubstituted heterocyclyl.

In still another embodiment of the compounds of Formula IIA, $R^{11}$ is substituted heterocyclyl, $R^{12}$ is alkyl, $R^{13}$ is acylated aminoalkyl, $R^{14}$ and $R^{15}$ are both unsubstituted arylalkyl, and $R^{16}$ is unsubstituted heterocyclyl.

In another embodiment, the compounds of Formula I, or pharmaceutically acceptable salts, solvates, stereoisomers and/or esters thereof, have the following structure IIB:

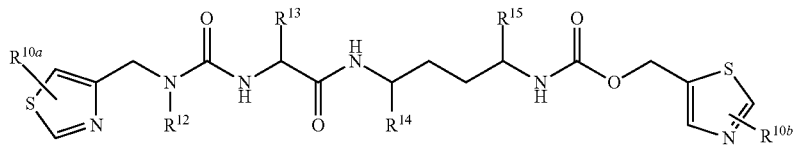

Formula IIB $R^{10a}$ and $R^{10b}$ are each independently H or —$C_{1-4}$ alkyl; $R^{12}$ is H or —$CH_3$; $R^{13}$ is H, —$C_{1-4}$ alkyl, —$(CH_2)_{0-1}CR^{17}R^{18}OR^{19}$, —$(CH_2)_{0-3}CR^{17}R^{18}NR^{20}R^{21}$, —$(CH_2)_{0-3}CR^{17}R^{18}NR^{17}C(O)$ $NR^{20}R^{21}$, —$(CH_2)_{1-3}C(O)R^{22}$, —$(CH_2)_{1-3}S(O)_2R^{22}$ or —$(CH_2)_{1-3}$—$R^{23}$; $R^{14}$ and $R^{15}$ are each independently H, —$C_{1-4}$ alkyl or arylalkyl; $R^{17}$ and $R^{18}$ are each independently H or —$C_{1-3}$ alkyl; $R^{19}$ is H, —$C_{1-4}$ alkyl or arylalkyl; $R^{20}$ and $R^{21}$ are each independently H, —$C_{1-3}$ alkyl, —$C(O)R^{17}$ or —$S(O)_2R^{17}$; or $R^{20}$ and $R^{21}$, taken together with the nitrogen atom to which they are attached, form an unsubstituted or substituted 5-6 membered heterocyclyl ring containing 1-2 heteroatoms selected from the group consisting of N and O; $R^{22}$ is H, —$OR^{19}$ or —$NR^{20}R^{21}$; and $R^{23}$ is an unsubstituted or substituted 5-6 membered heterocyclyl ring containing 1-2 heteroatoms selected from the group consisting of N and O.

In still another embodiment of the compounds of Formula IIB, $R^{13}$ is —$(CH_2)_{0-3}CR^{17}R^{18}NR^{20}R^{21}$, —$(CH_2)_{0-3}CR^{17}R^{18}NR^{17}C(O)$—$NR^{20}R^{21}$, or —$(CH_2)_{1-3}$—$R^{23}$ wherein $R^{20}$ and $R^{21}$ form a 5-6 membered heterocyclyl ring containing 1-2 heteroatoms selected from the group consisting of N and O or $R^{23}$ is an unsubstituted or substituted 5-6 membered heterocyclyl ring containing 1-2 heteroatoms selected from the group consisting of N and O, and the 5-6 membered heterocyclyl ring is optionally substituted with a $C_{1-2}$ alkyl.

In another embodiment, the compounds of Formula I, or pharmaceutically acceptable salts, solvates, stereoisomers and/or esters thereof, have the following structure IIC:

5-6 membered heterocyclyl ring containing 1-2 heteroatoms selected from the group consisting of N and O.

In still another embodiment of the compounds of Formula IIC, $R^{13}$ is —$(CH_2)_{0-3}CR^{17}R^{19}NR^{20}R^{21}$, —$(CH_2)_{0-3}CR^{17}R^{18}NR^{17}C(O)$—$NR^{20}R^{21}$, or —$(CH_2)_{1-3}$—$R^{23}$ wherein $R^{20}$ and $R^{21}$ form a 5-6 membered heterocyclyl ring containing 1-2 heteroatoms selected from the group consisting of N and O or $R^{23}$ is an unsubstituted or substituted 5-6 membered heterocyclyl ring containing 1-2 heteroatoms selected from the group consisting of N and O, and the 5-6 membered heterocyclyl ring is optionally substituted with a $C_{1-2}$ alkyl.

In still another embodiment of the compounds of Formula IIC, $R^{13}$ is —$(CH_2)_{0-3}CR^{17}R^{18}NR^{20}R^{21}$. In a particular embodiment, $R^{13}$ is a $C_{1-4}$alkylene-$NH_2$ group, $C_{1-4}$alkylene-NHP (wherein P is a protecting group such as Boc, Fmoc, Cbz, Ac, trifluoroacetyl, toluenesulfony group, benzyl, etc.), or $C_{1-4}$alkylene-N(alkyl)$_2$ group.

In still another embodiment of the compounds of Formula IIC, $R^{13}$ is —$(CH_2)_{0-3}CR^{17}R^{18}NR^{17}C(O)$—$NR^{20}R^{21}$. In a particular embodiment, $R^{13}$ is a $C_{1-4}$alkylene-$C(O)NH_2$ group or $C_{1-4}$alkylene-C(O)N(alkyl)$_2$ group.

In still another embodiment of the compounds of Formula IIC, $R^{13}$ is —$CH_2OH$, —$CH_2CH_2NHC(O)CH_3$ or Formula IIC

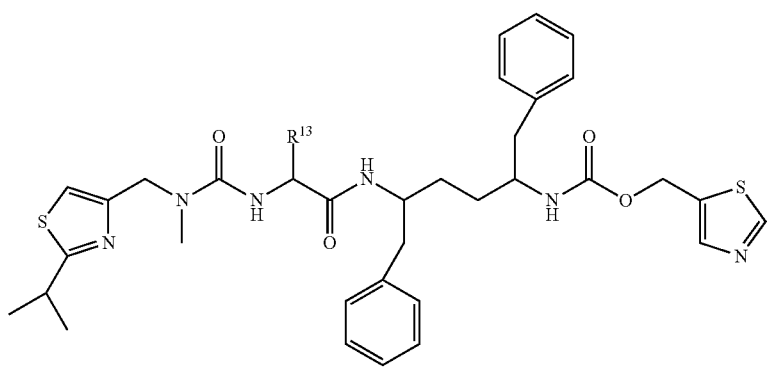

wherein: $R^{13}$ is H, —$C_{1-4}$ alkyl, —$(CH_2)_{0-1}CR^{17}R^{18}OR^{19}$, —$(CH_2)_{0-3}CR^{17}R^{18}NR^{20}R^{21}$, —$(CH_2)_{0-3}CR^{17}R^{18}NR^{17}C(O)NR^{20}R^{21}$, —$(CH_2)_{1-3}C(O)R^{22}$ or —$(CH_2)_{1-3}$—$R^{23}$; $R^{17}$ and $R^{18}$ are each independently H or $C_{1-3}$ alkyl; $R^{19}$ is H, —$C_{1-4}$ alkyl or arylalkyl; $R^{20}$ and $R^{21}$ are each independently H, —$C_{1-3}$ alkyl, —$C(O)R^{17}$ or —$S(O)_2R^{17}$; or $R^{20}$ and $R^{21}$, taken together with the nitrogen atom to which they are attached, form a 5-6 membered heterocyclyl ring containing 1-2 heteroatoms selected from the group consisting of N and O; $R^{22}$ is H, —$OR^{19}$ or —$NR^{20}R^{21}$; and $R^{23}$ is a

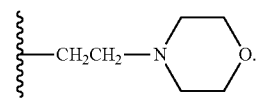

In another embodiment, the compounds of the present invention, or pharmaceutically acceptable salts, solvates, stereoisomers and/or esters thereof, have the following structure IID:

Formula IID

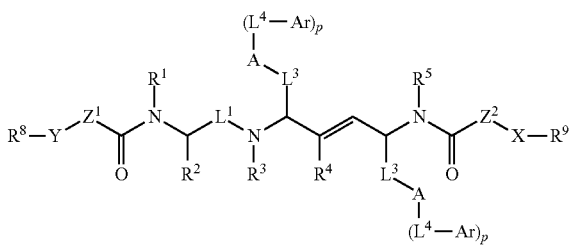

wherein,
$L^1$ is selected from the group consisting of —C(R$^6$)$_2$—, —C(O)—, —S(O$_2$)—, —N(R$^7$)—C(O)—, and —O—C(O)—;
each $L^3$ is independently a covalent bond, an alkylene, or substituted alkylene;
each $L^4$ is independently selected from the group consisting of a covalent bond, alkylene, substituted alkylene, —O—, —CH$_2$—O—, and —NH—;
each A is independently selected from the group consisting of H, alkyl, substituted alkyl, aryl, substituted aryl, heterocyclyl, and substituted heterocyclyl,
with the proviso that when A is H, p is 0;
$Z^1$ and $Z^2$ are each independently —O— or —N(R$^7$)—;
Y and X are independently selected from the group consisting of heterocyclyl and heterocyclylalkyl;
each Ar is independently selected from the group consisting of aryl, substituted aryl, heteroaryl, and substituted heteroaryl;
$R^1$, $R^3$, and $R^5$ are each independently selected from the group consisting of H, alkyl, substituted alkyl, arylalkyl, and substituted arylalkyl;
$R^2$ is independently selected from the group consisting of H, alkyl, substituted alkyl, alkoxyalkyl, hydroxyalkyl, arylheteroalkyl, substituted arylheteroalkyl, arylalkyl, substituted arylalkyl, heterocyclylalkyl, substituted heterocyclylalkyl, aminoalkyl, substituted aminoalkyl, -alkylene-C(O)—OH, -alkylene-C(O)—Oalkyl, -alkylene-C(O) amino, -alkylene-C(O)-alkyl;
$R^4$ and $R^6$ are independently selected from the group consisting of H, alkyl, substituted alkyl, and heteroalkyl;
each $R^7$ is independently selected from the group consisting of H, alkyl, substituted alkyl, heteroalkyl, carbocyclyl, substituted carbocyclyl, heterocyclyl, and substituted heterocyclyl;
$R^8$ and $R^9$ are each one or more substituents independently selected from the group consisting of H, alkyl, substituted alkyl, halogen, aryl, substituted aryl, heterocyclyl, substituted heterocyclyl, and —CN; and
each p is independently 0 or 1.

In another embodiment of the compounds of Formula IID, $L^1$ is —C(R$^6$)$_2$—.
In another embodiment of the compounds of Formula IID, $L^1$ is —CH$_2$—.
In another embodiment of the compounds of Formula IID, each $L^3$ is alkylene.
In another embodiment of the compounds of Formula IID, each $L^3$ is —CH$_2$—.
In another embodiment of the compounds of Formula IID, each A is aryl or substituted aryl.
In another embodiment of the compounds of Formula IID, each A is phenyl or substituted phenyl.
In another embodiment of the compounds of Formula IID, X is heterocyclylalkyl.
In another embodiment of the compounds of Formula IID, X is thiazolylmethyl.
In another embodiment of the compounds of Formula IID, Y is heterocyclylalkyl.
In another embodiment of the compounds of Formula IID, Y is thiazolylmethyl.
In another embodiment of the compounds of Formula IID, $Z^1$ is —N(R$^7$)—.
In another embodiment of the compounds of Formula IID, $Z^1$ is —NH—.
In another embodiment of the compounds of Formula IID, $Z^1$ is —N(alkyl)-.
In another embodiment of the compounds of Formula IID, $Z^1$ is —N(CH$_3$)—.
In another embodiment of the compounds of Formula IID, $Z^2$ is —O—.
In another embodiment of the compounds of Formula IID, $L^1$ is —C(R$^6$)$_2$— and X and Y are heterocyclylalkyl.
In another embodiment of the compounds of Formula IID, $L^1$ is —CH$_2$— and X and Y are heterocyclylalkyl.
In another embodiment of the compounds of Formula IID, $L^1$ is —CH$_2$— and X and Y are thiazolylmethyl.
In another embodiment of the compounds of Formula IID, $L^1$ is —C(R$^6$)$_2$— and $Z^1$ is —N(R$^7$)—.
In another embodiment of the compounds of Formula IID, $L^1$ is —CH$_2$— and $Z^1$ is —N(R$^7$)—.
In another embodiment of the compounds of Formula IID, $L^1$ is —CH$_2$— and $Z^1$ is —NH—.
In another embodiment of the compounds of Formula IID, U is —CH$_2$— and $Z^1$ is —N(alkyl)-.
In another embodiment of the compounds of Formula IID, $L^1$ is —CH$_2$— and $Z^1$ is —N(CH$_3$)—.
In another embodiment of the compounds of Formula IID, U is —C(R$^6$)$_2$— and $Z^2$ is —O—.
In another embodiment of the compounds of Formula IID, each $L^3$ is alkylene and each A is aryl or substituted aryl.
In another embodiment of the compounds of Formula IID, each $L^3$ is —CH$_2$— and each A is aryl or substituted aryl.
In another embodiment of the compounds of Formula IID, each $L^3$-A is benzyl or substituted benzyl.
In another embodiment of the compounds of Formula IID, X and Y are heterocyclylalkyl and $Z^1$ is —N(R$^7$)—.
In another embodiment of the compounds of Formula IID, X and Y are thiazolylmethyl and $Z^1$ is —N(R$^7$)—.
In another embodiment of the compounds of Formula IID, X and Y are thiazolylmethyl and $Z^1$ is —N(alkyl)-.
In another embodiment of the compounds of Formula IID, X and Y are thiazolylmethyl and $Z^1$ is —N(CH$_3$)—.
In another embodiment of the compounds of Formula IID, X and Y are thiazolylmethyl and $Z^1$ is —NH—.
In another embodiment of the compounds of Formula IID, X and Y are heterocyclylalkyl and $Z^2$ is —O—.
In another embodiment of the compounds of Formula IID, X and Y are thiazolylmethyl and $Z^2$ is —O—.
In another embodiment of the compounds of Formula IID, $Z^1$ is —N(R$^7$)— and $Z^2$ is —O—.
In another embodiment of the compounds of Formula IID, $Z^1$ is —N(alkyl)- and $Z^2$ is —O—.
In another embodiment of the compounds of Formula IID, $Z^1$, is —N(CH$_3$)— and $Z^2$ is —O—.
In another embodiment of the compounds of Formula IID, $Z^1$ is —NH— and $Z^2$ is —O—.
In another embodiment of the compounds of Formula IID, is —C(R$^6$)$_2$—, X and Y are heterocyclylalkyl, and $Z^1$ is —N(R$^7$)—.

In another embodiment of the compounds of Formula IID, $L^1$ is —$CH_2$—, X and Y are heterocyclylalkyl, and $Z^1$ is —$N(R^7)$—.

In another embodiment of the compounds of Formula IID, $L^1$ is —$CH_2$—, X and Y are thiazolylmethyl, and $Z^1$ is —$N(R^7)$—.

In another embodiment of the compounds of Formula IID, $L^1$ is —$CH_2$—, X and Y are thiazolylmethyl, and $Z^1$ is —N(alkyl)-.

In another embodiment of the compounds of Formula IID, $L^1$ is —$CH_2$—, X and Y are thiazolylmethyl, and $Z^1$ is —$N(CH_3)$—.

In another embodiment of the compounds of Formula IID, $L^1$ is —$CH_2$—, X and Y are thiazolylmethyl, and $Z^1$ is —NH—.

In another embodiment of the compounds of Formula IID, $L^1$ is —$C(R^6)_2$—; X and Y are heterocyclylalkyl; and $Z^2$ is —O—.

In another embodiment of the compounds of Formula IID, $L^1$ is —$CH_2$—; X and Y are heterocyclylalkyl; and $Z^2$ is —O—.

In another embodiment of the compounds of Formula IID, $L^1$ is —$CH_2$—; X and Y are thiazolylmethyl; and $Z^2$ is —O—.

In another embodiment of the compounds of Formula IID, $L^1$ is —$C(R^6)_2$—; each $L^3$ is alkylene; each A is aryl or substituted aryl; X and Y are heterocyclylalkyl; $Z^1$ is —$N(R^7)$—; and $Z^2$ is —O—.

In another embodiment of the compounds of Formula IID, $L^1$ is —$CH_2$—; each $L^3$-A is benzyl or substituted benzyl; X and Y are thiazolylmethyl; $Z^1$ is —$N(CH_3)$—; and $Z^2$ is —O—.

In another embodiment of the compounds of Formula IID, $L^1$ is —$CH_2$—; each $L^3$-A is benzyl or substituted benzyl; $Z^1$ is —$N(CH_3)$—; $Z^2$ is —O—; X is

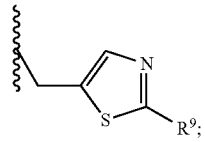

and
Y is

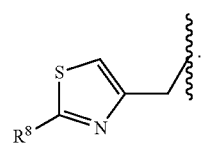

In another embodiment, the compounds of the present invention, or pharmaceutically acceptable salts, solvates, stereoisomers and/or esters thereof, have the following structure IV:

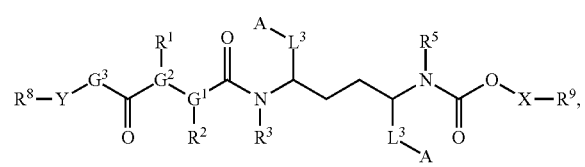

wherein, each $L^3$ is independently an alkylene or substituted alkylene;

each A is independently an aryl or substituted aryl;

X is heterocyclylalkyl;

Y is heterocyclylalkyl or alkyl;

$G^1$ and $G^2$ are independently CH or N, with the proviso that $G^1$ and $G^2$ are different;

$G^3$ is —$NR^7$— or —O—;

$R^1$, $R^3$, $R^5$, and $R^7$ are each independently selected from the group consisting of H, alkyl, substituted alkyl, arylalkyl, and substituted arylalkyl;

$R^2$ is independently selected from the group consisting of substituted alkyl, alkoxyalkyl, hydroxyalkyl, trialkylsiloxyalkyl, heterocyclylalkyl, substituted heterocyclylalkyl, aminoalkyl, substituted aminoalkyl, -alkylene-N($R^a$)—C(O)-alkyl, -alkylene-$NR^a$—C(O)—$N(R^a)_2$, -alkylene-$NR^a$—C(=N—$R^b$)—$N(R^a)_2$, -alkylene-C(=N—$R^b$)—$N(R^a)_2$, -alkylene-C(O)—OH, -alkylene-C(O)—Oalkyl, and -alkylene-C(O)—$N(R^e)_2$;

$R^8$ and $R^9$ are each one or more substituents independently selected from the group consisting of H, alkyl, substituted alkyl, halogen, and —CN;

each $R^a$ is independently selected from the group consisting of H, alkyl, and substituted alkyl;

$R^b$ is selected from the group consisting of H, alkyl, substituted alkyl, CN, and —$S(O_2)$-alkyl; and each $R^c$ is independently selected from the group consisting of H, alkyl, substituted alkyl, heterocyclyl, and —$S(O_2)$-alkyl.

In some embodiments of the compounds of Formula IV, each U is alkylene, for example any of those described herein, e.g. —$CH_2$— and each A is phenyl. In a particular embodiment, both -$L^3$-A moieties are benzyl.

In some embodiments of the compounds of Formula IV, X and Y are both heteroaryl (for example, any heteroaryl described herein). In a particular embodiment, both X and Y are thiazolyl.

In some embodiments of the compounds of Formula IV, $G^1$ is CH, and $G^2$ is N. In a particular embodiment, $G^2$ is N and $R^1$ is H. In another particular embodiment, $G^2$ is N, $R^1$ is H, and $G^3$ is $NR^7$. In yet another particular embodiment, $G^2$ is N, $R^1$ is H, and $G^3$ is NCH.

In some embodiments of the compounds of Formula IV, $R^2$ is substituted or unsubstituted aminoalkyl. In a particular embodiment, $R^2$ is substituted or unsubstituted aminoalkyl, $G^2$ is N and $R^1$ is H, and both X and Y are thiazolyl. In another particular embodiment, $R^2$ is —$CH_2CH_2$—$NHR^d$, wherein $R^d$ is selected from the group consisting of H, haloalkyl, —C(O)—$N(R^a)_2$, —C(=N—$R^b$)—$N(R^a)_2$, hydroxyalkyl, —$C(N(R^a)_2)$=$CHNO_2$, —C(O)-alkyl, $G^2$ is N and $R^1$ is H, and both X and Y are thiazolyl. In still another particular embodiment, $R^2$ is —$CH_2CH_2$—NH—C(O)-alkyl.

In specific embodiments, the compounds of Formula IV have the following structures:

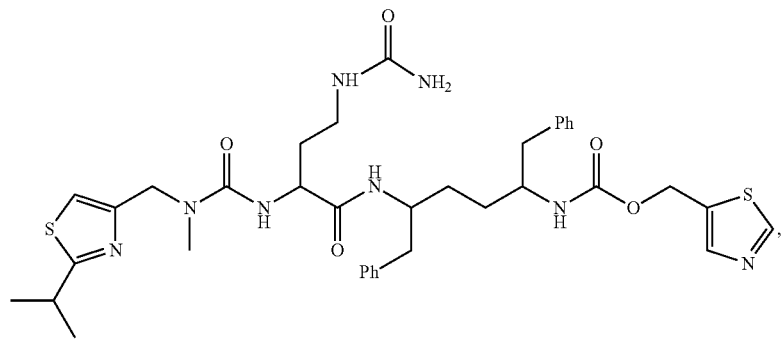
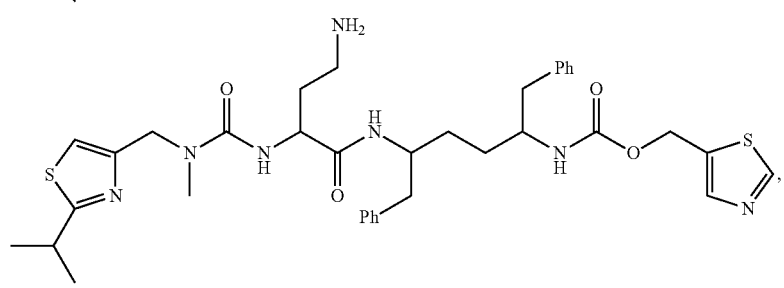
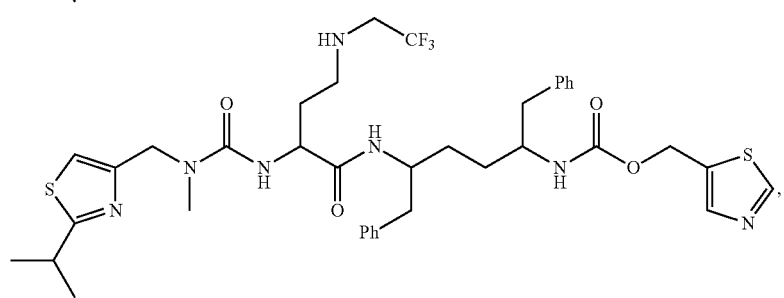
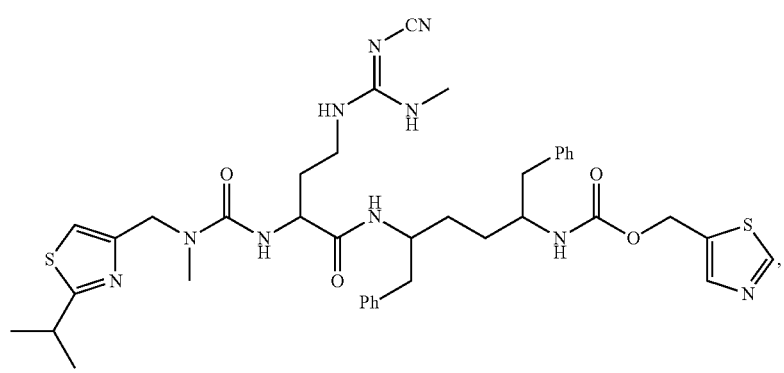
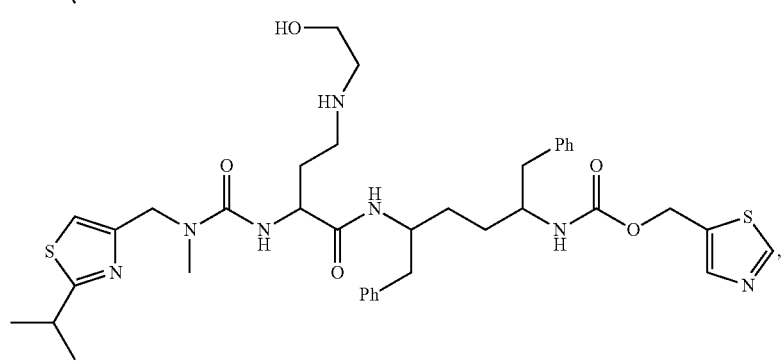

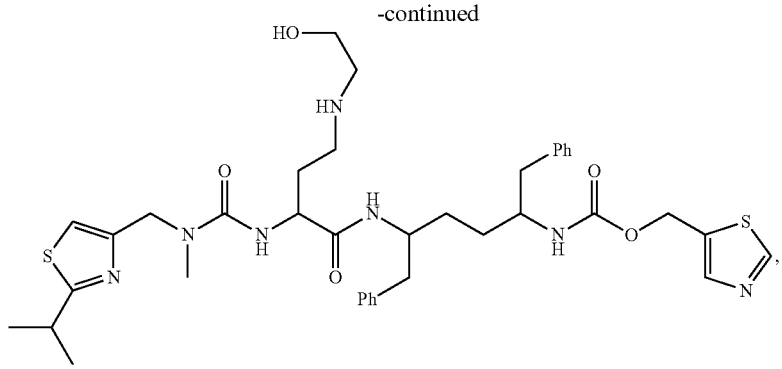

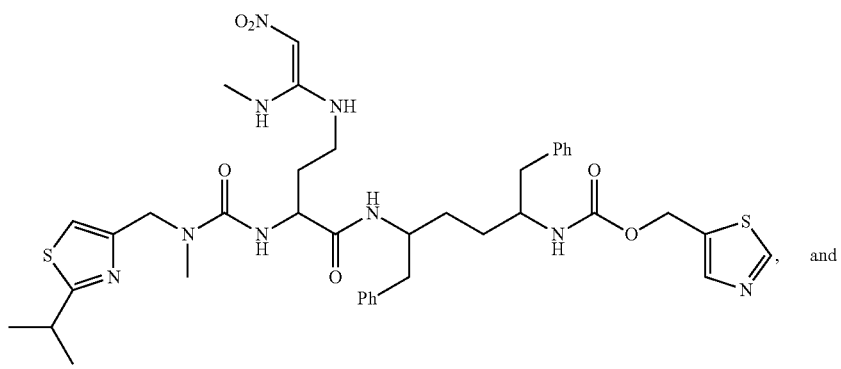

and

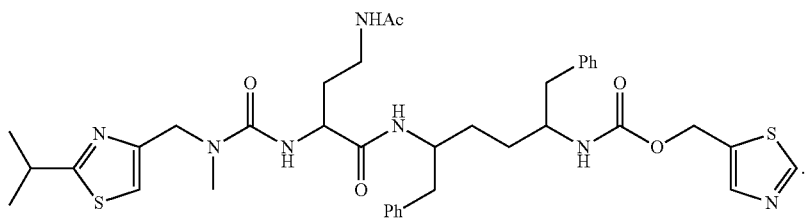

In other embodiments, the compounds of Formula IV have the following general formula:

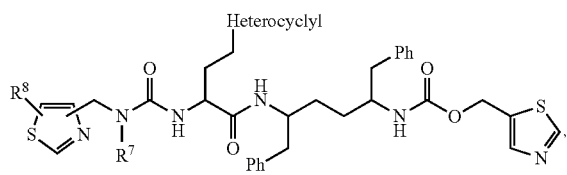

wherein said "Heterocyclyl" is substituted or unsubstituted. In a particular embodiment, said "Heterocyclyl" is a substituted or unsubstituted heteroaryl, for example, and of the heteroaryls described herein. In other embodiments, said "Heterocyclyl" is a substituted or unsubstituted heterocycloalkyl, including any heterocycloalkyl described herein. In a particular embodiment, the heterocyclyl is unsubstituted morpholinyl. In a more specific particular embodiment, the heterocyclyl is unsubstituted morpholinyl and $R^8$ is alkyl.

In other embodiments, the compounds of Formula IV have the following general formula:

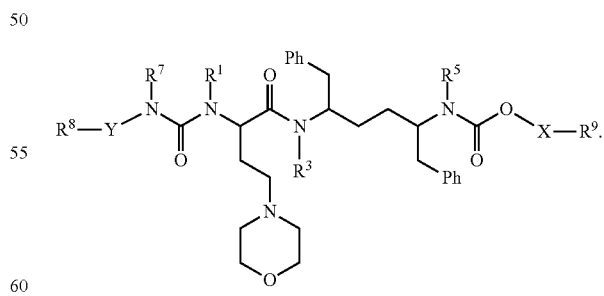

In a particular embodiment of the compounds of the above general formula, X and Y are both heteroarylalkyl.

In other specific embodiments, the compounds of Formula. IV have the following structures:

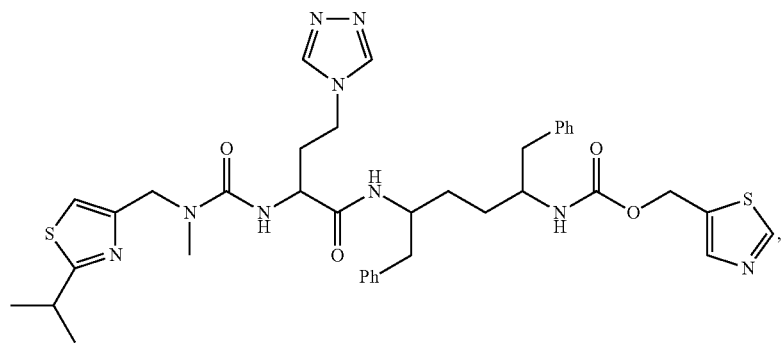
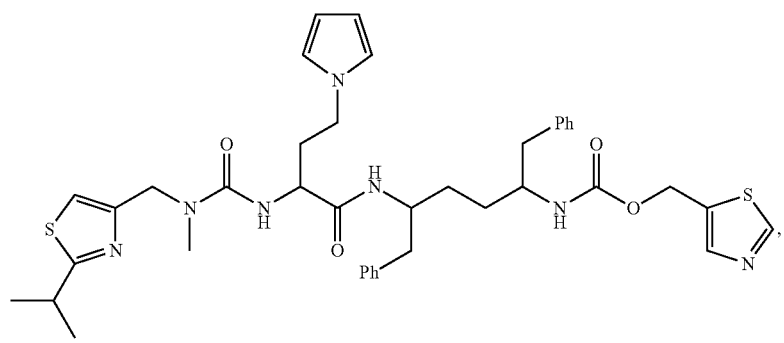
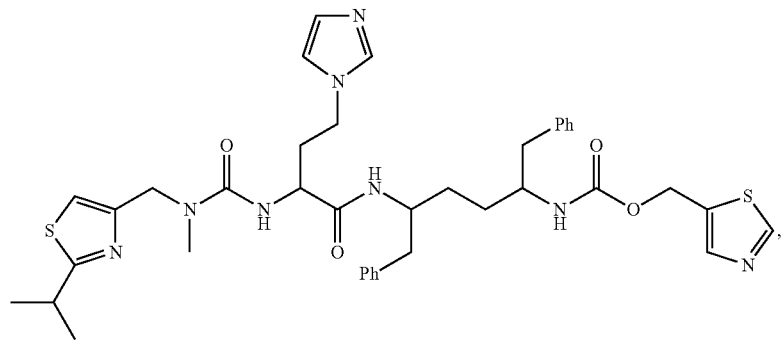
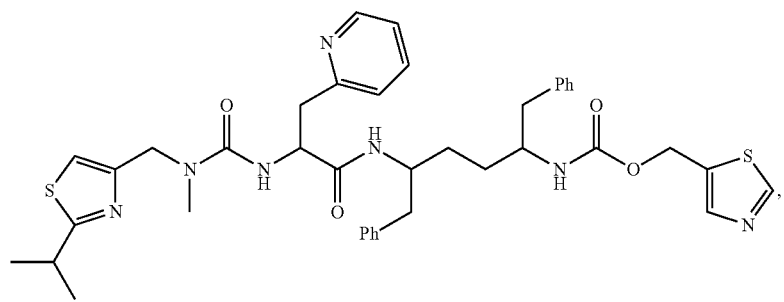
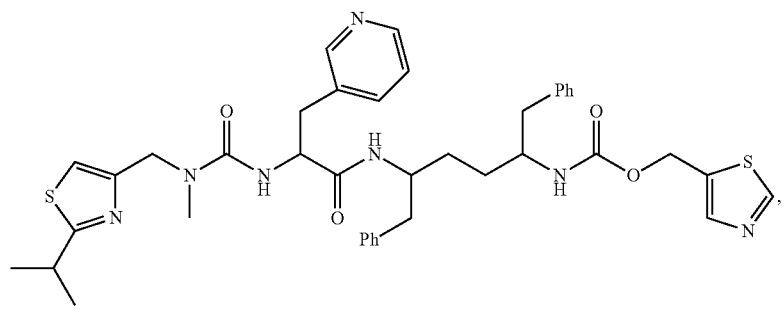

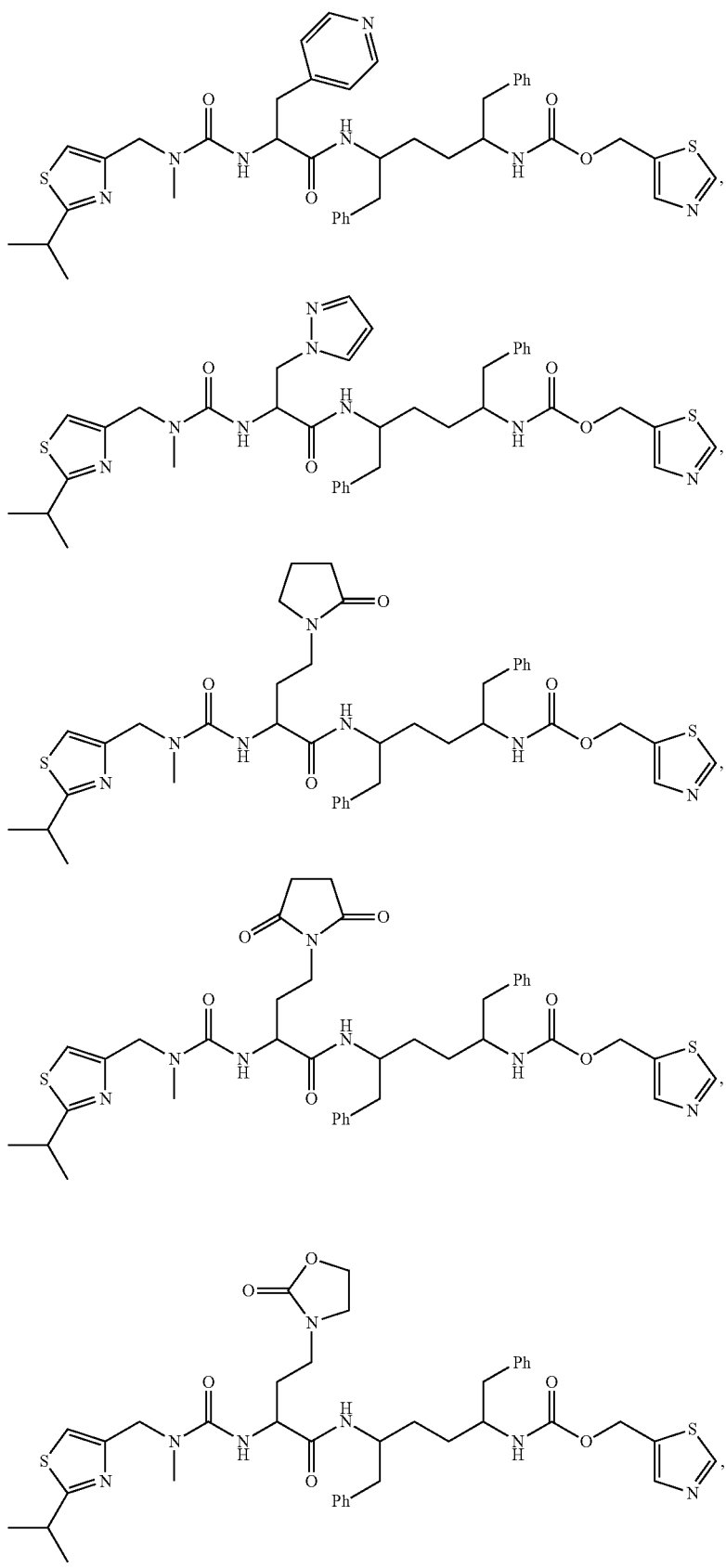

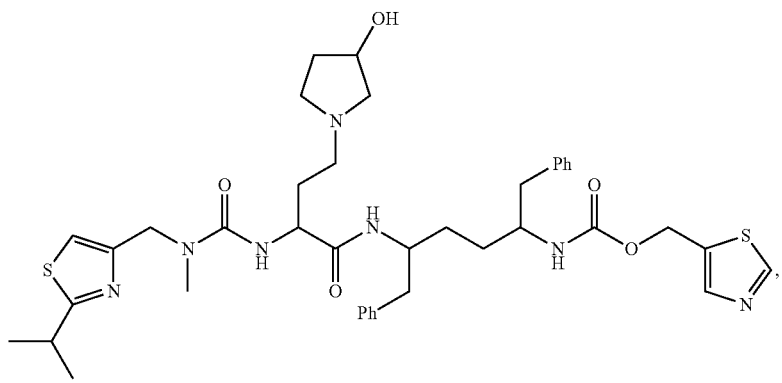
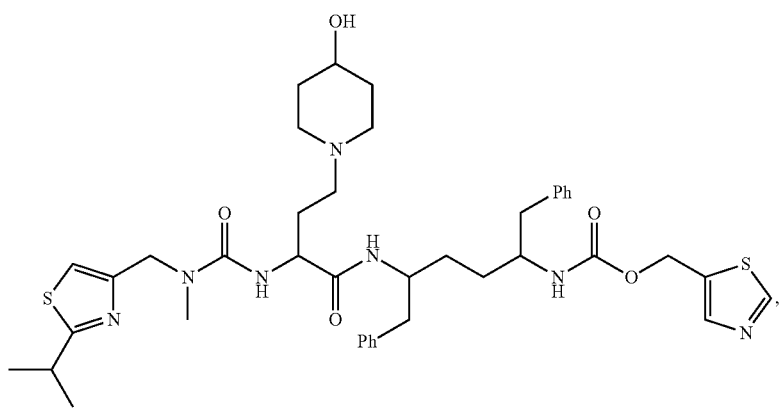
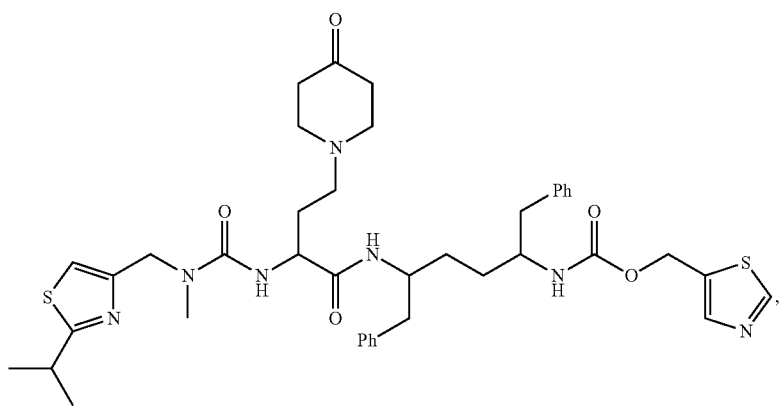
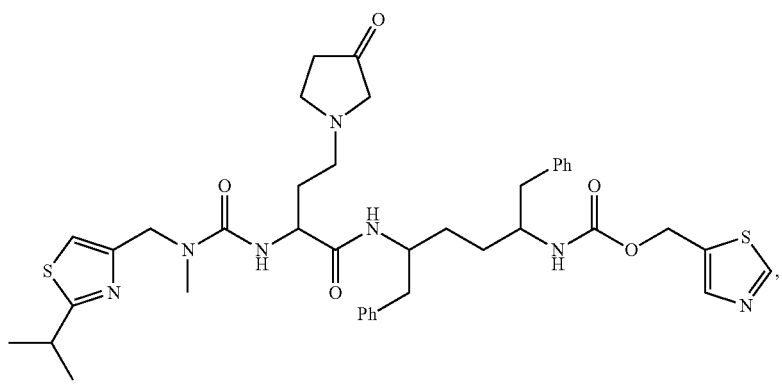

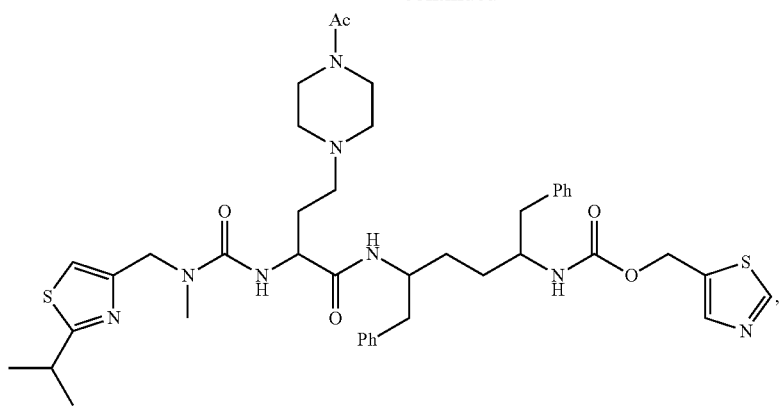
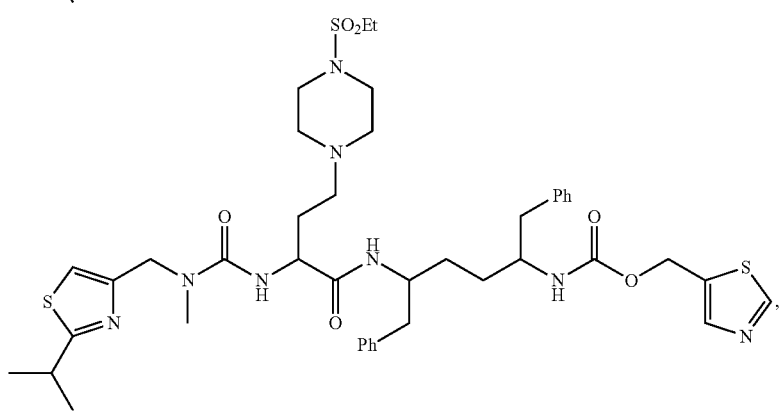
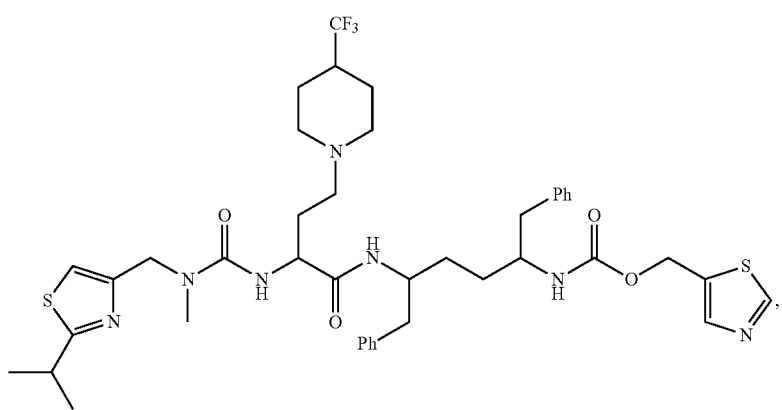
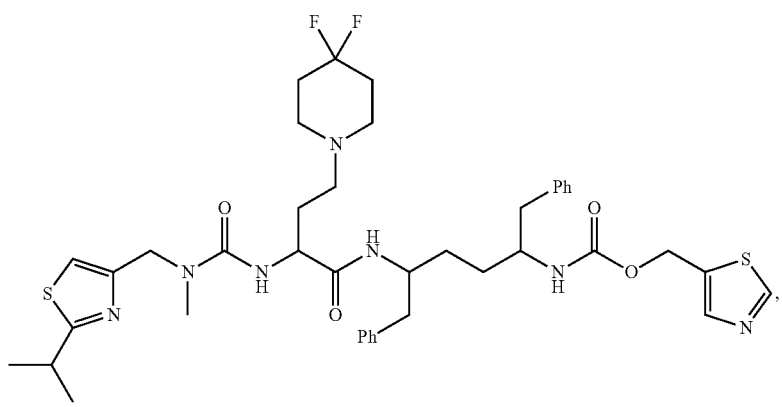

-continued
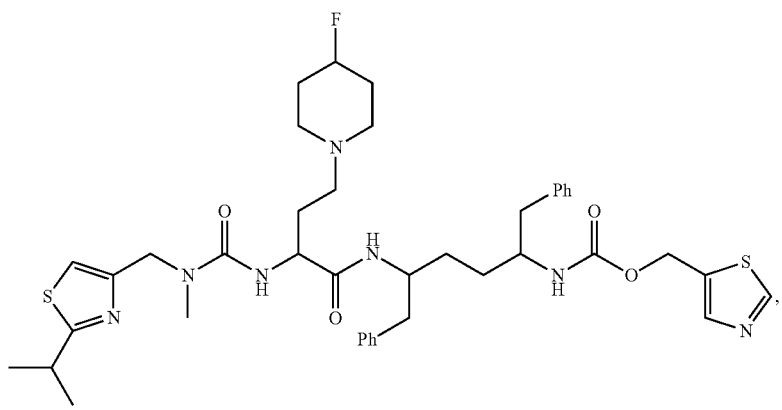
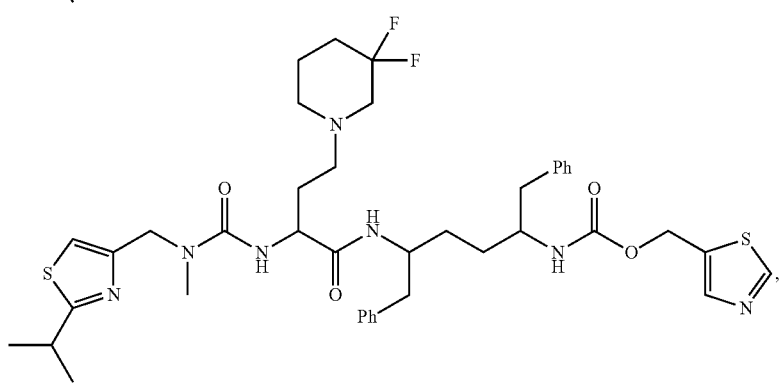
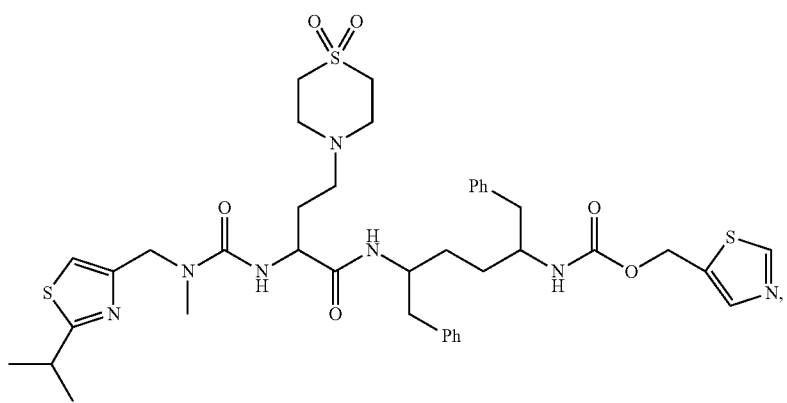
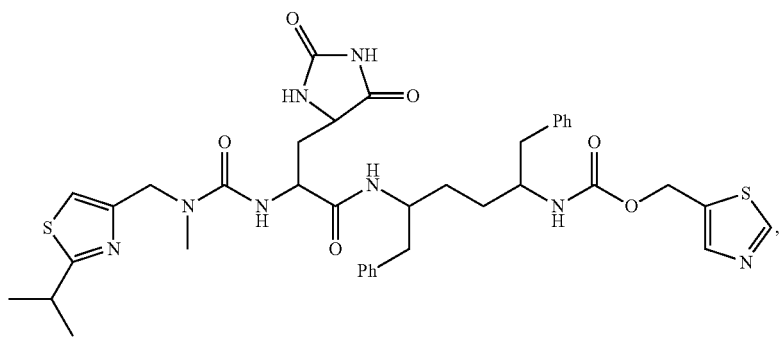

-continued
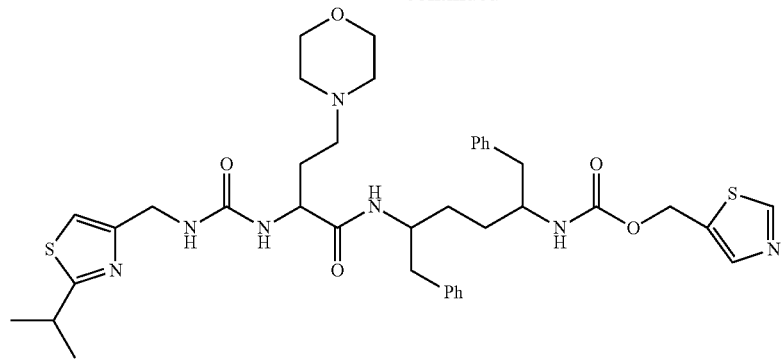
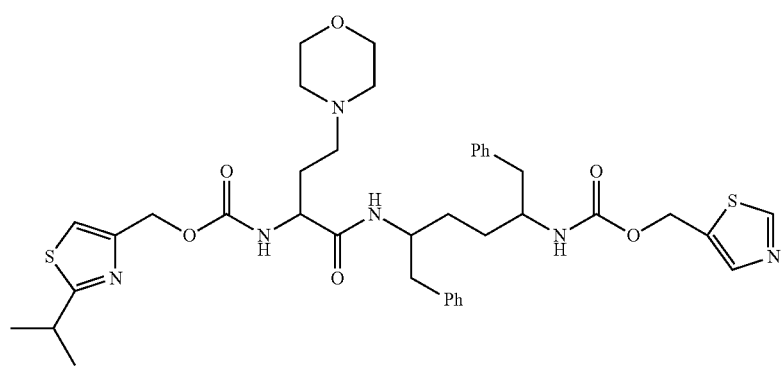
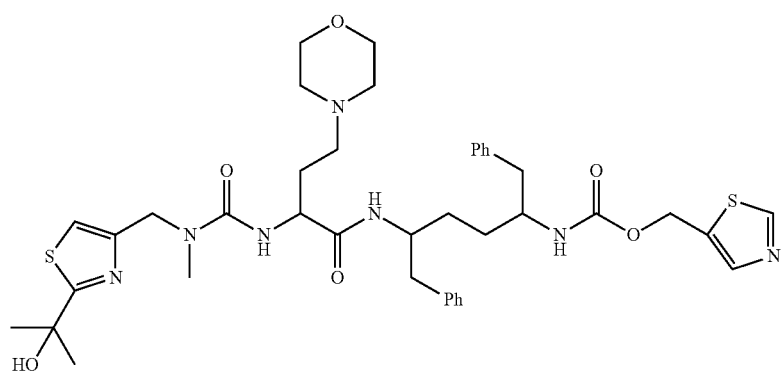
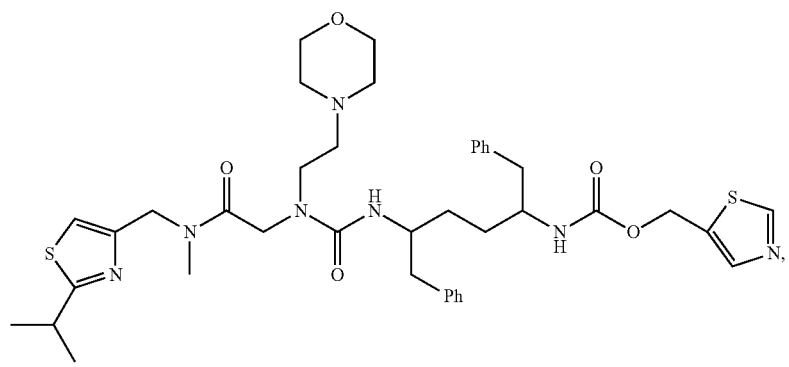

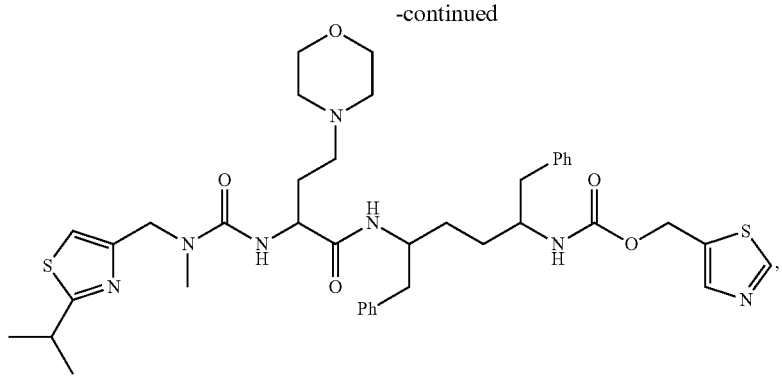

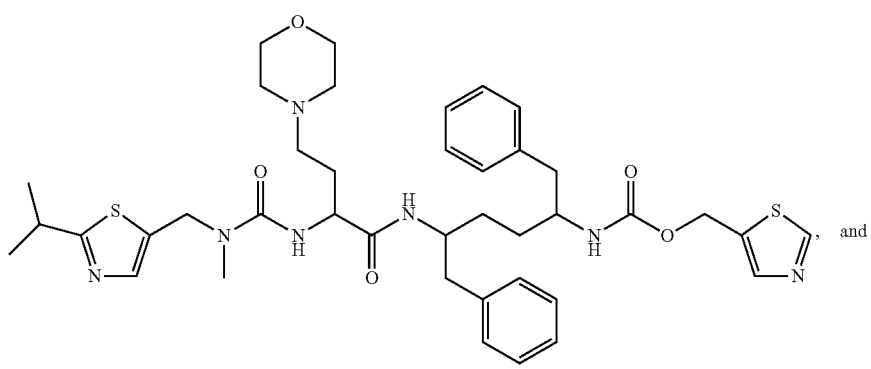, and

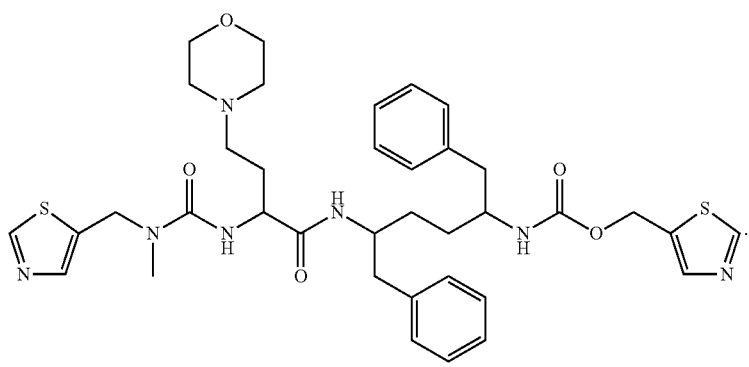

In other embodiments, the compounds of Formula IV have the following general formula:

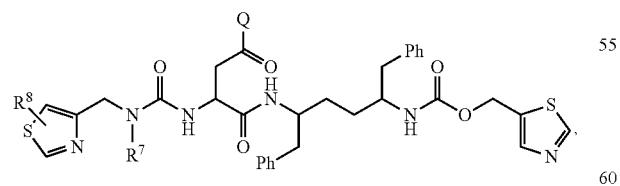

wherein Q is —OH or —N(R$^a$)$_2$. In a particular embodiment, Q is —OH. In another particular embodiment, Q is —N(R$^a$)$_2$. In yet another particular embodiment, Q is —NH-pyridyl, —NH-pyrrolyl, or —NH—S(O$_2$)-alkyl. In other specific embodiments, the compounds of the above general formula have the following structures:

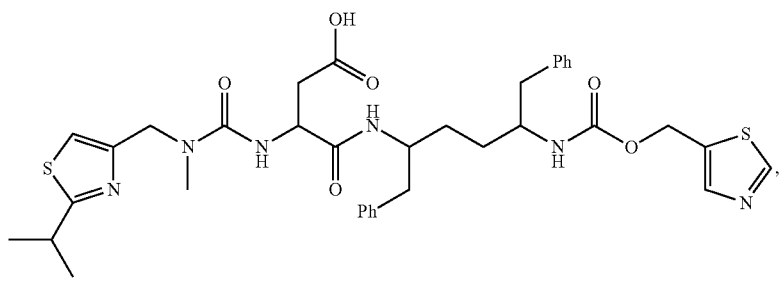
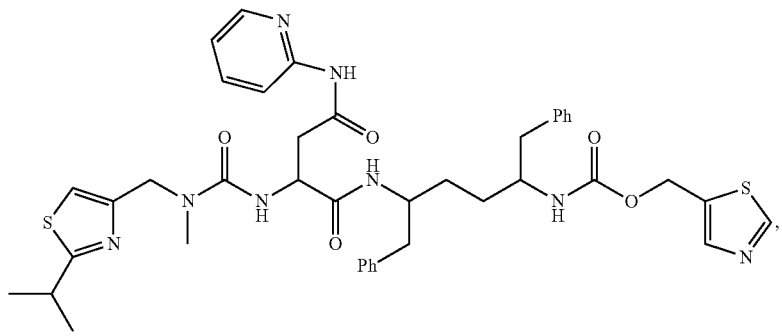
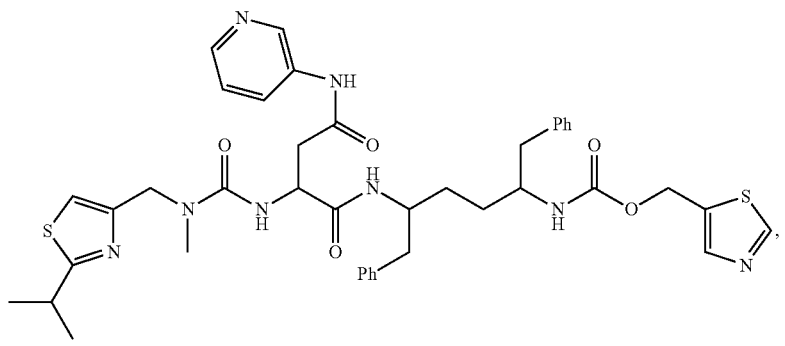
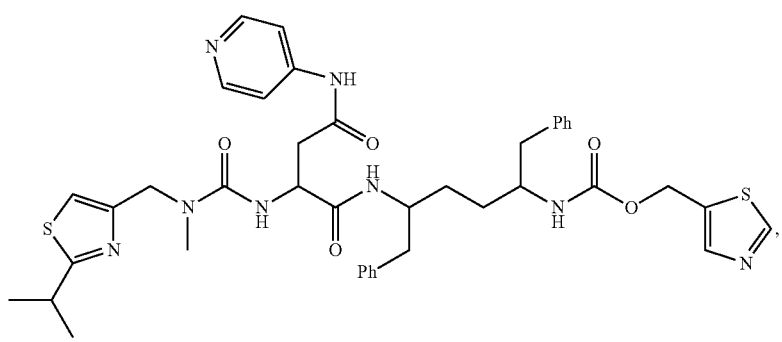
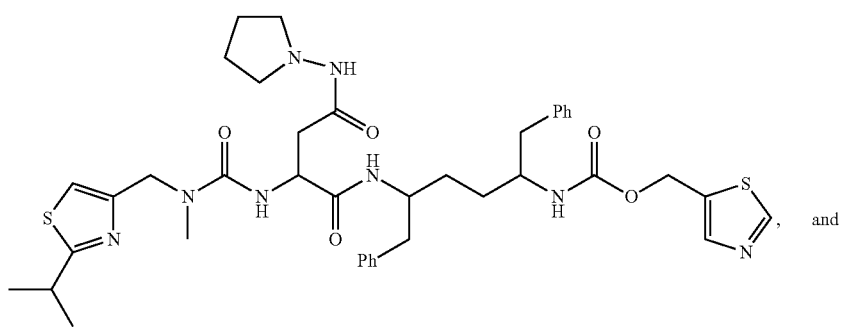

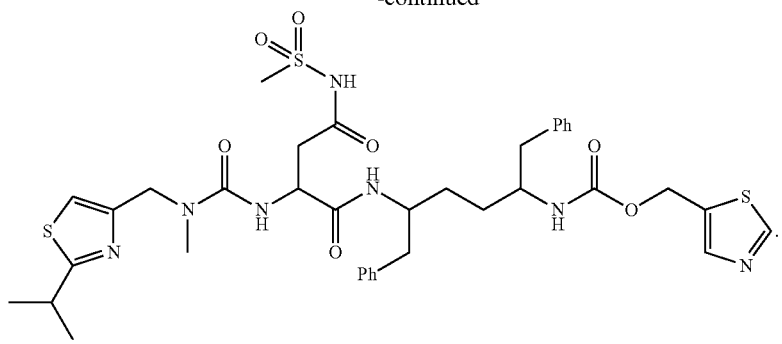

In other embodiments, the compounds of Formula IV have the following general formula:

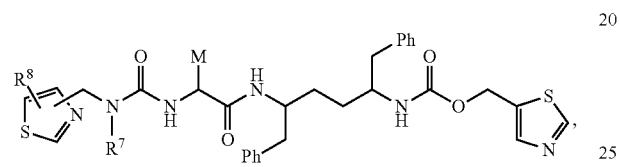

wherein M is substituted or unsubstituted alkyl. In particular embodiments, M is a substituted alkyl, for example hydroxyalkyl, substituted hydroxyalkyl, cyanoalkyl, substituted cyanoalkyl, and trialkylsiloxyalkyl. In other particular embodiments, the compounds of the above general formula have the following structures:

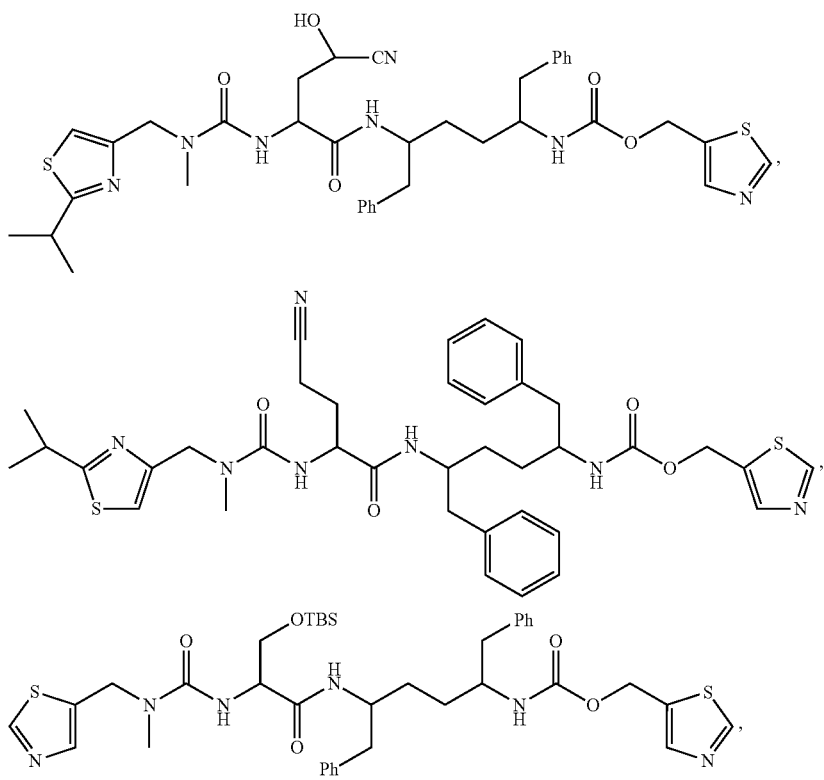

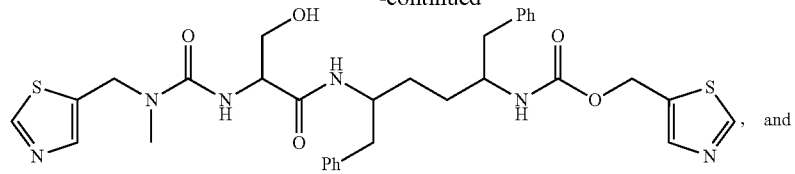

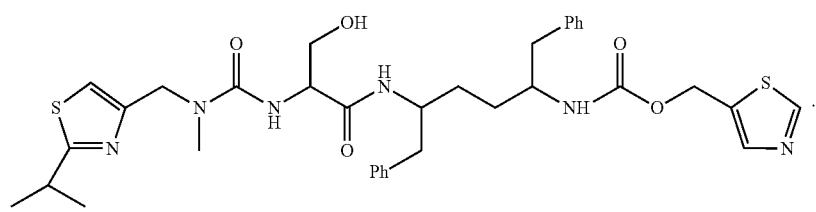

In still other embodiments, the compounds of Formula IV have the following general formula:

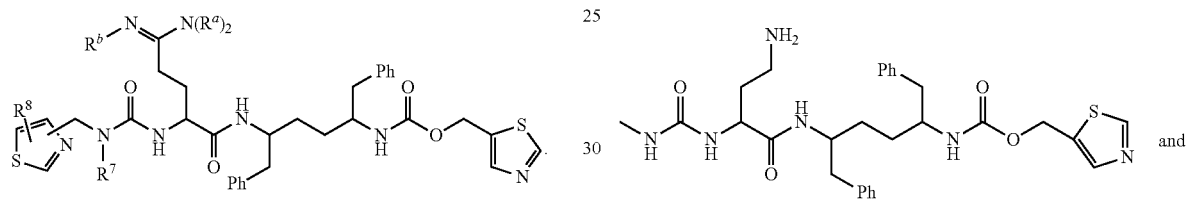

In particular embodiments, a compound of the above general formula has the following structure:

$R^8$—Y— is methyl. Specific particular embodiments of the above general structure include the following structures:

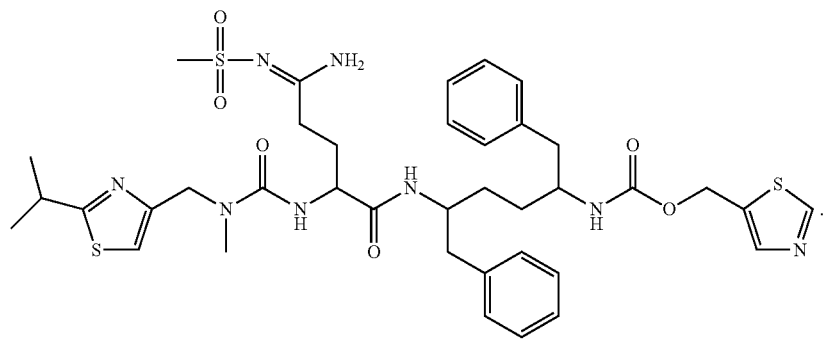 [SMILES: CC(C)c1nc(CN(C)C(=O)NC(CC/C(N)=N\S(C)(=O)=O)C(=O)NC(CCC(Cc2ccccc2)NC(=O)OCc2cncs2)Cc2ccccc2)cs1]

In still other embodiments of the compounds of Formula IV, Y is alkyl. In particular embodiments, such compounds have the following general formula:

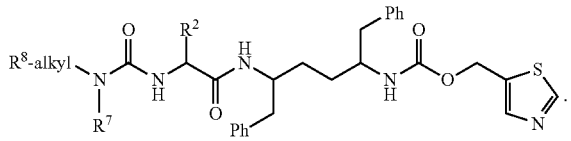

In specific embodiments, $R^8$—Y— is alkyl, for example any alkyl described herein. In a particular embodiment, -continued

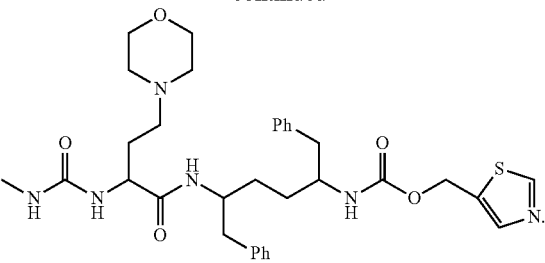

In still yet another embodiment, the compounds of Formula I are named below in tabular format (Table 6) as compounds of general Formula II:

Formula II

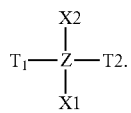

Compounds of general formula II are depicted as a "core" structure (Z) substituted with four moieties T1, T2, X1 and X2. The core structures Z are depicted in Table 1. The points of attachment of T1, T2, X1 and X2 are indicated on each of the core structures depicted in Table 1. Tables 2-5, respectively, show the structures of the T1, T2, X1 and X2 moieties. The point of attachment of the core structure Z is indicated in each of the structures of T1, T2, X1 and X2. Each core structure Z in Table 1, and each substituent T1, T2, X1 and X2 and Tables 2-5 is represented by a "code" comprising a letter and a number. Each structure of a compound of Formula II can be designated in tabular form by combining the "code" representing each structural moiety using the following syntax: Z.T1. T2.X1.X2. Thus, for example, Z1.T1A.T2B.X1A.X2A represents the following structure:

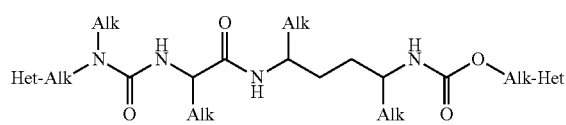

In the structures depicted in Tables 1-5, the term "Alk" means a substituted or unsubstituted alkyl, cycloalkyl, or alkylene group, wherein the terms "alkyl", "cycloalkyl", and "alkylene" are as defined herein. "Alk" means an alkyl or cycloalkyl group when depicted as monovalent, and an alkylene group when depicted as divalent. "Het" is a substituted or unsubstituted heterocyclyl or heterocyclylene group, wherein the term "heterocyclyl" is as defined herein, and the term "heterocyclylene" means a heterocyclyl group as defined herein, in which a hydrogen atom has been replaced by an open valence (in analogy to alkylene), thereby defining a divalent heterocyclyl. "Het" is a heterocyclyl when depicted as monovalent, and heterocyclylene when depicted as divalent. "Ar" is a substitute or unsubstituted aryl or arylene group, wherein the term "aryl" is as defined herein, and the term "arylene" means an aryl group as defined herein, in which a hydrogen atom has been replaced by an open valence (in analogy to alkylene), thereby defining a divalent aryl. "Ar" is aryl when depicted as monovalent, and arylene when depicted as divalent. When substituted, "Alk", "Het", and "Ar" can be substituted with any of the substituents defined or exemplified herein. For example, substituents of "Alk" can include ether, halogen, —OH, amide, amine, etc., substituents of "Het" can include alkyl, aryl, carbonyl, —OH, halogen, and substituents of "Ar" can include alkyl, aryl, —OH, halogen, etc., with the proviso that the resulting structure is chemically reasonable, and would provide compounds which are sufficiently stable for formulation in a pharmaceutically acceptable composition. When a structure or substructure shown in the tables below contains more than one "Alk", "Het" or "Ar" group, these groups are independently selected and can be the same or different. So, for example, each of the "Alk" groups of substructure T1A are independently selected and may be the same or different.

TABLE 1

Core Structures

| Code | Core Structure |
|------|----------------|
| Z1 | |
| Z2 | |
| Z3 | |
| Z4 | |
| Z5 | |
| Z6 | |

TABLE 2

T1 Structures

| Code | T1 Structure |
|------|--------------|
| T1A | |
| T1B | |
| T1C | |

TABLE 2-continued

T1 Structures

| Code | T1 Structure |
|---|---|
| T1D |  |

TABLE 3

T2 Structures

| Code | T2 Structure |
|---|---|
| T2A | —O-Alk-Het |
| T2B | —NH-Alk-Het |
| T2C | —N(Alk)-Alk-Het |
| T2D | —N(Alk)-Het |

TABLE 4

X1 Structures

| Code | X1 Structure |
|---|---|
| X1A | -Alk |
| X1B | -Alk-Ar |
| X1C | -Alk-Het |
| X1D | -Alk-Ar-O-Alk-Ar |
| X1E | -Alk-Ar-O-Alk-Het |

TABLE 5

X2 Structures

| Code | X2 Structure |
|---|---|
| X2A | -Alk |
| X2B | -Alk-Ar |
| X2C | -Alk-Het |
| X2D | -Alk-Ar-O-Alk-Ar |
| X2E | -Alk-Ar-O-Alk-Het |

TABLE 6

List of Compound Structures of Formula II

Z1.T1A.T2A.X1A.X2A, Z2.T1A.T2A.X1A.X2A,
Z3.T1A.T2A.X1A.X2A, Z4.T1A.T2A.X1A.X2A,
Z5.T1A.T2A.X1A.X2A, Z6.T1A.T2A.X1A.X2A,
Z1.T1B.T2A.X1A.X2A, Z2.T1B.T2A.X1A.X2A,
Z3.T1B.T2A.X1A.X2A, Z4.T1B.T2A.X1A.X2A,
Z5.T1B.T2A.X1A.X2A, Z6.T1B.T2A.X1A.X2A,
Z1.T1C.T2A.X1A.X2A, Z2.T1C.T2A.X1A.X2A,
Z3.T1C.T2A.X1A.X2A, Z4.T1C.T2A.X1A.X2A,
Z5.T1C.T2A.X1A.X2A, Z6.T1C.T2A.X1A.X2A,
Z1.T1D.T2A.X1A.X2A, Z2.T1D.T2A.X1A.X2A,
Z3.T1D.T2A.X1A.X2A, Z4.T1D.T2A.X1A.X2A,
Z5.T1D.T2A.X1A.X2A, Z6.T1D.T2A.X1A.X2A,
Z1.T1A.T2B.X1A.X2A, Z2.T1A.T2B.X1A.X2A,
Z3.T1A.T2B.X1A.X2A, Z4.T1A.T2B.X1A.X2A,
Z5.T1A.T2B.X1A.X2A, Z6.T1A.T2B.X1A.X2A,
Z1.T1B.T2B.X1A.X2A, Z2.T1B.T2B.X1A.X2A,
Z3.T1B.T2B.X1A.X2A, Z4.T1B.T2B.X1A.X2A,
Z5.T1B.T2B.X1A.X2A, Z6.T1B.T2B.X1A.X2A,
Z1.T1C.T2B.X1A.X2A, Z2.T1C.T2B.X1A.X2A,
Z3.T1C.T2B.X1A.X2A, Z4.T1C.T2B.X1A.X2A,
Z5.T1C.T2B.X1A.X2A, Z6.T1C.T2B.X1A.X2A,

TABLE 6-continued

List of Compound Structures of Formula II

Z1.T1D.T2B.X1A.X2A, Z2.T1D.T2B.X1A.X2A,
Z3.T1D.T2B.X1A.X2A, Z4.T1D.T2B.X1A.X2A,
Z5.T1D.T2B.X1A.X2A, Z6.T1D.T2B.X1A.X2A,
Z1.T1A.T2C.X1A.X2A, Z2.T1A.T2C.X1A.X2A,
Z3.T1A.T2C.X1A.X2A, Z4.T1A.T2C.X1A.X2A,
Z5.T1A.T2C.X1A.X2A, Z6.T1A.T2C.X1A.X2A,
Z1.T1B.T2C.X1A.X2A, Z2.T1B.T2C.X1A.X2A,
Z3.T1B.T2C.X1A.X2A, Z4.T1B.T2C.X1A.X2A,
Z5.T1B.T2C.X1A.X2A, Z6.T1B.T2C.X1A.X2A,
Z1.T1C.T2C.X1A.X2A, Z2.T1C.T2C.X1A.X2A,
Z3.T1C.T2C.X1A.X2A, Z4.T1C.T2C.X1A.X2A,
Z5.T1C.T2C.X1A.X2A, Z6.T1C.T2C.X1A.X2A,
Z1.T1D.T2C.X1A.X2A, Z2.T1D.T2C.X1A.X2A,
Z3.T1D.T2C.X1A.X2A, Z4.T1D.T2C.X1A.X2A,
Z5.T1D.T2C.X1A.X2A, Z6.T1D.T2C.X1A.X2A,
Z1.T1A.T2D.X1A.X2A, Z2.T1A.T2D.X1A.X2A,
Z3.T1A.T2D.X1A.X2A, Z4.T1A.T2D.X1A.X2A,
Z5.T1A.T2D.X1A.X2A, Z6.T1A.T2D.X1A.X2A,
Z1.T1B.T2D.X1A.X2A, Z2.T1B.T2D.X1A.X2A,
Z3.T1B.T2D.X1A.X2A, Z4.T1B.T2D.X1A.X2A,
Z5.T1B.T2D.X1A.X2A, Z6.T1B.T2D.X1A.X2A,
Z1.T1C.T2D.X1A.X2A, Z2.T1C.T2D.X1A.X2A,
Z3.T1C.T2D.X1A.X2A, Z4.T1C.T2D.X1A.X2A,
Z5.T1C.T2D.X1A.X2A, Z6.T1C.T2D.X1A.X2A,
Z1.T1D.T2D.X1A.X2A, Z2.T1D.T2D.X1A.X2A,
Z3.T1D.T2D.X1A.X2A, Z4.T1D.T2D.X1A.X2A,
Z5.T1D.T2D.X1A.X2A, Z6.T1D.T2D.X1A.X2A,
Z1.T1A.T2A.X1B.X2A, Z2.T1A.T2A.X1B.X2A,
Z3.T1A.T2A.X1B.X2A, Z4.T1A.T2A.X1B.X2A,
Z5.T1A.T2A.X1B.X2A, Z6.T1A.T2A.X1B.X2A,
Z1.T1B.T2A.X1B.X2A, Z2.T1B.T2A.X1B.X2A,
Z3.T1B.T2A.X1B.X2A, Z4.T1B.T2A.X1B.X2A,
Z5.T1B.T2A.X1B.X2A, Z6.T1B.T2A.X1B.X2A,
Z1.T1C.T2A.X1B.X2A, Z2.T1C.T2A.X1B.X2A,
Z3.T1C.T2A.X1B.X2A, Z4.T1C.T2A.X1B.X2A,
Z5.T1C.T2A.X1B.X2A, Z6.T1C.T2A.X1B.X2A,
Z1.T1D.T2A.X1B.X2A, Z2.T1D.T2A.X1B.X2A,
Z3.T1D.T2A.X1B.X2A, Z4.T1D.T2A.X1B.X2A,
Z5.T1D.T2A.X1B.X2A, Z6.T1D.T2A.X1B.X2A,
Z1.T1A.T2B.X1B.X2A, Z2.T1A.T2B.X1B.X2A,
Z3.T1A.T2B.X1B.X2A, Z4.T1A.T2B.X1B.X2A,
Z5.T1A.T2B.X1B.X2A, Z6.T1A.T2B.X1B.X2A,
Z1.T1B.T2B.X1B.X2A, Z2.T1B.T2B.X1B.X2A,
Z3.T1B.T2B.X1B.X2A, Z4.T1B.T2B.X1B.X2A,
Z5.T1B.T2B.X1B.X2A, Z6.T1B.T2B.X1B.X2A,
Z1.T1C.T2B.X1B.X2A, Z2.T1C.T2B.X1B.X2A,
Z3.T1C.T2B.X1B.X2A, Z4.T1C.T2B.X1B.X2A,
Z5.T1C.T2B.X1B.X2A, Z6.T1C.T2B.X1B.X2A,
Z1.T1D.T2B.X1B.X2A, Z2.T1D.T2B.X1B.X2A,
Z3.T1D.T2B.X1B.X2A, Z4.T1D.T2B.X1B.X2A,
Z5.T1D.T2B.X1B.X2A, Z6.T1D.T2B.X1B.X2A,
Z1.T1A.T2C.X1B.X2A, Z2.T1A.T2C.X1B.X2A,
Z3.T1A.T2C.X1B.X2A, Z4.T1A.T2C.X1B.X2A,
Z5.T1A.T2C.X1B.X2A, Z6.T1A.T2C.X1B.X2A,
Z1.T1B.T2C.X1B.X2A, Z2.T1B.T2C.X1B.X2A,
Z3.T1B.T2C.X1B.X2A, Z4.T1B.T2C.X1B.X2A,
Z5.T1B.T2C.X1B.X2A, Z6.T1B.T2C.X1B.X2A,
Z1.T1C.T2C.X1B.X2A, Z2.T1C.T2C.X1B.X2A,
Z3.T1C.T2C.X1B.X2A, Z4.T1C.T2C.X1B.X2A,
Z5.T1C.T2C.X1B.X2A, Z6.T1C.T2C.X1B.X2A,
Z1.T1D.T2C.X1B.X2A, Z2.T1D.T2C.X1B.X2A,
Z3.T1D.T2C.X1B.X2A, Z4.T1D.T2C.X1B.X2A,
Z5.T1D.T2C.X1B.X2A, Z6.T1D.T2C.X1B.X2A,
Z1.T1A.T2D.X1B.X2A, Z2.T1A.T2D.X1B.X2A,
Z3.T1A.T2D.X1B.X2A, Z4.T1A.T2D.X1B.X2A,
Z5.T1A.T2D.X1B.X2A, Z6.T1A.T2D.X1B.X2A,
Z1.T1B.T2D.X1B.X2A, Z2.T1B.T2D.X1B.X2A,
Z3.T1B.T2D.X1B.X2A, Z4.T1B.T2D.X1B.X2A,
Z5.T1B.T2D.X1B.X2A, Z6.T1B.T2D.X1B.X2A,
Z1.T1C.T2D.X1B.X2A, Z2.T1C.T2D.X1B.X2A,
Z3.T1C.T2D.X1B.X2A, Z4.T1C.T2D.X1B.X2A,
Z5.T1C.T2D.X1B.X2A, Z6.T1C.T2D.X1B.X2A,
Z1.T1D.T2D.X1B.X2A, Z2.T1D.T2D.X1B.X2A,
Z3.T1D.T2D.X1B.X2A, Z4.T1D.T2D.X1B.X2A,
Z5.T1D.T2D.X1B.X2A, Z6.T1D.T2D.X1B.X2A,
Z1.T1A.T2A.X1C.X2A, Z2.T1A.T2A.X1C.X2A,
Z3.T1A.T2A.X1C.X2A, Z4.T1A.T2A.X1C.X2A,
Z5.T1A.T2A.X1C.X2A, Z6.T1A.T2A.X1C.X2A,

TABLE 6-continued

List of Compound Structures of Formula II

Z1.T1B.T2A.X1C.X2A, Z2.T1B.T2A.X1C.X2A,
Z3.T1B.T2A.X1C.X2A, Z4.T1B.T2A.X1C.X2A,
Z5.T1B.T2A.X1C.X2A, Z6.T1B.T2A.X1C.X2A,
Z1.T1C.T2A.X1C.X2A, Z2.T1C.T2A.X1C.X2A,
Z3.T1C.T2A.X1C.X2A, Z4.T1C.T2A.X1C.X2A,
Z5.T1C.T2A.X1C.X2A, Z6.T1C.T2A.X1C.X2A,
Z1.T1D.T2A.X1C.X2A, Z2.T1D.T2A.X1C.X2A,
Z3.T1D.T2A.X1C.X2A, Z4.T1D.T2A.X1C.X2A,
Z5.T1D.T2A.X1C.X2A, Z6.T1D.T2A.X1C.X2A,
Z1.T1A.T2B.X1C.X2A, Z2.T1A.T2B.X1C.X2A,
Z3.T1A.T2B.X1C.X2A, Z4.T1A.T2B.X1C.X2A,
Z5.T1A.T2B.X1C.X2A, Z6.T1A.T2B.X1C.X2A,
Z1.T1B.T2B.X1C.X2A, Z2.T1B.T2B.X1C.X2A,
Z3.T1B.T2B.X1C.X2A, Z4.T1B.T2B.X1C.X2A,
Z5.T1B.T2B.X1C.X2A, Z6.T1B.T2B.X1C.X2A,
Z1.T1C.T2B.X1C.X2A, Z2.T1C.T2B.X1C.X2A,
Z3.T1C.T2B.X1C.X2A, Z4.T1C.T2B.X1C.X2A,
Z5.T1C.T2B.X1C.X2A, Z6.T1C.T2B.X1C.X2A,
Z1.T1D.T2B.X1C.X2A, Z2.T1D.T2B.X1C.X2A,
Z3.T1D.T2B.X1C.X2A, Z4.T1D.T2B.X1C.X2A,
Z5.T1D.T2B.X1C.X2A, Z6.T1D.T2B.X1C.X2A,
Z1.T1A.T2C.X1C.X2A, Z2.T1A.T2C.X1C.X2A,
Z3.T1A.T2C.X1C.X2A, Z4.T1A.T2C.X1C.X2A,
Z5.T1A.T2C.X1C.X2A, Z6.T1A.T2C.X1C.X2A,
Z1.T1B.T2C.X1C.X2A, Z2.T1B.T2C.X1C.X2A,
Z3.T1B.T2C.X1C.X2A, Z4.T1B.T2C.X1C.X2A,
Z5.T1B.T2C.X1C.X2A, Z6.T1B.T2C.X1C.X2A,
Z1.T1C.T2C.X1C.X2A, Z2.T1C.T2C.X1C.X2A,
Z3.T1C.T2C.X1C.X2A, Z4.T1C.T2C.X1C.X2A,
Z5.T1C.T2C.X1C.X2A, Z6.T1C.T2C.X1C.X2A,
Z1.T1D.T2C.X1C.X2A, Z2.T1D.T2C.X1C.X2A,
Z3.T1D.T2C.X1C.X2A, Z4.T1D.T2C.X1C.X2A,
Z5.T1D.T2C.X1C.X2A, Z6.T1D.T2C.X1C.X2A,
Z1.T1A.T2D.X1C.X2A, Z2.T1A.T2D.X1C.X2A,
Z3.T1A.T2D.X1C.X2A, Z4.T1A.T2D.X1C.X2A,
Z5.T1A.T2D.X1C.X2A, Z6.T1A.T2D.X1C.X2A,
Z1.T1B.T2D.X1C.X2A, Z2.T1B.T2D.X1C.X2A,
Z3.T1B.T2D.X1C.X2A, Z4.T1B.T2D.X1C.X2A,
Z5.T1B.T2D.X1C.X2A, Z6.T1B.T2D.X1C.X2A,
Z1.T1C.T2D.X1C.X2A, Z2.T1C.T2D.X1C.X2A,
Z3.T1C.T2D.X1C.X2A, Z4.T1C.T2D.X1C.X2A,
Z5.T1C.T2D.X1C.X2A, Z6.T1C.T2D.X1C.X2A,
Z1.T1D.T2D.X1C.X2A, Z2.T1D.T2D.X1C.X2A,
Z3.T1D.T2D.X1C.X2A, Z4.T1D.T2D.X1C.X2A,
Z5.T1D.T2D.X1C.X2A, Z6.T1D.T2D.X1C.X2A,
Z1.T1A.T2A.X1D.X2A, Z2.T1A.T2A.X1D.X2A,
Z3.T1A.T2A.X1D.X2A, Z4.T1A.T2A.X1D.X2A,
Z5.T1A.T2A.X1D.X2A, Z6.T1A.T2A.X1D.X2A,
Z1.T1B.T2A.X1D.X2A, Z2.T1B.T2A.X1D.X2A,
Z3.T1B.T2A.X1D.X2A, Z4.T1B.T2A.X1D.X2A,
Z5.T1B.T2A.X1D.X2A, Z6.T1B.T2A.X1D.X2A,
Z1.T1C.T2A.X1D.X2A, Z2.T1C.T2A.X1D.X2A,
Z3.T1C.T2A.X1D.X2A, Z4.T1C.T2A.X1D.X2A,
Z5.T1C.T2A.X1D.X2A, Z6.T1C.T2A.X1D.X2A,
Z1.T1D.T2A.X1D.X2A, Z2.T1D.T2A.X1D.X2A,
Z3.T1D.T2A.X1D.X2A, Z4.T1D.T2A.X1D.X2A,
Z5.T1D.T2A.X1D.X2A, Z6.T1D.T2A.X1D.X2A,
Z1.T1A.T2B.X1D.X2A, Z2.T1A.T2B.X1D.X2A,
Z3.T1A.T2B.X1D.X2A, Z4.T1A.T2B.X1D.X2A,
Z5.T1A.T2B.X1D.X2A, Z6.T1A.T2B.X1D.X2A,
Z1.T1B.T2B.X1D.X2A, Z2.T1B.T2B.X1D.X2A,
Z3.T1B.T2B.X1D.X2A, Z4.T1B.T2B.X1D.X2A,
Z5.T1B.T2B.X1D.X2A, Z6.T1B.T2B.X1D.X2A,
Z1.T1C.T2B.X1D.X2A, Z2.T1C.T2B.X1D.X2A,
Z3.T1C.T2B.X1D.X2A, Z4.T1C.T2B.X1D.X2A,
Z5.T1C.T2B.X1D.X2A, Z6.T1C.T2B.X1D.X2A,
Z1.T1D.T2B.X1D.X2A, Z2.T1D.T2B.X1D.X2A,
Z3.T1D.T2B.X1D.X2A, Z4.T1D.T2B.X1D.X2A,
Z5.T1D.T2B.X1D.X2A, Z6.T1D.T2B.X1D.X2A,
Z1.T1A.T2C.X1D.X2A, Z2.T1A.T2C.X1D.X2A,
Z3.T1A.T2C.X1D.X2A, Z4.T1A.T2C.X1D.X2A,
Z5.T1A.T2C.X1D.X2A, Z6.T1A.T2C.X1D.X2A,
Z1.T1B.T2C.X1D.X2A, Z2.T1B.T2C.X1D.X2A,
Z3.T1B.T2C.X1D.X2A, Z4.T1B.T2C.X1D.X2A,
Z5.T1B.T2C.X1D.X2A, Z6.T1B.T2C.X1D.X2A,
Z1.T1C.T2C.X1D.X2A, Z2.T1C.T2C.X1D.X2A,
Z3.T1C.T2C.X1D.X2A, Z4.T1C.T2C.X1D.X2A,
Z5.T1C.T2C.X1D.X2A, Z6.T1C.T2C.X1D.X2A,
Z1.T1D.T2C.X1D.X2A, Z2.T1D.T2C.X1D.X2A,
Z3.T1D.T2C.X1D.X2A, Z4.T1D.T2C.X1D.X2A,
Z5.T1D.T2C.X1D.X2A, Z6.T1D.T2C.X1D.X2A,
Z1.T1A.T2D.X1D.X2A, Z2.T1A.T2D.X1D.X2A,
Z3.T1A.T2D.X1D.X2A, Z4.T1A.T2D.X1D.X2A,
Z5.T1A.T2D.X1D.X2A, Z6.T1A.T2D.X1D.X2A,
Z1.T1B.T2D.X1D.X2A, Z2.T1B.T2D.X1D.X2A,
Z3.T1B.T2D.X1D.X2A, Z4.T1B.T2D.X1D.X2A,
Z5.T1B.T2D.X1D.X2A, Z6.T1B.T2D.X1D.X2A,
Z1.T1C.T2D.X1D.X2A, Z2.T1C.T2D.X1D.X2A,
Z3.T1C.T2D.X1D.X2A, Z4.T1C.T2D.X1D.X2A,
Z5.T1C.T2D.X1D.X2A, Z6.T1C.T2D.X1D.X2A,
Z1.T1D.T2D.X1D.X2A, Z2.T1D.T2D.X1D.X2A,
Z3.T1D.T2D.X1D.X2A, Z4.T1D.T2D.X1D.X2A,
Z5.T1D.T2D.X1D.X2A, Z6.T1D.T2D.X1D.X2A,
Z1.T1A.T2A.X1E.X2A, Z2.T1A.T2A.X1E.X2A,
Z3.T1A.T2A.X1E.X2A, Z4.T1A.T2A.X1E.X2A,
Z5.T1A.T2A.X1E.X2A, Z6.T1A.T2A.X1E.X2A,
Z1.T1B.T2A.X1E.X2A, Z2.T1B.T2A.X1E.X2A,
Z3.T1B.T2A.X1E.X2A, Z4.T1B.T2A.X1E.X2A,
Z5.T1B.T2A.X1E.X2A, Z6.T1B.T2A.X1E.X2A,
Z1.T1C.T2A.X1E.X2A, Z2.T1C.T2A.X1E.X2A,
Z3.T1C.T2A.X1E.X2A, Z4.T1C.T2A.X1E.X2A,
Z5.T1C.T2A.X1E.X2A, Z6.T1C.T2A.X1E.X2A,
Z1.T1D.T2A.X1E.X2A, Z2.T1D.T2A.X1E.X2A,
Z3.T1D.T2A.X1E.X2A, Z4.T1D.T2A.X1E.X2A,
Z5.T1D.T2A.X1E.X2A, Z6.T1D.T2A.X1E.X2A,
Z1.T1A.T2B.X1E.X2A, Z2.T1A.T2B.X1E.X2A,
Z3.T1A.T2B.X1E.X2A, Z4.T1A.T2B.X1E.X2A,
Z5.T1A.T2B.X1E.X2A, Z6.T1A.T2B.X1E.X2A,
Z1.T1B.T2B.X1E.X2A, Z2.T1B.T2B.X1E.X2A,
Z3.T1B.T2B.X1E.X2A, Z4.T1B.T2B.X1E.X2A,
Z5.T1B.T2B.X1E.X2A, Z6.T1B.T2B.X1E.X2A,
Z1.T1C.T2B.X1E.X2A, Z2.T1C.T2B.X1E.X2A,
Z3.T1C.T2B.X1E.X2A, Z4.T1C.T2B.X1E.X2A,
Z5.T1C.T2B.X1E.X2A, Z6.T1C.T2B.X1E.X2A,
Z1.T1D.T2B.X1E.X2A, Z2.T1D.T2B.X1E.X2A,
Z3.T1D.T2B.X1E.X2A, Z4.T1D.T2B.X1E.X2A,
Z5.T1D.T2B.X1E.X2A, Z6.T1D.T2B.X1E.X2A,
Z1.T1A.T2C.X1E.X2A, Z2.T1A.T2C.X1E.X2A,
Z3.T1A.T2C.X1E.X2A, Z4.T1A.T2C.X1E.X2A,
Z5.T1A.T2C.X1E.X2A, Z6.T1A.T2C.X1E.X2A,
Z1.T1B.T2C.X1E.X2A, Z2.T1B.T2C.X1E.X2A,
Z3.T1B.T2C.X1E.X2A, Z4.T1B.T2C.X1E.X2A,
Z5.T1B.T2C.X1E.X2A, Z6.T1B.T2C.X1E.X2A,
Z1.T1C.T2C.X1E.X2A, Z2.T1C.T2C.X1E.X2A,
Z3.T1C.T2C.X1E.X2A, Z4.T1C.T2C.X1E.X2A,
Z5.T1C.T2C.X1E.X2A, Z6.T1C.T2C.X1E.X2A,
Z1.T1D.T2C.X1E.X2A, Z2.T1D.T2C.X1E.X2A,
Z3.T1D.T2C.X1E.X2A, Z4.T1D.T2C.X1E.X2A,
Z5.T1D.T2C.X1E.X2A, Z6.T1D.T2C.X1E.X2A,
Z1.T1A.T2D.X1E.X2A, Z2.T1A.T2D.X1E.X2A,
Z3.T1A.T2D.X1E.X2A, Z4.T1A.T2D.X1E.X2A,
Z5.T1A.T2D.X1E.X2A, Z6.T1A.T2D.X1E.X2A,
Z1.T1B.T2D.X1E.X2A, Z2.T1B.T2D.X1E.X2A,
Z3.T1B.T2D.X1E.X2A, Z4.T1B.T2D.X1E.X2A,
Z5.T1B.T2D.X1E.X2A, Z6.T1B.T2D.X1E.X2A,
Z1.T1C.T2D.X1E.X2A, Z2.T1C.T2D.X1E.X2A,
Z3.T1C.T2D.X1E.X2A, Z4.T1C.T2D.X1E.X2A,
Z5.T1C.T2D.X1E.X2A, Z6.T1C.T2D.X1E.X2A,
Z1.T1D.T2D.X1E.X2A, Z2.T1D.T2D.X1E.X2A,
Z3.T1D.T2D.X1E.X2A, Z4.T1D.T2D.X1E.X2A,
Z5.T1D.T2D.X1E.X2A, Z6.T1D.T2D.X1E.X2A,
Z1.T1A.T2A.X1A.X2B, Z2.T1A.T2A.X1A.X2B,
Z3.T1A.T2A.X1A.X2B, Z4.T1A.T2A.X1A.X2B,
Z5.T1A.T2A.X1A.X2B, Z6.T1A.T2A.X1A.X2B,
Z1.T1B.T2A.X1A.X2B, Z2.T1B.T2A.X1A.X2B,
Z3.T1B.T2A.X1A.X2B, Z4.T1B.T2A.X1A.X2B,
Z5.T1B.T2A.X1A.X2B, Z6.T1B.T2A.X1A.X2B,
Z1.T1C.T2A.X1A.X2B, Z2.T1C.T2A.X1A.X2B,
Z3.T1C.T2A.X1A.X2B, Z4.T1C.T2A.X1A.X2B,
Z5.T1C.T2A.X1A.X2B, Z6.T1C.T2A.X1A.X2B,
Z1.T1D.T2A.X1A.X2B, Z2.T1D.T2A.X1A.X2B,
Z3.T1D.T2A.X1A.X2B, Z4.T1D.T2A.X1A.X2B,
Z5.T1D.T2A.X1A.X2B, Z6.T1D.T2A.X1A.X2B,
Z1.T1A.T2B.X1A.X2B, Z2.T1A.T2B.X1A.X2B,
Z3.T1A.T2B.X1A.X2B, Z4.T1A.T2B.X1A.X2B,
Z5.T1A.T2B.X1A.X2B, Z6.T1A.T2B.X1A.X2B,

TABLE 6-continued

List of Compound Structures of Formula II

Z1.T1B.T2B.X1A.X2B, Z2.T1B.T2B.X1A.X2B,
Z3.T1B.T2B.X1A.X2B, Z4.T1B.T2B.X1A.X2B,
Z5.T1B.T2B.X1A.X2B, Z6.T1B.T2B.X1A.X2B,
Z1.T1C.T2B.X1A.X2B, Z2.T1C.T2B.X1A.X2B,
Z3.T1C.T2B.X1A.X2B, Z4.T1C.T2B.X1A.X2B,
Z5.T1C.T2B.X1A.X2B, Z6.T1C.T2B.X1A.X2B,
Z1.T1D.T2B.X1A.X2B, Z2.T1D.T2B.X1A.X2B,
Z3.T1D.T2B.X1A.X2B, Z4.T1D.T2B.X1A.X2B,
Z5.T1D.T2B.X1A.X2B, Z6.T1D.T2B.X1A.X2B,
Z1.T1A.T2C.X1A.X2B, Z2.T1A.T2C.X1A.X2B,
Z3.T1A.T2C.X1A.X2B, Z4.T1A.T2C.X1A.X2B,
Z5.T1A.T2C.X1A.X2B, Z6.T1A.T2C.X1A.X2B,
Z1.T1B.T2C.X1A.X2B, Z2.T1B.T2C.X1A.X2B,
Z3.T1B.T2C.X1A.X2B, Z4.T1B.T2C.X1A.X2B,
Z5.T1B.T2C.X1A.X2B, Z6.T1B.T2C.X1A.X2B,
Z1.T1C.T2C.X1A.X2B, Z2.T1C.T2C.X1A.X2B,
Z3.T1C.T2C.X1A.X2B, Z4.T1C.T2C.X1A.X2B,
Z5.T1C.T2C.X1A.X2B, Z6.T1C.T2C.X1A.X2B,
Z1.T1D.T2C.X1A.X2B, Z2.T1D.T2C.X1A.X2B,
Z3.T1D.T2C.X1A.X2B, Z4.T1D.T2C.X1A.X2B,
Z5.T1D.T2C.X1A.X2B, Z6.T1D.T2C.X1A.X2B,
Z1.T1A.T2D.X1A.X2B, Z2.T1A.T2D.X1A.X2B,
Z3.T1A.T2D.X1A.X2B, Z4.T1A.T2D.X1A.X2B,
Z5.T1A.T2D.X1A.X2B, Z6.T1A.T2D.X1A.X2B,
Z1.T1B.T2D.X1A.X2B, Z2.T1B.T2D.X1A.X2B,
Z3.T1B.T2D.X1A.X2B, Z4.T1B.T2D.X1A.X2B,
Z5.T1B.T2D.X1A.X2B, Z6.T1B.T2D.X1A.X2B,
Z1.T1C.T2D.X1A.X2B, Z2.T1C.T2D.X1A.X2B,
Z3.T1C.T2D.X1A.X2B, Z4.T1C.T2D.X1A.X2B,
Z5.T1C.T2D.X1A.X2B, Z6.T1C.T2D.X1A.X2B,
Z1.T1D.T2D.X1A.X2B, Z2.T1D.T2D.X1A.X2B,
Z3.T1D.T2D.X1A.X2B, Z4.T1D.T2D.X1A.X2B,
Z5.T1D.T2D.X1A.X2B, Z6.T1D.T2D.X1A.X2B,
Z1.T1A.T2A.X1B.X2B, Z2.T1A.T2A.X1B.X2B,
Z3.T1A.T2A.X1B.X2B, Z4.T1A.T2A.X1B.X2B,
Z5.T1A.T2A.X1B.X2B, Z6.T1A.T2A.X1B.X2B,
Z1.T1B.T2A.X1B.X2B, Z2.T1B.T2A.X1B.X2B,
Z3.T1B.T2A.X1B.X2B, Z4.T1B.T2A.X1B.X2B,
Z5.T1B.T2A.X1B.X2B, Z6.T1B.T2A.X1B.X2B,
Z1.T1C.T2A.X1B.X2B, Z2.T1C.T2A.X1B.X2B,
Z3.T1C.T2A.X1B.X2B, Z4.T1C.T2A.X1B.X2B,
Z5.T1C.T2A.X1B.X2B, Z6.T1C.T2A.X1B.X2B,
Z1.T1D.T2A.X1B.X2B, Z2.T1D.T2A.X1B.X2B,
Z3.T1D.T2A.X1B.X2B, Z4.T1D.T2A.X1B.X2B,
Z5.T1D.T2A.X1B.X2B, Z6.T1D.T2A.X1B.X2B,
Z1.T1A.T2B.X1B.X2B, Z2.T1A.T2B.X1B.X2B,
Z3.T1A.T2B.X1B.X2B, Z4.T1A.T2B.X1B.X2B,
Z5.T1A.T2B.X1B.X2B, Z6.T1A.T2B.X1B.X2B,
Z1.T1B.T2B.X1B.X2B, Z2.T1B.T2B.X1B.X2B,
Z3.T1B.T2B.X1B.X2B, Z4.T1B.T2B.X1B.X2B,
Z5.T1B.T2B.X1B.X2B, Z6.T1B.T2B.X1B.X2B,
Z1.T1C.T2B.X1B.X2B, Z2.T1C.T2B.X1B.X2B,
Z3.T1C.T2B.X1B.X2B, Z4.T1C.T2B.X1B.X2B,
Z5.T1C.T2B.X1B.X2B, Z6.T1C.T2B.X1B.X2B,
Z1.T1D.T2B.X1B.X2B, Z2.T1D.T2B.X1B.X2B,
Z3.T1D.T2B.X1B.X2B, Z4.T1D.T2B.X1B.X2B,
Z5.T1D.T2B.X1B.X2B, Z6.T1D.T2B.X1B.X2B,
Z1.T1A.T2C.X1B.X2B, Z2.T1A.T2C.X1B.X2B,
Z3.T1A.T2C.X1B.X2B, Z4.T1A.T2C.X1B.X2B,
Z5.T1A.T2C.X1B.X2B, Z6.T1A.T2C.X1B.X2B,
Z1.T1B.T2C.X1B.X2B, Z2.T1B.T2C.X1B.X2B,
Z3.T1B.T2C.X1B.X2B, Z4.T1B.T2C.X1B.X2B,
Z5.T1B.T2C.X1B.X2B, Z6.T1B.T2C.X1B.X2B,
Z1.T1C.T2C.X1B.X2B, Z2.T1C.T2C.X1B.X2B,
Z3.T1C.T2C.X1B.X2B, Z4.T1C.T2C.X1B.X2B,
Z5.T1C.T2C.X1B.X2B, Z6.T1C.T2C.X1B.X2B,
Z1.T1D.T2C.X1B.X2B, Z2.T1D.T2C.X1B.X2B,
Z3.T1D.T2C.X1B.X2B, Z4.T1D.T2C.X1B.X2B,
Z5.T1D.T2C.X1B.X2B, Z6.T1D.T2C.X1B.X2B,
Z1.T1A.T2D.X1B.X2B, Z2.T1A.T2D.X1B.X2B,
Z3.T1A.T2D.X1B.X2B, Z4.T1A.T2D.X1B.X2B,
Z5.T1A.T2D.X1B.X2B, Z6.T1A.T2D.X1B.X2B,
Z1.T1B.T2D.X1B.X2B, Z2.T1B.T2D.X1B.X2B,
Z3.T1B.T2D.X1B.X2B, Z4.T1B.T2D.X1B.X2B,
Z5.T1B.T2D.X1B.X2B, Z6.T1B.T2D.X1B.X2B,
Z1.T1C.T2D.X1B.X2B, Z2.T1C.T2D.X1B.X2B,
Z3.T1C.T2D.X1B.X2B, Z4.T1C.T2D.X1B.X2B,
Z5.T1C.T2D.X1B.X2B, Z6.T1C.T2D.X1B.X2B,
Z1.T1D.T2D.X1B.X2B, Z2.T1D.T2D.X1B.X2B,
Z3.T1D.T2D.X1B.X2B, Z4.T1D.T2D.X1B.X2B,
Z5.T1D.T2D.X1B.X2B, Z6.T1D.T2D.X1B.X2B,
Z1.T1A.T2A.X1C.X2B, Z2.T1A.T2A.X1C.X2B,
Z3.T1A.T2A.X1C.X2B, Z4.T1A.T2A.X1C.X2B,
Z5.T1A.T2A.X1C.X2B, Z6.T1A.T2A.X1C.X2B,
Z1.T1B.T2A.X1C.X2B, Z2.T1B.T2A.X1C.X2B,
Z3.T1B.T2A.X1C.X2B, Z4.T1B.T2A.X1C.X2B,
Z5.T1B.T2A.X1C.X2B, Z6.T1B.T2A.X1C.X2B,
Z1.T1C.T2A.X1C.X2B, Z2.T1C.T2A.X1C.X2B,
Z3.T1C.T2A.X1C.X2B, Z4.T1C.T2A.X1C.X2B,
Z5.T1C.T2A.X1C.X2B, Z6.T1C.T2A.X1C.X2B,
Z1.T1D.T2A.X1C.X2B, Z2.T1D.T2A.X1C.X2B,
Z3.T1D.T2A.X1C.X2B, Z4.T1D.T2A.X1C.X2B,
Z5.T1D.T2A.X1C.X2B, Z6.T1D.T2A.X1C.X2B,
Z1.T1A.T2B.X1C.X2B, Z2.T1A.T2B.X1C.X2B,
Z3.T1A.T2B.X1C.X2B, Z4.T1A.T2B.X1C.X2B,
Z5.T1A.T2B.X1C.X2B, Z6.T1A.T2B.X1C.X2B,
Z1.T1B.T2B.X1C.X2B, Z2.T1B.T2B.X1C.X2B,
Z3.T1B.T2B.X1C.X2B, Z4.T1B.T2B.X1C.X2B,
Z5.T1B.T2B.X1C.X2B, Z6.T1B.T2B.X1C.X2B,
Z1.T1C.T2B.X1C.X2B, Z2.T1C.T2B.X1C.X2B,
Z3.T1C.T2B.X1C.X2B, Z4.T1C.T2B.X1C.X2B,
Z5.T1C.T2B.X1C.X2B, Z6.T1C.T2B.X1C.X2B,
Z1.T1D.T2B.X1C.X2B, Z2.T1D.T2B.X1C.X2B,
Z3.T1D.T2B.X1C.X2B, Z4.T1D.T2B.X1C.X2B,
Z5.T1D.T2B.X1C.X2B, Z6.T1D.T2B.X1C.X2B,
Z1.T1A.T2C.X1C.X2B, Z2.T1A.T2C.X1C.X2B,
Z3.T1A.T2C.X1C.X2B, Z4.T1A.T2C.X1C.X2B,
Z5.T1A.T2C.X1C.X2B, Z6.T1A.T2C.X1C.X2B,
Z1.T1B.T2C.X1C.X2B, Z2.T1B.T2C.X1C.X2B,
Z3.T1B.T2C.X1C.X2B, Z4.T1B.T2C.X1C.X2B,
Z5.T1B.T2C.X1C.X2B, Z6.T1B.T2C.X1C.X2B,
Z1.T1C.T2C.X1C.X2B, Z2.T1C.T2C.X1C.X2B,
Z3.T1C.T2C.X1C.X2B, Z4.T1C.T2C.X1C.X2B,
Z5.T1C.T2C.X1C.X2B, Z6.T1C.T2C.X1C.X2B,
Z1.T1D.T2C.X1C.X2B, Z2.T1D.T2C.X1C.X2B,
Z3.T1D.T2C.X1C.X2B, Z4.T1D.T2C.X1C.X2B,
Z5.T1D.T2C.X1C.X2B, Z6.T1D.T2C.X1C.X2B,
Z1.T1A.T2D.X1C.X2B, Z2.T1A.T2D.X1C.X2B,
Z3.T1A.T2D.X1C.X2B, Z4.T1A.T2D.X1C.X2B,
Z5.T1A.T2D.X1C.X2B, Z6.T1A.T2D.X1C.X2B,
Z1.T1B.T2D.X1C.X2B, Z2.T1B.T2D.X1C.X2B,
Z3.T1B.T2D.X1C.X2B, Z4.T1B.T2D.X1C.X2B,
Z5.T1B.T2D.X1C.X2B, Z6.T1B.T2D.X1C.X2B,
Z1.T1C.T2D.X1C.X2B, Z2.T1C.T2D.X1C.X2B,
Z3.T1C.T2D.X1C.X2B, Z4.T1C.T2D.X1C.X2B,
Z5.T1C.T2D.X1C.X2B, Z6.T1C.T2D.X1C.X2B,
Z1.T1D.T2D.X1C.X2B, Z2.T1D.T2D.X1C.X2B,
Z3.T1D.T2D.X1C.X2B, Z4.T1D.T2D.X1C.X2B,
Z5.T1D.T2D.X1C.X2B, Z6.T1D.T2D.X1C.X2B,
Z1.T1A.T2A.X1D.X2B, Z2.T1A.T2A.X1D.X2B,
Z3.T1A.T2A.X1D.X2B, Z4.T1A.T2A.X1D.X2B,
Z5.T1A.T2A.X1D.X2B, Z6.T1A.T2A.X1D.X2B,
Z1.T1B.T2A.X1D.X2B, Z2.T1B.T2A.X1D.X2B,
Z3.T1B.T2A.X1D.X2B, Z4.T1B.T2A.X1D.X2B,
Z5.T1B.T2A.X1D.X2B, Z6.T1B.T2A.X1D.X2B,
Z1.T1C.T2A.X1D.X2B, Z2.T1C.T2A.X1D.X2B,
Z3.T1C.T2A.X1D.X2B, Z4.T1C.T2A.X1D.X2B,
Z5.T1C.T2A.X1D.X2B, Z6.T1C.T2A.X1D.X2B,
Z1.T1D.T2A.X1D.X2B, Z2.T1D.T2A.X1D.X2B,
Z3.T1D.T2A.X1D.X2B, Z4.T1D.T2A.X1D.X2B,
Z5.T1D.T2A.X1D.X2B, Z6.T1D.T2A.X1D.X2B,
Z1.T1A.T2B.X1D.X2B, Z2.T1A.T2B.X1D.X2B,
Z3.T1A.T2B.X1D.X2B, Z4.T1A.T2B.X1D.X2B,
Z5.T1A.T2B.X1D.X2B, Z6.T1A.T2B.X1D.X2B,
Z1.T1B.T2B.X1D.X2B, Z2.T1B.T2B.X1D.X2B,
Z3.T1B.T2B.X1D.X2B, Z4.T1B.T2B.X1D.X2B,
Z5.T1B.T2B.X1D.X2B, Z6.T1B.T2B.X1D.X2B,
Z1.T1C.T2B.X1D.X2B, Z2.T1C.T2B.X1D.X2B,
Z3.T1C.T2B.X1D.X2B, Z4.T1C.T2B.X1D.X2B,
Z5.T1C.T2B.X1D.X2B, Z6.T1C.T2B.X1D.X2B,
Z1.T1D.T2B.X1D.X2B, Z2.T1D.T2B.X1D.X2B,
Z3.T1D.T2B.X1D.X2B, Z4.T1D.T2B.X1D.X2B,
Z5.T1D.T2B.X1D.X2B, Z6.T1D.T2B.X1D.X2B,
Z1.T1A.T2C.X1D.X2B, Z2.T1A.T2C.X1D.X2B,
Z3.T1A.T2C.X1D.X2B, Z4.T1A.T2C.X1D.X2B,
Z5.T1A.T2C.X1D.X2B, Z6.T1A.T2C.X1D.X2B,

TABLE 6-continued

List of Compound Structures of Formula II

Z1.T1B.T2C.X1D.X2B, Z2.T1B.T2C.X1D.X2B,
Z3.T1B.T2C.X1D.X2B, Z4.T1B.T2C.X1D.X2B,
Z5.T1B.T2C.X1D.X2B, Z6.T1B.T2C.X1D.X2B,
Z1.T1C.T2C.X1D.X2B, Z2.T1C.T2C.X1D.X2B,
Z3.T1C.T2C.X1D.X2B, Z4.T1C.T2C.X1D.X2B,
Z5.T1C.T2C.X1D.X2B, Z6.T1C.T2C.X1D.X2B,
Z1.T1D.T2C.X1D.X2B, Z2.T1D.T2C.X1D.X2B,
Z3.T1D.T2C.X1D.X2B, Z4.T1D.T2C.X1D.X2B,
Z5.T1D.T2C.X1D.X2B, Z6.T1D.T2C.X1D.X2B,
Z1.T1A.T2D.X1D.X2B, Z2.T1A.T2D.X1D.X2B,
Z3.T1A.T2D.X1D.X2B, Z4.T1A.T2D.X1D.X2B,
Z5.T1A.T2D.X1D.X2B, Z6.T1A.T2D.X1D.X2B,
Z1.T1B.T2D.X1D.X2B, Z2.T1B.T2D.X1D.X2B,
Z3.T1B.T2D.X1D.X2B, Z4.T1B.T2D.X1D.X2B,
Z5.T1B.T2D.X1D.X2B, Z6.T1B.T2D.X1D.X2B,
Z1.T1C.T2D.X1D.X2B, Z2.T1C.T2D.X1D.X2B,
Z3.T1C.T2D.X1D.X2B, Z4.T1C.T2D.X1D.X2B,
Z5.T1C.T2D.X1D.X2B, Z6.T1C.T2D.X1D.X2B,
Z1.T1D.T2D.X1D.X2B, Z2.T1D.T2D.X1D.X2B,
Z3.T1D.T2D.X1D.X2B, Z4.T1D.T2D.X1D.X2B,
Z5.T1D.T2D.X1D.X2B, Z6.T1D.T2D.X1D.X2B,
Z1.T1A.T2A.X1E.X2B, Z2.T1A.T2A.X1E.X2B,
Z3.T1A.T2A.X1E.X2B, Z4.T1A.T2A.X1E.X2B,
Z5.T1A.T2A.X1E.X2B, Z6.T1A.T2A.X1E.X2B,
Z1.T1B.T2A.X1E.X2B, Z2.T1B.T2A.X1E.X2B,
Z3.T1B.T2A.X1E.X2B, Z4.T1B.T2A.X1E.X2B,
Z5.T1B.T2A.X1E.X2B, Z6.T1B.T2A.X1E.X2B,
Z1.T1C.T2A.X1E.X2B, Z2.T1C.T2A.X1E.X2B,
Z3.T1C.T2A.X1E.X2B, Z4.T1C.T2A.X1E.X2B,
Z5.T1C.T2A.X1E.X2B, Z6.T1C.T2A.X1E.X2B,
Z1.T1D.T2A.X1E.X2B, Z2.T1D.T2A.X1E.X2B,
Z3.T1D.T2A.X1E.X2B, Z4.T1D.T2A.X1E.X2B,
Z5.T1D.T2A.X1E.X2B, Z6.T1D.T2A.X1E.X2B,
Z1.T1A.T2B.X1E.X2B, Z2.T1A.T2B.X1E.X2B,
Z3.T1A.T2B.X1E.X2B, Z4.T1A.T2B.X1E.X2B,
Z5.T1A.T2B.X1E.X2B, Z6.T1A.T2B.X1E.X2B,
Z1.T1B.T2B.X1E.X2B, Z2.T1B.T2B.X1E.X2B,
Z3.T1B.T2B.X1E.X2B, Z4.T1B.T2B.X1E.X2B,
Z5.T1B.T2B.X1E.X2B, Z6.T1B.T2B.X1E.X2B,
Z1.T1C.T2B.X1E.X2B, Z2.T1C.T2B.X1E.X2B,
Z3.T1C.T2B.X1E.X2B, Z4.T1C.T2B.X1E.X2B,
Z5.T1C.T2B.X1E.X2B, Z6.T1C.T2B.X1E.X2B,
Z1.T1D.T2B.X1E.X2B, Z2.T1D.T2B.X1E.X2B,
Z3.T1D.T2B.X1E.X2B, Z4.T1D.T2B.X1E.X2B,
Z5.T1D.T2B.X1E.X2B, Z6.T1D.T2B.X1E.X2B,
Z1.T1A.T2C.X1E.X2B, Z2.T1A.T2C.X1E.X2B,
Z3.T1A.T2C.X1E.X2B, Z4.T1A.T2C.X1E.X2B,
Z5.T1A.T2C.X1E.X2B, Z6.T1A.T2C.X1E.X2B,
Z1.T1B.T2C.X1E.X2B, Z2.T1B.T2C.X1E.X2B,
Z3.T1B.T2C.X1E.X2B, Z4.T1B.T2C.X1E.X2B,
Z5.T1B.T2C.X1E.X2B, Z6.T1B.T2C.X1E.X2B,
Z1.T1C.T2C.X1E.X2B, Z2.T1C.T2C.X1E.X2B,
Z3.T1C.T2C.X1E.X2B, Z4.T1C.T2C.X1E.X2B,
Z5.T1C.T2C.X1E.X2B, Z6.T1C.T2C.X1E.X2B,
Z1.T1D.T2C.X1E.X2B, Z2.T1D.T2C.X1E.X2B,
Z3.T1D.T2C.X1E.X2B, Z4.T1D.T2C.X1E.X2B,
Z5.T1D.T2C.X1E.X2B, Z6.T1D.T2C.X1E.X2B,
Z1.T1A.T2D.X1E.X2B, Z2.T1A.T2D.X1E.X2B,
Z3.T1A.T2D.X1E.X2B, Z4.T1A.T2D.X1E.X2B,
Z5.T1A.T2D.X1E.X2B, Z6.T1A.T2D.X1E.X2B,
Z1.T1B.T2D.X1E.X2B, Z2.T1B.T2D.X1E.X2B,
Z3.T1B.T2D.X1E.X2B, Z4.T1B.T2D.X1E.X2B,
Z5.T1B.T2D.X1E.X2B, Z6.T1B.T2D.X1E.X2B,
Z1.T1C.T2D.X1E.X2B, Z2.T1C.T2D.X1E.X2B,
Z3.T1C.T2D.X1E.X2B, Z4.T1C.T2D.X1E.X2B,
Z5.T1C.T2D.X1E.X2B, Z6.T1C.T2D.X1E.X2B,
Z1.T1D.T2D.X1E.X2B, Z2.T1D.T2D.X1E.X2B,
Z3.T1D.T2D.X1E.X2B, Z4.T1D.T2D.X1E.X2B,
Z5.T1D.T2D.X1E.X2B, Z6.T1D.T2D.X1E.X2B,
Z1.T1A.T2A.X1A.X2C, Z2.T1A.T2A.X1A.X2C,
Z3.T1A.T2A.X1A.X2C, Z4.T1A.T2A.X1A.X2C,
Z5.T1A.T2A.X1A.X2C, Z6.T1A.T2A.X1A.X2C,
Z1.T1B.T2A.X1A.X2C, Z2.T1B.T2A.X1A.X2C,
Z3.T1B.T2A.X1A.X2C, Z4.T1B.T2A.X1A.X2C,
Z5.T1B.T2A.X1A.X2C, Z6.T1B.T2A.X1A.X2C,
Z1.T1C.T2A.X1A.X2C, Z2.T1C.T2A.X1A.X2C,
Z3.T1C.T2A.X1A.X2C, Z4.T1C.T2A.X1A.X2C,
Z5.T1C.T2A.X1A.X2C, Z6.T1C.T2A.X1A.X2C,
Z1.T1D.T2A.X1A.X2C, Z2.T1D.T2A.X1A.X2C,
Z3.T1D.T2A.X1A.X2C, Z4.T1D.T2A.X1A.X2C,
Z5.T1D.T2A.X1A.X2C, Z6.T1D.T2A.X1A.X2C,
Z1.T1A.T2B.X1A.X2C, Z2.T1A.T2B.X1A.X2C,
Z3.T1A.T2B.X1A.X2C, Z4.T1A.T2B.X1A.X2C,
Z5.T1A.T2B.X1A.X2C, Z6.T1A.T2B.X1A.X2C,
Z1.T1B.T2B.X1A.X2C, Z2.T1B.T2B.X1A.X2C,
Z3.T1B.T2B.X1A.X2C, Z4.T1B.T2B.X1A.X2C,
Z5.T1B.T2B.X1A.X2C, Z6.T1B.T2B.X1A.X2C,
Z1.T1C.T2B.X1A.X2C, Z2.T1C.T2B.X1A.X2C,
Z3.T1C.T2B.X1A.X2C, Z4.T1C.T2B.X1A.X2C,
Z5.T1C.T2B.X1A.X2C, Z6.T1C.T2B.X1A.X2C,
Z1.T1D.T2B.X1A.X2C, Z2.T1D.T2B.X1A.X2C,
Z3.T1D.T2B.X1A.X2C, Z4.T1D.T2B.X1A.X2C,
Z5.T1D.T2B.X1A.X2C, Z6.T1D.T2B.X1A.X2C,
Z1.T1A.T2C.X1A.X2C, Z2.T1A.T2C.X1A.X2C,
Z3.T1A.T2C.X1A.X2C, Z4.T1A.T2C.X1A.X2C,
Z5.T1A.T2C.X1A.X2C, Z6.T1A.T2C.X1A.X2C,
Z1.T1B.T2C.X1A.X2C, Z2.T1B.T2C.X1A.X2C,
Z3.T1B.T2C.X1A.X2C, Z4.T1B.T2C.X1A.X2C,
Z5.T1B.T2C.X1A.X2C, Z6.T1B.T2C.X1A.X2C,
Z1.T1C.T2C.X1A.X2C, Z2.T1C.T2C.X1A.X2C,
Z3.T1C.T2C.X1A.X2C, Z4.T1C.T2C.X1A.X2C,
Z5.T1C.T2C.X1A.X2C, Z6.T1C.T2C.X1A.X2C,
Z1.T1D.T2C.X1A.X2C, Z2.T1D.T2C.X1A.X2C,
Z3.T1D.T2C.X1A.X2C, Z4.T1D.T2C.X1A.X2C,
Z5.T1D.T2C.X1A.X2C, Z6.T1D.T2C.X1A.X2C,
Z1.T1A.T2D.X1A.X2C, Z2.T1A.T2D.X1A.X2C,
Z3.T1A.T2D.X1A.X2C, Z4.T1A.T2D.X1A.X2C,
Z5.T1A.T2D.X1A.X2C, Z6.T1A.T2D.X1A.X2C,
Z1.T1B.T2D.X1A.X2C, Z2.T1B.T2D.X1A.X2C,
Z3.T1B.T2D.X1A.X2C, Z4.T1B.T2D.X1A.X2C,
Z5.T1B.T2D.X1A.X2C, Z6.T1B.T2D.X1A.X2C,
Z1.T1C.T2D.X1A.X2C, Z2.T1C.T2D.X1A.X2C,
Z3.T1C.T2D.X1A.X2C, Z4.T1C.T2D.X1A.X2C,
Z5.T1C.T2D.X1A.X2C, Z6.T1C.T2D.X1A.X2C,
Z1.T1D.T2D.X1A.X2C, Z2.T1D.T2D.X1A.X2C,
Z3.T1D.T2D.X1A.X2C, Z4.T1D.T2D.X1A.X2C,
Z5.T1D.T2D.X1A.X2C, Z6.T1D.T2D.X1A.X2C,
Z1.T1A.T2A.X1B.X2C, Z2.T1A.T2A.X1B.X2C,
Z3.T1A.T2A.X1B.X2C, Z4.T1A.T2A.X1B.X2C,
Z5.T1A.T2A.X1B.X2C, Z6.T1A.T2A.X1B.X2C,
Z1.T1B.T2A.X1B.X2C, Z2.T1B.T2A.X1B.X2C,
Z3.T1B.T2A.X1B.X2C, Z4.T1B.T2A.X1B.X2C,
Z5.T1B.T2A.X1B.X2C, Z6.T1B.T2A.X1B.X2C,
Z1.T1C.T2A.X1B.X2C, Z2.T1C.T2A.X1B.X2C,
Z3.T1C.T2A.X1B.X2C, Z4.T1C.T2A.X1B.X2C,
Z5.T1C.T2A.X1B.X2C, Z6.T1C.T2A.X1B.X2C,
Z1.T1D.T2A.X1B.X2C, Z2.T1D.T2A.X1B.X2C,
Z3.T1D.T2A.X1B.X2C, Z4.T1D.T2A.X1B.X2C,
Z5.T1D.T2A.X1B.X2C, Z6.T1D.T2A.X1B.X2C,
Z1.T1A.T2B.X1B.X2C, Z2.T1A.T2B.X1B.X2C,
Z3.T1A.T2B.X1B.X2C, Z4.T1A.T2B.X1B.X2C,
Z5.T1A.T2B.X1B.X2C, Z6.T1A.T2B.X1B.X2C,
Z1.T1B.T2B.X1B.X2C, Z2.T1B.T2B.X1B.X2C,
Z3.T1B.T2B.X1B.X2C, Z4.T1B.T2B.X1B.X2C,
Z5.T1B.T2B.X1B.X2C, Z6.T1B.T2B.X1B.X2C,
Z1.T1C.T2B.X1B.X2C, Z2.T1C.T2B.X1B.X2C,
Z3.T1C.T2B.X1B.X2C, Z4.T1C.T2B.X1B.X2C,
Z5.T1C.T2B.X1B.X2C, Z6.T1C.T2B.X1B.X2C,
Z1.T1D.T2B.X1B.X2C, Z2.T1D.T2B.X1B.X2C,
Z3.T1D.T2B.X1B.X2C, Z4.T1D.T2B.X1B.X2C,
Z5.T1D.T2B.X1B.X2C, Z6.T1D.T2B.X1B.X2C,
Z1.T1A.T2C.X1B.X2C, Z2.T1A.T2C.X1B.X2C,
Z3.T1A.T2C.X1B.X2C, Z4.T1A.T2C.X1B.X2C,
Z5.T1A.T2C.X1B.X2C, Z6.T1A.T2C.X1B.X2C,
Z1.T1B.T2C.X1B.X2C, Z2.T1B.T2C.X1B.X2C,
Z3.T1B.T2C.X1B.X2C, Z4.T1B.T2C.X1B.X2C,
Z5.T1B.T2C.X1B.X2C, Z6.T1B.T2C.X1B.X2C,
Z1.T1C.T2C.X1B.X2C, Z2.T1C.T2C.X1B.X2C,
Z3.T1C.T2C.X1B.X2C, Z4.T1C.T2C.X1B.X2C,
Z5.T1C.T2C.X1B.X2C, Z6.T1C.T2C.X1B.X2C,
Z1.T1D.T2C.X1B.X2C, Z2.T1D.T2C.X1B.X2C,
Z3.T1D.T2C.X1B.X2C, Z4.T1D.T2C.X1B.X2C,
Z5.T1D.T2C.X1B.X2C, Z6.T1D.T2C.X1B.X2C,
Z1.T1A.T2D.X1B.X2C, Z2.T1A.T2D.X1B.X2C,
Z3.T1A.T2D.X1B.X2C, Z4.T1A.T2D.X1B.X2C,
Z5.T1A.T2D.X1B.X2C, Z6.T1A.T2D.X1B.X2C,

TABLE 6-continued

List of Compound Structures of Formula II

Z1.T1B.T2D.X1B.X2C, Z2.T1B.T2D.X1B.X2C,
Z3.T1B.T2D.X1B.X2C, Z4.T1B.T2D.X1B.X2C,
Z5.T1B.T2D.X1B.X2C, Z6.T1B.T2D.X1B.X2C,
Z1.T1C.T2D.X1B.X2C, Z2.T1C.T2D.X1B.X2C,
Z3.T1C.T2D.X1B.X2C, Z4.T1C.T2D.X1B.X2C,
Z5.T1C.T2D.X1B.X2C, Z6.T1C.T2D.X1B.X2C,
Z1.T1D.T2D.X1B.X2C, Z2.T1D.T2D.X1B.X2C,
Z3.T1D.T2D.X1B.X2C, Z4.T1D.T2D.X1B.X2C,
Z5.T1D.T2D.X1B.X2C, Z6.T1D.T2D.X1B.X2C,
Z1.T1A.T2A.X1C.X2C, Z2.T1A.T2A.X1C.X2C,
Z3.T1A.T2A.X1C.X2C, Z4.T1A.T2A.X1C.X2C,
Z5.T1A.T2A.X1C.X2C, Z6.T1A.T2A.X1C.X2C,
Z1.T1B.T2A.X1C.X2C, Z2.T1B.T2A.X1C.X2C,
Z3.T1B.T2A.X1C.X2C, Z4.T1B.T2A.X1C.X2C,
Z5.T1B.T2A.X1C.X2C, Z6.T1B.T2A.X1C.X2C,
Z1.T1C.T2A.X1C.X2C, Z2.T1C.T2A.X1C.X2C,
Z3.T1C.T2A.X1C.X2C, Z4.T1C.T2A.X1C.X2C,
Z5.T1C.T2A.X1C.X2C, Z6.T1C.T2A.X1C.X2C,
Z1.T1D.T2A.X1C.X2C, Z2.T1D.T2A.X1C.X2C,
Z3.T1D.T2A.X1C.X2C, Z4.T1D.T2A.X1C.X2C,
Z5.T1D.T2A.X1C.X2C, Z6.T1D.T2A.X1C.X2C,
Z1.T1A.T2B.X1C.X2C, Z2.T1A.T2B.X1C.X2C,
Z3.T1A.T2B.X1C.X2C, Z4.T1A.T2B.X1C.X2C,
Z5.T1A.T2B.X1C.X2C, Z6.T1A.T2B.X1C.X2C,
Z1.T1B.T2B.X1C.X2C, Z2.T1B.T2B.X1C.X2C,
Z3.T1B.T2B.X1C.X2C, Z4.T1B.T2B.X1C.X2C,
Z5.T1B.T2B.X1C.X2C, Z6.T1B.T2B.X1C.X2C,
Z1.T1C.T2B.X1C.X2C, Z2.T1C.T2B.X1C.X2C,
Z3.T1C.T2B.X1C.X2C, Z4.T1C.T2B.X1C.X2C,
Z5.T1C.T2B.X1C.X2C, Z6.T1C.T2B.X1C.X2C,
Z1.T1D.T2B.X1C.X2C, Z2.T1D.T2B.X1C.X2C,
Z3.T1D.T2B.X1C.X2C, Z4.T1D.T2B.X1C.X2C,
Z5.T1D.T2B.X1C.X2C, Z6.T1D.T2B.X1C.X2C,
Z1.T1A.T2C.X1C.X2C, Z2.T1A.T2C.X1C.X2C,
Z3.T1A.T2C.X1C.X2C, Z4.T1A.T2C.X1C.X2C,
Z5.T1A.T2C.X1C.X2C, Z6.T1A.T2C.X1C.X2C,
Z1.T1B.T2C.X1C.X2C, Z2.T1B.T2C.X1C.X2C,
Z3.T1B.T2C.X1C.X2C, Z4.T1B.T2C.X1C.X2C,
Z5.T1B.T2C.X1C.X2C, Z6.T1B.T2C.X1C.X2C,
Z1.T1C.T2C.X1C.X2C, Z2.T1C.T2C.X1C.X2C,
Z3.T1C.T2C.X1C.X2C, Z4.T1C.T2C.X1C.X2C,
Z5.T1C.T2C.X1C.X2C, Z6.T1C.T2C.X1C.X2C,
Z1.T1D.T2C.X1C.X2C, Z2.T1D.T2C.X1C.X2C,
Z3.T1D.T2C.X1C.X2C, Z4.T1D.T2C.X1C.X2C,
Z5.T1D.T2C.X1C.X2C, Z6.T1D.T2C.X1C.X2C,
Z1.T1A.T2D.X1C.X2C, Z2.T1A.T2D.X1C.X2C,
Z3.T1A.T2D.X1C.X2C, Z4.T1A.T2D.X1C.X2C,
Z5.T1A.T2D.X1C.X2C, Z6.T1A.T2D.X1C.X2C,
Z1.T1B.T2D.X1C.X2C, Z2.T1B.T2D.X1C.X2C,
Z3.T1B.T2D.X1C.X2C, Z4.T1B.T2D.X1C.X2C,
Z5.T1B.T2D.X1C.X2C, Z6.T1B.T2D.X1C.X2C,
Z1.T1C.T2D.X1C.X2C, Z2.T1C.T2D.X1C.X2C,
Z3.T1C.T2D.X1C.X2C, Z4.T1C.T2D.X1C.X2C,
Z5.T1C.T2D.X1C.X2C, Z6.T1C.T2D.X1C.X2C,
Z1.T1D.T2D.X1C.X2C, Z2.T1D.T2D.X1C.X2C,
Z3.T1D.T2D.X1C.X2C, Z4.T1D.T2D.X1C.X2C,
Z5.T1D.T2D.X1C.X2C, Z6.T1D.T2D.X1C.X2C,
Z1.T1A.T2A.X1D.X2C, Z2.T1A.T2A.X1D.X2C,
Z3.T1A.T2A.X1D.X2C, Z4.T1A.T2A.X1D.X2C,
Z5.T1A.T2A.X1D.X2C, Z6.T1A.T2A.X1D.X2C,
Z1.T1B.T2A.X1D.X2C, Z2.T1B.T2A.X1D.X2C,
Z3.T1B.T2A.X1D.X2C, Z4.T1B.T2A.X1D.X2C,
Z5.T1B.T2A.X1D.X2C, Z6.T1B.T2A.X1D.X2C,
Z1.T1C.T2A.X1D.X2C, Z2.T1C.T2A.X1D.X2C,
Z3.T1C.T2A.X1D.X2C, Z4.T1C.T2A.X1D.X2C,
Z5.T1C.T2A.X1D.X2C, Z6.T1C.T2A.X1D.X2C,
Z1.T1D.T2A.X1D.X2C, Z2.T1D.T2A.X1D.X2C,
Z3.T1D.T2A.X1D.X2C, Z4.T1D.T2A.X1D.X2C,
Z5.T1D.T2A.X1D.X2C, Z6.T1D.T2A.X1D.X2C,
Z1.T1A.T2B.X1D.X2C, Z2.T1A.T2B.X1D.X2C,
Z3.T1A.T2B.X1D.X2C, Z4.T1A.T2B.X1D.X2C,
Z5.T1A.T2B.X1D.X2C, Z6.T1A.T2B.X1D.X2C,
Z1.T1B.T2B.X1D.X2C, Z2.T1B.T2B.X1D.X2C,
Z3.T1B.T2B.X1D.X2C, Z4.T1B.T2B.X1D.X2C,
Z5.T1B.T2B.X1D.X2C, Z6.T1B.T2B.X1D.X2C,
Z1.T1C.T2B.X1D.X2C, Z2.T1C.T2B.X1D.X2C,
Z3.T1C.T2B.X1D.X2C, Z4.T1C.T2B.X1D.X2C,
Z5.T1C.T2B.X1D.X2C, Z6.T1C.T2B.X1D.X2C,
Z1.T1D.T2B.X1D.X2C, Z2.T1D.T2B.X1D.X2C,
Z3.T1D.T2B.X1D.X2C, Z4.T1D.T2B.X1D.X2C,
Z5.T1D.T2B.X1D.X2C, Z6.T1D.T2B.X1D.X2C,
Z1.T1A.T2C.X1D.X2C, Z2.T1A.T2C.X1D.X2C,
Z3.T1A.T2C.X1D.X2C, Z4.T1A.T2C.X1D.X2C,
Z5.T1A.T2C.X1D.X2C, Z6.T1A.T2C.X1D.X2C,
Z1.T1B.T2C.X1D.X2C, Z2.T1B.T2C.X1D.X2C,
Z3.T1B.T2C.X1D.X2C, Z4.T1B.T2C.X1D.X2C,
Z5.T1B.T2C.X1D.X2C, Z6.T1B.T2C.X1D.X2C,
Z1.T1C.T2C.X1D.X2C, Z2.T1C.T2C.X1D.X2C,
Z3.T1C.T2C.X1D.X2C, Z4.T1C.T2C.X1D.X2C,
Z5.T1C.T2C.X1D.X2C, Z6.T1C.T2C.X1D.X2C,
Z1.T1D.T2C.X1D.X2C, Z2.T1D.T2C.X1D.X2C,
Z3.T1D.T2C.X1D.X2C, Z4.T1D.T2C.X1D.X2C,
Z5.T1D.T2C.X1D.X2C, Z6.T1D.T2C.X1D.X2C,
Z1.T1A.T2D.X1D.X2C, Z2.T1A.T2D.X1D.X2C,
Z3.T1A.T2D.X1D.X2C, Z4.T1A.T2D.X1D.X2C,
Z5.T1A.T2D.X1D.X2C, Z6.T1A.T2D.X1D.X2C,
Z1.T1B.T2D.X1D.X2C, Z2.T1B.T2D.X1D.X2C,
Z3.T1B.T2D.X1D.X2C, Z4.T1B.T2D.X1D.X2C,
Z5.T1B.T2D.X1D.X2C, Z6.T1B.T2D.X1D.X2C,
Z1.T1C.T2D.X1D.X2C, Z2.T1C.T2D.X1D.X2C,
Z3.T1C.T2D.X1D.X2C, Z4.T1C.T2D.X1D.X2C,
Z5.T1C.T2D.X1D.X2C, Z6.T1C.T2D.X1D.X2C,
Z1.T1D.T2D.X1D.X2C, Z2.T1D.T2D.X1D.X2C,
Z3.T1D.T2D.X1D.X2C, Z4.T1D.T2D.X1D.X2C,
Z5.T1D.T2D.X1D.X2C, Z6.T1D.T2D.X1D.X2C,
Z1.T1A.T2A.X1E.X2C, Z2.T1A.T2A.X1E.X2C,
Z3.T1A.T2A.X1E.X2C, Z4.T1A.T2A.X1E.X2C,
Z5.T1A.T2A.X1E.X2C, Z6.T1A.T2A.X1E.X2C,
Z1.T1B.T2A.X1E.X2C, Z2.T1B.T2A.X1E.X2C,
Z3.T1B.T2A.X1E.X2C, Z4.T1B.T2A.X1E.X2C,
Z5.T1B.T2A.X1E.X2C, Z6.T1B.T2A.X1E.X2C,
Z1.T1C.T2A.X1E.X2C, Z2.T1C.T2A.X1E.X2C,
Z3.T1C.T2A.X1E.X2C, Z4.T1C.T2A.X1E.X2C,
Z5.T1C.T2A.X1E.X2C, Z6.T1C.T2A.X1E.X2C,
Z1.T1D.T2A.X1E.X2C, Z2.T1D.T2A.X1E.X2C,
Z3.T1D.T2A.X1E.X2C, Z4.T1D.T2A.X1E.X2C,
Z5.T1D.T2A.X1E.X2C, Z6.T1D.T2A.X1E.X2C,
Z1.T1A.T2B.X1E.X2C, Z2.T1A.T2B.X1E.X2C,
Z3.T1A.T2B.X1E.X2C, Z4.T1A.T2B.X1E.X2C,
Z5.T1A.T2B.X1E.X2C, Z6.T1A.T2B.X1E.X2C,
Z1.T1B.T2B.X1E.X2C, Z2.T1B.T2B.X1E.X2C,
Z3.T1B.T2B.X1E.X2C, Z4.T1B.T2B.X1E.X2C,
Z5.T1B.T2B.X1E.X2C, Z6.T1B.T2B.X1E.X2C,
Z1.T1C.T2B.X1E.X2C, Z2.T1C.T2B.X1E.X2C,
Z3.T1C.T2B.X1E.X2C, Z4.T1C.T2B.X1E.X2C,
Z5.T1C.T2B.X1E.X2C, Z6.T1C.T2B.X1E.X2C,
Z1.T1D.T2B.X1E.X2C, Z2.T1D.T2B.X1E.X2C,
Z3.T1D.T2B.X1E.X2C, Z4.T1D.T2B.X1E.X2C,
Z5.T1D.T2B.X1E.X2C, Z6.T1D.T2B.X1E.X2C,
Z1.T1A.T2C.X1E.X2C, Z2.T1A.T2C.X1E.X2C,
Z3.T1A.T2C.X1E.X2C, Z4.T1A.T2C.X1E.X2C,
Z5.T1A.T2C.X1E.X2C, Z6.T1A.T2C.X1E.X2C,
Z1.T1B.T2C.X1E.X2C, Z2.T1B.T2C.X1E.X2C,
Z3.T1B.T2C.X1E.X2C, Z4.T1B.T2C.X1E.X2C,
Z5.T1B.T2C.X1E.X2C, Z6.T1B.T2C.X1E.X2C,
Z1.T1C.T2C.X1E.X2C, Z2.T1C.T2C.X1E.X2C,
Z3.T1C.T2C.X1E.X2C, Z4.T1C.T2C.X1E.X2C,
Z5.T1C.T2C.X1E.X2C, Z6.T1C.T2C.X1E.X2C,
Z1.T1D.T2C.X1E.X2C, Z2.T1D.T2C.X1E.X2C,
Z3.T1D.T2C.X1E.X2C, Z4.T1D.T2C.X1E.X2C,
Z5.T1D.T2C.X1E.X2C, Z6.T1D.T2C.X1E.X2C,
Z1.T1A.T2D.X1E.X2C, Z2.T1A.T2D.X1E.X2C,
Z3.T1A.T2D.X1E.X2C, Z4.T1A.T2D.X1E.X2C,
Z5.T1A.T2D.X1E.X2C, Z6.T1A.T2D.X1E.X2C,
Z1.T1B.T2D.X1E.X2C, Z2.T1B.T2D.X1E.X2C,
Z3.T1B.T2D.X1E.X2C, Z4.T1B.T2D.X1E.X2C,
Z5.T1B.T2D.X1E.X2C, Z6.T1B.T2D.X1E.X2C,
Z1.T1C.T2D.X1E.X2C, Z2.T1C.T2D.X1E.X2C,
Z3.T1C.T2D.X1E.X2C, Z4.T1C.T2D.X1E.X2C,
Z5.T1C.T2D.X1E.X2C, Z6.T1C.T2D.X1E.X2C,
Z1.T1D.T2D.X1E.X2C, Z2.T1D.T2D.X1E.X2C,
Z3.T1D.T2D.X1E.X2C, Z4.T1D.T2D.X1E.X2C,
Z5.T1D.T2D.X1E.X2C, Z6.T1D.T2D.X1E.X2C,
Z1.T1A.T2A.X1A.X2D, Z2.T1A.T2A.X1A.X2D,
Z3.T1A.T2A.X1A.X2D, Z4.T1A.T2A.X1A.X2D,
Z5.T1A.T2A.X1A.X2D, Z6.T1A.T2A.X1A.X2D,

TABLE 6-continued

List of Compound Structures of Formula II

Z1.T1B.T2A.X1A.X2D, Z2.T1B.T2A.X1A.X2D,
Z3.T1B.T2A.X1A.X2D, Z4.T1B.T2A.X1A.X2D,
Z5.T1B.T2A.X1A.X2D, Z6.T1B.T2A.X1A.X2D,
Z1.T1C.T2A.X1A.X2D, Z2.T1C.T2A.X1A.X2D,
Z3.T1C.T2A.X1A.X2D, Z4.T1C.T2A.X1A.X2D,
Z5.T1C.T2A.X1A.X2D, Z6.T1C.T2A.X1A.X2D,
Z1.T1D.T2A.X1A.X2D, Z2.T1D.T2A.X1A.X2D,
Z3.T1D.T2A.X1A.X2D, Z4.T1D.T2A.X1A.X2D,
Z5.T1D.T2A.X1A.X2D, Z6.T1D.T2A.X1A.X2D,
Z1.T1A.T2B.X1A.X2D, Z2.T1A.T2B.X1A.X2D,
Z3.T1A.T2B.X1A.X2D, Z4.T1A.T2B.X1A.X2D,
Z5.T1A.T2B.X1A.X2D, Z6.T1A.T2B.X1A.X2D,
Z1.T1B.T2B.X1A.X2D, Z2.T1B.T2B.X1A.X2D,
Z3.T1B.T2B.X1A.X2D, Z4.T1B.T2B.X1A.X2D,
Z5.T1B.T2B.X1A.X2D, Z6.T1B.T2B.X1A.X2D,
Z1.T1C.T2B.X1A.X2D, Z2.T1C.T2B.X1A.X2D,
Z3.T1C.T2B.X1A.X2D, Z4.T1C.T2B.X1A.X2D,
Z5.T1C.T2B.X1A.X2D, Z6.T1C.T2B.X1A.X2D,
Z1.T1D.T2B.X1A.X2D, Z2.T1D.T2B.X1A.X2D,
Z3.T1D.T2B.X1A.X2D, Z4.T1D.T2B.X1A.X2D,
Z5.T1D.T2B.X1A.X2D, Z6.T1D.T2B.X1A.X2D,
Z1.T1A.T2C.X1A.X2D, Z2.T1A.T2C.X1A.X2D,
Z3.T1A.T2C.X1A.X2D, Z4.T1A.T2C.X1A.X2D,
Z5.T1A.T2C.X1A.X2D, Z6.T1A.T2C.X1A.X2D,
Z1.T1B.T2C.X1A.X2D, Z2.T1B.T2C.X1A.X2D,
Z3.T1B.T2C.X1A.X2D, Z4.T1B.T2C.X1A.X2D,
Z5.T1B.T2C.X1A.X2D, Z6.T1B.T2C.X1A.X2D,
Z1.T1C.T2C.X1A.X2D, Z2.T1C.T2C.X1A.X2D,
Z3.T1C.T2C.X1A.X2D, Z4.T1C.T2C.X1A.X2D,
Z5.T1C.T2C.X1A.X2D, Z6.T1C.T2C.X1A.X2D,
Z1.T1D.T2C.X1A.X2D, Z2.T1D.T2C.X1A.X2D,
Z3.T1D.T2C.X1A.X2D, Z4.T1D.T2C.X1A.X2D,
Z5.T1D.T2C.X1A.X2D, Z6.T1D.T2C.X1A.X2D,
Z1.T1A.T2D.X1A.X2D, Z2.T1A.T2D.X1A.X2D,
Z3.T1A.T2D.X1A.X2D, Z4.T1A.T2D.X1A.X2D,
Z5.T1A.T2D.X1A.X2D, Z6.T1A.T2D.X1A.X2D,
Z1.T1B.T2D.X1A.X2D, Z2.T1B.T2D.X1A.X2D,
Z3.T1B.T2D.X1A.X2D, Z4.T1B.T2D.X1A.X2D,
Z5.T1B.T2D.X1A.X2D, Z6.T1B.T2D.X1A.X2D,
Z1.T1C.T2D.X1A.X2D, Z2.T1C.T2D.X1A.X2D,
Z3.T1C.T2D.X1A.X2D, Z4.T1C.T2D.X1A.X2D,
Z5.T1C.T2D.X1A.X2D, Z6.T1C.T2D.X1A.X2D,
Z1.T1D.T2D.X1A.X2D, Z2.T1D.T2D.X1A.X2D,
Z3.T1D.T2D.X1A.X2D, Z4.T1D.T2D.X1A.X2D,
Z5.T1D.T2D.X1A.X2D, Z6.T1D.T2D.X1A.X2D,
Z1.T1A.T2A.X1B.X2D, Z2.T1A.T2A.X1B.X2D,
Z3.T1A.T2A.X1B.X2D, Z4.T1A.T2A.X1B.X2D,
Z5.T1A.T2A.X1B.X2D, Z6.T1A.T2A.X1B.X2D,
Z1.T1B.T2A.X1B.X2D, Z2.T1B.T2A.X1B.X2D,
Z3.T1B.T2A.X1B.X2D, Z4.T1B.T2A.X1B.X2D,
Z5.T1B.T2A.X1B.X2D, Z6.T1B.T2A.X1B.X2D,
Z1.T1C.T2A.X1B.X2D, Z2.T1C.T2A.X1B.X2D,
Z3.T1C.T2A.X1B.X2D, Z4.T1C.T2A.X1B.X2D,
Z5.T1C.T2A.X1B.X2D, Z6.T1C.T2A.X1B.X2D,
Z1.T1D.T2A.X1B.X2D, Z2.T1D.T2A.X1B.X2D,
Z3.T1D.T2A.X1B.X2D, Z4.T1D.T2A.X1B.X2D,
Z5.T1D.T2A.X1B.X2D, Z6.T1D.T2A.X1B.X2D,
Z1.T1A.T2B.X1B.X2D, Z2.T1A.T2B.X1B.X2D,
Z3.T1A.T2B.X1B.X2D, Z4.T1A.T2B.X1B.X2D,
Z5.T1A.T2B.X1B.X2D, Z6.T1A.T2B.X1B.X2D,
Z1.T1B.T2B.X1B.X2D, Z2.T1B.T2B.X1B.X2D,
Z3.T1B.T2B.X1B.X2D, Z4.T1B.T2B.X1B.X2D,
Z5.T1B.T2B.X1B.X2D, Z6.T1B.T2B.X1B.X2D,
Z1.T1C.T2B.X1B.X2D, Z2.T1C.T2B.X1B.X2D,
Z3.T1C.T2B.X1B.X2D, Z4.T1C.T2B.X1B.X2D,
Z5.T1C.T2B.X1B.X2D, Z6.T1C.T2B.X1B.X2D,
Z1.T1D.T2B.X1B.X2D, Z2.T1D.T2B.X1B.X2D,
Z3.T1D.T2B.X1B.X2D, Z4.T1D.T2B.X1B.X2D,
Z5.T1D.T2B.X1B.X2D, Z6.T1D.T2B.X1B.X2D,
Z1.T1A.T2C.X1B.X2D, Z2.T1A.T2C.X1B.X2D,
Z3.T1A.T2C.X1B.X2D, Z4.T1A.T2C.X1B.X2D,
Z5.T1A.T2C.X1B.X2D, Z6.T1A.T2C.X1B.X2D,
Z1.T1B.T2C.X1B.X2D, Z2.T1B.T2C.X1B.X2D,
Z3.T1B.T2C.X1B.X2D, Z4.T1B.T2C.X1B.X2D,
Z5.T1B.T2C.X1B.X2D, Z6.T1B.T2C.X1B.X2D,
Z1.T1C.T2C.X1B.X2D, Z2.T1C.T2C.X1B.X2D,
Z3.T1C.T2C.X1B.X2D, Z4.T1C.T2C.X1B.X2D,
Z5.T1C.T2C.X1B.X2D, Z6.T1C.T2C.X1B.X2D,
Z1.T1D.T2C.X1B.X2D, Z2.T1D.T2C.X1B.X2D,
Z3.T1D.T2C.X1B.X2D, Z4.T1D.T2C.X1B.X2D,
Z5.T1D.T2C.X1B.X2D, Z6.T1D.T2C.X1B.X2D,
Z1.T1A.T2D.X1B.X2D, Z2.T1A.T2D.X1B.X2D,
Z3.T1A.T2D.X1B.X2D, Z4.T1A.T2D.X1B.X2D,
Z5.T1A.T2D.X1B.X2D, Z6.T1A.T2D.X1B.X2D,
Z1.T1B.T2D.X1B.X2D, Z2.T1B.T2D.X1B.X2D,
Z3.T1B.T2D.X1B.X2D, Z4.T1B.T2D.X1B.X2D,
Z5.T1B.T2D.X1B.X2D, Z6.T1B.T2D.X1B.X2D,
Z1.T1C.T2D.X1B.X2D, Z2.T1C.T2D.X1B.X2D,
Z3.T1C.T2D.X1B.X2D, Z4.T1C.T2D.X1B.X2D,
Z5.T1C.T2D.X1B.X2D, Z6.T1C.T2D.X1B.X2D,
Z1.T1D.T2D.X1B.X2D, Z2.T1D.T2D.X1B.X2D,
Z3.T1D.T2D.X1B.X2D, Z4.T1D.T2D.X1B.X2D,
Z5.T1D.T2D.X1B.X2D, Z6.T1D.T2D.X1B.X2D,
Z1.T1A.T2A.X1C.X2D, Z2.T1A.T2A.X1C.X2D,
Z3.T1A.T2A.X1C.X2D, Z4.T1A.T2A.X1C.X2D,
Z5.T1A.T2A.X1C.X2D, Z6.T1A.T2A.X1C.X2D,
Z1.T1B.T2A.X1C.X2D, Z2.T1B.T2A.X1C.X2D,
Z3.T1B.T2A.X1C.X2D, Z4.T1B.T2A.X1C.X2D,
Z5.T1B.T2A.X1C.X2D, Z6.T1B.T2A.X1C.X2D,
Z1.T1C.T2A.X1C.X2D, Z2.T1C.T2A.X1C.X2D,
Z3.T1C.T2A.X1C.X2D, Z4.T1C.T2A.X1C.X2D,
Z5.T1C.T2A.X1C.X2D, Z6.T1C.T2A.X1C.X2D,
Z1.T1D.T2A.X1C.X2D, Z2.T1D.T2A.X1C.X2D,
Z3.T1D.T2A.X1C.X2D, Z4.T1D.T2A.X1C.X2D,
Z5.T1D.T2A.X1C.X2D, Z6.T1D.T2A.X1C.X2D,
Z1.T1A.T2B.X1C.X2D, Z2.T1A.T2B.X1C.X2D,
Z3.T1A.T2B.X1C.X2D, Z4.T1A.T2B.X1C.X2D,
Z5.T1A.T2B.X1C.X2D, Z6.T1A.T2B.X1C.X2D,
Z1.T1B.T2B.X1C.X2D, Z2.T1B.T2B.X1C.X2D,
Z3.T1B.T2B.X1C.X2D, Z4.T1B.T2B.X1C.X2D,
Z5.T1B.T2B.X1C.X2D, Z6.T1B.T2B.X1C.X2D,
Z1.T1C.T2B.X1C.X2D, Z2.T1C.T2B.X1C.X2D,
Z3.T1C.T2B.X1C.X2D, Z4.T1C.T2B.X1C.X2D,
Z5.T1C.T2B.X1C.X2D, Z6.T1C.T2B.X1C.X2D,
Z1.T1D.T2B.X1C.X2D, Z2.T1D.T2B.X1C.X2D,
Z3.T1D.T2B.X1C.X2D, Z4.T1D.T2B.X1C.X2D,
Z5.T1D.T2B.X1C.X2D, Z6.T1D.T2B.X1C.X2D,
Z1.T1A.T2C.X1C.X2D, Z2.T1A.T2C.X1C.X2D,
Z3.T1A.T2C.X1C.X2D, Z4.T1A.T2C.X1C.X2D,
Z5.T1A.T2C.X1C.X2D, Z6.T1A.T2C.X1C.X2D,
Z1.T1B.T2C.X1C.X2D, Z2.T1B.T2C.X1C.X2D,
Z3.T1B.T2C.X1C.X2D, Z4.T1B.T2C.X1C.X2D,
Z5.T1B.T2C.X1C.X2D, Z6.T1B.T2C.X1C.X2D,
Z1.T1C.T2C.X1C.X2D, Z2.T1C.T2C.X1C.X2D,
Z3.T1C.T2C.X1C.X2D, Z4.T1C.T2C.X1C.X2D,
Z5.T1C.T2C.X1C.X2D, Z6.T1C.T2C.X1C.X2D,
Z1.T1D.T2C.X1C.X2D, Z2.T1D.T2C.X1C.X2D,
Z3.T1D.T2C.X1C.X2D, Z4.T1D.T2C.X1C.X2D,
Z5.T1D.T2C.X1C.X2D, Z6.T1D.T2C.X1C.X2D,
Z1.T1A.T2D.X1C.X2D, Z2.T1A.T2D.X1C.X2D,
Z3.T1A.T2D.X1C.X2D, Z4.T1A.T2D.X1C.X2D,
Z5.T1A.T2D.X1C.X2D, Z6.T1A.T2D.X1C.X2D,
Z1.T1B.T2D.X1C.X2D, Z2.T1B.T2D.X1C.X2D,
Z3.T1B.T2D.X1C.X2D, Z4.T1B.T2D.X1C.X2D,
Z5.T1B.T2D.X1C.X2D, Z6.T1B.T2D.X1C.X2D,
Z1.T1C.T2D.X1C.X2D, Z2.T1C.T2D.X1C.X2D,
Z3.T1C.T2D.X1C.X2D, Z4.T1C.T2D.X1C.X2D,
Z5.T1C.T2D.X1C.X2D, Z6.T1C.T2D.X1C.X2D,
Z1.T1D.T2D.X1C.X2D, Z2.T1D.T2D.X1C.X2D,
Z3.T1D.T2D.X1C.X2D, Z4.T1D.T2D.X1C.X2D,
Z5.T1D.T2D.X1C.X2D, Z6.T1D.T2D.X1C.X2D,
Z1.T1A.T2A.X1D.X2D, Z2.T1A.T2A.X1D.X2D,
Z3.T1A.T2A.X1D.X2D, Z4.T1A.T2A.X1D.X2D,
Z5.T1A.T2A.X1D.X2D, Z6.T1A.T2A.X1D.X2D,
Z1.T1B.T2A.X1D.X2D, Z2.T1B.T2A.X1D.X2D,
Z3.T1B.T2A.X1D.X2D, Z4.T1B.T2A.X1D.X2D,
Z5.T1B.T2A.X1D.X2D, Z6.T1B.T2A.X1D.X2D,
Z1.T1C.T2A.X1D.X2D, Z2.T1C.T2A.X1D.X2D,
Z3.T1C.T2A.X1D.X2D, Z4.T1C.T2A.X1D.X2D,
Z5.T1C.T2A.X1D.X2D, Z6.T1C.T2A.X1D.X2D,
Z1.T1D.T2A.X1D.X2D, Z2.T1D.T2A.X1D.X2D,
Z3.T1D.T2A.X1D.X2D, Z4.T1D.T2A.X1D.X2D,
Z5.T1D.T2A.X1D.X2D, Z6.T1D.T2A.X1D.X2D,
Z1.T1A.T2B.X1D.X2D, Z2.T1A.T2B.X1D.X2D,
Z3.T1A.T2B.X1D.X2D, Z4.T1A.T2B.X1D.X2D,
Z5.T1A.T2B.X1D.X2D, Z6.T1A.T2B.X1D.X2D,

TABLE 6-continued

List of Compound Structures of Formula II

Z1.T1B.T2B.X1D.X2D, Z2.T1B.T2B.X1D.X2D,
Z3.T1B.T2B.X1D.X2D, Z4.T1B.T2B.X1D.X2D,
Z5.T1B.T2B.X1D.X2D, Z6.T1B.T2B.X1D.X2D,
Z1.T1C.T2B.X1D.X2D, Z2.T1C.T2B.X1D.X2D,
Z3.T1C.T2B.X1D.X2D, Z4.T1C.T2B.X1D.X2D,
Z5.T1C.T2B.X1D.X2D, Z6.T1C.T2B.X1D.X2D,
Z1.T1D.T2B.X1D.X2D, Z2.T1D.T2B.X1D.X2D,
Z3.T1D.T2B.X1D.X2D, Z4.T1D.T2B.X1D.X2D,
Z5.T1D.T2B.X1D.X2D, Z6.T1D.T2B.X1D.X2D,
Z1.T1A.T2C.X1D.X2D, Z2.T1A.T2C.X1D.X2D,
Z3.T1A.T2C.X1D.X2D, Z4.T1A.T2C.X1D.X2D,
Z5.T1A.T2C.X1D.X2D, Z6.T1A.T2C.X1D.X2D,
Z1.T1B.T2C.X1D.X2D, Z2.T1B.T2C.X1D.X2D,
Z3.T1B.T2C.X1D.X2D, Z4.T1B.T2C.X1D.X2D,
Z5.T1B.T2C.X1D.X2D, Z6.T1B.T2C.X1D.X2D,
Z1.T1C.T2C.X1D.X2D, Z2.T1C.T2C.X1D.X2D,
Z3.T1C.T2C.X1D.X2D, Z4.T1C.T2C.X1D.X2D,
Z5.T1C.T2C.X1D.X2D, Z6.T1C.T2C.X1D.X2D,
Z1.T1D.T2C.X1D.X2D, Z2.T1D.T2C.X1D.X2D,
Z3.T1D.T2C.X1D.X2D, Z4.T1D.T2C.X1D.X2D,
Z5.T1D.T2C.X1D.X2D, Z6.T1D.T2C.X1D.X2D,
Z1.T1A.T2D.X1D.X2D, Z2.T1A.T2D.X1D.X2D,
Z3.T1A.T2D.X1D.X2D, Z4.T1A.T2D.X1D.X2D,
Z5.T1A.T2D.X1D.X2D, Z6.T1A.T2D.X1D.X2D,
Z1.T1B.T2D.X1D.X2D, Z2.T1B.T2D.X1D.X2D,
Z3.T1B.T2D.X1D.X2D, Z4.T1B.T2D.X1D.X2D,
Z5.T1B.T2D.X1D.X2D, Z6.T1B.T2D.X1D.X2D,
Z1.T1C.T2D.X1D.X2D, Z2.T1C.T2D.X1D.X2D,
Z3.T1C.T2D.X1D.X2D, Z4.T1C.T2D.X1D.X2D,
Z5.T1C.T2D.X1D.X2D, Z6.T1C.T2D.X1D.X2D,
Z1.T1D.T2D.X1D.X2D, Z2.T1D.T2D.X1D.X2D,
Z3.T1D.T2D.X1D.X2D, Z4.T1D.T2D.X1D.X2D,
Z5.T1D.T2D.X1D.X2D, Z6.T1D.T2D.X1D.X2D,
Z1.T1A.T2A.X1E.X2D, Z2.T1A.T2A.X1E.X2D,
Z3.T1A.T2A.X1E.X2D, Z4.T1A.T2A.X1E.X2D,
Z5.T1A.T2A.X1E.X2D, Z6.T1A.T2A.X1E.X2D,
Z1.T1B.T2A.X1E.X2D, Z2.T1B.T2A.X1E.X2D,
Z3.T1B.T2A.X1E.X2D, Z4.T1B.T2A.X1E.X2D,
Z5.T1B.T2A.X1E.X2D, Z6.T1B.T2A.X1E.X2D,
Z1.T1C.T2A.X1E.X2D, Z2.T1C.T2A.X1E.X2D,
Z3.T1C.T2A.X1E.X2D, Z4.T1C.T2A.X1E.X2D,
Z5.T1C.T2A.X1E.X2D, Z6.T1C.T2A.X1E.X2D,
Z1.T1D.T2A.X1E.X2D, Z2.T1D.T2A.X1E.X2D,
Z3.T1D.T2A.X1E.X2D, Z4.T1D.T2A.X1E.X2D,
Z5.T1D.T2A.X1E.X2D, Z6.T1D.T2A.X1E.X2D,
Z1.T1A.T2B.X1E.X2D, Z2.T1A.T2B.X1E.X2D,
Z3.T1A.T2B.X1E.X2D, Z4.T1A.T2B.X1E.X2D,
Z5.T1A.T2B.X1E.X2D, Z6.T1A.T2B.X1E.X2D,
Z1.T1B.T2B.X1E.X2D, Z2.T1B.T2B.X1E.X2D,
Z3.T1B.T2B.X1E.X2D, Z4.T1B.T2B.X1E.X2D,
Z5.T1B.T2B.X1E.X2D, Z6.T1B.T2B.X1E.X2D,
Z1.T1C.T2B.X1E.X2D, Z2.T1C.T2B.X1E.X2D,
Z3.T1C.T2B.X1E.X2D, Z4.T1C.T2B.X1E.X2D,
Z5.T1C.T2B.X1E.X2D, Z6.T1C.T2B.X1E.X2D,
Z1.T1D.T2B.X1E.X2D, Z2.T1D.T2B.X1E.X2D,
Z3.T1D.T2B.X1E.X2D, Z4.T1D.T2B.X1E.X2D,
Z5.T1D.T2B.X1E.X2D, Z6.T1D.T2B.X1E.X2D,
Z1.T1A.T2C.X1E.X2D, Z2.T1A.T2C.X1E.X2D,
Z3.T1A.T2C.X1E.X2D, Z4.T1A.T2C.X1E.X2D,
Z5.T1A.T2C.X1E.X2D, Z6.T1A.T2C.X1E.X2D,
Z1.T1B.T2C.X1E.X2D, Z2.T1B.T2C.X1E.X2D,
Z3.T1B.T2C.X1E.X2D, Z4.T1B.T2C.X1E.X2D,
Z5.T1B.T2C.X1E.X2D, Z6.T1B.T2C.X1E.X2D,
Z1.T1C.T2C.X1E.X2D, Z2.T1C.T2C.X1E.X2D,
Z3.T1C.T2C.X1E.X2D, Z4.T1C.T2C.X1E.X2D,
Z5.T1C.T2C.X1E.X2D, Z6.T1C.T2C.X1E.X2D,
Z1.T1D.T2C.X1E.X2D, Z2.T1D.T2C.X1E.X2D,
Z3.T1D.T2C.X1E.X2D, Z4.T1D.T2C.X1E.X2D,
Z5.T1D.T2C.X1E.X2D, Z6.T1D.T2C.X1E.X2D,
Z1.T1A.T2D.X1E.X2D, Z2.T1A.T2D.X1E.X2D,
Z3.T1A.T2D.X1E.X2D, Z4.T1A.T2D.X1E.X2D,
Z5.T1A.T2D.X1E.X2D, Z6.T1A.T2D.X1E.X2D,
Z1.T1B.T2D.X1E.X2D, Z2.T1B.T2D.X1E.X2D,
Z3.T1B.T2D.X1E.X2D, Z4.T1B.T2D.X1E.X2D,
Z5.T1B.T2D.X1E.X2D, Z6.T1B.T2D.X1E.X2D,
Z1.T1C.T2D.X1E.X2D, Z2.T1C.T2D.X1E.X2D,
Z3.T1C.T2D.X1E.X2D, Z4.T1C.T2D.X1E.X2D,
Z5.T1C.T2D.X1E.X2D, Z6.T1C.T2D.X1E.X2D,
Z1.T1D.T2D.X1E.X2D, Z2.T1D.T2D.X1E.X2D,
Z3.T1D.T2D.X1E.X2D, Z4.T1D.T2D.X1E.X2D,
Z5.T1D.T2D.X1E.X2D, Z6.T1D.T2D.X1E.X2D,
Z1.T1A.T2A.X1A.X2E, Z2.T1A.T2A.X1A.X2E,
Z3.T1A.T2A.X1A.X2E, Z4.T1A.T2A.X1A.X2E,
Z5.T1A.T2A.X1A.X2E, Z6.T1A.T2A.X1A.X2E,
Z1.T1B.T2A.X1A.X2E, Z2.T1B.T2A.X1A.X2E,
Z3.T1B.T2A.X1A.X2E, Z4.T1B.T2A.X1A.X2E,
Z5.T1B.T2A.X1A.X2E, Z6.T1B.T2A.X1A.X2E,
Z1.T1C.T2A.X1A.X2E, Z2.T1C.T2A.X1A.X2E,
Z3.T1C.T2A.X1A.X2E, Z4.T1C.T2A.X1A.X2E,
Z5.T1C.T2A.X1A.X2E, Z6.T1C.T2A.X1A.X2E,
Z1.T1D.T2A.X1A.X2E, Z2.T1D.T2A.X1A.X2E,
Z3.T1D.T2A.X1A.X2E, Z4.T1D.T2A.X1A.X2E,
Z5.T1D.T2A.X1A.X2E, Z6.T1D.T2A.X1A.X2E,
Z1.T1A.T2B.X1A.X2E, Z2.T1A.T2B.X1A.X2E,
Z3.T1A.T2B.X1A.X2E, Z4.T1A.T2B.X1A.X2E,
Z5.T1A.T2B.X1A.X2E, Z6.T1A.T2B.X1A.X2E,
Z1.T1B.T2B.X1A.X2E, Z2.T1B.T2B.X1A.X2E,
Z3.T1B.T2B.X1A.X2E, Z4.T1B.T2B.X1A.X2E,
Z5.T1B.T2B.X1A.X2E, Z6.T1B.T2B.X1A.X2E,
Z1.T1C.T2B.X1A.X2E, Z2.T1C.T2B.X1A.X2E,
Z3.T1C.T2B.X1A.X2E, Z4.T1C.T2B.X1A.X2E,
Z5.T1C.T2B.X1A.X2E, Z6.T1C.T2B.X1A.X2E,
Z1.T1D.T2B.X1A.X2E, Z2.T1D.T2B.X1A.X2E,
Z3.T1D.T2B.X1A.X2E, Z4.T1D.T2B.X1A.X2E,
Z5.T1D.T2B.X1A.X2E, Z6.T1D.T2B.X1A.X2E,
Z1.T1A.T2C.X1A.X2E, Z2.T1A.T2C.X1A.X2E,
Z3.T1A.T2C.X1A.X2E, Z4.T1A.T2C.X1A.X2E,
Z5.T1A.T2C.X1A.X2E, Z6.T1A.T2C.X1A.X2E,
Z1.T1B.T2C.X1A.X2E, Z2.T1B.T2C.X1A.X2E,
Z3.T1B.T2C.X1A.X2E, Z4.T1B.T2C.X1A.X2E,
Z5.T1B.T2C.X1A.X2E, Z6.T1B.T2C.X1A.X2E,
Z1.T1C.T2C.X1A.X2E, Z2.T1C.T2C.X1A.X2E,
Z3.T1C.T2C.X1A.X2E, Z4.T1C.T2C.X1A.X2E,
Z5.T1C.T2C.X1A.X2E, Z6.T1C.T2C.X1A.X2E,
Z1.T1D.T2C.X1A.X2E, Z2.T1D.T2C.X1A.X2E,
Z3.T1D.T2C.X1A.X2E, Z4.T1D.T2C.X1A.X2E,
Z5.T1D.T2C.X1A.X2E, Z6.T1D.T2C.X1A.X2E,
Z1.T1A.T2D.X1A.X2E, Z2.T1A.T2D.X1A.X2E,
Z3.T1A.T2D.X1A.X2E, Z4.T1A.T2D.X1A.X2E,
Z5.T1A.T2D.X1A.X2E, Z6.T1A.T2D.X1A.X2E,
Z1.T1B.T2D.X1A.X2E, Z2.T1B.T2D.X1A.X2E,
Z3.T1B.T2D.X1A.X2E, Z4.T1B.T2D.X1A.X2E,
Z5.T1B.T2D.X1A.X2E, Z6.T1B.T2D.X1A.X2E,
Z1.T1C.T2D.X1A.X2E, Z2.T1C.T2D.X1A.X2E,
Z3.T1C.T2D.X1A.X2E, Z4.T1C.T2D.X1A.X2E,
Z5.T1C.T2D.X1A.X2E, Z6.T1C.T2D.X1A.X2E,
Z1.T1D.T2D.X1A.X2E, Z2.T1D.T2D.X1A.X2E,
Z3.T1D.T2D.X1A.X2E, Z4.T1D.T2D.X1A.X2E,
Z5.T1D.T2D.X1A.X2E, Z6.T1D.T2D.X1A.X2E,
Z1.T1A.T2A.X1B.X2E, Z2.T1A.T2A.X1B.X2E,
Z3.T1A.T2A.X1B.X2E, Z4.T1A.T2A.X1B.X2E,
Z5.T1A.T2A.X1B.X2E, Z6.T1A.T2A.X1B.X2E,
Z1.T1B.T2A.X1B.X2E, Z2.T1B.T2A.X1B.X2E,
Z3.T1B.T2A.X1B.X2E, Z4.T1B.T2A.X1B.X2E,
Z5.T1B.T2A.X1B.X2E, Z6.T1B.T2A.X1B.X2E,
Z1.T1C.T2A.X1B.X2E, Z2.T1C.T2A.X1B.X2E,
Z3.T1C.T2A.X1B.X2E, Z4.T1C.T2A.X1B.X2E,
Z5.T1C.T2A.X1B.X2E, Z6.T1C.T2A.X1B.X2E,
Z1.T1D.T2A.X1B.X2E, Z2.T1D.T2A.X1B.X2E,
Z3.T1D.T2A.X1B.X2E, Z4.T1D.T2A.X1B.X2E,
Z5.T1D.T2A.X1B.X2E, Z6.T1D.T2A.X1B.X2E,
Z1.T1A.T2B.X1B.X2E, Z2.T1A.T2B.X1B.X2E,
Z3.T1A.T2B.X1B.X2E, Z4.T1A.T2B.X1B.X2E,
Z5.T1A.T2B.X1B.X2E, Z6.T1A.T2B.X1B.X2E,
Z1.T1B.T2B.X1B.X2E, Z2.T1B.T2B.X1B.X2E,
Z3.T1B.T2B.X1B.X2E, Z4.T1B.T2B.X1B.X2E,
Z5.T1B.T2B.X1B.X2E, Z6.T1B.T2B.X1B.X2E,
Z1.T1C.T2B.X1B.X2E, Z2.T1C.T2B.X1B.X2E,
Z3.T1C.T2B.X1B.X2E, Z4.T1C.T2B.X1B.X2E,
Z5.T1C.T2B.X1B.X2E, Z6.T1C.T2B.X1B.X2E,
Z1.T1D.T2B.X1B.X2E, Z2.T1D.T2B.X1B.X2E,
Z3.T1D.T2B.X1B.X2E, Z4.T1D.T2B.X1B.X2E,
Z5.T1D.T2B.X1B.X2E, Z6.T1D.T2B.X1B.X2E,
Z1.T1A.T2C.X1B.X2E, Z2.T1A.T2C.X1B.X2E,
Z3.T1A.T2C.X1B.X2E, Z4.T1A.T2C.X1B.X2E,
Z5.T1A.T2C.X1B.X2E, Z6.T1A.T2C.X1B.X2E,

TABLE 6-continued

List of Compound Structures of Formula II

Z1.T1B.T2C.X1B.X2E, Z2.T1B.T2C.X1B.X2E,
Z3.T1B.T2C.X1B.X2E, Z4.T1B.T2C.X1B.X2E,
Z5.T1B.T2C.X1B.X2E, Z6.T1B.T2C.X1B.X2E,
Z1.T1C.T2C.X1B.X2E, Z2.T1C.T2C.X1B.X2E,
Z3.T1C.T2C.X1B.X2E, Z4.T1C.T2C.X1B.X2E,
Z5.T1C.T2C.X1B.X2E, Z6.T1C.T2C.X1B.X2E,
Z1.T1D.T2C.X1B.X2E, Z2.T1D.T2C.X1B.X2E,
Z3.T1D.T2C.X1B.X2E, Z4.T1D.T2C.X1B.X2E,
Z5.T1D.T2C.X1B.X2E, Z6.T1D.T2C.X1B.X2E,
Z1.T1A.T2D.X1B.X2E, Z2.T1A.T2D.X1B.X2E,
Z3.T1A.T2D.X1B.X2E, Z4.T1A.T2D.X1B.X2E,
Z5.T1A.T2D.X1B.X2E, Z6.T1A.T2D.X1B.X2E,
Z1.T1B.T2D.X1B.X2E, Z2.T1B.T2D.X1B.X2E,
Z3.T1B.T2D.X1B.X2E, Z4.T1B.T2D.X1B.X2E,
Z5.T1B.T2D.X1B.X2E, Z6.T1B.T2D.X1B.X2E,
Z1.T1C.T2D.X1B.X2E, Z2.T1C.T2D.X1B.X2E,
Z3.T1C.T2D.X1B.X2E, Z4.T1C.T2D.X1B.X2E,
Z5.T1C.T2D.X1B.X2E, Z6.T1C.T2D.X1B.X2E,
Z1.T1D.T2D.X1B.X2E, Z2.T1D.T2D.X1B.X2E,
Z3.T1D.T2D.X1B.X2E, Z4.T1D.T2D.X1B.X2E,
Z5.T1D.T2D.X1B.X2E, Z6.T1D.T2D.X1B.X2E,
Z1.T1A.T2A.X1C.X2E, Z2.T1A.T2A.X1C.X2E,
Z3.T1A.T2A.X1C.X2E, Z4.T1A.T2A.X1C.X2E,
Z5.T1A.T2A.X1C.X2E, Z6.T1A.T2A.X1C.X2E,
Z1.T1B.T2A.X1C.X2E, Z2.T1B.T2A.X1C.X2E,
Z3.T1B.T2A.X1C.X2E, Z4.T1B.T2A.X1C.X2E,
Z5.T1B.T2A.X1C.X2E, Z6.T1B.T2A.X1C.X2E,
Z1.T1C.T2A.X1C.X2E, Z2.T1C.T2A.X1C.X2E,
Z3.T1C.T2A.X1C.X2E, Z4.T1C.T2A.X1C.X2E,
Z5.T1C.T2A.X1C.X2E, Z6.T1C.T2A.X1C.X2E,
Z1.T1D.T2A.X1C.X2E, Z2.T1D.T2A.X1C.X2E,
Z3.T1D.T2A.X1C.X2E, Z4.T1D.T2A.X1C.X2E,
Z5.T1D.T2A.X1C.X2E, Z6.T1D.T2A.X1C.X2E,
Z1.T1A.T2B.X1C.X2E, Z2.T1A.T2B.X1C.X2E,
Z3.T1A.T2B.X1C.X2E, Z4.T1A.T2B.X1C.X2E,
Z5.T1A.T2B.X1C.X2E, Z6.T1A.T2B.X1C.X2E,
Z1.T1B.T2B.X1C.X2E, Z2.T1B.T2B.X1C.X2E,
Z3.T1B.T2B.X1C.X2E, Z4.T1B.T2B.X1C.X2E,
Z5.T1B.T2B.X1C.X2E, Z6.T1B.T2B.X1C.X2E,
Z1.T1C.T2B.X1C.X2E, Z2.T1C.T2B.X1C.X2E,
Z3.T1C.T2B.X1C.X2E, Z4.T1C.T2B.X1C.X2E,
Z5.T1C.T2B.X1C.X2E, Z6.T1C.T2B.X1C.X2E,
Z1.T1D.T2B.X1C.X2E, Z2.T1D.T2B.X1C.X2E,
Z3.T1D.T2B.X1C.X2E, Z4.T1D.T2B.X1C.X2E,
Z5.T1D.T2B.X1C.X2E, Z6.T1D.T2B.X1C.X2E,
Z1.T1A.T2C.X1C.X2E, Z2.T1A.T2C.X1C.X2E,
Z3.T1A.T2C.X1C.X2E, Z4.T1A.T2C.X1C.X2E,
Z5.T1A.T2C.X1C.X2E, Z6.T1A.T2C.X1C.X2E,
Z1.T1B.T2C.X1C.X2E, Z2.T1B.T2C.X1C.X2E,
Z3.T1B.T2C.X1C.X2E, Z4.T1B.T2C.X1C.X2E,
Z5.T1B.T2C.X1C.X2E, Z6.T1B.T2C.X1C.X2E,
Z1.T1C.T2C.X1C.X2E, Z2.T1C.T2C.X1C.X2E,
Z3.T1C.T2C.X1C.X2E, Z4.T1C.T2C.X1C.X2E,
Z5.T1C.T2C.X1C.X2E, Z6.T1C.T2C.X1C.X2E,
Z1.T1D.T2C.X1C.X2E, Z2.T1D.T2C.X1C.X2E,
Z3.T1D.T2C.X1C.X2E, Z4.T1D.T2C.X1C.X2E,
Z5.T1D.T2C.X1C.X2E, Z6.T1D.T2C.X1C.X2E,
Z1.T1A.T2D.X1C.X2E, Z2.T1A.T2D.X1C.X2E,
Z3.T1A.T2D.X1C.X2E, Z4.T1A.T2D.X1C.X2E,
Z5.T1A.T2D.X1C.X2E, Z6.T1A.T2D.X1C.X2E,
Z1.T1B.T2D.X1C.X2E, Z2.T1B.T2D.X1C.X2E,
Z3.T1B.T2D.X1C.X2E, Z4.T1B.T2D.X1C.X2E,
Z5.T1B.T2D.X1C.X2E, Z6.T1B.T2D.X1C.X2E,
Z1.T1C.T2D.X1C.X2E, Z2.T1C.T2D.X1C.X2E,
Z3.T1C.T2D.X1C.X2E, Z4.T1C.T2D.X1C.X2E,
Z5.T1C.T2D.X1C.X2E, Z6.T1C.T2D.X1C.X2E,
Z1.T1D.T2D.X1C.X2E, Z2.T1D.T2D.X1C.X2E,
Z3.T1D.T2D.X1C.X2E, Z4.T1D.T2D.X1C.X2E,
Z5.T1D.T2D.X1C.X2E, Z6.T1D.T2D.X1C.X2E,
Z1.T1A.T2A.X1D.X2E, Z2.T1A.T2A.X1D.X2E,
Z3.T1A.T2A.X1D.X2E, Z4.T1A.T2A.X1D.X2E,
Z5.T1A.T2A.X1D.X2E, Z6.T1A.T2A.X1D.X2E,
Z1.T1B.T2A.X1D.X2E, Z2.T1B.T2A.X1D.X2E,
Z3.T1B.T2A.X1D.X2E, Z4.T1B.T2A.X1D.X2E,
Z5.T1B.T2A.X1D.X2E, Z6.T1B.T2A.X1D.X2E,
Z1.T1C.T2A.X1D.X2E, Z2.T1C.T2A.X1D.X2E,
Z3.T1C.T2A.X1D.X2E, Z4.T1C.T2A.X1D.X2E,
Z5.T1C.T2A.X1D.X2E, Z6.T1C.T2A.X1D.X2E,
Z1.T1D.T2A.X1D.X2E, Z2.T1D.T2A.X1D.X2E,
Z3.T1D.T2A.X1D.X2E, Z4.T1D.T2A.X1D.X2E,
Z5.T1D.T2A.X1D.X2E, Z6.T1D.T2A.X1D.X2E,
Z1.T1A.T2B.X1D.X2E, Z2.T1A.T2B.X1D.X2E,
Z3.T1A.T2B.X1D.X2E, Z4.T1A.T2B.X1D.X2E,
Z5.T1A.T2B.X1D.X2E, Z6.T1A.T2B.X1D.X2E,
Z1.T1B.T2B.X1D.X2E, Z2.T1B.T2B.X1D.X2E,
Z3.T1B.T2B.X1D.X2E, Z4.T1B.T2B.X1D.X2E,
Z5.T1B.T2B.X1D.X2E, Z6.T1B.T2B.X1D.X2E,
Z1.T1C.T2B.X1D.X2E, Z2.T1C.T2B.X1D.X2E,
Z3.T1C.T2B.X1D.X2E, Z4.T1C.T2B.X1D.X2E,
Z5.T1C.T2B.X1D.X2E, Z6.T1C.T2B.X1D.X2E,
Z1.T1D.T2B.X1D.X2E, Z2.T1D.T2B.X1D.X2E,
Z3.T1D.T2B.X1D.X2E, Z4.T1D.T2B.X1D.X2E,
Z5.T1D.T2B.X1D.X2E, Z6.T1D.T2B.X1D.X2E,
Z1.T1A.T2C.X1D.X2E, Z2.T1A.T2C.X1D.X2E,
Z3.T1A.T2C.X1D.X2E, Z4.T1A.T2C.X1D.X2E,
Z5.T1A.T2C.X1D.X2E, Z6.T1A.T2C.X1D.X2E,
Z1.T1B.T2C.X1D.X2E, Z2.T1B.T2C.X1D.X2E,
Z3.T1B.T2C.X1D.X2E, Z4.T1B.T2C.X1D.X2E,
Z5.T1B.T2C.X1D.X2E, Z6.T1B.T2C.X1D.X2E,
Z1.T1C.T2C.X1D.X2E, Z2.T1C.T2C.X1D.X2E,
Z3.T1C.T2C.X1D.X2E, Z4.T1C.T2C.X1D.X2E,
Z5.T1C.T2C.X1D.X2E, Z6.T1C.T2C.X1D.X2E,
Z1.T1D.T2C.X1D.X2E, Z2.T1D.T2C.X1D.X2E,
Z3.T1D.T2C.X1D.X2E, Z4.T1D.T2C.X1D.X2E,
Z5.T1D.T2C.X1D.X2E, Z6.T1D.T2C.X1D.X2E,
Z1.T1A.T2D.X1D.X2E, Z2.T1A.T2D.X1D.X2E,
Z3.T1A.T2D.X1D.X2E, Z4.T1A.T2D.X1D.X2E,
Z5.T1A.T2D.X1D.X2E, Z6.T1A.T2D.X1D.X2E,
Z1.T1B.T2D.X1D.X2E, Z2.T1B.T2D.X1D.X2E,
Z3.T1B.T2D.X1D.X2E, Z4.T1B.T2D.X1D.X2E,
Z5.T1B.T2D.X1D.X2E, Z6.T1B.T2D.X1D.X2E,
Z1.T1C.T2D.X1D.X2E, Z2.T1C.T2D.X1D.X2E,
Z3.T1C.T2D.X1D.X2E, Z4.T1C.T2D.X1D.X2E,
Z5.T1C.T2D.X1D.X2E, Z6.T1C.T2D.X1D.X2E,
Z1.T1D.T2D.X1D.X2E, Z2.T1D.T2D.X1D.X2E,
Z3.T1D.T2D.X1D.X2E, Z4.T1D.T2D.X1D.X2E,
Z5.T1D.T2D.X1D.X2E, Z6.T1D.T2D.X1D.X2E,
Z1.T1A.T2A.X1E.X2E, Z2.T1A.T2A.X1E.X2E,
Z3.T1A.T2A.X1E.X2E, Z4.T1A.T2A.X1E.X2E,
Z5.T1A.T2A.X1E.X2E, Z6.T1A.T2A.X1E.X2E,
Z1.T1B.T2A.X1E.X2E, Z2.T1B.T2A.X1E.X2E,
Z3.T1B.T2A.X1E.X2E, Z4.T1B.T2A.X1E.X2E,
Z5.T1B.T2A.X1E.X2E, Z6.T1B.T2A.X1E.X2E,
Z1.T1C.T2A.X1E.X2E, Z2.T1C.T2A.X1E.X2E,
Z3.T1C.T2A.X1E.X2E, Z4.T1C.T2A.X1E.X2E,
Z5.T1C.T2A.X1E.X2E, Z6.T1C.T2A.X1E.X2E,
Z1.T1D.T2A.X1E.X2E, Z2.T1D.T2A.X1E.X2E,
Z3.T1D.T2A.X1E.X2E, Z4.T1D.T2A.X1E.X2E,
Z5.T1D.T2A.X1E.X2E, Z6.T1D.T2A.X1E.X2E,
Z1.T1A.T2B.X1E.X2E, Z2.T1A.T2B.X1E.X2E,
Z3.T1A.T2B.X1E.X2E, Z4.T1A.T2B.X1E.X2E,
Z5.T1A.T2B.X1E.X2E, Z6.T1A.T2B.X1E.X2E,
Z1.T1B.T2B.X1E.X2E, Z2.T1B.T2B.X1E.X2E,
Z3.T1B.T2B.X1E.X2E, Z4.T1B.T2B.X1E.X2E,
Z5.T1B.T2B.X1E.X2E, Z6.T1B.T2B.X1E.X2E,
Z1.T1C.T2B.X1E.X2E, Z2.T1C.T2B.X1E.X2E,
Z3.T1C.T2B.X1E.X2E, Z4.T1C.T2B.X1E.X2E,
Z5.T1C.T2B.X1E.X2E, Z6.T1C.T2B.X1E.X2E,
Z1.T1D.T2B.X1E.X2E, Z2.T1D.T2B.X1E.X2E,
Z3.T1D.T2B.X1E.X2E, Z4.T1D.T2B.X1E.X2E,
Z5.T1D.T2B.X1E.X2E, Z6.T1D.T2B.X1E.X2E,
Z1.T1A.T2C.X1E.X2E, Z2.T1A.T2C.X1E.X2E,
Z3.T1A.T2C.X1E.X2E, Z4.T1A.T2C.X1E.X2E,
Z5.T1A.T2C.X1E.X2E, Z6.T1A.T2C.X1E.X2E,
Z1.T1B.T2C.X1E.X2E, Z2.T1B.T2C.X1E.X2E,
Z3.T1B.T2C.X1E.X2E, Z4.T1B.T2C.X1E.X2E,
Z5.T1B.T2C.X1E.X2E, Z6.T1B.T2C.X1E.X2E,
Z1.T1C.T2C.X1E.X2E, Z2.T1C.T2C.X1E.X2E,
Z3.T1C.T2C.X1E.X2E, Z4.T1C.T2C.X1E.X2E,
Z5.T1C.T2C.X1E.X2E, Z6.T1C.T2C.X1E.X2E,
Z1.T1D.T2C.X1E.X2E, Z2.T1D.T2C.X1E.X2E,
Z3.T1D.T2C.X1E.X2E, Z4.T1D.T2C.X1E.X2E,
Z5.T1D.T2C.X1E.X2E, Z6.T1D.T2C.X1E.X2E,
Z1.T1A.T2D.X1E.X2E, Z2.T1A.T2D.X1E.X2E,
Z3.T1A.T2D.X1E.X2E, Z4.T1A.T2D.X1E.X2E,
Z5.T1A.T2D.X1E.X2E, Z6.T1A.T2D.X1E.X2E,

TABLE 6-continued

List of Compound Structures of Formula II

Z1.T1B.T2D.X1E.X2E, Z2.T1B.T2D.X1E.X2E,
Z3.T1B.T2D.X1E.X2E, Z4.T1B.T2D.X1E.X2E,
Z5.T1B.T2D.X1E.X2E, Z6.T1B.T2D.X1E.X2E,
Z1.T1C.T2D.X1E.X2E, Z2.T1C.T2D.X1E.X2E,
Z3.T1C.T2D.X1E.X2E, Z4.T1C.T2D.X1E.X2E,
Z5.T1C.T2D.X1E.X2E, Z6.T1C.T2D.X1E.X2E,
Z1.T1D.T2D.X1E.X2E, Z2.T1D.T2D.X1E.X2E,
Z3.T1D.T2D.X1E.X2E, Z4.T1D.T2D.X1E.X2E,
Z5.T1D.T2D.X1E.X2E, and Z6.T1D.T2D.X1E.X2E.

In still another embodiment, selected compounds of Formula I are named below in tabular format (Table 12) as compounds of general Formula III (below):

Formula III where 1, 2, 3, 4 and 5 are defined in Tables 7-11, below. Each compound is designated in tabular form by combining the "code" representing each structural moiety using the following syntax: 1.2.3.4.5. Thus, for example, 1a.2a.3a.4a.5a represents the following structure:

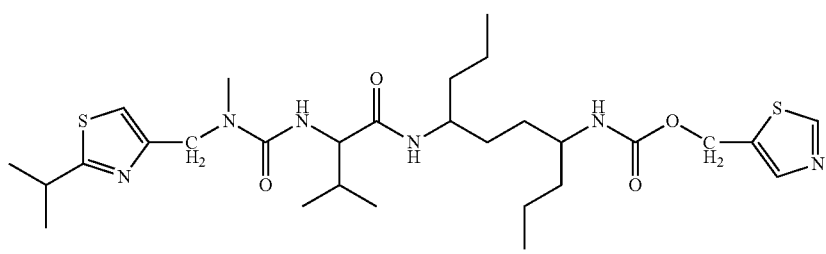 [SMILES: CCCC(CCC(CCC)NC(=O)C(NC(=O)N(C)Cc1csc(C(C)C)n1)C(C)C)NC(=O)OCc1cncs1]

TABLE 7

"1" Structures

| Code | "1" Structure |
|---|---|
| 1a | |
| 1b | |

TABLE 7-continued

"1" Structures

| Code | "1" Structure |
|---|---|
| 1c | |
| 1d | |
| 1e | |

TABLE 7-continued

"1" Structures

| Code | "1" Structure |
|---|---|
| 1f | |
| 1g | |

TABLE 7-continued

"1" Structures

| Code | "1" Structure |
|------|---------------|
| 1h | (structure) |
| 1i | (structure) |
| 1j | (structure) |
| 1k | (structure) |
| 1l | (structure) |
| 1m | (structure) |
| 1n | (structure) |
| 1o | (structure) |
| 1p | (structure) |
| 1q | (structure) |
| 1r | (structure) |
| 1s | (structure) |
| 1t | (structure) |
| 1u | (structure) |

TABLE 8

"2" Structures

| Code | "2" Structure |
|------|---------------|
| 2a | (structure) |

TABLE 8-continued

"2" Structures

| Code | "2" Structure |
|------|---------------|
| 2b | [structure: 2-isopropylthiazol-5-yl-CH2-N(CH3)-C(O)-NH-CH(iPr)-C(O)-] |
| 2c | [structure: pyridin-2-yl-CH2-N(CH3)-C(O)-NH-CH(iPr)-C(O)-] |
| 2d | [structure: pyrazin-2-yl-CH2-N(CH3)-C(O)-NH-CH(iPr)-C(O)-] |
| 2e | [structure: 2-isopropylthiazol-4-yl-CH2-N(CH3)-C(O)-NH-CH(CH(OH)CH3)-C(O)-] |
| 2f | [structure: 2-isopropylthiazol-5-yl-CH2-N(CH3)-C(O)-NH-CH(CH(OH)CH3)-C(O)-] |
| 2g | [structure: 2-isopropylthiazol-4-yl-CH2-N(CH3)-C(O)-NH-CH(CH2CH2-imidazol-1-yl)-C(O)-] |
| 2h | [structure: 2-isopropylthiazol-4-yl-CH2-N(CH3)-C(O)-NH-CH(CH2CH2-(4,4-difluoropiperidin-1-yl))-C(O)-] |
| 2i | [structure: thiazol-4-yl-CH2-N(cyclopropyl)-C(O)-NH-CH(CH(OH)CH3)-C(O)-] |
| 2j | [structure: 2-isopropylthiazol-5-yl-CH2-N(cyclopropyl)-C(O)-NH-CH(CH(OH)CH3)-C(O)-] |
| 2k | [structure: 2-isopropylthiazol-4-yl-CH2-N(CH3)-C(O)-NH-CH(CH2-morpholin-4-yl)-C(O)-] |
| 2l | [structure: 2-isopropylthiazol-4-yl-CH2-N(CH3)-C(O)-NH-CH(CH2CH2-(1,2,4-triazol-4-yl))-C(O)-] |
| 2m | [structure: 2-isopropylthiazol-4-yl-CH2-N(CH3)-C(O)-N(CH3)-CH(CH(OH)CH3)-C(O)-] |
| 2n | [structure: 2-isopropylthiazol-4-yl-CH2-N(CH3)-C(O)-N(cyclopropyl)-CH(CH(OH)CH3)-C(O)-] |
| 2o | [structure: 2-isopropylthiazol-5-yl-CH2-N(CH3)-C(O)-N(cyclopropyl)-CH(CH(OH)CH3)-C(O)-] |

TABLE 8-continued
"2" Structures
| Code | "2" Structure |
|---|---|
| 2p | 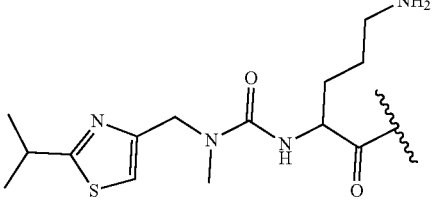 |
| 2q | 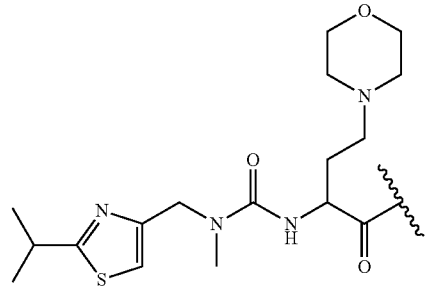 [SMILES: *C(=O)C(CCN1CCOCC1)NC(=O)N(C)Cc1csc(C(C)C)n1] |
| 2r | 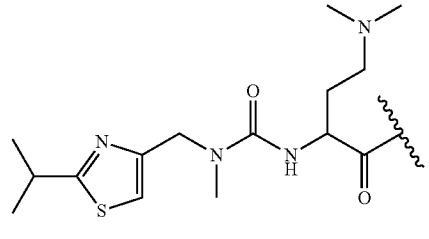 [SMILES: *C(=O)C(CCN(C)C)NC(=O)N(C)Cc1csc(C(C)C)n1] |
| 2s | 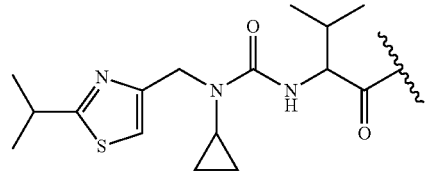 [SMILES: *C(=O)C(NC(=O)N(Cc1csc(C(C)C)n1)C1CC1)C(C)C] |
| 2t | 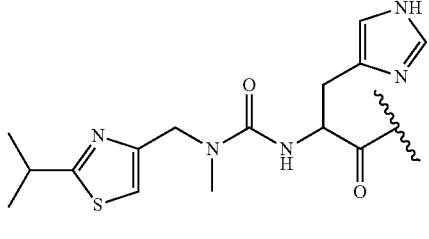 [SMILES: *C(=O)C(Cc1c[nH]cn1)NC(=O)N(C)Cc1csc(C(C)C)n1] |
| 2u | 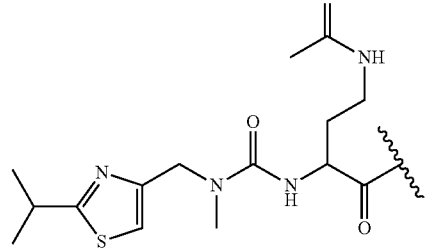 |
TABLE 8-continued
"2" Structures
| Code | "2" Structure |
|---|---|
| 2v | 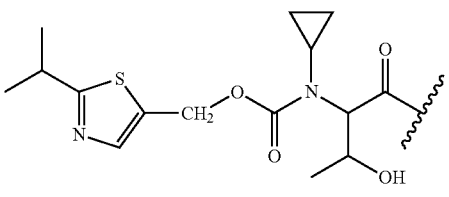 [SMILES: *C(=O)C(C(C)O)N(C(=O)OCc1cnc(C(C)C)s1)C1CC1] |
| 2w | 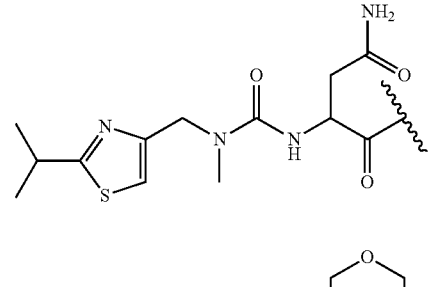 |
| 2x | 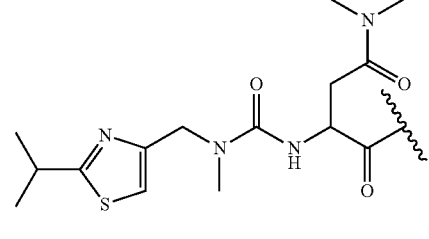 |
| 2y | 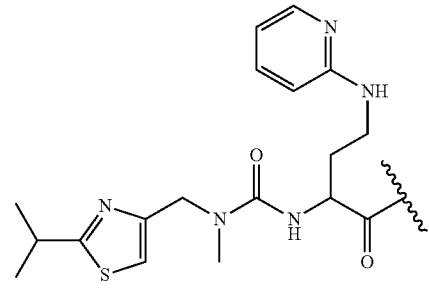 [SMILES: *C(=O)C(CCNc1ccccn1)NC(=O)N(C)Cc1csc(C(C)C)n1] |
TABLE 9
"3" Structures
| Code | "3" Structure |
|---|---|
| 3a | —O—CH$_2$-(5-thiazolyl) |
| 3b | —O—CH$_2$-(3-pyridyl) |
| 3c | —NH—CH$_2$-(5-thiazolyl) |
| 3d | —NH—CH$_2$-(3-pyridyl) |
| 3e | —N(CH$_3$)—CH$_2$-(5-thiazolyl) |
| 3f | —N(CH$_3$)—CH$_2$-(3-pyridyl) |
| 3g | —N(CH$_3$)-(5-thiazolyl) |
| 3h | —N(CH$_3$)-(3-pyridyl) |

TABLE 10

"4" Structures

| Code | "4" Structure |
|------|---------------|
| 4a | n-propyl |
| 4b | i-butyl |
| 4c | —CH$_2$-cyclohexyl |
| 4d | —CH$_2$-phenyl |
| 4e | —CH$_2$-(4-methoxyphenyl) |
| 4f | —CH$_2$-(3-fluorophenyl) |
| 4g | —CH$_2$-(4-pyridyl) |
| 4h | —CH$_2$-(3-pyridyl) |
| 4i | —CH$_2$-(2-pyridyl) |
| 4j | —CH$_2$CH$_2$-(4-morpholinyl) |
| 4k | 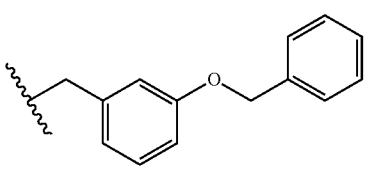 [SMILES: *Cc1cccc(OCc2ccccc2)c1] |
| 4l | 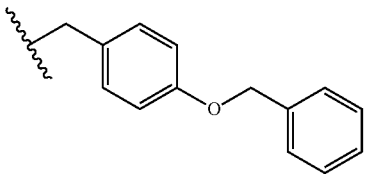 [SMILES: *Cc1ccc(OCc2ccccc2)cc1] |
| 4m | 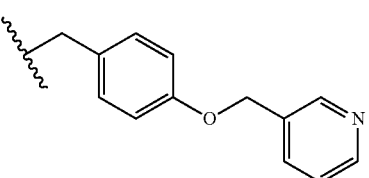 |
| 4n | 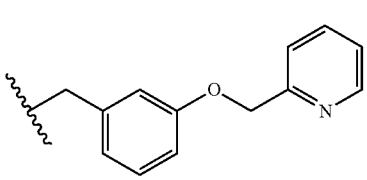 [SMILES: *Cc1cccc(OCc2ccccn2)c1] |
| 4o | 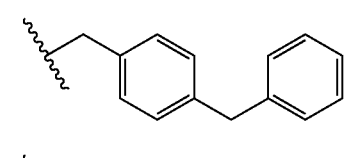 |
| 4p | 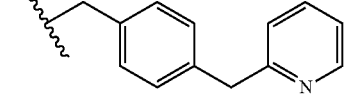 |

TABLE 11

"5" Structures

| Code | "5" Structure |
|------|---------------|
| 5a | n-propyl |
| 5b | i-butyl |
| 5c | —CH$_2$-cyclohexyl |
| 5d | —CH$_2$-phenyl |
| 5e | —CH$_2$-(4-methoxyphenyl) |
| 5f | —CH$_2$-(3-fluorophenyl) |
| 5g | —CH$_2$-(4-pyridyl) |
| 5h | —CH$_2$-(3-pyridyl) |

TABLE 11-continued

"5" Structures

| Code | "5" Structure |
|------|---------------|
| 5i | —CH$_2$-(2-pyridyl) |
| 5j | —CH$_2$CH$_2$-(4-morpholinyl) |
| 5k | 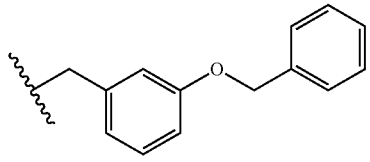 [SMILES: *Cc1cccc(OCc2ccccc2)c1] |
| 5l | 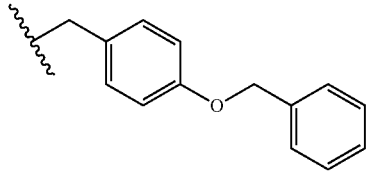 [SMILES: *Cc1ccc(OCc2ccccc2)cc1] |
| 5m | 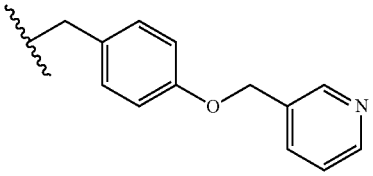 [SMILES: *Cc1ccc(OCc2cccnc2)cc1] |
| 5n | 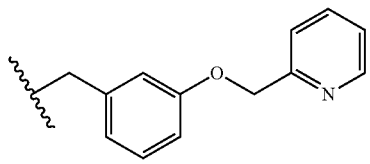 [SMILES: *Cc1cccc(OCc2ccccn2)c1] |
| 5o | 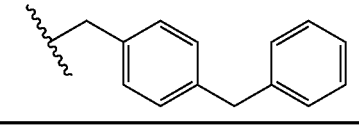 |

TABLE 12

List of Compound Structures of Formula II 1a.2a.3a.4a.5a., 1b.2a.3a.4a.5a., 1f.2a.3a.4a.5a., 1h.2a.3a.4a.5a., 1j.2a.3a.4a.5a., 1p.2a.3a.4a.5a., 1a.2b.3a.4a.5a., 1b.2b.3a.4a.5a., 1f.2b.3a.4a.5a., 1h.2b.3a.4a.5a., 1j.2b.3a.4a.5a., 1p.2b.3a.4a.5a., 1a.2e.3a.4a.5a., 1b.2e.3a.4a.5a., 1f.2e.3a.4a.5a., 1h.2e.3a.4a.5a., 1j.2e.3a.4a.5a., 1p.2e.3a.4a.5a., 1a.2f.3a.4a.5a., 1b.2f.3a.4a.5a., 1f.2f.3a.4a.5a., 1h.2f.3a.4a.5a., 1j.2f.3a.4a.5a., 1p.2f.3a.4a.5a., 1a.2i.3a.4a.5a., 1b.2i.3a.4a.5a., 1f.2i.3a.4a.5a., 1h.2i.3a.4a.5a., 1j.2i.3a.4a.5a., 1p.2i.3a.4a.5a., 1a.2m.3a.4a.5a., 1b.2m.3a.4a.5a., 1f.2m.3a.4a.5a., 1h.2m.3a.4a.5a., 1j.2m.3a.4a.5a., 1p.2m.3a.4a.5a., 1a.2o.3a.4a.5a., 1b.2o.3a.4a.5a., 1f.2o.3a.4a.5a., 1h.2o.3a.4a.5a., 1j.2o.3a.4a.5a., 1p.2o.3a.4a.5a., 1a.2u.3a.4a.5a., 1b.2u.3a.4a.5a., 1f.2u.3a.4a.5a., 1h.2u.3a.4a.5a., 1j.2u.3a.4a.5a., 1p.2u.3a.4a.5a., 1a.2y.3a.4a.5a., 1b.2y.3a.4a.5a., 1f.2y.3a.4a.5a., 1h.2y.3a.4a.5a., 1j.2y.3a.4a.5a., 1p.2y.3a.4a.5a., 1a.2a.3b.4a.5a., 1b.2a.3b.4a.5a., 1f.2a.3b.4a.5a., 1h.2a.3b.4a.5a., 1j.2a.3b.4a.5a., 1p.2a.3b.4a.5a., 1a.2b.3b.4a.5a., 1b.2b.3b.4a.5a., 1f.2b.3b.4a.5a., 1h.2b.3b.4a.5a., 1j.2b.3b.4a.5a., 1p.2b.3b.4a.5a., 1a.2e.3b.4a.5a., 1b.2e.3b.4a.5a., 1f.2e.3b.4a.5a., 1h.2e.3b.4a.5a., 1j.2e.3b.4a.5a., 1p.2e.3b.4a.5a., 1a.2f.3b.4a.5a., 1b.2f.3b.4a.5a., 1f.2f.3b.4a.5a., 1h.2f.3b.4a.5a., 1j.2f.3b.4a.5a., 1p.2f.3b.4a.5a., 1a.2i.3b.4a.5a., 1b.2i.3b.4a.5a., 1f.2i.3b.4a.5a., 1h.2i.3b.4a.5a., 1j.2i.3b.4a.5a., 1p.2i.3b.4a.5a., 1a.2m.3b.4a.5a., 1b.2m.3b.4a.5a., 1f.2m.3b.4a.5a., 1h.2m.3b.4a.5a., 1j.2m.3b.4a.5a., 1p.2m.3b.4a.5a., 1a.2o.3b.4a.5a., 1b.2o.3b.4a.5a., 1f.2o.3b.4a.5a., 1h.2o.3b.4a.5a., 1j.2o.3b.4a.5a., 1p.2o.3b.4a.5a., 1a.2u.3b.4a.5a., 1b.2u.3b.4a.5a., 1f.2u.3b.4a.5a., 1h.2u.3b.4a.5a.,

TABLE 12-continued

List of Compound Structures of Formula II 1j.2u.3b.4a.5a., 1p.2u.3b.4a.5a., 1a.2y.3b.4a.5a., 1b.2y.3b.4a.5a.,
1f.2y.3b.4a.5a., 1h.2y.3b.4a.5a., 1j.2y.3b.4a.5a., 1p.2y.3b.4a.5a.,
1a.2a.3e.4a.5a., 1b.2a.3e.4a.5a., 1f.2a.3e.4a.5a., 1h.2a.3e.4a.5a.,
1j.2a.3e.4a.5a., 1p.2a.3e.4a.5a., 1a.2b.3e.4a.5a., 1b.2b.3e.4a.5a.,
1f.2b.3e.4a.5a., 1h.2b.3e.4a.5a., 1j.2b.3e.4a.5a., 1p.2b.3e.4a.5a.,
1a.2e.3e.4a.5a., 1b.2e.3e.4a.5a., 1f.2e.3e.4a.5a., 1h.2e.3e.4a.5a.,
1j.2e.3e.4a.5a., 1p.2e.3e.4a.5a., 1a.2f.3e.4a.5a., 1b.2f.3e.4a.5a.,
1f.2f.3e.4a.5a., 1h.2f.3e.4a.5a., 1j.2f.3e.4a.5a., 1p.2f.3e.4a.5a.,
1a.2i.3e.4a.5a., 1b.2i.3e.4a.5a., 1f.2i.3e.4a.5a., 1h.2i.3e.4a.5a.,
1j.2i.3e.4a.5a., 1p.2i.3e.4a.5a., 1a.2m.3e.4a.5a., 1b.2m.3e.4a.5a.,
1f.2m.3e.4a.5a., 1h.2m.3e.4a.5a., 1j.2m.3e.4a.5a., 1p.2m.3e.4a.5a.,
1a.2o.3e.4a.5a., 1b.2o.3e.4a.5a., 1f.2o.3e.4a.5a., 1h.2o.3e.4a.5a.,
1j.2o.3e.4a.5a., 1p.2o.3e.4a.5a., 1a.2u.3e.4a.5a., 1b.2u.3e.4a.5a.,
1f.2u.3e.4a.5a., 1h.2u.3e.4a.5a., 1j.2u.3e.4a.5a., 1p.2u.3e.4a.5a.,
1a.2y.3e.4a.5a., 1b.2y.3e.4a.5a., 1f.2y.3e.4a.5a., 1h.2y.3e.4a.5a.,
1j.2y.3e.4a.5a., 1p.2y.3e.4a.5a., 1a.2a.3g.4a.5a., 1b.2a.3g.4a.5a.,
1f.2a.3g.4a.5a., 1h.2a.3g.4a.5a., 1j.2a.3g.4a.5a., 1p.2a.3g.4a.5a.,
1a.2b.3g.4a.5a., 1b.2b.3g.4a.5a., 1f.2b.3g.4a.5a., 1h.2b.3g.4a.5a.,
1j.2b.3g.4a.5a., 1p.2b.3g.4a.5a., 1a.2e.3g.4a.5a., 1b.2e.3g.4a.5a.,
1f.2e.3g.4a.5a., 1h.2e.3g.4a.5a., 1j.2e.3g.4a.5a., 1p.2e.3g.4a.5a.,
1a.2f.3g.4a.5a., 1b.2f.3g.4a.5a., 1f.2f.3g.4a.5a., 1h.2f.3g.4a.5a.,
1j.2f.3g.4a.5a., 1p.2f.3g.4a.5a., 1a.2i.3g.4a.5a., 1b.2i.3g.4a.5a.,
1f.2i.3g.4a.5a., 1h.2i.3g.4a.5a., 1j.2i.3g.4a.5a., 1p.2i.3g.4a.5a.,
1a.2m.3g.4a.5a., 1b.2m.3g.4a.5a., 1f.2m.3g.4a.5a., 1h.2m.3g.4a.5a.,
1j.2m.3g.4a.5a., 1p.2m.3g.4a.5a., 1a.2o.3g.4a.5a., 1b.2o.3g.4a.5a.,
1f.2o.3g.4a.5a., 1h.2o.3g.4a.5a., 1j.2o.3g.4a.5a., 1p.2o.3g.4a.5a.,
1a.2u.3g.4a.5a., 1b.2u.3g.4a.5a., 1f.2u.3g.4a.5a., 1h.2u.3g.4a.5a.,
1j.2u.3g.4a.5a., 1p.2u.3g.4a.5a., 1a.2y.3g.4a.5a., 1b.2y.3g.4a.5a.,
1f.2y.3g.4a.5a., 1h.2y.3g.4a.5a., 1j.2y.3g.4a.5a., 1p.2y.3g.4a.5a.,
1a.2a.3a.4d.5a., 1b.2a.3a.4d.5a., 1f.2a.3a.4d.5a., 1h.2a.3a.4d.5a.,
1j.2a.3a.4d.5a., 1p.2a.3a.4d.5a., 1a.2b.3a.4d.5a., 1b.2b.3a.4d.5a.,
1f.2b.3a.4d.5a., 1h.2b.3a.4d.5a., 1j.2b.3a.4d.5a., 1p.2b.3a.4d.5a.,
1a.2e.3a.4d.5a., 1b.2e.3a.4d.5a., 1f.2e.3a.4d.5a., 1h.2e.3a.4d.5a.,
1j.2e.3a.4d.5a., 1p.2e.3a.4d.5a., 1a.2f.3a.4d.5a., 1b.2f.3a.4d.5a.,
1f.2f.3a.4d.5a., 1h.2f.3a.4d.5a., 1j.2f.3a.4d.5a., 1p.2f.3a.4d.5a.,
1a.2i.3a.4d.5a., 1b.2i.3a.4d.5a., 1f.2i.3a.4d.5a., 1h.2i.3a.4d.5a.,
1j.2i.3a.4d.5a., 1p.2i.3a.4d.5a., 1a.2m.3a.4d.5a., 1b.2m.3a.4d.5a.,
1f.2m.3a.4d.5a., 1h.2m.3a.4d.5a., 1j.2m.3a.4d.5a., 1p.2m.3a.4d.5a.,
1a.2o.3a.4d.5a., 1b.2o.3a.4d.5a., 1f.2o.3a.4d.5a., 1h.2o.3a.4d.5a.,
1j.2o.3a.4d.5a., 1p.2o.3a.4d.5a., 1a.2u.3a.4d.5a., 1b.2u.3a.4d.5a.,
1f.2u.3a.4d.5a., 1h.2u.3a.4d.5a., 1j.2u.3a.4d.5a., 1p.2u.3a.4d.5a.,
1a.2y.3a.4d.5a., 1b.2y.3a.4d.5a., 1f.2y.3a.4d.5a., 1h.2y.3a.4d.5a.,
1j.2y.3a.4d.5a., 1p.2y.3a.4d.5a., 1a.2a.3b.4d.5a., 1b.2a.3b.4d.5a.,
1f.2a.3b.4d.5a., 1h.2a.3b.4d.5a., 1j.2a.3b.4d.5a., 1p.2a.3b.4d.5a.,
1a.2b.3b.4d.5a., 1b.2b.3b.4d.5a., 1f.2b.3b.4d.5a., 1h.2b.3b.4d.5a.,
1j.2b.3b.4d.5a., 1p.2b.3b.4d.5a., 1a.2e.3b.4d.5a., 1b.2e.3b.4d.5a.,
1f.2e.3b.4d.5a., 1h.2e.3b.4d.5a., 1j.2e.3b.4d.5a., 1p.2e.3b.4d.5a.,
1a.2f.3b.4d.5a., 1b.2f.3b.4d.5a., 1f.2f.3b.4d.5a., 1h.2f.3b.4d.5a.,
1j.2f.3b.4d.5a., 1p.2f.3b.4d.5a., 1a.2i.3b.4d.5a., 1b.2i.3b.4d.5a.,
1f.2i.3b.4d.5a., 1h.2i.3b.4d.5a., 1j.2i.3b.4d.5a., 1p.2i.3b.4d.5a.,
1a.2m.3b.4d.5a., 1b.2m.3b.4d.5a., 1f.2m.3b.4d.5a., 1h.2m.3b.4d.5a.,
1j.2m.3b.4d.5a., 1p.2m.3b.4d.5a., 1a.2o.3b.4d.5a., 1b.2o.3b.4d.5a.,
1f.2o.3b.4d.5a., 1h.2o.3b.4d.5a., 1j.2o.3b.4d.5a., 1p.2o.3b.4d.5a.,
1a.2u.3b.4d.5a., 1b.2u.3b.4d.5a., 1f.2u.3b.4d.5a., 1h.2u.3b.4d.5a.,
1j.2u.3b.4d.5a., 1p.2u.3b.4d.5a., 1a.2y.3b.4d.5a., 1b.2y.3b.4d.5a.,
1f.2y.3b.4d.5a., 1h.2y.3b.4d.5a., 1j.2y.3b.4d.5a., 1p.2y.3b.4d.5a.,
1a.2a.3e.4d.5a., 1b.2a.3e.4d.5a., 1f.2a.3e.4d.5a., 1h.2a.3e.4d.5a.,
1j.2a.3e.4d.5a., 1p.2a.3e.4d.5a., 1a.2b.3e.4d.5a., 1b.2b.3e.4d.5a.,
1f.2b.3e.4d.5a., 1h.2b.3e.4d.5a., 1j.2b.3e.4d.5a., 1p.2b.3e.4d.5a.,
1a.2e.3e.4d.5a., 1b.2e.3e.4d.5a., 1f.2e.3e.4d.5a., 1h.2e.3e.4d.5a.,
1j.2e.3e.4d.5a., 1p.2e.3e.4d.5a., 1a.2f.3e.4d.5a., 1b.2f.3e.4d.5a.,
1f.2f.3e.4d.5a., 1h.2f.3e.4d.5a., 1j.2f.3e.4d.5a., 1p.2f.3e.4d.5a.,
1a.2i.3e.4d.5a., 1b.2i.3e.4d.5a., 1f.2i.3e.4d.5a., 1h.2i.3e.4d.5a.,
1j.2i.3e.4d.5a., 1p.2i.3e.4d.5a., 1a.2m.3e.4d.5a., 1b.2m.3e.4d.5a.,
1f.2m.3e.4d.5a., 1h.2m.3e.4d.5a., 1j.2m.3e.4d.5a., 1p.2m.3e.4d.5a.,
1a.2o.3e.4d.5a., 1b.2o.3e.4d.5a., 1f.2o.3e.4d.5a., 1h.2o.3e.4d.5a.,
1j.2o.3e.4d.5a., 1p.2o.3e.4d.5a., 1a.2u.3e.4d.5a., 1b.2u.3e.4d.5a.,
1f.2u.3e.4d.5a., 1h.2u.3e.4d.5a., 1j.2u.3e.4d.5a., 1p.2u.3e.4d.5a.,
1a.2y.3e.4d.5a., 1b.2y.3e.4d.5a., 1f.2y.3e.4d.5a., 1h.2y.3e.4d.5a.,
1j.2y.3e.4d.5a., 1p.2y.3e.4d.5a., 1a.2a.3g.4d.5a., 1b.2a.3g.4d.5a.,
1f.2a.3g.4d.5a., 1h.2a.3g.4d.5a., 1j.2a.3g.4d.5a., 1p.2a.3g.4d.5a.,
1a.2b.3g.4d.5a., 1b.2b.3g.4d.5a., 1f.2b.3g.4d.5a., 1h.2b.3g.4d.5a.,
1j.2b.3g.4d.5a., 1p.2b.3g.4d.5a., 1a.2e.3g.4d.5a., 1b.2e.3g.4d.5a.,
1f.2e.3g.4d.5a., 1h.2e.3g.4d.5a., 1j.2e.3g.4d.5a., 1p.2e.3g.4d.5a.,
1a.2f.3g.4d.5a., 1b.2f.3g.4d.5a., 1f.2f.3g.4d.5a., 1h.2f.3g.4d.5a.,
1j.2f.3g.4d.5a., 1p.2f.3g.4d.5a., 1a.2i.3g.4d.5a., 1b.2i.3g.4d.5a.,
1f.2i.3g.4d.5a., 1h.2i.3g.4d.5a., 1j.2i.3g.4d.5a., 1p.2i.3g.4d.5a.,
1a.2m.3g.4d.5a., 1b.2m.3g.4d.5a., 1f.2m.3g.4d.5a., 1h.2m.3g.4d.5a.,
1j.2m.3g.4d.5a., 1p.2m.3g.4d.5a., 1a.2o.3g.4d.5a., 1b.2o.3g.4d.5a.,
1f.2o.3g.4d.5a., 1h.2o.3g.4d.5a., 1j.2o.3g.4d.5a., 1p.2o.3g.4d.5a.,
1a.2u.3g.4d.5a., 1b.2u.3g.4d.5a., 1f.2u.3g.4d.5a., 1h.2u.3g.4d.5a.,
1j.2u.3g.4d.5a., 1p.2u.3g.4d.5a., 1a.2y.3g.4d.5a., 1b.2y.3g.4d.5a.,
1f.2y.3g.4d.5a., 1h.2y.3g.4d.5a., 1j.2y.3g.4d.5a., 1p.2y.3g.4d.5a.,
1a.2a.3a.4f.5a., 1b.2a.3a.4f.5a., 1f.2a.3a.4f.5a., 1h.2a.3a.4f.5a.,
1j.2a.3a.4f.5a., 1p.2a.3a.4f.5a., 1a.2b.3a.4f.5a., 1b.2b.3a.4f.5a.,
1f.2b.3a.4f.5a., 1h.2b.3a.4f.5a., 1j.2b.3a.4f.5a., 1p.2b.3a.4f.5a.,
1a.2e.3a.4f.5a., 1b.2e.3a.4f.5a., 1f.2e.3a.4f.5a., 1h.2e.3a.4f.5a.,
1j.2e.3a.4f.5a., 1p.2e.3a.4f.5a., 1a.2f.3a.4f.5a., 1b.2f.3a.4f.5a.,
1f.2f.3a.4f.5a., 1h.2f.3a.4f.5a., 1j.2f.3a.4f.5a., 1p.2f.3a.4f.5a.,
1a.2i.3a.4f.5a., 1b.2i.3a.4f.5a., 1f.2i.3a.4f.5a., 1h.2i.3a.4f.5a.,
1j.2i.3a.4f.5a., 1p.2i.3a.4f.5a., 1a.2m.3a.4f.5a., 1b.2m.3a.4f.5a.,
1f.2m.3a.4f.5a., 1h.2m.3a.4f.5a., 1j.2m.3a.4f.5a., 1p.2m.3a.4f.5a.,
1a.2o.3a.4f.5a., 1b.2o.3a.4f.5a., 1f.2o.3a.4f.5a., 1h.2o.3a.4f.5a.,
1j.2o.3a.4f.5a., 1p.2o.3a.4f.5a., 1a.2u.3a.4f.5a., 1b.2u.3a.4f.5a.,
1f.2u.3a.4f.5a., 1h.2u.3a.4f.5a., 1j.2u.3a.4f.5a., 1p.2u.3a.4f.5a.,
1a.2y.3a.4f.5a., 1b.2y.3a.4f.5a., 1f.2y.3a.4f.5a., 1h.2y.3a.4f.5a.,
1j.2y.3a.4f.5a., 1p.2y.3a.4f.5a., 1a.2a.3b.4f.5a., 1b.2a.3b.4f.5a.,
1f.2a.3b.4f.5a., 1h.2a.3b.4f.5a., 1j.2a.3b.4f.5a., 1p.2a.3b.4f.5a.,
1a.2b.3b.4f.5a., 1b.2b.3b.4f.5a., 1f.2b.3b.4f.5a., 1h.2b.3b.4f.5a.,
1j.2b.3b.4f.5a., 1p.2b.3b.4f.5a., 1a.2e.3b.4f.5a., 1b.2e.3b.4f.5a.,
1f.2e.3b.4f.5a., 1h.2e.3b.4f.5a., 1j.2e.3b.4f.5a., 1p.2e.3b.4f.5a.,
1a.2f.3b.4f.5a., 1b.2f.3b.4f.5a., 1f.2f.3b.4f.5a., 1h.2f.3b.4f.5a.,
1j.2f.3b.4f.5a., 1p.2f.3b.4f.5a., 1a.2i.3b.4f.5a., 1b.2i.3b.4f.5a.,
1f.2i.3b.4f.5a., 1h.2i.3b.4f.5a., 1j.2i.3b.4f.5a., 1p.2i.3b.4f.5a.,
1a.2m.3b.4f.5a., 1b.2m.3b.4f.5a., 1f.2m.3b.4f.5a., 1h.2m.3b.4f.5a.,
1j.2m.3b.4f.5a., 1p.2m.3b.4f.5a., 1a.2o.3b.4f.5a., 1b.2o.3b.4f.5a.,
1f.2o.3b.4f.5a., 1h.2o.3b.4f.5a., 1j.2o.3b.4f.5a., 1p.2o.3b.4f.5a.,
1a.2u.3b.4f.5a., 1b.2u.3b.4f.5a., 1f.2u.3b.4f.5a., 1h.2u.3b.4f.5a.,
1j.2u.3b.4f.5a., 1p.2u.3b.4f.5a., 1a.2y.3b.4f.5a., 1b.2y.3b.4f.5a.,
1f.2y.3b.4f.5a., 1h.2y.3b.4f.5a., 1j.2y.3b.4f.5a., 1p.2y.3b.4f.5a.,
1a.2a.3e.4f.5a., 1b.2a.3e.4f.5a., 1f.2a.3e.4f.5a., 1h.2a.3e.4f.5a.,
1j.2a.3e.4f.5a., 1p.2a.3e.4f.5a., 1a.2b.3e.4f.5a., 1b.2b.3e.4f.5a.,
1f.2b.3e.4f.5a., 1h.2b.3e.4f.5a., 1j.2b.3e.4f.5a., 1p.2b.3e.4f.5a.,
1a.2e.3e.4f.5a., 1b.2e.3e.4f.5a., 1f.2e.3e.4f.5a., 1h.2e.3e.4f.5a.,
1j.2e.3e.4f.5a., 1p.2e.3e.4f.5a., 1a.2f.3e.4f.5a., 1b.2f.3e.4f.5a.,
1f.2f.3e.4f.5a., 1h.2f.3e.4f.5a., 1j.2f.3e.4f.5a., 1p.2f.3e.4f.5a.,
1a.2i.3e.4f.5a., 1b.2i.3e.4f.5a., 1f.2i.3e.4f.5a., 1h.2i.3e.4f.5a.,
1j.2i.3e.4f.5a., 1p.2i.3e.4f.5a., 1a.2m.3e.4f.5a., 1b.2m.3e.4f.5a.,
1f.2m.3e.4f.5a., 1h.2m.3e.4f.5a., 1j.2m.3e.4f.5a., 1p.2m.3e.4f.5a.,
1a.2o.3e.4f.5a., 1b.2o.3e.4f.5a., 1f.2o.3e.4f.5a., 1h.2o.3e.4f.5a.,
1j.2o.3e.4f.5a., 1p.2o.3e.4f.5a., 1a.2u.3e.4f.5a., 1b.2u.3e.4f.5a.,
1f.2u.3e.4f.5a., 1h.2u.3e.4f.5a., 1j.2u.3e.4f.5a., 1p.2u.3e.4f.5a.,
1a.2y.3e.4f.5a., 1b.2y.3e.4f.5a., 1f.2y.3e.4f.5a., 1h.2y.3e.4f.5a.,
1j.2y.3e.4f.5a., 1p.2y.3e.4f.5a., 1a.2a.3g.4f.5a., 1b.2a.3g.4f.5a.,
1f.2a.3g.4f.5a., 1h.2a.3g.4f.5a., 1j.2a.3g.4f.5a., 1p.2a.3g.4f.5a.,
1a.2b.3g.4f.5a., 1b.2b.3g.4f.5a., 1f.2b.3g.4f.5a., 1h.2b.3g.4f.5a.,
1j.2b.3g.4f.5a., 1p.2b.3g.4f.5a., 1a.2e.3g.4f.5a., 1b.2e.3g.4f.5a.,
1f.2e.3g.4f.5a., 1h.2e.3g.4f.5a., 1j.2e.3g.4f.5a., 1p.2e.3g.4f.5a.,
1a.2f.3g.4f.5a., 1b.2f.3g.4f.5a., 1f.2f.3g.4f.5a., 1h.2f.3g.4f.5a.,
1j.2f.3g.4f.5a., 1p.2f.3g.4f.5a., 1a.2i.3g.4f.5a., 1b.2i.3g.4f.5a.,
1f.2i.3g.4f.5a., 1h.2i.3g.4f.5a., 1j.2i.3g.4f.5a., 1p.2i.3g.4f.5a.,
1a.2m.3g.4f.5a., 1b.2m.3g.4f.5a., 1f.2m.3g.4f.5a., 1h.2m.3g.4f.5a.,
1j.2m.3g.4f.5a., 1p.2m.3g.4f.5a., 1a.2o.3g.4f.5a., 1b.2o.3g.4f.5a.,
1f.2o.3g.4f.5a., 1h.2o.3g.4f.5a., 1j.2o.3g.4f.5a., 1p.2o.3g.4f.5a.,
1a.2u.3g.4f.5a., 1b.2u.3g.4f.5a., 1f.2u.3g.4f.5a., 1h.2u.3g.4f.5a.,
1j.2u.3g.4f.5a., 1p.2u.3g.4f.5a., 1a.2y.3g.4f.5a., 1b.2y.3g.4f.5a.,
1f.2y.3g.4f.5a., 1h.2y.3g.4f.5a., 1j.2y.3g.4f.5a., 1p.2y.3g.4f.5a.,
1a.2a.3a.4g.5a., 1b.2a.3a.4g.5a., 1f.2a.3a.4g.5a., 1h.2a.3a.4g.5a.,
1j.2a.3a.4g.5a., 1p.2a.3a.4g.5a., 1a.2b.3a.4g.5a., 1b.2b.3a.4g.5a.,
1f.2b.3a.4g.5a., 1h.2b.3a.4g.5a., 1j.2b.3a.4g.5a., 1p.2b.3a.4g.5a.,
1a.2e.3a.4g.5a., 1b.2e.3a.4g.5a., 1f.2e.3a.4g.5a., 1h.2e.3a.4g.5a.,
1j.2e.3a.4g.5a., 1p.2e.3a.4g.5a., 1a.2f.3a.4g.5a., 1b.2f.3a.4g.5a.,
1f.2f.3a.4g.5a., 1h.2f.3a.4g.5a., 1j.2f.3a.4g.5a., 1p.2f.3a.4g.5a.,
1a.2i.3a.4g.5a., 1b.2i.3a.4g.5a., 1f.2i.3a.4g.5a., 1h.2i.3a.4g.5a.,
1j.2i.3a.4g.5a., 1p.2i.3a.4g.5a., 1a.2m.3a.4g.5a., 1b.2m.3a.4g.5a.,
1f.2m.3a.4g.5a., 1h.2m.3a.4g.5a., 1j.2m.3a.4g.5a., 1p.2m.3a.4g.5a.,
1a.2o.3a.4g.5a., 1b.2o.3a.4g.5a., 1f.2o.3a.4g.5a., 1h.2o.3a.4g.5a.,
1j.2o.3a.4g.5a., 1p.2o.3a.4g.5a., 1a.2u.3a.4g.5a., 1b.2u.3a.4g.5a.,
1f.2u.3a.4g.5a., 1h.2u.3a.4g.5a., 1j.2u.3a.4g.5a., 1p.2u.3a.4g.5a.,
1a.2y.3a.4g.5a., 1b.2y.3a.4g.5a., 1f.2y.3a.4g.5a., 1h.2y.3a.4g.5a.,
1j.2y.3a.4g.5a., 1p.2y.3a.4g.5a., 1a.2a.3b.4g.5a., 1b.2a.3b.4g.5a.,
1f.2a.3b.4g.5a., 1h.2a.3b.4g.5a., 1j.2a.3b.4g.5a., 1p.2a.3b.4g.5a.,
1a.2b.3b.4g.5a., 1b.2b.3b.4g.5a., 1f.2b.3b.4g.5a., 1h.2b.3b.4g.5a.,
1j.2b.3b.4g.5a., 1p.2b.3b.4g.5a., 1a.2e.3b.4g.5a., 1b.2e.3b.4g.5a.,
1f.2e.3b.4g.5a., 1h.2e.3b.4g.5a., 1j.2e.3b.4g.5a., 1p.2e.3b.4g.5a.,
1a.2f.3b.4g.5a., 1b.2f.3b.4g.5a., 1f.2f.3b.4g.5a., 1h.2f.3b.4g.5a.,

TABLE 12-continued

List of Compound Structures of Formula II 1j.2f.3b.4g.5a., 1p.2f.3b.4g.5a., 1a.2i.3b.4g.5a., 1b.2i.3b.4g.5a.,
1f.2i.3b.4g.5a., 1h.2i.3b.4g.5a., 1j.2i.3b.4g.5a., 1p.2i.3b.4g.5a.,
1a.2m.3b.4g.5a., 1b.2m.3b.4g.5a., 1f.2m.3b.4g.5a., 1h.2m.3b.4g.5a.,
1j.2m.3b.4g.5a., 1p.2m.3b.4g.5a., 1a.2o.3b.4g.5a., 1b.2o.3b.4g.5a.,
1f.2o.3b.4g.5a., 1h.2o.3b.4g.5a., 1j.2o.3b.4g.5a., 1p.2o.3b.4g.5a.,
1a.2u.3b.4g.5a., 1b.2u.3b.4g.5a., 1f.2u.3b.4g.5a., 1h.2u.3b.4g.5a.,
1j.2u.3b.4g.5a., 1p.2u.3b.4g.5a., 1a.2y.3b.4g.5a., 1b.2y.3b.4g.5a.,
1f.2y.3b.4g.5a., 1h.2y.3b.4g.5a., 1j.2y.3b.4g.5a., 1p.2y.3b.4g.5a.,
1a.2a.3e.4g.5a., 1b.2a.3e.4g.5a., 1f.2a.3e.4g.5a., 1h.2a.3e.4g.5a.,
1j.2a.3e.4g.5a., 1p.2a.3e.4g.5a., 1a.2b.3e.4g.5a., 1b.2b.3e.4g.5a.,
1f.2b.3e.4g.5a., 1h.2b.3e.4g.5a., 1j.2b.3e.4g.5a., 1p.2b.3e.4g.5a.,
1a.2e.3e.4g.5a., 1b.2e.3e.4g.5a., 1f.2e.3e.4g.5a., 1h.2e.3e.4g.5a.,
1j.2e.3e.4g.5a., 1p.2e.3e.4g.5a., 1a.2f.3e.4g.5a., 1b.2f.3e.4g.5a.,
1f.2f.3e.4g.5a., 1h.2f.3e.4g.5a., 1j.2f.3e.4g.5a., 1p.2f.3e.4g.5a.,
1a.2i.3e.4g.5a., 1b.2i.3e.4g.5a., 1f.2i.3e.4g.5a., 1h.2i.3e.4g.5a.,
1j.2i.3e.4g.5a., 1p.2i.3e.4g.5a., 1a.2m.3e.4g.5a., 1b.2m.3e.4g.5a.,
1f.2m.3e.4g.5a., 1h.2m.3e.4g.5a., 1j.2m.3e.4g.5a., 1p.2m.3e.4g.5a.,
1a.2o.3e.4g.5a., 1b.2o.3e.4g.5a., 1f.2o.3e.4g.5a., 1h.2o.3e.4g.5a.,
1j.2o.3e.4g.5a., 1p.2o.3e.4g.5a., 1a.2u.3e.4g.5a., 1b.2u.3e.4g.5a.,
1f.2u.3e.4g.5a., 1h.2u.3e.4g.5a., 1j.2u.3e.4g.5a., 1p.2u.3e.4g.5a.,
1a.2y.3e.4g.5a., 1b.2y.3e.4g.5a., 1f.2y.3e.4g.5a., 1h.2y.3e.4g.5a.,
1j.2y.3e.4g.5a., 1p.2y.3e.4g.5a., 1a.2a.3g.4g.5a., 1b.2a.3g.4g.5a.,
1f.2a.3g.4g.5a., 1h.2a.3g.4g.5a., 1j.2a.3g.4g.5a., 1p.2a.3g.4g.5a.,
1a.2b.3g.4g.5a., 1b.2b.3g.4g.5a., 1f.2b.3g.4g.5a., 1h.2b.3g.4g.5a.,
1j.2b.3g.4g.5a., 1p.2b.3g.4g.5a., 1a.2e.3g.4g.5a., 1b.2e.3g.4g.5a.,
1f.2e.3g.4g.5a., 1h.2e.3g.4g.5a., 1j.2e.3g.4g.5a., 1p.2e.3g.4g.5a.,
1a.2f.3g.4g.5a., 1b.2f.3g.4g.5a., 1f.2f.3g.4g.5a., 1h.2f.3g.4g.5a.,
1j.2f.3g.4g.5a., 1p.2f.3g.4g.5a., 1a.2i.3g.4g.5a., 1b.2i.3g.4g.5a.,
1f.2i.3g.4g.5a., 1h.2i.3g.4g.5a., 1j.2i.3g.4g.5a., 1p.2i.3g.4g.5a.,
1a.2m.3g.4g.5a., 1b.2m.3g.4g.5a., 1f.2m.3g.4g.5a., 1h.2m.3g.4g.5a.,
1j.2m.3g.4g.5a., 1p.2m.3g.4g.5a., 1a.2o.3g.4g.5a., 1b.2o.3g.4g.5a.,
1f.2o.3g.4g.5a., 1h.2o.3g.4g.5a., 1j.2o.3g.4g.5a., 1p.2o.3g.4g.5a.,
1a.2u.3g.4g.5a., 1b.2u.3g.4g.5a., 1f.2u.3g.4g.5a., 1h.2u.3g.4g.5a.,
1j.2u.3g.4g.5a., 1p.2u.3g.4g.5a., 1a.2y.3g.4g.5a., 1b.2y.3g.4g.5a.,
1f.2y.3g.4g.5a., 1h.2y.3g.4g.5a., 1j.2y.3g.4g.5a., 1p.2y.3g.4g.5a.,
1a.2a.3a.4h.5a., 1b.2a.3a.4h.5a., 1f.2a.3a.4h.5a., 1h.2a.3a.4h.5a.,
1j.2a.3a.4h.5a., 1p.2a.3a.4h.5a., 1a.2b.3a.4h.5a., 1b.2b.3a.4h.5a.,
1f.2b.3a.4h.5a., 1h.2b.3a.4h.5a., 1j.2b.3a.4h.5a., 1p.2b.3a.4h.5a.,
1a.2e.3a.4h.5a., 1b.2e.3a.4h.5a., 1f.2e.3a.4h.5a., 1h.2e.3a.4h.5a.,
1j.2e.3a.4h.5a., 1p.2e.3a.4h.5a., 1a.2f.3a.4h.5a., 1b.2f.3a.4h.5a.,
1f.2f.3a.4h.5a., 1h.2f.3a.4h.5a., 1j.2f.3a.4h.5a., 1p.2f.3a.4h.5a.,
1a.2i.3a.4h.5a., 1b.2i.3a.4h.5a., 1f.2i.3a.4h.5a., 1h.2i.3a.4h.5a.,
1j.2i.3a.4h.5a., 1p.2i.3a.4h.5a., 1a.2m.3a.4h.5a., 1b.2m.3a.4h.5a.,
1f.2m.3a.4h.5a., 1h.2m.3a.4h.5a., 1j.2m.3a.4h.5a., 1p.2m.3a.4h.5a.,
1a.2o.3a.4h.5a., 1b.2o.3a.4h.5a., 1f.2o.3a.4h.5a., 1h.2o.3a.4h.5a.,
1j.2o.3a.4h.5a., 1p.2o.3a.4h.5a., 1a.2u.3a.4h.5a., 1b.2u.3a.4h.5a.,
1f.2u.3a.4h.5a., 1h.2u.3a.4h.5a., 1j.2u.3a.4h.5a., 1p.2u.3a.4h.5a.,
1a.2y.3a.4h.5a., 1b.2y.3a.4h.5a., 1f.2y.3a.4h.5a., 1h.2y.3a.4h.5a.,
1j.2y.3a.4h.5a., 1p.2y.3a.4h.5a., 1a.2a.3b.4h.5a., 1b.2a.3b.4h.5a.,
1f.2a.3b.4h.5a., 1h.2a.3b.4h.5a., 1j.2a.3b.4h.5a., 1p.2a.3b.4h.5a.,
1a.2b.3b.4h.5a., 1b.2b.3b.4h.5a., 1f.2b.3b.4h.5a., 1h.2b.3b.4h.5a.,
1j.2b.3b.4h.5a., 1p.2b.3b.4h.5a., 1a.2e.3b.4h.5a., 1b.2e.3b.4h.5a.,
1f.2e.3b.4h.5a., 1h.2e.3b.4h.5a., 1j.2e.3b.4h.5a., 1p.2e.3b.4h.5a.,
1a.2f.3b.4h.5a., 1b.2f.3b.4h.5a., 1f.2f.3b.4h.5a., 1h.2f.3b.4h.5a.,
1j.2f.3b.4h.5a., 1p.2f.3b.4h.5a., 1a.2i.3b.4h.5a., 1b.2i.3b.4h.5a.,
1f.2i.3b.4h.5a., 1h.2i.3b.4h.5a., 1j.2i.3b.4h.5a., 1p.2i.3b.4h.5a.,
1a.2m.3b.4h.5a., 1b.2m.3b.4h.5a., 1f.2m.3b.4h.5a., 1h.2m.3b.4h.5a.,
1j.2m.3b.4h.5a., 1p.2m.3b.4h.5a., 1a.2o.3b.4h.5a., 1b.2o.3b.4h.5a.,
1f.2o.3b.4h.5a., 1h.2o.3b.4h.5a., 1j.2o.3b.4h.5a., 1p.2o.3b.4h.5a.,
1a.2u.3b.4h.5a., 1b.2u.3b.4h.5a., 1f.2u.3b.4h.5a., 1h.2u.3b.4h.5a.,
1j.2u.3b.4h.5a., 1p.2u.3b.4h.5a., 1a.2y.3b.4h.5a., 1b.2y.3b.4h.5a.,
1f.2y.3b.4h.5a., 1h.2y.3b.4h.5a., 1j.2y.3b.4h.5a., 1p.2y.3b.4h.5a.,
1a.2a.3e.4h.5a., 1b.2a.3e.4h.5a., 1f.2a.3e.4h.5a., 1h.2a.3e.4h.5a.,
1j.2a.3e.4h.5a., 1p.2a.3e.4h.5a., 1a.2b.3e.4h.5a., 1b.2b.3e.4h.5a.,
1f.2b.3e.4h.5a., 1h.2b.3e.4h.5a., 1j.2b.3e.4h.5a., 1p.2b.3e.4h.5a.,
1a.2e.3e.4h.5a., 1b.2e.3e.4h.5a., 1f.2e.3e.4h.5a., 1h.2e.3e.4h.5a.,
1j.2e.3e.4h.5a., 1p.2e.3e.4h.5a., 1a.2f.3e.4h.5a., 1b.2f.3e.4h.5a.,
1f.2f.3e.4h.5a., 1h.2f.3e.4h.5a., 1j.2f.3e.4h.5a., 1p.2f.3e.4h.5a.,
1a.2i.3e.4h.5a., 1b.2i.3e.4h.5a., 1f.2i.3e.4h.5a., 1h.2i.3e.4h.5a.,
1j.2i.3e.4h.5a., 1p.2i.3e.4h.5a., 1a.2m.3e.4h.5a., 1b.2m.3e.4h.5a.,
1f.2m.3e.4h.5a., 1h.2m.3e.4h.5a., 1j.2m.3e.4h.5a., 1p.2m.3e.4h.5a.,
1a.2o.3e.4h.5a., 1b.2o.3e.4h.5a., 1f.2o.3e.4h.5a., 1h.2o.3e.4h.5a.,
1j.2o.3e.4h.5a., 1p.2o.3e.4h.5a., 1a.2u.3e.4h.5a., 1b.2u.3e.4h.5a.,
1f.2u.3e.4h.5a., 1h.2u.3e.4h.5a., 1j.2u.3e.4h.5a., 1p.2u.3e.4h.5a.,
1a.2y.3e.4h.5a., 1b.2y.3e.4h.5a., 1f.2y.3e.4h.5a., 1h.2y.3e.4h.5a.,
1j.2y.3e.4h.5a., 1p.2y.3e.4h.5a., 1a.2a.3g.4h.5a., 1b.2a.3g.4h.5a.,
1f.2a.3g.4h.5a., 1h.2a.3g.4h.5a., 1j.2a.3g.4h.5a., 1p.2a.3g.4h.5a.,
1a.2b.3g.4h.5a., 1b.2b.3g.4h.5a., 1f.2b.3g.4h.5a., 1h.2b.3g.4h.5a.,
1j.2b.3g.4h.5a., 1p.2b.3g.4h.5a., 1a.2e.3g.4h.5a., 1b.2e.3g.4h.5a.,
1f.2e.3g.4h.5a., 1h.2e.3g.4h.5a., 1j.2e.3g.4h.5a., 1p.2e.3g.4h.5a.,
1a.2f.3g.4h.5a., 1b.2f.3g.4h.5a., 1f.2f.3g.4h.5a., 1h.2f.3g.4h.5a.,
1j.2f.3g.4h.5a., 1p.2f.3g.4h.5a., 1a.2i.3g.4h.5a., 1b.2i.3g.4h.5a.,
1f.2i.3g.4h.5a., 1h.2i.3g.4h.5a., 1j.2i.3g.4h.5a., 1p.2i.3g.4h.5a.,
1a.2m.3g.4h.5a., 1b.2m.3g.4h.5a., 1f.2m.3g.4h.5a., 1h.2m.3g.4h.5a.,
1j.2m.3g.4h.5a., 1p.2m.3g.4h.5a., 1a.2o.3g.4h.5a., 1b.2o.3g.4h.5a.,
1f.2o.3g.4h.5a., 1h.2o.3g.4h.5a., 1j.2o.3g.4h.5a., 1p.2o.3g.4h.5a.,
1a.2u.3g.4h.5a., 1b.2u.3g.4h.5a., 1f.2u.3g.4h.5a., 1h.2u.3g.4h.5a.,
1j.2u.3g.4h.5a., 1p.2u.3g.4h.5a., 1a.2y.3g.4h.5a., 1b.2y.3g.4h.5a.,
1f.2y.3g.4h.5a., 1h.2y.3g.4h.5a., 1j.2y.3g.4h.5a., 1p.2y.3g.4h.5a.,
1a.2a.3a.4i.5a., 1b.2a.3a.4i.5a., 1f.2a.3a.4i.5a., 1h.2a.3a.4i.5a.,
1j.2a.3a.4i.5a., 1p.2a.3a.4i.5a., 1a.2b.3a.4i.5a., 1b.2b.3a.4i.5a.,
1f.2b.3a.4i.5a., 1h.2b.3a.4i.5a., 1j.2b.3a.4i.5a., 1p.2b.3a.4i.5a.,
1a.2e.3a.4i.5a., 1b.2e.3a.4i.5a., 1f.2e.3a.4i.5a., 1h.2e.3a.4i.5a.,
1j.2e.3a.4i.5a., 1p.2e.3a.4i.5a., 1a.2f.3a.4i.5a., 1b.2f.3a.4i.5a.,
1f.2f.3a.4i.5a., 1h.2f.3a.4i.5a., 1j.2f.3a.4i.5a., 1p.2f.3a.4i.5a.,
1a.2i.3a.4i.5a., 1b.2i.3a.4i.5a., 1f.2i.3a.4i.5a., 1h.2i.3a.4i.5a.,
1j.2i.3a.4i.5a., 1p.2i.3a.4i.5a., 1a.2m.3a.4i.5a., 1b.2m.3a.4i.5a.,
1f.2m.3a.4i.5a., 1h.2m.3a.4i.5a., 1j.2m.3a.4i.5a., 1p.2m.3a.4i.5a.,
1a.2o.3a.4i.5a., 1b.2o.3a.4i.5a., 1f.2o.3a.4i.5a., 1h.2o.3a.4i.5a.,
1j.2o.3a.4i.5a., 1p.2o.3a.4i.5a., 1a.2u.3a.4i.5a., 1b.2u.3a.4i.5a.,
1f.2u.3a.4i.5a., 1h.2u.3a.4i.5a., 1j.2u.3a.4i.5a., 1p.2u.3a.4i.5a.,
1a.2y.3a.4i.5a., 1b.2y.3a.4i.5a., 1f.2y.3a.4i.5a., 1h.2y.3a.4i.5a.,
1j.2y.3a.4i.5a., 1p.2y.3a.4i.5a., 1a.2a.3b.4i.5a., 1b.2a.3b.4i.5a.,
1f.2a.3b.4i.5a., 1h.2a.3b.4i.5a., 1j.2a.3b.4i.5a., 1p.2a.3b.4i.5a.,
1a.2b.3b.4i.5a., 1b.2b.3b.4i.5a., 1f.2b.3b.4i.5a., 1h.2b.3b.4i.5a.,
1j.2b.3b.4i.5a., 1p.2b.3b.4i.5a., 1a.2e.3b.4i.5a., 1b.2e.3b.4i.5a.,
1f.2e.3b.4i.5a., 1h.2e.3b.4i.5a., 1j.2e.3b.4i.5a., 1p.2e.3b.4i.5a.,
1a.2f.3b.4i.5a., 1b.2f.3b.4i.5a., 1f.2f.3b.4i.5a., 1h.2f.3b.4i.5a.,
1j.2f.3b.4i.5a., 1p.2f.3b.4i.5a., 1a.2i.3b.4i.5a., 1b.2i.3b.4i.5a.,
1f.2i.3b.4i.5a., 1h.2i.3b.4i.5a., 1j.2i.3b.4i.5a., 1p.2i.3b.4i.5a.,
1a.2m.3b.4i.5a., 1b.2m.3b.4i.5a., 1f.2m.3b.4i.5a., 1h.2m.3b.4i.5a.,
1j.2m.3b.4i.5a., 1p.2m.3b.4i.5a., 1a.2o.3b.4i.5a., 1b.2o.3b.4i.5a.,
1f.2o.3b.4i.5a., 1h.2o.3b.4i.5a., 1j.2o.3b.4i.5a., 1p.2o.3b.4i.5a.,
1a.2u.3b.4i.5a., 1b.2u.3b.4i.5a., 1f.2u.3b.4i.5a., 1h.2u.3b.4i.5a.,
1j.2u.3b.4i.5a., 1p.2u.3b.4i.5a., 1a.2y.3b.4i.5a., 1b.2y.3b.4i.5a.,
1f.2y.3b.4i.5a., 1h.2y.3b.4i.5a., 1j.2y.3b.4i.5a., 1p.2y.3b.4i.5a.,
1a.2a.3e.4i.5a., 1b.2a.3e.4i.5a., 1f.2a.3e.4i.5a., 1h.2a.3e.4i.5a.,
1j.2a.3e.4i.5a., 1p.2a.3e.4i.5a., 1a.2b.3e.4i.5a., 1b.2b.3e.4i.5a.,
1f.2b.3e.4i.5a., 1h.2b.3e.4i.5a., 1j.2b.3e.4i.5a., 1p.2b.3e.4i.5a.,
1a.2e.3e.4i.5a., 1b.2e.3e.4i.5a., 1f.2e.3e.4i.5a., 1h.2e.3e.4i.5a.,
1j.2e.3e.4i.5a., 1p.2e.3e.4i.5a., 1a.2f.3e.4i.5a., 1b.2f.3e.4i.5a.,
1f.2f.3e.4i.5a., 1h.2f.3e.4i.5a., 1j.2f.3e.4i.5a., 1p.2f.3e.4i.5a.,
1a.2i.3e.4i.5a., 1b.2i.3e.4i.5a., 1f.2i.3e.4i.5a., 1h.2i.3e.4i.5a.,
1j.2i.3e.4i.5a., 1p.2i.3e.4i.5a., 1a.2m.3e.4i.5a., 1b.2m.3e.4i.5a.,
1f.2m.3e.4i.5a., 1h.2m.3e.4i.5a., 1j.2m.3e.4i.5a., 1p.2m.3e.4i.5a.,
1a.2o.3e.4i.5a., 1b.2o.3e.4i.5a., 1f.2o.3e.4i.5a., 1h.2o.3e.4i.5a.,
1j.2o.3e.4i.5a., 1p.2o.3e.4i.5a., 1a.2u.3e.4i.5a., 1b.2u.3e.4i.5a.,
1f.2u.3e.4i.5a., 1h.2u.3e.4i.5a., 1j.2u.3e.4i.5a., 1p.2u.3e.4i.5a.,
1a.2y.3e.4i.5a., 1b.2y.3e.4i.5a., 1f.2y.3e.4i.5a., 1h.2y.3e.4i.5a.,
1j.2y.3e.4i.5a., 1p.2y.3e.4i.5a., 1a.2a.3g.4i.5a., 1b.2a.3g.4i.5a.,
1f.2a.3g.4i.5a., 1h.2a.3g.4i.5a., 1j.2a.3g.4i.5a., 1p.2a.3g.4i.5a.,
1a.2b.3g.4i.5a., 1b.2b.3g.4i.5a., 1f.2b.3g.4i.5a., 1h.2b.3g.4i.5a.,
1j.2b.3g.4i.5a., 1p.2b.3g.4i.5a., 1a.2e.3g.4i.5a., 1b.2e.3g.4i.5a.,
1f.2e.3g.4i.5a., 1h.2e.3g.4i.5a., 1j.2e.3g.4i.5a., 1p.2e.3g.4i.5a.,
1a.2f.3g.4i.5a., 1b.2f.3g.4i.5a., 1f.2f.3g.4i.5a., 1h.2f.3g.4i.5a.,
1j.2f.3g.4i.5a., 1p.2f.3g.4i.5a., 1a.2i.3g.4i.5a., 1b.2i.3g.4i.5a.,
1f.2i.3g.4i.5a., 1h.2i.3g.4i.5a., 1j.2i.3g.4i.5a., 1p.2i.3g.4i.5a.,
1a.2m.3g.4i.5a., 1b.2m.3g.4i.5a., 1f.2m.3g.4i.5a., 1h.2m.3g.4i.5a.,
1j.2m.3g.4i.5a., 1p.2m.3g.4i.5a., 1a.2o.3g.4i.5a., 1b.2o.3g.4i.5a.,
1f.2o.3g.4i.5a., 1h.2o.3g.4i.5a., 1j.2o.3g.4i.5a., 1p.2o.3g.4i.5a.,
1a.2u.3g.4i.5a., 1b.2u.3g.4i.5a., 1f.2u.3g.4i.5a., 1h.2u.3g.4i.5a.,
1j.2u.3g.4i.5a., 1p.2u.3g.4i.5a., 1a.2y.3g.4i.5a., 1b.2y.3g.4i.5a.,
1f.2y.3g.4i.5a., 1h.2y.3g.4i.5a., 1j.2y.3g.4i.5a., 1p.2y.3g.4i.5a.,
1a.2a.3a.4a.5d., 1b.2a.3a.4a.5d., 1f.2a.3a.4a.5d., 1h.2a.3a.4a.5d.,
1j.2a.3a.4a.5d., 1p.2a.3a.4a.5d., 1a.2b.3a.4a.5d., 1b.2b.3a.4a.5d.,
1f.2b.3a.4a.5d., 1h.2b.3a.4a.5d., 1j.2b.3a.4a.5d., 1p.2b.3a.4a.5d.,
1a.2e.3a.4a.5d., 1b.2e.3a.4a.5d., 1f.2e.3a.4a.5d., 1h.2e.3a.4a.5d.,
1j.2e.3a.4a.5d., 1p.2e.3a.4a.5d., 1a.2f.3a.4a.5d., 1b.2f.3a.4a.5d.,
1f.2f.3a.4a.5d., 1h.2f.3a.4a.5d., 1j.2f.3a.4a.5d., 1p.2f.3a.4a.5d.,
1a.2i.3a.4a.5d., 1b.2i.3a.4a.5d., 1f.2i.3a.4a.5d., 1h.2i.3a.4a.5d.,
1j.2i.3a.4a.5d., 1p.2i.3a.4a.5d., 1a.2m.3a.4a.5d., 1b.2m.3a.4a.5d.,
1f.2m.3a.4a.5d., 1h.2m.3a.4a.5d., 1j.2m.3a.4a.5d., 1p.2m.3a.4a.5d.,
1a.2o.3a.4a.5d., 1b.2o.3a.4a.5d., 1f.2o.3a.4a.5d., 1h.2o.3a.4a.5d.,
1j.2o.3a.4a.5d., 1p.2o.3a.4a.5d., 1a.2u.3a.4a.5d., 1b.2u.3a.4a.5d.,
1f.2u.3a.4a.5d., 1h.2u.3a.4a.5d., 1j.2u.3a.4a.5d., 1p.2u.3a.4a.5d.,
1a.2y.3a.4a.5d., 1b.2y.3a.4a.5d., 1f.2y.3a.4a.5d., 1h.2y.3a.4a.5d.,

TABLE 12-continued

List of Compound Structures of Formula II 1j.2y.3a.4a.5d., 1p.2y.3a.4a.5d., 1a.2a.3b.4a.5d., 1b.2a.3b.4a.5d.,
1f.2a.3b.4a.5d., 1h.2a.3b.4a.5d., 1j.2a.3b.4a.5d., 1p.2a.3b.4a.5d.,
1a.2b.3b.4a.5d., 1b.2b.3b.4a.5d., 1f.2b.3b.4a.5d., 1h.2b.3b.4a.5d.,
1j.2b.3b.4a.5d., 1p.2b.3b.4a.5d., 1a.2e.3b.4a.5d., 1b.2e.3b.4a.5d.,
1f.2e.3b.4a.5d., 1h.2e.3b.4a.5d., 1j.2e.3b.4a.5d., 1p.2e.3b.4a.5d.,
1a.2f.3b.4a.5d., 1b.2f.3b.4a.5d., 1f.2f.3b.4a.5d., 1h.2f.3b.4a.5d.,
1j.2f.3b.4a.5d., 1p.2f.3b.4a.5d., 1a.2i.3b.4a.5d., 1b.2i.3b.4a.5d.,
1f.2i.3b.4a.5d., 1h.2i.3b.4a.5d., 1j.2i.3b.4a.5d., 1p.2i.3b.4a.5d.,
1a.2m.3b.4a.5d., 1b.2m.3b.4a.5d., 1f.2m.3b.4a.5d., 1h.2m.3b.4a.5d.,
1j.2m.3b.4a.5d., 1p.2m.3b.4a.5d., 1a.2o.3b.4a.5d., 1b.2o.3b.4a.5d.,
1f.2o.3b.4a.5d., 1h.2o.3b.4a.5d., 1j.2o.3b.4a.5d., 1p.2o.3b.4a.5d.,
1a.2u.3b.4a.5d., 1b.2u.3b.4a.5d., 1f.2u.3b.4a.5d., 1h.2u.3b.4a.5d.,
1j.2u.3b.4a.5d., 1p.2u.3b.4a.5d., 1a.2y.3b.4a.5d., 1b.2y.3b.4a.5d.,
1f.2y.3b.4a.5d., 1h.2y.3b.4a.5d., 1j.2y.3b.4a.5d., 1p.2y.3b.4a.5d.,
1a.2a.3e.4a.5d., 1b.2a.3e.4a.5d., 1f.2a.3e.4a.5d., 1h.2a.3e.4a.5d.,
1j.2a.3e.4a.5d., 1p.2a.3e.4a.5d., 1a.2b.3e.4a.5d., 1b.2b.3e.4a.5d.,
1f.2b.3e.4a.5d., 1h.2b.3e.4a.5d., 1j.2b.3e.4a.5d., 1p.2b.3e.4a.5d.,
1a.2e.3e.4a.5d., 1b.2e.3e.4a.5d., 1f.2e.3e.4a.5d., 1h.2e.3e.4a.5d.,
1j.2e.3e.4a.5d., 1p.2e.3e.4a.5d., 1a.2f.3e.4a.5d., 1b.2f.3e.4a.5d.,
1f.2f.3e.4a.5d., 1h.2f.3e.4a.5d., 1j.2f.3e.4a.5d., 1p.2f.3e.4a.5d.,
1a.2i.3e.4a.5d., 1b.2i.3e.4a.5d., 1f.2i.3e.4a.5d., 1h.2i.3e.4a.5d.,
1j.2i.3e.4a.5d., 1p.2i.3e.4a.5d., 1a.2m.3e.4a.5d., 1b.2m.3e.4a.5d.,
1f.2m.3e.4a.5d., 1h.2m.3e.4a.5d., 1j.2m.3e.4a.5d., 1p.2m.3e.4a.5d.,
1a.2o.3e.4a.5d., 1b.2o.3e.4a.5d., 1f.2o.3e.4a.5d., 1h.2o.3e.4a.5d.,
1j.2o.3e.4a.5d., 1p.2o.3e.4a.5d., 1a.2u.3e.4a.5d., 1b.2u.3e.4a.5d.,
1f.2u.3e.4a.5d., 1h.2u.3e.4a.5d., 1j.2u.3e.4a.5d., 1p.2u.3e.4a.5d.,
1a.2y.3e.4a.5d., 1b.2y.3e.4a.5d., 1f.2y.3e.4a.5d., 1h.2y.3e.4a.5d.,
1j.2y.3e.4a.5d., 1p.2y.3e.4a.5d., 1a.2a.3g.4a.5d., 1b.2a.3g.4a.5d.,
1f.2a.3g.4a.5d., 1h.2a.3g.4a.5d., 1j.2a.3g.4a.5d., 1p.2a.3g.4a.5d.,
1a.2b.3g.4a.5d., 1b.2b.3g.4a.5d., 1f.2b.3g.4a.5d., 1h.2b.3g.4a.5d.,
1j.2b.3g.4a.5d., 1p.2b.3g.4a.5d., 1a.2e.3g.4a.5d., 1b.2e.3g.4a.5d.,
1f.2e.3g.4a.5d., 1h.2e.3g.4a.5d., 1j.2e.3g.4a.5d., 1p.2e.3g.4a.5d.,
1a.2f.3g.4a.5d., 1b.2f.3g.4a.5d., 1f.2f.3g.4a.5d., 1h.2f.3g.4a.5d.,
1j.2f.3g.4a.5d., 1p.2f.3g.4a.5d., 1a.2i.3g.4a.5d., 1b.2i.3g.4a.5d.,
1f.2i.3g.4a.5d., 1h.2i.3g.4a.5d., 1j.2i.3g.4a.5d., 1p.2i.3g.4a.5d.,
1a.2m.3g.4a.5d., 1b.2m.3g.4a.5d., 1f.2m.3g.4a.5d., 1h.2m.3g.4a.5d.,
1j.2m.3g.4a.5d., 1p.2m.3g.4a.5d., 1a.2o.3g.4a.5d., 1b.2o.3g.4a.5d.,
1f.2o.3g.4a.5d., 1h.2o.3g.4a.5d., 1j.2o.3g.4a.5d., 1p.2o.3g.4a.5d.,
1a.2u.3g.4a.5d., 1b.2u.3g.4a.5d., 1f.2u.3g.4a.5d., 1h.2u.3g.4a.5d.,
1j.2u.3g.4a.5d., 1p.2u.3g.4a.5d., 1a.2y.3g.4a.5d., 1b.2y.3g.4a.5d.,
1f.2y.3g.4a.5d., 1h.2y.3g.4a.5d., 1j.2y.3g.4a.5d., 1p.2y.3g.4a.5d.,
1a.2a.3a.4d.5d., 1b.2a.3a.4d.5d., 1f.2a.3a.4d.5d., 1h.2a.3a.4d.5d.,
1j.2a.3a.4d.5d., 1p.2a.3a.4d.5d., 1a.2b.3a.4d.5d., 1b.2b.3a.4d.5d.,
1f.2b.3a.4d.5d., 1h.2b.3a.4d.5d., 1j.2b.3a.4d.5d., 1p.2b.3a.4d.5d.,
1a.2e.3a.4d.5d., 1b.2e.3a.4d.5d., 1f.2e.3a.4d.5d., 1h.2e.3a.4d.5d.,
1j.2e.3a.4d.5d., 1p.2e.3a.4d.5d., 1a.2f.3a.4d.5d., 1b.2f.3a.4d.5d.,
1f.2f.3a.4d.5d., 1h.2f.3a.4d.5d., 1j.2f.3a.4d.5d., 1p.2f.3a.4d.5d.,
1a.2i.3a.4d.5d., 1b.2i.3a.4d.5d., 1f.2i.3a.4d.5d., 1h.2i.3a.4d.5d.,
1j.2i.3a.4d.5d., 1p.2i.3a.4d.5d., 1a.2m.3a.4d.5d., 1b.2m.3a.4d.5d.,
1f.2m.3a.4d.5d., 1h.2m.3a.4d.5d., 1j.2m.3a.4d.5d., 1p.2m.3a.4d.5d.,
1a.2o.3a.4d.5d., 1b.2o.3a.4d.5d., 1f.2o.3a.4d.5d., 1h.2o.3a.4d.5d.,
1j.2o.3a.4d.5d., 1p.2o.3a.4d.5d., 1a.2u.3a.4d.5d., 1b.2u.3a.4d.5d.,
1f.2u.3a.4d.5d., 1h.2u.3a.4d.5d., 1j.2u.3a.4d.5d., 1p.2u.3a.4d.5d.,
1a.2y.3a.4d.5d., 1b.2y.3a.4d.5d., 1f.2y.3a.4d.5d., 1h.2y.3a.4d.5d.,
1j.2y.3a.4d.5d., 1p.2y.3a.4d.5d., 1a.2a.3b.4d.5d., 1b.2a.3b.4d.5d.,
1f.2a.3b.4d.5d., 1h.2a.3b.4d.5d., 1j.2a.3b.4d.5d., 1p.2a.3b.4d.5d.,
1a.2b.3b.4d.5d., 1b.2b.3b.4d.5d., 1f.2b.3b.4d.5d., 1h.2b.3b.4d.5d.,
1j.2b.3b.4d.5d., 1p.2b.3b.4d.5d., 1a.2e.3b.4d.5d., 1b.2e.3b.4d.5d.,
1f.2e.3b.4d.5d., 1h.2e.3b.4d.5d., 1j.2e.3b.4d.5d., 1p.2e.3b.4d.5d.,
1a.2f.3b.4d.5d., 1b.2f.3b.4d.5d., 1f.2f.3b.4d.5d., 1h.2f.3b.4d.5d.,
1j.2f.3b.4d.5d., 1p.2f.3b.4d.5d., 1a.2i.3b.4d.5d., 1b.2i.3b.4d.5d.,
1f.2i.3b.4d.5d., 1h.2i.3b.4d.5d., 1j.2i.3b.4d.5d., 1p.2i.3b.4d.5d.,
1a.2m.3b.4d.5d., 1b.2m.3b.4d.5d., 1f.2m.3b.4d.5d., 1h.2m.3b.4d.5d.,
1j.2m.3b.4d.5d., 1p.2m.3b.4d.5d., 1a.2o.3b.4d.5d., 1b.2o.3b.4d.5d.,
1f.2o.3b.4d.5d., 1h.2o.3b.4d.5d., 1j.2o.3b.4d.5d., 1p.2o.3b.4d.5d.,
1a.2u.3b.4d.5d., 1b.2u.3b.4d.5d., 1f.2u.3b.4d.5d., 1h.2u.3b.4d.5d.,
1j.2u.3b.4d.5d., 1p.2u.3b.4d.5d., 1a.2y.3b.4d.5d., 1b.2y.3b.4d.5d.,
1f.2y.3b.4d.5d., 1h.2y.3b.4d.5d., 1j.2y.3b.4d.5d., 1p.2y.3b.4d.5d.,
1a.2a.3e.4d.5d., 1b.2a.3e.4d.5d., 1f.2a.3e.4d.5d., 1h.2a.3e.4d.5d.,
1j.2a.3e.4d.5d., 1p.2a.3e.4d.5d., 1a.2b.3e.4d.5d., 1b.2b.3e.4d.5d.,
1f.2b.3e.4d.5d., 1h.2b.3e.4d.5d., 1j.2b.3e.4d.5d., 1p.2b.3e.4d.5d.,
1a.2e.3e.4d.5d., 1b.2e.3e.4d.5d., 1f.2e.3e.4d.5d., 1h.2e.3e.4d.5d.,
1j.2e.3e.4d.5d., 1p.2e.3e.4d.5d., 1a.2f.3e.4d.5d., 1b.2f.3e.4d.5d.,
1f.2f.3e.4d.5d., 1h.2f.3e.4d.5d., 1j.2f.3e.4d.5d., 1p.2f.3e.4d.5d.,
1a.2i.3e.4d.5d., 1b.2i.3e.4d.5d., 1f.2i.3e.4d.5d., 1h.2i.3e.4d.5d.,
1j.2i.3e.4d.5d., 1p.2i.3e.4d.5d., 1a.2m.3e.4d.5d., 1b.2m.3e.4d.5d.,
1f.2m.3e.4d.5d., 1h.2m.3e.4d.5d., 1j.2m.3e.4d.5d., 1p.2m.3e.4d.5d.,
1a.2o.3e.4d.5d., 1b.2o.3e.4d.5d., 1f.2o.3e.4d.5d., 1h.2o.3e.4d.5d.,
1j.2o.3e.4d.5d., 1p.2o.3e.4d.5d., 1a.2u.3e.4d.5d., 1b.2u.3e.4d.5d.,
1f.2u.3e.4d.5d., 1h.2u.3e.4d.5d., 1j.2u.3e.4d.5d., 1p.2u.3e.4d.5d.,
1a.2y.3e.4d.5d., 1b.2y.3e.4d.5d., 1f.2y.3e.4d.5d., 1h.2y.3e.4d.5d.,
1j.2y.3e.4d.5d., 1p.2y.3e.4d.5d., 1a.2a.3g.4d.5d., 1b.2a.3g.4d.5d.,
1f.2a.3g.4d.5d., 1h.2a.3g.4d.5d., 1j.2a.3g.4d.5d., 1p.2a.3g.4d.5d.,
1a.2b.3g.4d.5d., 1b.2b.3g.4d.5d., 1f.2b.3g.4d.5d., 1h.2b.3g.4d.5d.,
1j.2b.3g.4d.5d., 1p.2b.3g.4d.5d., 1a.2e.3g.4d.5d., 1b.2e.3g.4d.5d.,
1f.2e.3g.4d.5d., 1h.2e.3g.4d.5d., 1j.2e.3g.4d.5d., 1p.2e.3g.4d.5d.,
1a.2f.3g.4d.5d., 1b.2f.3g.4d.5d., 1f.2f.3g.4d.5d., 1h.2f.3g.4d.5d.,
1j.2f.3g.4d.5d., 1p.2f.3g.4d.5d., 1a.2i.3g.4d.5d., 1b.2i.3g.4d.5d.,
1f.2i.3g.4d.5d., 1h.2i.3g.4d.5d., 1j.2i.3g.4d.5d., 1p.2i.3g.4d.5d.,
1a.2m.3g.4d.5d., 1b.2m.3g.4d.5d., 1f.2m.3g.4d.5d., 1h.2m.3g.4d.5d.,
1j.2m.3g.4d.5d., 1p.2m.3g.4d.5d., 1a.2o.3g.4d.5d., 1b.2o.3g.4d.5d.,
1f.2o.3g.4d.5d., 1h.2o.3g.4d.5d., 1j.2o.3g.4d.5d., 1p.2o.3g.4d.5d.,
1a.2u.3g.4d.5d., 1b.2u.3g.4d.5d., 1f.2u.3g.4d.5d., 1h.2u.3g.4d.5d.,
1j.2u.3g.4d.5d., 1p.2u.3g.4d.5d., 1a.2y.3g.4d.5d., 1b.2y.3g.4d.5d.,
1f.2y.3g.4d.5d., 1h.2y.3g.4d.5d., 1j.2y.3g.4d.5d., 1p.2y.3g.4d.5d.,
1a.2a.3a.4f.5d., 1b.2a.3a.4f.5d., 1f.2a.3a.4f.5d., 1h.2a.3a.4f.5d.,
1j.2a.3a.4f.5d., 1p.2a.3a.4f.5d., 1a.2b.3a.4f.5d., 1b.2b.3a.4f.5d.,
1f.2b.3a.4f.5d., 1h.2b.3a.4f.5d., 1j.2b.3a.4f.5d., 1p.2b.3a.4f.5d.,
1a.2e.3a.4f.5d., 1b.2e.3a.4f.5d., 1f.2e.3a.4f.5d., 1h.2e.3a.4f.5d.,
1j.2e.3a.4f.5d., 1p.2e.3a.4f.5d., 1a.2f.3a.4f.5d., 1b.2f.3a.4f.5d.,
1f.2f.3a.4f.5d., 1h.2f.3a.4f.5d., 1j.2f.3a.4f.5d., 1p.2f.3a.4f.5d.,
1a.2i.3a.4f.5d., 1b.2i.3a.4f.5d., 1f.2i.3a.4f.5d., 1h.2i.3a.4f.5d.,
1j.2i.3a.4f.5d., 1p.2i.3a.4f.5d., 1a.2m.3a.4f.5d., 1b.2m.3a.4f.5d.,
1f.2m.3a.4f.5d., 1h.2m.3a.4f.5d., 1j.2m.3a.4f.5d., 1p.2m.3a.4f.5d.,
1a.2o.3a.4f.5d., 1b.2o.3a.4f.5d., 1f.2o.3a.4f.5d., 1h.2o.3a.4f.5d.,
1j.2o.3a.4f.5d., 1p.2o.3a.4f.5d., 1a.2u.3a.4f.5d., 1b.2u.3a.4f.5d.,
1f.2u.3a.4f.5d., 1h.2u.3a.4f.5d., 1j.2u.3a.4f.5d., 1p.2u.3a.4f.5d.,
1a.2y.3a.4f.5d., 1b.2y.3a.4f.5d., 1f.2y.3a.4f.5d., 1h.2y.3a.4f.5d.,
1j.2y.3a.4f.5d., 1p.2y.3a.4f.5d., 1a.2a.3b.4f.5d., 1b.2a.3b.4f.5d.,
1f.2a.3b.4f.5d., 1h.2a.3b.4f.5d., 1j.2a.3b.4f.5d., 1p.2a.3b.4f.5d.,
1a.2b.3b.4f.5d., 1b.2b.3b.4f.5d., 1f.2b.3b.4f.5d., 1h.2b.3b.4f.5d.,
1j.2b.3b.4f.5d., 1p.2b.3b.4f.5d., 1a.2e.3b.4f.5d., 1b.2e.3b.4f.5d.,
1f.2e.3b.4f.5d., 1h.2e.3b.4f.5d., 1j.2e.3b.4f.5d., 1p.2e.3b.4f.5d.,
1a.2f.3b.4f.5d., 1b.2f.3b.4f.5d., 1f.2f.3b.4f.5d., 1h.2f.3b.4f.5d.,
1j.2f.3b.4f.5d., 1p.2f.3b.4f.5d., 1a.2i.3b.4f.5d., 1b.2i.3b.4f.5d.,
1f.2i.3b.4f.5d., 1h.2i.3b.4f.5d., 1j.2i.3b.4f.5d., 1p.2i.3b.4f.5d.,
1a.2m.3b.4f.5d., 1b.2m.3b.4f.5d., 1f.2m.3b.4f.5d., 1h.2m.3b.4f.5d.,
1j.2m.3b.4f.5d., 1p.2m.3b.4f.5d., 1a.2o.3b.4f.5d., 1b.2o.3b.4f.5d.,
1f.2o.3b.4f.5d., 1h.2o.3b.4f.5d., 1a.2u.3b.4f.5d., 1b.2u.3b.4f.5d.,
1f.2u.3b.4f.5d., 1h.2u.3b.4f.5d., 1j.2u.3b.4f.5d., 1p.2u.3b.4f.5d.,
1a.2y.3b.4f.5d., 1b.2y.3b.4f.5d., 1f.2y.3b.4f.5d., 1h.2y.3b.4f.5d.,
1j.2y.3b.4f.5d., 1p.2y.3b.4f.5d., 1a.2a.3e.4f.5d., 1b.2a.3e.4f.5d.,
1f.2a.3e.4f.5d., 1h.2a.3e.4f.5d., 1j.2a.3e.4f.5d., 1p.2a.3e.4f.5d.,
1a.2b.3e.4f.5d., 1b.2b.3e.4f.5d., 1f.2b.3e.4f.5d., 1h.2b.3e.4f.5d.,
1j.2b.3e.4f.5d., 1p.2b.3e.4f.5d., 1a.2e.3e.4f.5d., 1b.2e.3e.4f.5d.,
1f.2e.3e.4f.5d., 1h.2e.3e.4f.5d., 1j.2e.3e.4f.5d., 1p.2e.3e.4f.5d.,
1a.2f.3e.4f.5d., 1b.2f.3e.4f.5d., 1f.2f.3e.4f.5d., 1h.2f.3e.4f.5d.,
1j.2f.3e.4f.5d., 1p.2f.3e.4f.5d., 1a.2i.3e.4f.5d., 1b.2i.3e.4f.5d.,
1f.2i.3e.4f.5d., 1h.2i.3e.4f.5d., 1j.2i.3e.4f.5d., 1p.2i.3e.4f.5d., 1a.2m.3e.4f.5d., 1b.2m.3e.4f.5d.,
1f.2m.3e.4f.5d., 1h.2m.3e.4f.5d., 1j.2m.3e.4f.5d., 1p.2m.3e.4f.5d.,
1a.2o.3e.4f.5d., 1b.2o.3e.4f.5d., 1f.2o.3e.4f.5d., 1h.2o.3e.4f.5d.,
1j.2o.3e.4f.5d., 1p.2o.3e.4f.5d., 1a.2u.3e.4f.5d., 1b.2u.3e.4f.5d.,
1f.2u.3e.4f.5d., 1h.2u.3e.4f.5d., 1j.2u.3e.4f.5d., 1p.2u.3e.4f.5d.,
1a.2y.3e.4f.5d., 1b.2y.3e.4f.5d., 1f.2y.3e.4f.5d., 1h.2y.3e.4f.5d.,
1j.2y.3e.4f.5d., 1p.2y.3e.4f.5d., 1a.2a.3g.4f.5d., 1b.2a.3g.4f.5d.,
1f.2a.3g.4f.5d., 1h.2a.3g.4f.5d., 1j.2a.3g.4f.5d., 1p.2a.3g.4f.5d.,
1a.2b.3g.4f.5d., 1b.2b.3g.4f.5d., 1f.2b.3g.4f.5d., 1h.2b.3g.4f.5d.,
1j.2b.3g.4f.5d., 1p.2b.3g.4f.5d., 1a.2e.3g.4f.5d., 1b.2e.3g.4f.5d.,
1f.2e.3g.4f.5d., 1h.2e.3g.4f.5d., 1j.2e.3g.4f.5d., 1p.2e.3g.4f.5d.,
1a.2f.3g.4f.5d., 1b.2f.3g.4f.5d., 1f.2f.3g.4f.5d., 1h.2f.3g.4f.5d.,
1j.2f.3g.4f.5d., 1p.2f.3g.4f.5d., 1a.2i.3g.4f.5d., 1b.2i.3g.4f.5d.,
1f.2i.3g.4f.5d., 1h.2i.3g.4f.5d., 1j.2i.3g.4f.5d., 1p.2i.3g.4f.5d.,
1a.2m.3g.4f.5d., 1b.2m.3g.4f.5d., 1f.2m.3g.4f.5d., 1h.2m.3g.4f.5d.,
1j.2m.3g.4f.5d., 1p.2m.3g.4f.5d., 1a.2o.3g.4f.5d., 1b.2o.3g.4f.5d.,
1f.2o.3g.4f.5d., 1h.2o.3g.4f.5d., 1j.2o.3g.4f.5d., 1p.2o.3g.4f.5d.,
1a.2u.3g.4f.5d., 1b.2u.3g.4f.5d., 1f.2u.3g.4f.5d., 1h.2u.3g.4f.5d.,
1j.2u.3g.4f.5d., 1p.2u.3g.4f.5d., 1a.2y.3g.4f.5d., 1b.2y.3g.4f.5d.,
1f.2y.3g.4f.5d., 1h.2y.3g.4f.5d., 1j.2y.3g.4f.5d., 1p.2y.3g.4f.5d.,
1a.2a.3a.4g.5d., 1b.2a.3a.4g.5d., 1f.2a.3a.4g.5d., 1h.2a.3a.4g.5d.,
1j.2a.3a.4g.5d., 1p.2a.3a.4g.5d., 1a.2b.3a.4g.5d., 1b.2b.3a.4g.5d.,
1f.2b.3a.4g.5d., 1h.2b.3a.4g.5d., 1j.2b.3a.4g.5d., 1p.2b.3a.4g.5d.,
1a.2e.3a.4g.5d., 1b.2e.3a.4g.5d., 1f.2e.3a.4g.5d., 1h.2e.3a.4g.5d.,
1j.2e.3a.4g.5d., 1p.2e.3a.4g.5d., 1a.2f.3a.4g.5d., 1b.2f.3a.4g.5d.,
1f.2f.3a.4g.5d., 1h.2f.3a.4g.5d., 1j.2f.3a.4g.5d., 1p.2f.3a.4g.5d.,
1a.2i.3a.4g.5d., 1b.2i.3a.4g.5d., 1f.2i.3a.4g.5d., 1h.2i.3a.4g.5d.,

TABLE 12-continued

List of Compound Structures of Formula II 1j.2i.3a.4g.5d., 1p.2i.3a.4g.5d., 1a.2m.3a.4g.5d., 1b.2m.3a.4g.5d.,
1f.2m.3a.4g.5d., 1h.2m.3a.4g.5d., 1j.2m.3a.4g.5d., 1p.2m.3a.4g.5d.,
1a.2o.3a.4g.5d., 1b.2o.3a.4g.5d., 1f.2o.3a.4g.5d., 1h.2o.3a.4g.5d.,
1j.2o.3a.4g.5d., 1p.2o.3a.4g.5d., 1a.2u.3a.4g.5d., 1b.2u.3a.4g.5d.,
1f.2u.3a.4g.5d., 1h.2u.3a.4g.5d., 1j.2u.3a.4g.5d., 1p.2u.3a.4g.5d.,
1a.2y.3a.4g.5d., 1b.2y.3a.4g.5d., 1f.2y.3a.4g.5d., 1h.2y.3a.4g.5d.,
1j.2y.3a.4g.5d., 1p.2y.3a.4g.5d., 1a.2a.3b.4g.5d., 1b.2a.3b.4g.5d.,
1f.2a.3b.4g.5d., 1h.2a.3b.4g.5d., 1j.2a.3b.4g.5d., 1p.2a.3b.4g.5d.,
1a.2b.3b.4g.5d., 1b.2b.3b.4g.5d., 1f.2b.3b.4g.5d., 1h.2b.3b.4g.5d.,
1j.2b.3b.4g.5d., 1p.2b.3b.4g.5d., 1a.2e.3b.4g.5d., 1b.2e.3b.4g.5d.,
1f.2e.3b.4g.5d., 1h.2e.3b.4g.5d., 1j.2e.3b.4g.5d., 1p.2e.3b.4g.5d.,
1a.2f.3b.4g.5d., 1b.2f.3b.4g.5d., 1f.2f.3b.4g.5d., 1h.2f.3b.4g.5d.,
1j.2f.3b.4g.5d., 1p.2f.3b.4g.5d., 1a.2i.3b.4g.5d., 1b.2i.3b.4g.5d.,
1f.2i.3b.4g.5d., 1h.2i.3b.4g.5d., 1j.2i.3b.4g.5d., 1p.2i.3b.4g.5d.,
1a.2m.3b.4g.5d., 1b.2m.3b.4g.5d., 1f.2m.3b.4g.5d., 1h.2m.3b.4g.5d.,
1j.2m.3b.4g.5d., 1p.2m.3b.4g.5d., 1a.2o.3b.4g.5d., 1b.2o.3b.4g.5d.,
1f.2o.3b.4g.5d., 1h.2o.3b.4g.5d., 1j.2o.3b.4g.5d., 1p.2o.3b.4g.5d.,
1a.2u.3b.4g.5d., 1b.2u.3b.4g.5d., 1f.2u.3b.4g.5d., 1h.2u.3b.4g.5d.,
1j.2u.3b.4g.5d., 1p.2u.3b.4g.5d., 1a.2y.3b.4g.5d., 1b.2y.3b.4g.5d.,
1f.2y.3b.4g.5d., 1h.2y.3b.4g.5d., 1j.2y.3b.4g.5d., 1p.2y.3b.4g.5d.,
1a.2a.3e.4g.5d., 1b.2a.3e.4g.5d., 1f.2a.3e.4g.5d., 1h.2a.3e.4g.5d.,
1j.2a.3e.4g.5d., 1p.2a.3e.4g.5d., 1a.2b.3e.4g.5d., 1b.2b.3e.4g.5d.,
1f.2b.3e.4g.5d., 1h.2b.3e.4g.5d., 1j.2b.3e.4g.5d., 1p.2b.3e.4g.5d.,
1a.2e.3e.4g.5d., 1b.2e.3e.4g.5d., 1f.2e.3e.4g.5d., 1h.2e.3e.4g.5d.,
1j.2e.3e.4g.5d., 1p.2e.3e.4g.5d., 1a.2f.3e.4g.5d., 1b.2f.3e.4g.5d.,
1f.2f.3e.4g.5d., 1h.2f.3e.4g.5d., 1j.2f.3e.4g.5d., 1p.2f.3e.4g.5d.,
1a.2i.3e.4g.5d., 1b.2i.3e.4g.5d., 1f.2i.3e.4g.5d., 1h.2i.3e.4g.5d.,
1j.2i.3e.4g.5d., 1p.2i.3e.4g.5d., 1a.2m.3e.4g.5d., 1b.2m.3e.4g.5d.,
1f.2m.3e.4g.5d., 1h.2m.3e.4g.5d., 1j.2m.3e.4g.5d., 1p.2m.3e.4g.5d.,
1a.2o.3e.4g.5d., 1b.2o.3e.4g.5d., 1f.2o.3e.4g.5d., 1h.2o.3e.4g.5d.,
1j.2o.3e.4g.5d., 1p.2o.3e.4g.5d., 1a.2u.3e.4g.5d., 1b.2u.3e.4g.5d.,
1f.2u.3e.4g.5d., 1h.2u.3e.4g.5d., 1j.2u.3e.4g.5d., 1p.2u.3e.4g.5d.,
1a.2y.3e.4g.5d., 1b.2y.3e.4g.5d., 1f.2y.3e.4g.5d., 1h.2y.3e.4g.5d.,
1j.2y.3e.4g.5d., 1p.2y.3e.4g.5d., 1a.2a.3g.4g.5d., 1b.2a.3g.4g.5d.,
1f.2a.3g.4g.5d., 1h.2a.3g.4g.5d., 1j.2a.3g.4g.5d., 1p.2a.3g.4g.5d.,
1a.2b.3g.4g.5d., 1b.2b.3g.4g.5d., 1f.2b.3g.4g.5d., 1h.2b.3g.4g.5d.,
1j.2b.3g.4g.5d., 1p.2b.3g.4g.5d., 1a.2e.3g.4g.5d., 1b.2e.3g.4g.5d.,
1f.2e.3g.4g.5d., 1h.2e.3g.4g.5d., 1j.2e.3g.4g.5d., 1p.2e.3g.4g.5d.,
1a.2f.3g.4g.5d., 1b.2f.3g.4g.5d., 1f.2f.3g.4g.5d., 1h.2f.3g.4g.5d.,
1j.2f.3g.4g.5d., 1p.2f.3g.4g.5d., 1a.2i.3g.4g.5d., 1b.2i.3g.4g.5d.,
1f.2i.3g.4g.5d., 1h.2i.3g.4g.5d., 1j.2i.3g.4g.5d., 1p.2i.3g.4g.5d.,
1a.2m.3g.4g.5d., 1b.2m.3g.4g.5d., 1f.2m.3g.4g.5d., 1h.2m.3g.4g.5d.,
1j.2m.3g.4g.5d., 1p.2m.3g.4g.5d., 1a.2o.3g.4g.5d., 1b.2o.3g.4g.5d.,
1f.2o.3g.4g.5d., 1h.2o.3g.4g.5d., 1j.2o.3g.4g.5d., 1p.2o.3g.4g.5d.,
1a.2u.3g.4g.5d., 1b.2u.3g.4g.5d., 1f.2u.3g.4g.5d., 1h.2u.3g.4g.5d.,
1j.2u.3g.4g.5d., 1p.2u.3g.4g.5d., 1a.2y.3g.4g.5d., 1b.2y.3g.4g.5d.,
1f.2y.3g.4g.5d., 1h.2y.3g.4g.5d., 1j.2y.3g.4g.5d., 1p.2y.3g.4g.5d.,
1a.2a.3a.4h.5d., 1b.2a.3a.4h.5d., 1f.2a.3a.4h.5d., 1h.2a.3a.4h.5d.,
1j.2a.3a.4h.5d., 1p.2a.3a.4h.5d., 1a.2b.3a.4h.5d., 1b.2b.3a.4h.5d.,
1f.2b.3a.4h.5d., 1h.2b.3a.4h.5d., 1j.2b.3a.4h.5d., 1p.2b.3a.4h.5d.,
1a.2e.3a.4h.5d., 1b.2e.3a.4h.5d., 1f.2e.3a.4h.5d., 1h.2e.3a.4h.5d.,
1j.2e.3a.4h.5d., 1p.2e.3a.4h.5d., 1a.2f.3a.4h.5d., 1b.2f.3a.4h.5d.,
1f.2f.3a.4h.5d., 1h.2f.3a.4h.5d., 1j.2f.3a.4h.5d., 1p.2f.3a.4h.5d.,
1a.2i.3a.4h.5d., 1b.2i.3a.4h.5d., 1f.2i.3a.4h.5d., 1h.2i.3a.4h.5d.,
1j.2i.3a.4h.5d., 1p.2i.3a.4h.5d., 1a.2m.3a.4h.5d., 1b.2m.3a.4h.5d.,
1f.2m.3a.4h.5d., 1h.2m.3a.4h.5d., 1j.2m.3a.4h.5d., 1p.2m.3a.4h.5d.,
1a.2o.3a.4h.5d., 1b.2o.3a.4h.5d., 1f.2o.3a.4h.5d., 1h.2o.3a.4h.5d.,
1j.2o.3a.4h.5d., 1p.2o.3a.4h.5d., 1a.2u.3a.4h.5d., 1b.2u.3a.4h.5d.,
1f.2u.3a.4h.5d., 1h.2u.3a.4h.5d., 1j.2u.3a.4h.5d., 1p.2u.3a.4h.5d.,
1a.2y.3a.4h.5d., 1b.2y.3a.4h.5d., 1f.2y.3a.4h.5d., 1h.2y.3a.4h.5d.,
1j.2y.3a.4h.5d., 1p.2y.3a.4h.5d., 1a.2a.3b.4h.5d., 1b.2a.3b.4h.5d.,
1f.2a.3b.4h.5d., 1h.2a.3b.4h.5d., 1j.2a.3b.4h.5d., 1p.2a.3b.4h.5d.,
1a.2b.3b.4h.5d., 1b.2b.3b.4h.5d., 1f.2b.3b.4h.5d., 1h.2b.3b.4h.5d.,
1j.2b.3b.4h.5d., 1p.2b.3b.4h.5d., 1a.2e.3b.4h.5d., 1b.2e.3b.4h.5d.,
1f.2e.3b.4h.5d., 1h.2e.3b.4h.5d., 1j.2e.3b.4h.5d., 1p.2e.3b.4h.5d.,
1a.2f.3b.4h.5d., 1b.2f.3b.4h.5d., 1f.2f.3b.4h.5d., 1h.2f.3b.4h.5d.,
1j.2f.3b.4h.5d., 1p.2f.3b.4h.5d., 1a.2i.3b.4h.5d., 1b.2i.3b.4h.5d.,
1f.2i.3b.4h.5d., 1h.2i.3b.4h.5d., 1j.2i.3b.4h.5d., 1p.2i.3b.4h.5d.,
1a.2m.3b.4h.5d., 1b.2m.3b.4h.5d., 1f.2m.3b.4h.5d., 1h.2m.3b.4h.5d.,
1j.2m.3b.4h.5d., 1p.2m.3b.4h.5d., 1a.2o.3b.4h.5d., 1b.2o.3b.4h.5d.,
1f.2o.3b.4h.5d., 1h.2o.3b.4h.5d., 1j.2o.3b.4h.5d., 1p.2o.3b.4h.5d.,
1a.2u.3b.4h.5d., 1b.2u.3b.4h.5d., 1f.2u.3b.4h.5d., 1h.2u.3b.4h.5d.,
1j.2u.3b.4h.5d., 1p.2u.3b.4h.5d., 1a.2y.3b.4h.5d., 1b.2y.3b.4h.5d.,
1f.2y.3b.4h.5d., 1h.2y.3b.4h.5d., 1j.2y.3b.4h.5d., 1p.2y.3b.4h.5d.,
1a.2a.3e.4h.5d., 1b.2a.3e.4h.5d., 1f.2a.3e.4h.5d., 1h.2a.3e.4h.5d.,
1j.2a.3e.4h.5d., 1p.2a.3e.4h.5d., 1a.2b.3e.4h.5d., 1b.2b.3e.4h.5d.,
1f.2b.3e.4h.5d., 1h.2b.3e.4h.5d., 1j.2b.3e.4h.5d., 1p.2b.3e.4h.5d.,
1a.2e.3e.4h.5d., 1b.2e.3e.4h.5d., 1f.2e.3e.4h.5d., 1h.2e.3e.4h.5d.,
1j.2e.3e.4h.5d., 1p.2e.3e.4h.5d., 1a.2f.3e.4h.5d., 1b.2f.3e.4h.5d.,
1f.2f.3e.4h.5d., 1h.2f.3e.4h.5d., 1j.2f.3e.4h.5d., 1p.2f.3e.4h.5d.,
1a.2i.3e.4h.5d., 1b.2i.3e.4h.5d., 1f.2i.3e.4h.5d., 1h.2i.3e.4h.5d.,
1j.2i.3e.4h.5d., 1p.2i.3e.4h.5d., 1a.2m.3e.4h.5d., 1b.2m.3e.4h.5d.,
1f.2m.3e.4h.5d., 1h.2m.3e.4h.5d., 1j.2m.3e.4h.5d., 1p.2m.3e.4h.5d.,
1a.2o.3e.4h.5d., 1b.2o.3e.4h.5d., 1f.2o.3e.4h.5d., 1h.2o.3e.4h.5d.,
1j.2o.3e.4h.5d., 1p.2o.3e.4h.5d., 1a.2u.3e.4h.5d., 1b.2u.3e.4h.5d.,
1f.2u.3e.4h.5d., 1h.2u.3e.4h.5d., 1j.2u.3e.4h.5d., 1p.2u.3e.4h.5d.,
1a.2y.3e.4h.5d., 1b.2y.3e.4h.5d., 1f.2y.3e.4h.5d., 1h.2y.3e.4h.5d.,
1j.2y.3e.4h.5d., 1p.2y.3e.4h.5d., 1a.2a.3g.4h.5d., 1b.2a.3g.4h.5d.,
1f.2a.3g.4h.5d., 1h.2a.3g.4h.5d., 1j.2a.3g.4h.5d., 1p.2a.3g.4h.5d.,
1a.2b.3g.4h.5d., 1b.2b.3g.4h.5d., 1f.2b.3g.4h.5d., 1h.2b.3g.4h.5d.,
1j.2b.3g.4h.5d., 1p.2b.3g.4h.5d., 1a.2e.3g.4h.5d., 1b.2e.3g.4h.5d.,
1f.2e.3g.4h.5d., 1h.2e.3g.4h.5d., 1j.2e.3g.4h.5d., 1p.2e.3g.4h.5d.,
1a.2f.3g.4h.5d., 1b.2f.3g.4h.5d., 1f.2f.3g.4h.5d., 1h.2f.3g.4h.5d.,
1j.2f.3g.4h.5d., 1p.2f.3g.4h.5d., 1a.2i.3g.4h.5d., 1b.2i.3g.4h.5d.,
1f.2i.3g.4h.5d., 1h.2i.3g.4h.5d., 1j.2i.3g.4h.5d., 1p.2i.3g.4h.5d.,
1a.2m.3g.4h.5d., 1b.2m.3g.4h.5d., 1f.2m.3g.4h.5d., 1h.2m.3g.4h.5d.,
1j.2m.3g.4h.5d., 1p.2m.3g.4h.5d., 1a.2o.3g.4h.5d., 1b.2o.3g.4h.5d.,
1f.2o.3g.4h.5d., 1h.2o.3g.4h.5d., 1j.2o.3g.4h.5d., 1p.2o.3g.4h.5d.,
1a.2u.3g.4h.5d., 1b.2u.3g.4h.5d., 1f.2u.3g.4h.5d., 1h.2u.3g.4h.5d.,
1j.2u.3g.4h.5d., 1p.2u.3g.4h.5d., 1a.2y.3g.4h.5d., 1b.2y.3g.4h.5d.,
1f.2y.3g.4h.5d., 1h.2y.3g.4h.5d., 1j.2y.3g.4h.5d., 1p.2y.3g.4h.5d.,
1a.2a.3a.4i.5d., 1b.2a.3a.4i.5d., 1f.2a.3a.4i.5d., 1h.2a.3a.4i.5d.,
1j.2a.3a.4i.5d., 1p.2a.3a.4i.5d., 1a.2b.3a.4i.5d., 1b.2b.3a.4i.5d.,
1f.2b.3a.4i.5d., 1h.2b.3a.4i.5d., 1j.2b.3a.4i.5d., 1p.2b.3a.4i.5d.,
1a.2e.3a.4i.5d., 1b.2e.3a.4i.5d., 1f.2e.3a.4i.5d., 1h.2e.3a.4i.5d.,
1j.2e.3a.4i.5d., 1p.2e.3a.4i.5d., 1a.2f.3a.4i.5d., 1b.2f.3a.4i.5d.,
1f.2f.3a.4i.5d., 1h.2f.3a.4i.5d., 1j.2f.3a.4i.5d., 1p.2f.3a.4i.5d.,
1a.2i.3a.4i.5d., 1b.2i.3a.4i.5d., 1f.2i.3a.4i.5d., 1h.2i.3a.4i.5d.,
1j.2i.3a.4i.5d., 1p.2i.3a.4i.5d., 1a.2m.3a.4i.5d., 1b.2m.3a.4i.5d.,
1f.2m.3a.4i.5d., 1h.2m.3a.4i.5d., 1j.2m.3a.4i.5d., 1p.2m.3a.4i.5d.,
1a.2o.3a.4i.5d., 1b.2o.3a.4i.5d., 1f.2o.3a.4i.5d., 1h.2o.3a.4i.5d.,
1j.2o.3a.4i.5d., 1p.2o.3a.4i.5d., 1a.2u.3a.4i.5d., 1b.2u.3a.4i.5d.,
1f.2u.3a.4i.5d., 1h.2u.3a.4i.5d., 1j.2u.3a.4i.5d., 1p.2u.3a.4i.5d.,
1a.2y.3a.4i.5d., 1b.2y.3a.4i.5d., 1f.2y.3a.4i.5d., 1h.2y.3a.4i.5d.,
1j.2y.3a.4i.5d., 1p.2y.3a.4i.5d., 1a.2a.3b.4i.5d., 1b.2a.3b.4i.5d.,
1f.2a.3b.4i.5d., 1h.2a.3b.4i.5d., 1j.2a.3b.4i.5d., 1p.2a.3b.4i.5d.,
1a.2b.3b.4i.5d., 1b.2b.3b.4i.5d., 1f.2b.3b.4i.5d., 1h.2b.3b.4i.5d.,
1j.2b.3b.4i.5d., 1p.2b.3b.4i.5d., 1a.2e.3b.4i.5d., 1b.2e.3b.4i.5d.,
1f.2e.3b.4i.5d., 1h.2e.3b.4i.5d., 1j.2e.3b.4i.5d., 1p.2e.3b.4i.5d.,
1a.2f.3b.4i.5d., 1b.2f.3b.4i.5d., 1f.2f.3b.4i.5d., 1h.2f.3b.4i.5d.,
1j.2f.3b.4i.5d., 1p.2f.3b.4i.5d., 1a.2i.3b.4i.5d., 1b.2i.3b.4i.5d.,
1f.2i.3b.4i.5d., 1h.2i.3b.4i.5d., 1j.2i.3b.4i.5d., 1p.2i.3b.4i.5d.,
1a.2m.3b.4i.5d., 1b.2m.3b.4i.5d., 1f.2m.3b.4i.5d., 1h.2m.3b.4i.5d.,
1j.2m.3b.4i.5d., 1p.2m.3b.4i.5d., 1a.2o.3b.4i.5d., 1b.2o.3b.4i.5d.,
1f.2o.3b.4i.5d., 1h.2o.3b.4i.5d., 1j.2o.3b.4i.5d., 1p.2o.3b.4i.5d.,
1a.2u.3b.4i.5d., 1b.2u.3b.4i.5d., 1f.2u.3b.4i.5d., 1h.2u.3b.4i.5d.,
1j.2u.3b.4i.5d., 1p.2u.3b.4i.5d., 1a.2y.3b.4i.5d., 1b.2y.3b.4i.5d.,
1f.2y.3b.4i.5d., 1h.2y.3b.4i.5d., 1j.2y.3b.4i.5d., 1p.2y.3b.4i.5d.,
1a.2a.3e.4i.5d., 1b.2a.3e.4i.5d., 1f.2a.3e.4i.5d., 1h.2a.3e.4i.5d.,
1j.2a.3e.4i.5d., 1p.2a.3e.4i.5d., 1a.2b.3e.4i.5d., 1b.2b.3e.4i.5d.,
1f.2b.3e.4i.5d., 1h.2b.3e.4i.5d., 1j.2b.3e.4i.5d., 1p.2b.3e.4i.5d.,
1a.2e.3e.4i.5d., 1b.2e.3e.4i.5d., 1f.2e.3e.4i.5d., 1h.2e.3e.4i.5d.,
1j.2e.3e.4i.5d., 1p.2e.3e.4i.5d., 1a.2f.3e.4i.5d., 1b.2f.3e.4i.5d.,
1f.2f.3e.4i.5d., 1h.2f.3e.4i.5d., 1j.2f.3e.4i.5d., 1p.2f.3e.4i.5d.,
1a.2i.3e.4i.5d., 1b.2i.3e.4i.5d., 1f.2i.3e.4i.5d., 1h.2i.3e.4i.5d.,
1j.2i.3e.4i.5d., 1p.2i.3e.4i.5d., 1a.2m.3e.4i.5d., 1b.2m.3e.4i.5d.,
1f.2m.3e.4i.5d., 1h.2m.3e.4i.5d., 1j.2m.3e.4i.5d., 1p.2m.3e.4i.5d.,
1a.2o.3e.4i.5d., 1b.2o.3e.4i.5d., 1f.2o.3e.4i.5d., 1h.2o.3e.4i.5d.,
1j.2o.3e.4i.5d., 1p.2o.3e.4i.5d., 1a.2u.3e.4i.5d., 1b.2u.3e.4i.5d.,
1f.2u.3e.4i.5d., 1h.2u.3e.4i.5d., 1j.2u.3e.4i.5d., 1p.2u.3e.4i.5d.,
1a.2y.3e.4i.5d., 1b.2y.3e.4i.5d., 1f.2y.3e.4i.5d., 1h.2y.3e.4i.5d.,
1j.2y.3e.4i.5d., 1p.2y.3e.4i.5d., 1a.2a.3g.4i.5d., 1b.2a.3g.4i.5d.,
1f.2a.3g.4i.5d., 1h.2a.3g.4i.5d., 1j.2a.3g.4i.5d., 1p.2a.3g.4i.5d.,
1a.2b.3g.4i.5d., 1b.2b.3g.4i.5d., 1f.2b.3g.4i.5d., 1h.2b.3g.4i.5d.,
1j.2b.3g.4i.5d., 1p.2b.3g.4i.5d., 1a.2e.3g.4i.5d., 1b.2e.3g.4i.5d.,
1f.2e.3g.4i.5d., 1h.2e.3g.4i.5d., 1j.2e.3g.4i.5d., 1p.2e.3g.4i.5d.,
1a.2f.3g.4i.5d., 1b.2f.3g.4i.5d., 1f.2f.3g.4i.5d., 1h.2f.3g.4i.5d.,
1j.2f.3g.4i.5d., 1p.2f.3g.4i.5d., 1a.2i.3g.4i.5d., 1b.2i.3g.4i.5d.,
1f.2i.3g.4i.5d., 1h.2i.3g.4i.5d., 1j.2i.3g.4i.5d., 1p.2i.3g.4i.5d.,
1a.2m.3g.4i.5d., 1b.2m.3g.4i.5d., 1f.2m.3g.4i.5d., 1h.2m.3g.4i.5d.,
1j.2m.3g.4i.5d., 1p.2m.3g.4i.5d., 1a.2o.3g.4i.5d., 1b.2o.3g.4i.5d.,
1f.2o.3g.4i.5d., 1h.2o.3g.4i.5d., 1j.2o.3g.4i.5d., 1p.2o.3g.4i.5d.,
1a.2u.3g.4i.5d., 1b.2u.3g.4i.5d., 1f.2u.3g.4i.5d., 1h.2u.3g.4i.5d.,
1j.2u.3g.4i.5d., 1p.2u.3g.4i.5d., 1a.2y.3g.4i.5d., 1b.2y.3g.4i.5d.,
1f.2y.3g.4i.5d., 1h.2y.3g.4i.5d., 1j.2y.3g.4i.5d., 1p.2y.3g.4i.5d.,
1a.2a.3a.4a.5f., 1b.2a.3a.4a.5f., 1f.2a.3a.4a.5f., 1h.2a.3a.4a.5f., TABLE 12-continued List of Compound Structures of Formula II 1j.2a.3a.4a.5f., 1p.2a.3a.4a.5f., 1a.2b.3a.4a.5f., 1b.2b.3a.4a.5f.,
1f.2b.3a.4a.5f., 1h.2b.3a.4a.5f., 1j.2b.3a.4a.5f., 1p.2b.3a.4a.5f.,
1a.2e.3a.4a.5f., 1b.2e.3a.4a.5f., 1f.2e.3a.4a.5f., 1h.2e.3a.4a.5f.,
1j.2e.3a.4a.5f., 1p.2e.3a.4a.5f., 1a.2f.3a.4a.5f., 1b.2f.3a.4a.5f.,
1f.2f.3a.4a.5f., 1h.2f.3a.4a.5f., 1j.2f.3a.4a.5f., 1p.2f.3a.4a.5f.,
1a.2i.3a.4a.5f., 1b.2i.3a.4a.5f., 1f.2i.3a.4a.5f., 1h.2i.3a.4a.5f.,
1j.2i.3a.4a.5f., 1p.2i.3a.4a.5f., 1a.2m.3a.4a.5f., 1b.2m.3a.4a.5f.,
1f.2m.3a.4a.5f., 1h.2m.3a.4a.5f., 1j.2m.3a.4a.5f., 1p.2m.3a.4a.5f.,
1a.2o.3a.4a.5f., 1b.2o.3a.4a.5f., 1f.2o.3a.4a.5f., 1h.2o.3a.4a.5f.,
1j.2o.3a.4a.5f., 1p.2o.3a.4a.5f., 1a.2u.3a.4a.5f., 1b.2u.3a.4a.5f.,
1f.2u.3a.4a.5f., 1h.2u.3a.4a.5f., 1j.2u.3a.4a.5f., 1p.2u.3a.4a.5f.,
1a.2y.3a.4a.5f., 1b.2y.3a.4a.5f., 1f.2y.3a.4a.5f., 1h.2y.3a.4a.5f.,
1j.2y.3a.4a.5f., 1p.2y.3a.4a.5f., 1a.2a.3b.4a.5f., 1b.2a.3b.4a.5f.,
1f.2a.3b.4a.5f., 1h.2a.3b.4a.5f., 1j.2a.3b.4a.5f., 1p.2a.3b.4a.5f.,
1a.2b.3b.4a.5f., 1b.2b.3b.4a.5f., 1f.2b.3b.4a.5f., 1h.2b.3b.4a.5f.,
1j.2b.3b.4a.5f., 1p.2b.3b.4a.5f., 1a.2e.3b.4a.5f., 1b.2e.3b.4a.5f.,
1f.2e.3b.4a.5f., 1h.2e.3b.4a.5f., 1j.2e.3b.4a.5f., 1p.2e.3b.4a.5f.,
1a.2f.3b.4a.5f., 1b.2f.3b.4a.5f., 1f.2f.3b.4a.5f., 1h.2f.3b.4a.5f.,
1j.2f.3b.4a.5f., 1p.2f.3b.4a.5f., 1a.2i.3b.4a.5f., 1b.2i.3b.4a.5f.,
1f.2i.3b.4a.5f., 1h.2i.3b.4a.5f., 1j.2i.3b.4a.5f., 1p.2i.3b.4a.5f.,
1a.2m.3b.4a.5f., 1b.2m.3b.4a.5f., 1f.2m.3b.4a.5f., 1h.2m.3b.4a.5f.,
1j.2m.3b.4a.5f., 1p.2m.3b.4a.5f., 1a.2o.3b.4a.5f., 1b.2o.3b.4a.5f.,
1f.2o.3b.4a.5f., 1h.2o.3b.4a.5f., 1j.2o.3b.4a.5f., 1p.2o.3b.4a.5f.,
1a.2u.3b.4a.5f., 1b.2u.3b.4a.5f., 1f.2u.3b.4a.5f., 1h.2u.3b.4a.5f.,
1j.2u.3b.4a.5f., 1p.2u.3b.4a.5f., 1a.2y.3b.4a.5f., 1b.2y.3b.4a.5f.,
1f.2y.3b.4a.5f., 1h.2y.3b.4a.5f., 1j.2y.3b.4a.5f., 1p.2y.3b.4a.5f.,
1a.2a.3e.4a.5f., 1b.2a.3e.4a.5f., 1f.2a.3e.4a.5f., 1h.2a.3e.4a.5f.,
1j.2a.3e.4a.5f., 1p.2a.3e.4a.5f., 1a.2b.3e.4a.5f., 1b.2b.3e.4a.5f.,
1f.2b.3e.4a.5f., 1h.2b.3e.4a.5f., 1j.2b.3e.4a.5f., 1p.2b.3e.4a.5f.,
1a.2e.3e.4a.5f., 1b.2e.3e.4a.5f., 1f.2e.3e.4a.5f., 1h.2e.3e.4a.5f.,
1j.2e.3e.4a.5f., 1p.2e.3e.4a.5f., 1a.2f.3e.4a.5f., 1p.2f.3e.4a.5f.,
1f.2f.3e.4a.5f., 1h.2f.3e.4a.5f., 1j.2f.3e.4a.5f., 1p.2f.3e.4a.5f.,
1a.2i.3e.4a.5f., 1b.2i.3e.4a.5f., 1f.2i.3e.4a.5f., 1h.2i.3e.4a.5f.,
1j.2i.3e.4a.5f., 1p.2i.3e.4a.5f., 1a.2m.3e.4a.5f., 1b.2m.3e.4a.5f.,
1f.2m.3e.4a.5f., 1h.2m.3e.4a.5f., 1j.2m.3e.4a.5f., 1p.2m.3e.4a.5f.,
1a.2o.3e.4a.5f., 1b.2o.3e.4a.5f., 1f.2o.3e.4a.5f., 1h.2o.3e.4a.5f.,
1j.2o.3e.4a.5f., 1p.2o.3e.4a.5f., 1a.2u.3e.4a.5f., 1b.2u.3e.4a.5f.,
1f.2u.3e.4a.5f., 1h.2u.3e.4a.5f., 1j.2u.3e.4a.5f., 1p.2u.3e.4a.5f.,
1a.2y.3e.4a.5f., 1b.2y.3e.4a.5f., 1f.2y.3e.4a.5f., 1h.2y.3e.4a.5f.,
1j.2y.3e.4a.5f., 1p.2y.3e.4a.5f., 1a.2a.3g.4a.5f., 1b.2a.3g.4a.5f.,
1f.2a.3g.4a.5f., 1h.2a.3g.4a.5f., 1j.2a.3g.4a.5f., 1p.2a.3g.4a.5f.,
1a.2b.3g.4a.5f., 1b.2b.3g.4a.5f., 1f.2b.3g.4a.5f., 1h.2b.3g.4a.5f.,
1j.2b.3g.4a.5f., 1p.2b.3g.4a.5f., 1a.2e.3g.4a.5f., 1b.2e.3g.4a.5f.,
1f.2e.3g.4a.5f., 1h.2e.3g.4a.5f., 1j.2e.3g.4a.5f., 1p.2e.3g.4a.5f.,
1a.2f.3g.4a.5f., 1b.2f.3g.4a.5f., 1f.2f.3g.4a.5f., 1h.2f.3g.4a.5f.,
1j.2f.3g.4a.5f., 1p.2f.3g.4a.5f., 1a.2i.3g.4a.5f., 1b.2i.3g.4a.5f.,
1f.2i.3g.4a.5f., 1h.2i.3g.4a.5f., 1j.2i.3g.4a.5f., 1p.2i.3g.4a.5f.,
1a.2m.3g.4a.5f., 1b.2m.3g.4a.5f., 1f.2m.3g.4a.5f., 1h.2m.3g.4a.5f.,
1j.2m.3g.4a.5f., 1p.2m.3g.4a.5f., 1a.2o.3g.4a.5f., 1b.2o.3g.4a.5f.,
1f.2o.3g.4a.5f., 1h.2o.3g.4a.5f., 1j.2o.3g.4a.5f., 1p.2o.3g.4a.5f.,
1a.2u.3g.4a.5f., 1b.2u.3g.4a.5f., 1f.2u.3g.4a.5f., 1h.2u.3g.4a.5f.,
1j.2u.3g.4a.5f., 1p.2u.3g.4a.5f., 1a.2y.3g.4a.5f., 1b.2y.3g.4a.5f.,
1f.2y.3g.4a.5f., 1h.2y.3g.4a.5f., 1j.2y.3g.4a.5f., 1p.2y.3g.4a.5f.,
1a.2a.3a.4d.5f., 1b.2a.3a.4d.5f., 1f.2a.3a.4d.5f., 1h.2a.3a.4d.5f.,
1j.2a.3a.4d.5f., 1p.2a.3a.4d.5f., 1a.2b.3a.4d.5f., 1b.2b.3a.4d.5f.,
1f.2b.3a.4d.5f., 1h.2b.3a.4d.5f., 1j.2b.3a.4d.5f., 1p.2b.3a.4d.5f.,
1a.2e.3a.4d.5f., 1b.2e.3a.4d.5f., 1f.2e.3a.4d.5f., 1h.2e.3a.4d.5f.,
1j.2e.3a.4d.5f., 1p.2e.3a.4d.5f., 1a.2f.3a.4d.5f., 1b.2f.3a.4d.5f.,
1f.2f.3a.4d.5f., 1h.2f.3a.4d.5f., 1j.2f.3a.4d.5f., 1p.2f.3a.4d.5f.,
1a.2i.3a.4d.5f., 1b.2i.3a.4d.5f., 1f.2i.3a.4d.5f., 1h.2i.3a.4d.5f.,
1j.2i.3a.4d.5f., 1p.2i.3a.4d.5f., 1a.2m.3a.4d.5f., 1b.2m.3a.4d.5f.,
1f.2m.3a.4d.5f., 1h.2m.3a.4d.5f., 1j.2m.3a.4d.5f., 1p.2m.3a.4d.5f.,
1a.2o.3a.4d.5f., 1b.2o.3a.4d.5f., 1f.2o.3a.4d.5f., 1h.2o.3a.4d.5f.,
1j.2o.3a.4d.5f., 1p.2o.3a.4d.5f., 1a.2u.3a.4d.5f., 1b.2u.3a.4d.5f.,
1f.2u.3a.4d.5f., 1h.2u.3a.4d.5f., 1j.2u.3a.4d.5f., 1p.2u.3a.4d.5f.,
1a.2y.3a.4d.5f., 1b.2y.3a.4d.5f., 1f.2y.3a.4d.5f., 1h.2y.3a.4d.5f.,
1j.2y.3a.4d.5f., 1p.2y.3a.4d.5f., 1a.2a.3b.4d.5f., 1b.2a.3b.4d.5f.,
1f.2a.3b.4d.5f., 1h.2a.3b.4d.5f., 1j.2a.3b.4d.5f., 1p.2a.3b.4d.5f.,
1a.2b.3b.4d.5f., 1b.2b.3b.4d.5f., 1f.2b.3b.4d.5f., 1h.2b.3b.4d.5f.,
1j.2b.3b.4d.5f., 1p.2b.3b.4d.5f., 1a.2e.3b.4d.5f., 1b.2e.3b.4d.5f.,
1f.2e.3b.4d.5f., 1h.2e.3b.4d.5f., 1j.2e.3b.4d.5f., 1p.2e.3b.4d.5f.,
1a.2f.3b.4d.5f., 1b.2f.3b.4d.5f., 1f.2f.3b.4d.5f., 1h.2f.3b.4d.5f.,
1j.2f.3b.4d.5f., 1p.2f.3b.4d.5f., 1a.2i.3b.4d.5f., 1b.2i.3b.4d.5f.,
1f.2i.3b.4d.5f., 1h.2i.3b.4d.5f., 1j.2i.3b.4d.5f., 1p.2i.3b.4d.5f.,
1a.2m.3b.4d.5f., 1b.2m.3b.4d.5f., 1f.2m.3b.4d.5f., 1h.2m.3b.4d.5f.,
1j.2m.3b.4d.5f., 1p.2m.3b.4d.5f., 1a.2o.3b.4d.5f., 1b.2o.3b.4d.5f.,
1f.2o.3b.4d.5f., 1h.2o.3b.4d.5f., 1j.2o.3b.4d.5f., 1p.2o.3b.4d.5f.,
1a.2u.3b.4d.5f., 1b.2u.3b.4d.5f., 1f.2u.3b.4d.5f., 1h.2u.3b.4d.5f.,
1j.2u.3b.4d.5f., 1p.2u.3b.4d.5f., 1a.2y.3b.4d.5f., 1b.2y.3b.4d.5f.,
1f.2y.3b.4d.5f., 1h.2y.3b.4d.5f., 1j.2y.3b.4d.5f., 1p.2y.3b.4d.5f.,
1a.2a.3e.4d.5f., 1b.2a.3e.4d.5f., 1f.2a.3e.4d.5f., 1h.2a.3e.4d.5f.,
1j.2a.3e.4d.5f., 1p.2a.3e.4d.5f., 1a.2b.3e.4d.5f., 1b.2b.3e.4d.5f.,
1f.2b.3e.4d.5f., 1h.2b.3e.4d.5f., 1j.2b.3e.4d.5f., 1p.2b.3e.4d.5f.,
1a.2e.3e.4d.5f., 1b.2e.3e.4d.5f., 1f.2e.3e.4d.5f., 1h.2e.3e.4d.5f.,
1j.2e.3e.4d.5f., 1p.2e.3e.4d.5f., 1a.2f.3e.4d.5f., 1b.2f.3e.4d.5f.,
1f.2f.3e.4d.5f., 1h.2f.3e.4d.5f., 1j.2f.3e.4d.5f., 1p.2f.3e.4d.5f.,
1a.2i.3e.4d.5f., 1b.2i.3e.4d.5f., 1f.2i.3e.4d.5f., 1h.2i.3e.4d.5f.,
1j.2i.3e.4d.5f., 1p.2i.3e.4d.5f., 1a.2m.3e.4d.5f., 1b.2m.3e.4d.5f.,
1f.2m.3e.4d.5f., 1h.2m.3e.4d.5f., 1j.2m.3e.4d.5f., 1p.2m.3e.4d.5f.,
1a.2o.3e.4d.5f., 1b.2o.3e.4d.5f., 1f.2o.3e.4d.5f., 1h.2o.3e.4d.5f.,
1j.2o.3e.4d.5f., 1p.2o.3e.4d.5f., 1a.2u.3e.4d.5f., 1b.2u.3e.4d.5f.,
1f.2u.3e.4d.5f., 1h.2u.3e.4d.5f., 1j.2u.3e.4d.5f., 1p.2u.3e.4d.5f.,
1a.2y.3e.4d.5f., 1b.2y.3e.4d.5f., 1f.2y.3e.4d.5f., 1h.2y.3e.4d.5f.,
1j.2y.3e.4d.5f., 1p.2y.3e.4d.5f., 1a.2a.3g.4d.5f., 1b.2a.3g.4d.5f.,
1f.2a.3g.4d.5f., 1h.2a.3g.4d.5f., 1j.2a.3g.4d.5f., 1p.2a.3g.4d.5f.,
1a.2b.3g.4d.5f., 1b.2b.3g.4d.5f., 1f.2b.3g.4d.5f., 1h.2b.3g.4d.5f.,
1j.2b.3g.4d.5f., 1p.2b.3g.4d.5f., 1a.2e.3g.4d.5f., 1b.2e.3g.4d.5f.,
1f.2e.3g.4d.5f., 1h.2e.3g.4d.5f., 1j.2e.3g.4d.5f., 1p.2e.3g.4d.5f.,
1a.2f.3g.4d.5f., 1b.2f.3g.4d.5f., 1f.2f.3g.4d.5f., 1h.2f.3g.4d.5f.,
1j.2f.3g.4d.5f., 1p.2f.3g.4d.5f., 1a.2i.3g.4d.5f., 1b.2i.3g.4d.5f.,
1f.2i.3g.4d.5f., 1h.2i.3g.4d.5f., 1j.2i.3g.4d.5f., 1p.2i.3g.4d.5f.,
1a.2m.3g.4d.5f., 1b.2m.3g.4d.5f., 1f.2m.3g.4d.5f., 1h.2m.3g.4d.5f.,
1j.2m.3g.4d.5f., 1p.2m.3g.4d.5f., 1a.2o.3g.4d.5f., 1b.2o.3g.4d.5f.,
1f.2o.3g.4d.5f., 1h.2o.3g.4d.5f., 1j.2o.3g.4d.5f., 1p.2o.3g.4d.5f.,
1a.2u.3g.4d.5f., 1b.2u.3g.4d.5f., 1f.2u.3g.4d.5f., 1h.2u.3g.4d.5f.,
1j.2u.3g.4d.5f., 1p.2u.3g.4d.5f., 1a.2y.3g.4d.5f., 1b.2y.3g.4d.5f.,
1f.2y.3g.4d.5f., 1h.2y.3g.4d.5f., 1j.2y.3g.4d.5f., 1p.2y.3g.4d.5f.,
1a.2a.3a.4f.5f., 1b.2a.3a.4f.5f., 1f.2a.3a.4f.5f., 1h.2a.3a.4f.5f.,
1j.2a.3a.4f.5f., 1p.2a.3a.4f.5f., 1a.2b.3a.4f.5f., 1b.2b.3a.4f.5f.,
1f.2b.3a.4f.5f., 1h.2b.3a.4f.5f., 1j.2b.3a.4f.5f., 1p.2b.3a.4f.5f.,
1a.2e.3a.4f.5f., 1b.2e.3a.4f.5f., 1f.2e.3a.4f.5f., 1h.2e.3a.4f.5f.,
1j.2e.3a.4f.5f., 1p.2e.3a.4f.5f., 1a.2f.3a.4f.5f., 1b.2f.3a.4f.5f.,
1f.2f.3a.4f.5f., 1h.2f.3a.4f.5f., 1j.2f.3a.4f.5f., 1p.2f.3a.4f.5f.,
1a.2i.3a.4f.5f., 1b.2i.3a.4f.5f., 1f.2i.3a.4f.5f., 1h.2i.3a.4f.5f.,
1j.2i.3a.4f.5f., 1p.2i.3a.4f.5f., 1a.2m.3a.4f.5f., 1b.2m.3a.4f.5f.,
1f.2m.3a.4f.5f., 1h.2m.3a.4f.5f., 1j.2m.3a.4f.5f., 1p.2m.3a.4f.5f.,
1a.2o.3a.4f.5f., 1b.2o.3a.4f.5f., 1f.2o.3a.4f.5f., 1h.2o.3a.4f.5f.,
1j.2o.3a.4f.5f., 1p.2o.3a.4f.5f., 1a.2u.3a.4f.5f., 1b.2u.3a.4f.5f.,
1f.2u.3a.4f.5f., 1h.2u.3a.4f.5f., 1j.2u.3a.4f.5f., 1p.2u.3a.4f.5f.,
1a.2y.3a.4f.5f., 1b.2y.3a.4f.5f., 1f.2y.3a.4f.5f., 1h.2y.3a.4f.5f.,
1j.2y.3a.4f.5f., 1p.2y.3a.4f.5f., 1a.2a.3b.4f.5f., 1b.2a.3b.4f.5f.,
1f.2a.3b.4f.5f., 1h.2a.3b.4f.5f., 1j.2a.3b.4f.5f., 1p.2a.3b.4f.5f.,
1a.2b.3b.4f.5f., 1b.2b.3b.4f.5f., 1f.2b.3b.4f.5f., 1h.2b.3b.4f.5f.,
1j.2b.3b.4f.5f., 1p.2b.3b.4f.5f., 1a.2e.3b.4f.5f., 1b.2e.3b.4f.5f.,
1f.2e.3b.4f.5f., 1h.2e.3b.4f.5f., 1j.2e.3b.4f.5f., 1p.2e.3b.4f.5f.,
1a.2f.3b.4f.5f., 1b.2f.3b.4f.5f., 1f.2f.3b.4f.5f., 1h.2f.3b.4f.5f.,
1j.2f.3b.4f.5f., 1p.2f.3b.4f.5f., 1a.2i.3b.4f.5f., 1b.2i.3b.4f.5f.,
1f.2i.3b.4f.5f., 1h.2i.3b.4f.5f., 1j.2i.3b.4f.5f., 1p.2i.3b.4f.5f.,
1a.2m.3b.4f.5f., 1b.2m.3b.4f.5f., 1f.2m.3b.4f.5f., 1h.2m.3b.4f.5f.,
1j.2m.3b.4f.5f., 1p.2m.3b.4f.5f., 1a.2o.3b.4f.5f., 1b.2o.3b.4f.5f.,
1f.2o.3b.4f.5f., 1h.2o.3b.4f.5f., 1j.2o.3b.4f.5f., 1p.2o.3b.4f.5f.,
1a.2u.3b.4f.5f., 1b.2u.3b.4f.5f., 1f.2u.3b.4f.5f., 1h.2u.3b.4f.5f.,
1j.2u.3b.4f.5f., 1p.2u.3b.4f.5f., 1a.2y.3b.4f.5f., 1b.2y.3b.4f.5f.,
1f.2y.3b.4f.5f., 1h.2y.3b.4f.5f., 1j.2y.3b.4f.5f., 1p.2y.3b.4f.5f.,
1a.2a.3e.4f.5f., 1b.2a.3e.4f.5f., 1f.2a.3e.4f.5f., 1h.2a.3e.4f.5f.,
1j.2a.3e.4f.5f., 1p.2a.3e.4f.5f., 1a.2b.3e.4f.5f., 1b.2b.3e.4f.5f.,
1f.2b.3e.4f.5f., 1h.2b.3e.4f.5f., 1j.2b.3e.4f.5f., 1p.2b.3e.4f.5f.,
1a.2e.3e.4f.5f., 1b.2e.3e.4f.5f., 1f.2e.3e.4f.5f., 1h.2e.3e.4f.5f.,
1j.2e.3e.4f.5f., 1p.2e.3e.4f.5f., 1a.2f.3e.4f.5f., 1b.2f.3e.4f.5f.,
1f.2f.3e.4f.5f., 1h.2f.3e.4f.5f., 1j.2f.3e.4f.5f., 1p.2f.3e.4f.5f.,
1a.2i.3e.4f.5f., 1b.2i.3e.4f.5f., 1f.2i.3e.4f.5f., 1h.2i.3e.4f.5f.,
1j.2i.3e.4f.5f., 1p.2i.3e.4f.5f., 1a.2m.3e.4f.5f., 1b.2m.3e.4f.5f.,
1f.2m.3e.4f.5f., 1h.2m.3e.4f.5f., 1j.2m.3e.4f.5f., 1p.2m.3e.4f.5f.,
1a.2o.3e.4f.5f., 1b.2o.3e.4f.5f., 1f.2o.3e.4f.5f., 1h.2o.3e.4f.5f.,
1j.2o.3e.4f.5f., 1p.2o.3e.4f.5f., 1a.2u.3e.4f.5f., 1b.2u.3e.4f.5f.,
1f.2u.3e.4f.5f., 1h.2u.3e.4f.5f., 1j.2u.3e.4f.5f., 1p.2u.3e.4f.5f.,
1a.2y.3e.4f.5f., 1b.2y.3e.4f.5f., 1f.2y.3e.4f.5f., 1h.2y.3e.4f.5f.,
1j.2y.3e.4f.5f., 1p.2y.3e.4f.5f., 1a.2a.3g.4f.5f., 1b.2a.3g.4f.5f.,
1f.2a.3g.4f.5f., 1h.2a.3g.4f.5f., 1j.2a.3g.4f.5f., 1p.2a.3g.4f.5f.,
1a.2b.3g.4f.5f., 1b.2b.3g.4f.5f., 1f.2b.3g.4f.5f., 1h.2b.3g.4f.5f.,
1j.2b.3g.4f.5f., 1p.2b.3g.4f.5f., 1a.2e.3g.4f.5f., 1b.2e.3g.4f.5f.,
1f.2e.3g.4f.5f., 1h.2e.3g.4f.5f., 1j.2e.3g.4f.5f., 1p.2e.3g.4f.5f.,
1a.2f.3g.4f.5f., 1b.2f.3g.4f.5f., 1f.2f.3g.4f.5f., 1h.2f.3g.4f.5f.,
1j.2f.3g.4f.5f., 1p.2f.3g.4f.5f., 1a.2i.3g.4f.5f., 1b.2i.3g.4f.5f.,
1f.2i.3g.4f.5f., 1h.2i.3g.4f.5f., 1j.2i.3g.4f.5f., 1p.2i.3g.4f.5f.,
1a.2m.3g.4f.5f., 1b.2m.3g.4f.5f., 1f.2m.3g.4f.5f., 1h.2m.3g.4f.5f.,

TABLE 12-continued

List of Compound Structures of Formula II 1j.2m.3g.4f.5f., 1p.2m.3g.4f.5f., 1a.2o.3g.4f.5f., 1b.2o.3g.4f.5f.,
1f.2o.3g.4f.5f., 1h.2o.3g.4f.5f., 1j.2o.3g.4f.5f., 1p.2o.3g.4f.5f.,
1a.2u.3g.4f.5f., 1b.2u.3g.4f.5f., 1f.2u.3g.4f.5f., 1h.2u.3g.4f.5f.,
1j.2u.3g.4f.5f., 1p.2u.3g.4f.5f., 1a.2y.3g.4f.5f., 1b.2y.3g.4f.5f.,
1f.2y.3g.4f.5f., 1h.2y.3g.4f.5f., 1j.2y.3g.4f.5f., 1p.2y.3g.4f.5f.,
1a.2a.3a.4g.5f., 1b.2a.3a.4g.5f., 1f.2a.3a.4g.5f., 1h.2a.3a.4g.5f.,
1j.2a.3a.4g.5f., 1p.2a.3a.4g.5f., 1a.2b.3a.4g.5f., 1b.2b.3a.4g.5f.,
1f.2b.3a.4g.5f., 1h.2b.3a.4g.5f., 1j.2b.3a.4g.5f., 1p.2b.3a.4g.5f.,
1a.2e.3a.4g.5f., 1b.2e.3a.4g.5f., 1f.2e.3a.4g.5f., 1h.2e.3a.4g.5f.,
1j.2e.3a.4g.5f., 1p.2e.3a.4g.5f., 1a.2f.3a.4g.5f., 1b.2f.3a.4g.5f.,
1f.2f.3a.4g.5f., 1h.2f.3a.4g.5f., 1j.2f.3a.4g.5f., 1p.2f.3a.4g.5f.,
1a.2i.3a.4g.5f., 1b.2i.3a.4g.5f., 1f.2i.3a.4g.5f., 1h.2i.3a.4g.5f.,
1j.2i.3a.4g.5f., 1p.2i.3a.4g.5f., 1a.2m.3a.4g.5f., 1b.2m.3a.4g.5f.,
1f.2m.3a.4g.5f., 1h.2m.3a.4g.5f., 1j.2m.3a.4g.5f., 1p.2m.3a.4g.5f.,
1a.2o.3a.4g.5f., 1b.2o.3a.4g.5f., 1f.2o.3a.4g.5f., 1h.2o.3a.4g.5f.,
1j.2o.3a.4g.5f., 1p.2o.3a.4g.5f., 1a.2u.3a.4g.5f., 1b.2u.3a.4g.5f.,
1f.2u.3a.4g.5f., 1h.2u.3a.4g.5f., 1j.2u.3a.4g.5f., 1p.2u.3a.4g.5f.,
1a.2y.3a.4g.5f., 1b.2y.3a.4g.5f., 1f.2y.3a.4g.5f., 1h.2y.3a.4g.5f.,
1j.2y.3a.4g.5f., 1p.2y.3a.4g.5f., 1a.2a.3b.4g.5f., 1b.2a.3b.4g.5f.,
1f.2a.3b.4g.5f., 1h.2a.3b.4g.5f., 1j.2a.3b.4g.5f., 1p.2a.3b.4g.5f.,
1a.2b.3b.4g.5f., 1b.2b.3b.4g.5f., 1f.2b.3b.4g.5f., 1h.2b.3b.4g.5f.,
1j.2b.3b.4g.5f., 1p.2b.3b.4g.5f., 1a.2e.3b.4g.5f., 1b.2e.3b.4g.5f.,
1f.2e.3b.4g.5f., 1h.2e.3b.4g.5f., 1j.2e.3b.4g.5f., 1p.2e.3b.4g.5f.,
1a.2f.3b.4g.5f., 1b.2f.3b.4g.5f., 1f.2f.3b.4g.5f., 1h.2f.3b.4g.5f.,
1j.2f.3b.4g.5f., 1p.2f.3b.4g.5f., 1a.2i.3b.4g.5f., 1b.2i.3b.4g.5f.,
1f.2i.3b.4g.5f., 1h.2i.3b.4g.5f., 1j.2i.3b.4g.5f., 1p.2i.3b.4g.5f.,
1a.2m.3b.4g.5f., 1b.2m.3b.4g.5f., 1f.2m.3b.4g.5f., 1h.2m.3b.4g.5f.,
1j.2m.3b.4g.5f., 1p.2m.3b.4g.5f., 1a.2o.3b.4g.5f., 1b.2o.3b.4g.5f.,
1f.2o.3b.4g.5f., 1h.2o.3b.4g.5f., 1j.2o.3b.4g.5f., 1p.2o.3b.4g.5f.,
1a.2u.3b.4g.5f., 1b.2u.3b.4g.5f., 1f.2u.3b.4g.5f., 1h.2u.3b.4g.5f.,
1j.2u.3b.4g.5f., 1p.2u.3b.4g.5f., 1a.2y.3b.4g.5f., 1b.2y.3b.4g.5f.,
1f.2y.3b.4g.5f., 1h.2y.3b.4g.5f., 1j.2y.3b.4g.5f., 1p.2y.3b.4g.5f.,
1a.2a.3e.4g.5f., 1b.2a.3e.4g.5f., 1f.2a.3e.4g.5f., 1h.2a.3e.4g.5f.,
1j.2a.3e.4g.5f., 1p.2a.3e.4g.5f., 1a.2b.3e.4g.5f., 1b.2b.3e.4g.5f.,
1f.2b.3e.4g.5f., 1h.2b.3e.4g.5f., 1j.2b.3e.4g.5f., 1p.2b.3e.4g.5f.,
1a.2e.3e.4g.5f., 1b.2e.3e.4g.5f., 1f.2e.3e.4g.5f., 1h.2e.3e.4g.5f.,
1j.2e.3e.4g.5f., 1p.2e.3e.4g.5f., 1a.2f.3e.4g.5f., 1b.2f.3e.4g.5f.,
1f.2f.3e.4g.5f., 1h.2f.3e.4g.5f., 1j.2f.3e.4g.5f., 1p.2f.3e.4g.5f.,
1a.2i.3e.4g.5f., 1b.2i.3e.4g.5f., 1f.2i.3e.4g.5f., 1h.2i.3e.4g.5f.,
1j.2i.3e.4g.5f., 1p.2i.3e.4g.5f., 1a.2m.3e.4g.5f., 1b.2m.3e.4g.5f.,
1f.2m.3e.4g.5f., 1h.2m.3e.4g.5f., 1j.2m.3e.4g.5f., 1p.2m.3e.4g.5f.,
1a.2o.3e.4g.5f., 1b.2o.3e.4g.5f., 1f.2o.3e.4g.5f., 1h.2o.3e.4g.5f.,
1j.2o.3e.4g.5f., 1p.2o.3e.4g.5f., 1a.2u.3e.4g.5f., 1b.2u.3e.4g.5f.,
1f.2u.3e.4g.5f., 1h.2u.3e.4g.5f., 1j.2u.3e.4g.5f., 1p.2u.3e.4g.5f.,
1a.2y.3e.4g.5f., 1b.2y.3e.4g.5f., 1f.2y.3e.4g.5f., 1h.2y.3e.4g.5f.,
1j.2y.3e.4g.5f., 1p.2y.3e.4g.5f., 1a.2a.3g.4g.5f., 1b.2a.3g.4g.5f.,
1f.2a.3g.4g.5f., 1h.2a.3g.4g.5f., 1j.2a.3g.4g.5f., 1p.2a.3g.4g.5f.,
1a.2b.3g.4g.5f., 1b.2b.3g.4g.5f., 1f.2b.3g.4g.5f., 1h.2b.3g.4g.5f.,
1j.2b.3g.4g.5f., 1p.2b.3g.4g.5f., 1a.2e.3g.4g.5f., 1b.2e.3g.4g.5f.,
1f.2e.3g.4g.5f., 1h.2e.3g.4g.5f., 1j.2e.3g.4g.5f., 1p.2e.3g.4g.5f.,
1a.2f.3g.4g.5f., 1b.2f.3g.4g.5f., 1f.2f.3g.4g.5f., 1h.2f.3g.4g.5f.,
1j.2f.3g.4g.5f., 1p.2f.3g.4g.5f., 1a.2i.3g.4g.5f., 1b.2i.3g.4g.5f.,
1f.2i.3g.4g.5f., 1h.2i.3g.4g.5f., 1j.2i.3g.4g.5f., 1p.2i.3g.4g.5f.,
1a.2m.3g.4g.5f., 1b.2m.3g.4g.5f., 1f.2m.3g.4g.5f., 1h.2m.3g.4g.5f.,
1j.2m.3g.4g.5f., 1p.2m.3g.4g.5f., 1a.2o.3g.4g.5f., 1b.2o.3g.4g.5f.,
1f.2o.3g.4g.5f., 1h.2o.3g.4g.5f., 1j.2o.3g.4g.5f., 1p.2o.3g.4g.5f.,
1a.2u.3g.4g.5f., 1b.2u.3g.4g.5f., 1f.2u.3g.4g.5f., 1h.2u.3g.4g.5f.,
1j.2u.3g.4g.5f., 1p.2u.3g.4g.5f., 1a.2y.3g.4g.5f., 1b.2y.3g.4g.5f.,
1f.2y.3g.4g.5f., 1h.2y.3g.4g.5f., 1j.2y.3g.4g.5f., 1p.2y.3g.4g.5f.,
1a.2a.3a.4h.5f., 1b.2a.3a.4h.5f., 1f.2a.3a.4h.5f., 1h.2a.3a.4h.5f.,
1j.2a.3a.4h.5f., 1p.2a.3a.4h.5f., 1a.2b.3a.4h.5f., 1b.2b.3a.4h.5f.,
1f.2b.3a.4h.5f., 1h.2b.3a.4h.5f., 1j.2b.3a.4h.5f., 1p.2b.3a.4h.5f.,
1a.2e.3a.4h.5f., 1b.2e.3a.4h.5f., 1f.2e.3a.4h.5f., 1h.2e.3a.4h.5f.,
1j.2e.3a.4h.5f., 1p.2e.3a.4h.5f., 1a.2f.3a.4h.5f., 1b.2f.3a.4h.5f.,
1f.2f.3a.4h.5f., 1h.2f.3a.4h.5f., 1j.2f.3a.4h.5f., 1p.2f.3a.4h.5f.,
1a.2i.3a.4h.5f., 1b.2i.3a.4h.5f., 1f.2i.3a.4h.5f., 1h.2i.3a.4h.5f.,
1j.2i.3a.4h.5f., 1p.2i.3a.4h.5f., 1a.2m.3a.4h.5f., 1b.2m.3a.4h.5f.,
1f.2m.3a.4h.5f., 1h.2m.3a.4h.5f., 1j.2m.3a.4h.5f., 1p.2m.3a.4h.5f.,
1a.2o.3a.4h.5f., 1b.2o.3a.4h.5f., 1f.2o.3a.4h.5f., 1h.2o.3a.4h.5f.,
1j.2o.3a.4h.5f., 1p.2o.3a.4h.5f., 1a.2u.3a.4h.5f., 1b.2u.3a.4h.5f.,
1f.2u.3a.4h.5f., 1h.2u.3a.4h.5f., 1j.2u.3a.4h.5f., 1p.2u.3a.4h.5f.,
1a.2y.3a.4h.5f., 1b.2y.3a.4h.5f., 1f.2y.3a.4h.5f., 1h.2y.3a.4h.5f.,
1j.2y.3a.4h.5f., 1p.2y.3a.4h.5f., 1a.2a.3b.4h.5f., 1b.2a.3b.4h.5f.,
1f.2a.3b.4h.5f., 1h.2a.3b.4h.5f., 1j.2a.3b.4h.5f., 1p.2a.3b.4h.5f.,
1a.2b.3b.4h.5f., 1b.2b.3b.4h.5f., 1f.2b.3b.4h.5f., 1h.2b.3b.4h.5f.,
1j.2b.3b.4h.5f., 1p.2b.3b.4h.5f., 1a.2e.3b.4h.5f., 1b.2e.3b.4h.5f.,
1f.2e.3b.4h.5f., 1h.2e.3b.4h.5f., 1j.2e.3b.4h.5f., 1p.2e.3b.4h.5f.,
1a.2f.3b.4h.5f., 1b.2f.3b.4h.5f., 1f.2f.3b.4h.5f., 1h.2f.3b.4h.5f.,
1j.2f.3b.4h.5f., 1p.2f.3b.4h.5f., 1a.2i.3b.4h.5f., 1b.2i.3b.4h.5f.,
1f.2i.3b.4h.5f., 1h.2i.3b.4h.5f., 1j.2i.3b.4h.5f., 1p.2i.3b.4h.5f.,
1a.2m.3b.4h.5f., 1b.2m.3b.4h.5f., 1f.2m.3b.4h.5f., 1h.2m.3b.4h.5f.,
1j.2m.3b.4h.5f., 1p.2m.3b.4h.5f., 1a.2o.3b.4h.5f., 1b.2o.3b.4h.5f.,
1f.2o.3b.4h.5f., 1h.2o.3b.4h.5f., 1j.2o.3b.4h.5f., 1p.2o.3b.4h.5f.,
1a.2u.3b.4h.5f., 1b.2u.3b.4h.5f., 1f.2u.3b.4h.5f., 1h.2u.3b.4h.5f.,
1j.2u.3b.4h.5f., 1p.2u.3b.4h.5f., 1a.2y.3b.4h.5f., 1b.2y.3b.4h.5f.,
1f.2y.3b.4h.5f., 1h.2y.3b.4h.5f., 1j.2y.3b.4h.5f., 1p.2y.3b.4h.5f.,
1a.2a.3e.4h.5f., 1b.2a.3e.4h.5f., 1f.2a.3e.4h.5f., 1h.2a.3e.4h.5f.,
1j.2a.3e.4h.5f., 1p.2a.3e.4h.5f., 1a.2b.3e.4h.5f., 1b.2b.3e.4h.5f.,
1f.2b.3e.4h.5f., 1h.2b.3e.4h.5f., 1j.2b.3e.4h.5f., 1p.2b.3e.4h.5f.,
1a.2e.3e.4h.5f., 1b.2e.3e.4h.5f., 1f.2e.3e.4h.5f., 1h.2e.3e.4h.5f.,
1j.2e.3e.4h.5f., 1p.2e.3e.4h.5f., 1a.2f.3e.4h.5f., 1b.2f.3e.4h.5f.,
1f.2f.3e.4h.5f., 1h.2f.3e.4h.5f., 1j.2f.3e.4h.5f., 1p.2f.3e.4h.5f.,
1a.2i.3e.4h.5f., 1b.2i.3e.4h.5f., 1f.2i.3e.4h.5f., 1h.2i.3e.4h.5f.,
1j.2i.3e.4h.5f., 1p.2i.3e.4h.5f., 1a.2m.3e.4h.5f., 1b.2m.3e.4h.5f.,
1f.2m.3e.4h.5f., 1h.2m.3e.4h.5f., 1j.2m.3e.4h.5f., 1p.2m.3e.4h.5f.,
1a.2o.3e.4h.5f., 1b.2o.3e.4h.5f., 1f.2o.3e.4h.5f., 1h.2o.3e.4h.5f.,
1j.2o.3e.4h.5f., 1p.2o.3e.4h.5f., 1a.2u.3e.4h.5f., 1b.2u.3e.4h.5f.,
1f.2u.3e.4h.5f., 1h.2u.3e.4h.5f., 1j.2u.3e.4h.5f., 1p.2u.3e.4h.5f.,
1a.2y.3e.4h.5f., 1b.2y.3e.4h.5f., 1f.2y.3e.4h.5f., 1h.2y.3e.4h.5f.,
1j.2y.3e.4h.5f., 1p.2y.3e.4h.5f., 1a.2a.3g.4h.5f., 1b.2a.3g.4h.5f.,
1f.2a.3g.4h.5f., 1h.2a.3g.4h.5f., 1j.2a.3g.4h.5f., 1p.2a.3g.4h.5f.,
1a.2b.3g.4h.5f., 1b.2b.3g.4h.5f., 1f.2b.3g.4h.5f., 1h.2b.3g.4h.5f.,
1j.2b.3g.4h.5f., 1p.2b.3g.4h.5f., 1a.2e.3g.4h.5f., 1b.2e.3g.4h.5f.,
1f.2e.3g.4h.5f., 1h.2e.3g.4h.5f., 1j.2e.3g.4h.5f., 1p.2e.3g.4h.5f.,
1a.2f.3g.4h.5f., 1b.2f.3g.4h.5f., 1f.2f.3g.4h.5f., 1h.2f.3g.4h.5f.,
1j.2f.3g.4h.5f., 1p.2f.3g.4h.5f., 1a.2i.3g.4h.5f., 1b.2i.3g.4h.5f.,
1f.2i.3g.4h.5f., 1h.2i.3g.4h.5f., 1j.2i.3g.4h.5f., 1p.2i.3g.4h.5f.,
1a.2m.3g.4h.5f., 1b.2m.3g.4h.5f., 1f.2m.3g.4h.5f., 1h.2m.3g.4h.5f.,
1j.2m.3g.4h.5f., 1p.2m.3g.4h.5f., 1a.2o.3g.4h.5f., 1b.2o.3g.4h.5f.,
1f.2o.3g.4h.5f., 1h.2o.3g.4h.5f., 1j.2o.3g.4h.5f., 1p.2o.3g.4h.5f.,
1a.2u.3g.4h.5f., 1b.2u.3g.4h.5f., 1f.2u.3g.4h.5f., 1h.2u.3g.4h.5f.,
1j.2u.3g.4h.5f., 1p.2u.3g.4h.5f., 1a.2y.3g.4h.5f., 1b.2y.3g.4h.5f.,
1f.2y.3g.4h.5f., 1h.2y.3g.4h.5f., 1j.2y.3g.4h.5f., 1p.2y.3g.4h.5f.,
1a.2a.3a.4i.5f., 1b.2a.3a.4i.5f., 1f.2a.3a.4i.5f., 1h.2a.3a.4i.5f.,
1j.2a.3a.4i.5f., 1p.2a.3a.4i.5f., 1a.2b.3a.4i.5f., 1b.2b.3a.4i.5f.,
1f.2b.3a.4i.5f., 1h.2b.3a.4i.5f., 1j.2b.3a.4i.5f., 1p.2b.3a.4i.5f.,
1a.2e.3a.4i.5f., 1b.2e.3a.4i.5f., 1f.2e.3a.4i.5f., 1h.2e.3a.4i.5f.,
1j.2e.3a.4i.5f., 1p.2e.3a.4i.5f., 1a.2f.3a.4i.5f., 1b.2f.3a.4i.5f.,
1f.2f.3a.4i.5f., 1h.2f.3a.4i.5f., 1j.2f.3a.4i.5f., 1p.2f.3a.4i.5f.,
1a.2i.3a.4i.5f., 1b.2i.3a.4i.5f., 1f.2i.3a.4i.5f., 1h.2i.3a.4i.5f.,
1j.2i.3a.4i.5f., 1p.2i.3a.4i.5f., 1a.2m.3a.4i.5f., 1b.2m.3a.4i.5f.,
1f.2m.3a.4i.5f., 1h.2m.3a.4i.5f., 1j.2m.3a.4i.5f., 1p.2m.3a.4i.5f.,
1a.2o.3a.4i.5f., 1b.2o.3a.4i.5f., 1f.2o.3a.4i.5f., 1h.2o.3a.4i.5f.,
1j.2o.3a.4i.5f., 1p.2o.3a.4i.5f., 1a.2u.3a.4i.5f., 1b.2u.3a.4i.5f.,
1f.2u.3a.4i.5f., 1h.2u.3a.4i.5f., 1j.2u.3a.4i.5f., 1p.2u.3a.4i.5f.,
1a.2y.3a.4i.5f., 1b.2y.3a.4i.5f., 1f.2y.3a.4i.5f., 1h.2y.3a.4i.5f.,
1j.2y.3a.4i.5f., 1p.2y.3a.4i.5f., 1a.2a.3b.4i.5f., 1b.2a.3b.4i.5f.,
1f.2a.3b.4i.5f., 1h.2a.3b.4i.5f., 1j.2a.3b.4i.5f., 1p.2a.3b.4i.5f.,
1a.2b.3b.4i.5f., 1b.2b.3b.4i.5f., 1f.2b.3b.4i.5f., 1h.2b.3b.4i.5f.,
1j.2b.3b.4i.5f., 1p.2b.3b.4i.5f., 1a.2e.3b.4i.5f., 1b.2e.3b.4i.5f.,
1f.2e.3b.4i.5f., 1h.2e.3b.4i.5f., 1j.2e.3b.4i.5f., 1p.2e.3b.4i.5f.,
1a.2f.3b.4i.5f., 1b.2f.3b.4i.5f., 1f.2f.3b.4i.5f., 1h.2f.3b.4i.5f.,
1j.2f.3b.4i.5f., 1p.2f.3b.4i.5f., 1a.2i.3b.4i.5f., 1b.2i.3b.4i.5f.,
1f.2i.3b.4i.5f., 1h.2i.3b.4i.5f., 1j.2i.3b.4i.5f., 1p.2i.3b.4i.5f.,
1a.2m.3b.4i.5f., 1b.2m.3b.4i.5f., 1f.2m.3b.4i.5f., 1h.2m.3b.4i.5f.,
1j.2m.3b.4i.5f., 1p.2m.3b.4i.5f., 1a.2o.3b.4i.5f., 1b.2o.3b.4i.5f.,
1f.2o.3b.4i.5f., 1h.2o.3b.4i.5f., 1j.2o.3b.4i.5f., 1p.2o.3b.4i.5f.,
1a.2u.3b.4i.5f., 1b.2u.3b.4i.5f., 1f.2u.3b.4i.5f., 1h.2u.3b.4i.5f.,
1j.2u.3b.4i.5f., 1p.2u.3b.4i.5f., 1a.2y.3b.4i.5f., 1b.2y.3b.4i.5f.,
1f.2y.3b.4i.5f., 1h.2y.3b.4i.5f., 1j.2y.3b.4i.5f., 1p.2y.3b.4i.5f.,
1a.2a.3e.4i.5f., 1b.2a.3e.4i.5f., 1f.2a.3e.4i.5f., 1h.2a.3e.4i.5f.,
1j.2a.3e.4i.5f., 1p.2a.3e.4i.5f., 1a.2b.3e.4i.5f., 1b.2b.3e.4i.5f.,
1f.2b.3e.4i.5f., 1h.2b.3e.4i.5f., 1j.2b.3e.4i.5f., 1p.2b.3e.4i.5f.,
1a.2e.3e.4i.5f., 1b.2e.3e.4i.5f., 1f.2e.3e.4i.5f., 1h.2e.3e.4i.5f.,
1j.2e.3e.4i.5f., 1p.2e.3e.4i.5f., 1a.2f.3e.4i.5f., 1b.2f.3e.4i.5f.,
1f.2f.3e.4i.5f., 1h.2f.3e.4i.5f., 1j.2f.3e.4i.5f., 1p.2f.3e.4i.5f.,
1a.2i.3e.4i.5f., 1b.2i.3e.4i.5f., 1f.2i.3e.4i.5f., 1h.2i.3e.4i.5f.,
1j.2i.3e.4i.5f., 1p.2i.3e.4i.5f., 1a.2m.3e.4i.5f., 1b.2m.3e.4i.5f.,
1f.2m.3e.4i.5f., 1h.2m.3e.4i.5f., 1j.2m.3e.4i.5f., 1p.2m.3e.4i.5f.,
1a.2o.3e.4i.5f., 1b.2o.3e.4i.5f., 1f.2o.3e.4i.5f., 1h.2o.3e.4i.5f.,
1j.2o.3e.4i.5f., 1p.2o.3e.4i.5f., 1a.2u.3e.4i.5f., 1b.2u.3e.4i.5f.,
1f.2u.3e.4i.5f., 1h.2u.3e.4i.5f., 1j.2u.3e.4i.5f., 1p.2u.3e.4i.5f.,
1a.2y.3e.4i.5f., 1b.2y.3e.4i.5f., 1f.2y.3e.4i.5f., 1h.2y.3e.4i.5f.,
1j.2y.3e.4i.5f., 1p.2y.3e.4i.5f., 1a.2a.3g.4i.5f., 1b.2a.3g.4i.5f.,
1f.2a.3g.4i.5f., 1h.2a.3g.4i.5f., 1j.2a.3g.4i.5f., 1p.2a.3g.4i.5f.,
1a.2b.3g.4i.5f., 1b.2b.3g.4i.5f., 1f.2b.3g.4i.5f., 1h.2b.3g.4i.5f.,

TABLE 12-continued

List of Compound Structures of Formula II 1j.2b.3g.4i.5f., 1p.2b.3g.4i.5f., 1a.2e.3g.4i.5f., 1b.2e.3g.4i.5f., 1f.2e.3g.4i.5f., 1h.2e.3g.4i.5f., 1j.2e.3g.4i.5f., 1p.2e.3g.4i.5f., 1a.2f.3g.4i.5f., 1b.2f.3g.4i.5f., 1f.2f.3g.4i.5f., 1h.2f.3g.4i.5f., 1j.2f.3g.4i.5f., 1p.2f.3g.4i.5f., 1a.2i.3g.4i.5f., 1b.2i.3g.4i.5f., 1f.2i.3g.4i.5f., 1h.2i.3g.4i.5f., 1j.2i.3g.4i.5f., 1p.2i.3g.4i.5f., 1a.2m.3g.4i.5f., 1b.2m.3g.4i.5f., 1f.2m.3g.4i.5f., 1h.2m.3g.4i.5f., 1j.2m.3g.4i.5f., 1p.2m.3g.4i.5f., 1a.2o.3g.4i.5f., 1b.2o.3g.4i.5f., 1f.2o.3g.4i.5f., 1h.2o.3g.4i.5f., 1j.2o.3g.4i.5f., 1p.2o.3g.4i.5f., 1a.2u.3g.4i.5f., 1b.2u.3g.4i.5f., 1f.2u.3g.4i.5f., 1h.2u.3g.4i.5f., 1j.2u.3g.4i.5f., 1p.2u.3g.4i.5f., 1a.2y.3g.4i.5f., 1b.2y.3g.4i.5f., 1f.2y.3g.4i.5f., 1h.2y.3g.4i.5f., 1j.2y.3g.4i.5f., 1p.2y.3g.4i.5f., 1a.2a.3a.4a.5g., 1b.2a.3a.4a.5g., 1f.2a.3a.4a.5g., 1h.2a.3a.4a.5g., 1j.2a.3a.4a.5g., 1p.2a.3a.4a.5g., 1a.2b.3a.4a.5g., 1b.2b.3a.4a.5g., 1f.2b.3a.4a.5g., 1h.2b.3a.4a.5g., 1j.2b.3a.4a.5g., 1p.2b.3a.4a.5g., 1a.2e.3a.4a.5g., 1b.2e.3a.4a.5g., 1f.2e.3a.4a.5g., 1h.2e.3a.4a.5g., 1j.2e.3a.4a.5g., 1p.2e.3a.4a.5g., 1a.2f.3a.4a.5g., 1b.2f.3a.4a.5g., 1f.2f.3a.4a.5g., 1h.2f.3a.4a.5g., 1j.2f.3a.4a.5g., 1p.2f.3a.4a.5g., 1a.2i.3a.4a.5g., 1b.2i.3a.4a.5g., 1f.2i.3a.4a.5g., 1h.2i.3a.4a.5g., 1j.2i.3a.4a.5g., 1p.2i.3a.4a.5g., 1a.2m.3a.4a.5g., 1b.2m.3a.4a.5g., 1f.2m.3a.4a.5g., 1h.2m.3a.4a.5g., 1j.2m.3a.4a.5g., 1p.2m.3a.4a.5g., 1a.2o.3a.4a.5g., 1b.2o.3a.4a.5g., 1f.2o.3a.4a.5g., 1h.2o.3a.4a.5g., 1j.2o.3a.4a.5g., 1p.2o.3a.4a.5g., 1a.2u.3a.4a.5g., 1b.2u.3a.4a.5g., 1f.2u.3a.4a.5g., 1h.2u.3a.4a.5g., 1j.2u.3a.4a.5g., 1p.2u.3a.4a.5g., 1a.2y.3a.4a.5g., 1b.2y.3a.4a.5g., 1f.2y.3a.4a.5g., 1h.2y.3a.4a.5g., 1j.2y.3a.4a.5g., 1p.2y.3a.4a.5g., 1a.2a.3b.4a.5g., 1b.2a.3b.4a.5g., 1f.2a.3b.4a.5g., 1h.2a.3b.4a.5g., 1j.2a.3b.4a.5g., 1p.2a.3b.4a.5g., 1a.2b.3b.4a.5g., 1b.2b.3b.4a.5g., 1f.2b.3b.4a.5g., 1h.2b.3b.4a.5g., 1j.2b.3b.4a.5g., 1p.2b.3b.4a.5g., 1a.2e.3b.4a.5g., 1b.2e.3b.4a.5g., 1f.2e.3b.4a.5g., 1h.2e.3b.4a.5g., 1j.2e.3b.4a.5g., 1p.2e.3b.4a.5g., 1a.2f.3b.4a.5g., 1b.2f.3b.4a.5g., 1f.2f.3b.4a.5g., 1h.2f.3b.4a.5g., 1j.2f.3b.4a.5g., 1p.2f.3b.4a.5g., 1a.2i.3b.4a.5g., 1b.2i.3b.4a.5g., 1f.2i.3b.4a.5g., 1h.2i.3b.4a.5g., 1j.2i.3b.4a.5g., 1p.2i.3b.4a.5g., 1a.2m.3b.4a.5g., 1b.2m.3b.4a.5g., 1f.2m.3b.4a.5g., 1h.2m.3b.4a.5g., 1j.2m.3b.4a.5g., 1p.2m.3b.4a.5g., 1a.2o.3b.4a.5g., 1b.2o.3b.4a.5g., 1f.2o.3b.4a.5g., 1h.2o.3b.4a.5g., 1j.2o.3b.4a.5g., 1p.2o.3b.4a.5g., 1a.2u.3b.4a.5g., 1b.2u.3b.4a.5g., 1f.2u.3b.4a.5g., 1h.2u.3b.4a.5g., 1j.2u.3b.4a.5g., 1p.2u.3b.4a.5g., 1a.2y.3b.4a.5g., 1b.2y.3b.4a.5g., 1f.2y.3b.4a.5g., 1h.2y.3b.4a.5g., 1j.2y.3b.4a.5g., 1p.2y.3b.4a.5g., 1a.2a.3e.4a.5g., 1b.2a.3e.4a.5g., 1f.2a.3e.4a.5g., 1h.2a.3e.4a.5g., 1j.2a.3e.4a.5g., 1p.2a.3e.4a.5g., 1a.2b.3e.4a.5g., 1b.2b.3e.4a.5g., 1f.2b.3e.4a.5g., 1h.2b.3e.4a.5g., 1j.2b.3e.4a.5g., 1p.2b.3e.4a.5g., 1a.2e.3e.4a.5g., 1b.2e.3e.4a.5g., 1f.2e.3e.4a.5g., 1h.2e.3e.4a.5g., 1j.2e.3e.4a.5g., 1p.2e.3e.4a.5g., 1a.2f.3e.4a.5g., 1b.2f.3e.4a.5g., 1f.2f.3e.4a.5g., 1h.2f.3e.4a.5g., 1j.2f.3e.4a.5g., 1p.2f.3e.4a.5g., 1a.2i.3e.4a.5g., 1b.2i.3e.4a.5g., 1f.2i.3e.4a.5g., 1h.2i.3e.4a.5g., 1j.2i.3e.4a.5g., 1p.2i.3e.4a.5g., 1a.2m.3e.4a.5g., 1b.2m.3e.4a.5g., 1f.2m.3e.4a.5g., 1h.2m.3e.4a.5g., 1j.2m.3e.4a.5g., 1p.2m.3e.4a.5g., 1a.2o.3e.4a.5g., 1b.2o.3e.4a.5g., 1f.2o.3e.4a.5g., 1h.2o.3e.4a.5g., 1j.2o.3e.4a.5g., 1p.2o.3e.4a.5g., 1a.2u.3e.4a.5g., 1b.2u.3e.4a.5g., 1f.2u.3e.4a.5g., 1h.2u.3e.4a.5g., 1j.2u.3e.4a.5g., 1p.2u.3e.4a.5g., 1a.2y.3e.4a.5g., 1b.2y.3e.4a.5g., 1f.2y.3e.4a.5g., 1h.2y.3e.4a.5g., 1j.2y.3e.4a.5g., 1p.2y.3e.4a.5g., 1a.2a.3g.4a.5g., 1b.2a.3g.4a.5g., 1f.2a.3g.4a.5g., 1h.2a.3g.4a.5g., 1j.2a.3g.4a.5g., 1p.2a.3g.4a.5g., 1a.2b.3g.4a.5g., 1b.2b.3g.4a.5g., 1f.2b.3g.4a.5g., 1h.2b.3g.4a.5g., 1j.2b.3g.4a.5g., 1p.2b.3g.4a.5g., 1a.2e.3g.4a.5g., 1b.2e.3g.4a.5g., 1f.2e.3g.4a.5g., 1h.2e.3g.4a.5g., 1j.2e.3g.4a.5g., 1p.2e.3g.4a.5g., 1a.2f.3g.4a.5g., 1b.2f.3g.4a.5g., 1f.2f.3g.4a.5g., 1h.2f.3g.4a.5g., 1j.2f.3g.4a.5g., 1p.2f.3g.4a.5g., 1a.2i.3g.4a.5g., 1b.2i.3g.4a.5g., 1f.2i.3g.4a.5g., 1h.2i.3g.4a.5g., 1j.2i.3g.4a.5g., 1p.2i.3g.4a.5g., 1a.2m.3g.4a.5g., 1b.2m.3g.4a.5g., 1f.2m.3g.4a.5g., 1h.2m.3g.4a.5g., 1j.2m.3g.4a.5g., 1p.2m.3g.4a.5g., 1a.2o.3g.4a.5g., 1b.2o.3g.4a.5g., 1f.2o.3g.4a.5g., 1h.2o.3g.4a.5g., 1j.2o.3g.4a.5g., 1p.2o.3g.4a.5g., 1a.2u.3g.4a.5g., 1b.2u.3g.4a.5g., 1f.2u.3g.4a.5g., 1h.2u.3g.4a.5g., 1j.2u.3g.4a.5g., 1p.2u.3g.4a.5g., 1a.2y.3g.4a.5g., 1b.2y.3g.4a.5g., 1f.2y.3g.4a.5g., 1h.2y.3g.4a.5g., 1j.2y.3g.4a.5g., 1p.2y.3g.4a.5g., 1a.2a.3a.4d.5g., 1b.2a.3a.4d.5g., 1f.2a.3a.4d.5g., 1h.2a.3a.4d.5g., 1j.2a.3a.4d.5g., 1p.2a.3a.4d.5g., 1a.2b.3a.4d.5g., 1b.2b.3a.4d.5g., 1f.2b.3a.4d.5g., 1h.2b.3a.4d.5g., 1j.2b.3a.4d.5g., 1p.2b.3a.4d.5g., 1a.2e.3a.4d.5g., 1b.2e.3a.4d.5g., 1f.2e.3a.4d.5g., 1h.2e.3a.4d.5g., 1j.2e.3a.4d.5g., 1p.2e.3a.4d.5g., 1a.2f.3a.4d.5g., 1b.2f.3a.4d.5g., 1f.2f.3a.4d.5g., 1h.2f.3a.4d.5g., 1j.2f.3a.4d.5g., 1p.2f.3a.4d.5g., 1a.2i.3a.4d.5g., 1b.2i.3a.4d.5g., 1f.2i.3a.4d.5g., 1h.2i.3a.4d.5g., 1j.2i.3a.4d.5g., 1p.2i.3a.4d.5g., 1a.2m.3a.4d.5g., 1b.2m.3a.4d.5g., 1f.2m.3a.4d.5g., 1h.2m.3a.4d.5g., 1j.2m.3a.4d.5g., 1p.2m.3a.4d.5g., 1a.2o.3a.4d.5g., 1b.2o.3a.4d.5g., 1f.2o.3a.4d.5g., 1h.2o.3a.4d.5g., 1j.2o.3a.4d.5g., 1p.2o.3a.4d.5g., 1a.2u.3a.4d.5g., 1b.2u.3a.4d.5g., 1f.2u.3a.4d.5g., 1h.2u.3a.4d.5g., 1j.2u.3a.4d.5g., 1p.2u.3a.4d.5g., 1a.2y.3a.4d.5g., 1b.2y.3a.4d.5g., 1f.2y.3a.4d.5g., 1h.2y.3a.4d.5g., 1j.2y.3a.4d.5g., 1p.2y.3a.4d.5g., 1a.2a.3b.4d.5g., 1b.2a.3b.4d.5g., 1f.2a.3b.4d.5g., 1h.2a.3b.4d.5g., 1j.2a.3b.4d.5g., 1p.2a.3b.4d.5g., 1a.2b.3b.4d.5g., 1b.2b.3b.4d.5g., 1f.2b.3b.4d.5g., 1h.2b.3b.4d.5g., 1j.2b.3b.4d.5g., 1p.2b.3b.4d.5g., 1a.2e.3b.4d.5g., 1b.2e.3b.4d.5g., 1f.2e.3b.4d.5g., 1h.2e.3b.4d.5g., 1j.2e.3b.4d.5g., 1p.2e.3b.4d.5g., 1a.2f.3b.4d.5g., 1b.2f.3b.4d.5g., 1f.2f.3b.4d.5g., 1h.2f.3b.4d.5g., 1j.2f.3b.4d.5g., 1p.2f.3b.4d.5g., 1a.2i.3b.4d.5g., 1b.2i.3b.4d.5g., 1f.2i.3b.4d.5g., 1h.2i.3b.4d.5g., 1j.2i.3b.4d.5g., 1p.2i.3b.4d.5g., 1a.2m.3b.4d.5g., 1b.2m.3b.4d.5g., 1f.2m.3b.4d.5g., 1h.2m.3b.4d.5g., 1j.2m.3b.4d.5g., 1p.2m.3b.4d.5g., 1a.2o.3b.4d.5g., 1b.2o.3b.4d.5g., 1f.2o.3b.4d.5g., 1h.2o.3b.4d.5g., 1j.2o.3b.4d.5g., 1p.2o.3b.4d.5g., 1a.2u.3b.4d.5g., 1b.2u.3b.4d.5g., 1f.2u.3b.4d.5g., 1h.2u.3b.4d.5g., 1j.2u.3b.4d.5g., 1p.2u.3b.4d.5g., 1a.2y.3b.4d.5g., 1b.2y.3b.4d.5g., 1f.2y.3b.4d.5g., 1h.2y.3b.4d.5g., 1j.2y.3b.4d.5g., 1p.2y.3b.4d.5g., 1a.2a.3e.4d.5g., 1b.2a.3e.4d.5g., 1f.2a.3e.4d.5g., 1h.2a.3e.4d.5g., 1j.2a.3e.4d.5g., 1p.2a.3e.4d.5g., 1a.2b.3e.4d.5g., 1b.2b.3e.4d.5g., 1f.2b.3e.4d.5g., 1h.2b.3e.4d.5g., 1j.2b.3e.4d.5g., 1p.2b.3e.4d.5g., 1a.2e.3e.4d.5g., 1b.2e.3e.4d.5g., 1f.2e.3e.4d.5g., 1h.2e.3e.4d.5g., 1j.2e.3e.4d.5g., 1p.2e.3e.4d.5g., 1a.2f.3e.4d.5g., 1b.2f.3e.4d.5g., 1f.2f.3e.4d.5g., 1h.2f.3e.4d.5g., 1j.2f.3e.4d.5g., 1p.2f.3e.4d.5g., 1a.2i.3e.4d.5g., 1b.2i.3e.4d.5g., 1f.2i.3e.4d.5g., 1h.2i.3e.4d.5g., 1j.2i.3e.4d.5g., 1p.2i.3e.4d.5g., 1a.2m.3e.4d.5g., 1b.2m.3e.4d.5g., 1f.2m.3e.4d.5g., 1h.2m.3e.4d.5g., 1j.2m.3e.4d.5g., 1p.2m.3e.4d.5g., 1a.2o.3e.4d.5g., 1b.2o.3e.4d.5g., 1f.2o.3e.4d.5g., 1h.2o.3e.4d.5g., 1j.2o.3e.4d.5g., 1p.2o.3e.4d.5g., 1a.2u.3e.4d.5g., 1b.2u.3e.4d.5g., 1f.2u.3e.4d.5g., 1h.2u.3e.4d.5g., 1j.2u.3e.4d.5g., 1p.2u.3e.4d.5g., 1a.2y.3e.4d.5g., 1b.2y.3e.4d.5g., 1f.2y.3e.4d.5g., 1h.2y.3e.4d.5g., 1j.2y.3e.4d.5g., 1p.2y.3e.4d.5g., 1a.2a.3g.4d.5g., 1b.2a.3g.4d.5g., 1f.2a.3g.4d.5g., 1h.2a.3g.4d.5g., 1j.2a.3g.4d.5g., 1p.2a.3g.4d.5g., 1a.2b.3g.4d.5g., 1b.2b.3g.4d.5g., 1f.2b.3g.4d.5g., 1h.2b.3g.4d.5g., 1j.2b.3g.4d.5g., 1p.2b.3g.4d.5g., 1a.2e.3g.4d.5g., 1b.2e.3g.4d.5g., 1f.2e.3g.4d.5g., 1h.2e.3g.4d.5g., 1j.2e.3g.4d.5g., 1p.2e.3g.4d.5g., 1a.2f.3g.4d.5g., 1b.2f.3g.4d.5g., 1f.2f.3g.4d.5g., 1h.2f.3g.4d.5g., 1j.2f.3g.4d.5g., 1p.2f.3g.4d.5g., 1a.2i.3g.4d.5g., 1b.2i.3g.4d.5g., 1f.2i.3g.4d.5g., 1h.2i.3g.4d.5g., 1j.2i.3g.4d.5g., 1p.2i.3g.4d.5g., 1a.2m.3g.4d.5g., 1b.2m.3g.4d.5g., 1f.2m.3g.4d.5g., 1h.2m.3g.4d.5g., 1j.2m.3g.4d.5g., 1p.2m.3g.4d.5g., 1a.2o.3g.4d.5g., 1b.2o.3g.4d.5g., 1f.2o.3g.4d.5g., 1h.2o.3g.4d.5g., 1j.2o.3g.4d.5g., 1p.2o.3g.4d.5g., 1a.2u.3g.4d.5g., 1b.2u.3g.4d.5g., 1f.2u.3g.4d.5g., 1h.2u.3g.4d.5g., 1j.2u.3g.4d.5g., 1p.2u.3g.4d.5g., 1a.2y.3g.4d.5g., 1b.2y.3g.4d.5g., 1f.2y.3g.4d.5g., 1h.2y.3g.4d.5g., 1j.2y.3g.4d.5g., 1p.2y.3g.4d.5g., 1a.2a.3a.4f.5g., 1b.2a.3a.4f.5g., 1f.2a.3a.4f.5g., 1h.2a.3a.4f.5g., 1j.2a.3a.4f.5g., 1p.2a.3a.4f.5g., 1a.2b.3a.4f.5g., 1b.2b.3a.4f.5g., 1f.2b.3a.4f.5g., 1h.2b.3a.4f.5g., 1j.2b.3a.4f.5g., 1p.2b.3a.4f.5g., 1a.2e.3a.4f.5g., 1b.2e.3a.4f.5g., 1f.2e.3a.4f.5g., 1h.2e.3a.4f.5g., 1j.2e.3a.4f.5g., 1p.2e.3a.4f.5g., 1a.2f.3a.4f.5g., 1b.2f.3a.4f.5g., 1f.2f.3a.4f.5g., 1h.2f.3a.4f.5g., 1j.2f.3a.4f.5g., 1p.2f.3a.4f.5g., 1a.2i.3a.4f.5g., 1b.2i.3a.4f.5g., 1f.2i.3a.4f.5g., 1h.2i.3a.4f.5g., 1j.2i.3a.4f.5g., 1p.2i.3a.4f.5g., 1a.2m.3a.4f.5g., 1b.2m.3a.4f.5g., 1f.2m.3a.4f.5g., 1h.2m.3a.4f.5g., 1j.2m.3a.4f.5g., 1p.2m.3a.4f.5g., 1a.2o.3a.4f.5g., 1b.2o.3a.4f.5g., 1f.2o.3a.4f.5g., 1h.2o.3a.4f.5g., 1j.2o.3a.4f.5g., 1p.2o.3a.4f.5g., 1a.2u.3a.4f.5g., 1b.2u.3a.4f.5g., 1f.2u.3a.4f.5g., 1h.2u.3a.4f.5g., 1j.2u.3a.4f.5g., 1p.2u.3a.4f.5g., 1a.2y.3a.4f.5g., 1b.2y.3a.4f.5g., 1f.2y.3a.4f.5g., 1h.2y.3a.4f.5g., 1j.2y.3a.4f.5g., 1p.2y.3a.4f.5g., 1a.2a.3b.4f.5g., 1b.2a.3b.4f.5g., 1f.2a.3b.4f.5g., 1h.2a.3b.4f.5g., 1j.2a.3b.4f.5g., 1p.2a.3b.4f.5g., 1a.2b.3b.4f.5g., 1b.2b.3b.4f.5g., 1f.2b.3b.4f.5g., 1h.2b.3b.4f.5g., 1j.2b.3b.4f.5g., 1p.2b.3b.4f.5g., 1a.2e.3b.4f.5g., 1b.2e.3b.4f.5g., 1f.2e.3b.4f.5g., 1h.2e.3b.4f.5g., 1j.2e.3b.4f.5g., 1p.2e.3b.4f.5g., 1a.2f.3b.4f.5g., 1b.2f.3b.4f.5g., 1f.2f.3b.4f.5g., 1h.2f.3b.4f.5g., 1j.2f.3b.4f.5g., 1p.2f.3b.4f.5g., 1a.2i.3b.4f.5g., 1b.2i.3b.4f.5g., 1f.2i.3b.4f.5g., 1h.2i.3b.4f.5g., 1j.2i.3b.4f.5g., 1p.2i.3b.4f.5g., 1a.2m.3b.4f.5g., 1b.2m.3b.4f.5g., 1f.2m.3b.4f.5g., 1h.2m.3b.4f.5g., 1j.2m.3b.4f.5g., 1p.2m.3b.4f.5g., 1a.2o.3b.4f.5g., 1b.2o.3b.4f.5g., 1f.2o.3b.4f.5g., 1h.2o.3b.4f.5g., 1j.2o.3b.4f.5g., 1p.2o.3b.4f.5g., 1a.2u.3b.4f.5g., 1b.2u.3b.4f.5g., 1f.2u.3b.4f.5g., 1h.2u.3b.4f.5g., 1j.2u.3b.4f.5g., 1p.2u.3b.4f.5g., 1a.2y.3b.4f.5g., 1b.2y.3b.4f.5g., 1f.2y.3b.4f.5g., 1h.2y.3b.4f.5g., 1j.2y.3b.4f.5g., 1p.2y.3b.4f.5g., 1a.2a.3e.4f.5g., 1b.2a.3e.4f.5g., 1f.2a.3e.4f.5g., 1h.2a.3e.4f.5g., 1j.2a.3e.4f.5g., 1p.2a.3e.4f.5g., 1a.2b.3e.4f.5g., 1b.2b.3e.4f.5g., 1f.2b.3e.4f.5g., 1h.2b.3e.4f.5g., 1j.2b.3e.4f.5g., 1p.2b.3e.4f.5g., 1a.2e.3e.4f.5g., 1b.2e.3e.4f.5g., 1f.2e.3e.4f.5g., 1h.2e.3e.4f.5g., 1j.2e.3e.4f.5g., 1p.2e.3e.4f.5g., 1a.2f.3e.4f.5g., 1b.2f.3e.4f.5g., 1f.2f.3e.4f.5g., 1h.2f.3e.4f.5g., 1j.2f.3e.4f.5g., 1p.2f.3e.4f.5g., 1a.2i.3e.4f.5g., 1b.2i.3e.4f.5g., 1f.2i.3e.4f.5g., 1h.2i.3e.4f.5g., 1j.2i.3e.4f.5g., 1p.2i.3e.4f.5g., 1a.2m.3e.4f.5g., 1b.2m.3e.4f.5g., 1f.2m.3e.4f.5g., 1h.2m.3e.4f.5g., 1j.2m.3e.4f.5g., 1p.2m.3e.4f.5g., 1a.2o.3e.4f.5g., 1b.2o.3e.4f.5g., 1f.2o.3e.4f.5g., 1h.2o.3e.4f.5g.,

TABLE 12-continued

List of Compound Structures of Formula II 1j.2o.3e.4f.5g., 1p.2o.3e.4f.5g., 1a.2u.3e.4f.5g., 1b.2u.3e.4f.5g., 1f.2u.3e.4f.5g., 1h.2u.3e.4f.5g., 1j.2u.3e.4f.5g., 1p.2u.3e.4f.5g., 1a.2y.3e.4f.5g., 1b.2y.3e.4f.5g., 1f.2y.3e.4f.5g., 1h.2y.3e.4f.5g., 1j.2y.3e.4f.5g., 1p.2y.3e.4f.5g., 1a.2a.3g.4f.5g., 1b.2a.3g.4f.5g., 1f.2a.3g.4f.5g., 1h.2a.3g.4f.5g., 1j.2a.3g.4f.5g., 1p.2a.3g.4f.5g., 1a.2b.3g.4f.5g., 1b.2b.3g.4f.5g., 1f.2b.3g.4f.5g., 1h.2b.3g.4f.5g., 1j.2b.3g.4f.5g., 1p.2b.3g.4f.5g., 1a.2e.3g.4f.5g., 1b.2e.3g.4f.5g., 1f.2e.3g.4f.5g., 1h.2e.3g.4f.5g., 1j.2e.3g.4f.5g., 1p.2e.3g.4f.5g., 1a.2f.3g.4f.5g., 1b.2f.3g.4f.5g., 1f.2f.3g.4f.5g., 1h.2f.3g.4f.5g., 1j.2f.3g.4f.5g., 1p.2f.3g.4f.5g., 1a.2i.3g.4f.5g., 1b.2i.3g.4f.5g., 1f.2i.3g.4f.5g., 1h.2i.3g.4f.5g., 1j.2i.3g.4f.5g., 1p.2i.3g.4f.5g., 1a.2m.3g.4f.5g., 1b.2m.3g.4f.5g., 1f.2m.3g.4f.5g., 1h.2m.3g.4f.5g., 1j.2m.3g.4f.5g., 1p.2m.3g.4f.5g., 1a.2o.3g.4f.5g., 1b.2o.3g.4f.5g., 1f.2o.3g.4f.5g., 1h.2o.3g.4f.5g., 1j.2o.3g.4f.5g., 1p.2o.3g.4f.5g., 1a.2u.3g.4f.5g., 1b.2u.3g.4f.5g., 1f.2u.3g.4f.5g., 1h.2u.3g.4f.5g., 1j.2u.3g.4f.5g., 1p.2u.3g.4f.5g., 1a.2y.3g.4f.5g., 1b.2y.3g.4f.5g., 1f.2y.3g.4f.5g., 1h.2y.3g.4f.5g., 1j.2y.3g.4f.5g., 1p.2y.3g.4f.5g., 1a.2a.3a.4g.5g., 1b.2a.3a.4g.5g., 1f.2a.3a.4g.5g., 1h.2a.3a.4g.5g., 1j.2a.3a.4g.5g., 1p.2a.3a.4g.5g., 1a.2b.3a.4g.5g., 1b.2b.3a.4g.5g., 1f.2b.3a.4g.5g., 1h.2b.3a.4g.5g., 1j.2b.3a.4g.5g., 1p.2b.3a.4g.5g., 1a.2e.3a.4g.5g., 1b.2e.3a.4g.5g., 1f.2e.3a.4g.5g., 1h.2e.3a.4g.5g., 1j.2e.3a.4g.5g., 1p.2e.3a.4g.5g., 1a.2f.3a.4g.5g., 1b.2f.3a.4g.5g., 1f.2f.3a.4g.5g., 1h.2f.3a.4g.5g., 1j.2f.3a.4g.5g., 1p.2f.3a.4g.5g., 1a.2i.3a.4g.5g., 1b.2i.3a.4g.5g., 1f.2i.3a.4g.5g., 1h.2i.3a.4g.5g., 1j.2i.3a.4g.5g., 1p.2i.3a.4g.5g., 1a.2m.3a.4g.5g., 1b.2m.3a.4g.5g., 1f.2m.3a.4g.5g., 1h.2m.3a.4g.5g., 1j.2m.3a.4g.5g., 1p.2m.3a.4g.5g., 1a.2o.3a.4g.5g., 1b.2o.3a.4g.5g., 1f.2o.3a.4g.5g., 1h.2o.3a.4g.5g., 1j.2o.3a.4g.5g., 1p.2o.3a.4g.5g., 1a.2u.3a.4g.5g., 1b.2u.3a.4g.5g., 1f.2u.3a.4g.5g., 1h.2u.3a.4g.5g., 1j.2u.3a.4g.5g., 1p.2u.3a.4g.5g., 1a.2y.3a.4g.5g., 1b.2y.3a.4g.5g., 1f.2y.3a.4g.5g., 1h.2y.3a.4g.5g., 1j.2y.3a.4g.5g., 1p.2y.3a.4g.5g., 1a.2a.3b.4g.5g., 1b.2a.3b.4g.5g., 1f.2a.3b.4g.5g., 1h.2a.3b.4g.5g., 1j.2a.3b.4g.5g., 1p.2a.3b.4g.5g., 1a.2b.3b.4g.5g., 1b.2b.3b.4g.5g., 1f.2b.3b.4g.5g., 1h.2b.3b.4g.5g., 1j.2b.3b.4g.5g., 1p.2b.3b.4g.5g., 1a.2e.3b.4g.5g., 1b.2e.3b.4g.5g., 1f.2e.3b.4g.5g., 1h.2e.3b.4g.5g., 1j.2e.3b.4g.5g., 1p.2e.3b.4g.5g., 1a.2f.3b.4g.5g., 1b.2f.3b.4g.5g., 1f.2f.3b.4g.5g., 1h.2f.3b.4g.5g., 1j.2f.3b.4g.5g., 1p.2f.3b.4g.5g., 1a.2i.3b.4g.5g., 1b.2i.3b.4g.5g., 1f.2i.3b.4g.5g., 1h.2i.3b.4g.5g., 1j.2i.3b.4g.5g., 1p.2i.3b.4g.5g., 1a.2m.3b.4g.5g., 1b.2m.3b.4g.5g., 1f.2m.3b.4g.5g., 1h.2m.3b.4g.5g., 1j.2m.3b.4g.5g., 1p.2m.3b.4g.5g., 1a.2o.3b.4g.5g., 1b.2o.3b.4g.5g., 1f.2o.3b.4g.5g., 1h.2o.3b.4g.5g., 1j.2o.3b.4g.5g., 1p.2o.3b.4g.5g., 1a.2u.3b.4g.5g., 1b.2u.3b.4g.5g., 1f.2u.3b.4g.5g., 1h.2u.3b.4g.5g., 1j.2u.3b.4g.5g., 1p.2u.3b.4g.5g., 1a.2y.3b.4g.5g., 1b.2y.3b.4g.5g., 1f.2y.3b.4g.5g., 1h.2y.3b.4g.5g., 1j.2y.3b.4g.5g., 1p.2y.3b.4g.5g., 1a.2a.3e.4g.5g., 1b.2a.3e.4g.5g., 1f.2a.3e.4g.5g., 1h.2a.3e.4g.5g., 1j.2a.3e.4g.5g., 1p.2a.3e.4g.5g., 1a.2b.3e.4g.5g., 1b.2b.3e.4g.5g., 1f.2b.3e.4g.5g., 1h.2b.3e.4g.5g., 1j.2b.3e.4g.5g., 1p.2b.3e.4g.5g., 1a.2e.3e.4g.5g., 1b.2e.3e.4g.5g., 1f.2e.3e.4g.5g., 1h.2e.3e.4g.5g., 1j.2e.3e.4g.5g., 1p.2e.3e.4g.5g., 1a.2f.3e.4g.5g., 1b.2f.3e.4g.5g., 1f.2f.3e.4g.5g., 1h.2f.3e.4g.5g., 1j.2f.3e.4g.5g., 1p.2f.3e.4g.5g., 1a.2i.3e.4g.5g., 1b.2i.3e.4g.5g., 1f.2i.3e.4g.5g., 1h.2i.3e.4g.5g., 1j.2i.3e.4g.5g., 1p.2i.3e.4g.5g., 1a.2m.3e.4g.5g., 1b.2m.3e.4g.5g., 1f.2m.3e.4g.5g., 1h.2m.3e.4g.5g., 1j.2m.3e.4g.5g., 1p.2m.3e.4g.5g., 1a.2o.3e.4g.5g., 1b.2o.3e.4g.5g., 1f.2o.3e.4g.5g., 1h.2o.3e.4g.5g., 1j.2o.3e.4g.5g., 1p.2o.3e.4g.5g., 1a.2u.3e.4g.5g., 1b.2u.3e.4g.5g., 1f.2u.3e.4g.5g., 1h.2u.3e.4g.5g., 1j.2u.3e.4g.5g., 1p.2u.3e.4g.5g., 1a.2y.3e.4g.5g., 1b.2y.3e.4g.5g., 1f.2y.3e.4g.5g., 1h.2y.3e.4g.5g., 1j.2y.3e.4g.5g., 1p.2y.3e.4g.5g., 1a.2a.3g.4g.5g., 1b.2a.3g.4g.5g., 1f.2a.3g.4g.5g., 1h.2a.3g.4g.5g., 1j.2a.3g.4g.5g., 1p.2a.3g.4g.5g., 1a.2b.3g.4g.5g., 1b.2b.3g.4g.5g., 1f.2b.3g.4g.5g., 1h.2b.3g.4g.5g., 1j.2b.3g.4g.5g., 1p.2b.3g.4g.5g., 1a.2e.3g.4g.5g., 1b.2e.3g.4g.5g., 1f.2e.3g.4g.5g., 1h.2e.3g.4g.5g., 1j.2e.3g.4g.5g., 1p.2e.3g.4g.5g., 1a.2f.3g.4g.5g., 1b.2f.3g.4g.5g., 1f.2f.3g.4g.5g., 1h.2f.3g.4g.5g., 1j.2f.3g.4g.5g., 1p.2f.3g.4g.5g., 1a.2i.3g.4g.5g., 1b.2i.3g.4g.5g., 1f.2i.3g.4g.5g., 1h.2i.3g.4g.5g., 1j.2i.3g.4g.5g., 1p.2i.3g.4g.5g., 1a.2m.3g.4g.5g., 1b.2m.3g.4g.5g., 1f.2m.3g.4g.5g., 1h.2m.3g.4g.5g., 1j.2m.3g.4g.5g., 1p.2m.3g.4g.5g., 1a.2o.3g.4g.5g., 1b.2o.3g.4g.5g., 1f.2o.3g.4g.5g., 1h.2o.3g.4g.5g., 1j.2o.3g.4g.5g., 1p.2o.3g.4g.5g., 1a.2u.3g.4g.5g., 1b.2u.3g.4g.5g., 1f.2u.3g.4g.5g., 1h.2u.3g.4g.5g., 1j.2u.3g.4g.5g., 1p.2u.3g.4g.5g., 1a.2y.3g.4g.5g., 1b.2y.3g.4g.5g., 1f.2y.3g.4g.5g., 1h.2y.3g.4g.5g., 1j.2y.3g.4g.5g., 1p.2y.3g.4g.5g., 1a.2a.3a.4h.5g., 1b.2a.3a.4h.5g., 1f.2a.3a.4h.5g., 1h.2a.3a.4h.5g., 1j.2a.3a.4h.5g., 1p.2a.3a.4h.5g., 1a.2b.3a.4h.5g., 1b.2b.3a.4h.5g., 1f.2b.3a.4h.5g., 1h.2b.3a.4h.5g., 1j.2b.3a.4h.5g., 1p.2b.3a.4h.5g., 1a.2e.3a.4h.5g., 1b.2e.3a.4h.5g., 1f.2e.3a.4h.5g., 1h.2e.3a.4h.5g., 1j.2e.3a.4h.5g., 1p.2e.3a.4h.5g., 1a.2f.3a.4h.5g., 1b.2f.3a.4h.5g., 1f.2f.3a.4h.5g., 1h.2f.3a.4h.5g., 1j.2f.3a.4h.5g., 1p.2f.3a.4h.5g., 1a.2i.3a.4h.5g., 1b.2i.3a.4h.5g., 1f.2i.3a.4h.5g., 1h.2i.3a.4h.5g., 1j.2i.3a.4h.5g., 1p.2i.3a.4h.5g., 1a.2m.3a.4h.5g., 1b.2m.3a.4h.5g., 1f.2m.3a.4h.5g., 1h.2m.3a.4h.5g., 1j.2m.3a.4h.5g., 1p.2m.3a.4h.5g., 1a.2o.3a.4h.5g., 1b.2o.3a.4h.5g., 1f.2o.3a.4h.5g., 1h.2o.3a.4h.5g., 1j.2o.3a.4h.5g., 1p.2o.3a.4h.5g., 1a.2u.3a.4h.5g., 1b.2u.3a.4h.5g., 1f.2u.3a.4h.5g., 1h.2u.3a.4h.5g., 1j.2u.3a.4h.5g., 1p.2u.3a.4h.5g., 1a.2y.3a.4h.5g., 1b.2y.3a.4h.5g., 1f.2y.3a.4h.5g., 1h.2y.3a.4h.5g., 1j.2y.3a.4h.5g., 1p.2y.3a.4h.5g., 1a.2a.3b.4h.5g., 1b.2a.3b.4h.5g., 1f.2a.3b.4h.5g., 1h.2a.3b.4h.5g., 1j.2a.3b.4h.5g., 1p.2a.3b.4h.5g., 1a.2b.3b.4h.5g., 1b.2b.3b.4h.5g., 1f.2b.3b.4h.5g., 1h.2b.3b.4h.5g., 1j.2b.3b.4h.5g., 1p.2b.3b.4h.5g., 1a.2e.3b.4h.5g., 1b.2e.3b.4h.5g., 1f.2e.3b.4h.5g., 1h.2e.3b.4h.5g., 1j.2e.3b.4h.5g., 1p.2e.3b.4h.5g., 1a.2f.3b.4h.5g., 1b.2f.3b.4h.5g., 1f.2f.3b.4h.5g., 1h.2f.3b.4h.5g., 1j.2f.3b.4h.5g., 1p.2f.3b.4h.5g., 1a.2i.3b.4h.5g., 1b.2i.3b.4h.5g., 1f.2i.3b.4h.5g., 1h.2i.3b.4h.5g., 1j.2i.3b.4h.5g., 1p.2i.3b.4h.5g., 1a.2m.3b.4h.5g., 1b.2m.3b.4h.5g., 1f.2m.3b.4h.5g., 1h.2m.3b.4h.5g., 1j.2m.3b.4h.5g., 1p.2m.3b.4h.5g., 1a.2o.3b.4h.5g., 1b.2o.3b.4h.5g., 1f.2o.3b.4h.5g., 1h.2o.3b.4h.5g., 1j.2o.3b.4h.5g., 1p.2o.3b.4h.5g., 1a.2u.3b.4h.5g., 1b.2u.3b.4h.5g., 1f.2u.3b.4h.5g., 1h.2u.3b.4h.5g., 1j.2u.3b.4h.5g., 1p.2u.3b.4h.5g., 1a.2y.3b.4h.5g., 1b.2y.3b.4h.5g., 1f.2y.3b.4h.5g., 1h.2y.3b.4h.5g., 1j.2y.3b.4h.5g., 1p.2y.3b.4h.5g., 1a.2a.3e.4h.5g., 1b.2a.3e.4h.5g., 1f.2a.3e.4h.5g., 1h.2a.3e.4h.5g., 1j.2a.3e.4h.5g., 1p.2a.3e.4h.5g., 1a.2b.3e.4h.5g., 1b.2b.3e.4h.5g., 1f.2b.3e.4h.5g., 1h.2b.3e.4h.5g., 1j.2b.3e.4h.5g., 1p.2b.3e.4h.5g., 1a.2e.3e.4h.5g., 1b.2e.3e.4h.5g., 1f.2e.3e.4h.5g., 1h.2e.3e.4h.5g., 1j.2e.3e.4h.5g., 1p.2e.3e.4h.5g., 1a.2f.3e.4h.5g., 1b.2f.3e.4h.5g., 1f.2f.3e.4h.5g., 1h.2f.3e.4h.5g., 1j.2f.3e.4h.5g., 1p.2f.3e.4h.5g., 1a.2i.3e.4h.5g., 1b.2i.3e.4h.5g., 1f.2i.3e.4h.5g., 1h.2i.3e.4h.5g., 1j.2i.3e.4h.5g., 1p.2i.3e.4h.5g., 1a.2m.3e.4h.5g., 1b.2m.3e.4h.5g., 1f.2m.3e.4h.5g., 1h.2m.3e.4h.5g., 1j.2m.3e.4h.5g., 1p.2m.3e.4h.5g., 1a.2o.3e.4h.5g., 1b.2o.3e.4h.5g., 1f.2o.3e.4h.5g., 1h.2o.3e.4h.5g., 1j.2o.3e.4h.5g., 1p.2o.3e.4h.5g., 1a.2u.3e.4h.5g., 1b.2u.3e.4h.5g., 1f.2u.3e.4h.5g., 1h.2u.3e.4h.5g., 1j.2u.3e.4h.5g., 1p.2u.3e.4h.5g., 1a.2y.3e.4h.5g., 1b.2y.3e.4h.5g., 1f.2y.3e.4h.5g., 1h.2y.3e.4h.5g., 1j.2y.3e.4h.5g., 1p.2y.3e.4h.5g., 1a.2a.3g.4h.5g., 1b.2a.3g.4h.5g., 1f.2a.3g.4h.5g., 1h.2a.3g.4h.5g., 1j.2a.3g.4h.5g., 1p.2a.3g.4h.5g., 1a.2b.3g.4h.5g., 1b.2b.3g.4h.5g., 1f.2b.3g.4h.5g., 1h.2b.3g.4h.5g., 1j.2b.3g.4h.5g., 1p.2b.3g.4h.5g., 1a.2e.3g.4h.5g., 1b.2e.3g.4h.5g., 1f.2e.3g.4h.5g., 1h.2e.3g.4h.5g., 1j.2e.3g.4h.5g., 1p.2e.3g.4h.5g., 1a.2f.3g.4h.5g., 1b.2f.3g.4h.5g., 1f.2f.3g.4h.5g., 1h.2f.3g.4h.5g., 1j.2f.3g.4h.5g., 1p.2f.3g.4h.5g., 1a.2i.3g.4h.5g., 1b.2i.3g.4h.5g., 1f.2i.3g.4h.5g., 1h.2i.3g.4h.5g., 1j.2i.3g.4h.5g., 1p.2i.3g.4h.5g., 1a.2m.3g.4h.5g., 1b.2m.3g.4h.5g., 1f.2m.3g.4h.5g., 1h.2m.3g.4h.5g., 1j.2m.3g.4h.5g., 1p.2m.3g.4h.5g., 1a.2o.3g.4h.5g., 1b.2o.3g.4h.5g., 1f.2o.3g.4h.5g., 1h.2o.3g.4h.5g., 1j.2o.3g.4h.5g., 1p.2o.3g.4h.5g., 1a.2u.3g.4h.5g., 1b.2u.3g.4h.5g., 1f.2u.3g.4h.5g., 1h.2u.3g.4h.5g., 1j.2u.3g.4h.5g., 1p.2u.3g.4h.5g., 1a.2y.3g.4h.5g., 1b.2y.3g.4h.5g., 1f.2y.3g.4h.5g., 1h.2y.3g.4h.5g., 1j.2y.3g.4h.5g., 1p.2y.3g.4h.5g., 1a.2a.3a.4i.5g., 1b.2a.3a.4i.5g., 1f.2a.3a.4i.5g., 1h.2a.3a.4i.5g., 1j.2a.3a.4i.5g., 1p.2a.3a.4i.5g., 1a.2b.3a.4i.5g., 1b.2b.3a.4i.5g., 1f.2b.3a.4i.5g., 1h.2b.3a.4i.5g., 1j.2b.3a.4i.5g., 1p.2b.3a.4i.5g., 1a.2e.3a.4i.5g., 1b.2e.3a.4i.5g., 1f.2e.3a.4i.5g., 1h.2e.3a.4i.5g., 1j.2e.3a.4i.5g., 1p.2e.3a.4i.5g., 1a.2f.3a.4i.5g., 1b.2f.3a.4i.5g., 1f.2f.3a.4i.5g., 1h.2f.3a.4i.5g., 1j.2f.3a.4i.5g., 1p.2f.3a.4i.5g., 1a.2i.3a.4i.5g., 1b.2i.3a.4i.5g., 1f.2i.3a.4i.5g., 1h.2i.3a.4i.5g., 1j.2i.3a.4i.5g., 1p.2i.3a.4i.5g., 1a.2m.3a.4i.5g., 1b.2m.3a.4i.5g., 1f.2m.3a.4i.5g., 1h.2m.3a.4i.5g., 1j.2m.3a.4i.5g., 1p.2m.3a.4i.5g., 1a.2o.3a.4i.5g., 1b.2o.3a.4i.5g., 1f.2o.3a.4i.5g., 1h.2o.3a.4i.5g., 1j.2o.3a.4i.5g., 1p.2o.3a.4i.5g., 1a.2u.3a.4i.5g., 1b.2u.3a.4i.5g., 1f.2u.3a.4i.5g., 1h.2u.3a.4i.5g., 1j.2u.3a.4i.5g., 1p.2u.3a.4i.5g., 1a.2y.3a.4i.5g., 1b.2y.3a.4i.5g., 1f.2y.3a.4i.5g., 1h.2y.3a.4i.5g., 1j.2y.3a.4i.5g., 1p.2y.3a.4i.5g., 1a.2a.3b.4i.5g., 1b.2a.3b.4i.5g., 1f.2a.3b.4i.5g., 1h.2a.3b.4i.5g., 1j.2a.3b.4i.5g., 1p.2a.3b.4i.5g., 1a.2b.3b.4i.5g., 1b.2b.3b.4i.5g., 1f.2b.3b.4i.5g., 1h.2b.3b.4i.5g., 1j.2b.3b.4i.5g., 1p.2b.3b.4i.5g., 1a.2e.3b.4i.5g., 1b.2e.3b.4i.5g., 1f.2e.3b.4i.5g., 1h.2e.3b.4i.5g., 1j.2e.3b.4i.5g., 1p.2e.3b.4i.5g., 1a.2f.3b.4i.5g., 1b.2f.3b.4i.5g., 1f.2f.3b.4i.5g., 1h.2f.3b.4i.5g., 1j.2f.3b.4i.5g., 1p.2f.3b.4i.5g., 1a.2i.3b.4i.5g., 1b.2i.3b.4i.5g., 1f.2i.3b.4i.5g., 1h.2i.3b.4i.5g., 1j.2i.3b.4i.5g., 1p.2i.3b.4i.5g., 1a.2m.3b.4i.5g., 1b.2m.3b.4i.5g., 1f.2m.3b.4i.5g., 1h.2m.3b.4i.5g., 1j.2m.3b.4i.5g., 1p.2m.3b.4i.5g., 1a.2o.3b.4i.5g., 1b.2o.3b.4i.5g., 1f.2o.3b.4i.5g., 1h.2o.3b.4i.5g., 1j.2o.3b.4i.5g., 1p.2o.3b.4i.5g., 1a.2u.3b.4i.5g., 1b.2u.3b.4i.5g., 1f.2u.3b.4i.5g., 1h.2u.3b.4i.5g., 1j.2u.3b.4i.5g., 1p.2u.3b.4i.5g., 1a.2y.3b.4i.5g., 1b.2y.3b.4i.5g., 1f.2y.3b.4i.5g., 1h.2y.3b.4i.5g., 1j.2y.3b.4i.5g., 1p.2y.3b.4i.5g., 1a.2a.3e.4i.5g., 1b.2a.3e.4i.5g., 1f.2a.3e.4i.5g., 1h.2a.3e.4i.5g., 1j.2a.3e.4i.5g., 1p.2a.3e.4i.5g., 1a.2b.3e.4i.5g., 1b.2b.3e.4i.5g., 1f.2b.3e.4i.5g., 1h.2b.3e.4i.5g., 1j.2b.3e.4i.5g., 1p.2b.3e.4i.5g., 1a.2e.3e.4i.5g., 1b.2e.3e.4i.5g., 1f.2e.3e.4i.5g., 1h.2e.3e.4i.5g.,

TABLE 12-continued

List of Compound Structures of Formula II 1j.2e.3e.4i.5g., 1p.2e.3e.4i.5g., 1a.2f.3e.4i.5g., 1b.2f.3e.4i.5g., 1f.2f.3e.4i.5g., 1h.2f.3e.4i.5g., 1j.2f.3e.4i.5g., 1p.2f.3e.4i.5g., 1a.2i.3e.4i.5g., 1b.2i.3e.4i.5g., 1f.2i.3e.4i.5g., 1h.2i.3e.4i.5g., 1j.2i.3e.4i.5g., 1p.2i.3e.4i.5g., 1a.2m.3e.4i.5g., 1b.2m.3e.4i.5g., 1f.2m.3e.4i.5g., 1h.2m.3e.4i.5g., 1j.2m.3e.4i.5g., 1p.2m.3e.4i.5g., 1a.2o.3e.4i.5g., 1b.2o.3e.4i.5g., 1f.2o.3e.4i.5g., 1h.2o.3e.4i.5g., 1j.2o.3e.4i.5g., 1p.2o.3e.4i.5g., 1a.2u.3e.4i.5g., 1b.2u.3e.4i.5g., 1f.2u.3e.4i.5g., 1h.2u.3e.4i.5g., 1j.2u.3e.4i.5g., 1p.2u.3e.4i.5g., 1a.2y.3e.4i.5g., 1b.2y.3e.4i.5g., 1f.2y.3e.4i.5g., 1h.2y.3e.4i.5g., 1j.2y.3e.4i.5g., 1p.2y.3e.4i.5g., 1a.2a.3g.4i.5g., 1b.2a.3g.4i.5g., 1f.2a.3g.4i.5g., 1h.2a.3g.4i.5g., 1j.2a.3g.4i.5g., 1p.2a.3g.4i.5g., 1a.2b.3g.4i.5g., 1b.2b.3g.4i.5g., 1f.2b.3g.4i.5g., 1h.2b.3g.4i.5g., 1j.2b.3g.4i.5g., 1p.2b.3g.4i.5g., 1a.2e.3g.4i.5g., 1b.2e.3g.4i.5g., 1f.2e.3g.4i.5g., 1h.2e.3g.4i.5g., 1j.2e.3g.4i.5g., 1p.2e.3g.4i.5g., 1a.2f.3g.4i.5g., 1b.2f.3g.4i.5g., 1f.2f.3g.4i.5g., 1h.2f.3g.4i.5g., 1j.2f.3g.4i.5g., 1p.2f.3g.4i.5g., 1a.2i.3g.4i.5g., 1b.2i.3g.4i.5g., 1f.2i.3g.4i.5g., 1h.2i.3g.4i.5g., 1j.2i.3g.4i.5g., 1p.2i.3g.4i.5g., 1a.2m.3g.4i.5g., 1b.2m.3g.4i.5g., 1f.2m.3g.4i.5g., 1h.2m.3g.4i.5g., 1j.2m.3g.4i.5g., 1p.2m.3g.4i.5g., 1a.2o.3g.4i.5g., 1b.2o.3g.4i.5g., 1f.2o.3g.4i.5g., 1h.2o.3g.4i.5g., 1j.2o.3g.4i.5g., 1p.2o.3g.4i.5g., 1a.2u.3g.4i.5g., 1b.2u.3g.4i.5g., 1f.2u.3g.4i.5g., 1h.2u.3g.4i.5g., 1j.2u.3g.4i.5g., 1p.2u.3g.4i.5g., 1a.2y.3g.4i.5g., 1b.2y.3g.4i.5g., 1f.2y.3g.4i.5g., 1h.2y.3g.4i.5g., 1j.2y.3g.4i.5g., 1p.2y.3g.4i.5g., 1a.2a.3a.4a.5h., 1b.2a.3a.4a.5h., 1f.2a.3a.4a.5h., 1h.2a.3a.4a.5h., 1j.2a.3a.4a.5h., 1p.2a.3a.4a.5h., 1a.2b.3a.4a.5h., 1b.2b.3a.4a.5h., 1f.2b.3a.4a.5h., 1h.2b.3a.4a.5h., 1j.2b.3a.4a.5h., 1p.2b.3a.4a.5h., 1a.2e.3a.4a.5h., 1b.2e.3a.4a.5h., 1f.2e.3a.4a.5h., 1h.2e.3a.4a.5h., 1j.2e.3a.4a.5h., 1p.2e.3a.4a.5h., 1a.2f.3a.4a.5h., 1b.2f.3a.4a.5h., 1f.2f.3a.4a.5h., 1h.2f.3a.4a.5h., 1j.2f.3a.4a.5h., 1p.2f.3a.4a.5h., 1a.2i.3a.4a.5h., 1b.2i.3a.4a.5h., 1f.2i.3a.4a.5h., 1h.2i.3a.4a.5h., 1j.2i.3a.4a.5h., 1p.2i.3a.4a.5h., 1a.2m.3a.4a.5h., 1b.2m.3a.4a.5h., 1f.2m.3a.4a.5h., 1h.2m.3a.4a.5h., 1j.2m.3a.4a.5h., 1p.2m.3a.4a.5h., 1a.2o.3a.4a.5h., 1b.2o.3a.4a.5h., 1f.2o.3a.4a.5h., 1h.2o.3a.4a.5h., 1j.2o.3a.4a.5h., 1p.2o.3a.4a.5h., 1a.2u.3a.4a.5h., 1b.2u.3a.4a.5h., 1f.2u.3a.4a.5h., 1h.2u.3a.4a.5h., 1j.2u.3a.4a.5h., 1p.2u.3a.4a.5h., 1a.2y.3a.4a.5h., 1b.2y.3a.4a.5h., 1f.2y.3a.4a.5h., 1h.2y.3a.4a.5h., 1j.2y.3a.4a.5h., 1p.2y.3a.4a.5h., 1a.2a.3b.4a.5h., 1b.2a.3b.4a.5h., 1f.2a.3b.4a.5h., 1h.2a.3b.4a.5h., 1j.2a.3b.4a.5h., 1p.2a.3b.4a.5h., 1a.2b.3b.4a.5h., 1b.2b.3b.4a.5h., 1f.2b.3b.4a.5h., 1h.2b.3b.4a.5h., 1j.2b.3b.4a.5h., 1p.2b.3b.4a.5h., 1a.2e.3b.4a.5h., 1b.2e.3b.4a.5h., 1f.2e.3b.4a.5h., 1h.2e.3b.4a.5h., 1j.2e.3b.4a.5h., 1p.2e.3b.4a.5h., 1a.2f.3b.4a.5h., 1b.2f.3b.4a.5h., 1f.2f.3b.4a.5h., 1h.2f.3b.4a.5h., 1j.2f.3b.4a.5h., 1p.2f.3b.4a.5h., 1a.2i.3b.4a.5h., 1b.2i.3b.4a.5h., 1f.2i.3b.4a.5h., 1h.2i.3b.4a.5h., 1j.2i.3b.4a.5h., 1p.2i.3b.4a.5h., 1a.2m.3b.4a.5h., 1b.2m.3b.4a.5h., 1f.2m.3b.4a.5h., 1h.2m.3b.4a.5h., 1j.2m.3b.4a.5h., 1p.2m.3b.4a.5h., 1a.2o.3b.4a.5h., 1b.2o.3b.4a.5h., 1f.2o.3b.4a.5h., 1h.2o.3b.4a.5h., 1j.2o.3b.4a.5h., 1p.2o.3b.4a.5h., 1a.2u.3b.4a.5h., 1b.2u.3b.4a.5h., 1f.2u.3b.4a.5h., 1h.2u.3b.4a.5h., 1j.2u.3b.4a.5h., 1p.2u.3b.4a.5h., 1a.2y.3b.4a.5h., 1b.2y.3b.4a.5h., 1f.2y.3b.4a.5h., 1h.2y.3b.4a.5h., 1j.2y.3b.4a.5h., 1p.2y.3b.4a.5h., 1a.2a.3e.4a.5h., 1b.2a.3e.4a.5h., 1f.2a.3e.4a.5h., 1h.2a.3e.4a.5h., 1j.2a.3e.4a.5h., 1p.2a.3e.4a.5h., 1a.2b.3e.4a.5h., 1b.2b.3e.4a.5h., 1f.2b.3e.4a.5h., 1h.2b.3e.4a.5h., 1j.2b.3e.4a.5h., 1p.2b.3e.4a.5h., 1a.2e.3e.4a.5h., 1b.2e.3e.4a.5h., 1f.2e.3e.4a.5h., 1h.2e.3e.4a.5h., 1j.2e.3e.4a.5h., 1p.2e.3e.4a.5h., 1a.2f.3e.4a.5h., 1b.2f.3e.4a.5h., 1f.2f.3e.4a.5h., 1h.2f.3e.4a.5h., 1j.2f.3e.4a.5h., 1p.2f.3e.4a.5h., 1a.2i.3e.4a.5h., 1b.2i.3e.4a.5h., 1f.2i.3e.4a.5h., 1h.2i.3e.4a.5h., 1j.2i.3e.4a.5h., 1p.2i.3e.4a.5h., 1a.2m.3e.4a.5h., 1b.2m.3e.4a.5h., 1f.2m.3e.4a.5h., 1h.2m.3e.4a.5h., 1j.2m.3e.4a.5h., 1p.2m.3e.4a.5h., 1a.2o.3e.4a.5h., 1b.2o.3e.4a.5h., 1f.2o.3e.4a.5h., 1h.2o.3e.4a.5h., 1j.2o.3e.4a.5h., 1p.2o.3e.4a.5h., 1a.2u.3e.4a.5h., 1b.2u.3e.4a.5h., 1f.2u.3e.4a.5h., 1h.2u.3e.4a.5h., 1j.2u.3e.4a.5h., 1p.2u.3e.4a.5h., 1a.2y.3e.4a.5h., 1b.2y.3e.4a.5h., 1f.2y.3e.4a.5h., 1h.2y.3e.4a.5h., 1j.2y.3e.4a.5h., 1p.2y.3e.4a.5h., 1a.2a.3g.4a.5h., 1b.2a.3g.4a.5h., 1f.2a.3g.4a.5h., 1h.2a.3g.4a.5h., 1j.2a.3g.4a.5h., 1p.2a.3g.4a.5h., 1a.2b.3g.4a.5h., 1b.2b.3g.4a.5h., 1f.2b.3g.4a.5h., 1h.2b.3g.4a.5h., 1j.2b.3g.4a.5h., 1p.2b.3g.4a.5h., 1a.2e.3g.4a.5h., 1b.2e.3g.4a.5h., 1f.2e.3g.4a.5h., 1h.2e.3g.4a.5h., 1j.2e.3g.4a.5h., 1p.2e.3g.4a.5h., 1a.2f.3g.4a.5h., 1b.2f.3g.4a.5h., 1f.2f.3g.4a.5h., 1h.2f.3g.4a.5h., 1j.2f.3g.4a.5h., 1p.2f.3g.4a.5h., 1a.2i.3g.4a.5h., 1b.2i.3g.4a.5h., 1f.2i.3g.4a.5h., 1h.2i.3g.4a.5h., 1j.2i.3g.4a.5h., 1p.2i.3g.4a.5h., 1a.2m.3g.4a.5h., 1b.2m.3g.4a.5h., 1f.2m.3g.4a.5h., 1h.2m.3g.4a.5h., 1j.2m.3g.4a.5h., 1p.2m.3g.4a.5h., 1a.2o.3g.4a.5h., 1b.2o.3g.4a.5h., 1f.2o.3g.4a.5h., 1h.2o.3g.4a.5h., 1j.2o.3g.4a.5h., 1p.2o.3g.4a.5h., 1a.2u.3g.4a.5h., 1b.2u.3g.4a.5h., 1f.2u.3g.4a.5h., 1h.2u.3g.4a.5h., 1j.2u.3g.4a.5h., 1p.2u.3g.4a.5h., 1a.2y.3g.4a.5h., 1b.2y.3g.4a.5h., 1f.2y.3g.4a.5h., 1h.2y.3g.4a.5h., 1j.2y.3g.4a.5h., 1p.2y.3g.4a.5h., 1a.2a.3a.4d.5h., 1b.2a.3a.4d.5h., 1f.2a.3a.4d.5h., 1h.2a.3a.4d.5h., 1j.2a.3a.4d.5h., 1p.2a.3a.4d.5h., 1a.2b.3a.4d.5h., 1b.2b.3a.4d.5h., 1f.2b.3a.4d.5h., 1h.2b.3a.4d.5h., 1j.2b.3a.4d.5h., 1p.2b.3a.4d.5h., 1a.2e.3a.4d.5h., 1b.2e.3a.4d.5h., 1f.2e.3a.4d.5h., 1h.2e.3a.4d.5h., 1j.2e.3a.4d.5h., 1p.2e.3a.4d.5h., 1a.2f.3a.4d.5h., 1b.2f.3a.4d.5h., 1f.2f.3a.4d.5h., 1h.2f.3a.4d.5h., 1j.2f.3a.4d.5h., 1p.2f.3a.4d.5h., 1a.2i.3a.4d.5h., 1b.2i.3a.4d.5h., 1f.2i.3a.4d.5h., 1h.2i.3a.4d.5h., 1j.2i.3a.4d.5h., 1p.2i.3a.4d.5h., 1a.2m.3a.4d.5h., 1b.2m.3a.4d.5h., 1f.2m.3a.4d.5h., 1h.2m.3a.4d.5h., 1j.2m.3a.4d.5h., 1p.2m.3a.4d.5h., 1a.2o.3a.4d.5h., 1b.2o.3a.4d.5h., 1f.2o.3a.4d.5h., 1h.2o.3a.4d.5h., 1j.2o.3a.4d.5h., 1p.2o.3a.4d.5h., 1a.2u.3a.4d.5h., 1b.2u.3a.4d.5h., 1f.2u.3a.4d.5h., 1h.2u.3a.4d.5h., 1j.2u.3a.4d.5h., 1p.2u.3a.4d.5h., 1a.2y.3a.4d.5h., 1b.2y.3a.4d.5h., 1f.2y.3a.4d.5h., 1h.2y.3a.4d.5h., 1j.2y.3a.4d.5h., 1p.2y.3a.4d.5h., 1a.2a.3b.4d.5h., 1b.2a.3b.4d.5h., 1f.2a.3b.4d.5h., 1h.2a.3b.4d.5h., 1j.2a.3b.4d.5h., 1p.2a.3b.4d.5h., 1a.2b.3b.4d.5h., 1b.2b.3b.4d.5h., 1f.2b.3b.4d.5h., 1h.2b.3b.4d.5h., 1j.2b.3b.4d.5h., 1p.2b.3b.4d.5h., 1a.2e.3b.4d.5h., 1b.2e.3b.4d.5h., 1f.2e.3b.4d.5h., 1h.2e.3b.4d.5h., 1j.2e.3b.4d.5h., 1p.2e.3b.4d.5h., 1a.2f.3b.4d.5h., 1b.2f.3b.4d.5h., 1f.2f.3b.4d.5h., 1h.2f.3b.4d.5h., 1j.2f.3b.4d.5h., 1p.2f.3b.4d.5h., 1a.2i.3b.4d.5h., 1b.2i.3b.4d.5h., 1f.2i.3b.4d.5h., 1h.2i.3b.4d.5h., 1j.2i.3b.4d.5h., 1p.2i.3b.4d.5h., 1a.2m.3b.4d.5h., 1b.2m.3b.4d.5h., 1f.2m.3b.4d.5h., 1h.2m.3b.4d.5h., 1j.2m.3b.4d.5h., 1p.2m.3b.4d.5h., 1a.2o.3b.4d.5h., 1b.2o.3b.4d.5h., 1f.2o.3b.4d.5h., 1h.2o.3b.4d.5h., 1j.2o.3b.4d.5h., 1p.2o.3b.4d.5h., 1a.2u.3b.4d.5h., 1b.2u.3b.4d.5h., 1f.2u.3b.4d.5h., 1h.2u.3b.4d.5h., 1j.2u.3b.4d.5h., 1p.2u.3b.4d.5h., 1a.2y.3b.4d.5h., 1b.2y.3b.4d.5h., 1f.2y.3b.4d.5h., 1h.2y.3b.4d.5h., 1j.2y.3b.4d.5h., 1p.2y.3b.4d.5h., 1a.2a.3e.4d.5h., 1b.2a.3e.4d.5h., 1f.2a.3e.4d.5h., 1h.2a.3e.4d.5h., 1j.2a.3e.4d.5h., 1p.2a.3e.4d.5h., 1a.2b.3e.4d.5h., 1b.2b.3e.4d.5h., 1f.2b.3e.4d.5h., 1h.2b.3e.4d.5h., 1j.2b.3e.4d.5h., 1p.2b.3e.4d.5h., 1a.2e.3e.4d.5h., 1b.2e.3e.4d.5h., 1f.2e.3e.4d.5h., 1h.2e.3e.4d.5h., 1j.2e.3e.4d.5h., 1p.2e.3e.4d.5h., 1a.2f.3e.4d.5h., 1b.2f.3e.4d.5h., 1f.2f.3e.4d.5h., 1h.2f.3e.4d.5h., 1j.2f.3e.4d.5h., 1p.2f.3e.4d.5h., 1a.2i.3e.4d.5h., 1b.2i.3e.4d.5h., 1f.2i.3e.4d.5h., 1h.2i.3e.4d.5h., 1j.2i.3e.4d.5h., 1p.2i.3e.4d.5h., 1a.2m.3e.4d.5h., 1b.2m.3e.4d.5h., 1f.2m.3e.4d.5h., 1h.2m.3e.4d.5h., 1j.2m.3e.4d.5h., 1p.2m.3e.4d.5h., 1a.2o.3e.4d.5h., 1b.2o.3e.4d.5h., 1f.2o.3e.4d.5h., 1h.2o.3e.4d.5h., 1j.2o.3e.4d.5h., 1p.2o.3e.4d.5h., 1a.2u.3e.4d.5h., 1b.2u.3e.4d.5h., 1f.2u.3e.4d.5h., 1h.2u.3e.4d.5h., 1j.2u.3e.4d.5h., 1p.2u.3e.4d.5h., 1a.2y.3e.4d.5h., 1b.2y.3e.4d.5h., 1f.2y.3e.4d.5h., 1h.2y.3e.4d.5h., 1j.2y.3e.4d.5h., 1p.2y.3e.4d.5h., 1a.2a.3g.4d.5h., 1b.2a.3g.4d.5h., 1f.2a.3g.4d.5h., 1h.2a.3g.4d.5h., 1j.2a.3g.4d.5h., 1p.2a.3g.4d.5h., 1a.2b.3g.4d.5h., 1b.2b.3g.4d.5h., 1f.2b.3g.4d.5h., 1h.2b.3g.4d.5h., 1j.2b.3g.4d.5h., 1p.2b.3g.4d.5h., 1a.2e.3g.4d.5h., 1b.2e.3g.4d.5h., 1f.2e.3g.4d.5h., 1h.2e.3g.4d.5h., 1j.2e.3g.4d.5h., 1p.2e.3g.4d.5h., 1a.2f.3g.4d.5h., 1b.2f.3g.4d.5h., 1f.2f.3g.4d.5h., 1h.2f.3g.4d.5h., 1j.2f.3g.4d.5h., 1p.2f.3g.4d.5h., 1a.2i.3g.4d.5h., 1b.2i.3g.4d.5h., 1f.2i.3g.4d.5h., 1h.2i.3g.4d.5h., 1j.2i.3g.4d.5h., 1p.2i.3g.4d.5h., 1a.2m.3g.4d.5h., 1b.2m.3g.4d.5h., 1f.2m.3g.4d.5h., 1h.2m.3g.4d.5h., 1j.2m.3g.4d.5h., 1p.2m.3g.4d.5h., 1a.2o.3g.4d.5h., 1b.2o.3g.4d.5h., 1f.2o.3g.4d.5h., 1h.2o.3g.4d.5h., 1j.2o.3g.4d.5h., 1p.2o.3g.4d.5h., 1a.2u.3g.4d.5h., 1b.2u.3g.4d.5h., 1f.2u.3g.4d.5h., 1h.2u.3g.4d.5h., 1j.2u.3g.4d.5h., 1p.2u.3g.4d.5h., 1a.2y.3g.4d.5h., 1b.2y.3g.4d.5h., 1f.2y.3g.4d.5h., 1h.2y.3g.4d.5h., 1j.2y.3g.4d.5h., 1p.2y.3g.4d.5h., 1a.2a.3a.4f.5h., 1b.2a.3a.4f.5h., 1f.2a.3a.4f.5h., 1h.2a.3a.4f.5h., 1j.2a.3a.4f.5h., 1p.2a.3a.4f.5h., 1a.2b.3a.4f.5h., 1b.2b.3a.4f.5h., 1f.2b.3a.4f.5h., 1h.2b.3a.4f.5h., 1j.2b.3a.4f.5h., 1p.2b.3a.4f.5h., 1a.2e.3a.4f.5h., 1b.2e.3a.4f.5h., 1f.2e.3a.4f.5h., 1h.2e.3a.4f.5h., 1j.2e.3a.4f.5h., 1p.2e.3a.4f.5h., 1a.2f.3a.4f.5h., 1b.2f.3a.4f.5h., 1f.2f.3a.4f.5h., 1h.2f.3a.4f.5h., 1j.2f.3a.4f.5h., 1p.2f.3a.4f.5h., 1a.2i.3a.4f.5h., 1b.2i.3a.4f.5h., 1f.2i.3a.4f.5h., 1h.2i.3a.4f.5h., 1j.2i.3a.4f.5h., 1p.2i.3a.4f.5h., 1a.2m.3a.4f.5h., 1b.2m.3a.4f.5h., 1f.2m.3a.4f.5h., 1h.2m.3a.4f.5h., 1j.2m.3a.4f.5h., 1p.2m.3a.4f.5h., 1a.2o.3a.4f.5h., 1b.2o.3a.4f.5h., 1f.2o.3a.4f.5h., 1h.2o.3a.4f.5h., 1j.2o.3a.4f.5h., 1p.2o.3a.4f.5h., 1a.2u.3a.4f.5h., 1b.2u.3a.4f.5h., 1f.2u.3a.4f.5h., 1h.2u.3a.4f.5h., 1j.2u.3a.4f.5h., 1p.2u.3a.4f.5h., 1a.2y.3a.4f.5h., 1b.2y.3a.4f.5h., 1f.2y.3a.4f.5h., 1h.2y.3a.4f.5h., 1j.2y.3a.4f.5h., 1p.2y.3a.4f.5h., 1a.2a.3b.4f.5h., 1b.2a.3b.4f.5h., 1f.2a.3b.4f.5h., 1h.2a.3b.4f.5h., 1j.2a.3b.4f.5h., 1p.2a.3b.4f.5h., 1a.2b.3b.4f.5h., 1b.2b.3b.4f.5h., 1f.2b.3b.4f.5h., 1h.2b.3b.4f.5h., 1j.2b.3b.4f.5h., 1p.2b.3b.4f.5h., 1a.2e.3b.4f.5h., 1b.2e.3b.4f.5h., 1f.2e.3b.4f.5h., 1h.2e.3b.4f.5h., 1j.2e.3b.4f.5h., 1p.2e.3b.4f.5h., 1a.2f.3b.4f.5h., 1b.2f.3b.4f.5h., 1f.2f.3b.4f.5h., 1h.2f.3b.4f.5h., 1j.2f.3b.4f.5h., 1p.2f.3b.4f.5h., 1a.2i.3b.4f.5h., 1b.2i.3b.4f.5h., 1f.2i.3b.4f.5h., 1h.2i.3b.4f.5h., 1j.2i.3b.4f.5h., 1p.2i.3b.4f.5h., 1a.2m.3b.4f.5h., 1b.2m.3b.4f.5h., 1f.2m.3b.4f.5h., 1h.2m.3b.4f.5h., 1j.2m.3b.4f.5h., 1p.2m.3b.4f.5h., 1a.2o.3b.4f.5h., 1b.2o.3b.4f.5h., 1f.2o.3b.4f.5h., 1h.2o.3b.4f.5h., 1j.2o.3b.4f.5h., 1p.2o.3b.4f.5h., 1a.2u.3b.4f.5h., 1b.2u.3b.4f.5h., 1f.2u.3b.4f.5h., 1h.2u.3b.4f.5h.,

TABLE 12-continued

List of Compound Structures of Formula II 1j.2u.3b.4f.5h., 1p.2u.3b.4f.5h., 1a.2y.3b.4f.5h., 1b.2y.3b.4f.5h., 1f.2y.3b.4f.5h., 1h.2y.3b.4f.5h., 1j.2y.3b.4f.5h., 1p.2y.3b.4f.5h., 1a.2a.3e.4f.5h., 1b.2a.3e.4f.5h., 1f.2a.3e.4f.5h., 1h.2a.3e.4f.5h., 1j.2a.3e.4f.5h., 1p.2a.3e.4f.5h., 1a.2b.3e.4f.5h., 1b.2b.3e.4f.5h., 1f.2b.3e.4f.5h., 1h.2b.3e.4f.5h., 1j.2b.3e.4f.5h., 1p.2b.3e.4f.5h., 1a.2e.3e.4f.5h., 1b.2e.3e.4f.5h., 1f.2e.3e.4f.5h., 1h.2e.3e.4f.5h., 1j.2e.3e.4f.5h., 1p.2e.3e.4f.5h., 1a.2f.3e.4f.5h., 1b.2f.3e.4f.5h., 1f.2f.3e.4f.5h., 1h.2f.3e.4f.5h., 1j.2f.3e.4f.5h., 1p.2f.3e.4f.5h., 1a.2i.3e.4f.5h., 1b.2i.3e.4f.5h., 1f.2i.3e.4f.5h., 1h.2i.3e.4f.5h., 1j.2i.3e.4f.5h., 1p.2i.3e.4f.5h., 1a.2m.3e.4f.5h., 1b.2m.3e.4f.5h., 1f.2m.3e.4f.5h., 1h.2m.3e.4f.5h., 1j.2m.3e.4f.5h., 1p.2m.3e.4f.5h., 1a.2o.3e.4f.5h., 1b.2o.3e.4f.5h., 1f.2o.3e.4f.5h., 1h.2o.3e.4f.5h., 1j.2o.3e.4f.5h., 1p.2o.3e.4f.5h., 1a.2u.3e.4f.5h., 1b.2u.3e.4f.5h., 1f.2u.3e.4f.5h., 1h.2u.3e.4f.5h., 1j.2u.3e.4f.5h., 1p.2u.3e.4f.5h., 1a.2y.3e.4f.5h., 1b.2y.3e.4f.5h., 1f.2y.3e.4f.5h., 1h.2y.3e.4f.5h., 1j.2y.3e.4f.5h., 1p.2y.3e.4f.5h., 1a.2a.3g.4f.5h., 1b.2a.3g.4f.5h., 1f.2a.3g.4f.5h., 1h.2a.3g.4f.5h., 1j.2a.3g.4f.5h., 1p.2a.3g.4f.5h., 1a.2b.3g.4f.5h., 1b.2b.3g.4f.5h., 1f.2b.3g.4f.5h., 1h.2b.3g.4f.5h., 1j.2b.3g.4f.5h., 1p.2b.3g.4f.5h., 1a.2e.3g.4f.5h., 1b.2e.3g.4f.5h., 1f.2e.3g.4f.5h., 1h.2e.3g.4f.5h., 1j.2e.3g.4f.5h., 1p.2e.3g.4f.5h., 1a.2f.3g.4f.5h., 1b.2f.3g.4f.5h., 1f.2f.3g.4f.5h., 1h.2f.3g.4f.5h., 1j.2f.3g.4f.5h., 1p.2f.3g.4f.5h., 1a.2i.3g.4f.5h., 1b.2i.3g.4f.5h., 1f.2i.3g.4f.5h., 1h.2i.3g.4f.5h., 1j.2i.3g.4f.5h., 1p.2i.3g.4f.5h., 1a.2m.3g.4f.5h., 1b.2m.3g.4f.5h., 1f.2m.3g.4f.5h., 1h.2m.3g.4f.5h., 1j.2m.3g.4f.5h., 1p.2m.3g.4f.5h., 1a.2o.3g.4f.5h., 1b.2o.3g.4f.5h., 1f.2o.3g.4f.5h., 1h.2o.3g.4f.5h., 1j.2o.3g.4f.5h., 1p.2o.3g.4f.5h., 1a.2u.3g.4f.5h., 1b.2u.3g.4f.5h., 1f.2u.3g.4f.5h., 1h.2u.3g.4f.5h., 1j.2u.3g.4f.5h., 1p.2u.3g.4f.5h., 1a.2y.3g.4f.5h., 1b.2y.3g.4f.5h., 1f.2y.3g.4f.5h., 1h.2y.3g.4f.5h., 1j.2y.3g.4f.5h., 1p.2y.3g.4f.5h., 1a.2a.3a.4g.5h., 1b.2a.3a.4g.5h., 1f.2a.3a.4g.5h., 1h.2a.3a.4g.5h., 1j.2a.3a.4g.5h., 1p.2a.3a.4g.5h., 1a.2b.3a.4g.5h., 1b.2b.3a.4g.5h., 1f.2b.3a.4g.5h., 1h.2b.3a.4g.5h., 1j.2b.3a.4g.5h., 1p.2b.3a.4g.5h., 1a.2e.3a.4g.5h., 1b.2e.3a.4g.5h., 1f.2e.3a.4g.5h., 1h.2e.3a.4g.5h., 1j.2e.3a.4g.5h., 1p.2e.3a.4g.5h., 1a.2f.3a.4g.5h., 1b.2f.3a.4g.5h., 1f.2f.3a.4g.5h., 1h.2f.3a.4g.5h., 1j.2f.3a.4g.5h., 1p.2f.3a.4g.5h., 1a.2i.3a.4g.5h., 1b.2i.3a.4g.5h., 1f.2i.3a.4g.5h., 1h.2i.3a.4g.5h., 1j.2i.3a.4g.5h., 1p.2i.3a.4g.5h., 1a.2m.3a.4g.5h., 1b.2m.3a.4g.5h., 1f.2m.3a.4g.5h., 1h.2m.3a.4g.5h., 1j.2m.3a.4g.5h., 1p.2m.3a.4g.5h., 1a.2o.3a.4g.5h., 1b.2o.3a.4g.5h., 1f.2o.3a.4g.5h., 1h.2o.3a.4g.5h., 1j.2o.3a.4g.5h., 1p.2o.3a.4g.5h., 1a.2u.3a.4g.5h., 1b.2u.3a.4g.5h., 1f.2u.3a.4g.5h., 1h.2u.3a.4g.5h., 1j.2u.3a.4g.5h., 1p.2u.3a.4g.5h., 1a.2y.3a.4g.5h., 1b.2y.3a.4g.5h., 1f.2y.3a.4g.5h., 1h.2y.3a.4g.5h., 1j.2y.3a.4g.5h., 1p.2y.3a.4g.5h., 1a.2a.3b.4g.5h., 1b.2a.3b.4g.5h., 1f.2a.3b.4g.5h., 1h.2a.3b.4g.5h., 1j.2a.3b.4g.5h., 1p.2a.3b.4g.5h., 1a.2b.3b.4g.5h., 1b.2b.3b.4g.5h., 1f.2b.3b.4g.5h., 1h.2b.3b.4g.5h., 1j.2b.3b.4g.5h., 1p.2b.3b.4g.5h., 1a.2e.3b.4g.5h., 1b.2e.3b.4g.5h., 1f.2e.3b.4g.5h., 1h.2e.3b.4g.5h., 1j.2e.3b.4g.5h., 1p.2e.3b.4g.5h., 1a.2f.3b.4g.5h., 1b.2f.3b.4g.5h., 1f.2f.3b.4g.5h., 1h.2f.3b.4g.5h., 1j.2f.3b.4g.5h., 1p.2f.3b.4g.5h., 1a.2i.3b.4g.5h., 1b.2i.3b.4g.5h., 1f.2i.3b.4g.5h., 1h.2i.3b.4g.5h., 1j.2i.3b.4g.5h., 1p.2i.3b.4g.5h., 1a.2m.3b.4g.5h., 1b.2m.3b.4g.5h., 1f.2m.3b.4g.5h., 1h.2m.3b.4g.5h., 1j.2m.3b.4g.5h., 1p.2m.3b.4g.5h., 1a.2o.3b.4g.5h., 1b.2o.3b.4g.5h., 1f.2o.3b.4g.5h., 1h.2o.3b.4g.5h., 1j.2o.3b.4g.5h., 1p.2o.3b.4g.5h., 1a.2u.3b.4g.5h., 1b.2u.3b.4g.5h., 1f.2u.3b.4g.5h., 1h.2u.3b.4g.5h., 1j.2u.3b.4g.5h., 1p.2u.3b.4g.5h., 1a.2y.3b.4g.5h., 1b.2y.3b.4g.5h., 1f.2y.3b.4g.5h., 1h.2y.3b.4g.5h., 1j.2y.3b.4g.5h., 1p.2y.3b.4g.5h., 1a.2a.3e.4g.5h., 1b.2a.3e.4g.5h., 1f.2a.3e.4g.5h., 1h.2a.3e.4g.5h., 1j.2a.3e.4g.5h., 1p.2a.3e.4g.5h., 1a.2b.3e.4g.5h., 1b.2b.3e.4g.5h., 1f.2b.3e.4g.5h., 1h.2b.3e.4g.5h., 1j.2b.3e.4g.5h., 1p.2b.3e.4g.5h., 1a.2e.3e.4g.5h., 1b.2e.3e.4g.5h., 1f.2e.3e.4g.5h., 1h.2e.3e.4g.5h., 1j.2e.3e.4g.5h., 1p.2e.3e.4g.5h., 1a.2f.3e.4g.5h., 1b.2f.3e.4g.5h., 1f.2f.3e.4g.5h., 1h.2f.3e.4g.5h., 1j.2f.3e.4g.5h., 1p.2f.3e.4g.5h., 1a.2i.3e.4g.5h., 1b.2i.3e.4g.5h., 1f.2i.3e.4g.5h., 1h.2i.3e.4g.5h., 1j.2i.3e.4g.5h., 1p.2i.3e.4g.5h., 1a.2m.3e.4g.5h., 1b.2m.3e.4g.5h., 1f.2m.3e.4g.5h., 1h.2m.3e.4g.5h., 1j.2m.3e.4g.5h., 1p.2m.3e.4g.5h., 1a.2o.3e.4g.5h., 1b.2o.3e.4g.5h., 1f.2o.3e.4g.5h., 1h.2o.3e.4g.5h., 1j.2o.3e.4g.5h., 1p.2o.3e.4g.5h., 1a.2u.3e.4g.5h., 1b.2u.3e.4g.5h., 1f.2u.3e.4g.5h., 1h.2u.3e.4g.5h., 1j.2u.3e.4g.5h., 1p.2u.3e.4g.5h., 1a.2y.3e.4g.5h., 1b.2y.3e.4g.5h., 1f.2y.3e.4g.5h., 1h.2y.3e.4g.5h., 1j.2y.3e.4g.5h., 1p.2y.3e.4g.5h., 1a.2a.3g.4g.5h., 1b.2a.3g.4g.5h., 1f.2a.3g.4g.5h., 1h.2a.3g.4g.5h., 1j.2a.3g.4g.5h., 1p.2a.3g.4g.5h., 1a.2b.3g.4g.5h., 1b.2b.3g.4g.5h., 1f.2b.3g.4g.5h., 1h.2b.3g.4g.5h., 1j.2b.3g.4g.5h., 1p.2b.3g.4g.5h., 1a.2e.3g.4g.5h., 1b.2e.3g.4g.5h., 1f.2e.3g.4g.5h., 1h.2e.3g.4g.5h., 1j.2e.3g.4g.5h., 1p.2e.3g.4g.5h., 1a.2f.3g.4g.5h., 1b.2f.3g.4g.5h., 1f.2f.3g.4g.5h., 1h.2f.3g.4g.5h., 1j.2f.3g.4g.5h., 1p.2f.3g.4g.5h., 1a.2i.3g.4g.5h., 1b.2i.3g.4g.5h., 1f.2i.3g.4g.5h., 1h.2i.3g.4g.5h., 1j.2i.3g.4g.5h., 1p.2i.3g.4g.5h., 1a.2m.3g.4g.5h., 1b.2m.3g.4g.5h., 1f.2m.3g.4g.5h., 1h.2m.3g.4g.5h., 1j.2m.3g.4g.5h., 1p.2m.3g.4g.5h., 1a.2o.3g.4g.5h., 1b.2o.3g.4g.5h., 1f.2o.3g.4g.5h., 1h.2o.3g.4g.5h., 1j.2o.3g.4g.5h., 1p.2o.3g.4g.5h., 1a.2u.3g.4g.5h., 1b.2u.3g.4g.5h., 1f.2u.3g.4g.5h., 1h.2u.3g.4g.5h., 1j.2u.3g.4g.5h., 1p.2u.3g.4g.5h., 1a.2y.3g.4g.5h., 1b.2y.3g.4g.5h., 1f.2y.3g.4g.5h., 1h.2y.3g.4g.5h., 1j.2y.3g.4g.5h., 1p.2y.3g.4g.5h., 1a.2a.3a.4h.5h., 1b.2a.3a.4h.5h., 1f.2a.3a.4h.5h., 1h.2a.3a.4h.5h., 1j.2a.3a.4h.5h., 1p.2a.3a.4h.5h., 1a.2b.3a.4h.5h., 1b.2b.3a.4h.5h., 1f.2b.3a.4h.5h., 1h.2b.3a.4h.5h., 1j.2b.3a.4h.5h., 1p.2b.3a.4h.5h., 1a.2e.3a.4h.5h., 1b.2e.3a.4h.5h., 1f.2e.3a.4h.5h., 1h.2e.3a.4h.5h., 1j.2e.3a.4h.5h., 1p.2e.3a.4h.5h., 1a.2f.3a.4h.5h., 1b.2f.3a.4h.5h., 1f.2f.3a.4h.5h., 1h.2f.3a.4h.5h., 1j.2f.3a.4h.5h., 1p.2f.3a.4h.5h., 1a.2i.3a.4h.5h., 1b.2i.3a.4h.5h., 1f.2i.3a.4h.5h., 1h.2i.3a.4h.5h., 1j.2i.3a.4h.5h., 1p.2i.3a.4h.5h., 1a.2m.3a.4h.5h., 1b.2m.3a.4h.5h., 1f.2m.3a.4h.5h., 1h.2m.3a.4h.5h., 1j.2m.3a.4h.5h., 1p.2m.3a.4h.5h., 1a.2o.3a.4h.5h., 1b.2o.3a.4h.5h., 1f.2o.3a.4h.5h., 1h.2o.3a.4h.5h., 1j.2o.3a.4h.5h., 1p.2o.3a.4h.5h., 1a.2u.3a.4h.5h., 1b.2u.3a.4h.5h., 1f.2u.3a.4h.5h., 1h.2u.3a.4h.5h., 1j.2u.3a.4h.5h., 1p.2u.3a.4h.5h., 1a.2y.3a.4h.5h., 1b.2y.3a.4h.5h., 1f.2y.3a.4h.5h., 1h.2y.3a.4h.5h., 1j.2y.3a.4h.5h., 1p.2y.3a.4h.5h., 1a.2a.3b.4h.5h., 1b.2a.3b.4h.5h., 1f.2a.3b.4h.5h., 1h.2a.3b.4h.5h., 1j.2a.3b.4h.5h., 1p.2a.3b.4h.5h., 1a.2b.3b.4h.5h., 1b.2b.3b.4h.5h., 1f.2b.3b.4h.5h., 1h.2b.3b.4h.5h., 1j.2b.3b.4h.5h., 1p.2b.3b.4h.5h., 1a.2e.3b.4h.5h., 1b.2e.3b.4h.5h., 1f.2e.3b.4h.5h., 1h.2e.3b.4h.5h., 1j.2e.3b.4h.5h., 1p.2e.3b.4h.5h., 1a.2f.3b.4h.5h., 1b.2f.3b.4h.5h., 1f.2f.3b.4h.5h., 1h.2f.3b.4h.5h., 1j.2f.3b.4h.5h., 1p.2f.3b.4h.5h., 1a.2i.3b.4h.5h., 1b.2i.3b.4h.5h., 1f.2i.3b.4h.5h., 1h.2i.3b.4h.5h., 1j.2i.3b.4h.5h., 1p.2i.3b.4h.5h., 1a.2m.3b.4h.5h., 1b.2m.3b.4h.5h., 1f.2m.3b.4h.5h., 1h.2m.3b.4h.5h., 1j.2m.3b.4h.5h., 1p.2m.3b.4h.5h., 1a.2o.3b.4h.5h., 1b.2o.3b.4h.5h., 1f.2o.3b.4h.5h., 1h.2o.3b.4h.5h., 1j.2o.3b.4h.5h., 1p.2o.3b.4h.5h., 1a.2u.3b.4h.5h., 1b.2u.3b.4h.5h., 1f.2u.3b.4h.5h., 1h.2u.3b.4h.5h., 1j.2u.3b.4h.5h., 1p.2u.3b.4h.5h., 1a.2y.3b.4h.5h., 1b.2y.3b.4h.5h., 1f.2y.3b.4h.5h., 1h.2y.3b.4h.5h., 1j.2y.3b.4h.5h., 1p.2y.3b.4h.5h., 1a.2a.3e.4h.5h., 1b.2a.3e.4h.5h., 1f.2a.3e.4h.5h., 1h.2a.3e.4h.5h., 1j.2a.3e.4h.5h., 1p.2a.3e.4h.5h., 1a.2b.3e.4h.5h., 1b.2b.3e.4h.5h., 1f.2b.3e.4h.5h., 1h.2b.3e.4h.5h., 1j.2b.3e.4h.5h., 1p.2b.3e.4h.5h., 1a.2e.3e.4h.5h., 1b.2e.3e.4h.5h., 1f.2e.3e.4h.5h., 1h.2e.3e.4h.5h., 1j.2e.3e.4h.5h., 1p.2e.3e.4h.5h., 1a.2f.3e.4h.5h., 1b.2f.3e.4h.5h., 1f.2f.3e.4h.5h., 1h.2f.3e.4h.5h., 1j.2f.3e.4h.5h., 1p.2f.3e.4h.5h., 1a.2i.3e.4h.5h., 1b.2i.3e.4h.5h., 1f.2i.3e.4h.5h., 1h.2i.3e.4h.5h., 1j.2i.3e.4h.5h., 1p.2i.3e.4h.5h., 1a.2m.3e.4h.5h., 1b.2m.3e.4h.5h., 1f.2m.3e.4h.5h., 1h.2m.3e.4h.5h., 1j.2m.3e.4h.5h., 1p.2m.3e.4h.5h., 1a.2o.3e.4h.5h., 1b.2o.3e.4h.5h., 1f.2o.3e.4h.5h., 1h.2o.3e.4h.5h., 1j.2o.3e.4h.5h., 1p.2o.3e.4h.5h., 1a.2u.3e.4h.5h., 1b.2u.3e.4h.5h., 1f.2u.3e.4h.5h., 1h.2u.3e.4h.5h., 1j.2u.3e.4h.5h., 1p.2u.3e.4h.5h., 1a.2y.3e.4h.5h., 1b.2y.3e.4h.5h., 1f.2y.3e.4h.5h., 1h.2y.3e.4h.5h., 1j.2y.3e.4h.5h., 1p.2y.3e.4h.5h., 1a.2a.3g.4h.5h., 1b.2a.3g.4h.5h., 1f.2a.3g.4h.5h., 1h.2a.3g.4h.5h., 1j.2a.3g.4h.5h., 1p.2a.3g.4h.5h., 1a.2b.3g.4h.5h., 1b.2b.3g.4h.5h., 1f.2b.3g.4h.5h., 1h.2b.3g.4h.5h., 1j.2b.3g.4h.5h., 1p.2b.3g.4h.5h., 1a.2e.3g.4h.5h., 1b.2e.3g.4h.5h., 1f.2e.3g.4h.5h., 1h.2e.3g.4h.5h., 1j.2e.3g.4h.5h., 1p.2e.3g.4h.5h., 1a.2f.3g.4h.5h., 1b.2f.3g.4h.5h., 1f.2f.3g.4h.5h., 1h.2f.3g.4h.5h., 1j.2f.3g.4h.5h., 1p.2f.3g.4h.5h., 1a.2i.3g.4h.5h., 1b.2i.3g.4h.5h., 1f.2i.3g.4h.5h., 1h.2i.3g.4h.5h., 1j.2i.3g.4h.5h., 1p.2i.3g.4h.5h., 1a.2m.3g.4h.5h., 1b.2m.3g.4h.5h., 1f.2m.3g.4h.5h., 1h.2m.3g.4h.5h., 1j.2m.3g.4h.5h., 1p.2m.3g.4h.5h., 1a.2o.3g.4h.5h., 1b.2o.3g.4h.5h., 1f.2o.3g.4h.5h., 1h.2o.3g.4h.5h., 1j.2o.3g.4h.5h., 1p.2o.3g.4h.5h., 1a.2u.3g.4h.5h., 1b.2u.3g.4h.5h., 1f.2u.3g.4h.5h., 1h.2u.3g.4h.5h., 1j.2u.3g.4h.5h., 1p.2u.3g.4h.5h., 1a.2y.3g.4h.5h., 1b.2y.3g.4h.5h., 1f.2y.3g.4h.5h., 1h.2y.3g.4h.5h., 1j.2y.3g.4h.5h., 1p.2y.3g.4h.5h., 1a.2a.3a.4i.5h., 1b.2a.3a.4i.5h., 1f.2a.3a.4i.5h., 1h.2a.3a.4i.5h., 1j.2a.3a.4i.5h., 1p.2a.3a.4i.5h., 1a.2b.3a.4i.5h., 1b.2b.3a.4i.5h., 1f.2b.3a.4i.5h., 1h.2b.3a.4i.5h., 1j.2b.3a.4i.5h., 1p.2b.3a.4i.5h., 1a.2e.3a.4i.5h., 1b.2e.3a.4i.5h., 1f.2e.3a.4i.5h., 1h.2e.3a.4i.5h., 1j.2e.3a.4i.5h., 1p.2e.3a.4i.5h., 1a.2f.3a.4i.5h., 1b.2f.3a.4i.5h., 1f.2f.3a.4i.5h., 1h.2f.3a.4i.5h., 1j.2f.3a.4i.5h., 1p.2f.3a.4i.5h., 1a.2i.3a.4i.5h., 1b.2i.3a.4i.5h., 1f.2i.3a.4i.5h., 1h.2i.3a.4i.5h., 1j.2i.3a.4i.5h., 1p.2i.3a.4i.5h., 1a.2m.3a.4i.5h., 1b.2m.3a.4i.5h., 1f.2m.3a.4i.5h., 1h.2m.3a.4i.5h., 1j.2m.3a.4i.5h., 1p.2m.3a.4i.5h., 1a.2o.3a.4i.5h., 1b.2o.3a.4i.5h., 1f.2o.3a.4i.5h., 1h.2o.3a.4i.5h., 1j.2o.3a.4i.5h., 1p.2o.3a.4i.5h., 1a.2u.3a.4i.5h., 1b.2u.3a.4i.5h., 1f.2u.3a.4i.5h., 1h.2u.3a.4i.5h., 1j.2u.3a.4i.5h., 1p.2u.3a.4i.5h., 1a.2y.3a.4i.5h., 1b.2y.3a.4i.5h., 1f.2y.3a.4i.5h., 1h.2y.3a.4i.5h., 1j.2y.3a.4i.5h., 1p.2y.3a.4i.5h., 1a.2a.3b.4i.5h., 1b.2a.3b.4i.5h., 1f.2a.3b.4i.5h., 1h.2a.3b.4i.5h., 1j.2a.3b.4i.5h., 1p.2a.3b.4i.5h., 1a.2b.3b.4i.5h., 1b.2b.3b.4i.5h., 1f.2b.3b.4i.5h., 1h.2b.3b.4i.5h., 1j.2b.3b.4i.5h., 1p.2b.3b.4i.5h., 1a.2e.3b.4i.5h., 1b.2e.3b.4i.5h., 1f.2e.3b.4i.5h., 1h.2e.3b.4i.5h., 1j.2e.3b.4i.5h., 1p.2e.3b.4i.5h., 1a.2f.3b.4i.5h., 1b.2f.3b.4i.5h., 1f.2f.3b.4i.5h., 1h.2f.3b.4i.5h.,

TABLE 12-continued

List of Compound Structures of Formula II 1j.2f.3b.4i.5h., 1p.2f.3b.4i.5h., 1a.2i.3b.4i.5h., 1b.2i.3b.4i.5h., 1f.2i.3b.4i.5h., 1h.2i.3b.4i.5h., 1j.2i.3b.4i.5h., 1p.2i.3b.4i.5h., 1a.2m.3b.4i.5h., 1b.2m.3b.4i.5h., 1f.2m.3b.4i.5h., 1h.2m.3b.4i.5h., 1j.2m.3b.4i.5h., 1p.2m.3b.4i.5h., 1a.2o.3b.4i.5h., 1b.2o.3b.4i.5h., 1f.2o.3b.4i.5h., 1h.2o.3b.4i.5h., 1j.2o.3b.4i.5h., 1p.2o.3b.4i.5h., 1a.2u.3b.4i.5h., 1b.2u.3b.4i.5h., 1f.2u.3b.4i.5h., 1h.2u.3b.4i.5h., 1j.2u.3b.4i.5h., 1p.2u.3b.4i.5h., 1a.2y.3b.4i.5h., 1b.2y.3b.4i.5h., 1f.2y.3b.4i.5h., 1h.2y.3b.4i.5h., 1j.2y.3b.4i.5h., 1p.2y.3b.4i.5h., 1a.2a.3e.4i.5h., 1b.2a.3e.4i.5h., 1f.2a.3e.4i.5h., 1h.2a.3e.4i.5h., 1j.2a.3e.4i.5h., 1p.2a.3e.4i.5h., 1a.2b.3e.4i.5h., 1b.2b.3e.4i.5h., 1f.2b.3e.4i.5h., 1h.2b.3e.4i.5h., 1j.2b.3e.4i.5h., 1p.2b.3e.4i.5h., 1a.2e.3e.4i.5h., 1b.2e.3e.4i.5h., 1f.2e.3e.4i.5h., 1h.2e.3e.4i.5h., 1j.2e.3e.4i.5h., 1p.2e.3e.4i.5h., 1a.2f.3e.4i.5h., 1b.2f.3e.4i.5h., 1f.2f.3e.4i.5h., 1h.2f.3e.4i.5h., 1j.2f.3e.4i.5h., 1p.2f.3e.4i.5h., 1a.2i.3e.4i.5h., 1b.2i.3e.4i.5h., 1f.2i.3e.4i.5h., 1h.2i.3e.4i.5h., 1j.2i.3e.4i.5h., 1p.2i.3e.4i.5h., 1a.2m.3e.4i.5h., 1b.2m.3e.4i.5h., 1f.2m.3e.4i.5h., 1h.2m.3e.4i.5h., 1j.2m.3e.4i.5h., 1p.2m.3e.4i.5h., 1a.2o.3e.4i.5h., 1b.2o.3e.4i.5h., 1f.2o.3e.4i.5h., 1h.2o.3e.4i.5h., 1j.2o.3e.4i.5h., 1p.2o.3e.4i.5h., 1a.2u.3e.4i.5h., 1b.2u.3e.4i.5h., 1f.2u.3e.4i.5h., 1h.2u.3e.4i.5h., 1j.2u.3e.4i.5h., 1p.2u.3e.4i.5h., 1a.2y.3e.4i.5h., 1b.2y.3e.4i.5h., 1f.2y.3e.4i.5h., 1h.2y.3e.4i.5h., 1j.2y.3e.4i.5h., 1p.2y.3e.4i.5h., 1a.2a.3g.4i.5h., 1b.2a.3g.4i.5h., 1f.2a.3g.4i.5h., 1h.2a.3g.4i.5h., 1j.2a.3g.4i.5h., 1p.2a.3g.4i.5h., 1a.2b.3g.4i.5h., 1b.2b.3g.4i.5h., 1f.2b.3g.4i.5h., 1h.2b.3g.4i.5h., 1j.2b.3g.4i.5h., 1p.2b.3g.4i.5h., 1a.2e.3g.4i.5h., 1b.2e.3g.4i.5h., 1f.2e.3g.4i.5h., 1h.2e.3g.4i.5h., 1j.2e.3g.4i.5h., 1p.2e.3g.4i.5h., 1a.2f.3g.4i.5h., 1b.2f.3g.4i.5h., 1f.2f.3g.4i.5h., 1h.2f.3g.4i.5h., 1j.2f.3g.4i.5h., 1p.2f.3g.4i.5h., 1a.2i.3g.4i.5h., 1b.2i.3g.4i.5h., 1f.2i.3g.4i.5h., 1h.2i.3g.4i.5h., 1j.2i.3g.4i.5h., 1p.2i.3g.4i.5h., 1a.2m.3g.4i.5h., 1b.2m.3g.4i.5h., 1f.2m.3g.4i.5h., 1h.2m.3g.4i.5h., 1j.2m.3g.4i.5h., 1p.2m.3g.4i.5h., 1a.2o.3g.4i.5h., 1b.2o.3g.4i.5h., 1f.2o.3g.4i.5h., 1h.2o.3g.4i.5h., 1j.2o.3g.4i.5h., 1p.2o.3g.4i.5h., 1a.2u.3g.4i.5h., 1b.2u.3g.4i.5h., 1f.2u.3g.4i.5h., 1h.2u.3g.4i.5h., 1j.2u.3g.4i.5h., 1p.2u.3g.4i.5h., 1a.2y.3g.4i.5h., 1b.2y.3g.4i.5h., 1f.2y.3g.4i.5h., 1h.2y.3g.4i.5h., 1j.2y.3g.4i.5h., 1p.2y.3g.4i.5h., 1a.2a.3a.4a.5i., 1b.2a.3a.4a.5i., 1f.2a.3a.4a.5i., 1h.2a.3a.4a.5i., 1j.2a.3a.4a.5i., 1p.2a.3a.4a.5i., 1a.2b.3a.4a.5i., 1b.2b.3a.4a.5i., 1f.2b.3a.4a.5i., 1h.2b.3a.4a.5i., 1j.2b.3a.4a.5i., 1p.2b.3a.4a.5i., 1a.2e.3a.4a.5i., 1b.2e.3a.4a.5i., 1f.2e.3a.4a.5i., 1h.2e.3a.4a.5i., 1j.2e.3a.4a.5i., 1p.2e.3a.4a.5i., 1a.2f.3a.4a.5i., 1b.2f.3a.4a.5i., 1f.2f.3a.4a.5i., 1h.2f.3a.4a.5i., 1j.2f.3a.4a.5i., 1p.2f.3a.4a.5i., 1a.2i.3a.4a.5i., 1b.2i.3a.4a.5i., 1f.2i.3a.4a.5i., 1h.2i.3a.4a.5i., 1j.2i.3a.4a.5i., 1p.2i.3a.4a.5i., 1a.2m.3a.4a.5i., 1b.2m.3a.4a.5i., 1f.2m.3a.4a.5i., 1h.2m.3a.4a.5i., 1j.2m.3a.4a.5i., 1p.2m.3a.4a.5i., 1a.2o.3a.4a.5i., 1b.2o.3a.4a.5i., 1f.2o.3a.4a.5i., 1h.2o.3a.4a.5i., 1j.2o.3a.4a.5i., 1p.2o.3a.4a.5i., 1a.2u.3a.4a.5i., 1b.2u.3a.4a.5i., 1f.2u.3a.4a.5i., 1h.2u.3a.4a.5i., 1j.2u.3a.4a.5i., 1p.2u.3a.4a.5i., 1a.2y.3a.4a.5i., 1b.2y.3a.4a.5i., 1f.2y.3a.4a.5i., 1h.2y.3a.4a.5i., 1j.2y.3a.4a.5i., 1p.2y.3a.4a.5i., 1a.2a.3b.4a.5i., 1b.2a.3b.4a.5i., 1f.2a.3b.4a.5i., 1h.2a.3b.4a.5i., 1j.2a.3b.4a.5i., 1p.2a.3b.4a.5i., 1a.2b.3b.4a.5i., 1b.2b.3b.4a.5i., 1f.2b.3b.4a.5i., 1h.2b.3b.4a.5i., 1j.2b.3b.4a.5i., 1p.2b.3b.4a.5i., 1a.2e.3b.4a.5i., 1b.2e.3b.4a.5i., 1f.2e.3b.4a.5i., 1h.2e.3b.4a.5i., 1j.2e.3b.4a.5i., 1p.2e.3b.4a.5i., 1a.2f.3b.4a.5i., 1b.2f.3b.4a.5i., 1f.2f.3b.4a.5i., 1h.2f.3b.4a.5i., 1j.2f.3b.4a.5i., 1p.2f.3b.4a.5i., 1a.2i.3b.4a.5i., 1b.2i.3b.4a.5i., 1f.2i.3b.4a.5i., 1h.2i.3b.4a.5i., 1j.2i.3b.4a.5i., 1p.2i.3b.4a.5i., 1a.2m.3b.4a.5i., 1b.2m.3b.4a.5i., 1f.2m.3b.4a.5i., 1h.2m.3b.4a.5i., 1j.2m.3b.4a.5i., 1p.2m.3b.4a.5i., 1a.2o.3b.4a.5i., 1b.2o.3b.4a.5i., 1f.2o.3b.4a.5i., 1h.2o.3b.4a.5i., 1j.2o.3b.4a.5i., 1p.2o.3b.4a.5i., 1a.2u.3b.4a.5i., 1b.2u.3b.4a.5i., 1f.2u.3b.4a.5i., 1h.2u.3b.4a.5i., 1j.2u.3b.4a.5i., 1p.2u.3b.4a.5i., 1a.2y.3b.4a.5i., 1b.2y.3b.4a.5i., 1f.2y.3b.4a.5i., 1h.2y.3b.4a.5i., 1j.2y.3b.4a.5i., 1p.2y.3b.4a.5i., 1a.2a.3e.4a.5i., 1b.2a.3e.4a.5i., 1f.2a.3e.4a.5i., 1h.2a.3e.4a.5i., 1j.2a.3e.4a.5i., 1p.2a.3e.4a.5i., 1a.2b.3e.4a.5i., 1b.2b.3e.4a.5i., 1f.2b.3e.4a.5i., 1h.2b.3e.4a.5i., 1j.2b.3e.4a.5i., 1p.2b.3e.4a.5i., 1a.2e.3e.4a.5i., 1b.2e.3e.4a.5i., 1f.2e.3e.4a.5i., 1h.2e.3e.4a.5i., 1j.2e.3e.4a.5i., 1p.2e.3e.4a.5i., 1a.2f.3e.4a.5i., 1b.2f.3e.4a.5i., 1f.2f.3e.4a.5i., 1h.2f.3e.4a.5i., 1j.2f.3e.4a.5i., 1p.2f.3e.4a.5i., 1a.2i.3e.4a.5i., 1b.2i.3e.4a.5i., 1f.2i.3e.4a.5i., 1h.2i.3e.4a.5i., 1j.2i.3e.4a.5i., 1p.2i.3e.4a.5i., 1a.2m.3e.4a.5i., 1b.2m.3e.4a.5i., 1f.2m.3e.4a.5i., 1h.2m.3e.4a.5i., 1j.2m.3e.4a.5i., 1p.2m.3e.4a.5i., 1a.2o.3e.4a.5i., 1b.2o.3e.4a.5i., 1f.2o.3e.4a.5i., 1h.2o.3e.4a.5i., 1j.2o.3e.4a.5i., 1p.2o.3e.4a.5i., 1a.2u.3e.4a.5i., 1b.2u.3e.4a.5i., 1f.2u.3e.4a.5i., 1h.2u.3e.4a.5i., 1j.2u.3e.4a.5i., 1p.2u.3e.4a.5i., 1a.2y.3e.4a.5i., 1b.2y.3e.4a.5i., 1f.2y.3e.4a.5i., 1h.2y.3e.4a.5i., 1j.2y.3e.4a.5i., 1p.2y.3e.4a.5i., 1a.2a.3g.4a.5i., 1b.2a.3g.4a.5i., 1f.2a.3g.4a.5i., 1h.2a.3g.4a.5i., 1j.2a.3g.4a.5i., 1p.2a.3g.4a.5i., 1a.2b.3g.4a.5i., 1b.2b.3g.4a.5i., 1f.2b.3g.4a.5i., 1h.2b.3g.4a.5i., 1j.2b.3g.4a.5i., 1p.2b.3g.4a.5i., 1a.2e.3g.4a.5i., 1b.2e.3g.4a.5i., 1f.2e.3g.4a.5i., 1h.2e.3g.4a.5i., 1j.2e.3g.4a.5i., 1p.2e.3g.4a.5i., 1a.2f.3g.4a.5i., 1b.2f.3g.4a.5i., 1f.2f.3g.4a.5i., 1h.2f.3g.4a.5i., 1j.2f.3g.4a.5i., 1p.2f.3g.4a.5i., 1a.2i.3g.4a.5i., 1b.2i.3g.4a.5i., 1f.2i.3g.4a.5i., 1h.2i.3g.4a.5i., 1j.2i.3g.4a.5i., 1p.2i.3g.4a.5i., 1a.2m.3g.4a.5i., 1b.2m.3g.4a.5i., 1f.2m.3g.4a.5i., 1h.2m.3g.4a.5i., 1j.2m.3g.4a.5i., 1p.2m.3g.4a.5i., 1a.2o.3g.4a.5i., 1b.2o.3g.4a.5i., 1f.2o.3g.4a.5i., 1h.2o.3g.4a.5i., 1j.2o.3g.4a.5i., 1p.2o.3g.4a.5i., 1a.2u.3g.4a.5i., 1b.2u.3g.4a.5i., 1f.2u.3g.4a.5i., 1h.2u.3g.4a.5i., 1j.2u.3g.4a.5i., 1p.2u.3g.4a.5i., 1a.2y.3g.4a.5i., 1b.2y.3g.4a.5i., 1f.2y.3g.4a.5i., 1h.2y.3g.4a.5i., 1j.2y.3g.4a.5i., 1p.2y.3g.4a.5i., 1a.2a.3a.4d.5i., 1b.2a.3a.4d.5i., 1f.2a.3a.4d.5i., 1h.2a.3a.4d.5i., 1j.2a.3a.4d.5i., 1p.2a.3a.4d.5i., 1a.2b.3a.4d.5i., 1b.2b.3a.4d.5i., 1f.2b.3a.4d.5i., 1h.2b.3a.4d.5i., 1j.2b.3a.4d.5i., 1p.2b.3a.4d.5i., 1a.2e.3a.4d.5i., 1b.2e.3a.4d.5i., 1f.2e.3a.4d.5i., 1h.2e.3a.4d.5i., 1j.2e.3a.4d.5i., 1p.2e.3a.4d.5i., 1a.2f.3a.4d.5i., 1b.2f.3a.4d.5i., 1f.2f.3a.4d.5i., 1h.2f.3a.4d.5i., 1j.2f.3a.4d.5i., 1p.2f.3a.4d.5i., 1a.2i.3a.4d.5i., 1b.2i.3a.4d.5i., 1f.2i.3a.4d.5i., 1h.2i.3a.4d.5i., 1j.2i.3a.4d.5i., 1p.2i.3a.4d.5i., 1a.2m.3a.4d.5i., 1b.2m.3a.4d.5i., 1f.2m.3a.4d.5i., 1h.2m.3a.4d.5i., 1j.2m.3a.4d.5i., 1p.2m.3a.4d.5i., 1a.2o.3a.4d.5i., 1b.2o.3a.4d.5i., 1f.2o.3a.4d.5i., 1h.2o.3a.4d.5i., 1j.2o.3a.4d.5i., 1p.2o.3a.4d.5i., 1a.2u.3a.4d.5i., 1b.2u.3a.4d.5i., 1f.2u.3a.4d.5i., 1h.2u.3a.4d.5i., 1j.2u.3a.4d.5i., 1p.2u.3a.4d.5i., 1a.2y.3a.4d.5i., 1b.2y.3a.4d.5i., 1f.2y.3a.4d.5i., 1h.2y.3a.4d.5i., 1j.2y.3a.4d.5i., 1p.2y.3a.4d.5i., 1a.2a.3b.4d.5i., 1b.2a.3b.4d.5i., 1f.2a.3b.4d.5i., 1h.2a.3b.4d.5i., 1j.2a.3b.4d.5i., 1p.2a.3b.4d.5i., 1a.2b.3b.4d.5i., 1b.2b.3b.4d.5i., 1f.2b.3b.4d.5i., 1h.2b.3b.4d.5i., 1j.2b.3b.4d.5i., 1p.2b.3b.4d.5i., 1a.2e.3b.4d.5i., 1b.2e.3b.4d.5i., 1f.2e.3b.4d.5i., 1h.2e.3b.4d.5i., 1j.2e.3b.4d.5i., 1p.2e.3b.4d.5i., 1a.2f.3b.4d.5i., 1b.2f.3b.4d.5i., 1f.2f.3b.4d.5i., 1h.2f.3b.4d.5i., 1j.2f.3b.4d.5i., 1p.2f.3b.4d.5i., 1a.2i.3b.4d.5i., 1b.2i.3b.4d.5i., 1f.2i.3b.4d.5i., 1h.2i.3b.4d.5i., 1j.2i.3b.4d.5i., 1p.2i.3b.4d.5i., 1a.2m.3b.4d.5i., 1b.2m.3b.4d.5i., 1f.2m.3b.4d.5i., 1h.2m.3b.4d.5i., 1j.2m.3b.4d.5i., 1p.2m.3b.4d.5i., 1a.2o.3b.4d.5i., 1b.2o.3b.4d.5i., 1f.2o.3b.4d.5i., 1h.2o.3b.4d.5i., 1j.2o.3b.4d.5i., 1p.2o.3b.4d.5i., 1a.2u.3b.4d.5i., 1b.2u.3b.4d.5i., 1f.2u.3b.4d.5i., 1h.2u.3b.4d.5i., 1j.2u.3b.4d.5i., 1p.2u.3b.4d.5i., 1a.2y.3b.4d.5i., 1b.2y.3b.4d.5i., 1f.2y.3b.4d.5i., 1h.2y.3b.4d.5i., 1j.2y.3b.4d.5i., 1p.2y.3b.4d.5i., 1a.2a.3e.4d.5i., 1b.2a.3e.4d.5i., 1f.2a.3e.4d.5i., 1h.2a.3e.4d.5i., 1j.2a.3e.4d.5i., 1p.2a.3e.4d.5i., 1a.2b.3e.4d.5i., 1b.2b.3e.4d.5i., 1f.2b.3e.4d.5i., 1h.2b.3e.4d.5i., 1j.2b.3e.4d.5i., 1p.2b.3e.4d.5i., 1a.2e.3e.4d.5i., 1b.2e.3e.4d.5i., 1f.2e.3e.4d.5i., 1h.2e.3e.4d.5i., 1j.2e.3e.4d.5i., 1p.2e.3e.4d.5i., 1a.2f.3e.4d.5i., 1b.2f.3e.4d.5i., 1f.2f.3e.4d.5i., 1h.2f.3e.4d.5i., 1j.2f.3e.4d.5i., 1p.2f.3e.4d.5i., 1a.2i.3e.4d.5i., 1b.2i.3e.4d.5i., 1f.2i.3e.4d.5i., 1h.2i.3e.4d.5i., 1j.2i.3e.4d.5i., 1p.2i.3e.4d.5i., 1a.2m.3e.4d.5i., 1b.2m.3e.4d.5i., 1f.2m.3e.4d.5i., 1h.2m.3e.4d.5i., 1j.2m.3e.4d.5i., 1p.2m.3e.4d.5i., 1a.2o.3e.4d.5i., 1b.2o.3e.4d.5i., 1f.2o.3e.4d.5i., 1h.2o.3e.4d.5i., 1j.2o.3e.4d.5i., 1p.2o.3e.4d.5i., 1a.2u.3e.4d.5i., 1b.2u.3e.4d.5i., 1f.2u.3e.4d.5i., 1h.2u.3e.4d.5i., 1j.2u.3e.4d.5i., 1p.2u.3e.4d.5i., 1a.2y.3e.4d.5i., 1b.2y.3e.4d.5i., 1f.2y.3e.4d.5i., 1h.2y.3e.4d.5i., 1j.2y.3e.4d.5i., 1p.2y.3e.4d.5i., 1a.2a.3g.4d.5i., 1b.2a.3g.4d.5i., 1f.2a.3g.4d.5i., 1h.2a.3g.4d.5i., 1j.2a.3g.4d.5i., 1p.2a.3g.4d.5i., 1a.2b.3g.4d.5i., 1b.2b.3g.4d.5i., 1f.2b.3g.4d.5i., 1h.2b.3g.4d.5i., 1j.2b.3g.4d.5i., 1p.2b.3g.4d.5i., 1a.2e.3g.4d.5i., 1b.2e.3g.4d.5i., 1f.2e.3g.4d.5i., 1h.2e.3g.4d.5i., 1j.2e.3g.4d.5i., 1p.2e.3g.4d.5i., 1a.2f.3g.4d.5i., 1b.2f.3g.4d.5i., 1f.2f.3g.4d.5i., 1h.2f.3g.4d.5i., 1j.2f.3g.4d.5i., 1p.2f.3g.4d.5i., 1a.2i.3g.4d.5i., 1b.2i.3g.4d.5i., 1f.2i.3g.4d.5i., 1h.2i.3g.4d.5i., 1j.2i.3g.4d.5i., 1p.2i.3g.4d.5i., 1a.2m.3g.4d.5i., 1b.2m.3g.4d.5i., 1f.2m.3g.4d.5i., 1h.2m.3g.4d.5i., 1j.2m.3g.4d.5i., 1p.2m.3g.4d.5i., 1a.2o.3g.4d.5i., 1b.2o.3g.4d.5i., 1f.2o.3g.4d.5i., 1h.2o.3g.4d.5i., 1j.2o.3g.4d.5i., 1p.2o.3g.4d.5i., 1a.2u.3g.4d.5i., 1b.2u.3g.4d.5i., 1f.2u.3g.4d.5i., 1h.2u.3g.4d.5i., 1j.2u.3g.4d.5i., 1p.2u.3g.4d.5i., 1a.2y.3g.4d.5i., 1b.2y.3g.4d.5i., 1f.2y.3g.4d.5i., 1h.2y.3g.4d.5i., 1j.2y.3g.4d.5i., 1p.2y.3g.4d.5i., 1a.2a.3a.4f.5i., 1b.2a.3a.4f.5i., 1f.2a.3a.4f.5i., 1h.2a.3a.4f.5i., 1j.2a.3a.4f.5i., 1p.2a.3a.4f.5i., 1a.2b.3a.4f.5i., 1b.2b.3a.4f.5i., 1f.2b.3a.4f.5i., 1h.2b.3a.4f.5i., 1j.2b.3a.4f.5i., 1p.2b.3a.4f.5i., 1a.2e.3a.4f.5i., 1b.2e.3a.4f.5i., 1f.2e.3a.4f.5i., 1h.2e.3a.4f.5i., 1j.2e.3a.4f.5i., 1p.2e.3a.4f.5i., 1a.2f.3a.4f.5i., 1b.2f.3a.4f.5i., 1f.2f.3a.4f.5i., 1h.2f.3a.4f.5i., 1j.2f.3a.4f.5i., 1p.2f.3a.4f.5i., 1a.2i.3a.4f.5i., 1b.2i.3a.4f.5i., 1f.2i.3a.4f.5i., 1h.2i.3a.4f.5i., 1j.2i.3a.4f.5i., 1p.2i.3a.4f.5i., 1a.2m.3a.4f.5i., 1b.2m.3a.4f.5i., 1f.2m.3a.4f.5i., 1h.2m.3a.4f.5i., 1j.2m.3a.4f.5i., 1p.2m.3a.4f.5i., 1a.2o.3a.4f.5i., 1b.2o.3a.4f.5i., 1f.2o.3a.4f.5i., 1h.2o.3a.4f.5i., 1j.2o.3a.4f.5i., 1p.2o.3a.4f.5i., 1a.2u.3a.4f.5i., 1b.2u.3a.4f.5i., 1f.2u.3a.4f.5i., 1h.2u.3a.4f.5i., 1j.2u.3a.4f.5i., 1p.2u.3a.4f.5i., 1a.2y.3a.4f.5i., 1b.2y.3a.4f.5i., 1f.2y.3a.4f.5i., 1h.2y.3a.4f.5i.,

TABLE 12-continued

List of Compound Structures of Formula II 1j.2y.3a.4f.5i., 1p.2y.3a.4f.5i., 1a.2a.3b.4f.5i., 1b.2a.3b.4f.5i.,
1f.2a.3b.4f.5i., 1h.2a.3b.4f.5i., 1j.2a.3b.4f.5i., 1p.2a.3b.4f.5i.,
1a.2b.3b.4f.5i., 1b.2b.3b.4f.5i., 1f.2b.3b.4f.5i., 1h.2b.3b.4f.5i.,
1j.2b.3b.4f.5i., 1p.2b.3b.4f.5i., 1a.2e.3b.4f.5i., 1b.2e.3b.4f.5i.,
1f.2e.3b.4f.5i., 1h.2e.3b.4f.5i., 1j.2e.3b.4f.5i., 1p.2e.3b.4f.5i.,
1a.2f.3b.4f.5i., 1b.2f.3b.4f.5i., 1f.2f.3b.4f.5i., 1h.2f.3b.4f.5i.,
1j.2f.3b.4f.5i., 1p.2f.3b.4f.5i., 1a.2i.3b.4f.5i., 1b.2i.3b.4f.5i.,
1f.2i.3b.4f.5i., 1h.2i.3b.4f.5i., 1j.2i.3b.4f.5i., 1p.2i.3b.4f.5i.,
1a.2m.3b.4f.5i., 1b.2m.3b.4f.5i., 1f.2m.3b.4f.5i., 1h.2m.3b.4f.5i.,
1j.2m.3b.4f.5i., 1p.2m.3b.4f.5i., 1a.2o.3b.4f.5i., 1b.2o.3b.4f.5i.,
1f.2o.3b.4f.5i., 1h.2o.3b.4f.5i., 1j.2o.3b.4f.5i., 1p.2o.3b.4f.5i.,
1a.2u.3b.4f.5i., 1b.2u.3b.4f.5i., 1f.2u.3b.4f.5i., 1h.2u.3b.4f.5i.,
1j.2u.3b.4f.5i., 1p.2u.3b.4f.5i., 1a.2y.3b.4f.5i., 1b.2y.3b.4f.5i.,
1f.2y.3b.4f.5i., 1h.2y.3b.4f.5i., 1j.2y.3b.4f.5i., 1p.2y.3b.4f.5i.,
1a.2a.3e.4f.5i., 1b.2a.3e.4f.5i., 1f.2a.3e.4f.5i., 1h.2a.3e.4f.5i.,
1j.2a.3e.4f.5i., 1p.2a.3e.4f.5i., 1a.2b.3e.4f.5i., 1b.2b.3e.4f.5i.,
1f.2b.3e.4f.5i., 1h.2b.3e.4f.5i., 1j.2b.3e.4f.5i., 1p.2b.3e.4f.5i.,
1a.2e.3e.4f.5i., 1b.2e.3e.4f.5i., 1f.2e.3e.4f.5i., 1h.2e.3e.4f.5i.,
1j.2e.3e.4f.5i., 1p.2e.3e.4f.5i., 1a.2f.3e.4f.5i., 1b.2f.3e.4f.5i.,
1f.2f.3e.4f.5i., 1h.2f.3e.4f.5i., 1j.2f.3e.4f.5i., 1p.2f.3e.4f.5i.,
1a.2i.3e.4f.5i., 1b.2i.3e.4f.5i., 1f.2i.3e.4f.5i., 1h.2i.3e.4f.5i.,
1j.2i.3e.4f.5i., 1p.2i.3e.4f.5i., 1a.2m.3e.4f.5i., 1b.2m.3e.4f.5i.,
1f.2m.3e.4f.5i., 1h.2m.3e.4f.5i., 1j.2m.3e.4f.5i., 1p.2m.3e.4f.5i.,
1a.2o.3e.4f.5i., 1b.2o.3e.4f.5i., 1f.2o.3e.4f.5i., 1h.2o.3e.4f.5i.,
1j.2o.3e.4f.5i., 1p.2o.3e.4f.5i., 1a.2u.3e.4f.5i., 1b.2u.3e.4f.5i.,
1f.2u.3e.4f.5i., 1h.2u.3e.4f.5i., 1j.2u.3e.4f.5i., 1p.2u.3e.4f.5i.,
1a.2y.3e.4f.5i., 1b.2y.3e.4f.5i., 1f.2y.3e.4f.5i., 1h.2y.3e.4f.5i.,
1j.2y.3e.4f.5i., 1p.2y.3e.4f.5i., 1a.2a.3g.4f.5i., 1b.2a.3g.4f.5i.,
1f.2a.3g.4f.5i., 1h.2a.3g.4f.5i., 1j.2a.3g.4f.5i., 1p.2a.3g.4f.5i.,
1a.2b.3g.4f.5i., 1b.2b.3g.4f.5i., 1f.2b.3g.4f.5i., 1h.2b.3g.4f.5i.,
1j.2b.3g.4f.5i., 1p.2b.3g.4f.5i., 1a.2e.3g.4f.5i., 1b.2e.3g.4f.5i.,
1f.2e.3g.4f.5i., 1h.2e.3g.4f.5i., 1j.2e.3g.4f.5i., 1p.2e.3g.4f.5i.,
1a.2f.3g.4f.5i., 1b.2f.3g.4f.5i., 1f.2f.3g.4f.5i., 1h.2f.3g.4f.5i.,
1j.2f.3g.4f.5i., 1p.2f.3g.4f.5i., 1a.2i.3g.4f.5i., 1b.2i.3g.4f.5i.,
1f.2i.3g.4f.5i., 1h.2i.3g.4f.5i., 1j.2i.3g.4f.5i., 1p.2i.3g.4f.5i.,
1a.2m.3g.4f.5i., 1b.2m.3g.4f.5i., 1f.2m.3g.4f.5i., 1h.2m.3g.4f.5i.,
1j.2m.3g.4f.5i., 1p.2m.3g.4f.5i., 1a.2o.3g.4f.5i., 1b.2o.3g.4f.5i.,
1f.2o.3g.4f.5i., 1h.2o.3g.4f.5i., 1j.2o.3g.4f.5i., 1p.2o.3g.4f.5i.,
1a.2u.3g.4f.5i., 1b.2u.3g.4f.5i., 1f.2u.3g.4f.5i., 1h.2u.3g.4f.5i.,
1j.2u.3g.4f.5i., 1p.2u.3g.4f.5i., 1a.2y.3g.4f.5i., 1b.2y.3g.4f.5i.,
1f.2y.3g.4f.5i., 1h.2y.3g.4f.5i., 1j.2y.3g.4f.5i., 1p.2y.3g.4f.5i.,
1a.2a.3a.4g.5i., 1b.2a.3a.4g.5i., 1f.2a.3a.4g.5i., 1h.2a.3a.4g.5i.,
1j.2a.3a.4g.5i., 1p.2a.3a.4g.5i., 1a.2b.3a.4g.5i., 1b.2b.3a.4g.5i.,
1f.2b.3a.4g.5i., 1h.2b.3a.4g.5i., 1j.2b.3a.4g.5i., 1p.2b.3a.4g.5i.,
1a.2e.3a.4g.5i., 1b.2e.3a.4g.5i., 1f.2e.3a.4g.5i., 1h.2e.3a.4g.5i.,
1j.2e.3a.4g.5i., 1p.2e.3a.4g.5i., 1a.2f.3a.4g.5i., 1b.2f.3a.4g.5i.,
1f.2f.3a.4g.5i., 1h.2f.3a.4g.5i., 1j.2f.3a.4g.5i., 1p.2f.3a.4g.5i.,
1a.2i.3a.4g.5i., 1b.2i.3a.4g.5i., 1f.2i.3a.4g.5i., 1h.2i.3a.4g.5i.,
1j.2i.3a.4g.5i., 1p.2i.3a.4g.5i., 1a.2m.3a.4g.5i., 1b.2m.3a.4g.5i.,
1f.2m.3a.4g.5i., 1h.2m.3a.4g.5i., 1j.2m.3a.4g.5i., 1p.2m.3a.4g.5i.,
1a.2o.3a.4g.5i., 1b.2o.3a.4g.5i., 1f.2o.3a.4g.5i., 1h.2o.3a.4g.5i.,
1j.2o.3a.4g.5i., 1p.2o.3a.4g.5i., 1a.2u.3a.4g.5i., 1b.2u.3a.4g.5i.,
1f.2u.3a.4g.5i., 1h.2u.3a.4g.5i., 1j.2u.3a.4g.5i., 1p.2u.3a.4g.5i.,
1a.2y.3a.4g.5i., 1b.2y.3a.4g.5i., 1f.2y.3a.4g.5i., 1h.2y.3a.4g.5i.,
1j.2y.3a.4g.5i., 1p.2y.3a.4g.5i., 1a.2a.3b.4g.5i., 1b.2a.3b.4g.5i.,
1f.2a.3b.4g.5i., 1h.2a.3b.4g.5i., 1j.2a.3b.4g.5i., 1p.2a.3b.4g.5i.,
1a.2b.3b.4g.5i., 1b.2b.3b.4g.5i., 1f.2b.3b.4g.5i., 1h.2b.3b.4g.5i.,
1j.2b.3b.4g.5i., 1p.2b.3b.4g.5i., 1a.2e.3b.4g.5i., 1b.2e.3b.4g.5i.,
1f.2e.3b.4g.5i., 1h.2e.3b.4g.5i., 1j.2e.3b.4g.5i., 1p.2e.3b.4g.5i.,
1a.2f.3b.4g.5i., 1b.2f.3b.4g.5i., 1f.2f.3b.4g.5i., 1h.2f.3b.4g.5i.,
1j.2f.3b.4g.5i., 1p.2f.3b.4g.5i., 1a.2i.3b.4g.5i., 1b.2i.3b.4g.5i.,
1f.2i.3b.4g.5i., 1h.2i.3b.4g.5i., 1j.2i.3b.4g.5i., 1p.2i.3b.4g.5i.,
1a.2m.3b.4g.5i., 1b.2m.3b.4g.5i., 1f.2m.3b.4g.5i., 1h.2m.3b.4g.5i.,
1j.2m.3b.4g.5i., 1p.2m.3b.4g.5i., 1a.2o.3b.4g.5i., 1b.2o.3b.4g.5i.,
1f.2o.3b.4g.5i., 1h.2o.3b.4g.5i., 1j.2o.3b.4g.5i., 1p.2o.3b.4g.5i.,
1a.2u.3b.4g.5i., 1b.2u.3b.4g.5i., 1f.2u.3b.4g.5i., 1h.2u.3b.4g.5i.,
1j.2u.3b.4g.5i., 1p.2u.3b.4g.5i., 1a.2y.3b.4g.5i., 1b.2y.3b.4g.5i.,
1f.2y.3b.4g.5i., 1h.2y.3b.4g.5i., 1j.2y.3b.4g.5i., 1p.2y.3b.4g.5i.,
1a.2a.3e.4g.5i., 1b.2a.3e.4g.5i., 1f.2a.3e.4g.5i., 1h.2a.3e.4g.5i.,
1j.2a.3e.4g.5i., 1p.2a.3e.4g.5i., 1a.2b.3e.4g.5i., 1b.2b.3e.4g.5i.,
1f.2b.3e.4g.5i., 1h.2b.3e.4g.5i., 1j.2b.3e.4g.5i., 1p.2b.3e.4g.5i.,
1a.2e.3e.4g.5i., 1b.2e.3e.4g.5i., 1f.2e.3e.4g.5i., 1h.2e.3e.4g.5i.,
1j.2e.3e.4g.5i., 1p.2e.3e.4g.5i., 1a.2f.3e.4g.5i., 1b.2f.3e.4g.5i.,
1f.2f.3e.4g.5i., 1h.2f.3e.4g.5i., 1j.2f.3e.4g.5i., 1p.2f.3e.4g.5i.,
1a.2i.3e.4g.5i., 1b.2i.3e.4g.5i., 1f.2i.3e.4g.5i., 1h.2i.3e.4g.5i.,
1j.2i.3e.4g.5i., 1p.2i.3e.4g.5i., 1a.2m.3e.4g.5i., 1b.2m.3e.4g.5i.,
1f.2m.3e.4g.5i., 1h.2m.3e.4g.5i., 1j.2m.3e.4g.5i., 1p.2m.3e.4g.5i.,
1a.2o.3e.4g.5i., 1b.2o.3e.4g.5i., 1f.2o.3e.4g.5i., 1h.2o.3e.4g.5i.,
1j.2o.3e.4g.5i., 1p.2o.3e.4g.5i., 1a.2u.3e.4g.5i., 1b.2u.3e.4g.5i.,
1f.2u.3e.4g.5i., 1h.2u.3e.4g.5i., 1j.2u.3e.4g.5i., 1p.2u.3e.4g.5i.,
1a.2y.3e.4g.5i., 1b.2y.3e.4g.5i., 1f.2y.3e.4g.5i., 1h.2y.3e.4g.5i.,
1j.2y.3e.4g.5i., 1p.2y.3e.4g.5i., 1a.2a.3g.4g.5i., 1b.2a.3g.4g.5i.,
1f.2a.3g.4g.5i., 1h.2a.3g.4g.5i., 1j.2a.3g.4g.5i., 1p.2a.3g.4g.5i.,
1a.2b.3g.4g.5i., 1b.2b.3g.4g.5i., 1f.2b.3g.4g.5i., 1h.2b.3g.4g.5i.,
1j.2b.3g.4g.5i., 1p.2b.3g.4g.5i., 1a.2e.3g.4g.5i., 1b.2e.3g.4g.5i.,
1f.2e.3g.4g.5i., 1h.2e.3g.4g.5i., 1j.2e.3g.4g.5i., 1p.2e.3g.4g.5i.,
1a.2f.3g.4g.5i., 1b.2f.3g.4g.5i., 1f.2f.3g.4g.5i., 1h.2f.3g.4g.5i.,
1j.2f.3g.4g.5i., 1p.2f.3g.4g.5i., 1a.2i.3g.4g.5i., 1b.2i.3g.4g.5i.,
1f.2i.3g.4g.5i., 1h.2i.3g.4g.5i., 1j.2i.3g.4g.5i., 1p.2i.3g.4g.5i.,
1a.2m.3g.4g.5i., 1b.2m.3g.4g.5i., 1f.2m.3g.4g.5i., 1h.2m.3g.4g.5i.,
1j.2m.3g.4g.5i., 1p.2m.3g.4g.5i., 1a.2o.3g.4g.5i., 1b.2o.3g.4g.5i.,
1f.2o.3g.4g.5i., 1h.2o.3g.4g.5i., 1j.2o.3g.4g.5i., 1p.2o.3g.4g.5i.,
1a.2u.3g.4g.5i., 1b.2u.3g.4g.5i., 1f.2u.3g.4g.5i., 1h.2u.3g.4g.5i.,
1j.2u.3g.4g.5i., 1p.2u.3g.4g.5i., 1a.2y.3g.4g.5i., 1b.2y.3g.4g.5i.,
1f.2y.3g.4g.5i., 1h.2y.3g.4g.5i., 1j.2y.3g.4g.5i., 1p.2y.3g.4g.5i.,
1a.2a.3a.4h.5i., 1b.2a.3a.4h.5i., 1f.2a.3a.4h.5i., 1h.2a.3a.4h.5i.,
1j.2a.3a.4h.5i., 1p.2a.3a.4h.5i., 1a.2b.3a.4h.5i., 1b.2b.3a.4h.5i.,
1f.2b.3a.4h.5i., 1h.2b.3a.4h.5i., 1j.2b.3a.4h.5i., 1p.2b.3a.4h.5i.,
1a.2e.3a.4h.5i., 1b.2e.3a.4h.5i., 1f.2e.3a.4h.5i., 1h.2e.3a.4h.5i.,
1j.2e.3a.4h.5i., 1p.2e.3a.4h.5i., 1a.2f.3a.4h.5i., 1b.2f.3a.4h.5i.,
1f.2f.3a.4h.5i., 1h.2f.3a.4h.5i., 1j.2f.3a.4h.5i., 1p.2f.3a.4h.5i.,
1a.2i.3a.4h.5i., 1b.2i.3a.4h.5i., 1f.2i.3a.4h.5i., 1h.2i.3a.4h.5i.,
1j.2i.3a.4h.5i., 1p.2i.3a.4h.5i., 1a.2m.3a.4h.5i., 1b.2m.3a.4h.5i.,
1f.2m.3a.4h.5i., 1h.2m.3a.4h.5i., 1j.2m.3a.4h.5i., 1p.2m.3a.4h.5i.,
1a.2o.3a.4h.5i., 1b.2o.3a.4h.5i., 1f.2o.3a.4h.5i., 1h.2o.3a.4h.5i.,
1j.2o.3a.4h.5i., 1p.2o.3a.4h.5i., 1a.2u.3a.4h.5i., 1b.2u.3a.4h.5i.,
1f.2u.3a.4h.5i., 1h.2u.3a.4h.5i., 1j.2u.3a.4h.5i., 1p.2u.3a.4h.5i.,
1a.2y.3a.4h.5i., 1b.2y.3a.4h.5i., 1f.2y.3a.4h.5i., 1h.2y.3a.4h.5i.,
1j.2y.3a.4h.5i., 1p.2y.3a.4h.5i., 1a.2a.3b.4h.5i., 1b.2a.3b.4h.5i.,
1f.2a.3b.4h.5i., 1h.2a.3b.4h.5i., 1j.2a.3b.4h.5i., 1p.2a.3b.4h.5i.,
1a.2b.3b.4h.5i., 1b.2b.3b.4h.5i., 1f.2b.3b.4h.5i., 1h.2b.3b.4h.5i.,
1j.2b.3b.4h.5i., 1p.2b.3b.4h.5i., 1a.2e.3b.4h.5i., 1b.2e.3b.4h.5i.,
1f.2e.3b.4h.5i., 1h.2e.3b.4h.5i., 1j.2e.3b.4h.5i., 1p.2e.3b.4h.5i.,
1a.2f.3b.4h.5i., 1b.2f.3b.4h.5i., 1f.2f.3b.4h.5i., 1h.2f.3b.4h.5i.,
1j.2f.3b.4h.5i., 1p.2f.3b.4h.5i., 1a.2i.3b.4h.5i., 1b.2i.3b.4h.5i.,
1f.2i.3b.4h.5i., 1h.2i.3b.4h.5i., 1j.2i.3b.4h.5i., 1p.2i.3b.4h.5i.,
1a.2m.3b.4h.5i., 1b.2m.3b.4h.5i., 1f.2m.3b.4h.5i., 1h.2m.3b.4h.5i.,
1j.2m.3b.4h.5i., 1p.2m.3b.4h.5i., 1a.2o.3b.4h.5i., 1b.2o.3b.4h.5i.,
1f.2o.3b.4h.5i., 1h.2o.3b.4h.5i., 1j.2o.3b.4h.5i., 1p.2o.3b.4h.5i.,
1a.2u.3b.4h.5i., 1b.2u.3b.4h.5i., 1f.2u.3b.4h.5i., 1h.2u.3b.4h.5i.,
1j.2u.3b.4h.5i., 1p.2u.3b.4h.5i., 1a.2y.3b.4h.5i., 1b.2y.3b.4h.5i.,
1f.2y.3b.4h.5i., 1h.2y.3b.4h.5i., 1j.2y.3b.4h.5i., 1p.2y.3b.4h.5i.,
1a.2a.3e.4h.5i., 1b.2a.3e.4h.5i., 1f.2a.3e.4h.5i., 1h.2a.3e.4h.5i.,
1j.2a.3e.4h.5i., 1p.2a.3e.4h.5i., 1a.2b.3e.4h.5i., 1b.2b.3e.4h.5i.,
1f.2b.3e.4h.5i., 1h.2b.3e.4h.5i., 1j.2b.3e.4h.5i., 1p.2b.3e.4h.5i.,
1a.2e.3e.4h.5i., 1b.2e.3e.4h.5i., 1f.2e.3e.4h.5i., 1h.2e.3e.4h.5i.,
1j.2e.3e.4h.5i., 1p.2e.3e.4h.5i., 1a.2f.3e.4h.5i., 1b.2f.3e.4h.5i.,
1f.2f.3e.4h.5i., 1h.2f.3e.4h.5i., 1j.2f.3e.4h.5i., 1p.2f.3e.4h.5i.,
1a.2i.3e.4h.5i., 1b.2i.3e.4h.5i., 1f.2i.3e.4h.5i., 1h.2i.3e.4h.5i.,
1j.2i.3e.4h.5i., 1p.2i.3e.4h.5i., 1a.2m.3e.4h.5i., 1b.2m.3e.4h.5i.,
1f.2m.3e.4h.5i., 1h.2m.3e.4h.5i., 1j.2m.3e.4h.5i., 1p.2m.3e.4h.5i.,
1a.2o.3e.4h.5i., 1b.2o.3e.4h.5i., 1f.2o.3e.4h.5i., 1h.2o.3e.4h.5i.,
1j.2o.3e.4h.5i., 1p.2o.3e.4h.5i., 1a.2u.3e.4h.5i., 1b.2u.3e.4h.5i.,
1f.2u.3e.4h.5i., 1h.2u.3e.4h.5i., 1j.2u.3e.4h.5i., 1p.2u.3e.4h.5i.,
1a.2y.3e.4h.5i., 1b.2y.3e.4h.5i., 1f.2y.3e.4h.5i., 1h.2y.3e.4h.5i.,
1j.2y.3e.4h.5i., 1p.2y.3e.4h.5i., 1a.2a.3g.4h.5i., 1b.2a.3g.4h.5i.,
1f.2a.3g.4h.5i., 1h.2a.3g.4h.5i., 1j.2a.3g.4h.5i., 1p.2a.3g.4h.5i.,
1a.2b.3g.4h.5i., 1b.2b.3g.4h.5i., 1f.2b.3g.4h.5i., 1h.2b.3g.4h.5i.,
1j.2b.3g.4h.5i., 1p.2b.3g.4h.5i., 1a.2e.3g.4h.5i., 1b.2e.3g.4h.5i.,
1f.2e.3g.4h.5i., 1h.2e.3g.4h.5i., 1j.2e.3g.4h.5i., 1p.2e.3g.4h.5i.,
1a.2f.3g.4h.5i., 1b.2f.3g.4h.5i., 1f.2f.3g.4h.5i., 1h.2f.3g.4h.5i.,
1j.2f.3g.4h.5i., 1p.2f.3g.4h.5i., 1a.2i.3g.4h.5i., 1b.2i.3g.4h.5i.,
1f.2i.3g.4h.5i., 1h.2i.3g.4h.5i., 1j.2i.3g.4h.5i., 1p.2i.3g.4h.5i.,
1a.2m.3g.4h.5i., 1b.2m.3g.4h.5i., 1f.2m.3g.4h.5i., 1h.2m.3g.4h.5i.,
1j.2m.3g.4h.5i., 1p.2m.3g.4h.5i., 1a.2o.3g.4h.5i., 1b.2o.3g.4h.5i.,
1f.2o.3g.4h.5i., 1h.2o.3g.4h.5i., 1j.2o.3g.4h.5i., 1p.2o.3g.4h.5i.,
1a.2u.3g.4h.5i., 1b.2u.3g.4h.5i., 1f.2u.3g.4h.5i., 1h.2u.3g.4h.5i.,
1j.2u.3g.4h.5i., 1p.2u.3g.4h.5i., 1a.2y.3g.4h.5i., 1b.2y.3g.4h.5i.,
1f.2y.3g.4h.5i., 1h.2y.3g.4h.5i., 1j.2y.3g.4h.5i., 1p.2y.3g.4h.5i.,
1a.2a.3a.4i.5i., 1b.2a.3a.4i.5i., 1f.2a.3a.4i.5i., 1h.2a.3a.4i.5i.,
1j.2a.3a.4i.5i., 1p.2a.3a.4i.5i., 1a.2b.3a.4i.5i., 1b.2b.3a.4i.5i.,
1f.2b.3a.4i.5i., 1h.2b.3a.4i.5i., 1j.2b.3a.4i.5i., 1p.2b.3a.4i.5i.,
1a.2e.3a.4i.5i., 1b.2e.3a.4i.5i., 1f.2e.3a.4i.5i., 1h.2e.3a.4i.5i.,
1j.2e.3a.4i.5i., 1p.2e.3a.4i.5i., 1a.2f.3a.4i.5i., 1b.2f.3a.4i.5i.,
1f.2f.3a.4i.5i., 1h.2f.3a.4i.5i., 1j.2f.3a.4i.5i., 1p.2f.3a.4i.5i.,
1a.2i.3a.4i.5i., 1b.2i.3a.4i.5i., 1f.2i.3a.4i.5i., 1h.2i.3a.4i.5i.,

TABLE 12-continued

List of Compound Structures of Formula II 1j.2i.3a.4i.5i., 1p.2i.3a.4i.5i., 1a.2m.3a.4i.5i., 1b.2m.3a.4i.5i.,
1f.2m.3a.4i.5i., 1h.2m.3a.4i.5i., 1j.2m.3a.4i.5i., 1p.2m.3a.4i.5i.,
1a.2o.3a.4i.5i., 1b.2o.3a.4i.5i., 1f.2o.3a.4i.5i., 1h.2o.3a.4i.5i.,
1j.2o.3a.4i.5i., 1p.2o.3a.4i.5i., 1a.2u.3a.4i.5i., 1b.2u.3a.4i.5i.,
1f.2u.3a.4i.5i., 1h.2u.3a.4i.5i., 1j.2u.3a.4i.5i., 1p.2u.3a.4i.5i.,
1a.2y.3a.4i.5i., 1b.2y.3a.4i.5i., 1f.2y.3a.4i.5i., 1h.2y.3a.4i.5i.,
1j.2y.3a.4i.5i., 1p.2y.3a.4i.5i., 1a.2a.3b.4i.5i., 1b.2a.3b.4i.5i.,
1f.2a.3b.4i.5i., 1h.2a.3b.4i.5i., 1j.2a.3b.4i.5i., 1p.2a.3b.4i.5i.,
1a.2b.3b.4i.5i., 1b.2b.3b.4i.5i., 1f.2b.3b.4i.5i., 1h.2b.3b.4i.5i.,
1j.2b.3b.4i.5i., 1p.2b.3b.4i.5i., 1a.2e.3b.4i.5i., 1b.2e.3b.4i.5i.,
1f.2e.3b.4i.5i., 1h.2e.3b.4i.5i., 1j.2e.3b.4i.5i., 1p.2e.3b.4i.5i.,
1a.2f.3b.4i.5i., 1b.2f.3b.4i.5i., 1f.2f.3b.4i.5i., 1h.2f.3b.4i.5i.,
1j.2f.3b.4i.5i., 1p.2f.3b.4i.5i., 1a.2i.3b.4i.5i., 1b.2i.3b.4i.5i.,
1f.2i.3b.4i.5i., 1h.2i.3b.4i.5i., 1j.2i.3b.4i.5i., 1p.2i.3b.4i.5i.,
1a.2m.3b.4i.5i., 1b.2m.3b.4i.5i., 1f.2m.3b.4i.5i., 1h.2m.3b.4i.5i.,
1j.2m.3b.4i.5i., 1p.2m.3b.4i.5i., 1a.2o.3b.4i.5i., 1b.2o.3b.4i.5i.,
1f.2o.3b.4i.5i., 1h.2o.3b.4i.5i., 1j.2o.3b.4i.5i., 1p.2o.3b.4i.5i.,
1a.2u.3b.4i.5i., 1b.2u.3b.4i.5i., 1f.2u.3b.4i.5i., 1h.2u.3b.4i.5i.,
1j.2u.3b.4i.5i., 1p.2u.3b.4i.5i., 1a.2y.3b.4i.5i., 1b.2y.3b.4i.5i.,
1f.2y.3b.4i.5i., 1h.2y.3b.4i.5i., 1j.2y.3b.4i.5i., 1p.2y.3b.4i.5i.,
1a.2a.3e.4i.5i., 1b.2a.3e.4i.5i., 1f.2a.3e.4i.5i., 1h.2a.3e.4i.5i.,
1j.2a.3e.4i.5i., 1p.2a.3e.4i.5i., 1a.2b.3e.4i.5i., 1b.2b.3e.4i.5i.,
1f.2b.3e.4i.5i., 1h.2b.3e.4i.5i., 1j.2b.3e.4i.5i., 1p.2b.3e.4i.5i.,
1a.2e.3e.4i.5i., 1b.2e.3e.4i.5i., 1f.2e.3e.4i.5i., 1h.2e.3e.4i.5i.,
1j.2e.3e.4i.5i., 1p.2e.3e.4i.5i., 1a.2f.3e.4i.5i., 1b.2f.3e.4i.5i.,
1f.2f.3e.4i.5i., 1h.2f.3e.4i.5i., 1j.2f.3e.4i.5i., 1p.2f.3e.4i.5i.,
1a.2i.3e.4i.5i., 1b.2i.3e.4i.5i., 1f.2i.3e.4i.5i., 1h.2i.3e.4i.5i.,
1j.2i.3e.4i.5i., 1p.2i.3e.4i.5i., 1a.2m.3e.4i.5i., 1b.2m.3e.4i.5i.,
1f.2m.3e.4i.5i., 1h.2m.3e.4i.5i., 1j.2m.3e.4i.5i., 1p.2m.3e.4i.5i.,
1a.2o.3e.4i.5i., 1b.2o.3e.4i.5i., 1f.2o.3e.4i.5i., 1h.2o.3e.4i.5i.,
1j.2o.3e.4i.5i., 1p.2o.3e.4i.5i., 1a.2u.3e.4i.5i., 1b.2u.3e.4i.5i.,
1f.2u.3e.4i.5i., 1h.2u.3e.4i.5i., 1j.2u.3e.4i.5i., 1p.2u.3e.4i.5i.,
1a.2y.3e.4i.5i., 1b.2y.3e.4i.5i., 1f.2y.3e.4i.5i., 1h.2y.3e.4i.5i.,
1j.2y.3e.4i.5i., 1p.2y.3e.4i.5i., 1a.2a.3g.4i.5i., 1b.2a.3g.4i.5i.,
1f.2a.3g.4i.5i., 1h.2a.3g.4i.5i., 1j.2a.3g.4i.5i., 1p.2a.3g.4i.5i.,
1a.2b.3g.4i.5i., 1b.2b.3g.4i.5i., 1f.2b.3g.4i.5i., 1h.2b.3g.4i.5i.,
1j.2b.3g.4i.5i., 1p.2b.3g.4i.5i., 1a.2e.3g.4i.5i., 1b.2e.3g.4i.5i.,
1f.2e.3g.4i.5i., 1h.2e.3g.4i.5i., 1j.2e.3g.4i.5i., 1p.2e.3g.4i.5i.,
1a.2f.3g.4i.5i., 1b.2f.3g.4i.5i., 1f.2f.3g.4i.5i., 1h.2f.3g.4i.5i.,
1j.2f.3g.4i.5i., 1p.2f.3g.4i.5i., 1a.2i.3g.4i.5i., 1b.2i.3g.4i.5i.,
1f.2i.3g.4i.5i., 1h.2i.3g.4i.5i., 1j.2i.3g.4i.5i., 1p.2i.3g.4i.5i.,
1a.2m.3g.4i.5i., 1b.2m.3g.4i.5i., 1f.2m.3g.4i.5i., 1h.2m.3g.4i.5i.,
1j.2m.3g.4i.5i., 1p.2m.3g.4i.5i., 1a.2o.3g.4i.5i., 1b.2o.3g.4i.5i.,
1f.2o.3g.4i.5i., 1h.2o.3g.4i.5i., 1j.2o.3g.4i.5i., 1p.2o.3g.4i.5i.,
1a.2u.3g.4i.5i., 1b.2u.3g.4i.5i., 1f.2u.3g.4i.5i., 1h.2u.3g.4i.5i.,
1j.2u.3g.4i.5i., 1p.2u.3g.4i.5i., 1a.2y.3g.4i.5i., 1b.2y.3g.4i.5i.,
1f.2y.3g.4i.5i., 1h.2y.3g.4i.5i., 1j.2y.3g.4i.5i., and 1p.2y.3g.4i.5i..

In still yet another embodiment, the compound of the present invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM.

In still yet another embodiment, the compound of the present invention has an inhibition activity against an isozyme of P450, e.g., 3 A in a range represented by 1050 from about 2000 nM to about 100 nM, from about 1000 nM to about 100 nM, from about 900 nM to about 200 nM, from about 800 nM to about 300 nM, from about 700 nM to about 200 nM, from about 600 nM to about 200 nM, from about 500 nM to about 200 nM, from about 700 nM to about 300 nM, from about 600 nM to about 300 nM, from about 700 nM to about 400 nM, from about 600 nM to about 400 nM, from about 400 nM to about 100 nM, from about 300 nM to about 100 nM, or from about 600 nM to about 150 nM.

In still yet another embodiment, the compound of the present invention has an inhibition activity against P450 at a level equal to or better than the inhibition activity of a compound as represented by an $IC_{50}$ of less than about 2000 nM, less than about 1500 nM, less than about 1000 nM, less than about 900 nM, less than about 800 nM, less than about 700 nM, less than about 650 nM, less than about 600 nM, less than about 550 nM, less than about 500 nM, less than about 400 nM, less than about 350 nM, less than about 300 nM, less than about 250 nM, less than about 200 nM, less than about 100 nM, or less than about 50 nM, provided that such compound also does not substantially exhibit biological activities other than its inhibition activity against P450. For example, the compound of the present invention can have a reduced or not significant activity of protease inhibition, including without any limitation a level of protease inhibition as represented by HIV $EC_{50}$ of greater than about 1000 nM, greater than about 900 nM, greater than about 800 nM, greater than about 700 nM, greater than about 600 nM, greater than about 500 nM, greater than about 400 nM, greater than about 300 nM, greater than about 200 nM, greater than about 100 nM, greater than about 50 nM, greater than about 40 nM, greater than about 30 nM, greater than about 20 nM, greater than about 10 nM, greater than about 5 nM, or greater than about 1 nM.

In yet another embodiment, the compound of the present invention has an inhibition activity specifically against one or more isozymes of P450 including without limitation 1A2, 2B6, 2C8, 2C19, 2C9, 2D6, 2E1, and 3A4, 5, 7, etc.

In yet another embodiment, the compound of the present invention has an inhibition activity specifically against an isozyme of P450 that is involved in metabolizing anti-viral drugs, e.g., indinavir, nelfinavir, ritonavir, saquinavir etc.

In still yet another embodiment, the compound of the present invention has an inhibition activity specifically against one or more isozymes of P450, but not the other(s). For example, the compound of the present invention can have an inhibition activity specifically against P450 3A, but a reduced, insubstantial, or minimum inhibition activity against another isozyme of P450, e.g., P450 2C9.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, e.g. a compound of the present invention, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients provided by the present invention the formulations of this invention may include other agents conventional in the art having regard to the type of formulation in question, for example those suitable for oral administration may include flavoring agents.

The invention further provides veterinary compositions comprising at least one active ingredient, e.g., a compound of the present invention together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In yet another embodiment, the present application discloses pharmaceutical compositions comprising a compound of the present invention, or a pharmaceutically acceptable salt, solvate, and/or ester thereof, and a pharmaceutically acceptable carrier or excipient.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be any agent that is accessible to oxidative metabolism by cytochrome P450 enzymes, especially cytochrome P450 monooxygenase, e.g., 1A2, 2B6, 2C8, 2C19, 2C9, 2D6, 2E1, 3A4,5,7, etc.

In another example, the therapeutic agent used in combination with the compound of the present invention can be any anti-viral agent, e.g., anti-HIV, anti-HCV, etc., anti-bacterial agent, anti-fungal agent, immuno-modulator, e.g., immunosuppressant, anti-neoplastic agent, chemotherapeutic agent, agents useful for treating cardiovascular conditions, neurological conditions, etc.

In yet another example, the therapeutic agent used in combination with the compound of the present invention can be any proton pump inhibitor, anti-epileptics, NSAID, oral hypoglycemic agent, angiotensin II, sulfonylureas, beta blocker, antidepressant, antipsychotics, or anesthetics, or a combination thereof.

In yet another example, the therapeutic agent used in combination with the compound of the present invention can be any 1) macrolide antibiotics, e.g., clarithromycin, erythromycin, telithromycin, 2) anti-arrhythmics, e.g., quinidine=>3-OH, 3) benzodiazepines, e.g., alprazolam, diazepam=>3OH, midazolam, triazolam, 4) immune modulators, e.g., cyclosporine, tacrolimus (FK506), 5) HIV anti-virals, e.g., indinavir, nelfinavir, ritonavir, saquinavir, 6) prokinetic, e.g., cisapride, 7) antihistamines, e.g., astemizole, chlorpheniramine, terfenidine, 8) calcium channel blockers, e.g., amlodipine, diltiazem, felodipine, lercanidipine, nifedipine, nisoldipine, nitrendipine, verapamil, 9) HMG CoA reductase inhibitors, e.g., atorvastatin, cerivastatin, lovastatin, simvastatin, or 10) steroid 6beta-OH, e.g., estradiol, hydrocortisone, progesterone, testosterone.

In still yet another example, the therapeutic agent used in combination with the compound of the present invention can be any alfentanyl, aprepitant, aripiprazole, buspirone, cafergot, caffeine, TMU, cilostazol, cocaine, codeine-N-demethylation, dapsone, dextromethorphan, docetaxel, domperidone, eplerenone, fentanyl, finasteride, gleevec, haloperidol, irinotecan, LAAM, lidocaine, methadone, nateglinide, ondansetron, pimozide, propranolol, quetiapine, quinine, salmeterol, sildenafil, sirolimus, tamoxifen, taxol, terfenadine, trazodone, vincristine, zaleplon, or zolpidem or a combination thereof.

In one embodiment, the present application discloses pharmaceutical compositions comprising a compound of the present invention, or a pharmaceutically acceptable salt, solvate, and/or ester thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and a pharmaceutically acceptable carrier or expedient.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, Racivir (±-FTC), D-d4FC, phosphazide, fozivudine tidoxil, apricitibine AVX754, amdoxovir, KP-1461, and fosalvudine tidoxil (formerly HDP 99.0003), tenofovir disoproxil fumarate, adefovir dipivoxil, GS-9131, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, BA 011, enfuvirtide, sifuvirtide, FB006M, TRI-1144, AMD-070, SP01A, BMS-488043, BlockAide/CR, immunitin, benzimidazole derivatives, benzo-1,2,4-thiadiazine derivatives, phenylalanine derivatives, aplaviroc, vicriviroc, and maraviroc, cyclosporine, FK-506, rapamycin, taxol, taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017 and a pharmaceutically acceptable carrier or expedient.

In still another embodiment, the present invention provides pharmaceutical compositions comprising a compound of the present invention, or a pharmaceutically acceptable salt, solvate, and/or ester thereof, in combination with two or three additional therapeutic agents. For example, a compound of the present invention, or a pharmaceutically acceptable salt, solvate, and/or ester thereof, is combined with two or three additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. The two or three additional therapeutic agents can be different therapeutic agents selected from the same class of therapeutic agents, or they can be selected from different classes of therapeutic agents. The compounds of the present invention in such ternary or quaternary combinations can include any of the compounds of Formula I disclosed herein, for example a compounds of Formula IIA-D or Formula IV. In a particular embodiment, the pharmaceutical compositions of the present invention comprises a compound of Formula IV, or a pharmaceutically acceptable salt, solvate, and/or ester thereof, combined with two or three additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. In a still more particular embodiment, the pharmaceutical composition of the present invention comprises Example P, S, or X, or a pharmaceutically acceptable salt, solvate, and/or ester thereof, in combination with two or three additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. For example, such combinations can comprise Example P, S, or X, or a pharmaceutically acceptable salt, solvate, and/or ester thereof in combination with two or three additional therapeutic agents selected from the group consisting of tenofovir disoproxil fumarate, GS-9131, emtricitabine, elvitegravir, efavrenz, atazanavir, darunavir, raltegravir, and rilpivirine (or pharmaceutically acceptable salts, solvates, and/or esters thereof).

Specific embodiments of ternary combinations comprise, for example, Example P/tenofovir disoproxil fumarate/GS-9131, Example P/tenofovir disoproxil fumarate/emtricitabine, Example P/tenofovir disoproxil fumarate/elvitegravir, Example P/tenofovir disoproxil fumarate/efavrenz, Example P/tenofovir disoproxil fumarate/atazanavir, Example P/tenofovir disoproxil fumarate/darunavir, Example P/tenofovir disoproxil fumarate/raltegravir, Example P/tenofovir disoproxil fumarate/rilpivirine, Example P/GS-9131/emtricitabine, Example P/GS-9131/elvitegravir, Example P/GS-9131/efavrenz, Example P/GS-9131/atazanavir, Example P/GS-9131/darunavir, Example P/GS-9131/raltegravir, Example P/GS-9131/rilpivirine, Example P/emtricitabine/elvitegravir, Example P/emtricitabine/efavrenz, Example P/emtricitabine/atazanavir, Example P/emtricitabine/darunavir, Example P/emtricitabine/raltegravir, Example P/emtricitabine/rilpivirine, Example P/elvitegravir/efavrenz, Example P/elvitegravir/atazanavir, Example P/elvitegravir/darunavir, Example P/elvitegravir/raltegravir, Example P/elvitegravir/rilpivirine, Example P/efavrenz/atazanavir, Example P/efavrenz/darunavir, Example P/efavrenz/raltegravir, Example P/efavrenz/rilpivirine, Example P/atazanavir/darunavir, Example P/atazanavir/raltegravir, Example P/atazanavir/rilpivirine, Example P/darunavir/raltegravir, Example P/darunavir/rilpivirine, Example P/raltegravir/rilpivirine, Example S/tenofovir disoproxil fumarate/GS-9131, Example S/tenofovir disoproxil fumarate/emtricitabine, Example S/tenofovir disoproxil fumarate/elvitegravir, Example S/tenofovir disoproxil fumarate/efavrenz, Example S/tenofovir disoproxil fumarate/atazanavir, Example S/tenofovir disoproxil fumarate/darunavir, Example S/tenofovir disoproxil fumarate/raltegravir, Example S/tenofovir disoproxil fumarate/rilpivirine, Example S/GS-9131/emtricitabine, Example S/GS-9131/elvitegravir, Example S/GS-9131/efavrenz, Example S/GS-9131/atazanavir, Example S/GS-9131/darunavir, Example S/GS-9131/raltegravir, Example S/GS-9131/rilpivirine, Example S/emtricitabine/elvitegravir, Example S/emtricitabine/efavrenz, Example S/emtricitabine/atazanavir, Example S/emtricitabine/darunavir, Example S/emtricitabine/raltegravir, Example S/emtricitabine/rilpivirine, Example S/elvitegravir/efavrenz, Example S/elvitegravir/atazanavir, Example S/elvitegravir/darunavir, Example S/elvitegravir/raltegravir, Example S/elvitegravir/rilpivirine, Example S/efavrenz/atazanavir, Example S/efavrenz/darunavir, Example S/efavrenz/raltegravir, Example S/efavrenz/rilpivirine, Example S/atazanavir/darunavir, Example S/atazanavir/raltegravir, Example S/atazanavir/rilpivirine, Example S/darunavir/raltegravir, Example S/darunavir/rilpivirine, Example S/raltegravir/rilpivirine, Example X/tenofovir disoproxil fumarate/GS-9131, Example X/tenofovir disoproxil fumarate/emtricitabine, Example X/tenofovir disoproxil fumarate/elvitegravir, Example X/tenofovir disoproxil fumarate/efavrenz, Example X/tenofovir disoproxil fumarate/atazanavir, Example X/tenofovir disoproxil fumarate/darunavir, Example X/tenofovir disoproxil fumarate/raltegravir, Example X/tenofovir disoproxil fumarate/rilpivirine, Example X/GS-9131/emtricitabine, Example X/GS-9131/elvitegravir, Example X/GS-9131/efavrenz, Example X/GS-9131/atazanavir, Example X/GS-9131/darunavir, Example X/GS-9131/raltegravir, Example X/GS-9131/rilpivirine, Example X/emtricitabine/elvitegravir, Example X/emtricitabine/efavrenz, Example X/emtricitabine/atazanavir, Example X/emtricitabine/darunavir, Example X/emtricitabine/raltegravir, Example X/emtricitabine/rilpivirine, Example X/elvitegravir/efavrenz, Example X/elvitegravir/atazanavir, Example X/elvitegravir/darunavir, Example X/elvitegravir/raltegravir, Example X/elvitegravir/rilpivirine, Example X/efavrenz/atazanavir, Example X/efavrenz/darunavir, Example X/efavrenz/raltegravir, Example X/efavrenz/rilpivirine, Example X/atazanavir/darunavir, Example X/atazanavir/raltegravir, Example X/atazanavir/rilpivirine, Example X/darunavir/raltegravir, Example X/darunavir/rilpivirine, and Example X/raltegravir/rilpivirine (including pharmaceutically acceptable salts, solvates, and/or esters of any of the above).

Specific embodiments of quaternary combinations comprise, for example, Example P/tenofovir disoproxil fumarate/GS-9131/emtricitabine, Example P/tenofovir disoproxil fumarate/GS-9131/elvitegravir, Example P/tenofovir disoproxil fumarate/GS-9131/efavrenz, Example P/tenofovir disoproxil fumarate/GS-9131/atazanavir, Example P/tenofovir disoproxil fumarate/GS-9131/darunavir, Example P/tenofovir disoproxil fumarate/GS-9131/raltegravir, Example P/tenofovir disoproxil fumarate/GS-9131/rilpivirine, Example P/tenofovir disoproxil fumarate/emtricitabine/elvitegravir, Example P/tenofovir disoproxil fumarate/emtricitabine/efavrenz, Example P/tenofovir disoproxil fumarate/emtricitabine/atazanavir, Example P/tenofovir disoproxil fumarate/emtricitabine/darunavir, Example P/tenofovir disoproxil fumarate/emtricitabine/raltegravir, Example P/tenofovir disoproxil fumarate/emtricitabine/rilpivirine, Example P/tenofovir disoproxil fumarate/elvitegravir/efavrenz, Example P/tenofovir disoproxil fumarate/elvitegravir/atazanavir, Example P/tenofovir disoproxil fumarate/elvitegravir/darunavir, Example P/tenofovir disoproxil fumarate/elvitegravir/raltegravir, Example P/tenofovir disoproxil fumarate/elvitegravir/rilpivirine, Example P/tenofovir disoproxil fumarate/efavrenz/atazanavir, Example P/tenofovir disoproxil fumarate/efavrenz/darunavir, Example P/tenofovir disoproxil fumarate/efavrenz/raltegravir, Example P/tenofovir disoproxil fumarate/efavrenz/rilpivirine, Example P/tenofovir disoproxil fumarate/atazanavir/darunavir, Example P/tenofovir disoproxil fumarate/atazanavir/raltegravir, Example P/tenofovir disoproxil fumarate/atazanavir/rilpivirine, Example P/tenofovir disoproxil fumarate/darunavir/raltegravir, Example P/tenofovir disoproxil fumarate/darunavir/rilpivirine, Example P/tenofovir disoproxil fumarate/raltegravir/rilpivirine, Example P/GS-9131/emtricitabine/elvitegravir, Example P/GS-9131/emtricitabine/efavrenz, Example P/GS-9131/emtricitabine/atazanavir, Example P/GS-9131/emtricitabine/darunavir, Example P/GS-9131/emtricitabine/raltegravir, Example P/GS-9131/emtricitabine/rilpivirine, Example P/GS-9131/elvitegravir/efavrenz, Example P/GS-9131/elvitegravir/atazanavir, Example P/GS-9131/elvitegravir/darunavir, Example P/GS-9131/elvitegravir/raltegravir, Example P/GS-9131/elvitegravir/rilpivirine, Example P/GS-9131/efavrenz/atazanavir, Example P/GS-9131/efavrenz/darunavir, Example P/GS-9131/efavrenz/raltegravir, Example P/GS-9131/efavrenz/rilpivirine, Example P/GS-9131/atazanavir/darunavir, Example P/GS-9131/atazanavir/raltegravir, Example P/GS-9131/atazanavir/rilpivirine, Example P/GS-9131/darunavir/raltegravir, Example P/GS-9131/darunavir/rilpivirine, Example P/GS-9131/raltegravir/rilpivirine, Example P/emtricitabine/elvitegravir/efavrenz, Example P/emtricitabine/elvitegravir/atazanavir, Example P/emtricitabine/elvitegravir/darunavir, Example P/emtricitabine/elvitegravir/raltegravir, Example P/emtricitabine/elvitegravir/rilpivirine, Example P/emtricitabine/efavrenz/atazanavir, Example P/emtricitabine/efavrenz/darunavir, Example P/emtricitabine/efavrenz/raltegravir, Example P/emtricitabine/efavrenz/rilpivirine, Example P/emtricitabine/atazanavir/darunavir, Example P/emtricitabine/atazanavir/raltegravir, Example P/emtricitabine/atazanavir/rilpivirine, Example P/emtricitabine/darunavir/raltegravir, Example P/emtricitabine/darunavir/rilpivirine, Example P/emtricitabine/raltegravir/rilpivirine, Example P/elvitegravir/efavrenz/atazanavir, Example P/elvitegravir/efavrenz/darunavir, Example P/elvitegravir/efavrenz/raltegravir, Example P/elvitegravir/efavrenz/rilpivirine, Example P/elvitegravir/atazanavir/darunavir, Example P/elvitegravir/atazanavir/raltegravir, Example P/elvitegravir/atazanavir/rilpivirine, Example P/elvitegravir/darunavir/raltegravir, Example P/elvitegravir/darunavir/rilpivirine, Example P/elvitegravir/raltegravir/rilpivirine, Example P/efavrenz/atazanavir/darunavir, Example P/efavrenz/atazanavir/raltegravir, Example P/efavrenz/atazanavir/rilpivirine, Example P/efavrenz/darunavir/raltegravir, Example P/efavrenz/darunavir/rilpivirine, Example P/efavrenz/raltegravir/rilpivirine, Example P/atazanavir/darunavir/raltegravir, Example P/atazanavir/darunavir/rilpivirine, Example P/darunavir/raltegravir/rilpivirine, Example S/tenofovir disoproxil fumarate/GS-9131/emtricitabine, Example S/tenofovir disoproxil fumarate/GS-9131/elvitegravir, Example S/tenofovir disoproxil fumarate/GS-9131/efavrenz, Example S/tenofovir disoproxil fumarate/GS-9131/atazanavir, Example S/tenofovir disoproxil fumarate/GS-9131/darunavir, Example S/tenofovir disoproxil fumarate/GS-9131/raltegravir, Example S/tenofovir disoproxil fumarate/GS-9131/rilpivirine, Example S/tenofovir disoproxil fumarate/emtricitabine/elvitegravir, Example S/tenofovir disoproxil fumarate/emtricitabine/efavrenz, Example S/tenofovir disoproxil fumarate/emtricitabine/atazanavir, Example S/tenofovir disoproxil fumarate/emtricitabine/darunavir, Example S/tenofovir disoproxil fumarate/emtricitabine/raltegravir, Example S/tenofovir disoproxil fumarate/emtricitabine/rilpivirine, Example S/tenofovir disoproxil fumarate/elvitegravir/efavrenz, Example S/tenofovir disoproxil fumarate/elvitegravir/atazanavir, Example S/tenofovir disoproxil fumarate/elvitegravir/darunavir, Example S/tenofovir disoproxil fumarate/elvitegravir/raltegravir, Example S/tenofovir disoproxil fumarate/elvitegravir/rilpivirine, Example S/tenofovir disoproxil fumarate/efavrenz/atazanavir, Example S/tenofovir disoproxil fumarate/efavrenz/darunavir, Example S/tenofovir disoproxil fumarate/efavrenz/raltegravir, Example S/tenofovir disoproxil fumarate/efavrenz/rilpivirine, Example S/tenofovir disoproxil fumarate/atazanavir/darunavir, Example S/tenofovir disoproxil fumarate/atazanavir/raltegravir, Example S/tenofovir disoproxil fumarate/atazanavir/rilpivirine, Example S/tenofovir disoproxil fumarate/darunavir/raltegravir, Example S/tenofovir disoproxil fumarate/darunavir/rilpivirine, Example S/tenofovir disoproxil fumarate/raltegravir/rilpivirine, Example S/GS-9131/emtricitabine/elvitegravir, Example S/GS-9131/emtricitabine/efavrenz, Example S/GS-9131/emtricitabine/atazanavir, Example S/GS-9131/emtricitabine/darunavir, Example S/GS-9131/emtricitabine/raltegravir, Example S/GS-9131/emtricitabine/rilpivirine, Example S/GS-9131/elvitegravir/efavrenz, Example S/GS-9131/elvitegravir/atazanavir, Example S/GS-9131/elvitegravir/darunavir, Example S/GS-9131/elvitegravir/raltegravir, Example S/GS-9131/elvitegravir/rilpivirine, Example S/GS-9131/efavrenz/atazanavir, Example S/GS-9131/efavrenz/darunavir, Example S/GS-9131/efavrenz/raltegravir, Example S/GS-9131/efavrenz/rilpivirine, Example S/GS-9131/atazanavir/darunavir, Example S/GS-9131/atazanavir/raltegravir, Example S/GS-9131/atazanavir/rilpivirine, Example S/GS-9131/darunavir/raltegravir, Example S/GS-9131/darunavir/rilpivirine, Example S/GS-9131/raltegravir/rilpivirine, Example S/emtricitabine/elvitegravir/efavrenz, Example S/emtricitabine/elvitegravir/atazanavir, Example S/emtricitabine/elvitegravir/darunavir, Example S/emtricitabine/elvitegravir/raltegravir, Example S/emtricitabine/elvitegravir/rilpivirine, Example S/emtricitabine/efavrenz/atazanavir, Example S/emtricitabine/efavrenz/darunavir, Example S/emtricitabine/efavrenz/raltegravir, Example S/emtricitabine/efavrenz/rilpivirine, Example S/emtricitabine/atazanavir/darunavir, Example S/emtricitabine/atazanavir/raltegravir, Example S/emtricitabine/atazanavir/rilpivirine, Example S/emtricitabine/darunavir/raltegravir, Example S/emtricitabine/darunavir/rilpivirine, Example S/emtricitabine/raltegravir/rilpivirine, Example S/elvitegravir/efavrenz/atazanavir, Example S/elvitegravir/efavrenz/darunavir, Example S/elvitegravir/efavrenz/raltegravir, Example S/elvitegravir/efavrenz/rilpivirine, Example S/elvitegravir/atazanavir/darunavir, Example S/elvitegravir/atazanavir/raltegravir, Example S/elvitegravir/atazanavir/rilpivirine, Example S/elvitegravir/darunavir/raltegravir, Example S/elvitegravir/darunavir/rilpivirine, Example S/elvitegravir/raltegravir/rilpivirine, Example S/efavrenz/atazanavir/darunavir, Example S/efavrenz/atazanavir/raltegravir, Example S/efavrenz/atazanavir/rilpivirine, Example S/efavrenz/darunavir/raltegravir, Example S/efavrenz/darunavir/rilpivirine, Example S/efavrenz/raltegravir/rilpivirine, Example S/atazanavir/darunavir/raltegravir, Example S/atazanavir/darunavir/rilpivirine, Example S/darunavir/raltegravir/rilpivirine, Example X/tenofovir disoproxil fumarate/GS-9131/emtricitabine, Example X/tenofovir disoproxil fumarate/GS-9131/elvitegravir, Example X/tenofovir disoproxil fumarate/GS-9131/efavrenz, Example X/tenofovir disoproxil fumarate/GS-9131/atazanavir, Example X/tenofovir disoproxil fumarate/GS-9131/darunavir, Example X/tenofovir disoproxil fumarate/GS-9131/raltegravir, Example X/tenofovir disoproxil fumarate/GS-9131/rilpivirine, Example X/tenofovir disoproxil fumarate/emtricitabine/elvitegravir, Example X/tenofovir disoproxil fumarate/emtricitabine/efavrenz, Example X/tenofovir disoproxil fumarate/erntricitabine/atazanavir, Example X/tenofovir disoproxil fumarate/emtricitabine/darunavir, Example X/tenofovir disoproxil fumarate/emtricitabine/raltegravir, Example X/tenofovir disoproxil fumarate/emtricitabine/rilpivirine, Example X/tenofovir disoproxil fumarate/elvitegravir/efavrenz, Example X/tenofovir disoproxil fumarate/elvitegravir/atazanavir, Example X/tenofovir disoproxil fumarate/elvitegravir/darunavir, Example X/tenofovir disoproxil fumarate/elvitegravir/raltegravir, Example X/tenofovir disoproxil fumarate/elvitegravir/rilpivirine, Example X/tenofovir disoproxil fumarate/efavrenz/atazanavir, Example X/tenofovir disoproxil fumarate/efavrenz/darunavir, Example X/tenofovir disoproxil fumarate/efavrenz/raltegravir, Example X/tenofovir disoproxil fumarate/efavrenz/rilpivirine, Example X/tenofovir disoproxil fumarate/atazanavir/darunavir, Example X/tenofovir disoproxil fumarate/atazanavir/raltegravir, Example X/tenofovir disoproxil fumarate/atazanavir/rilpivirine, Example X/tenofovir disoproxil fumarate/darunavir/raltegravir, Example X/tenofovir disoproxil fumarate/darunavir/rilpivirine, Example X/tenofovir disoproxil fumarate/raltegravir/rilpivirine, Example X/GS-9131/emtricitabine/elvitegravir, Example X/GS-9131/emtricitabine/efavrenz, Example X/GS-9131/emtricitabine/atazanavir, Example X/GS-9131/emtricitabine/darunavir, Example X/GS-9131/emtricitabine/raltegravir, Example X/GS-9131/emtricitabine/rilpivirine, Example X/GS-9131/elvitegravir/efavrenz, Example X/GS-9131/elvitegravir/atazanavir, Example X/GS-9131/elvitegravir/darunavir, Example X/GS-9131/elvitegravir/raltegravir, Example X/GS-9131/elvitegravir/rilpivirine, Example X/GS-9131/efavrenz/atazanavir, Example X/GS-9131/efavrenz/darunavir, Example X/GS-9131/efavrenz/raltegravir, Example X/GS-9131/efavrenz/rilpivirine, Example X/GS-9131/atazanavir/darunavir, Example X/GS-9131/atazanavir/raltegravir, Example X/GS-9131/atazanavir/rilpivirine, Example X/GS-9131/darunavir/raltegravir, Example X/GS-9131/darunavir/rilpivirine, Example X/GS-9131/raltegravir/rilpivirine, Example X/emtricitabine/elvitegravir/efavrenz, Example X/emtricitabine/elvitegravir/atazanavir, Example X/emtricitabine/elvitegravir/darunavir, Example X/emtricitabine/elvitegravir/raltegravir, Example X/emtricitabine/elvitegravir/rilpivirine, Example X/emtricitabine/efavrenz/atazanavir, Example X/emtricitabine/efavrenz/darunavir, Example X/emtricitabine/efavrenz/raltegravir, Example X/emtricitabine/efavrenz/rilpivirine, Example X/emtricitabine/atazanavir/darunavir, Example X/emtricitabine/atazanavir/raltegravir, Example X/emtricitabine/atazanavir/rilpivirine, Example X/emtricitabine/darunavir/raltegravir, Example X/emtricitabine/darunavir/rilpivirine, Example X/emtricitabine/raltegravir/rilpivirine, Example X/elvitegravir/efavrenz/atazanavir, Example X/elvitegravir/efavrenz/darunavir, Example X/elvitegravir/efavrenz/raltegravir, Example X/elvitegravir/efavrenz/rilpivirine, Example X/elvitegravir/atazanavir/darunavir, Example X/elvitegravir/atazanavir/raltegravir, Example X/elvitegravir/atazanavir/rilpivirine, Example X/elvitegravir/darunavir/raltegravir, Example X/elvitegravir/darunavir/rilpivirine, Example X/elvitegravir/raltegravir/rilpivirine, Example X/efavrenz/atazanavir/darunavir, Example X/efavrenz/atazanavir/raltegravir, Example X/efavrenz/atazanavir/rilpivirine, Example X/efavrenz/darunavir/raltegravir, Example X/efavrenz/darunavir/rilpivirine, Example X/efavrenz/raltegravir/rilpivirine, Example X/atazanavir/darunavir/raltegravir, Example X/atazanavir/darunavir/rilpivirine, and Example X/darunavir/raltegravir/rilpivirine (including pharmaceutically acceptable salts, solvates, and/or esters of any of the above).

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention can be used alone, e.g., for inhibiting cytochrome P450 monooxygenase. In another embodiment, the compounds of the present invention are used in combination with other active therapeutic ingredients or agents. Preferably, the other active therapeutic ingredients or agents are metabolized or accessible to the oxidative metabolism by cytochrome P450 enzymes, e.g., monooxygenase enzymes such as 1A2, 2B6, 2C8, 2C19, 2C9, 2D6, 2E1, 3A4, 5, 7, etc.

Combinations of the compounds of the present invention are typically selected based on the condition to be treated, cross-reactivities of ingredients and pharmaco-properties of the combination. For example, when treating an infection (e.g., HIV or HCV), the compositions of the invention are combined with anti-infective agents (such as those described herein).

In one embodiment, non-limiting examples of suitable combinations include combinations of one or more compounds of the present invention with one or more anti-viral agents, e.g., anti-HIV, anti-HCV, etc., anti-bacterial agents, anti-fungal agents, immuno-modulators, e.g., immunosuppressant, anti-neoplastic agents, chemotherapeutic agents, agents useful for treating cardiovascular conditions, neurological conditions, etc.

In another embodiment, non-limiting examples of suitable combinations include combinations of one or more compounds of the present invention with one or more proton pump inhibitors, anti-epileptics, NSAIDs, oral hypoglycemic agents, angiotensin II, sulfonylureas, beta blockers, antidepressants, antipsychotics, or anesthetics, or a combination thereof.

In yet another embodiment, non-limiting examples of suitable combinations include combinations of one or more compounds of the present invention with one or more 1) macrolide antibiotics, e.g., clarithromycin, erythromycin, telithromycin, 2) anti-arrhythmics, e.g., quinidine=>3-OH, 3) benzodiazepines, e.g., alprazolam, diazepam=>3OH, midazolam, triazolam, 4) immune modulators, e.g., cyclosporine, tacrolimus (FK506), 5) HIV antivirals, e.g., indinavir, nelfinavir, ritonavir, saquinavir, 6) prokinetic, e.g., cisapride, 7) antihistamines, e.g., astemizole, chlorpheniramine, terfenidine, 8) calcium channel blockers, e.g., amlodipine, diltiazem, felodipine, lercanidipine, nifedipine, nisoldipine, nitrendipine, verapamil, 9) HMG CoA reductase inhibitors, e.g., atorvastatin, cerivastatin, lovastatin, simvastatin, or 10) steroid 6beta-OH, e.g., estradiol, hydrocortisone, progesterone, testosterone.

In still yet another embodiment, non-limiting examples of suitable combinations include combinations of one or more compounds of the present invention with one or more compounds selected from the group consisting of alfentanyl, aprepitant, aripiprazole, buspirone, cafergot, caffeine=>TMU, cilostazol, cocaine, codeine-N-demethylation, dapsone, dextromethorphan, docetaxel, domperidone, eplerenone, fentanyl, finasteride, gleevec, haloperidol, irinotecan, LAAM, lidocaine, methadone, nateglinide, odanestron, pimozide, propranolol, quetiapine, quinine, salmeterol, sildenafil, sirolimus, tamoxifen, taxol, terfenadine, trazodone, vincristine, zaleplon, and zolpidem or a combination thereof.

In still yet another embodiment, non-limiting examples of suitable combinations include combinations of one or more compounds of the present invention with one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, and other drugs for treating HIV, interferons, ribavirin analogs, HCV NS3 protease inhibitors, alpha-glucosidase 1 inhibitors, hepatoprotectants, nucleoside or nucleotide inhibitors of HCV, non-nucleoside inhibitors of HCV, and other drugs for treating HCV.

More specifically, one or more compounds of the present invention may be combined with one or more compounds selected from the group consisting of 1) amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, 800334649, KNI-272, DPC-681, DPC-684, GW640385X, DG17, GS-8374, PPL-100, DG35, and AG 1859, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, KP-1461, and fosalvudine tidoxil (formerly HDP 99.0003), 4) a HIV nucleotide inhibitor of reverse transcriptase, e.g., tenofovir disoproxil fumarate and adefovir dipivoxil, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, 5-1360, zintevir (AR-177), L-870812, and L-870810, MK-0518 (raltegravir), elvitegravir, BMS-538158, GSK364735C, BMS-707035, MK-2048, and BA 011, 6) a gp41 inhibitor, e.g., enfuvirtide, sifuvirtide, FB006M, and TRI-1144, 7) a CXCR4 inhibitor, e.g., AMD-070, 8) an entry inhibitor, e.g., SP01A, 9) a gp120 inhibitor, e.g., BMS-488043 or BlockAide/CR, 10) a G6PD and NADH-oxidase inhibitor, e.g., immunitin, 11) a CCR5 inhibitor, e.g., aplaviroc, vicriviroc, maraviroc, PRO-140, INCB15050, PF-232798 (Pfizer), and CCR5 mAb004, 12) other drugs for treating HIV, e.g., BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040), 13) an interferon, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta, 14) a ribavirin analog, e.g., rebetol, copegus, viramidine (taribavirin), 15) a NS5b polymerase inhibitor, e.g., NM-283, valopicitabine, R1626, PS1-6130 (R1656), HCV-796, BILB 1941, XTL-2125, MK-0608, NM-107, R7128 (R4048), VCH-759, PF-868554, and GSK625433, 16) A NS3 protease inhibitor, e.g., SCH-503034 (SCH-7), VX-950 (telaprevir), BILN-2065, BMS-605339, and ITMN-191, 17) an alpha-glucosidase 1 inhibitor, e.g., MX-3253 (celgosivir), UT-231B, 18) hepatoprotectants, e.g., IDN-6556, ME 3738, LB-84451, and MitoQ, 19) a non-nucleoside inhibitor of HCV, e.g., benzimidazole derivatives, benzo-1,2,4-thiadiazine derivatives, phenylalanine derivatives, A-831, GS-9190, and A-689; and 20) other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

It is also contemplated that the compounds of the present invention can be used with any other active therapeutic agent or ingredient which is appreciably metabolized by cytochrome P450 monooxygenase enzymes, e.g. cytochrome P450 monooxygenase 3A, thereby reducing the amount or rate at which the other active therapeutic agent or ingredient is metabolized, whereby the pharmacokinetics of the other active therapeutic agent or ingredient is improved.

Such improvements can include elevating the blood plasma levels of the other therapeutic agent or ingredient or maintaining a more therapeutically effective blood plasma level of the other therapeutic active agent or ingredient—compared to blood plasma levels of the other therapeutic agent or ingredient administered without the compound of the present invention.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In yet another embodiment, the present application provides a method for improving the pharmacokinetics of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof.

In yet another embodiment, the present application provides a method for improving the pharmacokinetics of a drug which is metabolized by cytochrome P450 monooxygenase, comprising administering to a patient treated with said drug, a therapeutically effective amount of a combination comprising said drug and a compound of the present invention, or a pharmaceutically acceptable salt, solvate, and/or ester thereof.

In yet another embodiment, the present application provides a method for improving the pharmacokinetics of a drug which is metabolized by cytochrome P450 monooxygenase 3A, comprising administering to a patient treated with said drug, a therapeutically effective amount of a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase, comprising administering to a patient treated with said drug, a therapeutically effective amount of a combination comprising said drug and a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase 3A, comprising administering to a patient treated with said drug, a therapeutically effective amount of a compound of the present invention, or a pharmaceutically acceptable salt, solvate, and/or ester thereof.

In yet another embodiment, the present application provides a method for increasing blood plasma levels of a drug which is metabolized by cytochrome P450 monooxygenase, comprising administering to a patient treated with said drug, a therapeutically effective amount of a compound of the present invention, or a pharmaceutically acceptable salt, solvate, and/or ester thereof, and wherein the amount of the compound of the present invention administered is effective to inhibit cytochrome P450 monooxygenase.

In yet another embodiment, the present application provides a method for inhibiting cytochrome P450 monooxygenase in a patient comprising administering to a patient in need thereof an amount of a compound of the present invention, or a pharmaceutically acceptable salt, solvate, and/or ester thereof, effective to inhibit cytochrome P450 monooxygenase.

In yet another embodiment, the present application provides a method for inhibiting cytochrome P450 monooxygenase 3A in a patient comprising administering to a patient in need thereof an amount of a compound of the present invention, or a pharmaceutically acceptable salt, solvate, and/or ester thereof, effective to inhibit cytochrome P450 monooxygenase 3A.

In yet another embodiment, the present application provides a method for inhibiting cytochrome P450 monooxygenase comprising contacting cytochrome P450 monooxygenase with an amount of a compound of the present invention, or a pharmaceutically acceptable salt, solvate, and/or ester thereof, effective to inhibit cytochrome P450 monooxygenase.

In yet another embodiment, the present application provides a method for inhibiting cytochrome P450 monooxygenase 3A comprising contacting cytochrome P450 monooxygenase 3A with an amount of a compound of the present invention, or a pharmaceutically acceptable salt, solvate, and/or ester thereof, effective to inhibit cytochrome P450 monooxygenase 3A.

In yet another embodiment, the present application provides a method for treating an HIV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

In yet another embodiment, the present application provides a method for treating an HIV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, and GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILK 355 BS, VRX 840773, RDEA806, zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), amdoxovir, KP-1461, fosalvudine tidoxil (formerly HDP 99.0003), tenofovir disoproxil fumarate, adefovir dipivoxil, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, and BA 011, enfuvirtide, sifuvirtide, FB006M, and TRI-1144, AMD-070, an entry inhibitor, SP01A, BMS-488043, BlockAide/CR, a G6PD and NADH-oxidase inhibitor, immunitin, aplaviroc, vicriviroc, maraviroc, maraviroc, PRO-140, INCB15050, PF-232798 (Pfizer), CCR5 mAb004, BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS119, ALG 889, and PA-1050040 (PA-040).

In yet another embodiment, the present application provides a method for treating an HCV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen actimmune, IFN-omega with DUROS, locteron, albuferon, rebif, Oral interferon alpha, IFNalpha-2b XL, AVI-005, PEG-Infergen, and pegylated IFN-beta, rebetol, copegus, viramidine (taribavirin), NM-283, valopicitabine, R1626, PSI-6130 (R1656), HCV-796, BILB 1941, XTL-2125, MK-0608, NM-107, R7128 (R4048), VCH-759, PF-868554, GSK625433, SCH-503034 (SCH-7), VX-950 (telaprevir), BILN-2065, BMS-605339, ITMN-191, MX-3253 (celgosivir), UT-231B, IDN-6556, ME 3738, LB-84451, MitoQ, benzimidazole derivatives, benzo-1,2,4-thiadiazine derivatives, phenylalanine derivatives, A-831, A-689, zadaxin, nitazoxanide (alinea), BIVN-401 (virostat), PIN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In still yet another embodiment, the present application provides for the use of a compound of the present invention, or a pharmaceutically acceptable salt, solvate, and/or ester thereof, for the preparation of a medicament for inhibiting cytochrome P450 monooxygenase in a patient.

In still yet another embodiment, the present application provides for the use of a compound of the present invention, or a pharmaceutically acceptable salt, solvate, and/or ester thereof, for the preparation of a medicament for treating an HIV infection.

In still yet another embodiment, the present application provides for the use of a compound of the present invention, or a pharmaceutically acceptable salt, solvate, and/or ester thereof, for the preparation of a medicament for increasing blood plasma levels of the drug which is metabolized by cytochrome P450 monooxygenase.

In still yet another embodiment, the present application provides for the use of a compound of the present invention, or a pharmaceutically acceptable salt, solvate, and/or ester thereof, for the preparation of a medicament for improving the pharmacokinetics of a drug which is metabolized by cytochrome P450 monooxygenase.

EXAMPLES

Preparation of Example A

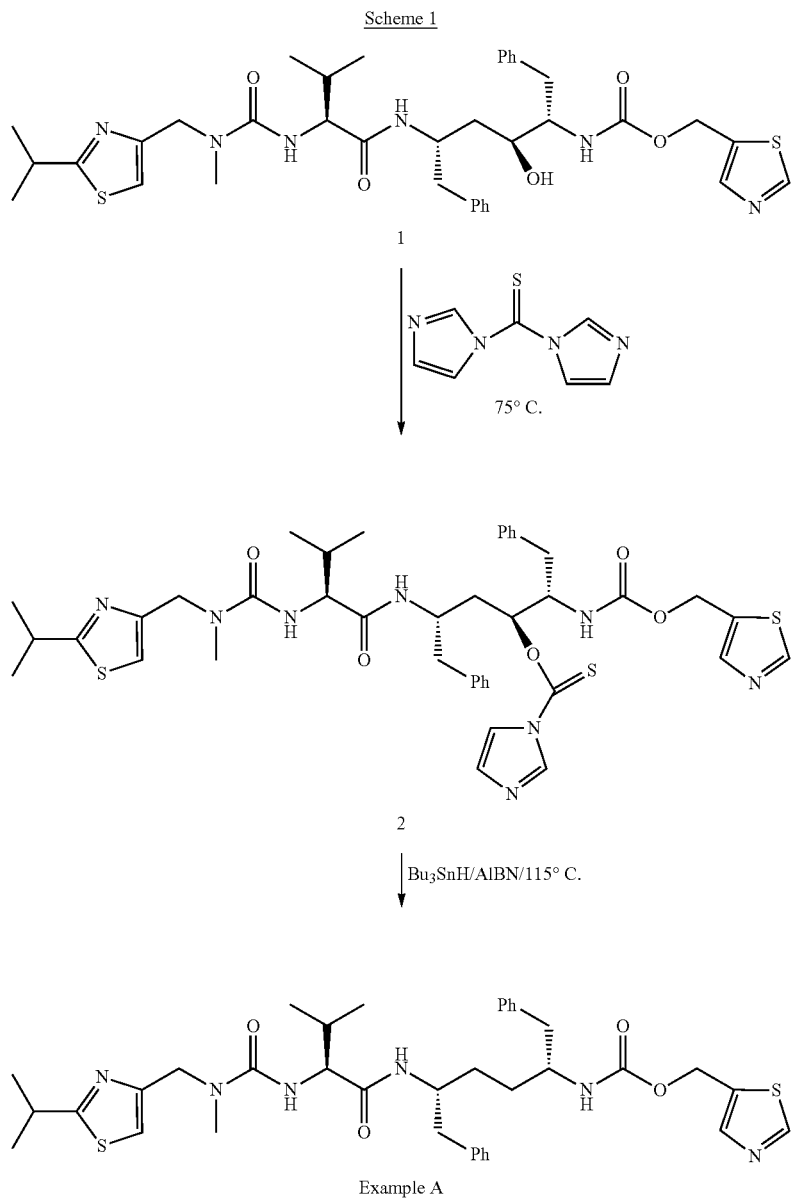 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1 ; S=C(n1ccnc1)n1ccnc1 ; CC(C)c1nc(CN(C)C(=O)N[C@H](C(=O)N[C@@H](Cc2ccccc2)C[C@H](OC(=S)n2ccnc2)[C@H](Cc2ccccc2)NC(=O)OCc2cncs2)C(C)C)cs1 ; CC(C)c1nc(CN(C)C(=O)N[C@H](C(=O)N[C@H](CC[C@H](Cc2ccccc2)NC(=O)OCc2cncs2)Cc2ccccc2)C(C)C)cs1]

Compound 2

To a solution of Compound 1 (ritonavir) (1.8 g, 2.5 mmol) in 1,2-dichloroethane (15 mL) was added 1,1'-thiocarbonyldiimidazole (890 mg, 5.0 mmol). The mixture was heated at 75° C. for 6 hours and cooled to 25° C. Evaporation under reduced pressure gave a white solid. Purification by flash column chromatography (stationary phase: silica gel; eluent: EtOAc) gave Compound 2 (1.6 g). m/z: 831.1 (M+H)$^+$.

Example A

To the refluxing solution of tributyltin hydride (0.78 mL, 2.9 mmol) in toluene (130 mL) was added a solution of Compound 2 (1.6 g, 1.9 mmol) and 2,2'-azobisisobutyronitrile (31 mg, 0.19 mmol) in toluene (30 mL) over 30 minutes. The mixture was heated at 115° C. for 6 hours and cooled to 25° C. Toluene was removed under reduced pressure. Purification by flash column chromatography (stationary phase: silica gel; eluent: hexane/EtOAc 1/10) gave Example A (560 mg). m/z: 705.2 (M+H)$^+$. $^1$H-NMR (CDCl$_3$) δ 8.79 (1H, s), 7.82 (1H, s), 7.26-7.05 (10H, m), 6.98 (1H, s), 6.28 (1H, m), 6.03 (1H, m), 5.27 (1H, m), 5.23 (2H, s), 4.45-4.22 (2H, m), 4.17 (1H, m), 3.98 (1H, m), 3.75 (1H, m), 3.25 (1H, m), 2.91 (3H, s), 2.67 (4H, m), 2.36 (1H, m), 1.6-1.2 (10H, m), 0.85 (6H, m).

Preparation of Example B

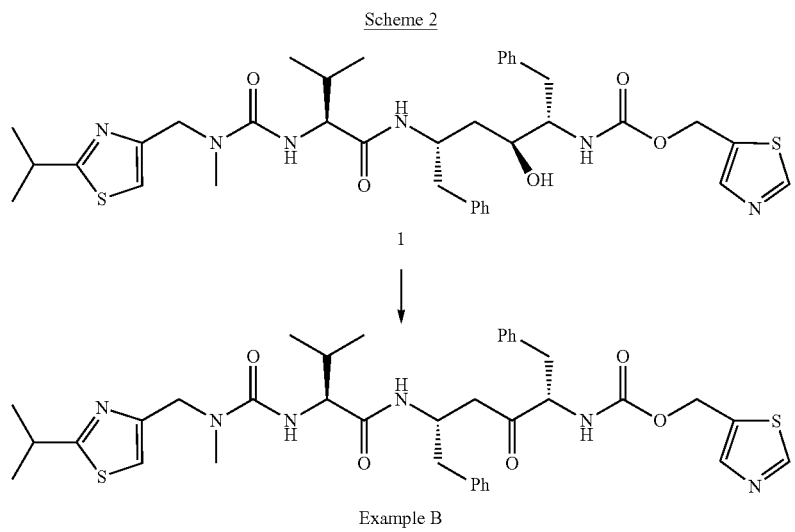

Example B

To a solution of Compound 1 (ritonavir) (98 mg, 0.136 mmol) in dichloromethane (4 mL) was added Dess-Martin periodinane (61 mg, 0.143 mmol). The mixture was stirred at room temperature for 6 hours. The mixture was then partitioned between dichloromethane and brine, the dichloromethane layer was separated, dried and evaporated to dryness. Purification with CombiFlash® (stationary phase: silica gel; eluent: 40-80% EtOAc/Hexane gradient) gave Example B as a white solid. Example B was further purified by trituration with MeOH/hexane to give 83 mg of a white solid. m/z: 719 (M+H)$^+$.

Preparation of Example C

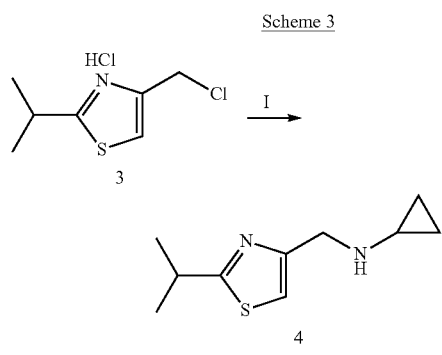

I. cyclopropylamine, MeCN, rt

Compound 3

Compound 3 was prepared according to the procedures of *J. Med. Chem.* 1998, 41, 602, herein incorporated by reference in its entirety for all purposes.

Compound 4

A flask was charged with cyclopropylamine (8.2 mL, 117.8 mmol) at room temperature. A solution of Compound 3 (1 g, 4.71 mmol) in MeCN (8.5 mL) was added dropwise over 5 min. to produce a clear yellow solution that was allowed to stand at room temperature overnight. Volatiles were removed in vacuo, and the resulting residue was purified via silica gel chromatography (gradient elution, 0 to 50% EtOAc/hexane) to afford 0.65 g (70%) of 4 as a yellow liquid (LC/MS m/z 197 (M+H)$^+$; 218 (M+Na)$^+$).

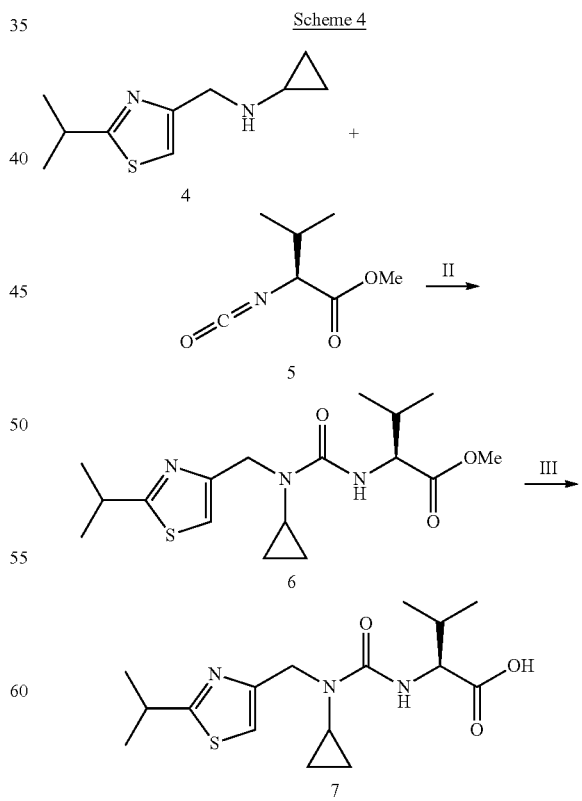

II. rt, DCM; III. 1M LiOH, THF/H$_2$O

Compound 5

Compound 5 was purchased from Aldrich or alternatively prepared according to the procedures of *J. Org. Chem.* 1994, 59, 1937, herein incorporated by reference in its entirety for all purposes.

Compound 6

To a solution of Compound 4 in DCM (3 mL) at room temperature was added 5 (0.1 mL, 0.695 mmol). The resulting clear solution was allowed to stand at room temperature for 2 h. The solvent was removed in vacuo, and the residue was chromatographed directly using silica gel chromatography (gradient elution, 0 to 50% EtOAc/hexane) to produce 0.218 g (89%) of 6 (LC/MS m/z 354 (M+H)$^+$; 729 (2M+Na)$^+$) as a colorless glass.

Compound 7

Compound 6 was taken up in THF (5 mL) at room temperature, and LiOH (1 M in H$_2$O) was added. The resulting reaction mixture was then stirred vigorously for 1.5 h. The reaction mixture was acidified with 1 M HCl to a pH of 3 (monitored using pH test strips). The acidified reaction mixture was then extracted several times with EtOAc. The combined organic phases were washed with brine, dried over anhydrous Na$_2$SO$_4$, and concentrated in vacuo to produce 0.20 g (quantitative yield) of 7 (LC/MS m/z 340 (M+H)$^+$) as a colorless film. This material was used without further purification.

Example C

Compounds 7 (0.034 g, 0.100 mmol) and 8, (0.034 g, 0.083 mmol) were diluted in THF (2 mL) at room temperature. To the resulting solution were added N,N-diisopropylethylamine (0.022 mL, 0.125 mmol), EDC (0.018 mL, 0.099 mmol) and HOBt (0.013 g, 0.099 mmol). The solution was then allowed to stand overnight at room temperature. The solvent was removed in vacuo and the residue was taken up in MeCN (0.5 mL) and passed through an Acrodisc LC13 PVDF filter (0.45 µM) prior to purification by preparatory HPLC to afford 0.043 g (71%) of Example C as a fluffy white solid. ($^1$H-NMR (300 MHz, CDCl$_3$) δ 8.79 (s, 1H); 7.82 (s, 1H); 7.27-7.02 (m, 10H); 6.81 (s, 1H); 5.97 (br d, J=8.7 Hz, 1H); 5.76 (br d, J=7.2 Hz, 1H); 5.21 (dt, J=7.5, 12.6 Hz, 2H); 5.02, br d, J=8.4 Hz, 1H); 4.58 (s, 2H); 4.16 (m, 1H); 3.99 (br t, J=6.6 Hz, 1H); 3.79 (m, 1H); 3.27 (pent, J=6.6 Hz, 1H); 2.85-2.50 (m, 3H); 2.23 (m, 1H); 1.82 (br s, 2H); 1.60-1.22 (m, 4H); 1.36 (d, J=6.6 Hz, 6H); 0.91 (d, J=6.6 Hz, 3H); 0.90-0.7 (m, 4H); 0.80 (d, J=6.6 Hz, 3H); LC/MS m/z 731 (M$^+$)).

Scheme 5

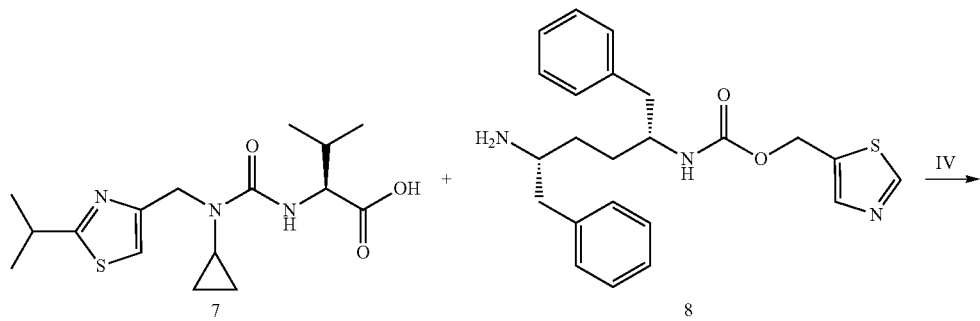

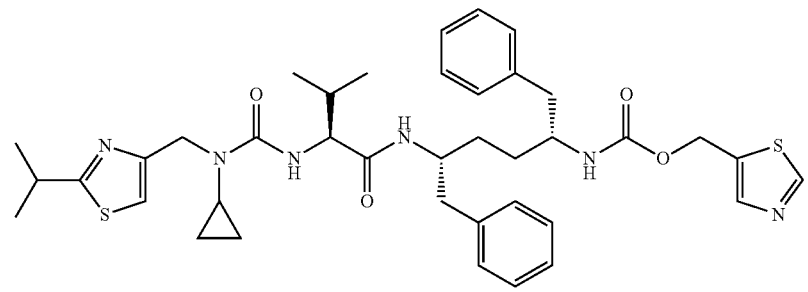

Example C

IV. EDC, HOBt, DIPEA, THF

Preparation of Examples D-I

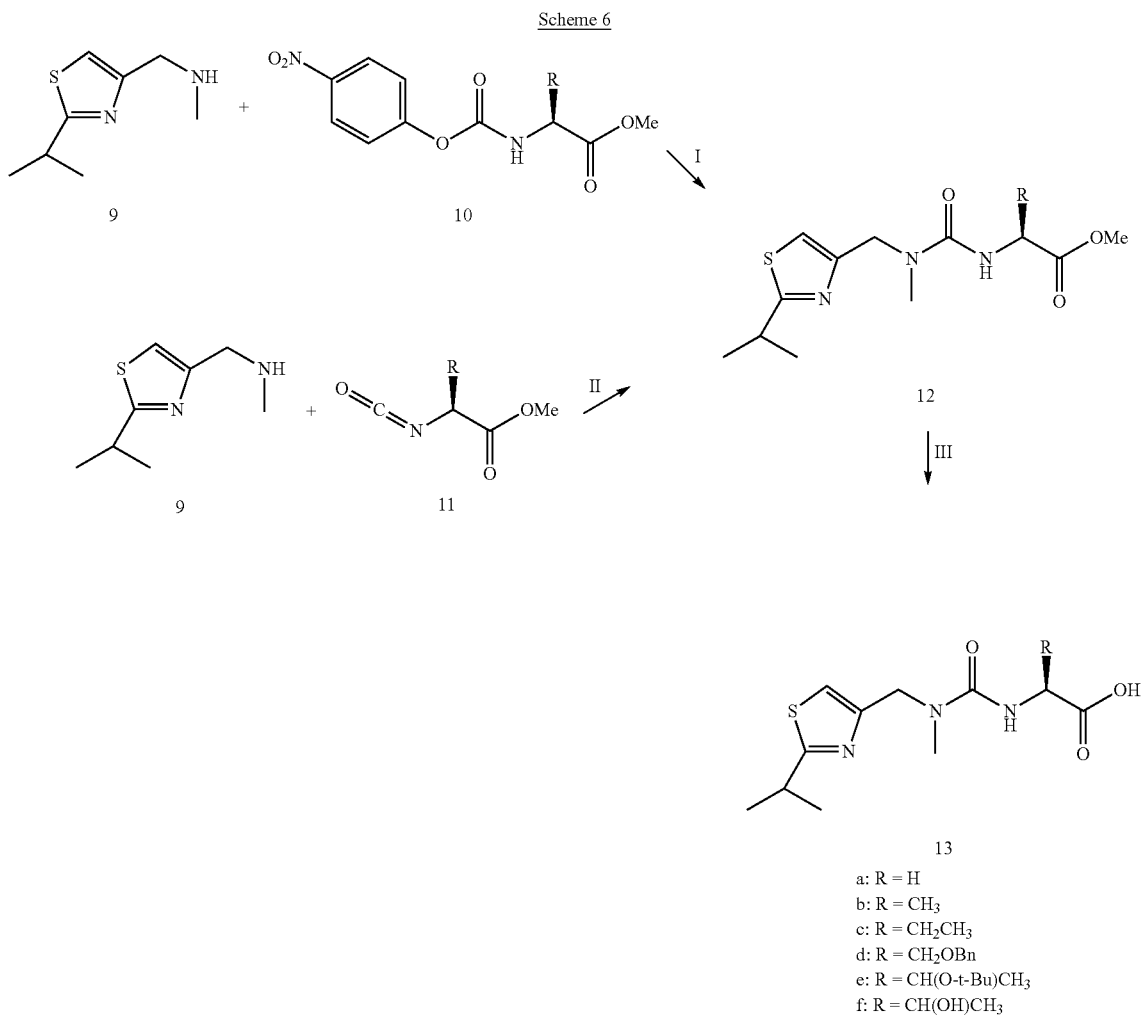

Scheme 6 a: R = H
b: R = CH₃
c: R = CH₂CH₃
d: R = CH₂OBn
e: R = CH(O-t-Bu)CH₃
f: R = CH(OH)CH₃

I. Et₃N/DMAP/THF/65° C.; II. CH₂Cl₂/25° C.; III.
a. NaOH/dioxane/H₂O;
b. HCl

Compound 9

Compound 9 was prepared according to the procedures of *J. Med. Chem.* 1998, 41, 602.

Compound 10

The structures of Compound 10 were prepared according to the procedures of *J. Med. Chem.* 1998, 41, 602.

Compound 11

The structures of Compound 11 were purchased from Aldrich or prepared according to the procedures of *J. Org. Chem.* 1994, 59, 1937.

Compound 12

Method 1: To a solution of Compound 9 (0.8 mmol) in THF (2 mL) was added a carbamate of Compound 10 (0.6 mmol), followed by DMAP (16 mg) and triethylamine (0.25 mL). The resulting mixture was heated at 70° C. for two hours and diluted with EtOAc. The organic phase was separated, and washed sequentially with saturated aqueous Na₂CO₃, water, and brine, then concentrated under reduced pressure. Purification of the residue by flash column chromatography (silica gel, 1/1-1/3 hexanes/EtOAc gradient) gave compounds of Structure 12.

Method 2: To a solution of Compound 9 (2.4 mmol) in CH₂Cl₂ (2 mL) was added an isocyanate of Compound 11 (2 mmol). The resulting mixture was stirred for 4 hours and concentrated. Purification of the residue by flash column chromatography (silica gel, hexane/EtOAc 1/1-1/3) gave structures of Compound 12.

Compound 13

To a solution of structures of Compound 12 (1.8 mmol) in dioxane (8 mL) and water (8 mL) was added sodium hydroxide (3.6 mmol). The resulting reaction mixture was stirred for 1 hour and acidified with HCl in dioxane (3.6 mmol). The reaction mixture was extracted with EtOAc and the organic phase was dried with anhydrous MgSO₄. Concentration of the dried organic phase gave structures of Compound 13.

Scheme 7

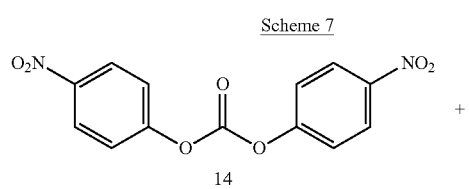

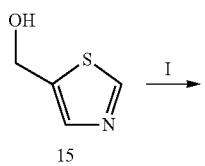

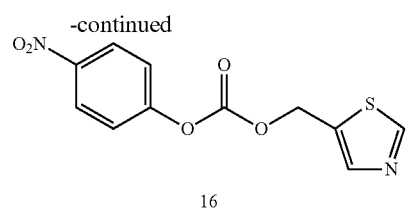

I. Et$_3$N/DCM

Compound 16

To a solution of Compound 15 (obtained commercially from Molekula) (17 mmol) in DCM (40 mL) was added Compound 14 (19 mmol), followed by triethylamine (26 mmol). The resulting reaction mixture was stirred for 12 hour and concentrated under reduced pressure. The reaction mixture was diluted with EtOAc and washed sequentially with saturated aqueous Na$_2$CO$_3$, water, and brine. The solvent was removed under reduced pressure. Purification of the residue by flash column chromatography (silica gel, eluent: hexanes/EtOAc=1/1) gave Compound 16 (4.7 g).

Scheme 8

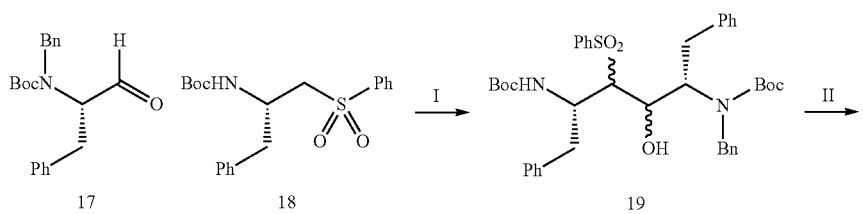

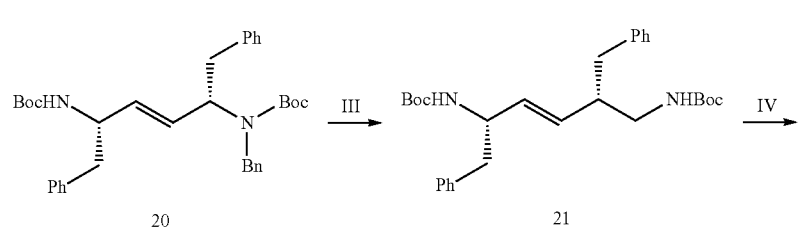

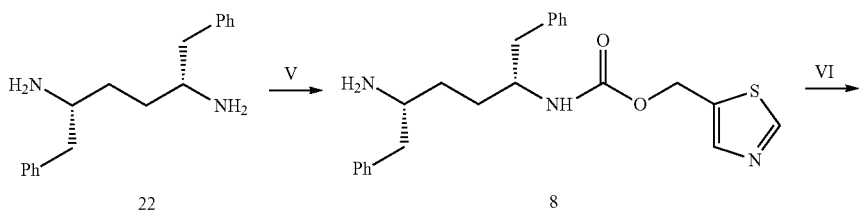

-continued

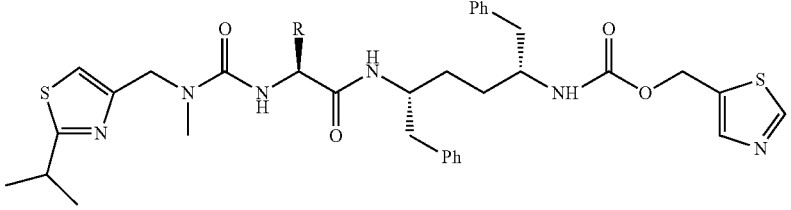

Examples:
D: R = H
E: R = CH₃
F: R = CH₂CH₃
G: R = CH₂OBn
H: R = CH(O-t-Bu)CH₃
I: R = CH(OH)CH₃

I. a. n-BuLi/-78 C.; b. i-Bu₂Al(OMe); II. a. Ac₂O/pyridine; b. Na-Hg/MeOH/THF; III. Na/NH₃/-33 C.;
IV. a. H₂/10% Pd/C; b. TFA/DCM; V. 16/Et₃N; VI. acid of structure 13/EDC/HOBt Compound 17

Compound 17 was prepared according to the procedures of *Tetrahedron* 1997, 53, 4769, herein incorporated by reference in its entirety for all purposes.

Compound 18

Compound 18 was prepared according to the procedures of *J. Org. Chem.* 1987, 52, 3759, herein incorporated by reference in its entirety for all purposes.

Compound 19

A suspension of Compound 18 (7.4 mmol) in THF (200 mL) was heated under reflux until a clear solution was obtained. The solution was cooled to −78° C. and n-butyl-lithium (14.8 mmol) was added dropwise to provide a solution of the dianion of sulfone 18.

To a DIBAL-H solution (7.8 mmol) at 0° C. was added a solution of MeOH (7.8 mmol) in THF (5 mL). The mixture was stirred for 5 minutes and cooled to −78° C. A solution of Compound 17 (6.6 mmol) in THF (5 mL) was added to the above DIBAL-H/MeOH solution, and the resulting reaction mixture was stirred for another 5 minutes. The resulting solution of aldehyde complexes was transferred to solution of the dianion of sulfone 18. The resulting mixture was stirred at −78° C. for 30 minutes, quenched with an aqueous solution of NH₄Cl, and warmed to 25° C. The mixture was then extracted with EtOAc, and concentrated to give Compound 19 as a mixture of diastereomers. (m/z 737.3 (M+Na)⁺.

Example 20

To a solution of Compound 19 in DCM (20 mL) was added Ac₂O (1.5 mL), followed by pyridine (3 mL). The resulting mixture was stirred for 12 hours and concentrated. The concentrate was dissolved in MeOH (30 mL) and cooled to 0° C. NaH₂PO₄ (4.9 g) was added to the solution, followed by freshly prepared Na—Hg (6%, 6 g). The resulting mixture was warmed to 25° C. and stirred for 12 hours. Water (50 mL) was then added, and the mixture was filtered and concentrated. The concentrate was diluted with EtOAc and washed with brine. The organic phase was concentrated. Purification by flash column chromatography (silica gel, eluent: hexanes/EtOAc=10/1) gave Compound 20 (1.4 g).

Compound 21

To liquid ammonia (25 mL) at −33° C. was added a solution of Compound 20 (1.4 g) in THF (2.5 mL). Sodium was slowly added until the blue color of the solution persisted. The resulting mixture was stirred for 1 hour. Solid NH₄Cl (6 g) was then added slowly, the mixture was warmed to 25° C., and the ammonia was evaporated. The mixture was diluted with EtOAc, and washed sequentially with water and brine. The solvent was removed under reduced pressure. Purification of the resulting residue by flash column chromatography (silica gel, eluent: hexanes/EtOAc=5/1) gave Compound 21 (1.15 g).

Compound 22

A mixture of Compound 21 (1.15 g) and 10% Pd/C (160 mg) in MeOH (20 mL) was hydrogenated for 12 hours. CELITE was added and the resulting mixture was stirred for 5 minutes. The mixture was then filtered and concentrated to give an intermediate (1 g). The intermediate (700 mg) was dissolved in DCM (20 mL) and TFA (4 mL), and the resulting mixture was stirred for 4 hours, then concentrated under reduced pressure. The concentrated mixture was diluted with EtOAc, and washed sequentially with saturated aqueous Na₂CO₃, water, and brine. Concentration of the washed EtOAc mixture gave Compound 22 (420 mg).

Compound 8

To a solution of Compound 22 (1.57 mmol) in CH₃CN (16 mL) was added Compound 16 (1.57 mmol), followed by diisopropylethylamine (3.14 mmol). The resulting mixture was stirred for 12 hours. The mixture was then diluted with EtOAc, and washed sequentially with saturated aqueous Na₂CO₃, water and brine. Purification by reverse-phase HPLC (Phenomenex Synergi® Comb-HTS column, eluent: 25%-100% CH₃CN in water) gave Compound 8 (460 mg).

Example D

To the solution of Compound 13a (R═H, 0.08 mmol) and Compound 8 (0.06 mmol) in THF (1 mL) were added HOBt (15 mg), EDC (26 mg), and disopropylethylamine (0.25 mL). The mixture was stirred for 12 hours and concentrated. Purification by reverse phase HPLC (Phenomenex Synergi® Comb-HTS column, eluent: 25%-100% CH₃CN in water) gave Example D (27 mg). m/z 663.1 (M+H)⁺. ¹H-NMR (CDCl₃) δ 8.79 (1H, s), 7.83 (1H, s), 7.25-7.04 (10H, m), 6.98 (1H, s), 6.25 (1H, m), 5.25 (3H, m), 4.40 (2H, s), 4.12 (1H, m), 3.8 (3H, m), 3.22 (1H, m), 2.95 (3H, s), 2.70 (4H, m), 1.60 (4H, m), 1.26 (6H, d, J=7 Hz).

Example E

Example E was prepared following the procedure for Example D (30 mg), except that Compound 13b was used instead of Compound 13a. m/z 677.1 (M+H)⁺.

Example F

Compound F was prepared following the procedure for Example D (40 mg), except that Compound 13c was used instead of Compound 13a. m/z 691.2 (M+H)⁺. ¹H-NMR (CDCl₃) δ 8.80 (1H, s), 7.83 (1H, s), 7.25-7.06 (10H, m), 6.98 (1H, s), 6.35 (1H, m), 6.23 (1H, m), 5.24 (2H, s), 5.12 (1H, m), 4.34 (2H, s), 4.10 (2H, m), 3.78 (1H, m), 3.23 (1H, m), 2.90 (3H, s), 2.68 (4H, m), 1.90 (2H, m), 1.7-1.4 (4H, m), 1.36 (6H, d, J=7.0 Hz), 0.90 (3H, t, J=7.3 Hz)

Example G

Example G was prepared following the procedure for Example D (84 mg), except that Compound 13d was used instead of Compound 13a. m/z 783.2 (M+H)⁺.

Example H

Example H was prepared following the procedure for Example D (90 mg), except that Compound 13e was used instead of Compound 13a. m/z 763.2 (M+H)⁺.

Example I

Example H (24 mg) was dissolved in TFA (2 mL) and the mixture was stirred for 12 hours, then concentrated. Purification by reverse phase HPLC (Phenomenex Synergi® Comb-FITS column, eluent: 25%-100% CH₃CN in water) gave Example 1 (14 mg). m/z 707.2 (M+H)⁺. ¹H-NMR (CDCl₃) δ 8.82 (1H, s), 7.85 (1H, s), 7.26-7.04 (10H, m), 7.0 (1H, s), 5.25 (2H, s), 4.86 (1H, m), 4.56 (1H, m), 4.37 (2H, m), 4.13 (1H, m), 4.06 (1H, m), 3.86 (1H, m), 3.32 (1H, m), 2.99 (3H, s), 2.8-2.6 (4H, m), 1.6-1.4 (4H, m), 1.37 (6H, m), 1.15 (3H, m).

Preparation of Example I

Scheme 9

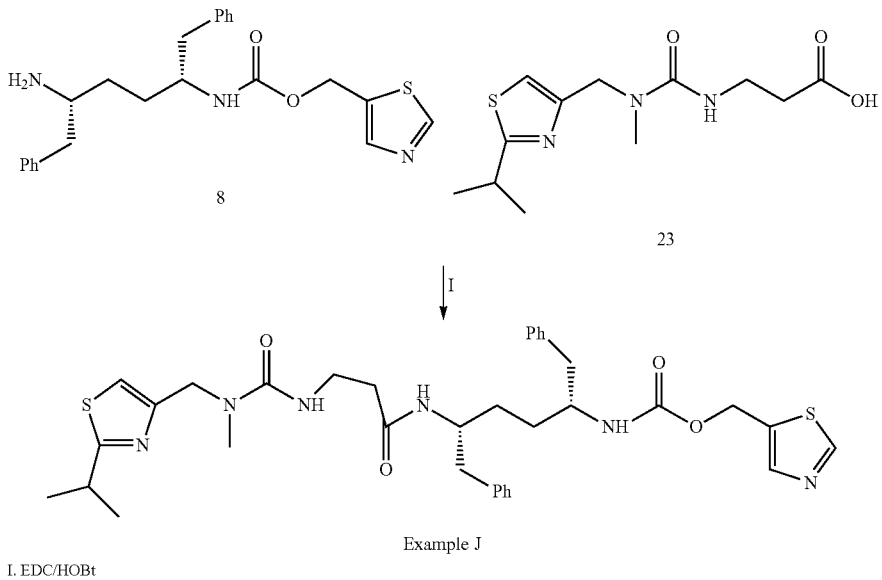

Example I

Compound 23 was prepared following the procedure for Compound 13, with the exception that methyl 3-isocyanatopropionate was used instead of Compound 11.

Example J was prepared following the procedure for Example D (37 mg), except that Compound 23 was used instead of Compound 13a. m/z 677.2 (M+H)⁺.

Preparation of Example K

Scheme 10

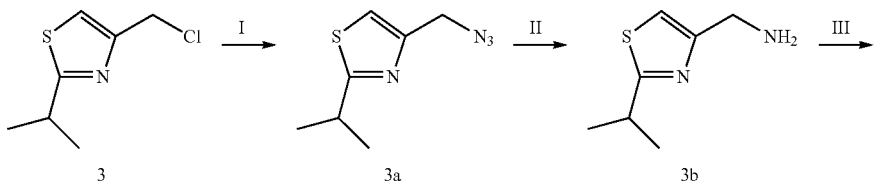

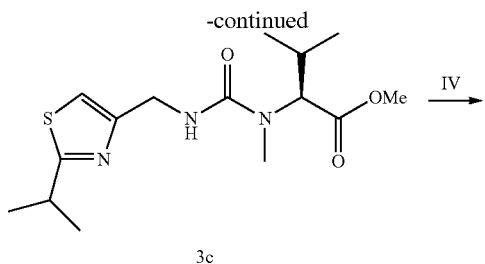

3c

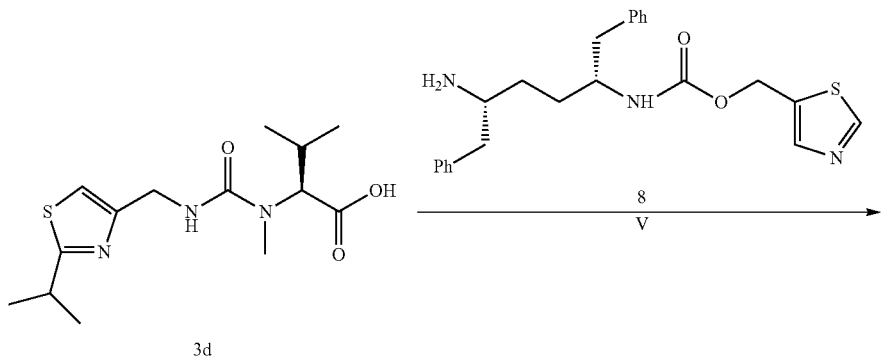

3d

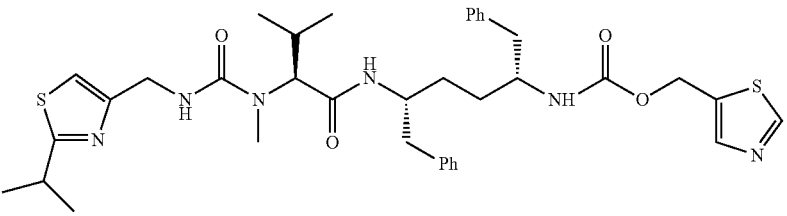

K

1. NaN₃/DMF; II. PPh₃/H₂O; III. a. Cl₃COCOOCCl₃; b. HCl-NH₂CHiPrCO₂Et;
IV. a. NaOH; b. HCl; V. EDC/HOBt/compound 8

Example K

Compound 3a

Compound 5a was prepared following the literature procedure of *Synthesis* 823, 1976, herein incorporated by reference in its entirety for all purposes.

Compound 3b

To the solution of Compound 3a (700 mg, 3.9 mmol) in THF (10 mL) was added water (69 μL, 3.9 mmol), followed by triphenylphosphine (1.06 g, 4.0 mmol). The mixture was stirred for 12 hours. Solvents were removed and the mixture was dried to give Compound 3b, which was used for next step without further purification.

Compound 3c

To a solution of triphosgene (110 mg, 0.37 mmol) in CH₂Cl₂ (2 mL) at 0° C. was added a solution of Compound 3b (1 mmol) and iPrNEt₂ (0.38 mL, 2.2 mmol) in CH₂Cl₂ (3.5 mL) over 30 minutes period. The mixture was stirred for 30 minutes, and a solution of amino N-methyl leucine methyl ester HCl salt (182 mg, 1 mmol) and iPrNEt₂ (0.34 mL, 2.2 mmol) in CH₂Cl₂ (2 mL) was added. The mixture was stirred for 12 hours, and diluted with EtOAc. The solution was washed with sat. Na₂CO₃ (2×), water (2×), and brine, and dried over Na₂SO₄. Concentration and purification with silica gel flash column gave Compound 5c (300 mg).

Compound 3d

Compound 3d was prepared following the procedure for Compound 13, with the exception that Compound 3c was used instead of Compound 12.

Example K

Example K was prepared following the procedure for Example D (7 mg), except that Compound 3d was used instead of Compound 13a. m/z 705.2 (M+H)⁺. ¹H-NMR (CDCl₃) δ 8.8 (1H, m), 7.86 (1H, s), 7.26-6.8 (1H, m), 6.10 (1H, m), 5.5-5.10 (4H, m), 4.46 (2H, m), 4.2-3.75 (3H, m), 3.25 (1H, m), 2.82/2.4 (3H), 2.8-2.5 (4H, m), 2.17 (1H, m), 1.7-1.2 (10H, m), 0.8 (6H, m).

Preparation of Example L

Scheme 11

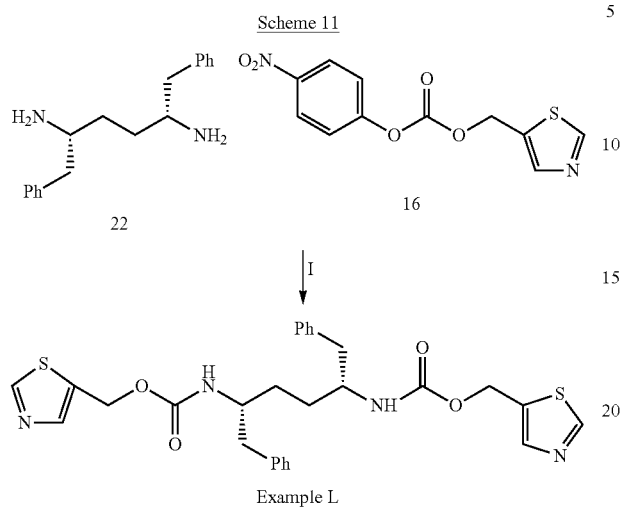

Example L

I. Et₃N

Example L

To a solution of Compound 22 (1.57 mmol) in CH₃CN (16 mL) was added Compound 16 (3.14 mmol), followed by triethylamine (4.71 mmol). The resulting mixture was stirred for 12 hours. The reaction mixture was diluted with EtOAc and washed sequentially with saturated aqueous $Na_2CO_3$, water, and brine. The solvent was removed under reduced pressure. Purification of the residue by flash column chromatography (silica gel, eluent: hexanes/EtOAc=1/1) gave Example L (460 mg). m/z 551.2 (M+H)⁺. ¹H-NMR (CDCl₃) δ 8.81 (2H, s), 7.85 (2H, s), 7.26-7.0 (10H, m), 5.24 (4H, s), 4.50 (2H, m), 3.87 (2H, m), 2.73 (4H, m), 1.4-1.2 (4H, m).

Alternate Preparation of Compound 22

Scheme 12

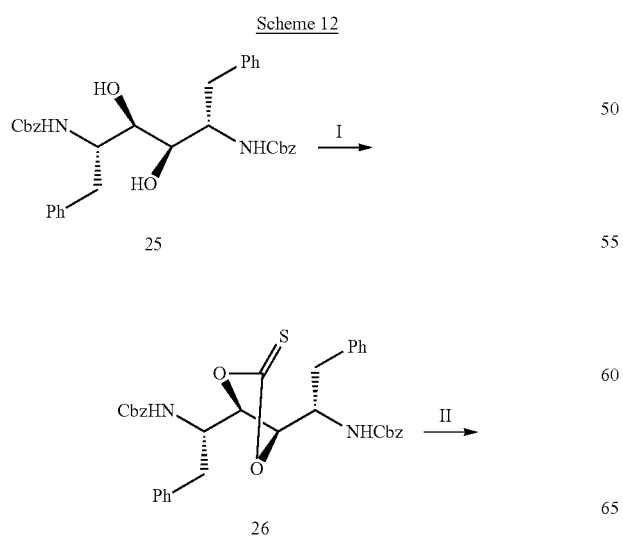

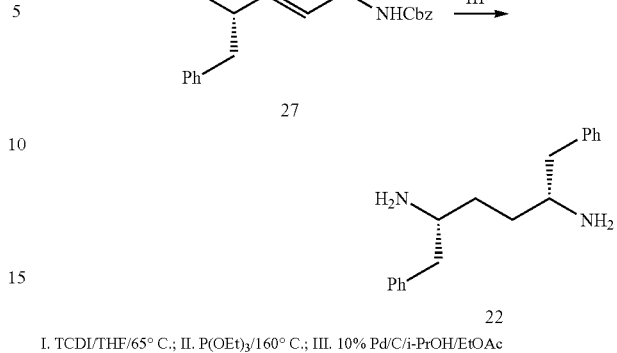

I. TCDI/THF/65° C.; II. P(OEt)₃/160° C.; III. 10% Pd/C/i-PrOH/EtOAc

Compound 25

Compound 25 was prepared following the literature procedure described in *J. Org. Chem.* 1996, 61, 444 (herein incorporated by reference in its entirety), except that the L-isomer was prepared instead of the D-isomer.

Compound 26

A mixture of Compound 25 (7.4 g) and 1,1'-thiocarbonyldiimidaxole (4.5 g) in THF (260 mL) was heated at 65° C. for 54 hours. Solvent was removed from the mixture under reduced pressure. Purification by flash column chromatography (silica gel, hexanes/EtOAc=1/1) gave Compound 26 (7.33 g).

Compound 27

The mixture of Compound 26 (7.3 g) and triethylphosphite (100 mL) was heated at 160° C. for 4 hours. Excess reagents were removed under reduced pressure. Purification by flash column chromatography (silica gel, hexanes/EtOAc=3/1) gave Compound 27 (5 g).

Compound 22

A mixture of Compound 27 (250 mg) in i-PrOH/EtOAc (5 mL/5 mL) was hydrogenated for 14 hours in the presence of 10% Pd/C (75 mg). CELITE was added to the mixture, and the mixture was stirred for 5 minutes. Filtration and evaporation of solvents gave Compound 22 (116 mg).

The skilled practitioner will recognize that the procedure outlined in Scheme 12 can be used to prepare a variety of 1,4-substituted 1,4-diamines analogous to Compound 22. For example, an amine-protected 2,3-dihydroxy-1,4-diamine analogous to Compound 25 can be prepared:

Analogs of Compound 25

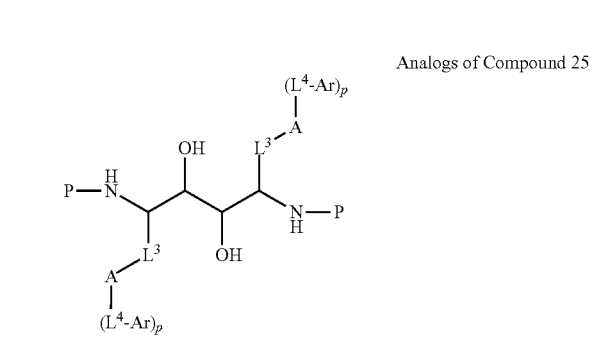

wherein $L^3$, A, Ar, and P are as defined herein, and protecting group "P" is any amine protecting group described in described in *Protective Groups in Organic Synthesis*, Theodora W. Greene and Peter G. M. Wuts (John Wiley & Sons, Inc., New York, 1999, ISBN 0-471-16019-9), which is herein incorporated by reference in its entirety for all purposes. The analogs of Compound 25 can then be transformed, according to the methods outlined in Scheme 12, to form analogs of Compound 26:

Analogs of Compound 26

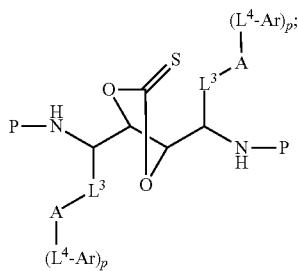

analogs of Compound 27:

Analogs of Compound 27

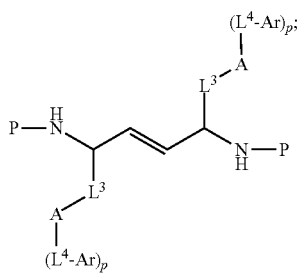

and
analogs of Compound 22:

Analogs of Compound 22

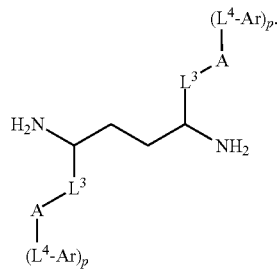

Preparation of Examples M and N

Scheme 13

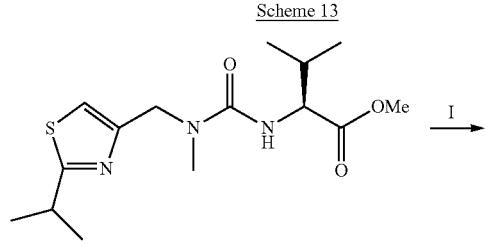

28

-continued

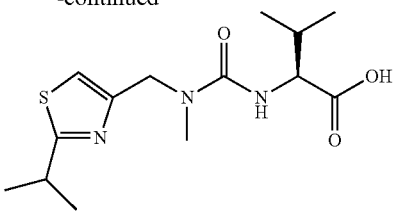

29

I. a. LiOH, THF/H$_2$O, 25° C.; b. HCl

Compound 29

Compound 28 was prepared using a procedure similar to that used to prepare Compound 6 (described in Scheme 4) except that Compound 9 was used instead of Compound 4.

To a solution of Compound 28 (0.757 g, 2.31 mmol) in THF (9 mL) at room temperature was added freshly prepared 1M LiOH (4.6 mL, 4.6 mmol). After 1.5 h, 1 M HCl (7 mL, 7 mmol) was added and the reaction mixture extracted thoroughly with EtOAc (5×15 mL). The combined organic layers were dried over anhydrous Na$_2$SO$_4$ and the volatiles removed in vacuo to afford 0.677 g (93%) of Compound 29 as a colorless glassy solid (LC/MS m/z 314.0 (M+H)$^+$) that was used in the following procedures without further purification.

Scheme 14

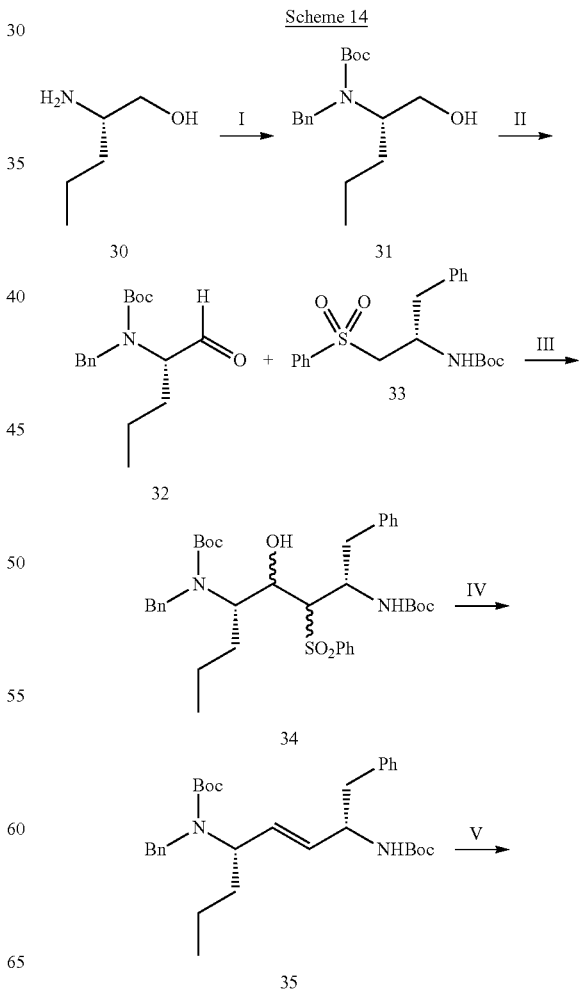

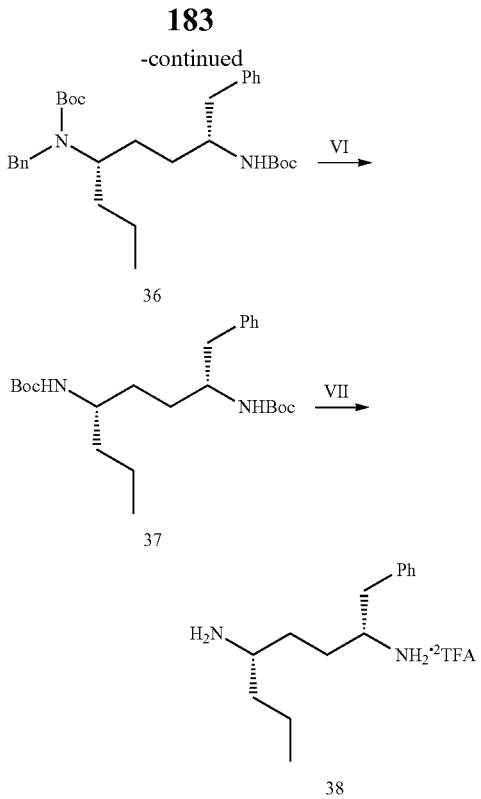

I. a. PhCHO, MeOH; b. NaBH₄; c. Boc₂O, THF/H₂O. II. Pyr•SO₃, Et₃N, DMSO 0° C. III. n-BuLi, MeOAl(i-Bu)₂, THF, -78° C. IV. a. Ac₂O, pyr, CH₂Cl₂, b. 6% Na/Hg, Na₂HPO₄, MeOH. V. H₂, 10% Pd/C, MeOH. VI. Na/NH₃, THF, -35° C. VII. 20% TFA/DCM.

Compound 30

Compound 30 was purchased from Aldrich Chemical Co., and used without further purification.

Compound 31

To a solution of Compound 30 (8.25 g, 80 mmol) in MeOH (50 mL), was added benzaldehyde (8.1 mL, 80 mmol) and the resulting solution was allowed to stir at room temperature. After 2 h, the reaction mixture was cooled to 0° C. and NaBH₄ (3.33 g, 88 mmol) was added in portions. After allowing the reaction mixture to warm to room temperature over 2 h, glacial acetic acid (2 mL) was added. The resulting viscous solution was concentrated in vacuo. EtOAc and H₂O (50 mL each) were added and the aqueous phase was extracted with EtOAc. The combined organic phases were washed with saturated NaHCO₃, brine, and concentrated in vacuo. The resulting material was taken up in THF (25 mL) and H₂O (25 mL) at room temperature and Boc₂O (15.1 g, 69.2 mmol) was added to produce an opaque suspension that was stirred vigorously for 2 h at room temperature. THF was removed in vacuo, and the aqueous layer was extracted with EtOAc. The combined organic layers were washed with brine and dried over anhydrous MgSO₄ and concentrated in vacuo. Chromatography on SiO₂ (3/1 Hex/EtOAC) afforded 18.5 g (79%) of Compound 31 as a colorless oil (LC/MS m/z 293.9 (M+H)⁺.

Compound 32

Compound 31 (5.95 g, 20.3 mmol) and Et₃N (9.9 mL, 71 mmol) were diluted in DMSO (65 mL) and allowed to age at room temperature for 30 min before cooling to 0° C. Pyridine•SO₃ was added in one portion and the reaction mixture was maintained at 5° C. to prevent freezing. After 45 min, the reaction mixture was poured into icewater and extracted with EtOAc. The combined organic layers were washed with saturated NaHCO₃, H₂O, and dried over anhydrous MgSO₄ prior to concentration in vacuo (bath temperature 25° C.) to produce 4.39 g (74%) of Compound 32 as a clear, yellow colored oil that was used without further purification. ¹H-NMR (CDCl₃, 300 MHz) δ (major rotamer) 9.36 (br s, 1H); 5.01 (d, J=15 Hz, 1H); 4.12 (d, J=15 Hz, 1H); 3.45 (m, 1H); 2.04-1.88 (m, 1H); 1.80-1.58 (m, 1H); 1.54-1.20 (m, 2H); 1.47 (s, 9H); 0.91 (t, J=7.2 Hz, 3H). (minor rotamer) 9.46 (br s, 1H); 4.71 (d, J=15 Hz, 1H); 4.20 (d, J=15 Hz, 1H); 3.78 (m, 1H); 2.04-1.88 (m, 1H); 1.80-1.58 (m, 1H); 1.54-1.20 (m, 2H); 1.47 (s, 9H); 0.91 (t, J=7.2 Hz, 3H).

Compound 34

A suspension of Compound 33 (6.23 g, 16.6 mmol) in THF (500 mL) was heated under reflux until a homogeneous solution was obtained. The solution was cooled to -78° C. and 1.6M n-BuLi (19.7 mL, 31.5 mmol) was introduced to produce a clear yellow solution. Meanwhile, DIBAL-OMe was prepared by dilution of DIBAL-H (1M in hexanes, 18.1 mL, 18.1 mmol) in THF (8 mL) and cooling to 0° C. prior to addition of MeOH (0.73 mL, 18.1 mmol). This solution was allowed to age while Compound 32 (4.39 g, 15.1 mmol) was diluted in THF (15 mL) and cooled to -78° C. The DIBAL-OMe solution was cannulated to the solution of Compound 32 and allowed to age for 5 min prior to cannulation to the sulfur dianion solution. The resulting clear yellow solution was allowed to age at -78° C. for 1 h. The reaction was quenched by addition of saturated NH₄Cl (100 mL) at -78° C. and allowed to warm to room temperature. Water was added until all precipitated solids were dissolved and the layers separated. The THF layer was concentrated in vacuo while the aqueous layer was extracted with EtOAc. The recombined organic layers were washed with brine, and the resulting emulsion was treated with solid NaOH until homogeneous bilayers resulted. The aqueous layer was extracted with EtOAc and the combined organics dried over anhydrous Na₂SO₄. Concentration in vacuo produced 9.57 g (95%) of Compound 34 as an amorphous white solid (LC/MS m/z: 689.3 (M+Na)⁺) that was used in the following procedures without further purification.

Compound 35

Crude Compound 34 was suspended in CH₂Cl₂ (65 mL) followed by addition of pyridine (6.7 mL, 83 mmol) and acetic anhydride (3.5 mL, 36.5 mmol). The resulting solution was allowed to age at room temperature overnight. MeOH (6 mL) was added and after 10 min, the reaction was poured into brine. Addition of water produced a bilayer that was separated and the aqueous phase was repeatedly extracted with CH₂Cl₂. The combined organic layers were dried over anhydrous MgSO₄ and concentrated in vacuo to produce 8.95 g (88%) of a white solid that was immediately taken up in MeOH (100 mL). Na₂HPO₄ (11.4 g, 80.3 mmol) was added and the resulting slurry was cooled to 0° C. prior to addition of Na—Hg (6%, 14.5 g, 37.8 mmol) in portions. After aging at room temperature overnight, H₂O (30 mL) was added and the reaction was filtered through a celite pad. MeOH was removed in vacuo and the aqueous residue was extracted with EtOAc. The combined organic layers were washed with brine, dried over anhydrous MgSO₄ and concentrated in vacuo to a yellow oil that was purified by chromatography on SiO₂ (0-15% EtOAc/hexanes) to afford 2.14 g (34%) of Compound 35 as a colorless oil (LC/MS m/z: 531.2 (M+Na)⁺).

Compound 36

Compound 35 (1.73 g, 3.4 mmol) was diluted in MeOH (7.5 mL) and 10% Pd/C (0.36 g, 0.34 mmol) was added. The atmosphere was replaced with a 1-12 balloon and the reaction mixture allowed to age at room temperature. After 2 h, the reaction mixture was filtered through a pad of celite, the filtrate was washed several times with MeOH, and the combined organic layers were concentrated in vacuo to afford 1.45 g (83%) of Compound 36 as a colorless oil (LC/MS m/z: 533.2 (M+Na)$^+$) that was used in the following procedures without further purification.

Compound 37

Compound 36 (0.528 g, 1.03 mmol) was diluted in THF (3 mL) and added to liquefied ammonia (approx. 20 mL) at −35° C. Small pieces of Na were added until a blue color persisted. After 1.5 h, solid NH$_4$Cl was added in portions until the remaining Na was destroyed and the ammonia was allowed to escape at ambient temperature. Water and EtOAc (20 mL each) were added, and the aqueous layer was extracted with EtOAc. The combined organic layers were washed with brine, dried over Na$_2$SO$_4$ and concentrated in vacuo to afford 0.395 g (91%) of Compound 37 as an amorphous white solid that was used without further purification in the following procedures (LC/MS m/z: 421.1 (M+H)$^+$; 443.2 (M+Na)$^+$).

Compound 38

Compound 37 (0.362 g, 0.861 mmol) was diluted in CH$_2$Cl$_2$ (3.2 mL). Trifluoroacetic acid (0.8 mL) was added and the clear solution was allowed to age overnight. Following concentration in vacuo, the residue was azeotroped with toluene several times to remove residual TFA. 0.382 g (99%) of the bis-trifluoroacetate salt of Compound 38 was collected as a colorless oil that was used without further purification (LC/MS m/z: 221.1 (M+H)$^+$).

3/2 (w/w) mixture of anhydrous Na$_2$SO$_4$/anhydrous Na$_2$CO$_3$ and concentrated in vacuo. Chromatography on SiO$_2$ (0-20% MeOH/CH$_2$Cl$_2$) afforded 0.043 g (14%) of Compound 39 as a colorless film (LC/MS m/z: 362.1 (M+H)$^+$) and 0.105 g (34%) of Compound 40 as a colorless film (LC/MS m/z: 362.1 (M+H)$^+$).

Example M

A flask was charged with Compound 39 (0.048 g, 0.133 mmol) and Compound 29 was added as a 0.2 M solution in THF (0.8 mL, 0.160 mmol). THF (1 mL) was added, followed by DIPEA (0.026 mL, 0.145 mmol), HOBt (0.022 g, 0.160 mmol) and finally EDC (0.028 mL, 0.160 mmol). The clear, colorless solution was allowed to age overnight. Volatiles were removed in vacuo and the residue chromatographed on SiO$_2$ (0-20% MeOH/CH$_2$Cl$_2$). Fractions containing the desired compound were concentrated in vacuo and submitted to preparatory LC/MS purification to afford 0.018 g (20%) of Example M as a colorless film LC/MS m/z: 657.2 (M+H)$^+$; $^1$H-NMR (CDCl$_3$, 300 MHz) δ 8.95 (s, 1H); 7.88 (br s, 1H); 7.27-7.04 (m, 5H); 7.04 (s, TH); 6.60-6.20 (m, 2H); 5.22 (m, 2H); 5.12 (d, J=9.3 Hz, 1H); 4.50 (m, 2H); 4.01 (br s, 1H); 3.83 (m, 2H); 3.38 (m, 1H); 3.10-2.94 (m, 3H); 2.74 (m, 2H); 2.23 (m, 1H); 1.64-1.15 (m, 8H); 1.40 (d, J=6.9 Hz, 6H); 0.96 (m, 6H); 0.83 (t, J=6.9 Hz, 3H).

Example N

Example N was prepared using procedures similar to those used to prepare Example M, using the following

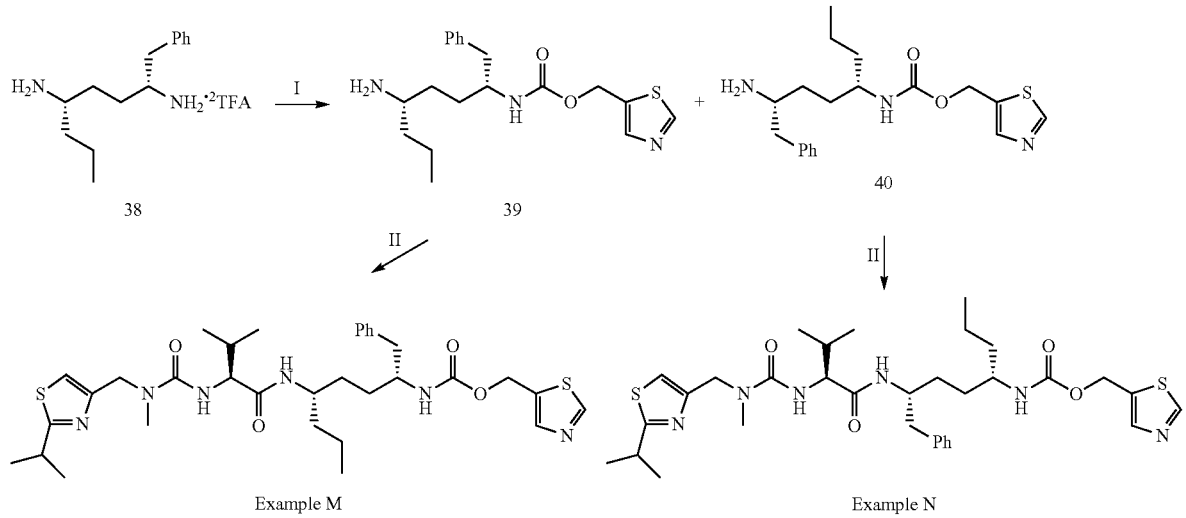

Scheme 15

Example M   Example N

I. carbonate 16, DIPEA, MeCN; II. acid 29, EDC, HOBt, DIPEA, THF

Compounds 39 and 40

Compound 38 (0.382 g, 0.852 mmol) was diluted in MeCN (10 mL) and N,N-diisopropylethylamine (0.60 mL, 3.41 mmol) was added, followed by a solution of Compound 16 in MeCN (1.5 mL). The clear, yellow solution was allowed to age at room temperature for 4 h and the volatiles were removed in vacuo. The residue was taken up in a 3/1 CHCl$_3$/IPA (v/v, 13 mL) and treated with saturated Na$_2$CO$_3$ (3 mL). The resulting suspension was diluted with H$_2$O (3 mL), and the aqueous phase thoroughly extracted with 3/1 CHCl$_3$/IPA. The combined organic layers were dried over a reagents: Compound 40 (0.055 g, 0.152 mmol); Compound 29 (0.92 mL of 0.2 M THF solution, 0.183 mmol); THF (1 mL); DIPEA (0.040 mL, 0.228 mmol); HOBt (0.025 g, 0.182 mmol); EDC (0.032 mL, 0.182 mmol). 0.087 g (87%) of Example N was isolated as a colorless film (LC/MS m/z: 657.2 (M+H)$^+$; $^1$H-NMR CDCl$_3$, 300 MHz) δ 8.84 (s, 1H); 7.86 (s, 1H); 7.27-7.04 (m, 5H); 7.04 (s, 1H); 6.28 (br s, 1H); 6.12 (br s, 1H); 5.25 (m, 2H); 5.11 (d, J=9.0 Hz, 1H); 4.62-4.32 (m, 2H); 4.19 (m, 1H); 4.01 (br s, 1H); 3.53 (m, 1H); 3.10-2.90 (m, 3H); 2.72 (d, J=6.0 Hz, 2H); 2.29 (m, 1H); 1.65-1.18 (m, 8H); 1.39 (d, J=6.9 Hz, 6H); 1.00-0.78 (m, 9H).

Preparation of Examples O and P

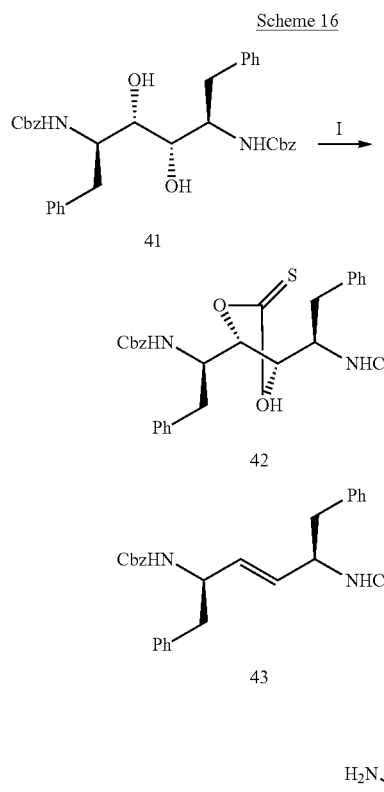

Scheme 16

I. TCDI/THF/65° C.; II. P(OEt)₃/160° C.; III. H₂, 10% Pd/C.

Compound 41

Compound 41 was prepared following the procedure described in *J. Org. Chem.* 1996, 61, 444-450.

Compound 42

A mixture of Compound 41 (1.73 g, 3 mmol) and 1,1'-thiocarbonyldiimidazole (1.14 g, 6.1 mmol) in THF (60 mL) was heated at 65° C. for 72 hours. Solvent was removed under reduced pressure. The mixture was diluted with EtOAc, and washed successively with 1N HCl, water, and brine, and dried over MgSO₄. Purification by flash column chromatography (silica gel, hexanes/EtOAc=1/1) gave Compound 42 (980 mg). m/z: 611.1 (M+H)⁺.

Compound 43

A mixture of Compound 42 (980 mg) and triethyl phosphite (10 mL) was heated at 160° C. for 14 hours. The excess reagents were removed under reduced pressure. Recrystallization from a mixture of hexanes (11 mL) and EtOAc (3.6 mL) gave Compound 57 (580 mg). m/z: 557.3 (M+Na)⁺.

Compound 44

A mixture of Compound 43 (580 mg) in i-PrOH/EtOAc (12 mL/12 mL) was hydrogenated under high pressure (100 psi) for 24 hours in the presence of 10% Pd/C (200 mg). Celite was added and the mixture was stirred for 5 minutes. Filtration and evaporation gave Compound 44 (285 mg). m/z: 269.1 (M+H)⁺.

The skilled practitioner will recognize that the procedure outlined in Scheme 16 can be used to prepare a variety of 1,4-substituted 1,4-diamines analogous to Compound 44. For example, an amine-protected 2,3-dihydroxy-1,4-diamine analogous to Compound 41 can be prepared:

Analogs of Compound 41

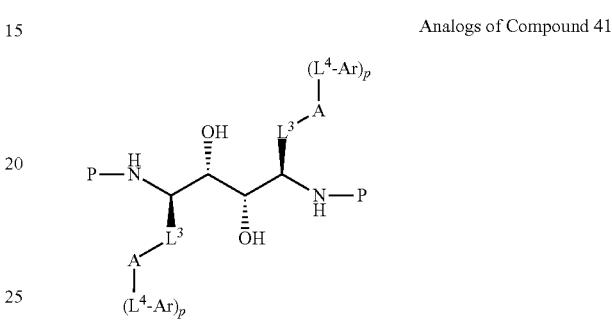

wherein $L^3$, A, Ar, and P are as defined herein, and protecting group "P" is any amine protecting group described in described in *Protective Groups in Organic Synthesis*, Theodora W. Greene and Peter G. M. Wuts (John Wiley & Sons, Inc., New York, 1999, ISBN 0-471-46019-9). The analogs of Compound 41 can then be transformed, according to the methods outlined in Scheme 16, to form analogs of Compound 42:

Analogs of Compound 42

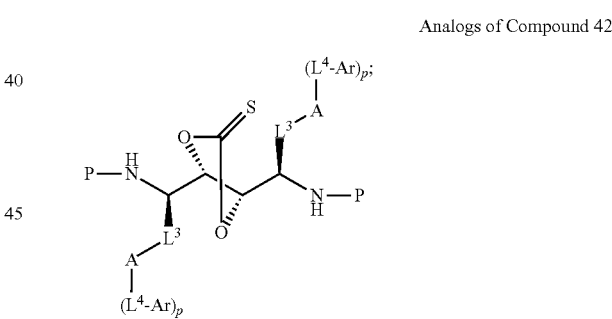

analogs of Compound 43:

Analogs of Compound 43

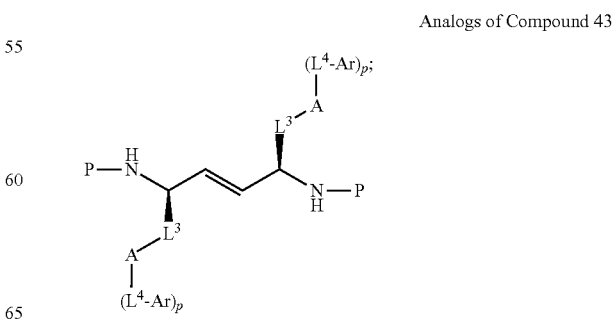

and analogs of Compound 44:

Analogs of Compound 44

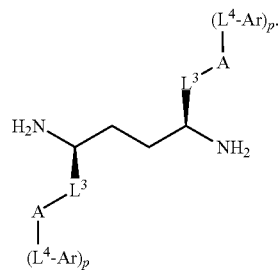

It will also be recognized that stereochemical configurations other than those shown (i.e., enantiomers or diasteriomers) can be prepared by the selection of analogs of Compound 41 having the appropriate stereochemical configuration at the chiral centers.

Scheme 17

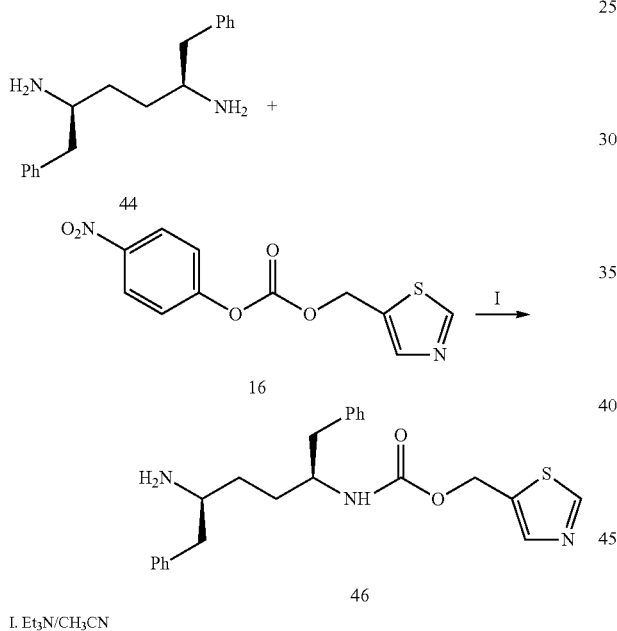

I. Et₃N/CH₃CN

Compound 46

To the solution of Compound 45 (950 mg, 3.5 mmol) in CH₃CN (36 mL) at 0° C. was added Compound 16 (892 mg, 3.2 mmol), followed by diisopropylethylamine (1.2 mL, 7 mmol). The mixture was stirred for 12 hours at 25° C. The mixture was diluted with EtOAc, and washed successively with saturated Na₂CO₃, water, and brine. Purification by flash column chromatography (silica gel, 100% EtOAc to CH₂Cl₂/MeOH=4/1) gave Compound 46 (770 mg). m/z: 410.1 (M+H)⁻.

The skilled practitioner will recognize that the procedure outlined in Scheme 17 can be used to prepare a variety of compounds analogous to Compound 46. For example, 1,4-diamines analogous to Compound 44 can be prepared as discussed above:

Analogs of Compound 44

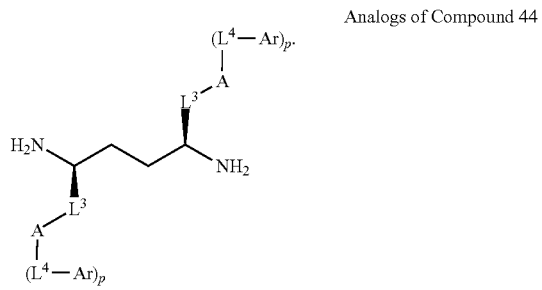

The analogs of Compound 44 can then be reacted with analogs of Compound 16:

Analogs of Compound 16

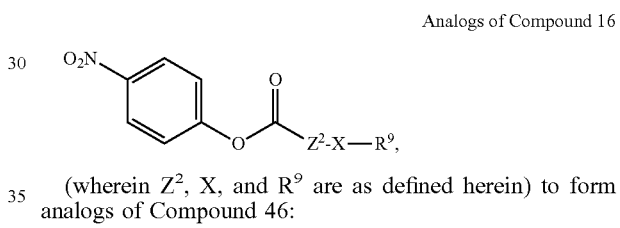

(wherein Z², X, and R⁹ are as defined herein) to form analogs of Compound 46:

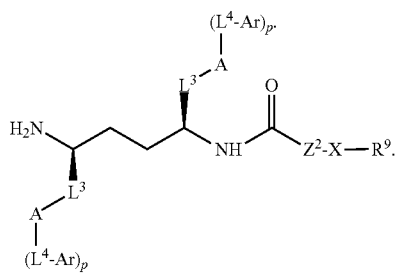

It will also be recognized that stereochemical configurations other than those shown (i.e., enantiomers or diasteriomers) can be prepared by the selection of analogs of Compound 44 having the appropriate stereochemical configuration at the chiral centers.

Scheme 18

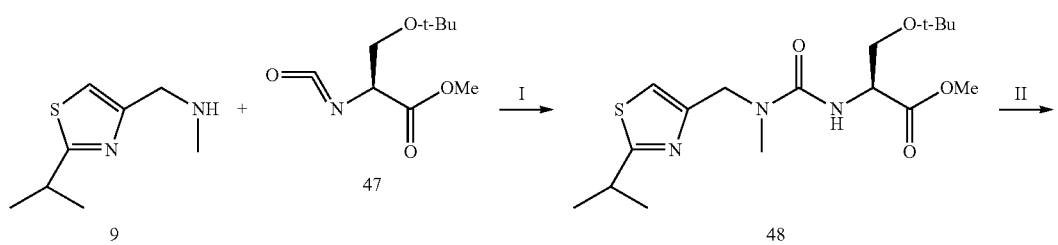

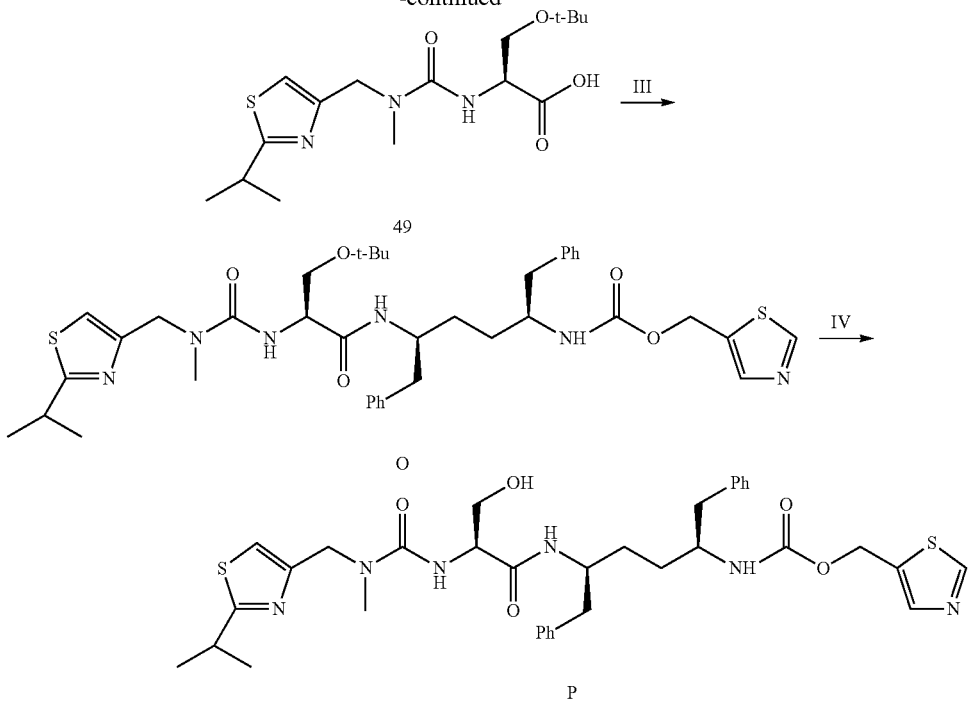

I. $CH_2Cl_2/25°$ C.; II. a. $NaOH/dioxane/H_2O$; b. HCl; III. amine 46/EDC/HOBt; IV. a. TFA; b. NaOH Compound 47

Compound 47 is commercially available from TCI.

Compound 48

To a solution of Compound 9 (500 mg, 3 mmol) in $CH_2Cl_2$ (3 mL) was added Compound 47 (500 mg, 2.5 mmol). The mixture was stirred for 14 hours. Purification by flash column chromatography (hexanes/EtOAc=1/1.5) gave Compound 48 (242 mg). m/z: 372.1 $(M+H)^+$.

Compound 49

To a solution of Compound 48 (240 mg, 0.65 mmol) in dioxane (4 mL) and water (4 mL) was added sodium hydroxide (40 mg, 1 mmol). The mixture was stirred for 1 hour and acidified with 4 N HCl in dioxane (0.25 mL, 1 mmol). The mixture was extracted with EtOAc and organic phase was dried with $MgSO_4$. Concentration gave Compound 49 (200 mg). m/z: 356.2 $(M-H)^+$.

Example O

To a solution of corresponding acid 49 (30 mg, 0.08 mmol) and Compound 46 (22 mg, 0.05 mmol) in THF (1 mL) were added HOBt (15 mg, 0.11 mmol), EDC (20 μL, 0.11 mmol), and disopropylethylamine (0.2 mL). The mixture was stirred for 12 hours and concentrated. Purification by flash column chromatography (hexanes/EtOAc=1/5 to 0/100) gave Example O (17 mg). m/z: 749.3 $(M+H)^+$.

Example P

To Example O (17 mg) was added TFA (2 mL). The mixture was stirred for 3 hours and concentrated. The mixture was diluted with THF (2 mL) and 1.0 N NaOH solution was added until pH 11. The mixture was stirred for 10 minutes, and extracted with EtOAc. The organic phase was washed with water and brine. Purification by flash column chromatography (EtOAc) gave Example P (12 mg). $^1$H-NMR ($CDCl_3$) δ 8.76 (1H, s), 7.79 (1H, s), 7.25-6.9 (11H, m), 6.51 (1H, broad), 5.42 (1H, m), 5.18 (2H, m), 4.42 (2H, m), 4.22 (1H, m), 4.10 (1H, m), 3.95 (1H, m), 3.79 (1H, m), 3.58 (1H, m), 3.23 (1H, m), 2.93 (3H, s), 2.9-2.5 (4H, m), 1.6-1.2 (10H, m); m/z: 693.2 $(M+H)^+$.

Preparation of Examples Q, R, and S

Scheme 19

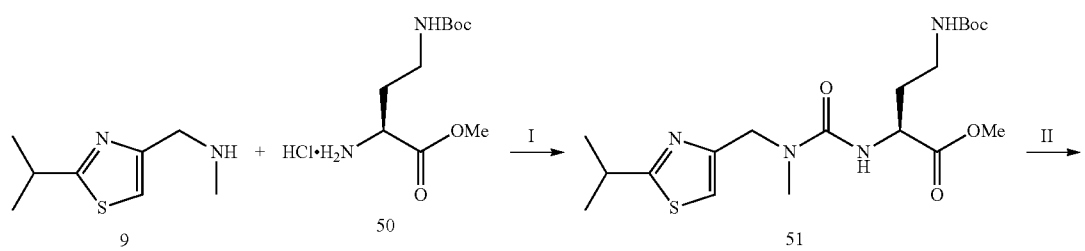

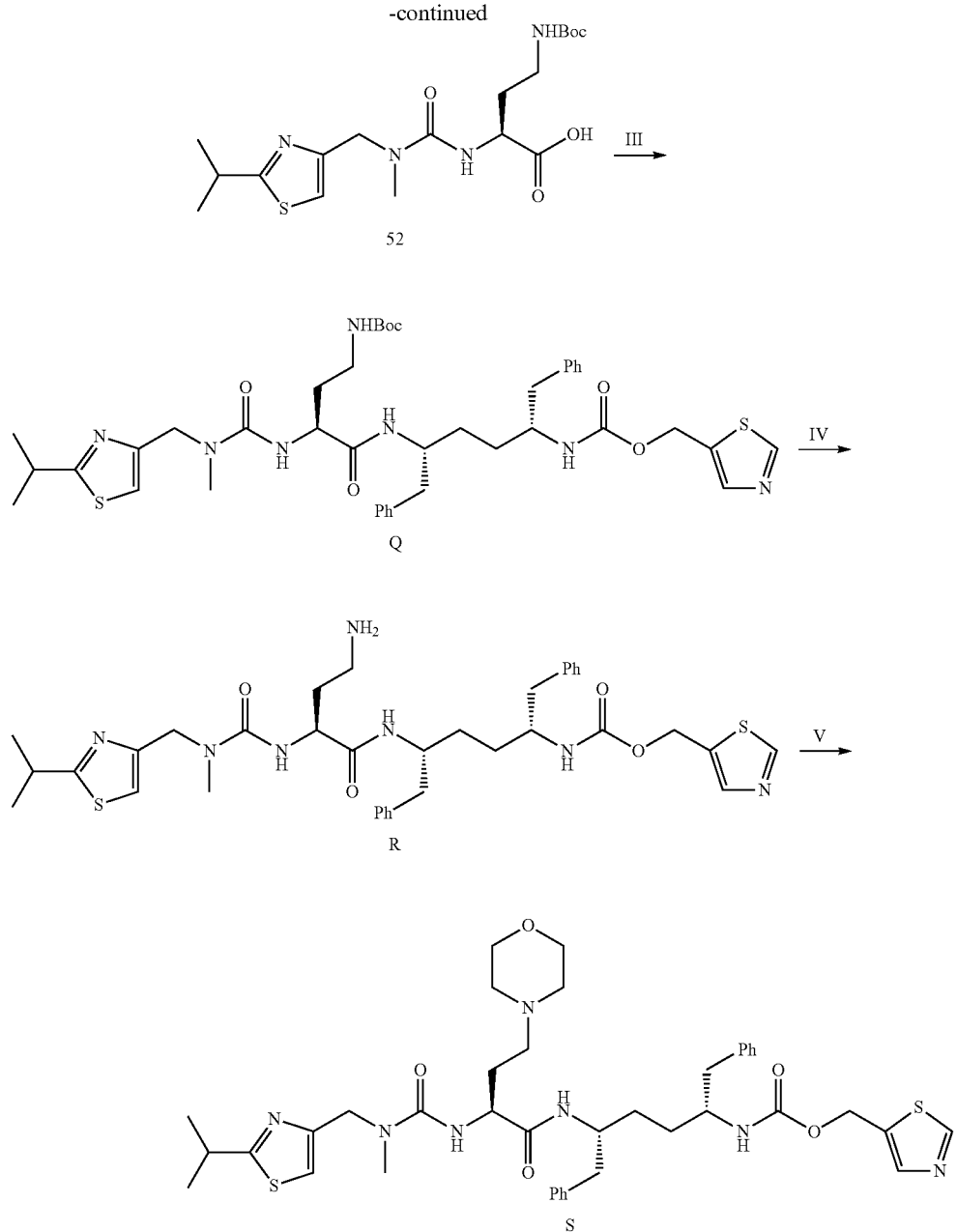

I. CDI, DIPEA, CH$_2$Cl$_2$; II. LiOH, THF/H$_2$O; III. Cmpd. 8, DIPEA, EDC, HOBt, THF; IV. a. HCl/dioxane; b. Na$_2$CO$_3$; V. (BrCH$_2$CH$_2$)$_2$O, NaHCO$_3$, DMF Compound 50

Compound 50 is commercially available from Chem Impex International, and used without further purification.

Compound 51

Compound 50 (7.0 g, 26.0 mmol) was dissolved in CH$_2$Cl$_2$ (330 mL) and 1,1-carbonyldiimidazole (4.22 g, 26.0 mmol) was added, followed by i-Pr$_2$NEt (19 mL, 104 mmol). The solution was stirred at 25° C. for 12 hours. Compound 9 (4.44 g, 26.0 mmol) was dissolved in 20 mL of CH$_2$Cl$_2$ and added to the reaction mixture. The solution was stirred at 25° C. for 7 hours. The solvent was removed in vacuo and the residue was diluted with ethyl acetate and washed with water and brine. The organic layers were dried (Na$_2$SO$_4$), filtered, and evaporated. Purification by Combi-flash® (stationary phase: silica gel; eluent: 66-100% EtOAc/Hexane gradient) gave Compound 51 (7.34 g). m/z: 429.0 (M+H)$^+$.

Compound 52

Compound 51 (7.34 g, 17.13 mmol) was dissolved in THF (90 mL) and 1M aqueous LiOH (35 mL) was added. The mixture was stirred at 25° C. for 0.5 hour. The reaction was quenched with 1M HCl (51 mL) and the mixture was adjusted to pH 2. The mixture was extracted with ethyl acetate. The organic layers were dried over Na$_2$SO$_4$, filtered, and evaporated to provide Compound 52 (7.00 g). The recovered Compound 52 was used in the next step without further purification. m/z: 415.0 (M+H)$^+$.

The skilled practitioner will recognize that the procedure outlined in Scheme 19 can be used to prepare a variety of compounds analogous to Compounds 51 and 52. For example, amines analogous to Compound 9 can be reacted with the appropriate amino ester analogous to Compound 50:

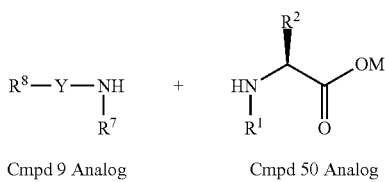

Cmpd 9 Analog        Cmpd 50 Analog to form compounds analogous to Compound 51, which are further reacted to form compounds analogous to Compound 52:

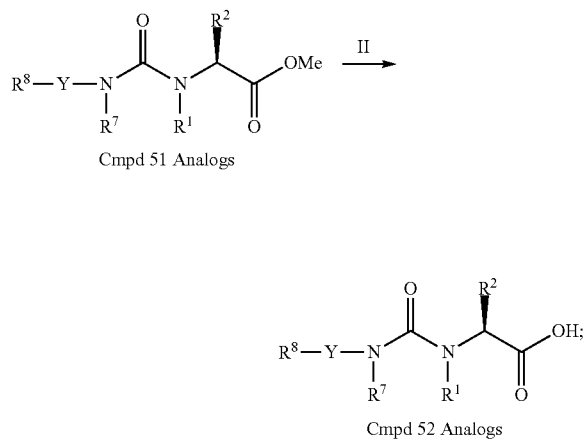

Cmpd 51 Analogs

Cmpd 52 Analogs wherein $R^1$, $R^2$, $R^7$, $R^8$ and Y are as defined herein.

It will also be recognized that stereochemical configurations other than those shown (i.e., enantiomers or diastereomers) can be prepared by the selection of analogs of Compound 50 having the appropriate stereochemical configuration at the chiral center.

Example O

Compound 52 (2.57 g, 6.21 mmol) was dissolved in THF (67 mL). Compound 8 (2.10 g, 5.13 mmol) was added, followed by HOBt (1.04 g, 7.70 mmol), i-Pr$_2$NEt (3.67 mL, 20.52 mmol), and EDC (1.82 mL, 10.26 mmol). The mixture was stirred at 25° C. for 12 hours. The solvent was removed under reduced pressure. The residue was diluted with ethyl acetate and washed sequentially with saturated aqueous Na$_2$CO$_3$, water, and brine. The organic phase was dried over Na$_2$SO$_4$, filtered, and evaporated. Purification by flash column chromatography (stationary phase: silica gel; eluent: 5% iPrOH/CH$_2$Cl$_2$) gave Example Q (3.02 g). m/z: 806.2 (M+H)$^+$.

Example R

Example Q (3.02 g, 3.74 mmol) was suspended in 4.0 N HCl/dioxane solution (30 mL) and stirred at 25° C. for 3 hours. Solvent was removed under reduced pressure and Et$_2$O was poured into the reaction mixture. The resulting suspension was stirred vigorously for 1.5 hours. The solid was allowed to settle and the ether layer was decanted. Washing of the precipitate with Et$_2$O was repeated two more times. The product was dried in vacuo to afford a white solid (3.18 g, quantitative yield). Saturated aqueous Na$_2$CO$_3$ solution was added to above solid (3.18 g) with stirring until solid disappeared. The aqueous solution was extracted with ethyl acetate. The organic phases were dried over Na$_2$SO$_4$, filtered, and evaporated to afford Example R as a yellow foam (2.44 g, 81%). The recovered Example R was used without further purification in the next step. m/z: 706.1 (M+H)$^+$.

Example S

Method I

Example R (1.00 g, 1.42 mmol) was dissolved in DMF (20 mL) and bromoethyl ether (196 µL, 1.56 mmol) was added dropwise, followed by NaHCO$_3$ (0.239 g, 2.84 mmol). The reaction mixture was stirred at 25° C. for 2 hours. The solution was heated to 65° C. and stirred for 12 hours. The solvent was removed under reduced pressure. The residue was diluted with EtOAc and washed sequentially with water and brine. The organic phase was dried over Na$_2$SO$_4$ filtered, and evaporated. Purification by reverse-phase HPLC (Phenomenex Synergi® Comb-HTS column, eluent: 5-95% CH$_3$CN/water) gave Compound 70 (580 mg, 53%). $^1$H NMR (CDCl$_3$) δ 8.98 (s, 1H); 7.90 (s, 1H); 7.75 (m, 1H); 7.40-7.00 (m, 11H), 6.55 (br s, 1H); 5.58 (m, 1H); 5.28, 5.19 (d$_{AB}$, J=14 Hz, 2H); 4.70-4.37 (m, 3H); 3.99 (m, 5H); 3.76 (br s, 1H); 3.65-3.30 (m, 3H); 2.97 (m, 5H); 2.90-2.60 (m, 6H); 2.28 (br s, 1H); 1.91 (br s, 1H); 1.60-1.30 (m, 10H). m/z: 776.2 (M+H)$^+$.

Method II

Scheme 20

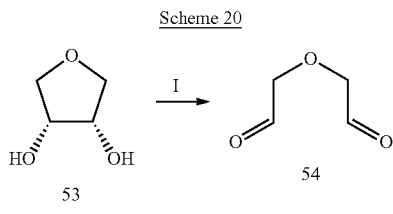

I. NaIO$_4$, H$_2$O

Compound 54

Compound 54 was prepared following the procedure described in *J. Med. Chem.* 1993, 36, 1384 (herein incorporated by reference in its entirety for all purposes).

To solution of Compound 53 (0.550 g, 5.28 mmol) (Sigma-Aldrich) in H$_2$O (8.8 mL) at 0° C. was added NaIO$_4$ (1.016 g, 4.75 mmol). The mixture was allowed to slowly warm to 25° C. and stirred for 12 hours. Solid NaHCO$_3$ was added to the reaction mixture until pH 7. CHCl$_3$ (16 mL) was added and the mixture was allowed to stir for 5 minutes. The mixture was filtered and the solid was washed with CHCl$_3$ (6 mL). The combined H$_2$O/CHCl$_3$ solution was used directly in the next step without further purification.

Scheme 21

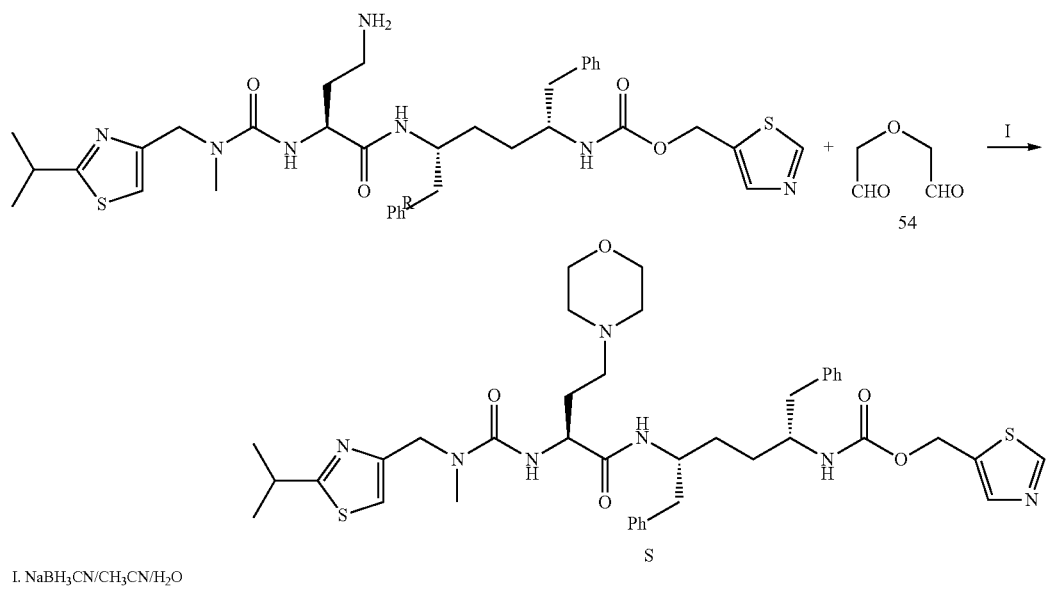

I. NaBH₃CN/CH₃CN/H₂O

Example S

To a solution of Example R (70 mg, 0.1 mmol) in CH₃CN (5 mL) was added sodium cyanoborohydride (50 mg) in water (5 mL). To the above mixture was added a solution of dialdehyde Compound 54 (0.6 mmol) in CHCl₃/H₂O (4 mL/1 mL). The mixture was stirred for 12 hours, and basified with saturated Na₂CO₃ solution. The mixture was extracted with EtOAc, and organic phase was washed with water and brine, and dried over. Na₂SO₄. Purification by reverse-phase HPLC (Phenomenex Synergi® Comb-HTS column) gave Example S (57 mg).

Method III

Scheme 22

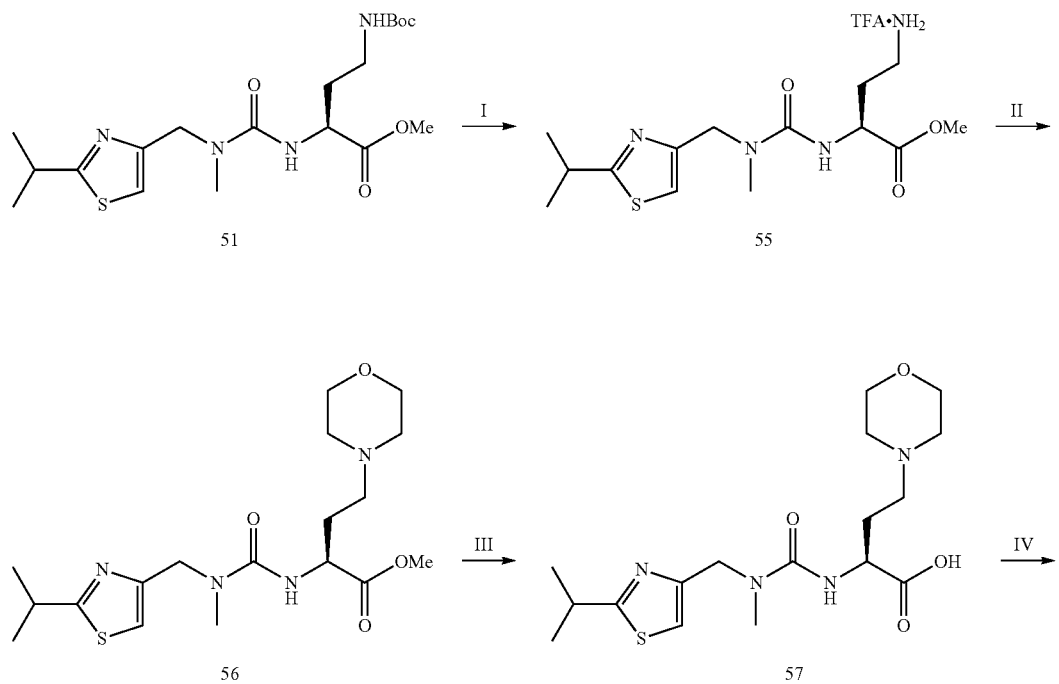

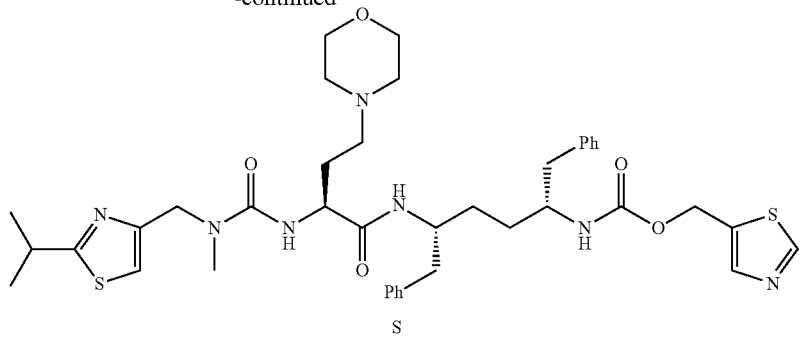

I. TFA, CH₂Cl₂; II. Cmpd 54, NaBH₃CN, H₂O/CH₃CN; III. LiOH, THF/H₂O; IV. amine Cmpd 8, DIPEA, EDC, HOBt, THF Compound 55

Compound 51 (0.28 g, 0.66 mmol) was dissolved in CH₂Cl₂ (4 mL) and TFA (1 mL) was added dropwise. The reaction was allowed to stir at 25° C. for 1 hour. The solvent was removed under reduced pressure to afford Compound 55 (0.39 g). m/z: 329.0 (M+H)⁺.

Compound 56

To a solution of Compound 55 (0.39 g, 0.89 mmol) in CH₃CN (45 mL) was added NaBH₃CN (0.45 g, 7.12 mmol) and H₂O (45 mL). A solution of Compound 54 (0.55 g, 5.34 mmol) in CHCl₃/H₂O (40 mL) was added. The mixture was stirred at 25° C. for 12 hours. The reaction mixture was made basic with saturated aqueous Na₂CO₃ and extracted sequentially with ethyl acetate and dichloromethane. The combined organic layers were washed sequentially with H₂O and brine, dried over Na₂SO₄, filtered, and evaporated. Purification by Combiflash® (stationary phase: silica gel; eluent: 0-10% MeOH/CH₂Cl₂ gradient) gave Compound 56 (0.17 g). m/z: 399.1 (M+H)⁺.

Compound 57

Compound 56 (377 mg, 0.95 mmol) was dissolved in THF (4 mL) and 1M aqueous LiOH (1.90 mL) was added. The mixture was stirred at 25° C. for 1 hour. The reaction was neutralized with 1M HCl. THF was removed under reduced pressure and the aqueous solution was lyophilized to afford Compound 57 (365 mg). The material was used directly in the next step without further purification. m/z: 385.1 (M+H)⁺.

Example S

Example S (185 mg, 57%) was prepared following the same procedure as for Example Q, except that Compound 57 (160 mg, 0.42 mmol) was used instead of Compound 52. mass m/z: 776.2 (M+H)⁺.

The skilled practitioner will recognize that the procedure outlined in Scheme 22 can be used to prepare a variety of compounds analogous to Compounds 55-57:

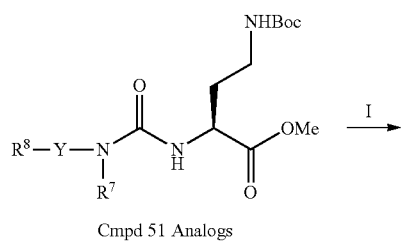

Cmpd 51 Analogs

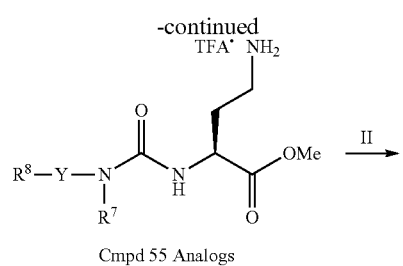

Cmpd 55 Analogs

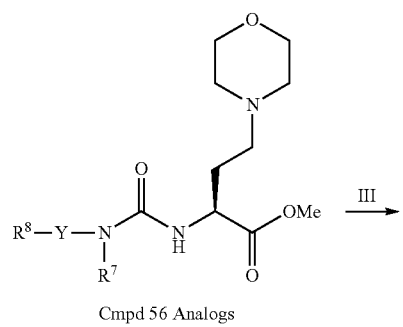

Cmpd 56 Analogs

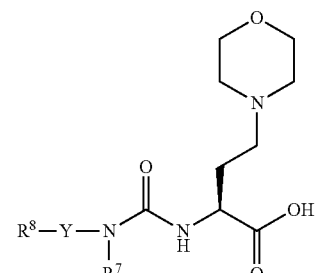

Cmpd 57 Analogs

I. TFA, CH₂Cl₂; II. Ex. R, NaBH₃CN, H₂O/CH₃CN; III. LiOH, THF/H₂O wherein R⁷, R⁸ and Y are as defined herein.

It will also be recognized that stereochemical configurations other than those shown (i.e., enantiomers or diastereomers) can be prepared by the selection of analogs of Compound 51 having the appropriate stereochemical configuration at the chiral center.

Method IV

Scheme 23

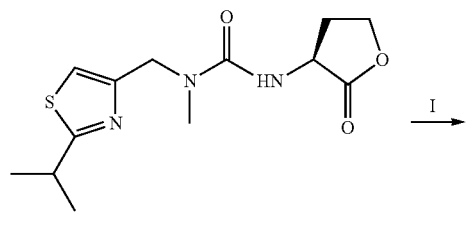

122

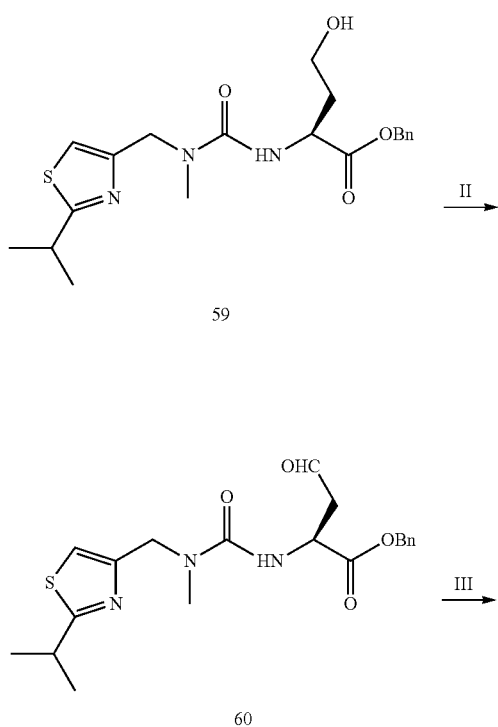

59

60

61

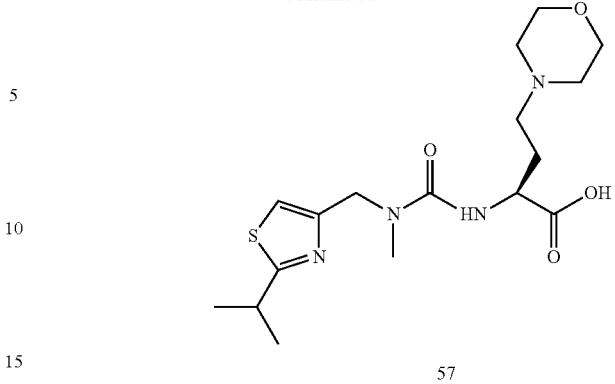

57

I. a. NaOH/H2O; b. BnBr; II. SO3/pyridine; III. morpholine/NaBH(OAc)3; IV. a. NaOH; b. HCl Compound 59

To a solution of Compound 122 (33 g, 112 mmol) (see Scheme 69) in ethanol (366 mL) at 0° C. was added a solution of sodium hydroxide (4.7 g, 117 mmol) in water (62 mL). The mixture was stirred for one hour at 25° C., and solvents were removed under reduced pressure. The mixture was coevaporated with ethanol (3×400 mL), and dried at 60° C. for two hours under high vacuum to give a white solid. To the solution of above solid in DMF (180 mL) was added benzyl bromide (16.2 mL, 136 mmol). The mixture was stirred for 16 hours under darkness, and was quenched with water (300 mL). The mixture was extracted with EtOAc (4×300 mL). The combined organic phase was washed with water (5×) and brine, and dried over $Na_2SO_4$. Concentration gave Compound 59 (48 g), which was used in the next step without further purification.

Compound 60

A mixture of Compound 59 (33 g, 74 mmol) in DMSO (225 mL) and $Et_3N$ (36 mL) was stirred for 30 minutes. The mixture was cooled to 0-10° C., $SO_3$-pyridine (45 g) was added, and the stirring was continued for 60 minutes. Ice (300 g) was added, and the mixture was stirred for 30 minutes. EtOAc (300 mL) was added and sat. $Na_2CO_3$ was added until pH was 9~10. The organic phase was separated from the aqueous phase, and the aqueous phase was extracted with EtOAc (2×300 ml). The combined organic phases were washed with sat $Na_2CO_3$ (2×), water (3×), and brine. The mixture was dried over $Na_2SO_4$ and concentrated to give Compound 60 (32 g), which was used directly in next step without further purification.

Compound 61

To a solution of Compound 60 (32 g) in $CH_3CN$ (325 mL) was added morpholine (12.9 mL, 148 mmol), with a water bath around the reaction vessel, followed by HOAc (8.9 mL, 148 mmol), and $NaBH(OAc)_3$ (47 g, 222 mmol). The mixture was stirred for 12 hours. $CH_3CN$ was removed under reduced pressure, and the mixture was diluted with EtOAc (300 mL). Sat. $Na_2CO_3$ was added until the pH was 9~10. The organic phase was separated from the aqueous phase, and the aqueous phase was extracted with EtOAc (2×300 mL). The combined organic phases were washed with sat $Na_2CO_3$ (2×), water (1×), and brine (1×). The mixture was dried over $Na_2SO_4$. The resulting residue was concentrated and purified by silica gel column chromatography (EtOAc to DCM/iPrOH=10/1) to give Compound 61 (30 g).

Compound 57

To a solution of Compound 61 (26.5 g, 56 mmol) in ethanol (160 mL) at 0° C. was added a solution of sodium hydroxide (2.5 g, 62 mmol) in water (30 mL). The mixture was stirred for one hour at 25° C., and solvents were removed under reduced pressure. The mixture was diluted with water (200 mL), and was washed with CH$_2$Cl$_2$ (6×100 mL). The water phase was acidified with 12 N HCl (5.2 mL), and was dried under reduced pressure to give Compound 57 (22 g).

Example S

Compound 57 was converted to Example S using the procedure described in Method III, above.

Preparation of Compounds T and U stirring until the solid disappeared. The aqueous solution was extracted with ethyl acetate. The organic phases were dried over Na$_2$SO$_4$, filtered, and evaporated to afford Example R as a yellow foam (2.44 g, 81%). This material was used without further purification in the next step. m/z: 706.1 (M+H)$^+$.

Example R (300 mg, 0.43 mmol) was dissolved in THF (5.5 mL). Acetic acid (37 μL, 0.64 mmol) was added, followed by HOBt (85 mg, 0.64 mmol), iPr$_2$NEt (304 μL, 1.70 mmol), and EDC (151 μL, 0.85 mmol). The reaction mixture was allowed to stir at 25° C. for 12 hours. The solvent was removed under reduced pressure. The residue was diluted with EtOAc and washed sequentially with saturated aqueous Na$_2$CO$_3$, water, and brine. The organic phase was dried over Na$_2$SO$_4$, filtered, and evaporated.

Scheme 24

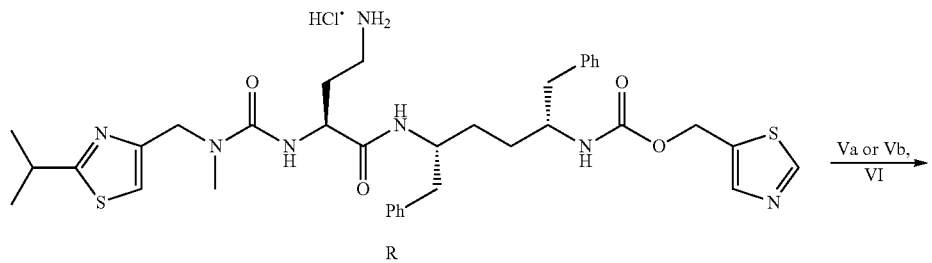

Va. CH$_3$COCl, DIPEA, CH$_2$Cl$_2$; Vb. CH$_3$COOH, DIPEA, EDC, HOBt, THF; VI. MsCl, DIPEA, CH$_2$Cl$_2$;
Compounds: Ex. T: X = NHAc
Ex. U: X = NHMs Example T Method I The hydrochloride salt of Example R (100 mg, 0.13 mmol) was suspended in CH$_2$Cl$_2$ (2 mL) and dissolved by addition of iPr$_2$NEt (69 μL). Acetyl chloride (11 μL) was added dropwise and the mixture was allowed to stir at 25° C. for 4 hours.

The solvent was removed in vacuo. Purification of the residue by flash column chromatography (stationary phase: silica gel; eluent: 8% iPrOH/CH$_2$Cl$_2$) gave Example T (39 mg, 40%). m/z: 748.2 (M+H)$^+$. $^1$H NMR (CDCl$_3$) δ 8.85 (s, 1H); 7.87 (s, 1H); 7.73 (s, 1H); 7.40-7.00 (m, 13H); 6.45 (br s, 1H); 5.70 (m, 1H); 5.32, 5.22 (d$_{AB}$, J=13 Hz, 2H); 4.51 (s, 2H); 4.20-3.90 (m, 4H); 3.78 (m, 1H); 3.38 (m, 2H); 3.20-2.50 (m, 8H); 1.95 (s, 4H); 1.82 (m, 2H); 1.41 (m, 6H).

Method II

Saturated aqueous Na$_2$CO$_3$ solution was added to the hydrochloride salt of Example R (3.18 g, 3.46 mmol) while Purification by Combiflash® (stationary phase: silica gel; eluent: 10% MeOH/CH$_2$Cl$_2$) gave Example T (249 mg, 77%). m/z: 748.2 (M+H)$^+$.

Example U

Example R (100 mg, 0.13 mmol) was suspended in CH$_2$Cl$_2$ (2 mL) and dissolved by addition of iPr$_2$NEt (69 μL). Methanesulfonyl chloride (12 μL) was added dropwise and the mixture was allowed to stir at 25° C. for 4 hours. The solvent was removed in vacuo. Purification of the residue by flash column chromatography (stationary phase: silica gel; eluent: 8% iPrOH/CH$_2$Cl$_2$) gave Example U (55 mg, 54%). m/z: 784.2 (M+H)$^+$. $^1$H NMR (CDCl$_3$) δ 8.90 (s, 1H); 7.88 (s, 1H); 7.40-7.00 (m, 12H); 6.54 (br s, 1H); 6.19 (br s, 1H); 5.25 (s, 2H); 4.53 (s, 2H); 4.38 (m, 1H); 4.12 (m, 1H); 3.79 (m, 1H); 3.79 (m, 1H); 3.48 (m, 1H); 2.99 (s, 3H); 2.90 (m, 3H); 2.73 (m, 6H); 2.00 (m, 1H); 1.79 (m, 1H); 1.60-1.18 (m, 10H).

Preparation of Examples V, W, X and Y

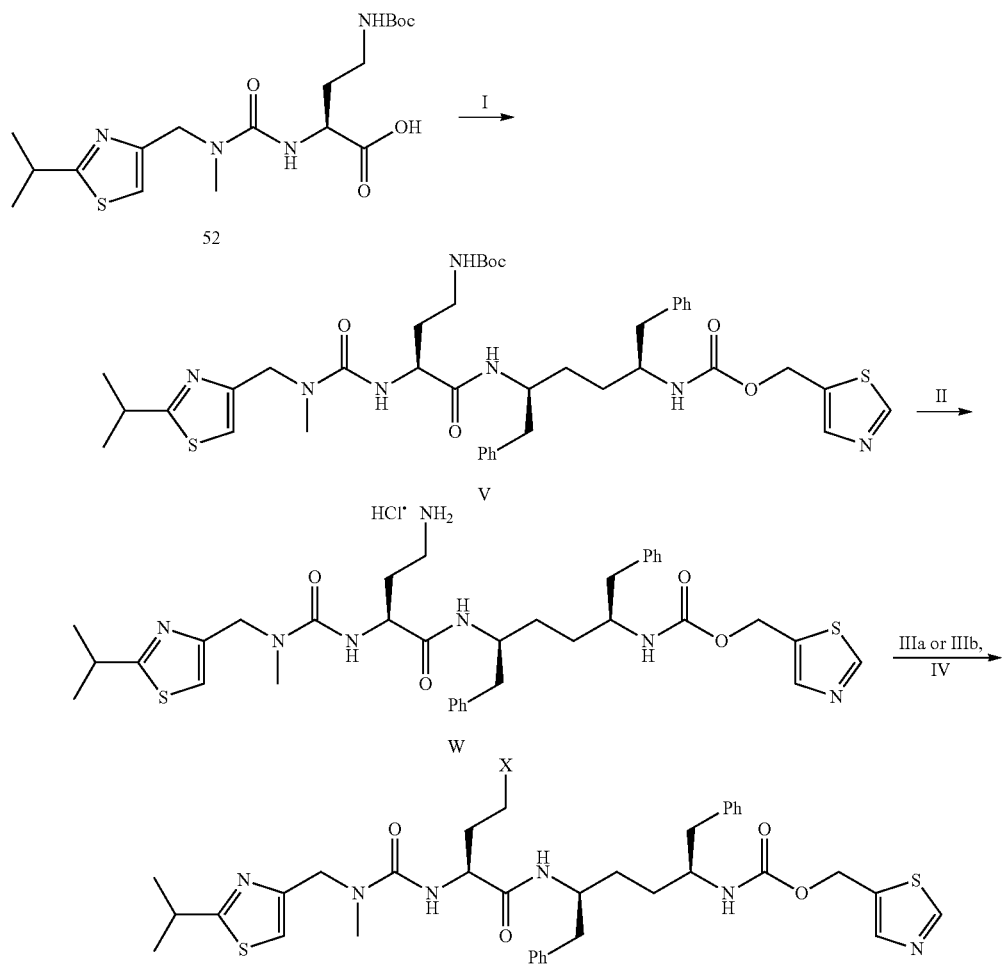

I. Cmpd. 46, DIPEA, EDC, HOBt, THF; II. HCl/dioxane; IIIa. CH₃COCl, DIPEA, CH₂Cl₂; IIIb. CH₃COOH, DIPEA, EDC, HOBt, THF; IV. MsCl, DIPEA, CH₂Cl₂
Compounds: Ex. X: X = NHAc
Ex. Y: X = NHMs

Example V

Example V (692 mg) was prepared following the same procedure used for preparing Example Q, except that Compound 46 was used instead of Compound 8. m/z: 8061 (M+H)$^+$.

Example W

Example W (770 mg, quantitative yield) was prepared following the same procedure for Example R except that Example V was used instead of Example Q. m/z: 706.2 (M+H)$^+$. $^1$H NMR (CD$_3$OD) δ 9.86 (s, 1H); 8.23 (s, 1H); 7.66 (s, 1H); 7.40-7.00 (m, 10H); 5.29, 5.17 (d$_{AB}$, J=13 Hz, 2H); 4.80-4.60 (m, 2H); 4.18 (s, 2H); 4.26 (m, 2H); 3.67 (br s, 1H); 3.55 (m, 2H); 3.03 (m, 3H); 2.90-2.60 (m, 8H); 2.53 (s, 2H); 2.00-1.80 (m, 2H); 1.85-1.30 (m, 10H).

Example X

Method I

Example X (107 mg, 55%) was prepared following the Method I procedure for Example T except that Example W was used instead of Example R. m/z: 748.2 (M+H)$^+$. $^1$H NMR (CDCl$_3$) δ 8.80 (s, 1H); 7.85 (s, 1H); 7.40 (m, 1H); 7.38-7.00 (m, 10H), 6.94 (s, 1H); 6.30 (m, 2H); 5.75 (m, 1H); 5.30, 5.23 (d$_{AB}$, J=13 Hz, 2H); 4.54, 4.46 (d$_{AB}$, J=8 Hz, 2H); 4.20-3.90 (m, 2H); 3.74 (br s, 1H); 3.46 (br s, 1H); 3.28 (m, 1H); 2.98 (s, 3H); 2.83 (m, 3H); 2.72 (m, TH); 2.62 (m, 1H); 2.05-1.20 (m, 15H).

Method II

Example X (205 mg, 65%) was prepared following the Method II procedure for Example T except that Example W was used instead of Example R. m/z: 748.2 (M+H)$^+$.

Example Y

Example Y (106 mg, 50%) was prepared following the same procedure for Example U, except that Example W was used instead of Example R. m/z: 784.2 (M+H)+. 1H NMR (CDCl3) δ 8.81 (s, 1H); 7.85 (s, 1H); 7.40-7.05 (m, 10H), 6.98 (s, 1H); 6.22 (br s, 1H); 5.78 (s, 1H); 5.25 (m, 4H); 4.29 (m, 2H); 4.33 (br s, 1H); 4.12 (br s, 1H); 3.77 (br s, 1H); 3.10 (br s, 1H); 2.98 (s, 3H); 2.90 (s, 3H); 2.73 (m, 6H); 2.00-1.20 (m, 12H).

Preparation of Examples Z-AD

Scheme 26

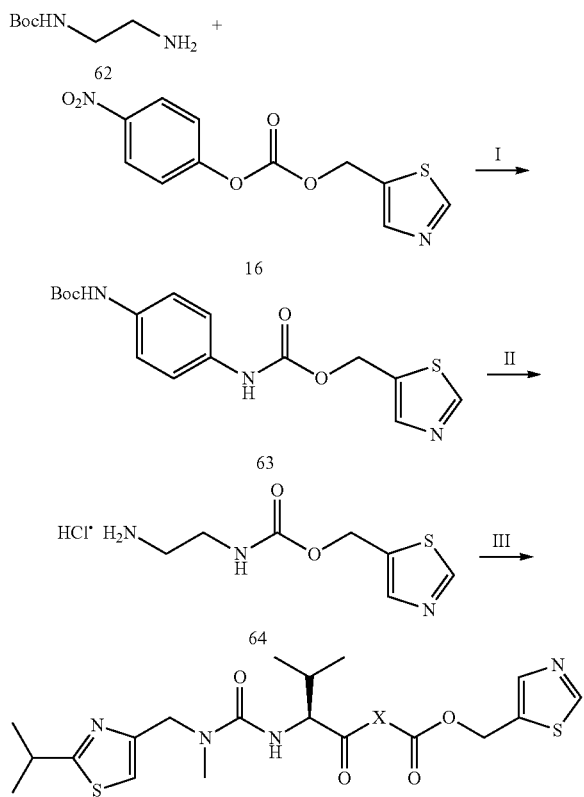

Examples:
Z: X = NH(CH2)2NH
AA: X = NH(CH2)3NH
AB: X = 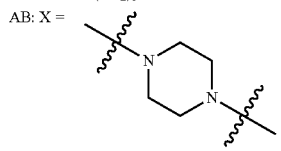

AC: X = 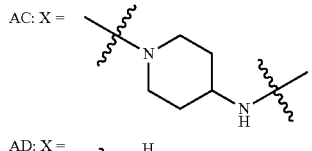

AD: X = 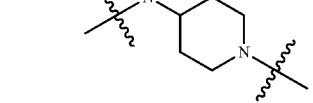

I. DIPEA, CH3CN; II. HCl/dioxane, EtOAc; III. acid 29, DIPEA, EDC, HOBt, THF

Compound 62

Tert-butyl 2-aminoethylcarbamate (62) is commercially available from Aldrich, and was used without further purification.

Compound 63

To a solution of Compound 62 (2M mmol) in CH3CN (15 mL) was added Compound 16 (1.82 mmol), followed by the addition of N,N-diisopropylethylamine (0.61 mL). The mixture was stirred at 25° C. for 12 hours. The solvent was removed in vacuo, and the residue was diluted with ethyl acetate and washed sequentially with saturated aqueous Na2CO3, water, and brine. The organic layers were dried with Na2SO4, filtered, and evaporated. Purification by Combiflash® (stationary phase: silica gel; eluent: 25-100% EtOAc/hexane gradient) gave Compound 63. m/z: 301.9 (M+H)+.

Compound 64

To a solution of Compound 63 (1.05 mmol) in EtOAc (3 mL) was added 4N HCl/dioxane solution (1.1 mL). The mixture was allowed to stir at 25° C. for 12 hours. The solvent was removed under reduced pressure, and Compound 64 was obtained as a white powder. This material was used in the next step without further purification. m/z: 216.0 (M+H)+.

Example Z

Compound 64 (70 mg, 0.29 mmol) was dissolved in THF (2.2 mL). Compound 29 (91 mg, 0.29 mmol) was added to the reaction flask as a 1.0M solution in THF, followed by HOBt (59 mg, 0.44 mmol), N,N-diisopropylethylamine (207 µL, 1.16 mmol), and EDC (103 µL, 0.58 mmol). The reaction was allowed to stir for 12 hours at 25° C. and concentrated under reduced pressure. The residue was diluted with EtOAc and washed sequentially with saturated aqueous Na2CO3, water, and brine. The organic layers were dried with Na2SO4, filtered, and evaporated. Purification by Combiflash® (stationary phase: silica gel; eluent: 0-10% MeOH/CH2Cl2 gradient) gave Example Z (54 mg, 38%). m/z: 497.1 (M+H)+. 1H NMR (CDCl3) δ 8.78 (s, 1H); 7.83 (s, 1H); 6.99 (s, 1H); 6.80 (br s, 1H); 6.22 (br s, 1H); 5.87 (br s, 1H); 5.25 (s, 2H); 4.43 (s, 2H); 3.97 (m, 1H); 3.34 (m, 4H); 2.95 (s, 3H); 2.22 (m, 2H); 1.38 (d, J=7 Hz, 6H); 0.97 (d, J=7 Hz, 6H).

Example AA

Example AA was prepared following the procedures for steps I-III (Scheme 20) for Example Z, with the exception that tert-butyl 3-aminopropylcarbamate was used instead of tert-butyl 2-aminoethylcarbamate (Compound 62). After Combiflash® purification, 38 mg (34%) of Example AA was obtained. m/z: 511.1 (M+H)+. 1H NMR (CDCl3) δ 8.78 (s, 1H); 7.84 (s, 1H); 6.96 (s, 2H); 6.17 (br s, 1H); 5.80 (m, 1H); 5.26 (m, 2H); 4.44 (s, 2H); 4.09 (m, 1H); 3.40-3.10 (m, 5H); 2.97 (s, 3H); 2.20 (m, 1H); 1.60 (m, 2H); 1.36 (d, J=7 Hz, 6H); 0.96 (d, J=7 Hz, 6H).

Example AB

Example AB was prepared following the procedures for steps I-III (Scheme 20) for Example Z, with the exception that tert-butyl 1-piperazinecarboxylate was used instead of tert-butyl 2-aminoethylcarbamate (Compound 62). After Combiflash® purification, 64 mg (45%) of Example AB was obtained. m/z: 523.1 (M+H)+. 1H NMR (CDCl3) δ 8.82 (s, 1H); 7.89 (s, 1H); 6.96 (s, 1H); 5.93 (br s, 1H); 5.35 (s, 2H);

4.62 (m, 1H); 4.50 (m, 2H); 3.80-3.40 (m, 8H); 3.34 (m, 1H); 3.00 (s, 3H); 1.97 (m, 1H); 1.40 (d, J=7 Hz, 6H); 0.96, 0.93 (d, J=7 Hz, 6H).

Example AC

Example AC was prepared following the procedures for steps I-III (Scheme 20) for Example Z, with the exception that tert-butyl 4-amino-1-piperidinecarboxylate was used instead of tert-butyl 2-aminoethylcarbamate (Compound 62). After Combiflash® purification, 60 mg (44%) of Example AC was obtained. m/z: 537.1 (M+H)$^+$. $^1$H NMR (CDCl$_3$) δ 8.82 (s, 1H); 7.87 (s, 1H); 6.97 (s, 1H); 5.82 (br s, 1H); 5.30 (m, 3H); 4.80-4.40 (m, 5H); 4.03 (m, 1H); 3.72 (br s, 1H); 3.34 (m, 1H); 3.18 (m, 1H); 3.01 (s, 3H); 2.79 (m, 1H); 2.20-1.90 (m, 4H); 1.40 (d, J=7 Hz, 6H); 0.97, 0.90 (d, J=7 Hz, 6H).

Example AD

Example AD was prepared following the procedures I-III for Example Z, with the exception that tert-butyl 4-piperidinylcarbamate was used instead of tert-butyl 2-aminoethylcarbamate (Compound 62). After Combiflash® purification, 49 mg (36%) of Example AD was obtained. m/z: 537.1 (M+H)$^+$. $^1$H NMR (CDCl$_3$) δ 8.82 (s, 1H); 7.87 (s, 1H); 7.01 (s, 1H); 6.33 (br s, 1H); 6.11 (br s, 1H); 5.32 (s, 2H); 4.47 (s, 2H); 4.20-3.80 (m, 4H); 3.35 (m, 1H); 3.10-2.80 (m, 6H); 2.21 (m, 2H); 1.90 (m, 2H); 1.40 (d, J=7 Hz, 6H); 0.97 (d, J=7 Hz, 6H).

Preparation of Examples AE-AG

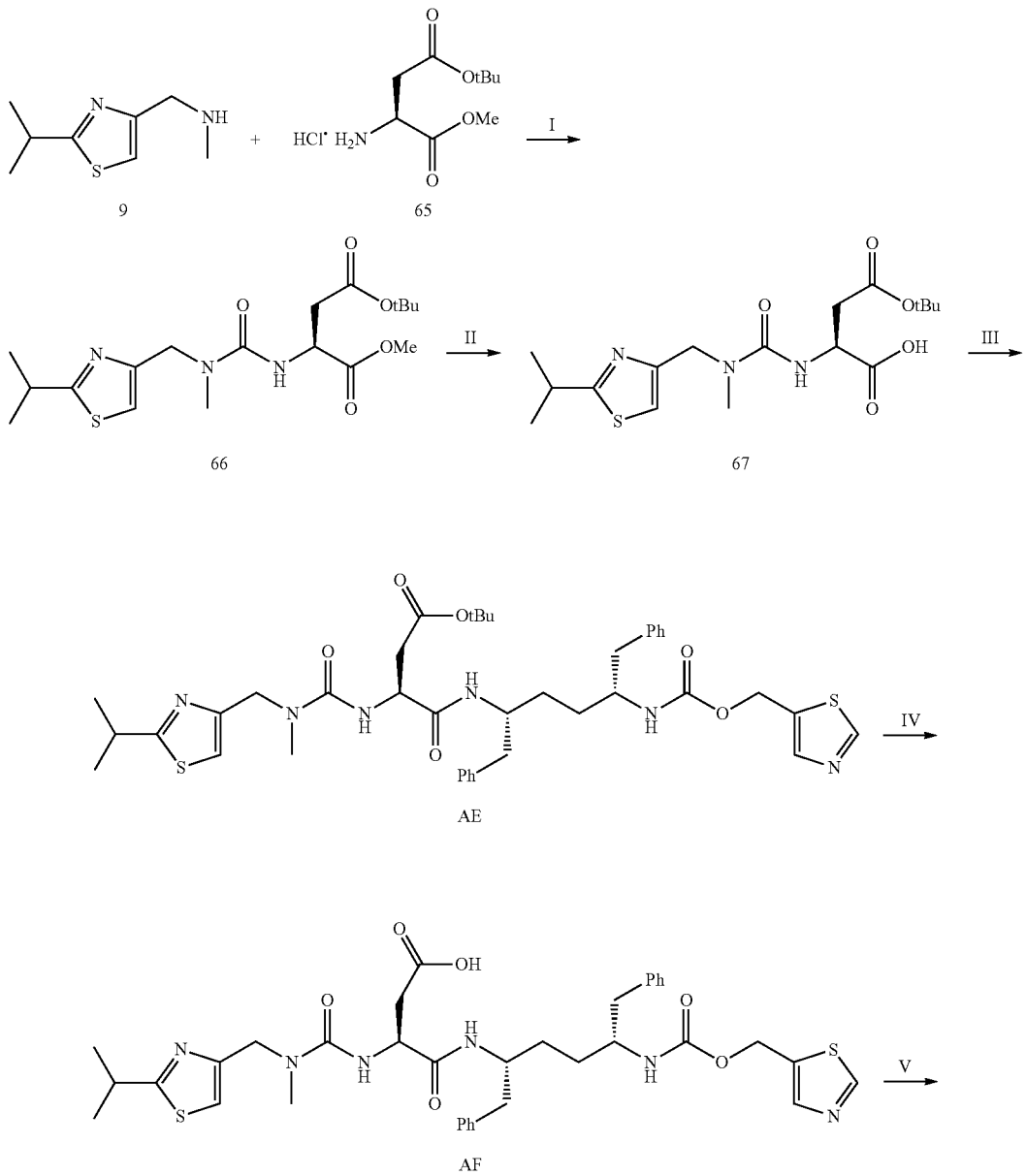

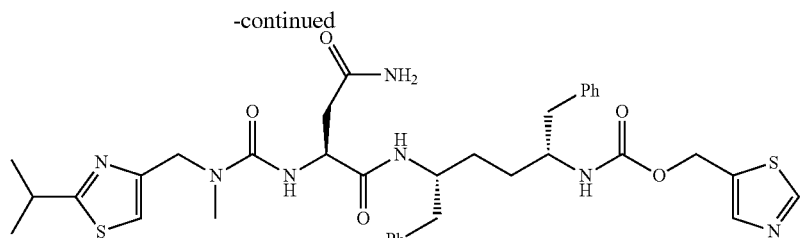

AG

I. CDI, DIPEA, CH₂Cl₂; II. NaOH, THF/H₂O; III. Cmpd. 8, DIPEA, EDC, HOBt, THF; IV. neat TFA; V. (Boc)₂O, NH₄HCO₃, pyridine, dioxane, DMF Compound 65

Compound 65 is commercially available from Chem Impex International, and was used without further purification.

Compound 66

Compound 65 (956 mg, 4.0 mmol) was dissolved in CH₂Cl₂ (45 mL) and 1,1-carbonyldiimidiazole (648 mg, 4.0 mmol) was added, followed by i-Pr₂NEt (2.8 mL, 16 mmol). The solution was stirred at 25° C. for 12 hours. Compound 9 (679 mg, 4.0 mmol) was dissolved in CH₂Cl₂ (5 mL) and added to the reaction. The mixture was allowed to stir for 5 hours. Then, the solvent was removed under reduced pressure. The residue was diluted with ethyl acetate and filtered through celite. The ethyl acetate was then removed in vacuo. Purification by flash column chromatography (stationary phase: silica gel; eluent: EtOAc) gave Compound 66 (841 mg). m/z: 400.0 (M+H)⁺.

Compound 67

Compound 66 (841 mg, 2.11 mmol) was dissolved in THF (9 mL) and 2N aqueous NaOH was added. The solution was stirred at 25° C. for 2 hours. The reaction was adjusted to pH 2 with 1N HCl. The mixture was extracted with ethyl acetate, dried over Na₂SO₄, filtered, and evaporated. Compound 67 (772 mg) was used directly in the next step without further purification. m/z: 386.0 (M+H)⁺.

Example AE

Compound 67 (569 mg, 1.48 mmol) was dissolved in THF (17 mL). Compound 8 (970 mg, 2.37 mmol) was added, followed by HOBt (300 mg, 2.22 mmol), i-Pr₂NEt (1.06 mL, 5.92 mmol), and EDC (0.52 mL, 2.96 mmol). The mixture was stirred at 25° C. for 36 hours. The solvent was removed under reduced pressure. The resulting residue was diluted with ethyl acetate and washed sequentially with saturated aqueous Na₂CO₃, water, and brine. The organic phase was dried over Na₂SO₄, filtered, and evaporated. Purification by flash column chromatography (stationary phase: silica gel; eluent: 8% iPrOH/CH₂Cl₂) gave Example AE (3.02 g). m/z: 777.2 (M+H)⁺.

Example AF

Example AE (100 mg, 0.13 mmol) was dissolved in neat TFA (3 mL). The mixture was stirred at 25° C. for 2 hours. The solvent was removed under reduced pressure. Purification by reverse-phase HPLC (Phenomenex Synergi® Comb-HTS column, eluent: 5-95% CH₃CN/H₂O gradient) gave Example AF (20 mg, 21%). m/z: 721.2 (M+H)⁺. ¹H NMR (CDCl₃) δ 8.92 (s, 1H); 7.91 (s, 1H); 7.40-7.00 (m, 11H); 6.41 (br s, 1H); 6.12 (br s, 1H); 5.40-5.00 (m, 3H); 4.70-4.50 (m, 3H); 4.05 (br s, 1H); 3.81 (br s, 1H); 3.51 (br s, 1H); 2.97 (s, 3H); 2.90-2.60 (m, 6H); 1.41 (d, J=7 Hz, 10H).

Example AG

Example AF (70 mg, 0.10 mmol) was dissolved in dioxane (0.5 mL). DMF (83 µL), pyridine (25 µL, 0.29 mmol), di-tert-butyldicarbonate (27 mg, 0.13 mmol), and ammonium bicarbonate (15 mg, 0.19 mmol) were added. The mixture was stirred at 25° C. for 48 hours, then diluted with ethyl acetate and washed sequentially with water and brine. The organic phase was dried over Na₂SO₄, filtered, and evaporated. Purification by reverse-phase HPLC (Phenomenex Synergi® Comb-HTS column, eluent: 5-95% CH₃CN/H₂O gradient) gave Example AG (35 mg, 50%). ¹H NMR (CDCl₃) δ 8.80 (s, 1H); 7.84 (s, 1H); 7.40-7.00 (m, 10H); 7.08 (s, 1H); 6.83 (m, 1H); 6.65 (m, 1H); 5.40-5.10 (m, 4H); 4.60-4.40 (m, 3H); 4.06 (m, 1H); 3.79 (m, 1H); 3.36 (m, 1H); 2.97 (s, 3H); 2.90-2.60 (m, 6H); 2.45 (m, 1H); 1.70-1.20 (m, 10H).

Preparation of Compounds 68 and 69

Scheme 28

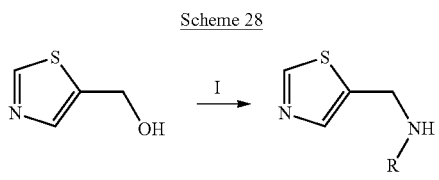

15

68: R = methyl
69: R = cyclopropyl

I. a. MsCl, TEA, CH₃CN; b. MeNH₂/H₂O; c. cyclopropyl amine

Compound 15

Compound 15 is commercially available from Molekula, and was used without further purification.

Compound 68

Compound 15 (6.81 g, 59.1 mmol) was dissolved in CH₃CN (340 mL) and methanesulfonyl chloride (7.03 mL, 65.1 mmol) was added, followed by triethylamine (9.03 mL, 65.1 mmol). After the mixture was stirred for 20 min, 40% wt. methylamine/water (516 mL) was added to the reaction mixture. The solution was stirred for 12 hours at 25° C. Solvent was removed under reduced pressure and the residue was partitioned between saturated aqueous Na₂CO₃ and CH₂Cl₂. The organic phase was separated, dried over Na₂SO₄, filtered, and evaporated. Purification by flash chromatography (stationary phase: silica gel; eluent: 0-10% MeOH/CH₂Cl₂ gradient) gave Compound 68 (5.07 g). m/z: 128.9 (M+H)⁺.

Compound 69

Compound 15 (10.0 g, 80 mmol) was dissolved in CH₃CN (500 mL) and methanesulfonyl chloride (7.0 mL, 88 mmol) was added, followed by triethylamine (12.3 mL, 88 mmol). After the mixture was stirred for 2 h, cyclopropylamine (140 mL, 2000 mmol) in CH₃CN (500 mL) was added to the reaction mixture. The solution was stirred for 36 hours at 25° C. Solvent was removed under reduced pressure and the slurry was partitioned between saturated aqueous Na₂CO₃ and 3:1 CH₂Cl₂:i-PrOH. The organic phase was separated, dried over Na₂SO₄, filtered, and evaporated. Compound 69 (12.81 g) was used in the next step without further purification. m/z: 155.0 (M+H)⁺.

Preparation of Examples AH and AI

Compound 71

Compound 70 (2.14 g, 6.23 mmol) was dissolved in THF (25 mL) and 1M aqueous LiOH (12.5 mL) was added. The mixture was stirred at 25° C. for 2 hours. The reaction was quenched with 1M HCl (15 mL) and the mixture was adjusted to pH 2. The mixture was extracted with ethyl acetate. The organic layers were dried over Na₂SO₄, filtered, and evaporated to provide Compound 71 (1.96 g). This material was used in the next step without further purification. m/z: 330.0 (M+H)⁺.

Example AH

Compound 71 (43 mg, 0.13 mmol) was dissolved in THF (1.5 mL). Compound 8 (50 mg, 0.12 mmol) was added, followed by HOBt (24 mg, 0.18 mmol), iPr₂NEt (86 μL,

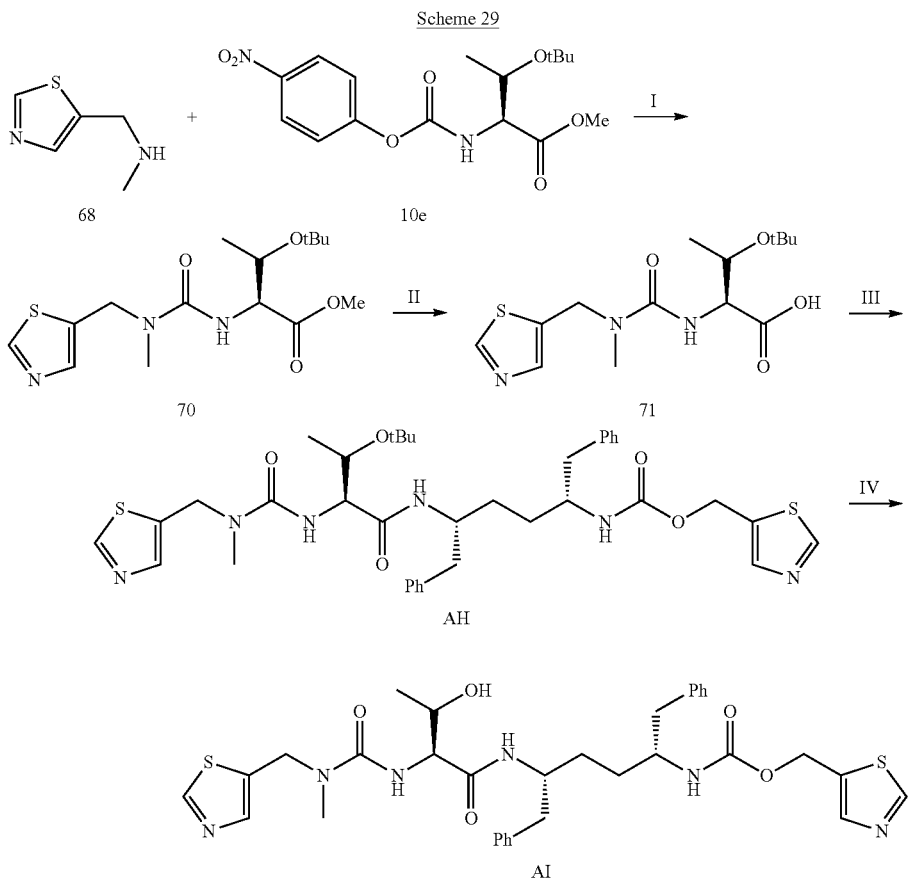

Scheme 29

I. DIPEA, CH₂Cl₂; II. LiOH, THF/H₂O; III. Cmpd. 8, HOBt, EDC, DIPEA, THF; IV. a. neat TFA; b. NaOH, THF, H₂O Compound 70

Compound 68 (1.00 g, 7.80 mmol) was dissolved in THF (25 mL) and Compound 10e (2.51 g, 7.09 mmol) was added, followed by N,N-dimethaminopyridine (200 mg, 1.63 mmol), and triethylamine (4.34 mL, 31.2 mmol). The mixture was allowed to stir at 60° C. for 6 hours. Solvent was removed under reduced pressure. The residue was diluted with ethyl acetate and washed sequentially with saturated aqueous Na₂CO₃, H₂O, and brine. The organic layer was dried over Na₂SO₄, filtered, and evaporated. The resulting residue was purified by Combiflash® (stationary phase: silica gel; eluent: 20-100% EtOAc/Hexane gradient) to give Compound 70 (2.14 g). m/z: 343.9 (M+H)⁺.

0.48 mmol), and EDC (42 μL, 0.24 mmol). The mixture was stirred at 25° C. for 12 hours. The solvent was removed under reduced pressure, and the resulting residue was diluted with ethyl acetate and washed sequentially with saturated aqueous Na₂CO₃, water, and brine. The organic phase was dried over Na₂SO₄, filtered, and evaporated. Purification by flash column chromatography (stationary phase: silica gel; eluent: 1-10% MeOH/CH₂Cl₂ gradient) gave Example AH (66 mg). m/z: 721.2 (M+H)⁺.

Compound AI

Example AH (66 mg, 0.09 mmol) was dissolved in TEA and allowed to stir at 25° C. for 3 hours. The solvent was removed under reduced pressure and the residue was diluted with THF (3 mL) and 2N aqueous NaOH was added until pH 12. The mixture was allowed to stir for 20 min and extracted with EtOAc. The organic layer was washed sequentially with water and brine, dried over $Na_2SO_4$, filtered, and evaporated. Purification by flash chromatography (stationary phase: silica gel; eluent: 0-20% i-PrOH/$CH_2Cl_2$ gradient) gave Example AI (71 mg, 97%). m/z: 665.2 (M+H)F. $^1$H NMR ($CDCl_3$) δ 8.84 (s, 1H); 8.80 (s, 1H); 7.85 (s, 1H); 7.79 (s, 1H); 7.40-7.00 (m, 10H); 6.69 (m, 1H); 5.34 (m, 1H); 5.24 (s, 2H); 4.86 (m, 2H); 4.73, 4.59 ($d_{AB}$, J=16 Hz, 2H); 4.30 (s, 1H); 4.15 (m, 2H); 3.86 (br s, 1H); 2.88 (s, 3H); 2.85-2.60 (m, 4H); 2.01 (s, 1H); 1.58 (s, 2H); 1.44 (s, 2H); 1.09 (d, J=6 Hz, 3H).

Preparation of Examples AJ and AK

Compound 73

Compound 73 was prepared following procedure for Compound 49, except that Compound 72 was used instead of Compound 48.

Example AJ

Example AJ (70 mg) was prepared following the same procedure used to prepare Example AH, with the exception that Compound 73 (41 mg, 0.13 mmol) was used instead of Compound 71, m/z: 707.2 (M+H)$^+$.

Example AK

Example AK (43 mg, 67%) was prepared following the same procedure used to prepare Example AI, with the

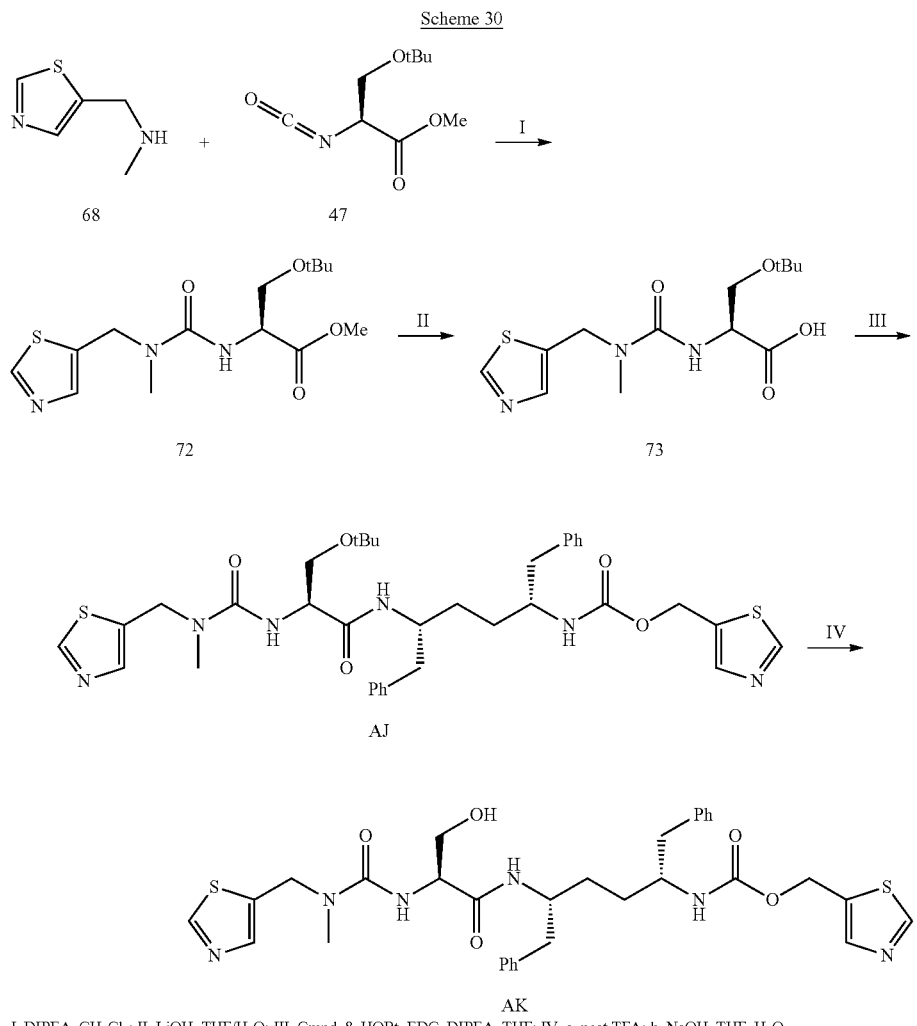

Compound 47

Compound 47 is commercially available from TCI America, and was used without further purification.

Compound 72

Compound 72 was prepared following procedure for Compound 48 (Method II), except that Compound 68 was used instead of Compound 9.

exception that Example AI (70 mg, 0.10 mmol) was used instead of Example AH. m/z: 651.2 (M+H)$^+$. $^1$H NMR ($CDCl_3$) δ 8.83 (s, 2H); 7.84 (s, 1H); 7.79 (s, 1H); 7.40-7.00 (m, 10H); 6.65 (br s, 1H); 5.47 (br s, 1H); 5.24 (s, 2H); 4.90 (m, 1H); 4.82-4.50 (m, 2H); 4.30-4.00 (m, 3H); 3.84 (br s, 1H); 3.49 (m, 1H); 2.87 (s, 3H); 2.75 (br s, 5H); 1.60-1.20 (m, 4H).

Preparation of Examples AL and AM

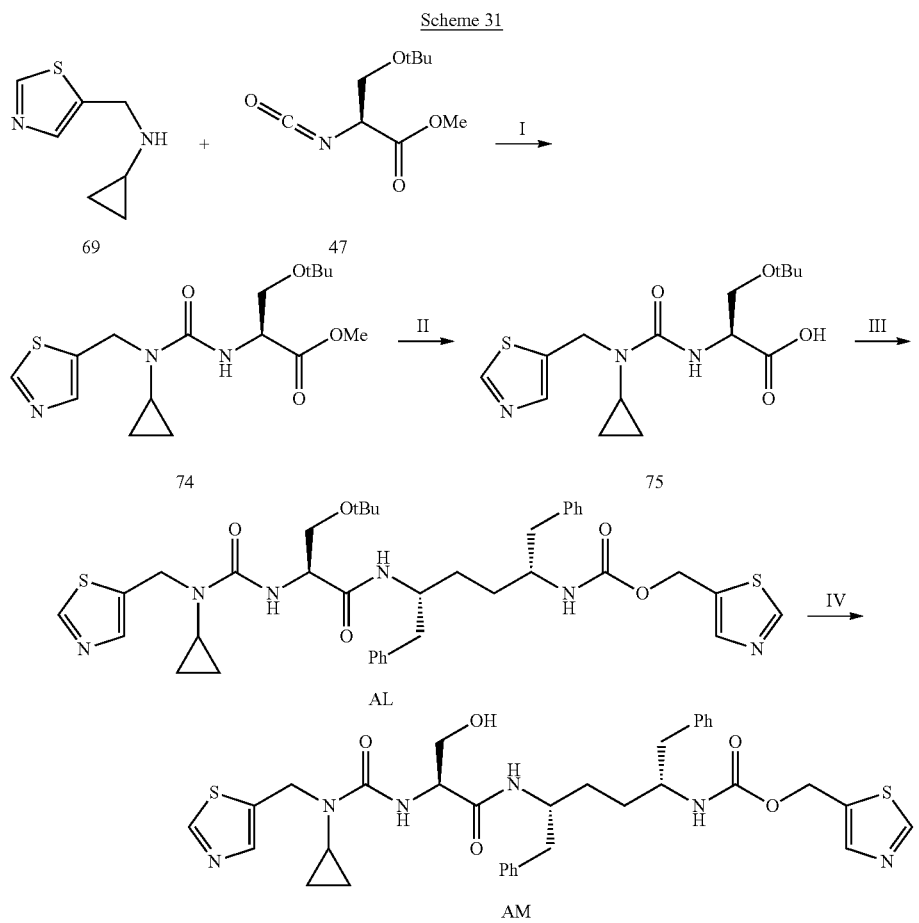

I. DIPEA, CH$_2$Cl$_2$; II. LiOH, THF/H$_2$O; III. Cmpd. 8, HOBt, EDC, DIPEA, THF; IV. a. neat TFA; b. NaOH, THF, H$_2$O Compound 74

Compound 69 (1.56 g, 10.1 mmol) was dissolved in CH$_2$Cl$_2$ (10 mL). Compound 47 (1.7 g, 8.5 mmol) in CH$_2$Cl$_2$ (20 mL) was added, followed by iPr$_2$NEt (3.02 mL, 16.9 mmol). The reaction was stirred at 25° C. for 12 hours. The solvent was removed under reduced pressure. The residue was diluted with ethyl acetate and washed sequentially with water and brine, dried over Na$_2$SO$_4$, filtered, and evaporated. Purification by Combiflash® (stationary phase: silica gel; eluent: 50-100% EtOAc/hexane gradient) gave Compound 74 (2.92 g). m/z: 356.0 (M+H)$^+$.

Compound 75

Compound 74 (0.97 mmol) was taken up in THF (3 mL) and treated with freshly prepared 1M LiOH (2 mmol) and stirred vigorously for 1 h. The reaction was quenched with 1M HCl (2.5 mmol) and extracted with EtOAc (3×15 mL). The combined organics were washed with brine (25 mL), dried over anhydrous Na$_2$SO$_4$ and concentrated in vacuo to produce 0.331 g (quant) of Compound 75 as a colorless film (m/z 342.0 (M+H)$^+$).

Example AL

Example AL (2.20 g) was prepared following the same procedure used to prepare Example AH, with the exception that Compound 75 (2.00 g, 4.88 mmol) was used instead of Compound 71. m/z: 733.2 (M+H)$^+$.

Example AM

Example AM (1.88 g, 92%) was prepared following the same procedure used to prepare Example AI, with the exception that Example AL (2.20 g, 3.01 mmol) was used instead of Example AH. m/z: 677.2 (M+H)$^+$. $^1$H NMR (CDCl$_3$) δ 8.79 (s, 1H); 8.72 (s, 1H); 7.82 (s, 1H); 7.77 (s, 1H); 7.40-7.00 (m, 10H); 6.59 (m, 1H); 6.31 (m, 1H); 5.23 (s, 2H); 5.00 (m, 1H); 4.72, 4.60 (d$_{AB}$, J=15 Hz, 2H); 4.18 (s, 2H); 4.03 (m, 1H); 3.84 (br s, 1H); 3.48 (m, 1H); 2.85-2.60 (m, 4H); 2.37 (br s, 2H); 1.58 (s, 2H); 1.41 (s, 2H); 0.93 (m, 2H); 0.76 (m, 2H).

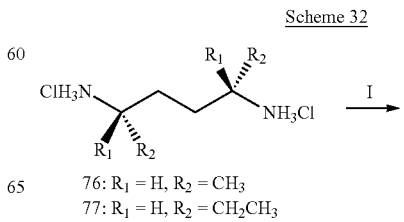

Scheme 32

76: R$_1$ = H, R$_2$ = CH$_3$
77: R$_1$ = H, R$_2$ = CH$_2$CH$_3$

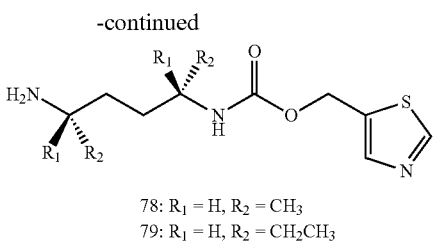

78: $R_1$ = H, $R_2$ = $CH_3$
79: $R_1$ = H, $R_2$ = $CH_2CH_3$

I. compound 16, DIPEA, MeCN (50 mL) and water is added until the aqueous layer is homogeneous. The aqueous layer is extracted with 3/1 $CHCl_3$/IPA (3×25 mL). The combined organics are washed with saturated $Na_2CO_3$ (50 mL), water (50 mL) and brine (50 mL) and are dried over anhydrous $Na_2SO_4$. The solvent is removed in vacuo and the residue purified by column chromatography on $SiO_2$ (100% EtOAc, then 0 to 20% MeOH/DCM) to produce 0.63 g (31%) of 78 as an off-white solid. (m/z 258.0 $(M+H)^+$).

Compound 79

Compound 79 (m/z 286.1 $(M+H)^+$) was prepared following the procedure for Compound 78 except that Compound 77 was used instead of Compound 76.

Scheme 33

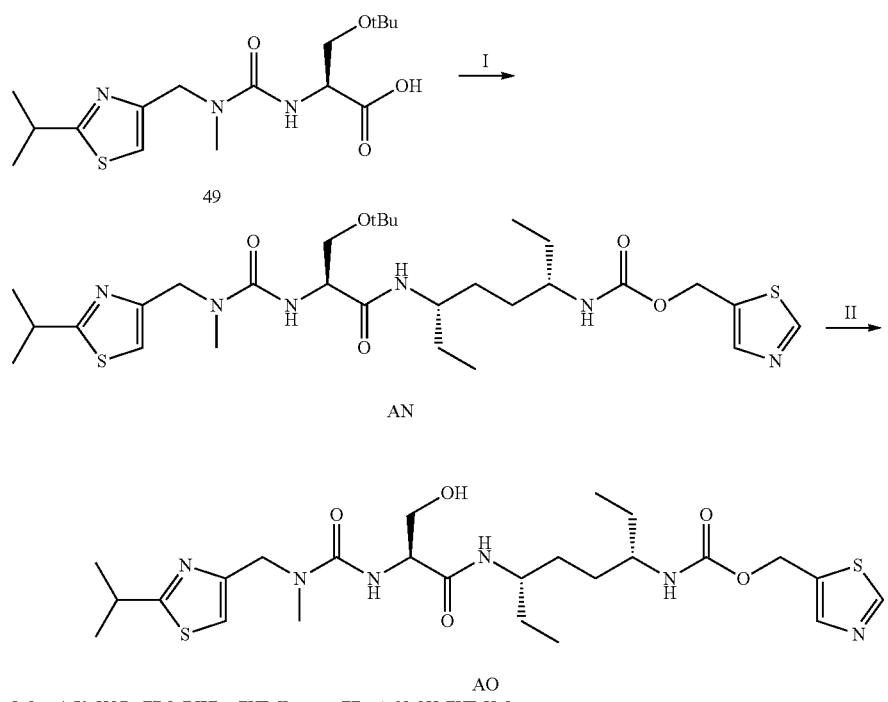

I. Cmpd. 79, HOBt, EDC, DIPEA, THF; II. a. neat TFA; b. NaOH, THF, $H_2O$

Compound 76

Compound 76 (m/z 117.0 $(M+H)^+$ of diamine) was prepared using a procedure similar to that used to prepare Compound 22 (described in Scheme 12) except that CBZ-L-alininol was used instead of CBZ-L-phenylalininol and Step III was performed with 1 M HCl added.

Compound 77

Compound 77 (m/z 145.0 $(M+H)^+$ of diamine) was prepared using a procedure similar to that used to prepare Compound 76 except that (S)-(+)-2-CBZ-amino-1-butanol was used instead of CBZ-L-alininol.

Compound 78

Compound 76 (7.93 mmol) is added to a solution of NaOH (16.7 mmol) in $H_2O$ (5 mL) that is cooled to 0° C. and diluted with MeCN (40 mL). DIPEA is added (2.1 mL, 11.9 mmol). Compound 16 (7.9 mmol) is taken up in MeCN (40 mL) and added to the reaction solution dropwise via an addition funnel over 1 h. The resulting solution is allowed to warm to room temperature overnight. The solvent is removed in vacuo and the residue taken up in 3/1 $CHCl_3$/IPA (50 mL). The resulting solution is washed with sat. $Na_2CO_3$ Example AN Example AN (68 mg) was prepared following the same procedure used to prepare Example AH, with the exceptions that Compound 49 (68 mg, 0.19 mmol) was used instead of Compound 71, and Compound 79 (50 mg, 0.18 mmol) was used instead of Compound 8. m/z: 625.2 $(M+H)^+$.

Example AO

Example AO (66 mg, 76%) was prepared following the same procedure used to prepare Example AI, with the exception that Example AN (43 mg, 0.13 mmol) was used instead of Example AH. m/z: 569.2 $(M+H)^+$. $^1$H NMR ($CDCl_3$) δ 8.85 (s, 1H); 7.89 (s, 1H); 7.08 (s, 1H); 6.81 (m, 1H); 5.29 (s, 2H); 4.87 (m, 1H); 4.63, 4.48 ($d_{AB}$, J=16 Hz, 2H); 4.31 (m, 1H); 4.11 (m, 1H); 3.76 (m, 2H); 3.44 (m, 2H); 3.02 (m, 4H); 1.60-1.20 (m, 14H); 1.00-0.70 (m, 6H).

Preparation of Examples AP and AO

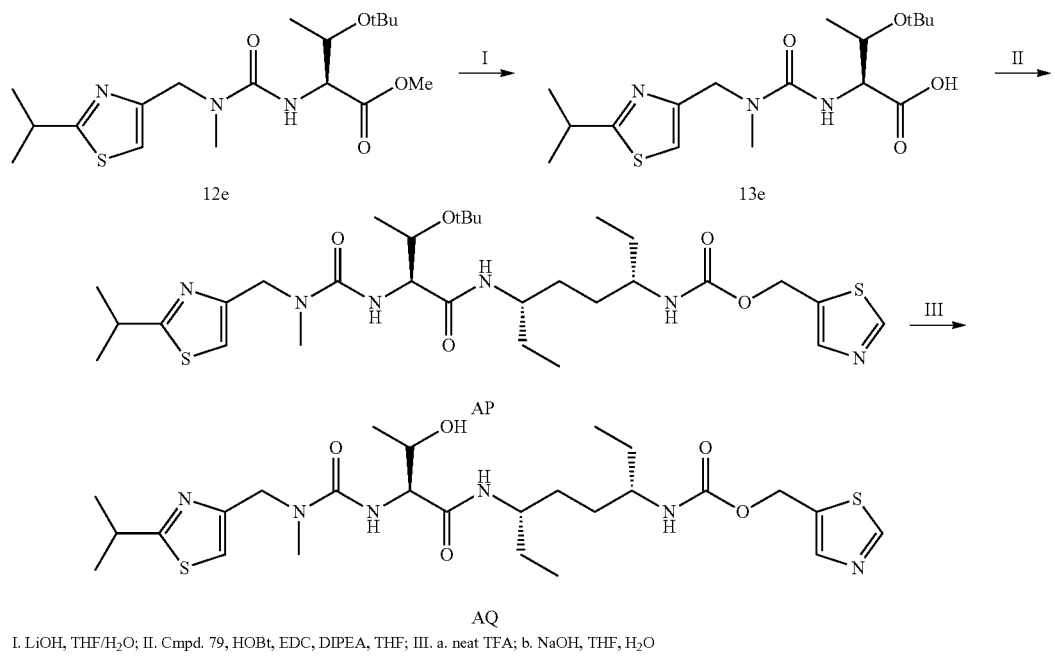

I. LiOH, THF/H₂O; II. Cmpd. 79, HOBt, EDC, DIPEA, THF; III. a. neat TFA; b. NaOH, THF, H₂O Compound 13e Compound 13e (1.39 g) was prepared following the same procedure used to prepare Compound 71, with the exception that Compound 12e (1.53 g, 3.97 mmol) was used instead of Compound 70 m/z: 372.0 (M+H)⁺.

Example AP

Example AP (87 mg) was prepared following the same procedure used to prepare Example AH, with the exception that Compound 13e (71 mg, 0.19 mmol) was used instead of Compound 71, and Compound 79 (50 mg, 0.18 mmol) was used instead of Compound 8. m/z: 639.2 (M+H)⁺.

Compound AQ

Example AQ (61 mg, 76%) was prepared following the same procedure used to prepare Example AI, with the exception that Example AP (87 mg, 0.14 mmol) was used instead of Example AH. m/z: 583.2 (M+H)⁺. ¹H NMR (CDCl₃) δ 8.81 (s, 1H); 7.87 (s, 1H); 7.01 (s, 1H); 6.87 (m, 1H); 6.52 (s, 1H); 5.28 (m, 2H); 4.47 (m, 1H); 4.59, 4.43 (d$_{AB}$, J=16 Hz, 2H); 4.45 (m, 1H); 4.17 (br s, 1H); 3.75 (br s, 1H); 3.52 (br s, 1H); 3.35 (br s, 1H); 3.01 (m, 3H); 2.07 (br s, 1H); 1.60-1.10 (m, 17H); 1.00-0.70 (m, 6H).

Preparation of Example AR

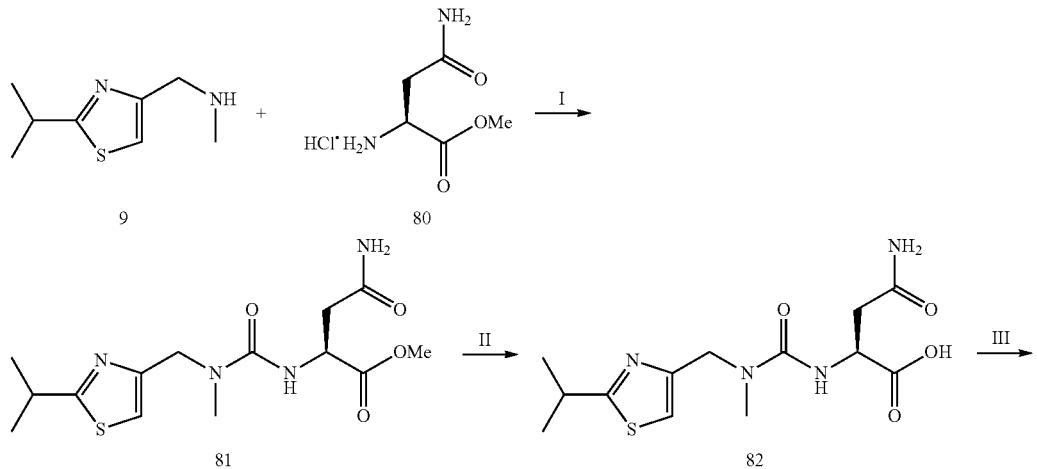

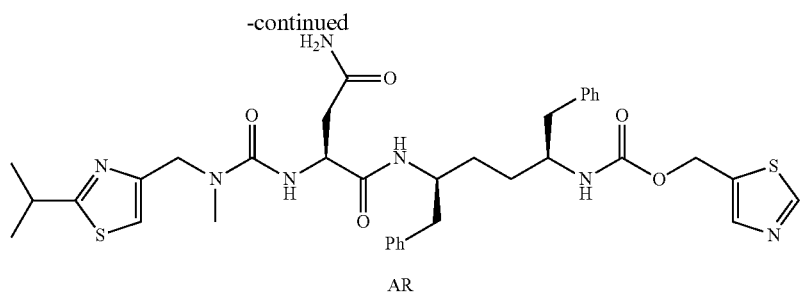

AR

I. CDI, DIPEA, CH₂Cl₂; II. LiOH, THF/H₂O; III. Cmpd. 46, DIPEA, EDC, HOBt, THF

Compound 80

Compound 80 is commercially available from Chem Impex International, and was used without further purification.

Compound 81

Compound 80 (2.0 g, 11.0 mmol) was dissolved in CH₂Cl₂ (170 mL) and 1,1-carbonyldiimidazole (1.78 g, 11.0 mmol) was added, followed by iPr₂NEt (7.83 mL, 43.8 mmol). The solution was allowed to stir at 25° C. for 12 hours. Compound 9 (1.86 g, 11.0 mmol) was dissolved in 20 mL of CH₂Cl₂ and added to the reaction mixture. The solution was stirred at 25° C. for 12 hours. The solvent was removed in vacuo and the residue was diluted with ethyl acetate and washed water and brine. The organic layers were dried over Na₂SO₄, filtered, and evaporated. Purification by Combiflash® (stationary phase: silica gel; eluent: 66-100% EtOAc/Hexane gradient) gave Compound 81 (0.252 mg). m/z: 343.0 (M+H)⁺.

Compound 82

Compound 82 (0.252 g, 0.74 mmol) was dissolved in THF (4 mL) and 1M aqueous LiOH (1.48 mL) was added. The mixture was stirred at 25° C. for 3 hours. The reaction was quenched with 1M HCl (2 mL) and the mixture was adjusted to pH 2. The mixture was extracted with ethyl acetate. The organic layers were dried over Na₂SO₄, filtered, and evaporated to afford Compound 82 (0.18 g). This material was used in the next step without further purification. m/z: 329.1 (M+H)⁺.

Example AR

Compound 82 (182 mg, 0.55 mmol) was dissolved in THF (7.15 mL). Compound 46 (225 mg, 0.55 mmol) was added, followed by HOBt (112 mg, 0.83 mmol), iPr₂NEt (393 µL, 2.20 mmol), and EDC (194 µL, 1.10 mmol). The mixture was stirred at 25° C. for 12 hours. The solvent was removed under reduced pressure. The residue was diluted ethyl acetate and washed sequentially with saturated aqueous Na₂CO₃, water, and brine. The organic phase was dried over Na₂SO₄, filtered, and evaporated. Purification by flash column chromatography (stationary phase: silica gel; eluent: 5-10% MeOH/CH₂Cl₂ gradient) gave Example AR (208 mg, 53%). m/z: 720.2 (M+H)⁺. ¹H NMR (CDCl₃) δ 8.80 (s, 1H); 7.84 (s, 1H); 7.40-7.00 (m, 10H); 6.97 (s, 1H); 6.83 (m, 1H); 6.65 (br s, 1H); 5.99 (m, 1H); 5.40-5.10 (m, 4H); 4.52 (m, 3H); 4.06 (m, 1H); 3.79 (m, 1H); 3.34 (m, 1H); 2.97 (s, 3H); 2.90-2.60 (m, 5H); 2.50-2.40 (br s, 1H); 1.80-1.20 (m, 10H).

Preparation of Example AS

Scheme 36

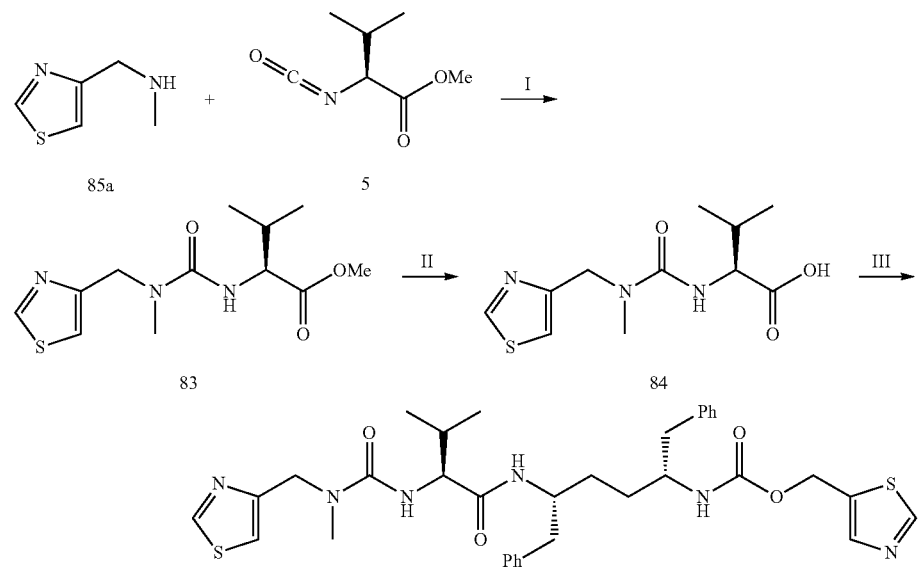

AS

I. DIPEA, CH₂Cl₂; II. LiOH, THF/H₂O; III. Cmpd. 8, HOBt, EDC, DIPEA, THF

Compound 85a

Compound 85a was prepared following the same procedure as Compound 4, except that 4-chloromethylthiazole (purchased from TCI America) was used instead of Compound 3, and methylamine was used instead of isopropylamine.

Compound 83

To compound 85a (0.40 g, 3.12 mmol) in CH$_2$Cl$_2$ (9 mL) was added N,N-diisopropylethylamine (1.04 mL, 5.85 mmol), followed by Compound 5 (280 µL, 1.95 mmol). The reaction mixture was stirred for 3.5 hours at 25° C. Solvent was removed under reduced pressure. Purification by Combiflash® (stationary phase: silica gel; eluent: 90-100% EtOAc/Hexane gradient) gave Compound 83 (0.51 g). m/z: 286.0 (M+H)$^+$.

Compound 84

Compound 83 (0.51 g, 1.77 mmol) was dissolved in THF (10 mL) and 1M aqueous LiOH (3.54 mL) was added. The mixture was stirred at 25° C. for 2 hours. The reaction was quenched with 1M HCl (4.8 mL) and the mixture was adjusted to pH 2. The mixture was extracted with ethyl acetate. The organic layers were dried over Na$_2$SO$_4$, filtered, and evaporated to afford Compound 84 (0.430 g). This material was used in the next step without further purification. m/z: 272.0 (M+H)$^+$.

Example AS

Compound 84 (150 mg, 0.55 mmol) was dissolved in THF (7.15 mL). Compound 8 (225 mg, 0.55 mmol) was added, followed by HOBt (112 mg, 0.83 mmol), iPr$_2$NEt (393 µL, 2.20 mmol), and EDC (198 µL, 1.11 mmol). The mixture was stirred at 25° C. for 12 hours. The solvent was removed under reduced pressure. The residue was diluted ethyl acetate and washed sequentially with saturated aqueous Na$_2$CO$_3$, water, and brine. The organic phase was dried over Na$_2$SO$_4$, filtered, and evaporated. Purification by flash column chromatography (stationary phase: silica gel; eluent: 7% i-PrOH/CH$_2$Cl$_2$) gave Example AS (219 mg, 60%). m/z: 663.1 (M+H)$^+$. $^1$H NMR (CDCl$_3$) δ 8.87 (s, 1H); 8.76 (s, 1H); 7.84 (s, 1H); 7.40-7.00 (m, 10H); 6.22 (br s, 1H); 5.73 (br s, 1H); 5.22 (m, 2H); 4.50 (m, 2H); 4.16 (br s, 1H); 4.05 (br s, 1H); 3.75 (m, 1H); 2.93 (s, 3H); 2.90-2.60 (m, 5H); 2.90 (m, 1H); 2.31 (m, 1H); 1.60-1.30 (m, 4H); 1.00-0.80 (m, 6H).

Preparation of Example AT

Scheme 37

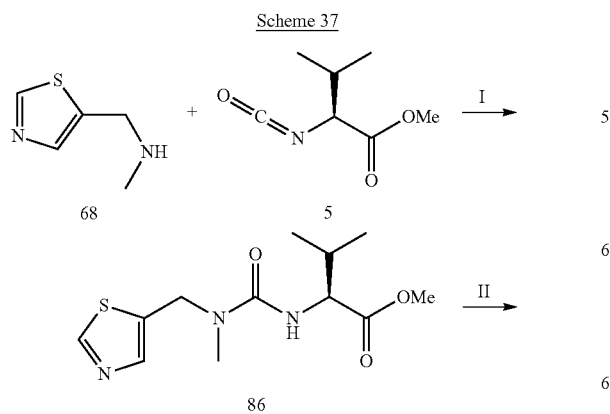

I. DIPEA, CH$_2$Cl$_2$; II. LiOH, THF/H$_2$O; III. Cmpd 8, HOBt, EDC, DIPEA, THF

Compound 87

Compound 87 (386 mg) was prepared from Compound 86 following the same procedure used to prepare Compound 7 from Compound 6, except that Compound 68 was used was used instead of Compound 4. m/z 286.0 (M+H)$^+$.

Preparation of Example AU

Scheme 38

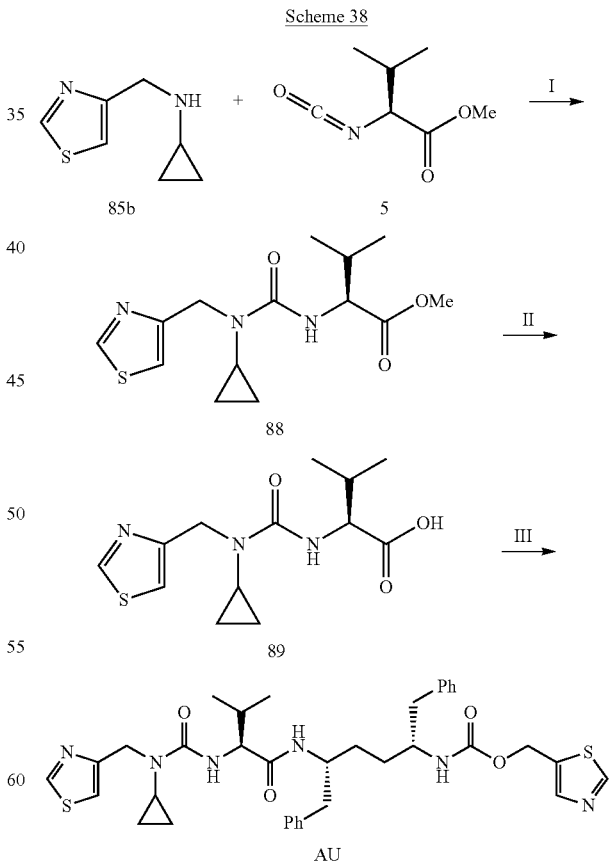

I. DIPEA, CH$_2$Cl$_2$; II. LiOH, THF/H$_2$O; III. Cmpd. 8, HOBt, EDC, DIPEA, THF Compound 85b Compound 85b was prepared following the same procedure as Compound 4, except that 4-chloromethylthiazole (obtained from TCI America) was used instead of Compound 3.

Compound 88

Compound 88 (341 mg) was prepared following the same procedure used to prepare Compound 83, with the exception that Compound 85b (300 mg, 1.95 mmol) was used instead of Compound 85a. m/z: 312.0 (M+H)$^+$.

Compound 89

Compound 89 (341 mg) was prepared following the same procedure for 84, with the exception that Compound 88 (293 mg, 0.99 mmol) was used instead of Compound 83. m/z: 298.0 (M+H)$^+$.

Example AU

Example AU (226 mg, 64%) was prepared following the same procedure used to prepare Example AS, with the exception that Compound 89 (150 mg, 0.51 mmol) was used instead of Compound 84. m/z: 689.1 (M+H)$^+$. $^1$H NMR (CDCl$_3$) δ 8.87 (s, 1H); 8.74 (s, 1H); 7.83 (s, 1H); 7.40-7.00 (m, 10H); 6.21 (m, 1H); 5.73 (m, 1H); 5.29 (m, 1H); 5.17 (m, 2H); 4.88 (d, J=16 Hz, 1H); 4.47 (d, J=16 Hz, 1H); 4.18 (m, 1H); 3.75 (br s, 1H); 2.90-2.60 (m, 6H); 2.51 (br s, 1H); 2.31 (m, 1H); 1.60-1.30 (m, 4H); 1.00-0.80 (m, 10H).

Preparation of Example AV

Compound 90

Compound 90 (190 mg) was prepared following the procedure used to prepare Compound 4, except that 4-(chloromethyl)-2-methylthiazole was used instead of Compound 3. m/z 141.1 (M−H).

Compound 91

Compound 91 (400 mg) was prepared following the same procedure used to prepare Compound 6 except that Compound 90 was used instead of Compound 4. m/z 300.0 (M+H)$^+$.

Compound 92

Compound 92 (188 mg) was prepared following the same procedure as Compound 7 except that Compound 91 was used instead of Compound 6. m/z 284.0 (M−H)$^-$.

Example AV

Example AV (107 mg) was prepared following the procedure used to prepare Example C, except Compound 92 was used instead of Compound 7. $^1$H NMR (CDCl$_3$) δ 8.76 (s, 1H), 7.78 (s, 1H), 7.27-7.07 (m, 10H), 6.93 (s, 1H), 6.25 (m, 2H), 5.39 (m, 1H), 5.19 (m, 2H), 4.37-4.32 (m, 2H), 4.06 (m, 1H), 3.81 (br s, 1H), 2.83 (m, 4H), 2.65 (br s, 7H), 2.28-2.22 (m, 1H), 1.51-1.37 (m, 4H), 0.82 (m, 6H): m/z 677.2 (M+H)$^+$.

Scheme 39

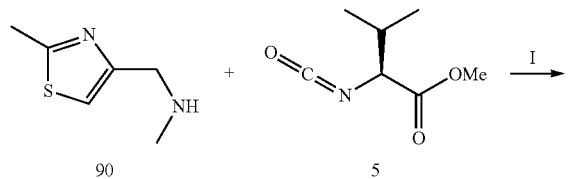

90     5

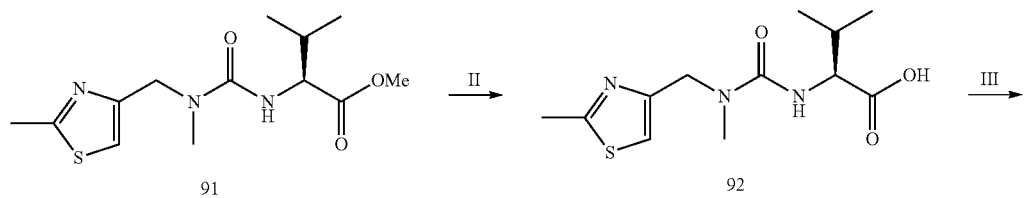

91     92

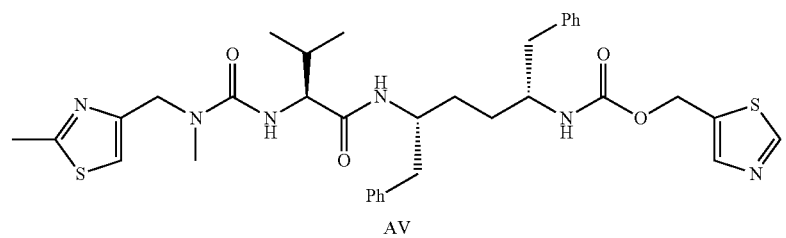

AV

I. DIPEA, CH$_2$Cl$_2$; II. LiOH, THF/H$_2$O; III. Cmpd. 8, HOBt, EDC, DIPEA, THF Preparation of Example AW

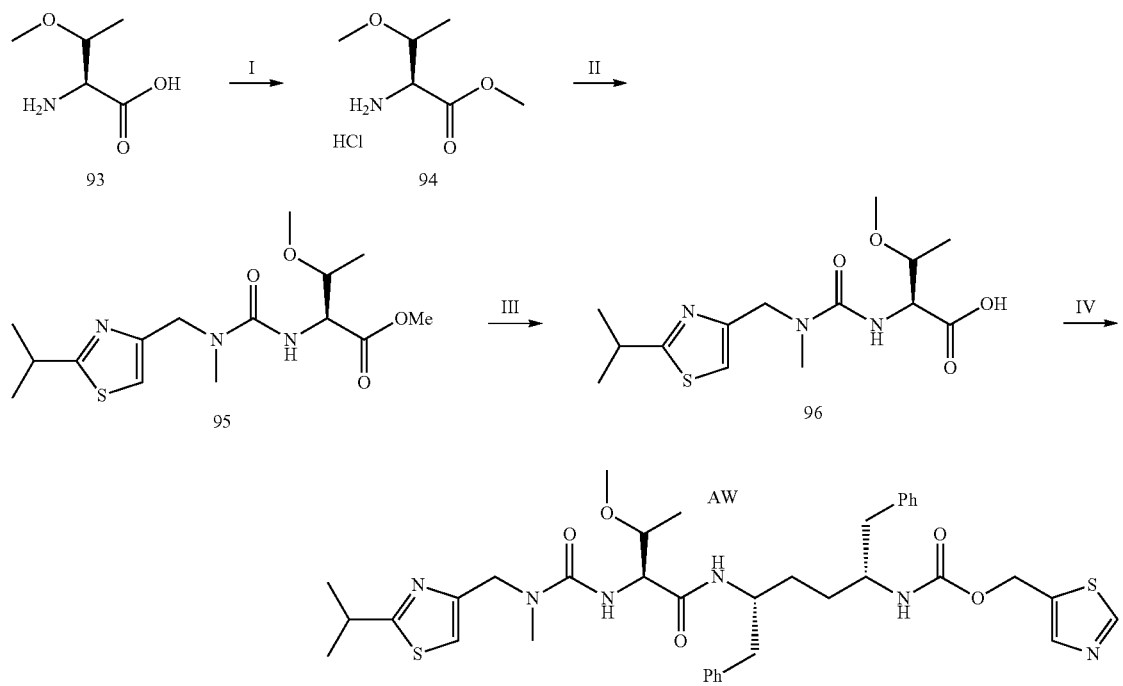

I. SOCl₂/MeOH; II. DIPEA, CH₂Cl₂; III. LiOH, THF/H₂O; IV. Cmpd 8, HOBt, EDC, IPEA, THF Compound 93

Compound 93 is commercially available from TCI, and was used without further purification.

Compound 94

To a solution of Compound 93 (500 mg, 3.76 mmol) in methanol (20 mL) was added thionyl chloride (0.5 mL, 6.6 mmol) dropwise. The mixture was stirred at 60° C. for 20 minutes, and concentrated in vacuo to gave Compound 94.

Compound 95

To a stirred solution of Compound 94 (3.7 mmol) and diisopropylethylamine (1.4 mL, 8.3 mmol) in dichloromethane (50 mL) was added CDI (609 mg, 3.7 mmol). The mixture was stirred for 12 hours. Compound 9 was added, and the mixture was stirred for 12 additional hours. Concentration and purification by flash column chromatography (0-100%: EtOAc/hexane) gave Compound 95 (100 mg). m/z 344.3 (M+H)⁺.

Compound 96

Compound 96 (39 mg) was prepared following the same procedure used to prepare Compound 7 except that Compound 95 was used instead of Compound 6. m/z 328.3 (M−H)⁻.

Example AW

Example AW (107 mg) was prepared following the procedure for Example C, except that Compound 96 was used instead of Compound 7. $^1$H NMR (CDCl₃) δ 8.79 (s, 1H), 7.82 (s, 1H), 7.27-7.09 (m, 10H), 6.95 (s, 1H), 6.23 (m, 1H), 6.14 (s, 1H), 5.22 (s, 3H), 4.45 (m, 2H), 4.35-4.0 (m, 3H), 3.8 (m, 1H), 3.6 (m, 1H), 3.25 (s, 3H), 3.21 (m, 2H), 2.95 (s, 3H), 2.8-2.6 (m, 4H), 2.0-4.4 (m, 4H), 1.25 (m, 4H), 1.05 (m, 4H): m/z 721.3 (M+H)⁺.

Preparation of Examples AX and AY

Scheme 41

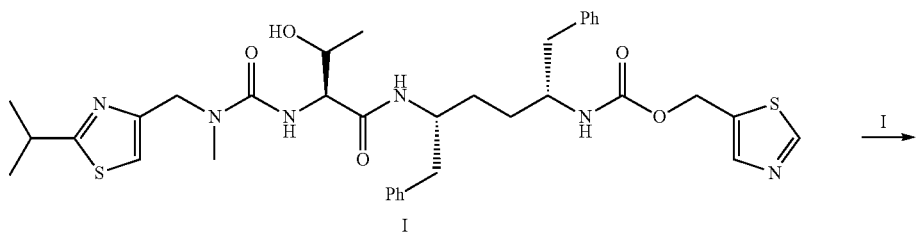

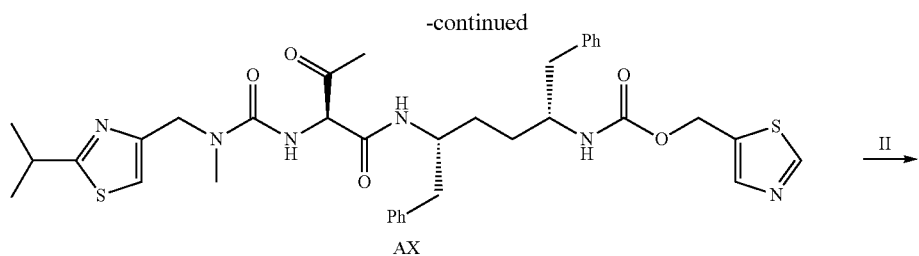

AX

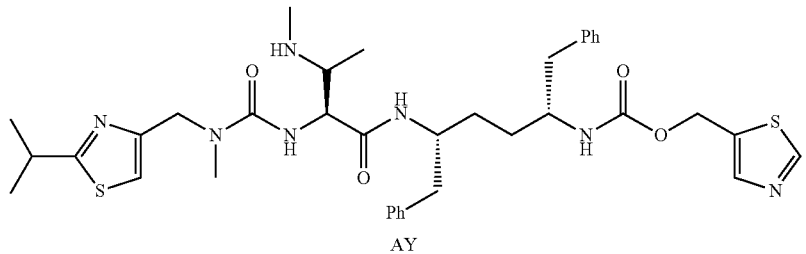

AY

I. DMSO, Et₃N, SO₃ pyridine: II. NaBH(OAc)₃, AcOH, Methylamine/MeOH

Example AX

To a solution of Example I (650 mg, 1.00 mmol) in DMSO (3.5 mL) was added triethylamine (0.5 mL). The mixture was stirred for 30 minutes. Pyridine SO₃ was added to the mixture at 5° C. then stirred for 60 minutes. The mixture was poured on to ice-water, then stirred for 30 minutes. The mixture was diluted with EtOAc and washed with water, sat. NaHCO₃, and brine. Concentration gave Example AX. m/z 705.2 (M+H)⁺.

Example AY

To a stirred solution of Example AX (70 mg, 0.099 mmol) and methylamine (1.5 mL, 2M) in MeOH (1.5 mL) was added AcOH (119 mg, 1.99 mmol). The mixture was stirred for 2 hours. NaSH(OAc)₃ (94 mg) was added, and the mixture was stirred for 2 hours. Concentration and purification by prep. HPLC gave Example AY (30 mg). ¹H NMR (CDCl₃) δ 8.79 (s, 1H), 7.82 (s, 1H), 7.27-7.09 (m, 10H), 6.95 (s, 1H), 6.23 (m, 1H), 6.14 (s, 1H), 5.22 (s, 2H), 4.45 (m, 1H), 4.35-4.0 (m, 4H), 3.8 (m, 1H), 3.6 (m, 1H), 3.21 (m, 1H), 2.95 (s, 3H), 2.93 (s, 3H), 2.8-2.6 (m, 4H), 2.0-1.4 (m, 4H), 1.25 (m, 4H), 1.05 (m, 4H): m/z 720.3 (M+H)⁺.

Preparation of Example AZ

Scheme 42

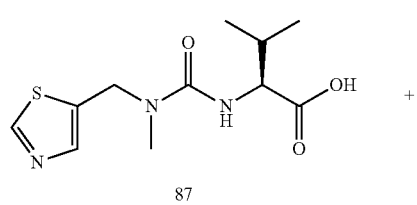

87

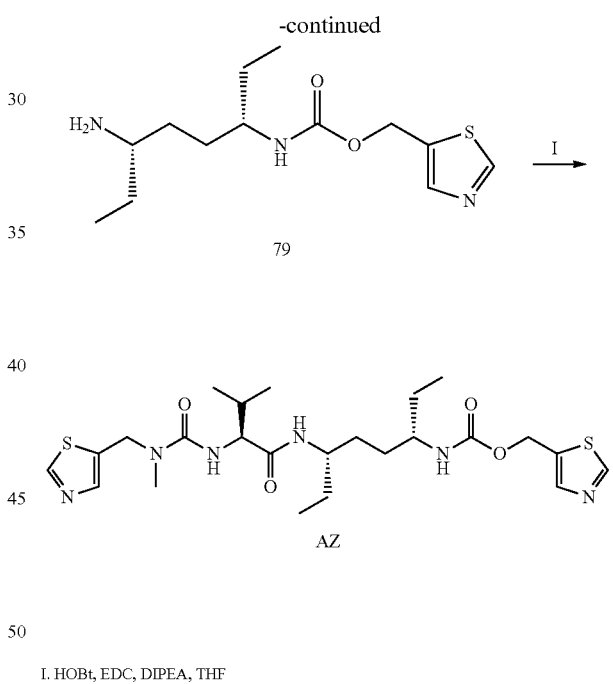

79

AZ

I. HOBt, EDC, DIPEA, THF

Example AZ

Compound AZ (61 mg) was prepared following the procedure for Example C, except that Compound 87 was used instead of Compound 7 and Compound 79 was used instead of Compound 8. ¹H NMR (CDCl₃) δ 8.77 (s, 1H), 8.72 (s, 1H), 7.78 (s, 1H), 7.71 (s, 1H), 6.23 (d, 1H), 5.28-5.24 (m, 2H), 4.85 (d, 1H), 4.71-4.57 (m, 2H), 4.08-4.03 (m, 1H), 3.78 (br s, 1H), 3.51 (br s, 1H), 2.87 (s, 3H), 2.33 (br s, 1H), 2.13-2.06 (m, 1H), 1.49-1.33 (m, 8H), 0.93-0.80 (m, 12H): m/z 539.2 (M+H)⁺.

Preparation of Examples BA and BB

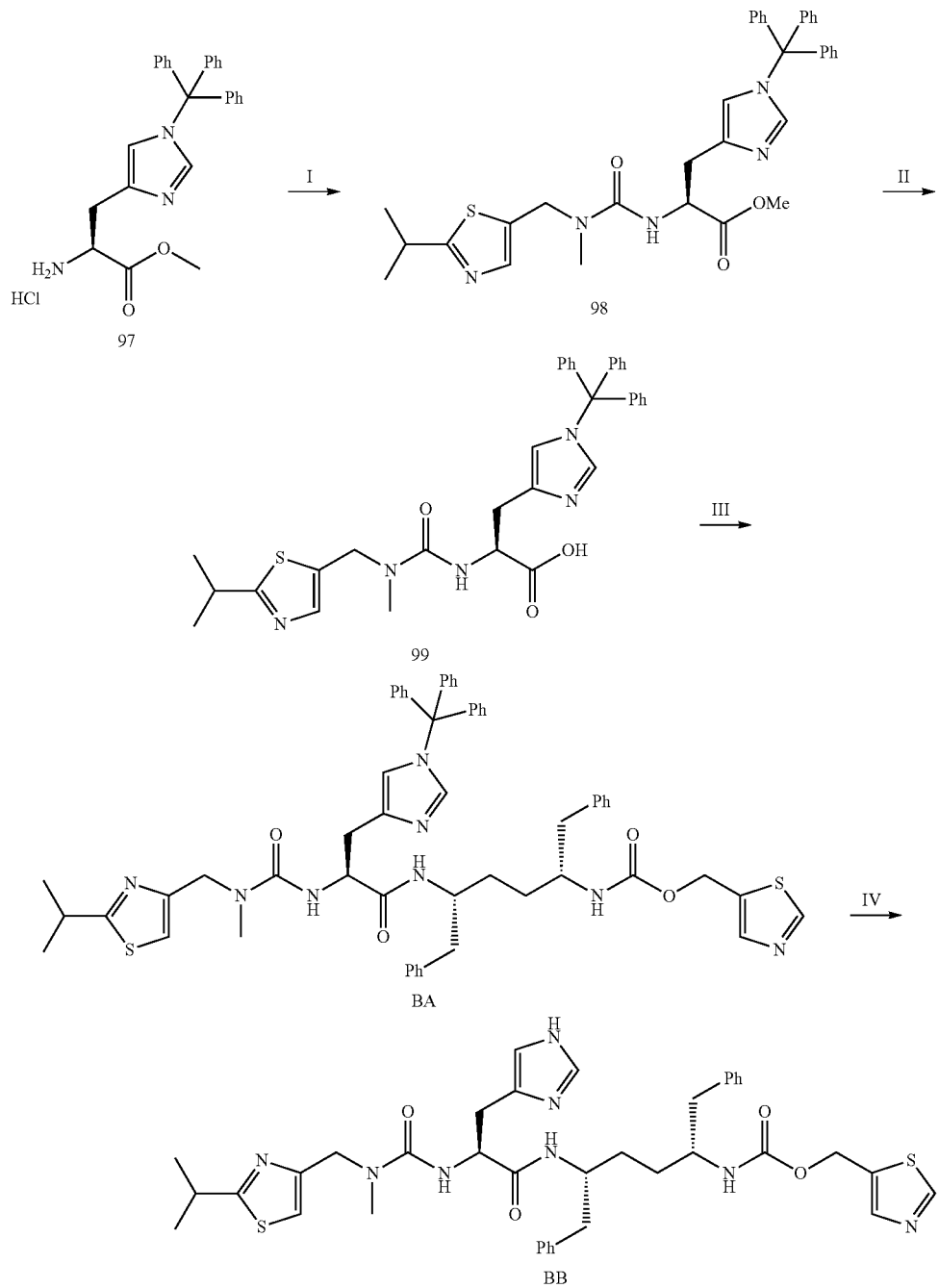

Scheme 43

I. a. CDI/iPr₂NEt; b. Compound 9; II. a. NaOH/THF/H₂O; b. HCl; III. Cmpd 8/EDC/HOBt, IPEA, THF; IV. Et₃SiH, TFA Compound 97

Compound 97 is commercially available from TCI, and was used as received.

Compound 98

To a stirred solution of Compound 97 (1 g, 2.2 mmol) and diisopropylethylamine (1.6 mL, 8.9 mmol) in dichloromethane (26 mL) was added CDT (362 mg, 2.2 mmol). The mixture was stirred for 12 hours. Compound 9 was added, and the mixture was stirred for 12 additional hours. Concentration and purification by flash column chromatography (0-8%: MeOH/DCM) gave Compound 98 (1.2 g). m/z 608.1 $(M+H)^+$.

Compound 99

Compound 99 (1.2 g) was prepared following the same procedure used to prepare Compound 67, with the exception that Compound 98 was used instead of Compound 66. m/z 592.2 $(M-H)^+$.

Example BA

Example BA (111 mg) was prepared following the procedure used to prepare Example C, except that Compound 99 was used instead of Compound 7. m/z 986.1 (M+H)$^+$.

Example BB

To a stirred solution of Example BA (111 mg, 0.113 mmol) and TFA (1.4 mL) was added Et$_3$SiH (0.1 mL). The mixture was stirred for 60 minutes, then concentrated and partitioned with EtOAc and sat. NaHCO$_3$, followed by extraction with EtOAc (2×) and drying over Na$_2$SO$_4$. Concentration and purification by flash column chromatography (0-15%: MeOH/DCM) gave Example BB (50 mg).

$^1$H-NMR (CDCl$_3$) δ 8.75 (s, 1H), 7.79 (s, 1H), 7.42 (s, 1H), 7.22-7.12 (m, 9H), 6.99-6.96 (m, 2H), 6.86 (s, 1H), 6.71 (m, 2H), 5.51 (br s, 1H), 5.17 (m, 2H), 4.57-4.52 (m, 1H), 4.39-4.35 (m, 2H), 4.07 (m, 1H), 3.74 (br s 1H), 3.28-3.19 (m, 1H), 3.09-2.76 (m, 6H), 3.65-2.58 (m, 3H), 1.49 (m, 2H), 1.36-1.20 (m, 8H); m/z 743.2 (M+H)$^+$.

Preparation of Example BC

Scheme 44

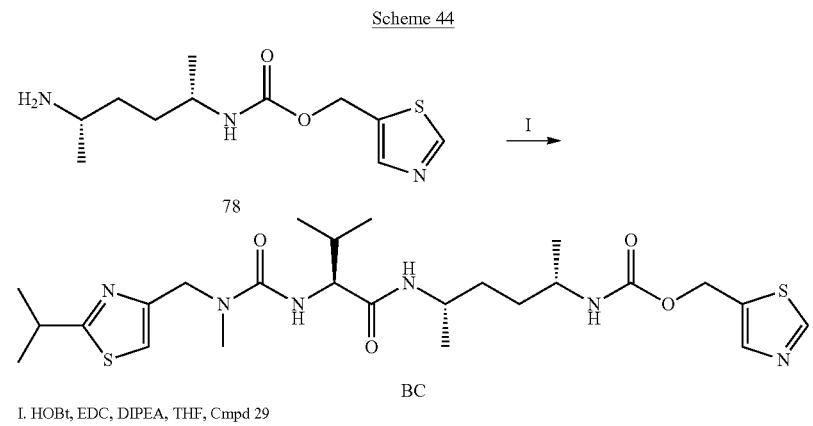

I. HOBt, EDC, DIPEA, THF, Cmpd 29

Example BC

Example BC (95 mg) was prepared following the procedure used to prepare Example C, except that Compound 29 was used instead of Compound 7, and Compound 78 was used instead of Compound 8. $^1$H NMR (CDCl$_3$) δ 8.75 (s, 1H), 7.80 (s, 1H), 6.93 (s, 1H), 6.28 (d, 1H), 6.18 (m, 1H), 5.26-5.21 (m, 3H), 4.47-4.30 (m, 2H), 4.11-4.00 (m, 1H), 3.91 (br s, 1H), 3.59 (br s, 1H), 3.28 (m, 1H), 2.97-2.90 (m, 3H), 2.26-2.19 (m, 1H), 1.39-1.24 (m, 10H), 1.09-1.01 (m, 6H), 0.94-0.86 (m, 6H): m/z 553.1 (M+H)$^+$.

Preparation of Examples BD and BE

Scheme 45

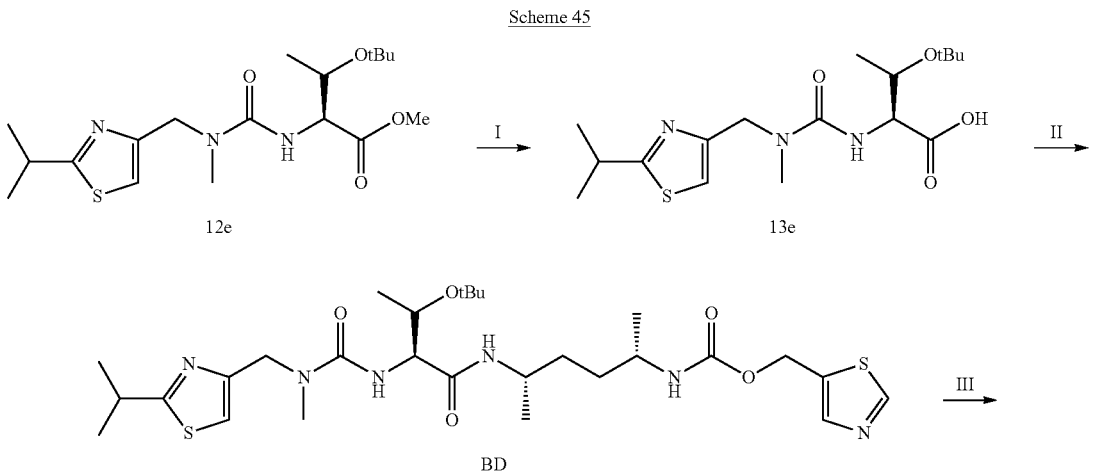

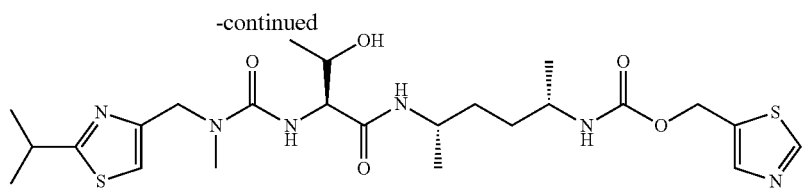

BE

I. LiOH, THF/H₂O; II. Cmpd. 78, HOBt, EDC, DIPEA, THF; III. a. neat TFA; b. NaOH, THF, H₂O Example BD Example BD (148 mg) was prepared following the procedure used to prepare Example C, except that Compound 13e was used instead of Compound 7, and Compound 78 was used instead of amine 8. m/z 611.1 (M+H)$^+$.

Example BE

Example BD (148 mg, 0.242 mmol) was dissolved in TFA (3 mL) and allowed to stir at 25° C. for 3 hours. The solvent was removed under reduced pressure and the residue was diluted with THF (3 mL) and 2N aqueous NaOH was added until pH 10. The mixture was allowed to stir for 20 min and extracted with EtOAc. The organic layer was washed sequentially with water and brine, dried over Na₂SO₄, filtered, and evaporated. Purification by flash chromatography (0-10% MeOH/CH₂Cl₂) gave Example BE (109 mg). $^1$H NMR (CDCl₃) δ 8.75 (s, 1H), 7.80 (s, 1H), 6.97-6.94 (d, 1H), 6.90 (s, 1H), 6.32 (br s, 1H), 5.26-5.22 (m, 2H), 5.12 (d, 1H), 4.51-4.39 (m, 3H), 4.25-4.22 (m, 2H), 3.87 (br s, 1H), 3.62 (br s, 1H), 3.27-3.18 (m, 1H), 2.94 (s, 3H), 1.41-1.31 (m, 10H), 1.13-1.00 (m, 9H). m/z: 555.1 (M+H)$^+$.

Preparation of Example BF

Scheme 46

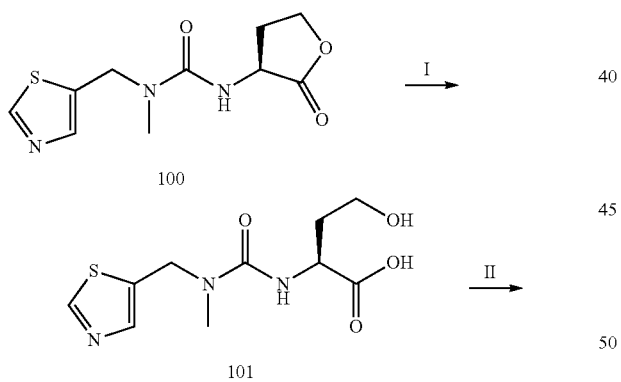

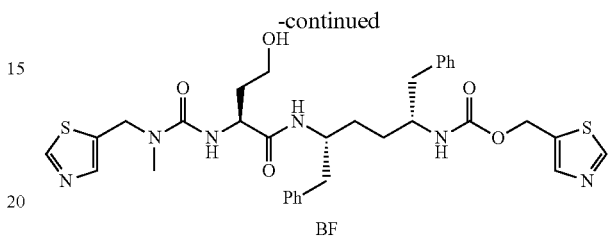

BF

I. LiOH, THF/H₂O; II. Cmpd. 8, HOBt, EDC, DIPEA, THF

Compound 100

Compound 100 was prepared using the same method used to prepare Compound 122, except that Compound 9 was replaced with Compound 68 (see Scheme 70).

Compound 101

Compound 100 (108 mg, 0.423 mmol) was dissolved in THF (2 mL), then 847 µl of 1 M LiOH/H₂O was added. After stirring overnight, 843 µl of 1 N HCl was added. Concentration gave Compound 101.

Example BF

Example BE (24 mg) was prepared following the procedure used to prepare Example C, except that Compound 101 was used instead of Compound 7.

$^1$H NMR (CDCl₃) δ 8.77 (s, 1H), 8.73 (s, 1H), 7.80 (s, 1H), 7.74 (s, 1H), 7.27-7.10 (m, 10H), 6.55-6.52 (d, 1H), 5.84 (d, 1H), 5.21-5.19 (m, 3H), 4.77-4.53 (m, 2H), 4.39 (br s, 1H), 4.11-3.99 (m, 2H), 3.81 (br s, 1H), 3.58 (m, 2H), 2.86 (s, 3H), 2.81-1.72 (m, 5H), 2.04 (m, 1H), 1.85 (m, 1H), 1.66-1.37 (m, 6H): m/z 665.2 (M+H)$^+$.

Preparation of Example BG

Scheme 47

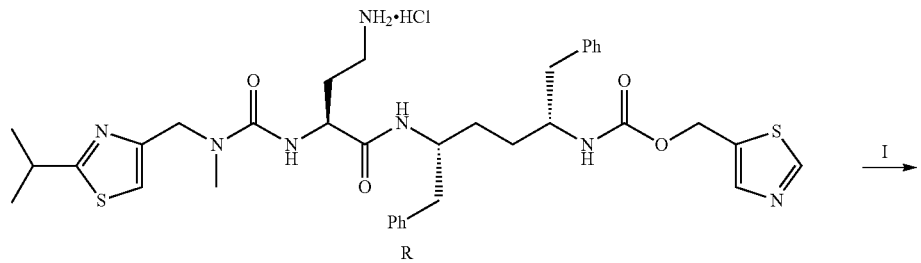

R

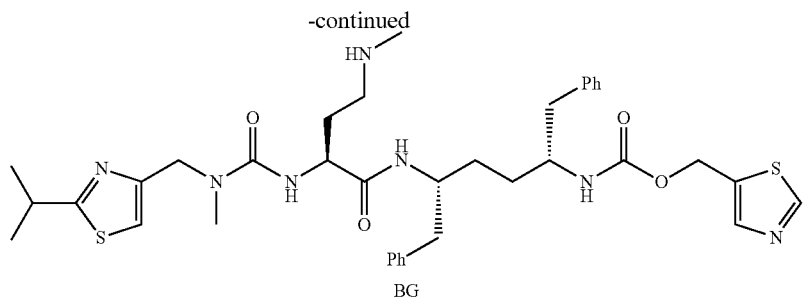

BG

I. Ethyltrifluoroacetate, MeI, Cs₂CO₃, THF

Example BG

Example R (102 mg, 0.137 mmol) was dissolved in THF (2 mL), then 2 mL of ethyltrifluoroactate was added. Then 1.3 eq of MeI and excess Cs$_2$CO$_3$ were added. After stirring for 1 day, the mixture was partitioned with EtOAc and sat. Na$_2$CO$_3$, extracted with EtOAc (2×), and dried over Na$_2$SO$_4$. Purification by flash chromatography (0-20% MeOH/CH$_2$Cl$_2$) gave Example BG (6.5 mg). $^1$H NMR (CD$_3$OD) δ 9.94 (s, 1H), 8.27 (s, 1H), 7.73 (s, 1H), 7.30-7.10 (m, 10H), 5.29, 5.17 (d 2H), 4.72 (s, 3H), 4.29 (m, 1H), 4.15 (br s, 1H), 3.83 (br s, 1H), 3.61 (m, 2H), 3.07 (s, 3H), 2.93 (m, 2H), 2.82-2.70 (m, 4H), 2.68-2.58 (m, 2H), 2.42 (s, 3H), 2.05 (m, 2H), 1.70-1.40 (m, 10H). m/z: 720.2 (M+H)$^+$.

Preparation of Example BH

Scheme 48

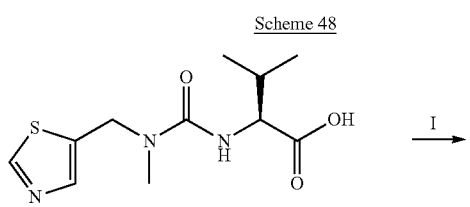

87

I. amine 59, HOBt, EDC, DIPEA, THF

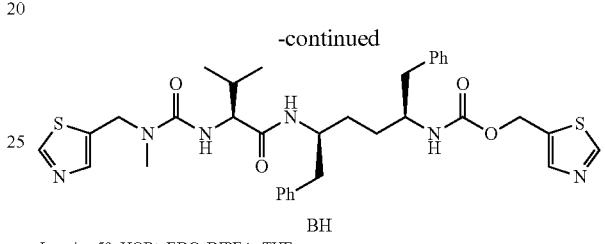

BH

Example BH

Example BH (78 mg) was prepared following the procedure used to prepare Example C, except that Compound 87 was used instead of Compound 7, and Compound 46 was used instead of Compound 8. $^1$H NMR (CDCl$_3$) δ 8.73 (s, 1H), 8.68 (s, 1H), 7.76 (s, 1H), 7.68 (s, 1H), 7.18-7.09 (m, 10H), 6.26 (m, 1H), 5.76 (m, 1H), 5.22-5.18 (m, 4H), 4.71-4.65 (d, 1H), 4.46-4.40 (d, 1H), 4.11-4.04 (m, 2H), 3.81 (br s, 1H), 3.14 (br s, 1H), 2.83 (s, 3H), 2.76-2.52 (m, 4H), 1.88 (m, 1H), 1.51-1.37 (m, 2H), 0.73-0.69 (m, 6H) m/z 663.2 (M+H)$^+$.

Preparation of Examples BI and BJ

Scheme 49

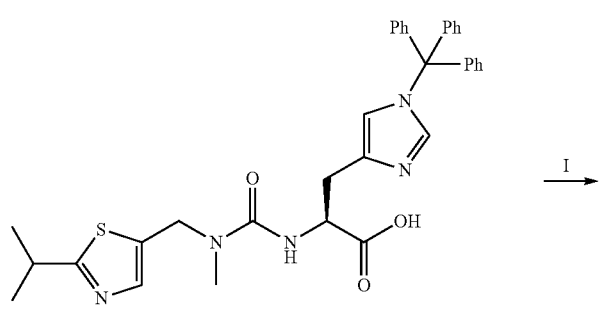

99

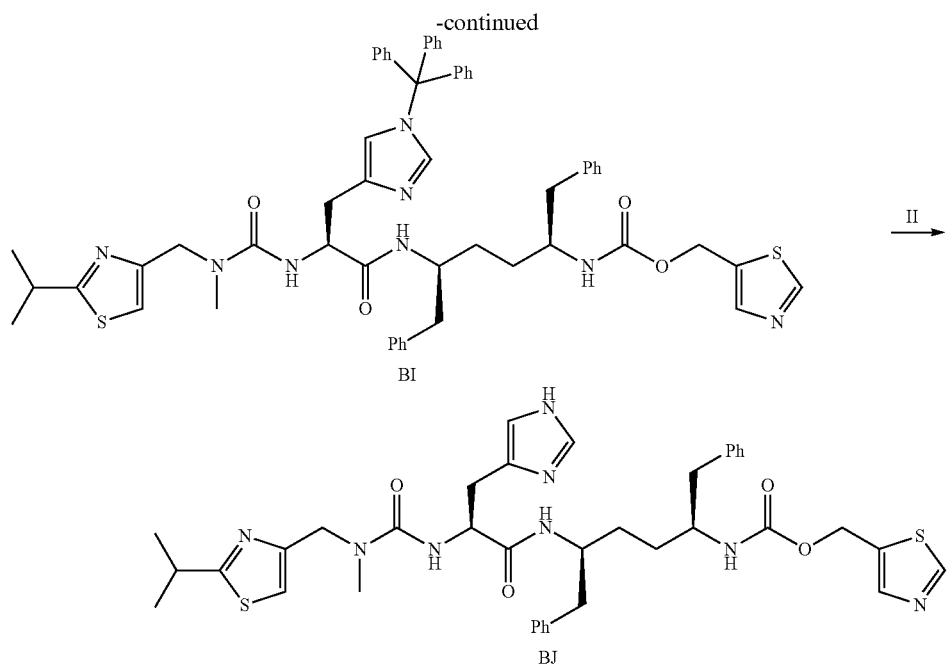

I. Cmpd. 46/EDC/HOBt, IPEA, THF: II. Et₃SiH, TFA

Example BI

Example BI (1.78 g) was prepared following the procedure used to prepare Example C, except that Compound 99 was used instead of Compound 7, and Compound 46 was used instead of Compound 8. m/z 986.1 (M+H)⁺.

Example BJ

Example BJ (728 mg) was prepared following the procedure used to prepare Example BB, except that Example BI was used instead of Example BA. $^1$H-NMR (CDCl$_3$) δ 8.75 (s, 1H), 7.79 (s, 1H), 7.42 (s, 1H), 7.22-7.12 (m, 9H), 6.99-6.96 (m, 2H), 6.86 (s, 1H), 6.71 (m, 2H), 5.51 (br s, 1H), 5.17 (m, 2H), 4.57-4.52 (m, 1H), 4.39-4.35 (m, 2H), 4.07 (m, 1H), 3.74 (br s 1H), 3.28-3.19 (m, 1H), 3.09-2.76 (m, 6H), 3.65-2.58 (m, 3H), 1.49 (m, 2H), 1.36-1.20 (m, 8H); m/z 743.2 (M+H)⁺.

Preparation of Compounds 104-115

Scheme 50

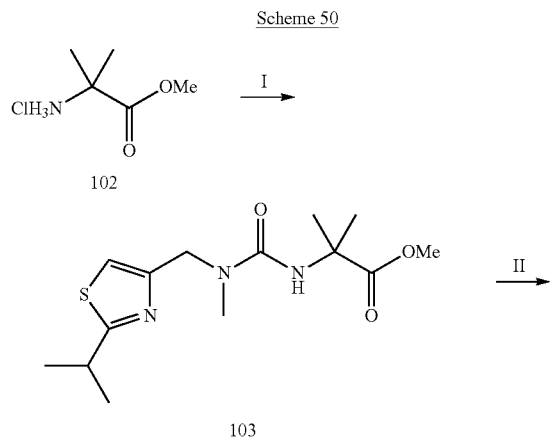

I. a. CDI, DIPEA, MeCN; b. Cmpd. 9, MeCN, II. 1M LiOH, THF.

Compound 102

Compound 102 is commercially available from Aldrich Chemical Co., and was used without further purification.

Compound 103

Compound 102 (5.5 mmol) was suspended in MeCN (55 mL) and DIPEA (8.25 mmol) was added. Carbonyl diimidazole (5.5 mmol) was diluted in MeCN (20 mL) and the solution added slowly to the reaction mixture over 45 min. The resulting mixture was allowed to age overnight. Compound 9 (5.5 mmol) was diluted in MeCN (10 mL) and treated with DIPEA (8.25 mmol) before being added to the reaction mixture, which was then allowed to age overnight. The volatiles were removed in vacuo and the residue taken up in EtOAc (50 mL) and washed with 1M HCl (50 mL). The layers were separated and the aqueous layer extracted with EtOAc (3×50 mL). The combined organic layers were washed with sat. Na$_2$CO$_3$ until the pH of the washes was ~pH 8. A brine wash (30 mL) was followed by drying over anhydrous MgSO$_4$. Following concentration in vacuo, the residue was purified on SiO$_2$ (0-65% EtOAc/hex) to provide 0.340 g (20%) of Compound 103 as an amorphous white solid (m/z 314.0 (M+H)⁺).

Compound 104

Compound 103 (1.1 mmol) was diluted in THF (5 mL) and treated with freshly prepared 1M LiOH (2.2 mmol). The biphasic reaction was stirred vigorously for 2 h before being quenched with 1M HCl (3 mmol). The reaction was extracted with EtOAc (5×15 mL) and the combined organics were washed with brine (30 mL), dried over anhydrous Na$_2$SO$_4$ and concentrated to provide 0.282 g (86%) of Compound 104 as an amorphous white powder that was used with further purification $^1$H-NMR (CDCl$_3$, 300 MHz): 7.06 (s, 1H); 4.37 (s, 1H); 3.28 (p, J=6.9 Hz, 1H); 3.00 (s, 3H); 1.62 (s, 6H); 1.39 (d, J=6.9 Hz, 6H).

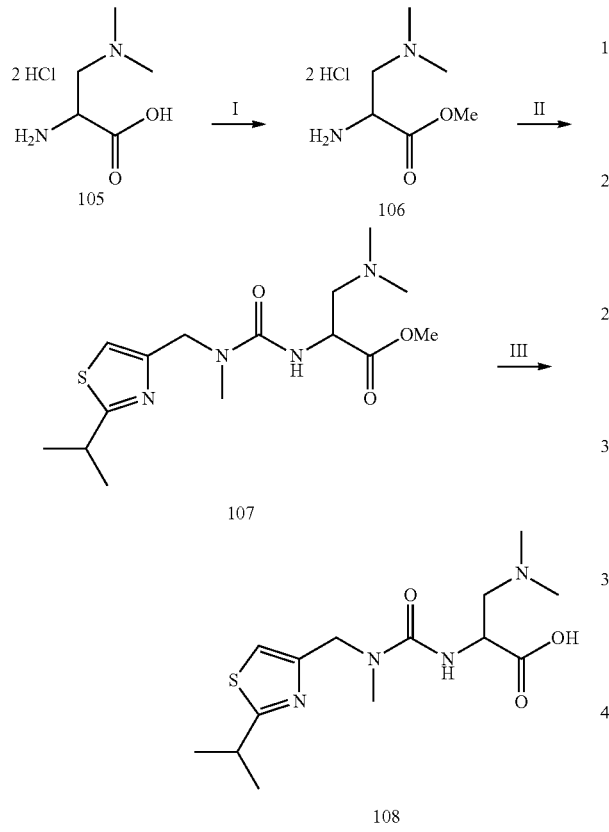

I. HCl, MeOH; II. a. CDI, DIPEA, MeCN; b. Cmpd. 9, MeCN. III. 1M LiOH, THF.

Compound 105

Compound 105 is commercially available from Aldrich Chemical Co., and was used without further purification.

Compound 106

Racemic Compound 105 (12.2 mmol) was diluted in MeOH (100 mL). HCl/dioxane solution (4M, 25 mmol) was added and the solution was refluxed overnight. Volatiles were removed in vacuo to produce 2.60 g (97%) of Compound 106 as a racemic mixture. The foamy white solid was used without further purification (m/z 147.0 (M+H)$^+$).

Compound 107

Compound 106 (5 mmol) was diluted in MeCN (65 mL) and treated with DIPEA (25 mmol). The resulting solution was added slowly via addition funnel to a solution of CDT (5 mmol) in MeCN (30 mL) and allowed to age overnight. Compound 9 (5 mmol) and DIPEA (3 mmol) were added to the reaction solution which was allowed to age overnight. The volatiles were removed in vacuo and the residue was taken up in EtOAc and sat. Na$_2$CO$_3$ (30 mL each). The aqueous layer was extracted with EtOAc (3×25 mL) and the combined organics were washed with brine (50 mL) and dried over anhydrous MgSO$_4$. Following concentration in vacuo, purification by column chromatography on SiO$_2$ (0-10% MeOH/DCM) provided 0.36 g (21%) of racemic Compound 107 as a yellow oil (m/z 343.1 (M+H)$^+$).

Compound 108

Compound 107 (1.05 mmol) was taken up in THF (5 mL) and treated with freshly prepared 1M LiOH solution (2.1 mmol). The solution was stirred vigorously for 2 h and quenched with 1M HCl (2.1 mmol). The volatiles were removed in vacuo, and the resulting oil was azeotroped with toluene until a quantitative yield of racemic Compound 108 was produced as an amorphous white solid that was used without further purification (m/z 329.1 (M+H)$^+$).

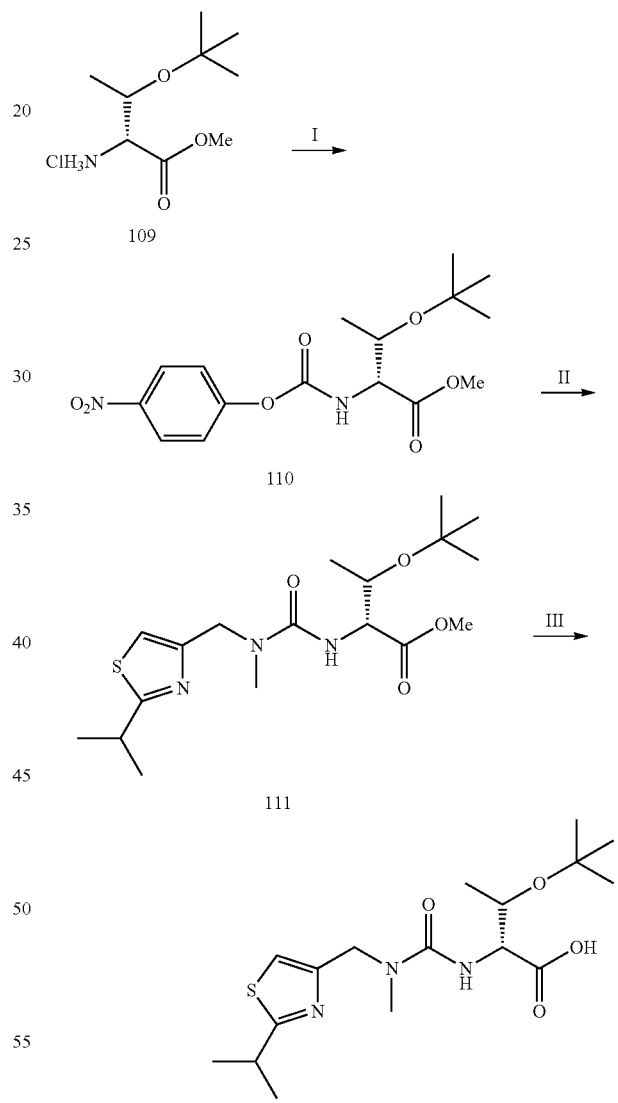

I. p-O$_2$NC$_6$H$_4$O(CO)Cl, NMM, DCM, 0° C. to rt; II. Cmpd. 9, Et$_3$N, DMAP, THF, 70° C.; III. 1M LiOH, THF Compound 109

Compound 109 is commercially available from Bachem, and was used as received.

Compound 110

Compound 109 (4.1 mmol) was diluted in DCM (5 mL) and treated with N-methylmorpholine (8.2 mmol). This solution was added slowly to a DCM (5 mL) solution of 4-nitrophenyl chloroformate (4.1 mmol) at 0° C. The reaction was then allowed to warm to room temperature overnight. The volatiles were removed in vacuo and the residue was taken up in EtOAc and sat. $Na_2CO_3$. The aqueous layer was extracted with EtOAc (3×10 mL) and the combined organics were washed with brine (30 mL) prior to being dried over anhydrous $Na_2SO_4$. Following concentration in vacuo, the residue was purified by column chromatography on $SiO_2$ (0-25% EtOAc/Hex) to produce 0.75 g (51%) of Compound 110 as an amorphous white solid (m/z 354.8 $(M+H)^+$).

Compound 111

Compound 110 (1.1 mmol) was diluted in THF (3.5 mL). Compound 9 (1.4 mmol) was diluted in THF (3 mL), treated with $Et_3N$ (2.8 mmol) and transferred to the reaction solution. DMAP (0.11 mmol) was added and the reaction was heated to 70° C. for 2 h. After cooling to room temperature, EtOAc (10 mL) and sat. $Na_2CO_3$ were added. The aqueous phase was extracted with EtOAc (3×10 mL) and the combined organics were washed with saturated $Na_2CO_3$, $H_2O$, and brine (15 mL each). After drying over anhydrous $MgSO_4$, volatiles were removed in vacuo and the residue was purified by column chromatography on $SiO_2$ (0-50% EA/hex) to produce 0.346 g (82%) of Compound III (m/z 386.0 $(M+H)^+$).

Compound 112

Compound III (0.88 mmol) was taken up in THF (4 mL) and treated with freshly prepared 1M LiOH (1.8 mmol). The reaction mixture was stirred vigorously for 1.5 h and quenched with 1M HCl (2.5 mmol). The reaction mixture was extracted with EtOAc (3×10 mL), and the combined organics were washed with brine (30 mL) and dried over anhydrous $Na_2SO_4$. Concentration in vacuo produced 0.300 g (92%) of Compound 112 as a colorless film that was used without further purification (m/z 372.0 $(M+H)^+$).

Scheme 53

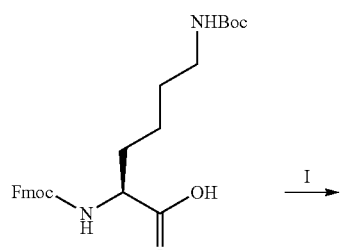

113

-continued

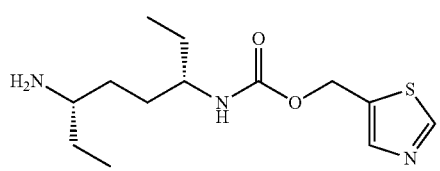

I. TMSCHN$_2$, THF/MeOH;
II. piperidine, DMF

Compound 113

Compound 113 is commercially available from Chem-Impex, and was used without further purification.

Compound 114

Compound 113 (3.2 mmol) was diluted in THF (15 mL). TMSCHN$_2$ (3.2 mmol) was added slowly, followed by MeOH (5 mL). The solution rapidly became colorless, and heavy evolution of gas was observed. After aging overnight, the volatiles were removed in vacuo and the residue purified by column chromatography on $SiO_2$ (0-50% EtOAc/hex) to produce 0.805 g (52%) of Compound 114 (m/z 505.2 $(M+Na)^+$).

Compound 115

Compound 114 (1.7 mmol) was diluted in DMF (4 mL) and piperidine (1 mL) was added. After 30 min, the volatiles were removed in vacuo and the residue was purified by column chromatography on $SiO_2$ (0-5% MeOH/DCM) to provide 0.414 (94%) of Compound 115 as an amorphous white solid (m/z 261.0 $(M+H)^+$).

Preparation of Example BK

Scheme 54

79

↓I

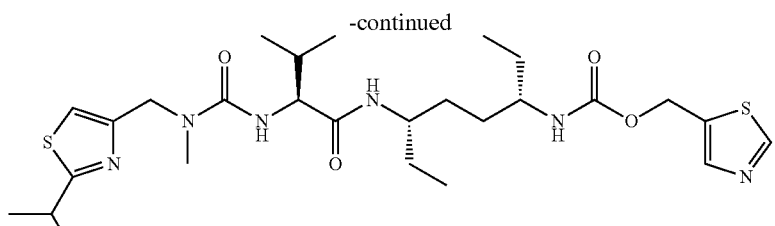

BK

I. Cmpd. 29/EDC/HOBt/DIPEA/THF.

Compound BK

Compound 79 (0.70 mmol) and Compound 29 (0.91 mmol) were combined in THF (7 mL). HOBt (0.91 mmol), DIPEA (1.05 mmol) and EDC (0.91 mmol) were added consecutively at room temperature and the reaction was allowed to age overnight. The volatiles were removed in vacuo and the residue taken up in 3/1 CHCl$_3$/IPA and sat. Na$_2$CO$_3$ (15 mL each). The aqueous layer was extracted with 3/1 CHCl$_3$/IPA (3×10 mL) and the combined organics were washed with sat. Na$_2$CO$_3$, water, and brine (15 mL each). Following drying over anhydrous MgSO$_4$, the volatiles were removed in vacuo and the residue was purified by column chromatography on SiO$_2$ (0-10% MeOH/DCM) to produce 8.5 mg (2%) of Compound BK m/z 581.2 (M+H)$^+$; $^1$H-NMR (CDCl$_3$, 300 MHz): 8.91 (s, 1H); 7.89 (s, 1H); 7.15 (s, 1H); 6.52-6.0 (br m, 2H); 5.26 (s, 2H); 5.18 (br d, J=8.1 Hz, 1H); 4.55 (s, 2H); 4.06 (br s, 1H); 3.79 (br s, 1H); 3.48 (m, 2H); 3.09 (s, 3H, minor rotamer); 3.01 (s, 3H, major rotamer); 2.34 (m, 1H); 1.60-1.30 (m, 8H); 1.42 (d, J=6.9 Hz, 6H); 0.98 (t, J=7.2 Hz, 6H); 0.86 (m, 6H).

Preparation of Example BL

Scheme 55

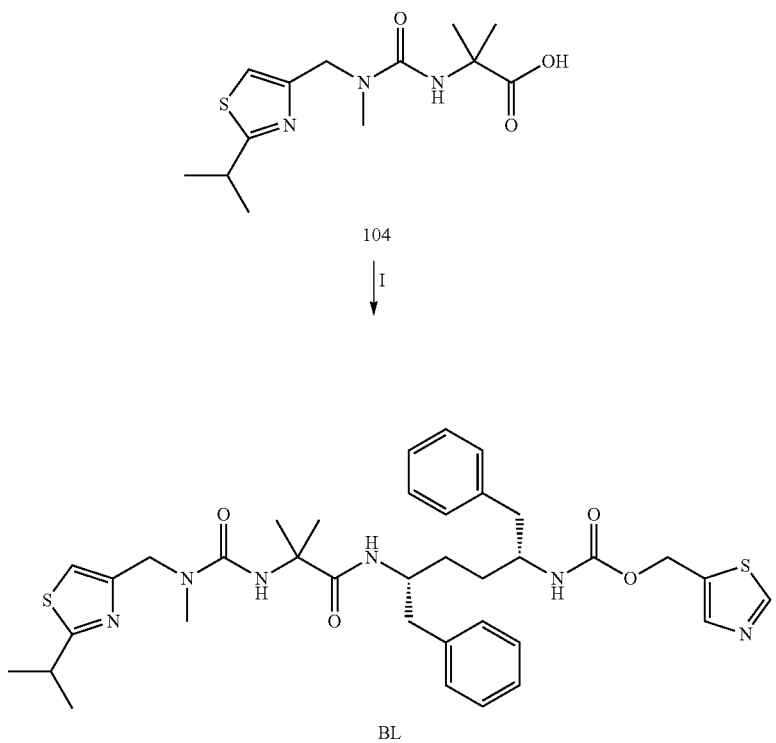

BL

I. Cmpd. 8/EDC/HOBt/DIPEA/THF.

Example BL

Example BL was prepared in a similar fashion to Example BK using Compound 104 (026 mmol) and Compound 8 (0.29 mmol) to produce 0.087 g (64%) of Example BL as an amorphous white solid m/z 691.3 (M+H)$^+$; $^1$H-NMR (CDCl$_3$, 300 MHz): 8.82 (s, 1H); 7.82 (s, 1H); 7.30-7.10 (m, 11H); 7.06 (s, 1H); 6.54 (d, J=9.6 Hz, 1H); 5.89 (d, J=8.4 Hz, 1H); 5.22 (s, 1H); 5.07 (m, 1H); 4.45 (AB d, J=16.5 Hz, 1H); 4.37 (AB d, J=15.6 Hz, 1H); 4.07 (m, 1H); 3.68 (m, 1H); 3.40 (m, 1H); 3.06 (s, 3H, minor rotamer); 2.89 (s, 3H, major rotamer); 2.90-2.54 (m, 4H); 1.60-1.25 (m, 16H).

Preparation of Example BMa and BMb

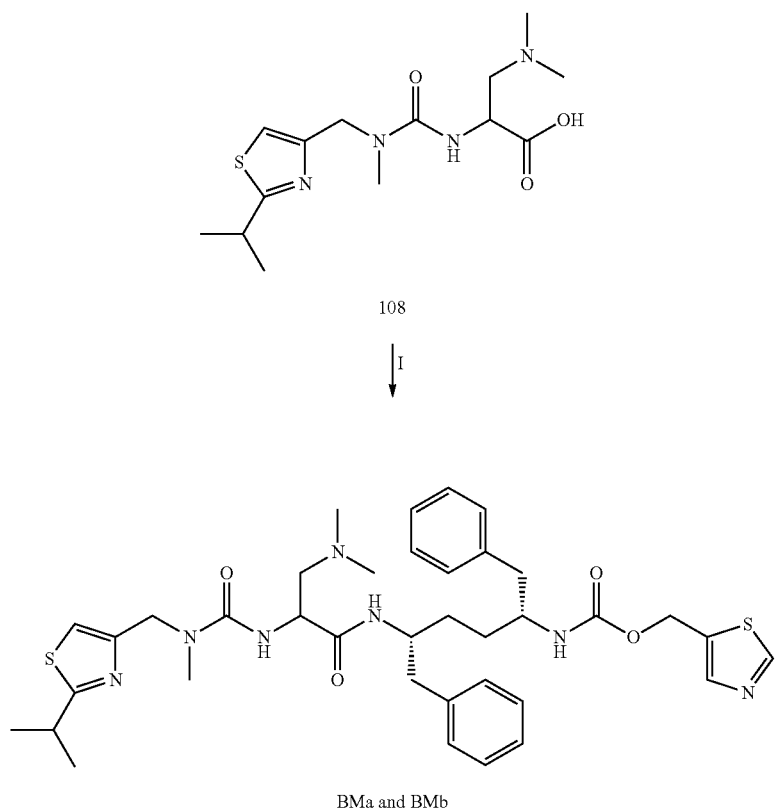

Scheme 56

108

BMa and BMb

I. Cmpd. 8/EDC/HOBt/DIPEA/THF.

Examples BMa and BMb

Examples BMa and BMb were prepared in a similar fashion to Compound BK using racemic Compound 108 (0.36 mmol) and Compound 8 (0.28 mmol). The enantiomeric products were separated by preparatory HPLC (Chiralcel OD-H (250×4.6 mm, 70:30 Heptane/IPA, 30 min) to produce 0.008 g (4%) of enantiomer BMa (HPLC R$_T$=11.71 min) m/z 720.3 (M+H)$^+$; $^1$H-NMR (CDCl$_3$, 300 MHz): 8.73 (s, 1H); 7.78 (s, 1H); 7.41 (br s, 1H); 7.30-7.00 (m, 11H); 6.94 (s, 1H); 5.40 (br s, 1H); 5.18 (br s, 2H); 4.56 (AB d, J=15 Hz, 1H); 4.48 (AB d, J=16 Hz, 1H); 4.39 (br s, 1H); 4.05 (br s, 1H); 3.73 (br s, 1H); 3.25 (s, 3H, minor rotamer); 3.23 (m, 1H); 2.98 (s, 3H, major rotamer); 2.82-2.30 (m, 10H); 1.60-1.20 (m, 6H); 1.32 (d, J=7 Hz, 6H) and 0.010 g (5%) of enantiomer BMb (HPLC R$_T$=15.41 min). (m/z 720.3 (M+H)$^+$; $^1$H-NMR (CDCl$_3$, 300 MHz): 8.78 (s, 1H); 7.83 (s, 1H); 7.38 (br d, J=8 Hz, 1H); 7.30-7.7.05 (m, 11H); 7.02 (s, 1H); 5.52 (d, J=9 Hz, 1H); 5.25 (AB d, J=13 Hz, 1H); 5.21 (AB d, J=13 Hz, 1H); 4.85-4.62 (m, 2H); 4.44 (d, J=16 Hz, 1H); 3.99 (br s, 1H); 3.78 (br s, 1H); 3.37 (br s, 3H, minor rotamer); 3.26 (m, 1H); 3.07 (s, 3H, major rotamer); 2.77 (s, 6H); 2.86-2.60 (m, 4H); 1.6-1.3 (m, 6H); 1.35 (d, J=7 Hz, 6H).

Preparation of Examples BN and BO

Scheme 57

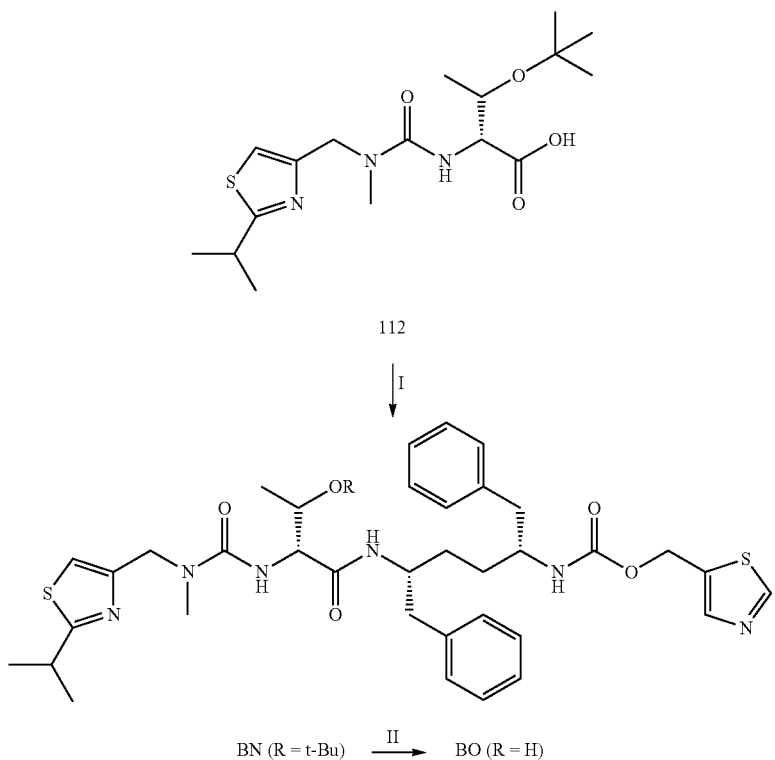

BN (R = t-Bu) →(II)→ BO (R = H)

I. Cmpd. 8/EDC/HOBt/DIPEA/THF;
II. TFA, 1M NaOH.

Example BN

Example BN was prepared in a similar fashion to Example BK using Compound 112 (0.78 mmol) and Compound 8 (0.60 mmol) to produce 0.227 g (50%) of Compound BN as colorless film. (m/z 763.3 (M+H)+).

Example BO

Example BO was prepared in a similar fashion to Example AM using Example BN (0.29 mmol) to produce 0.149 g (72%) of Example BO as an amorphous white solid.

(m/z 707.3 (M+H)+; $^1$H-NMR (CDCl$_3$, 300 MHz): 8.82 (s, 1H); 7.84 (s, 1H); 7.26-7.03 (m, 11H); 6.99 (s, 1H); 6.69 (d, J=9.6, 1H); 6.42 (br s, 1H); 5.47 (br d, J=8.7 Hz, 1H); 5.27 (AB d, J=13 Hz, 1H); 5.22 (AB d, J=13 Hz, 1H); 4.55 (AB d, J=16 Hz, 1H); 4.43 (AB d, J=16 Hz, 1H); 4.18 (m, 1H); 4.00 (m, 2H); 3.72 (br s, 1H); 2.25 (m, 1H); 2.99 (s, 3H); 2.84-2.60 (m, 3H); 2.54-2.42 (m, 1H); 1.64-1.12 (m, 4H); 1.37 (d, J=7 Hz, 6H); 1.11 (d, J=6 Hz, 3H).

Preparation of Examples BP-BR

Scheme 58

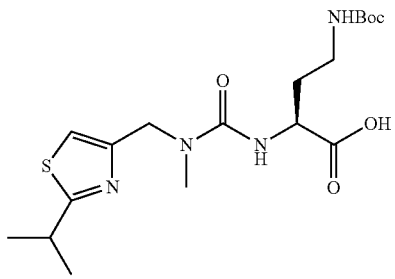

52

↓I

-continued

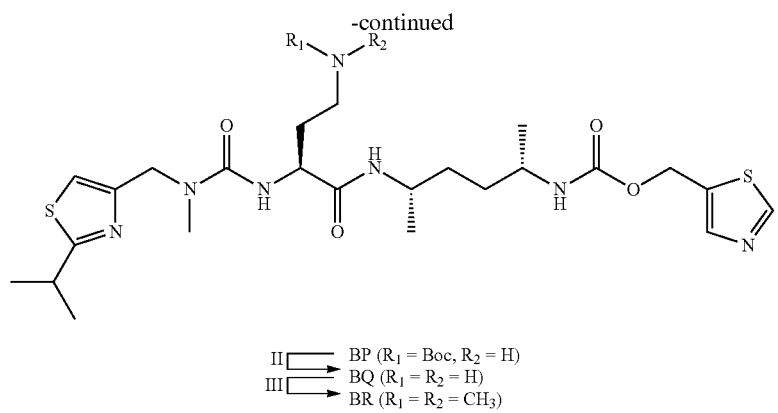

II ⎡⎯⎯→ BP (R₁ = Boc, R₂ = H)
III ⎣⎯⎯→ BQ (R₁ = R₂ = H)
⎯⎯→ BR (R₁ = R₂ = CH₃)

I. Cmpd. 78/EDC/HOBt/DIPEA/THF;
II. 4M HCl/dioxane;
III. HCHO, NaHB(OAc)₃, MeOH

Example BP

Example BP was prepared in a similar fashion to Example BK using Compound 52 (0.22 mmol) and Compound 78 (0.20 mmol) to produce 0.091 g (71%) of Example BP as colorless film (m/z 654.2 (M+H)$^+$).

Example BQ

Example BP (0.14 mmol) was treated with 4M HCl in dioxane (2 mL) to produce a white precipitate within 5 min. The solvents were removed, and the solid was taken up in MeOH. Concentration in vacuo afforded 0.083 g (99%) of the HCl salt of Example BQ as a colorless film (m/z 554.1 (M+H)$^+$; $^1$H-NMR (CD₃OD, 300 MHz): 10.03 (s, 1H); 8.41 (s, 1H); 7.81 (s, 1H); 5.48 (s, 2H, minor rotamer); 5.35 (s, 2H, major rotamer); 4.74 (s, 2H); 4.34 (br s, 1H); 3.90 (br s, 1H); 3.78-3.54 (m, 2H); 3.20-2.98 (m, 5H); 2.20 (br s, 1H); 2.07 (br s, 1H); 1.60-1.4 (m, 10H); 1.12 (m, 6H).

Example BR

Example BQ (0.11 mmol) was taken up in MeOH (1.5 mL). Formaldehyde (37% in H₂O, 13.4 mmol) was added and aged 10 min. NaHB(OAc)₃ (0.324 mmol) was added, and the reaction mixture was allowed to age at room temperature overnight. More formaldehyde (13.4 mmol) and NaHB(OAc)₃ (0.324 mmol) were added and allowed to age an additional 6 h at room temperature. The solvents were removed in vacuo and the product was isolated by preparatory HPLC to produce 0.058 g (77%) of the TFA salt of Example BR as an amorphous solid. m/z 582.3 (M+H)$^+$; $^1$H-NMR (CD₃OD, 300 MHz): 9.07 (s, 1H); 7.91 (s, 1H); 7.25 (s, 1H); 5.47 (s, 2H, minor rotamer); 5.28 (s, 2H, major rotamer); 4.59 (AB d, J=16 Hz, 1H); 4.53 (AB d, J=16 Hz, 1H); 4.31 (dd, J=9.2, 5 Hz, 1H); 3.88 (m, 1H); 3.59 (m, 1H); 3.32 (m, 1H); 3.20 (m, 2H); 2.98 (s, 3H); 2.89 (br s, 6H); 2.23 (m, 1H); 2.00 (m, 1H); 1.44 (m, 4H); 1.37 (d, J=7 Hz, 6H); 1.10 (m, 6H).

Preparation of Examples BS and BT

Scheme 59

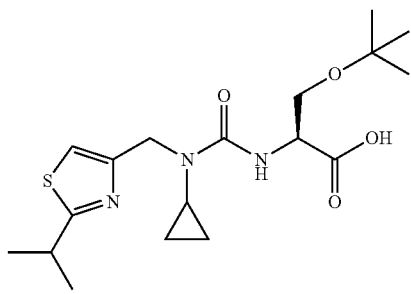

116

↓ I

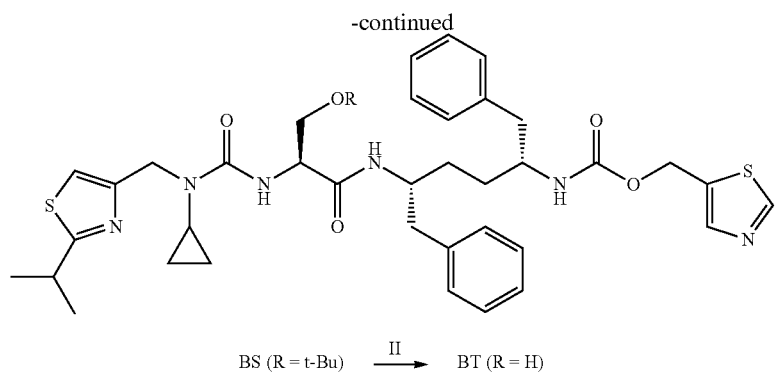

BS (R = t-Bu) →[II] BT (R = H)

I. Cmpd. 8/EDC/HOBt/DIPEA/THF;
II. TFA, 1M NaOH.

Compound 116

Compound 116 was prepared in a similar fashion to Compound 75 using Compound 4 (0.76 mmol) and Compound 47 (0.64 mmol) to produce 0.218 g (90%) of Compound 116 as a foamy white solid (m/z 384.1 (M+H)$^+$).

Example BS

Example BS was prepared in a similar fashion to Example BK using Compound 116 (0.28 mmol) and Compound 8 (0.25 mmol) to produce 0.139 g (72%) of Example BS as a colorless film (m/z 775.3 (M+H)$^+$).

Example BT

Example BT was prepared in a similar fashion to Example AM using Example BS (0.18 mmol) to produce 0.080 g (62%) of Example BT as an amorphous white solid. m/z 719.3 (M+H)$^+$; $^1$H-NMR (CDCl$_3$, 300 MHz): 8.79 (s, 1H); 7.82 (s, 1H); 7.27-7.0 (m, 10H); 6.98-6.82 (m, 1H); 6.85 (s, 1H); 6.44 (br s, 1H); 5.30 (s, 2H, minor rotamer); 5.22 (s, 2H, major rotamer); 5.04 (br s, 1H); 4.62 (AB d, J=15 Hz, TH); 4.54 (AB d, J=15 Hz, 1H); 4.27 (br s, 1H); 4.11 (br s, 1H); 3.97 (br d, J=10 Hz, 1H); 3.82, br s, 1H); 3.57 (br s, 1H); 3.40-3.10 (m, 2H); 2.80-2.60 (m, 4H); 2.55 (m, 1H); 1.54 (m, 2H); 1.46-1.30 (m, 2H); 1.35 (d, J=7 Hz, 6H); 0.94-0.72 (m, 4H).

Preparation of Examples BU and BV

Scheme 60

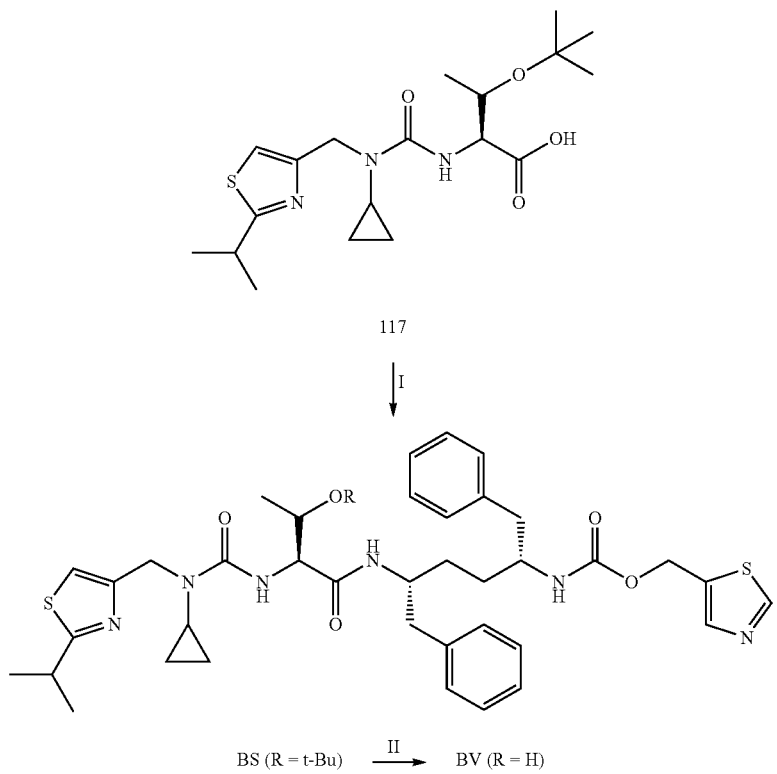

BS (R = t-Bu) →[II] BV (R = H)

I. Cmpd. 8/EDC/HOBt/DIPEA/THF;
II. TFA, 1M NaOH.

Compound 117

Compound 117 was prepared in a similar fashion to Compound 13d except that Compound 4 (1.5 mmol) and the L-enantiomer of Compound 10d (1.15 mmol) were used to ultimately produce 0.328 g (88%) of Compound 190 as a foamy white solid (m/z 398.1 (M+H)⁺).

Example BU

Example BU was prepared in a similar fashion to Example AL using Compound 117 (0.33 mmol) and Compound 8 (0.30 mmol) to produce 0.196 g (84%) of Example BU as an amorphous white solid (m/z 789.3 (M+H)⁺).

Example BV

Example BV was prepared in a similar fashion to Example AM using Example BU (0.29 mmol) to produce 0.140 g (77%) of Example BV as an amorphous white solid. m/z 733.3 (M+H)⁺; ¹H-NMR (CDCl₃, 300 MHz): 8.80 (s, 1H); 7.84 (s, 1H); 7.27-7.10 (m, 10H); 6.70-6.10 (m, 1H); 6.86 (s, 1H); 6.20 (br d, J=7 Hz, 1H); 4.81 (br d, J=7 Hz, 1H); 4.82 (s, 2H); 4.34 (br d, J=7 Hz, 1H); 4.16 (br s, 1H); 4.07 (br d, J=6 Hz, 1H); 3.86 (br s, 1H); 3.38 (br s, 1H); 2.69 (m, 6H); 1.62-1.50 (m, 2H); 1.50-1.34 (m, 2H); 1.38 (m, 6H); 1.13 (d, J=6 Hz, 3H); 0.98-0.76 (m, 4H).

Preparation of Examples BW and BX

Scheme 61

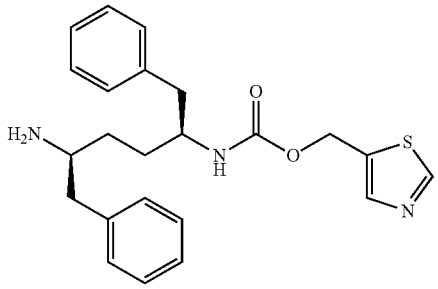

46

↓ I

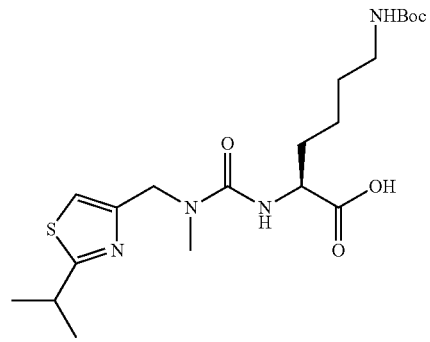

BW (R = t-Bu) —II→ BX (R = H)

I. Cmpd. 75/EDC/HOBt/DIPEA/THF;
II. TFA, 1M NaOH.

Example BW

Example BW was prepared in a similar fashion to Example BK using Compound 75 (0.27 mmol) and Compound 46 (0.24 mmol) to provide 0.154 g (86%) of Example BW as an amorphous white solid (m/z 733.3 (M+H)⁺).

Example BX

Example BX was prepared in a similar fashion to Example AM using Example BW (0.21 mmol) to provide 0.091 g (98%) of the TFA salt of Example BX as an amorphous white solid. m/z 677.5 (M+H)⁺; ¹H-NMR (CDCl₃, 300 MHz): 8.83 (s, 1H); 8.77 (s, 1H); 7.84 (s, 1H); 7.77 (s, 1H); 7.27-7.00 (m, 10H); 6.62 (d, J=9 Hz, 1H); 6.44 (d, J=6 Hz, 1H); 5.35 (d, J=10 Hz, 1H); 5.24 (s, 2H); 4.69 (AB d, J=15 Hz, 1H); 4.62 (AB d, J=16 Hz, 1H); 4.14 (br m, 2H); 3.96-3.78 (m, 2H); 3.51 (dd, J=11, 4.5 Hz, 1H); 3.38 (br s, 1H); 2.82-2.58 (m, 4H); 2.41 (m, 1H); 1.70-1.24 (m, 4H); 1.20-0.88 (m, 2H); 0.88-0.54 (m, 2H).

Preparation of Examples BY and BZ

Scheme 62

118

↓ I

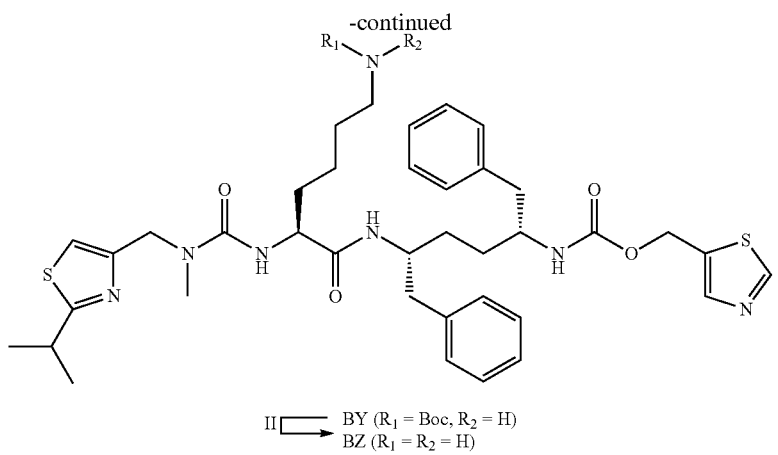

I. Cmpd. 8/EDC/HOBt/DIPEA/THF;
II. 4M HCl/dioxane.

Compound 118

Compound 118 was prepared in a similar fashion to Compound 104 except that Compound 115 (0.40 mmol) was used instead of Compound 102, which was reacted with Compound 9 (0.48 mmol) to ultimately provide 0.075 g (89%) of Compound 118 as a foamy white solid (m/z 443.4 (M+H)$^+$).

Example BY

Example BY was prepared in a similar fashion to Example BM using Compound 118 (0.17 mmol) and Compound 8 (0.15 mmol) to produce 0.079 g (62%) of Example BY as an amorphous white solid (m/z 834.3 (M+H)$^+$).

Example BZ

Example BZ was prepared in a similar fashion to Example BQ using Example BY (0.095 mmol) to provide 0.082 g (99%) of the HCl salt of Example BZ as an amorphous white solid m/z 734.2 (M+H)$^+$, $^1$H-NMR (DMSO-d$_6$, 300 MHz): 8.08 (s, 1H); 7.86 (br m, 3H); 7.58 (d, J=9 Hz, 1H); 7.25-7.00 (m, 11H); 6.32 (br s, 1H); 5.16 (s, 2H); 4.99 (br m, 4H); 4.48 (AB d, J=15 Hz, 1H); 4.43 (AB d, J=15 Hz, 1H); 4.02 (m, 1H); 3.89 (m, 1H); 3.63 (m, 1H); 3.22 (hep, J=7 Hz, 1H); 2.87 (s, 3H); 2.76-2.56 (m, 4H); 1.58-1.15 (m, 10H); 1.29 (d, J=7 Hz, 6H).

Preparation of Example CA

Scheme 63

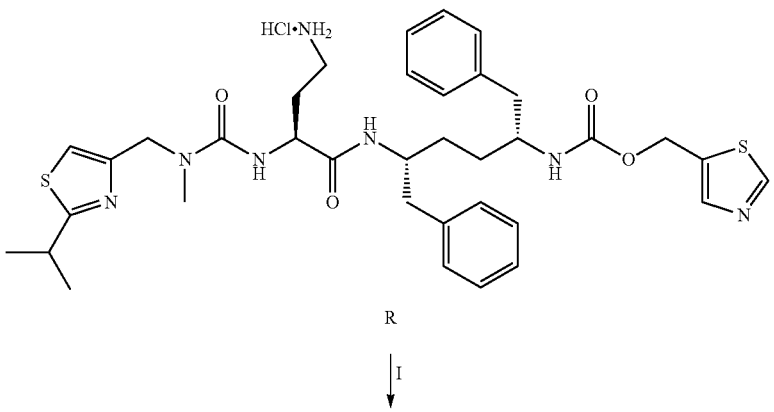

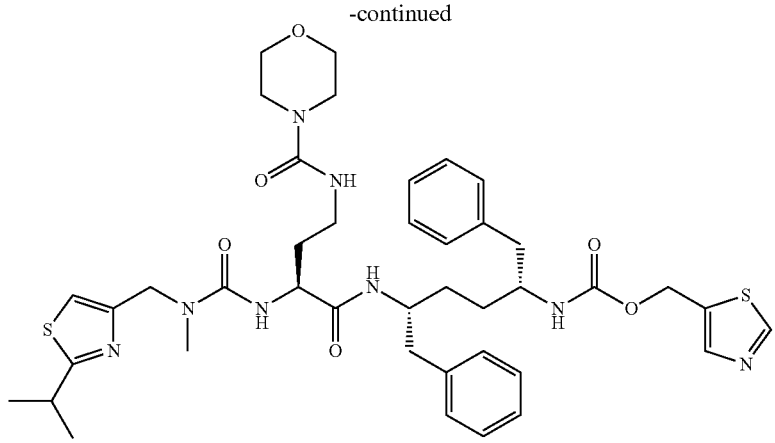

CA

I. 4-morpholinecarbonyl chloride, DIPEA, DCM.

Example CA

Example R (0.11 mmol) was diluted in DCM (1 mL) and treated with 4-morpholinecarbonyl chloride (0.13 mmol) and DIPEA (0.16 mmol). After 2 h, volatiles were removed in vacuo and the residue was purified by column chromatography on $SiO_2$ (0-20% MeOH/DCM) to afford 0.068 g (76%) of Example CA as an amorphous white solid m/z 819.1 (M+H)+; $^1$H-NMR (CDCl$_3$, 300 MHz): 8.82 (s, 1H); 7.85 (s, 1H); 7.27-7.07 (m, 12H); 6.94 (s, 1H); 6.26 (br s, 1H); 5.73 (d, J=8 Hz, 1H); 5.28 (AB d, J=13 Hz, 1H); 5.22 (AB d, J=13 Hz, 1H); 4.50 (AB d, J=16 Hz, 1H); 4.44 (AB d, J=16 Hz, 1H); 4.17 (m, 1H); 3.98 (br s, 1H) 3.76 (br s, 1H); 3.68 (br s, 1H); 3.60 (m, 4H); 3.40 (m, 2H); 3.32 (m, 4H); 2.97 (s, 3H); 2.87 (dd, J=13, 5 Hz, 2H); 2.73, (m, 2H); 2.57 (m, 2H); 1.79 (m, 2H); 1.60-1.20 (m, 6H); 1.37 (d, J=7 Hz, 6H).

Preparation of Compound CB

Scheme 64

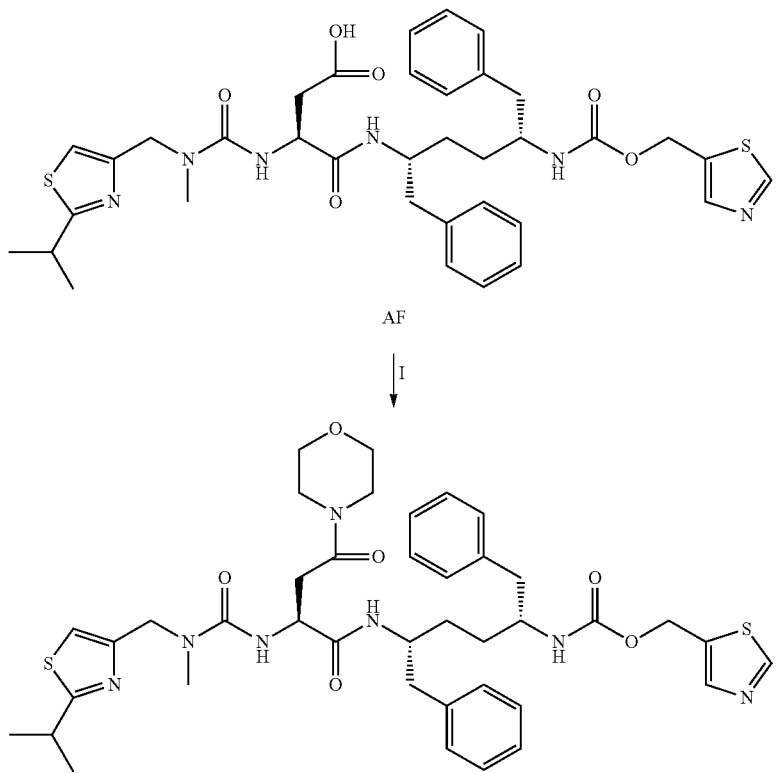

I. morpholine, EDC, HOBt, THF.

Example CB

Example AF (0.15 mmol) was diluted in THF (1 mL) and treated with morpholine (0.61 mmol), HOBt (0.18 mmol) and finally EDC (0.18 mmol). The reaction mixture was allowed to age overnight. The reaction mixture was then diluted in EtOAc and sat. $Na_2CO_3$. The aqueous layer was extracted with EtOAc and the combined organic layers were washed with brine, dried over anhydrous $MgSO_4$ and concentrated in vacuo. The resulting residue was purified via preparatory HPLC to provide 0.024 g (20%) of Example CB as an amorphous white solid. m/z 790.4 (M+H)+; $^1$H-NMR (CDCl$_3$, 300 MHz): 8.81 (s, 1H); 7.84 (s, 1H); 7.27-7.10 (m, 10H); 6.96 (s, 1H); 6.78 (d, J=8 Hz, 1H); 6.67 (s, 1H); 5.36 (d, J=9 Hz, 1H); 5.27 (AB d, J=13 Hz, 1H); 5.20 (AB d, J=13 Hz, 1H); 4.59 (s, 1H); 4.51 (s, 2H); 4.02 (m, 1H); 3.80-3.30 (m, 10H); 2.98 (s, 3H); 2.90-2.45 (m, 6H); 1.52 (m, 2H); 1.39 (d, J=7 Hz, 6H); 1.32 (m, 2H).

Preparation of Compound CC

Example CC

Example CC was prepared in a similar fashion to Example CB except that N-methylpiperazine (0.16 mmol) was reacted with Compound AF (0.10 mmol) instead of morpholine and DIPEA (0.19 mmol) was added to produce 0.009 g (11%) of Example CC as an amorphous white solid m/z 803.4 (M+H)+; $^1$H-NMR (CDCl$_3$, 300 MHz): 8.80 (s, 1H); 7.84 (s, 1H); 7.27-7.10 (m, 11H); 6.91 (s, 1H); 6.78 (m, 2H); 5.27 (AB d, J=13 Hz, 1H); 5.21 (AB d, J=13 Hz, 1H); 4.59 (m, 1H); 4.49 (AB d, J=16 Hz, 4.44 (AB d, J=16 Hz, 1H); 4.01 (m, 1H); 3.90-3.40 (m, 4H); 3.27 (hep, J=7 Hz, 1H); 3.10-2.90 (m, 1H); 2.97 (s, 3H); 2.90-2.30 (m, 11H); 1.60-1.25 (m, 6H); 1.37 (d, J=7 Hz, 6H).

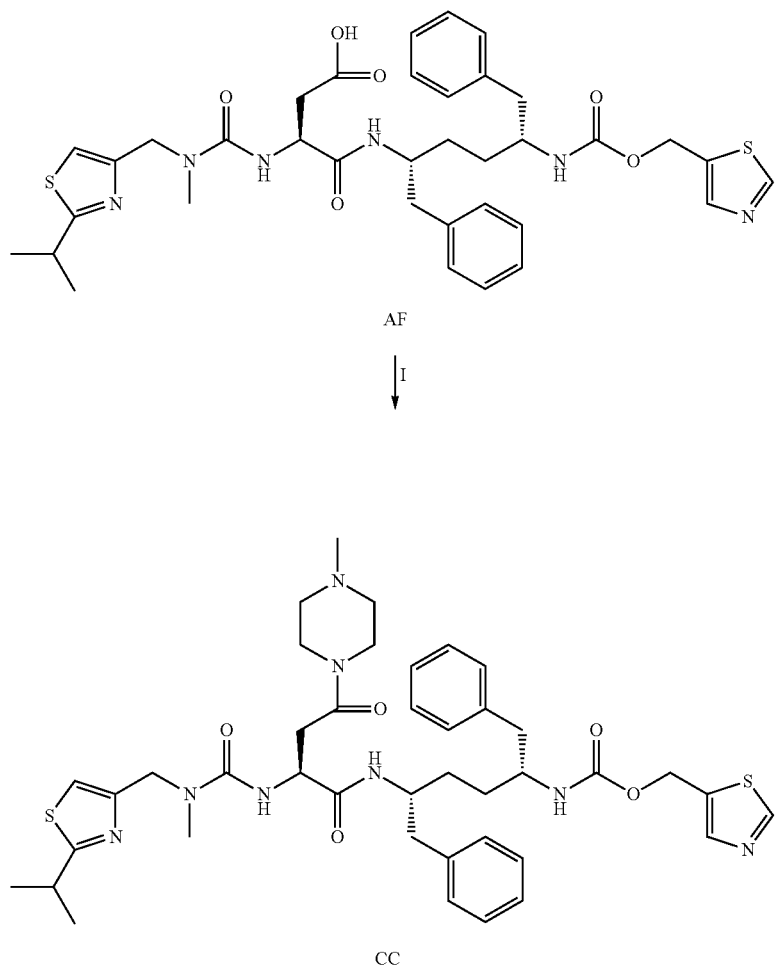

Scheme 65

I. N-methylpiperazine, EDC, HOBt, DIPEA, THF.

Preparation of Example CD

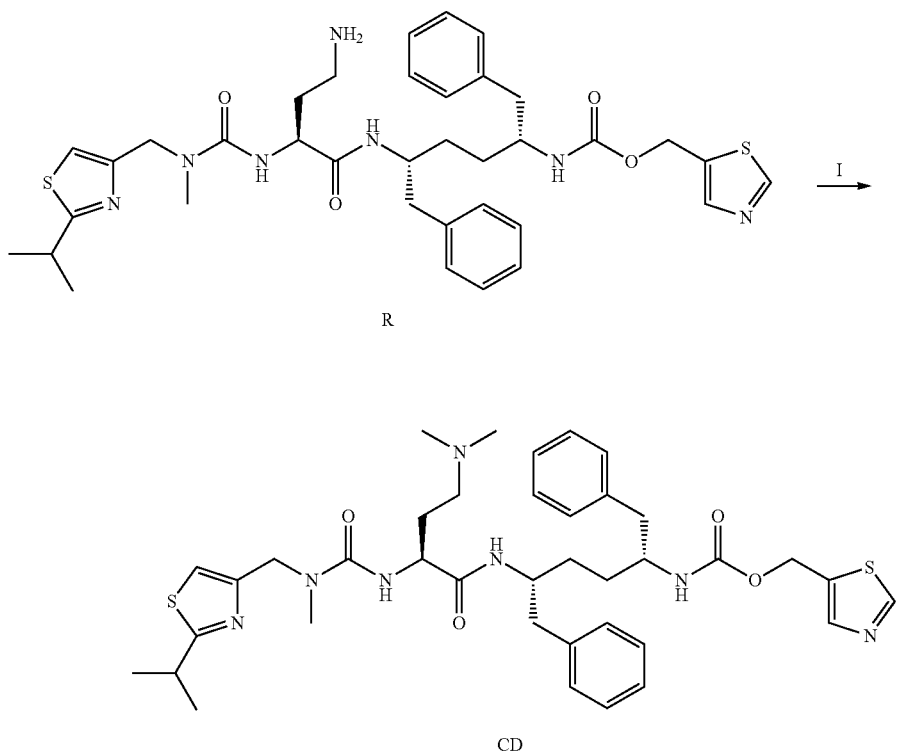

I. HCHO/NaBH(OAc)₃/MeOH

Example CD

To a solution of Example R (30.5 mg, 0.043 mmol) in methanol (1.5 mL) was added formaldehyde (1 mL, 37% in H₂O). After stirring for 10 minutes, NaBH(OAc)₃ (49 mg, 023 mmol) was added and the resulting mixture was stirred for 10 h. The reaction was monitored with LC/MS. When LC/MS indicated the absence of starting material Example R, the reaction mixture was evaporated to dryness, and filtered through a cotton plug. The crude product was then purified through CombiFlash (10% MeOH/CH₂Cl₂) to give 29.7 mg of Example CD $^1$H-NMR (CDCl₃, 500 MHz): 8.78 (s, 1H); 7.83 (s, 1H); 7.12-7.22 (m, 10H); 6.85 (s, 1H); 5.83 (d, 1H, J=8.5 Hz), 5.23 (d$_{AB}$, 2H, J=13.1 Hz); 4.49 (d$_{AB}$, 2H, J=16.5 Hz); 4.29 (m, 1H); 4.15 (m, 1H); 3.75 (m, 1H); 3.30 (m, 1H); 2.93 (s, 3H); 2.87 (dd, 1H, J1=5.5 Hz, J2=13.5 Hz); 2.72 (m, 2H); 2.66 (dd, J1=7.3 Hz, J2=13.3 Hz), 2.47 (br s, 1H), 2.36 (br s, 1H), 2.23 (s, 6H), 1.91 (m, 2H), 1.56 (m, 2H), 1.40 (m, 2H), 1.40 (d, 6H, J=6.8 Hz). m/z 734 (M+H)⁺; 756 (M+Na)⁺;

Preparation of Example CE

Scheme 67

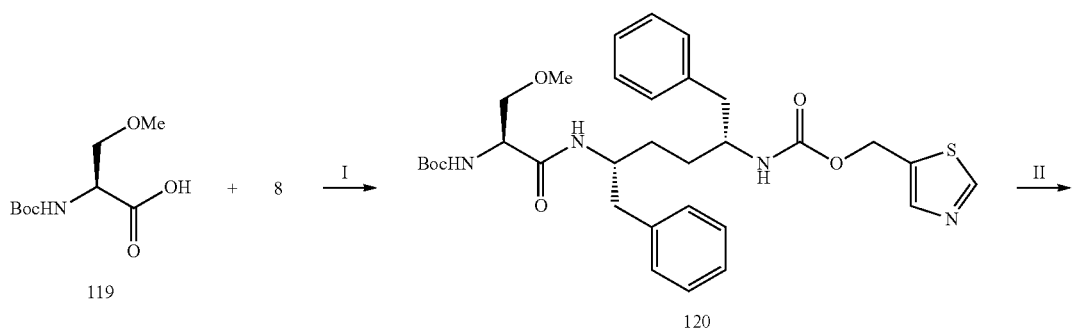

-continued

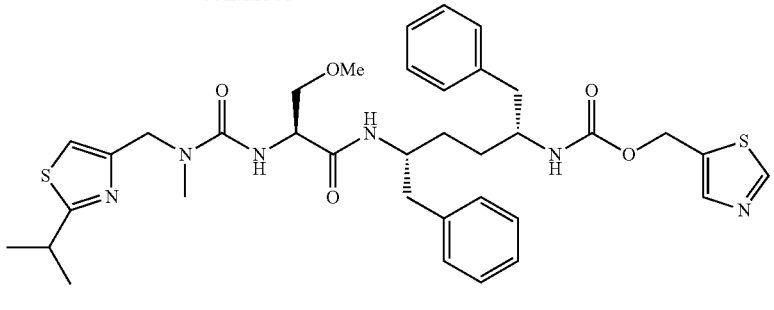

CE

I. EDC, HOBt, iPr₂NEt, THF
II. a. HCl;/dioxane; b. CDI, iPr₂NEt, Compound 9, CH₂Cl₂

Compound 119

Compound 119 is commercially available from Aldrich, and was used as received.

Compound 120

A mixture of Compound 119 (200 mg, 0.91 mmol), Compound 8 (373.7 mg, 0.91 mmol), EDC (212 mg, 1.37 mmol), HOBt (160.3 mg, 1.19 mmol) and iPr₂NEt (794.7 µL, 4.56 mmol) in THF was stirred for 10 h at room temperature. The mixture was then evaporated to a small volume and purified by CombiFlash (eluted with 1 to 10% MeOH/CH₂Cl₂). The fractions containing the target Compounds were collected and re-purified by CombiFlash (40-100% EtOAc/hexanes) to give 449 mg of Compound 120 as oil. (m/z 611.0 (M+H)).

Example CE

Compound 120 (449 mg, 0.74 mmol) was treated with HCl/dioxane (3 mL). The resulting mixture was evaporated to dryness and lyophilized to provide 373.6 mg of a white solid.

To a solution of the above white compound (52.5 mg, 0.096 mmol) in CH₂Cl₂ (10 mL) was added Compound 9 (19.8 mg, 0.096 mmol), CDI (15.6 mg, 0.096 mmol) followed by iPr₂NEt (33.4 µL, 0.192 mmol). The mixture was stirred for 20 h before it was evaporated to dryness. The mixture was added CH₂Cl₂, then filtered through a cotton plug. The filtrate was evaporated to dryness and purified with CombiFlash. The fractions with Example CE was collected and re-purified on the TLC to give 15.1 mg of Example CE. ¹H-NMR (CDCl₃, 300 MHz): 8.79 (s, 1H); 7.82 (s, 1H); 7.09-7.27 (m, 10H), 6.94 (s, 1H); 6.25 (d, 2H, J=8.7 Hz); 5.23 (s, 2H); 5.17 (br s, 1H); 4.43 (d$_{AB}$, 2H, J=16.5 Hz); 4.29 (m, 1H); 4.13 (m, 1H), 3.76 (m, 2H); 3.48 (m, 1H); 3.29 (s, 3H); 3.25 (m, 1H), 2.94 (s, 3H), 2.65-2.82 (m, 4H), 1.75 (m, 2H), 1.54 (m, 2H), 1.39 (d, 5H, J=6.9 Hz). m/z 707 (M+H)⁺; 729 (M+Na)⁺.

Preparation of Example Cf

Scheme 68

CF

Example CF

Example CF was prepared using the same method as Example CE, except that Compound 9 was replaced with Compound 68. ¹H-NMR (CDCl₃, 300 MHz): 8.79 (s, 1H); 8.74 (s, 1H), 7.81 (s, 1H), 7.73 (s, 1H); 7.12-7.27 (m, 10H); 6.15 (d, 1H, J=8.7 Hz), 5.39 (d, 1H, J=6.8 Hz); 5.21 (s, 2H), 5.06 (d, J=9.1 Hz, 1H); 4.64 (d$_{AB}$, 2H, J=15.5 Hz); 4.28 (m, 1H); 4.134 (m, 1H), 3.79 (m, 1H), 3.70 (m, 1H); 3.34 (m, 1H); 3.28 (s, 3H); 2.87 (s, 3H); 2.72 (m, 4H); 1.57 (m, 2H); 1.50 (m, 2H). (m/z 665.2 (M+H)⁺; 687.3 (M+Na)⁺.

Preparation of Compound CG

Scheme 69

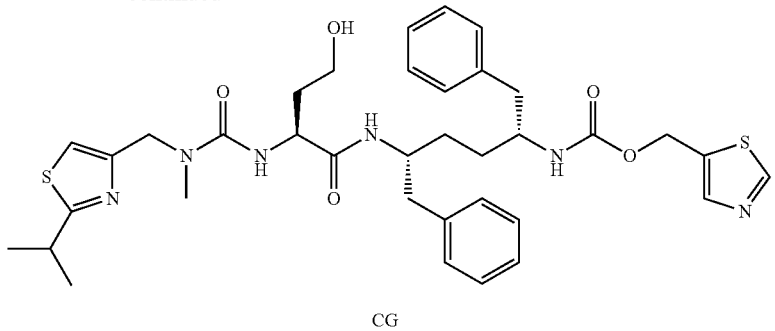

CG

I. a. CDI, DIPEA, MeCN; b. compound 9, MeCN.
II. 1M LiOH, THF.
III. EDCl, HOBt, iPr2NEt, compound 8

Compound 121

Compound 121 is commercially available from Aldrich, and was used as received.

Compound 122

To a suspension of Compound 121 (2.05 g, 11.3 mmol) in CH$_2$Cl$_2$ (40 mL) was added. iPr$_2$NEt (5.87 mL, 33.9 mmol) followed by CDT (1.86 g, 11.3 mmol). The resulting mixture was stirred at room temperature for 6 h, then Compound 9 (2.33 g, 11.3 mmol) was added. The resulting mixture was stirred for another 10 h before it was evaporated to dryness. The mixture was re-dissolved in CH$_2$Cl$_2$ and the solid was removed by filtration. The filtrate was evaporated to dryness and purified by CombiFlash (eluted with 20-80% EtOAc/hexanes) to give 3.2 g of Compound 207 as a pale yellow oil. m/z 298.0 (M+H)$^+$.

Compound 123

To a solution of Compound 122 (3.2 g, 10.8 mmol) in THF (100 mL) was added freshly prepared 1M LiOH (10.8 mmol). The biphasic reaction was stirred vigorously at room temperature for 16 h before being quenched with 1M HCl. The pH of the mixture was adjusted to 2.5-3, and then evaporated to a small volume. The mixture was partitioned between CH$_2$Cl$_2$ and brine (50 mL), the aqueous layer was separated and extracted with CH$_2$Cl$_2$ twice. The combined CH$_2$Cl$_2$ layers were dried over anhydrous Na$_2$SO$_4$ and concentrated to give 3.37 g of Compound 123 a pale yellow oil that is used with further purification. m/z 316.0 (M+H)$^+$, 338 (M+Na)$^+$;

Example CG

Example CG was prepared following the same procedure for Example C instead that Compound 123 was used instead of Compound 7. $^1$H-NMR (CDCl$_3$, 500 MHz): 8.80 (s, 1H); 7.83 (s, 1H), 7.11-7.26 (m, 10H), 6.96 (s, 1H); 7.12-7.27 (m, 10H); 6.52 (br s, 1H), 6.40 (br s, 1H), 5.23 (s, 2H), 5.20 (m, 1H), 4.44 (d$_{AB}$, 2H, J=155 Hz), 4.39 (m, 1H), 4.11 (m, 1H), 3.80 (m, 1H), 3.61 (m, 2H), 3.28 (sep, 1H, J=7.0 Hz); 2.94 (s, 3H), 2.79 (dd, 1H, J1=6.1 Hz, J2=13.4 Hz); 2.71 (m, 3H), 1.93 (m, 1H), 1.71 (m, 1H), 1.54 (m, 1H), 1.38 (d, 6H, J=7.0 Hz) 1.37 (m, 1H). (:)$^+$; m/z 707.3 (M+H)$^+$), 729.2 (M+Na)$^+$.

Preparation of Compound 100

Scheme 70

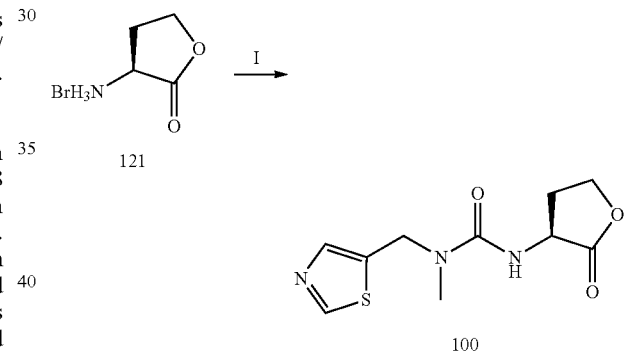

I. a. CDI, DIPEA, MeCN;

Compound 100 was prepared using the same method used to prepare Compound 122, except that Compound 9 was replaced with Compound 68.

Preparation of Example CH

Scheme 71

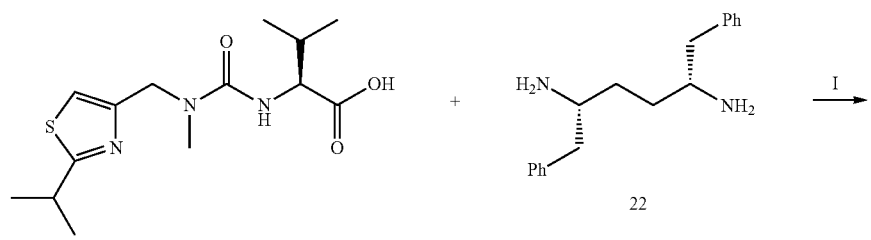

-continued

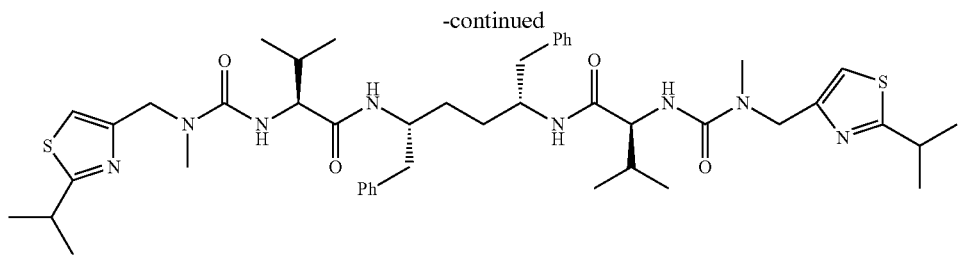

124

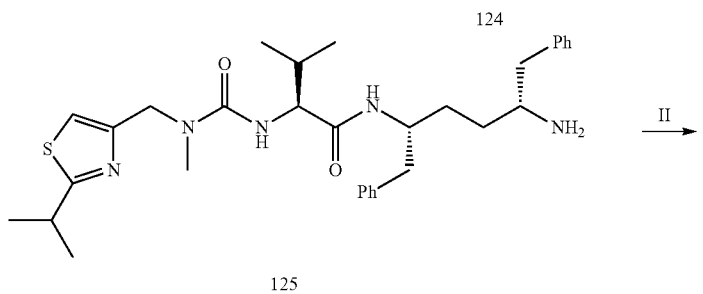

125

II →

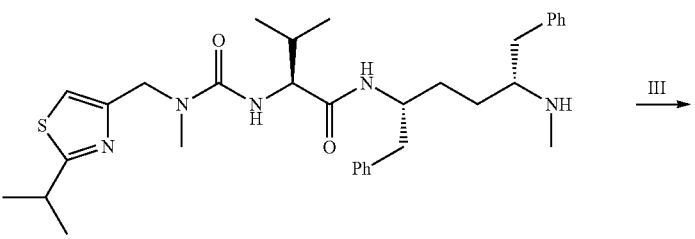

126

III →

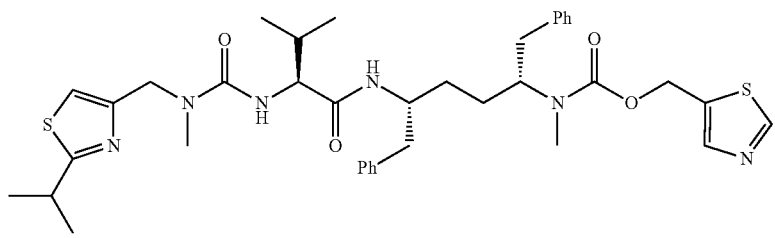

CH

I. EDCI/HOBt/iPr₂NEt/THF; II. HCHO/NaBH(OAc)₃/HOAc/CH₃CN;
III. Cmpd. 16/iPr₂NEt/CH₃CN Compounds 124 and 125

To a solution of Compound 29 (135 mg, 0.43 mmol) and Compound 22 (116 mg, 0.43 mmol) in THF (5 mL) were added HOBt (70 mg, 0.52 mmol), EDC (94 µL, 0.52 mmol), and diisopropylethylamine (150 µL, 0.83 mmol). The mixture was stirred for 12 hours and concentrated. Purification by reverse HPLC gave Compound 124 (70 mg) and Compound 125 (120 mg). Compound 124: $^1$H-NMR (CDCl$_3$) δ 7.2-7.1 (10H, m), 7.0 (2H, s), 6.45 (2H, m), 6.15 (2H, m), 4.45 (4H, s), 4.1 (2H, m), 3.96 (2H, m), 3.3 (2H, m), 2.98 (6H, s), 2.7 (4H, m), 2.1 (2H, m), 1.6-1.3 (16H, m), 0.90 (12H, m). m/z 859.3 (M+H)$^+$; Compound 125: m/z 564.3 (M+H)$^+$.

Compound 126

To a solution of Compound 125 (120 mg, 0.21 mmol) in CH$_3$CN (1 mL) was added 37% formaldehyde solution (17 µL, 0.23 mmol), followed by HOAc (24 µl, 0.42 mmol). The mixture was stirred for 2 hours, and NaBH(OAc)$_3$ (140 mg, 0.63 mmol) was added. The mixture was stirred for 2 additional hours and diluted with EtOAc. The organic phase was washed with saturated Na$_2$CO$_3$ solution, water, and brine, and dried over Na$_2$SO$_4$. Concentration gave Compound 126, which was used in the next step without further purification. m/z 578.3 (M+H)$^+$.

Example CH

Example CH (26 mg) was prepared following the procedure used to prepare Example L, except that Compound 126 was used instead of Compound 22. $^1$H-NMR (CDCl$_3$) δ 8.91 (1H, m), 7.82 (1H, m), 7.2-7.0 (11H, m), 6.4 (1H, m), 6.2 (1H, m), 5.23-5.05 (2H, m), 4.44 (2H, s), 4.44 (1H, m), 4.2 (1H, m), 3.95 (1H, m), 3.32 (1H, m), 2.98 (3H, s), 2.8-2.5 (7H, m), 2.15 (1H, m), 1.7-1.2 (10H, m), 0.88 (6H, m). m/z 719.3 (M+H)$^+$.

Preparation of Example CI

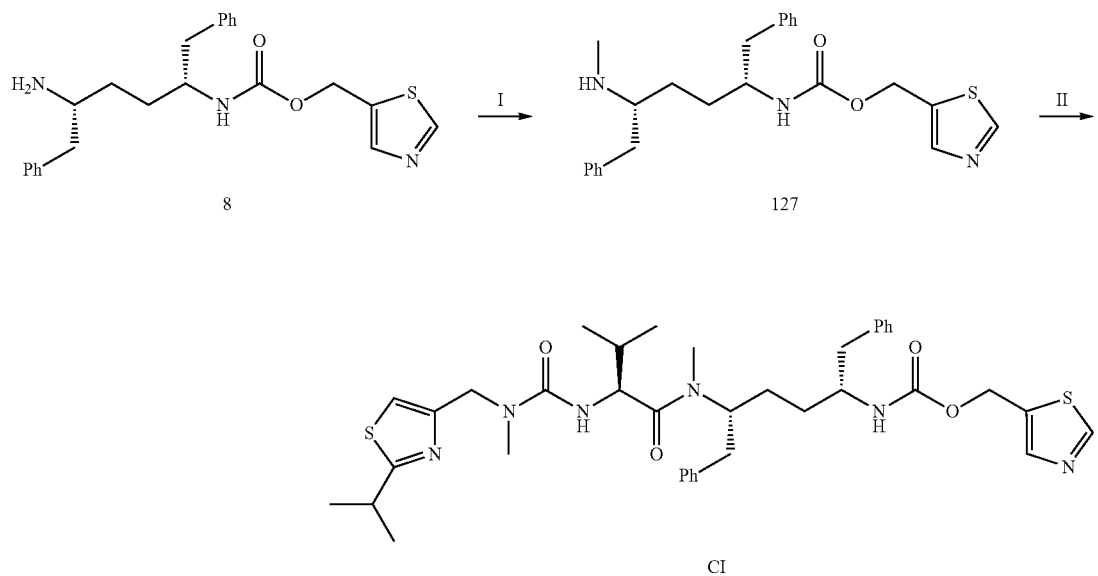

I. HCHO/NaBH(OAc)₃/HOAc/CH₃CN; II. Cmpd. 29/EDCl/HOBt/iPr₂NEt/THF

Compound 127

Compound 127 (110 mg) was prepared following the procedure used to prepare Compound 126, except that Compound 8 was used instead of Compound 125. m/z 424.4 (M+H)⁺.

Example CI

Example CI (7 mg) was prepared following the procedure used to prepare Example C, except that Compounds 127 and 29 were used instead of Compounds 8 and 7. ¹H-NMR (CDCl₃) δ 9.0 (1H, s), 8.92 (1H, s), 7.4-7.0 (11H, m), 5.25 (2H, m), 4.6-4.0 (5H, m), 3.4 (1H, m), 3.1-2.6 (10H, m), 1.9 (1H, m), 1.8 (10H, m), 0.9 (6H, m); m/z 719.2 (M+H)⁺.

Preparation of Compound CI

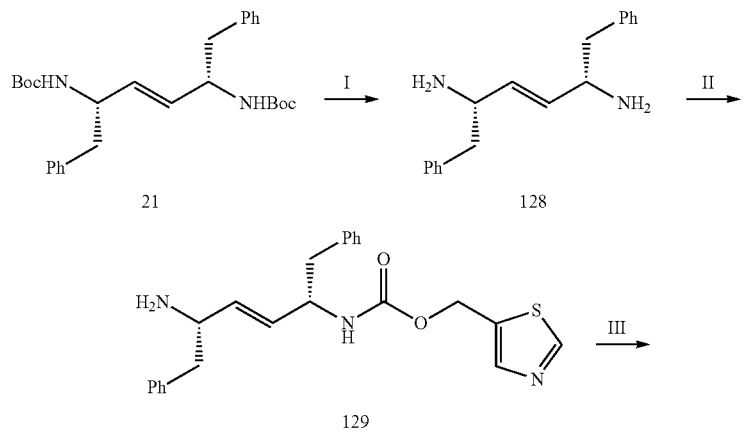

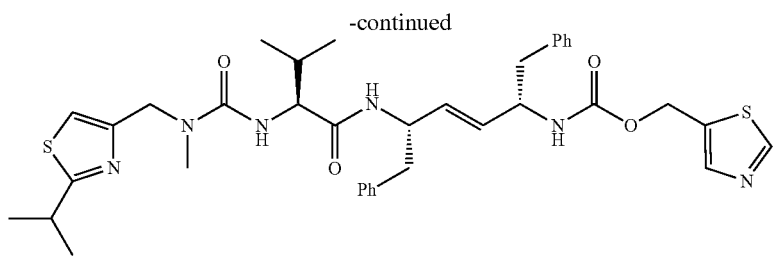

CJ

I. a. TFA/CH$_2$Cl$_2$; b. Na$_2$CO$_3$; II. Cmpd. 16/iPr$_2$NEt/CH$_3$CN;
III. Cmpd. 29/EDCl/HOBt/iPr$_2$NEt/THF Compound 128

To a solution of Compound 21 (100 mg) in dichloromethane (5 mL) was added TFA (1 mL). The mixture was stirred for 3 hours, and excess reagents were evaporated. The oil was diluted with EtOAc, and then was washed with saturated Na$_2$CO$_3$ solution (2×), water (2×), and brine, and dried over Na$_2$SO$_4$. Concentration gave Compound 128 (46 mg). m/z 267.1 (M+H)$^+$.

Compound 129

Compound 129 (44 mg) was prepared following the procedure for Compound 8, except that Compound 128 was used instead of Compound 22. m/z 408.10 (M+H)$^+$.

Example CJ

Example CJ (55 mg) was prepared following the procedure for Example C, except that Compounds 129 and 29 were used instead of Compounds 8 and 7. $^1$H-NMR (CDCl$_3$) δ 8.81 (1H, s), 7.85 (1H, s), 7.2-7.0 (11H, m), 6.4 (1H, m), 6.12 (1H, m), 5.44 (2H, m), 5.26 (2H, s), 4.85 (1H, m), 4.70 (1H, m), 4.4 (3H, m), 4.06 (1H, m), 3.25 (1H, m), 2.98 (3H, s), 2.78 (4H, m), 2.21 (1H, m), 1.38 (6H, m), 0.88 (6H, m); m/z 703.2 (M+H)$^+$.

Preparation of Compounds CK and CL

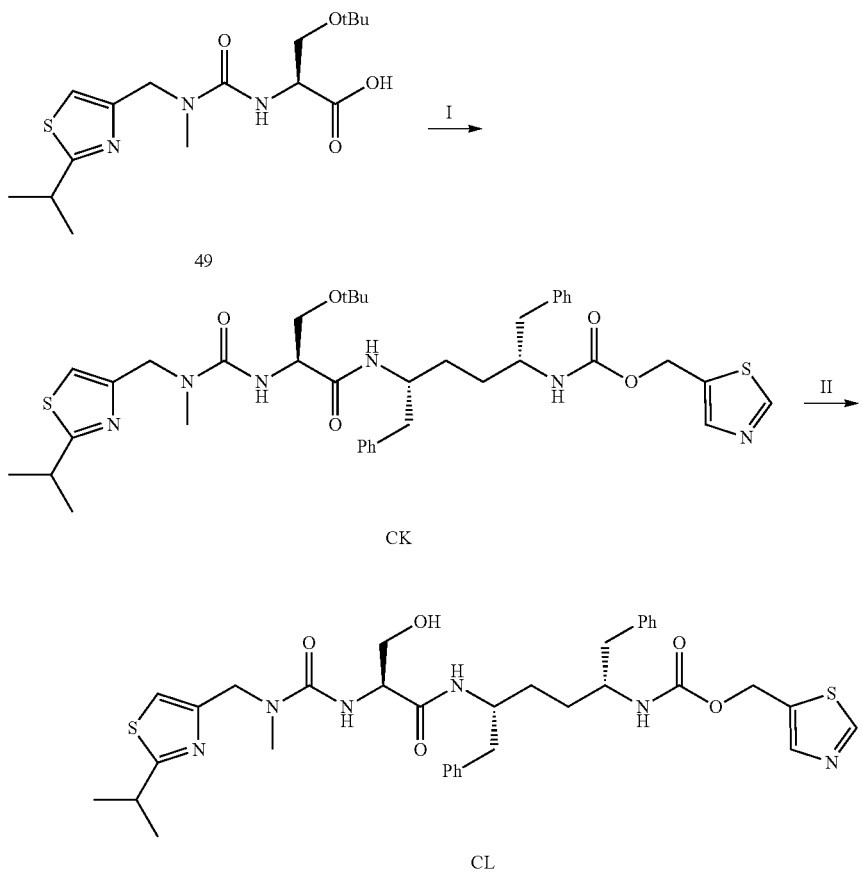

Scheme 74

I. Cmpd 8/EDC/HOBt; II. a. TFA; b. NaOH/THF

Example CK

Example CK (88 mg) was prepared following the procedure used to prepare Example C, except that Compound 49 was used instead of Compound 7. m/z 749.2 (M+H)$^+$.

Example CL

A mixture of Example CK (85 mg) and TFA (5 mL) was stirred for 3 hours. Excess TFA was evaporated and the mixture was dried under high vacuum. The mixture was dissolved in THF (5 mL), and 1.0 N sodium hydroxide solution was added until the pH was 11. The solution was stirred for 10 minutes, and extracted with EtOAc. The organic phase was washed with water, brine, and dried over Na$_2$SO$_4$.

Concentration and purification by flash column chromatography (EtOAc) gave Example CL (66 mg). $^1$H-NMR (CDCl$_3$) δ 8.81 (1H, s), 7.84 (1H, s), 7.30-6.96 (11H, m), 5.22 (2H, s), 4.90 (1H, m), 4.45 (1H, m), 4.35-4.0 (4H, m), 3.8 (1H, m), 3.6 (1H, m), 3.21 (1H, m), 2.95 (3H, s), 2.8-2.6 (4H, m), 2.0-1.4 (4H, m), 1.25 (6H, m). m/z 693.2 (M+H)$^+$.

mL, 6.6 mmol), dropwise. The mixture was stirred at 0° C. for 30 minutes and brought to reflux for 3 hours. Concentration gave Compound 131 as a white solid.

Compound 132

To a stirred solution of Compound 131 (3 mmol) and diisopropylethylamine (2 mL, 12 mmol) in dichloromethane (35 mL) was added CDI (486 mg, 3 mmol). The mixture was stirred for 12 hours. Compound 9 was added, and the mixture was stirred for 12 additional hours. Concentration and purification by flash column chromatography (CH$_2$Cl$_2$/iPrOH=10/1) gave Compound 132 (414 mg). m/z 380.0 (M+H)$^+$.

Compound 133

Compound 133 was prepared following the procedure for Compound 67, except that Compound 132 was used instead of Compound 66. m/z 364.0 (M−H)$^+$.

Example CM

Example CM (600 mg) was prepared following the procedure for Example C, except Compound 133 was used Preparation of Example CM

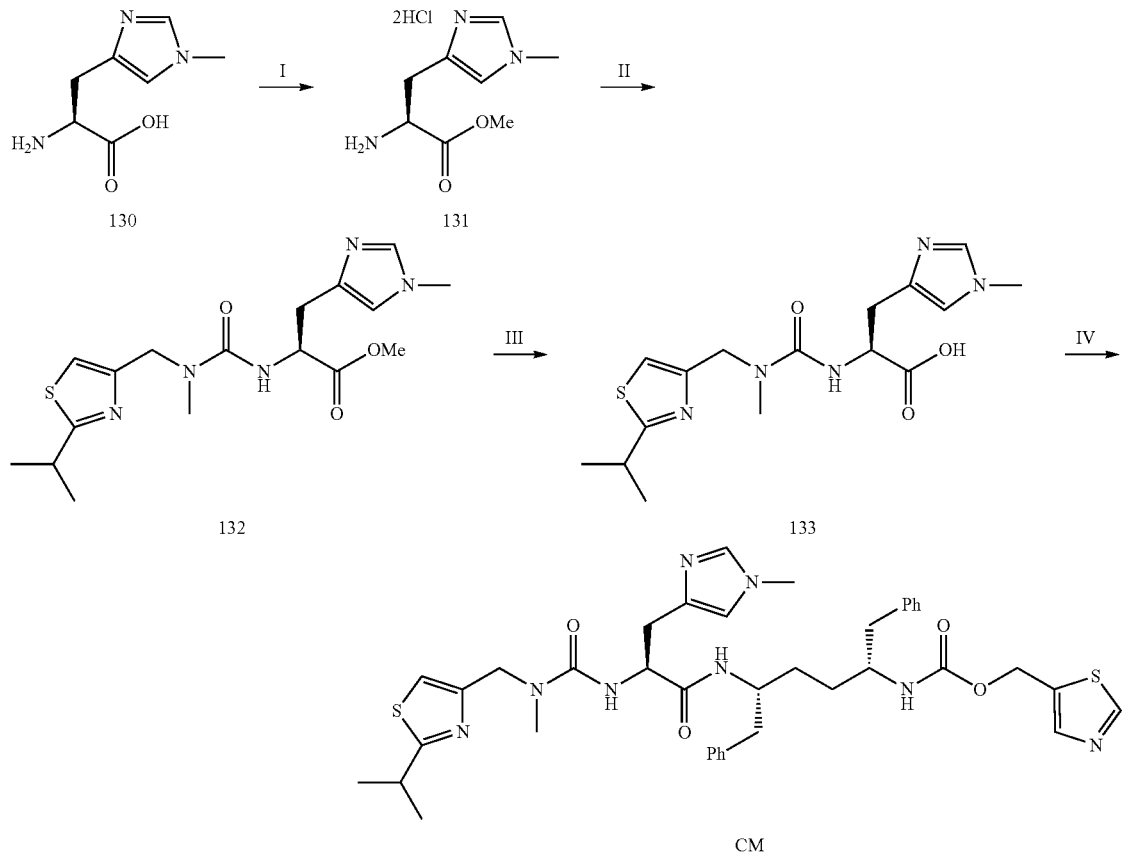

I. SOCl$_2$/MeOH; II. a. CDI/iPr$_2$NEt; b. Cmpd. 9; III. a. NaOH/THF/H$_2$O; b. HCl;
IV. Cmpd. 8/EDC/HOBt;

Compound 130

Compound 130 is commercially available from (TCI), and was used as received.

Compound 131

To the solution of Compound 130 (510 mg, 3 mmol) in methanol (12 mL) at 0° C. was added thionyl chloride (0.5 instead of Compound 7. $^1$H-NMR (CDCl$_3$) δ 9.18 (1H, s), 8.35 (1H, s), 7.95 (1H, s), 7.6 (1H, m), 7.3-7.0 (11H, m), 5.22 (2H, m), 4.70 (1H, m), 4.50 (2H, m), 4.05 (1H, m), 3.86 (3H, s), 3.80 (2H, m), 3.55 (1H, m), 3.10 (1H, m), 2.90 (3H, s), 2.70 (4H, m), 1.45 (10H, m); m/z 757.3 (M+H)$^+$.

Preparation of Examples O, P, CN, and CO

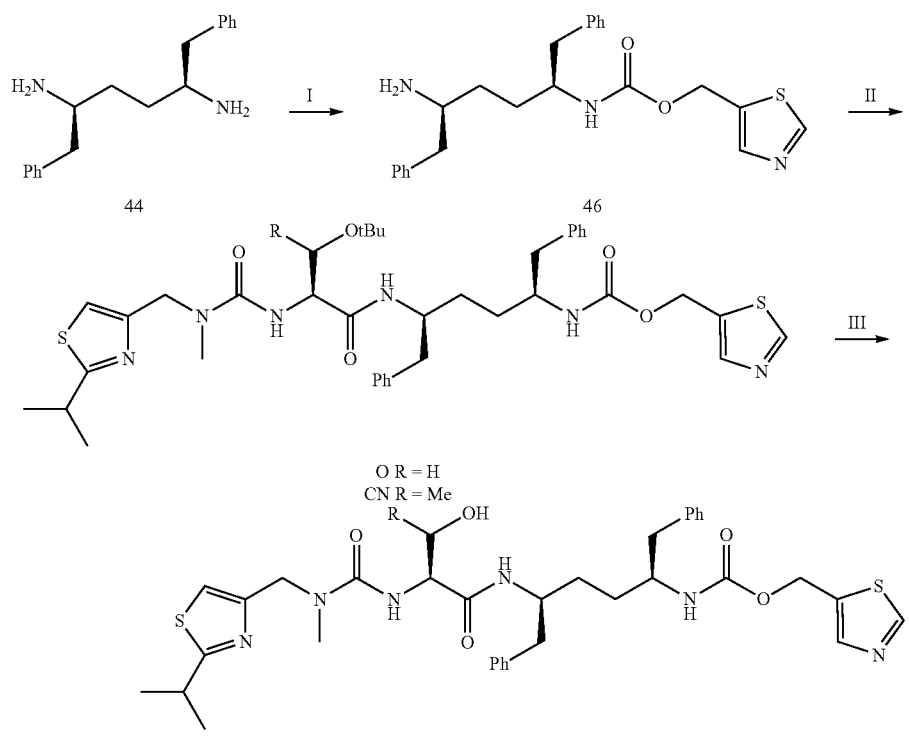

I. Cmpd. 16/iPr2NEt; II. Cmpd. 13d or Cmpd. 49/EDC/HOBt; III. a. TFA; b. NaOH/THF

Example O

Example O (17 mg) was prepared following the procedure for Example C, except Compounds 46 and 49 were used instead of Compounds 8 and 7. m/z 749.3 (M+H)+.

Example CN

Example CN (22 mg) was prepared following the procedure used to prepare Example C, except Compounds 46 and 13e were used instead of Compounds 8 and 7. m/z 763.2 (M+H)+.

Example P

Example P (12 mg) was prepared following the procedure used to prepare Example CL, except Example O was used instead of Example CK. $^1$H-NMR (CDCl$_3$) δ 8.76 (1H, s), 7.79 (1H, s), 7.25-6.9 (11H, m), 6.51 (1H, broad), 5.42 (1H, m), 5.18 (2H, m), 4.42 (2H, m), 4.22 (1H, m), 4.10 (1H, m), 3.95 (1H, m), 3.79 (1H, m), 3.58 (1H, m), 3.23 (1H, m), 2.93 (3H, s), 2.9-2.5 (4H, m), 1.6-1.2 (10H, m); m/z: 693.2 (M+H)+.

Compound CO

Example CO (13 mg) was prepared following the procedure used to prepare Example CL, except Example CN was used instead of Compound CK.

$^1$H-NMR (CDCl$_3$) δ 8.85 (1H, m), 7.88 (1H, m), 7.3-7.0 (11H, m), 6.55 (1H, m), 6.24 (1H, m), 5.45 (1H, m), 5.23 (2H, m), 4.6 (2H, m), 4.2 (1H, m), 4.0 (2H, m), 3.7 (1H, m), 3.5 (1H, m), 3.02 (3H, s), 2.70 (4H, m), 1.6-1.0 (13H, m); m/z: 707.3 (M+H)+.

Preparation of Examples CP-CS

Scheme 77

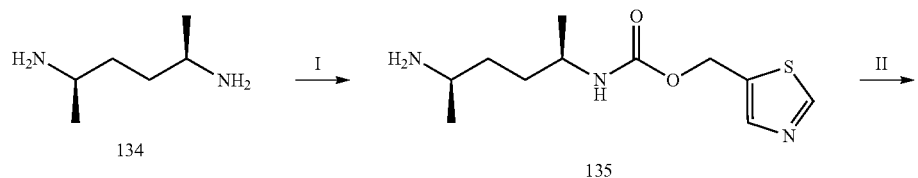

-continued

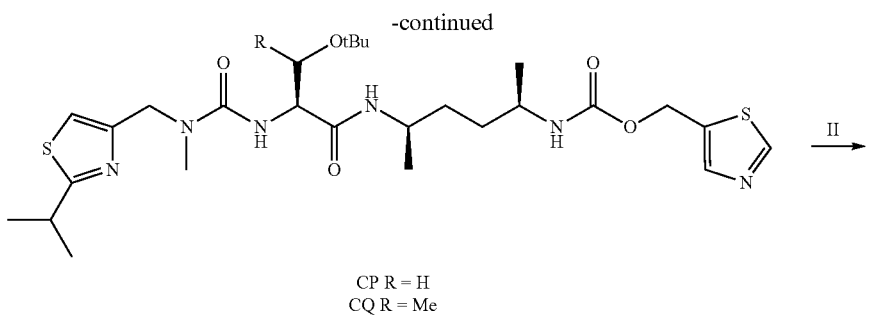

CP R = H
CQ R = Me

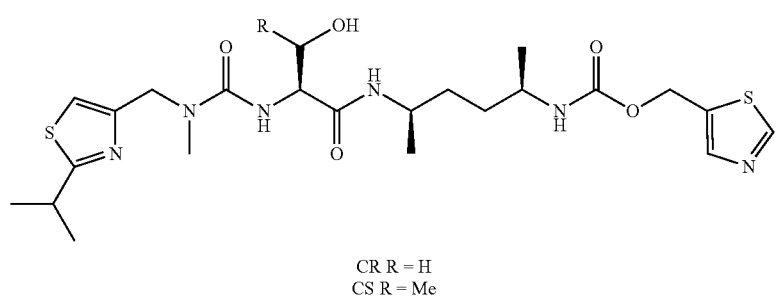

CR R = H
CS R = Me

I. Cmpd. 16/iPr₂NEt; II. Cmpd. 13d or 49/EDC/HOBt; III. a. TFA; b. NaOH/THF

Compound 134

Compound 134 was prepared using procedure described for Compound 76, except that CBZ-D-alaninol was used instead of CBZ-L-alaninol.

Compound 135

Compound 135 was prepared following the procedure used to prepare Compound 8, except Compound 134 was used instead of Compound 22.

Example CP

Example CP (12 mg) was prepared following the procedure used to prepare Example C, except Compounds 135 and 49 were used instead of Compounds 8 and 7. m/z 597.2 (M+H)$^+$.

Example CO

Example CQ (11 mg) was prepared following the procedure used to prepare Example C, except Compounds 135 and 13d were used instead of Compounds 8 and 7. m/z 611.2 (M+H)$^+$.

Example CR

Example CR (7 mg) was prepared following the procedure used to prepare Example P, except that Example CP was used instead of Example O. $^1$H-NMR (CDCl$_3$) δ 8.82 (1H, s), 7.88 (1H, s), 7.02 (1H, s), 6.92 (1H, m), 5.28 (2H, s), 5.10 (1H, m), 4.5 (2H, m), 4.15 (2H, m), 3.88 (1H, m), 3.8-3.5 (2H, m), 3.35 (1H, m), 3.0 (3H, s), 1.5-1.0 (16H, m); m/z: 541.1 (M+H)$^+$.

Example CS

Example CS (8 mg) was prepared following the procedure used to prepare Example CO, except that Example CQ was used instead of Example CN. $^1$H-NMR (CDCl$_3$) δ 8.83 (1H, s), 7.88 (1H, s), 6.98 (1H, s), 6.81 (1H, m), 6.58 (1H, m), 5.28 (2H, s), 5.18 (1H, m), 4.4-4.3 (2H, m), 4.03 (1H, m), 3.85 (1H, m), 3.58 (2H, m), 3.3 (1H, m), 2.99 (3H, s), 1.5-0.98 (19H, m); m/z: 555.2 (M+H)$^+$.

Preparation of Examples CT-CV

Scheme 78

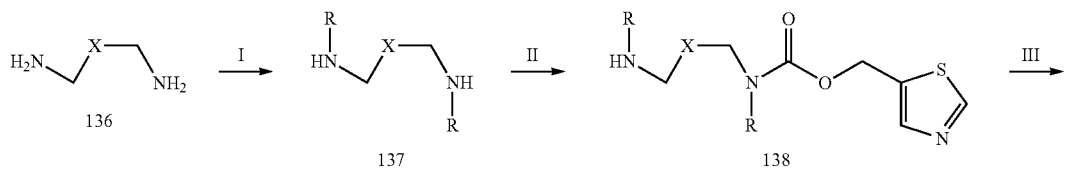

-continued

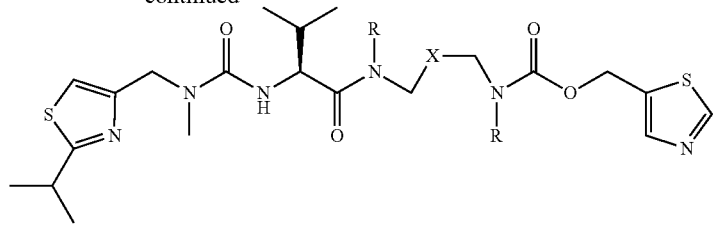

CT X = CH₂CH₂; R = H
CU X = CH₂CH₂; R = Bn
CV X = CH₂; R = Bn

I. PhCHO/NaBH₄; II. Cmpd 16/iPr₂NEt; II. Cmpd 13d/EDC/HOBt;

Compound 136

Compounds 136a-c are commercially available (Sigma-Aldrich).

Compound 137

To a solution of Compound 136 (20 mmol) in methanol (25 mL) was added benzaldehyde (40 mmol) dropwise. The mixture was stirred for 2 hours and was cooled to 0° C. Sodium borohydride (44 mmol) was added in portions. The mixture was warmed to 25° C. and stirred for 2 hours. Acetic acid (10 mL) was added and the mixture was stirred for 10 minutes. Methanol was removed and the mixture was partitioned between EtOAc and 3 N NaOH solution. The organic layer was separated and water phase was extracted with EtOAc (2x). The combined organic layers was washed with water, brine, and dried over Na₂SO₄. Concentration gave Compound 137.

Compound 138

Compound 138 was prepared following the procedure used to prepare Compound 8, except that Compound 137 was used instead of Compound 22.

Example CT

Example CT (70 mg) was prepared following the procedure used to prepare Example C, except that Compounds 29 and 138a was used instead of Compounds 7 and 8. ¹H-NMR (CDCl₃) δ 8.79 (1H, s), 7.86 (1H, s), 6.97 (1H, s), 6.49 (1H, m), 6.15 (1H, m), 5.28 (2H, s), 5.20 (1H, m), 4.44 (2H, m), 4.05 (1H, m), 3.25 (5H, m), 3.0 (3H, s), 2.24 (1H, m), 1.8-1.45 (4H, m), 1.38 (6H, m), 0.97 (6H, m); m/z: 525.2 (M+H)⁺.

Example CU

Example CU (140 mg) was prepared following the procedure used to prepare Example C, except that Compounds 29 and 138b was used instead of Compounds 7 and 8. ¹H-NMR (CDCl₃) δ 8.78 (1H, s), 7.85 (1H, m), 7.4-7.05 (10H, m), 6.93 (1H, s), 5.90 (1H, m), 5.35 (2H, s), 4.9-4.6 (2H, m), 4.6-4.4 (4H, m), 4.2 (1H, m), 3.4-3.05 (5H, m), 3.0 (3H, s), 2.0 (1H, m), 1.8-1.3 (10H, m), 0.90 (6H, m); m/z: 705.2 (M+H)⁺.

Example CV

Example CV (145 mg) was prepared following the procedure used to prepare Example C, except that Compounds 29 and 138c was used instead of Compounds 7 and 8. ¹H-NMR (CDCl₃) δ 8.76 (1H, m), 7.86 (1H, m), 7.4-7.02 (10H, m), 6.97 (1H, m), 5.75 (1H, m), 5.38 (2H, m), 4.95-4.3 (6H, m), 4.15 (1H, m), 3.4-3.0 (5H, m), 3.0 (3H, s), 2.2-1.6 (3H, m), 1.4 (6H, m), 0.88 (6H, m); m/z: 691.2 (M+H)⁺.

Preparation of Example CW

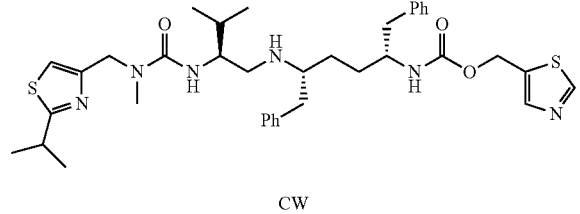 [SMILES: CC(C)c1nc(CN(C)C(=O)N[C@H](CN[C@H](CC[C@H](Cc2ccccc2)NC(=O)OCc2cncs2)Cc2ccccc2)C(C)C)cs1 ; "CW"]

CW

Example CW could be prepared, e.g. by reacting Compound 8 with a compound having the following structure:

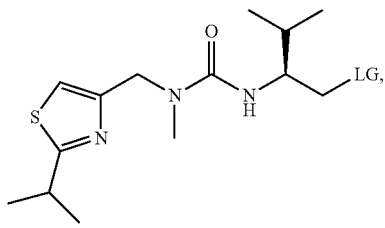

where "LG" is a leaving group such as a halogen. Such compounds could be prepared by one-carbon degradation of the corresponding carboxylic acid or ester (e.g., Compounds 28 or 29) by known methods such as the Hunsdieker reaction or the Kochi reaction or similar methods.

Preparation of Example CX

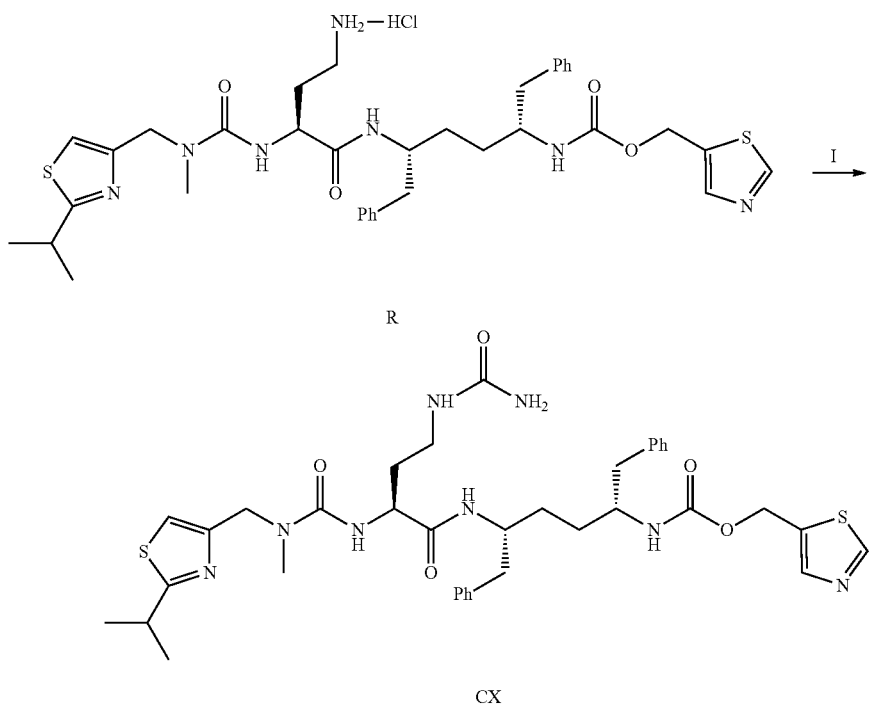

I. a. TMSNCO/iPr₂NEt/THF; b. MeOH

Example R

Example R (hydrochloride salt) was synthesized following the procedure described in WO 2008/010921 A2 (herein incorporated by reference in its entirety for all purposes) or as described above.

Example CX

To a suspension of Example R (hydrochloride salt) (150 mg, 0.2 mmol) in THF (2 mL) was added diisopropylethylamine (70 •l, 0.4 mmol). The mixture was stirred until a clear solution was obtained. To this solution was added trimethylsilyl isocyanate (30 •l, 0.22 mmol) dropwise, and the mixture was stirred for 12 hours. The solvent was removed and the mixture was coevaporated twice with 5 mL of MeOH. Purification with preparative thin layer chromatography (preparative TLC) gave Example CX (86 mg). m/z: 749.2 (M+H)⁺. $^1$H NMR (CD$_3$OD) δ 8.99 (s, 1H); 7.83 (s, 1H); 7.72 (m, 1H); 7.30-7.00 (m, 11H); 5.22 (s, 2H); 4.54 (s, 2H); 4.19 (s, 1H); 4.07 (m, 1H); 3.75 (m, 1H); 3.28 (m, 1H); 3.30-2.90 (m, 2H); 2.97 (s, 3H); 2.71 (m, 4H); 1.79 (m, 2H); 1.50 (m, 4H); 1.38 (d, 6H, J=7 Hz).

Preparation of Example CY

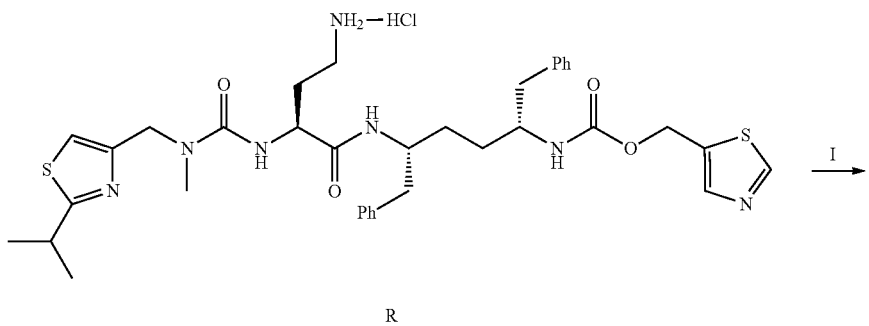

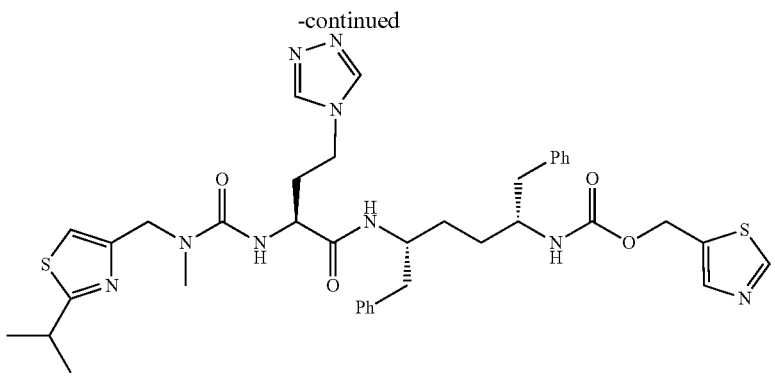

CY

I. diformylhydrazine/pyridine/Et₃N/TMSCl/100 C.

Example CY

To a solution of Example R (hydrochloride salt) (269 mg, 0.36 mmol) in pyridine (3 mL) was added diformylhydrazine (95 mg, 1.1 mmol), followed by chlorotrimethylsilane (2.7 mL) and triethylamine (0.34 mL). The mixture was heated at 100° C. for 14 hours, and solvents were removed. The mixture was quenched with water, and extracted three times with EtOAc. The organic layer was dried over $Na_2SO_4$ and concentrated to give a white solid. Purification by HPLC and preparative TLC (5% MeOH in dichloromethane) gave Example CY (5 mg). m/z: 758.3 (M+H)⁺. ¹H NMR ($CD_3OD$) δ 8.98 (s, 1H); 8.50 (s, 2H); 7.83 (s, 1H); 7.30-7.00 (m, 11H); 5.21 (s, 2H); 4.54 (m, 2H); 4.11 (m, 4H); 3.76 (m, 1H); 3.28 (m, 1H); 2.95 (s, 3H); 2.69 (m, 4H); 2.04 (m, 2H); 1.70-1.20 (m, 10H).

Preparation of Example CZ

Scheme 81

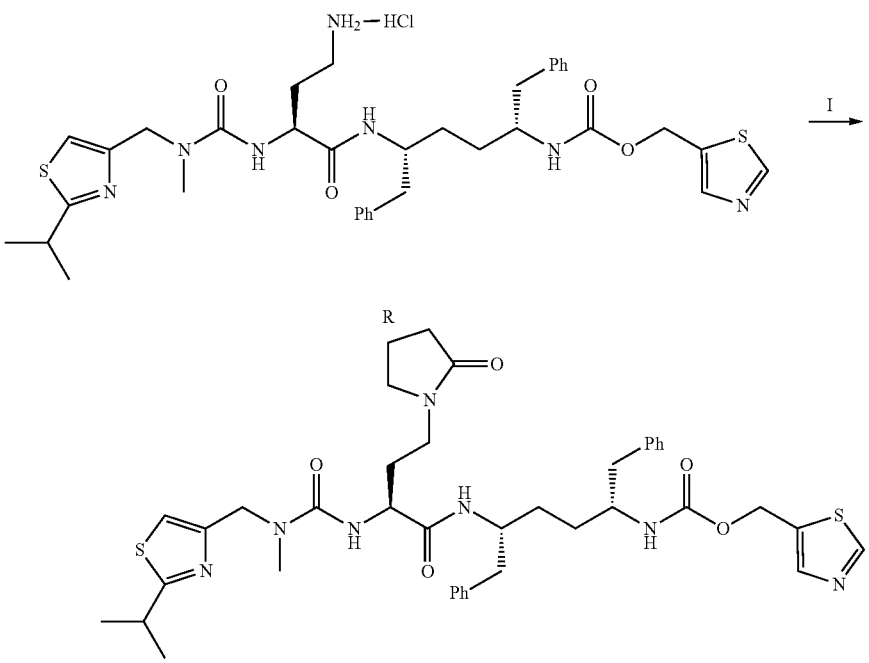

CZ

I. Methyl 4-bromobutyrate/NaHCO₃/DMF/60 C.

Example CZ

To a suspension of Example R (hydrochloride salt) (200 mg, 0.27 mmol) and sodium bicarbonate (92 mg, 1.1 mmol) in DMF (2 mL) was added a solution of methyl 4-bromobutyrate (74 •l, 0.54 mmol) in DMF (1 mL). The mixture was heated at 65° C. for 20 hours and the solvent was removed under reduced pressure. The mixture was quenched with water, and extracted with EtOAc. The organic layer was washed three times with water, twice with sodium carbonate solution, and once with brine, and dried over $Na_2SO_4$. Concentration followed by purification using HPLC gave Example CZ as a white solid (23 mg). m/z: 774.3 $(M+H)^+$. $^1H$ NMR ($CD_3OD$) δ 8.99 (s, 1H); 7.84 (s, 1H); 7.30-7.00 (m, 11H); 5.22 (s, 2H); 4.55 (m, 2H); 4.09 (m, 2H); 3.90-3.60 (m, 1H); 3.55-3.10 (m, 5H); 2.98 (s, 3H); 2.71 (m, 4H); 2.37 (m, 2H); 2.04 (m, 2H); 1.81 (m, 2H); 1.70-1.20 (m, 10H).

Preparation of Example DA acetate (153 mg, 1.9 mmol), followed by 2,5-dimethoxyTHF (44 •l, 0.34 mmol). The mixture was heated at 125° C. for 90 minutes, and the solvent was removed under reduced pressure. The residue was quenched with saturated sodium bicarbonate solution and extracted with EtOAc. The organic layer was washed sequentially with saturated $NaHCO_3$ solution, water, and brine, and dried over $Na_2SO_4$, Concentration and purification by HPLC gave a white solid, which was further purified by preparative TLC to give Example DA (25 mg). m/z: 756.3 $(M+H)^+$. $^1H$ NMR ($CD_3OD$) δ 8.96 (s, 1H); 7.82 (s, 1H); 7.30-7.00 (m, 11H); 6.62 (s, 2H); 6.02 (s, 2H); 5.20 (s, 2H); 4.51 (s, 2H); 4.20-3.95 (m, 2H); 3.88 (m, 2H); 3.75 (m, 1H); 3.26 (m, 1H); 2.93 (s, 3H); 2.70 (m, 4H); 2.01 (m, 2H); 1.70-1.20 (m, 10H).

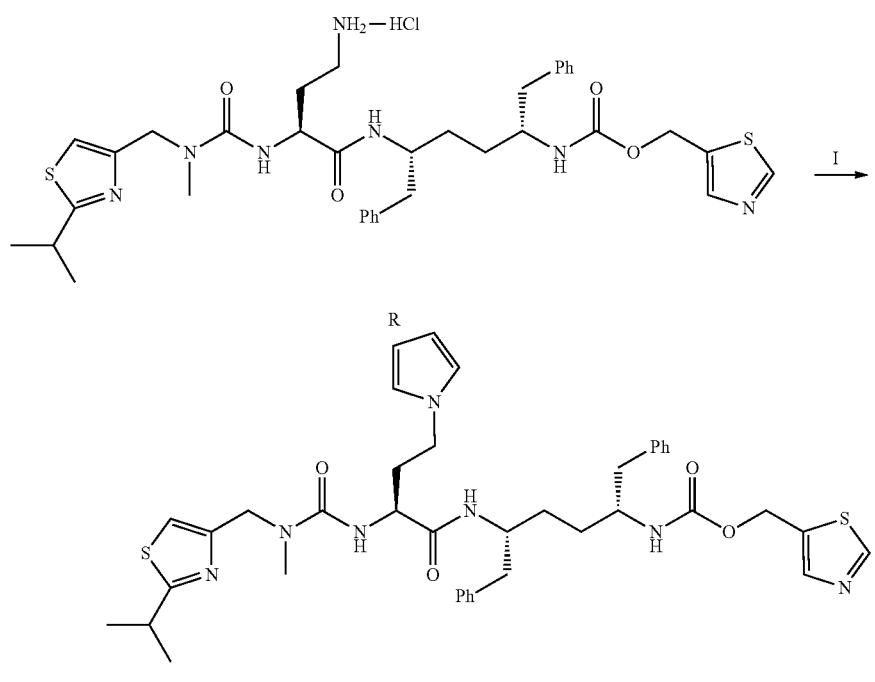

I. 2,5-dimethoxyTHF/NaOAc/HOAc/125 C.

Example DA

To a suspension of Example R (hydrochloride salt) (250 mg, 0.34 mmol) in acetic acid (0.73 mL) was added sodium Preparation of Example DB

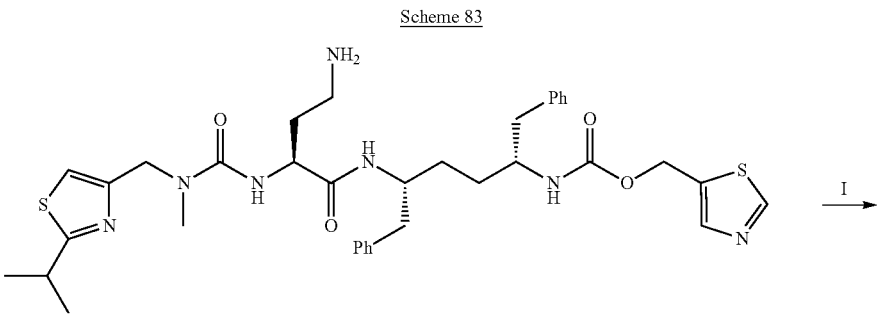

R

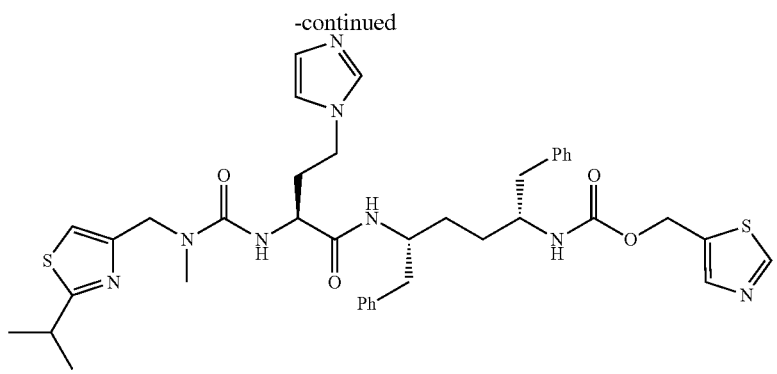

DB

I. NH₃—H₂O/formaldehyde/glyoxal/n-PrOH/80 C.

Example DB

To Example R (220 mg, 0.34 mmol) in propanol (1.9 mL) was added aqueous ammonia (39 mg, 0.34 mmol, 28-30%). The mixture was stirred for 5 minutes. To the above mixture was added a solution of glyoxal (53 mg, 0.37 mmol, 40% wt) and formaldehyde (30 mg, 0.37 mmol, 37% wt) in propanol (3.7 mL) dropwise. The mixture was heated at 80° C. for 5 hours. The solvent was removed under reduced pressure, and the residue was diluted with EtOAc. The organic layer was washed with water and brine, and dried over Na₂SO₄. Concentration of the organic layer and purification by HPLC gave Example DB as a white powder (101 mg). m/z: 757.3 (M+H)⁺. ¹H NMR (CD₃OD) δ 8.97 (s, 1H); 7.82 (s, 1H); 7.60 (s, 1H); 7.30-7.00 (m, 12H); 6.96 (s, 1H); 5.20 (s, 2H); 4.53 (m, 2H); 4.20-3.90 (m, 4H); 3.76 (m, 1H); 3.28 (m, 1H); 2.95 (s, 3H); 2.70 (m, 4H); 2.02 (m, 2H); 1.70-1.20 (m, 10H).

Preparation of Example DC

Scheme 84

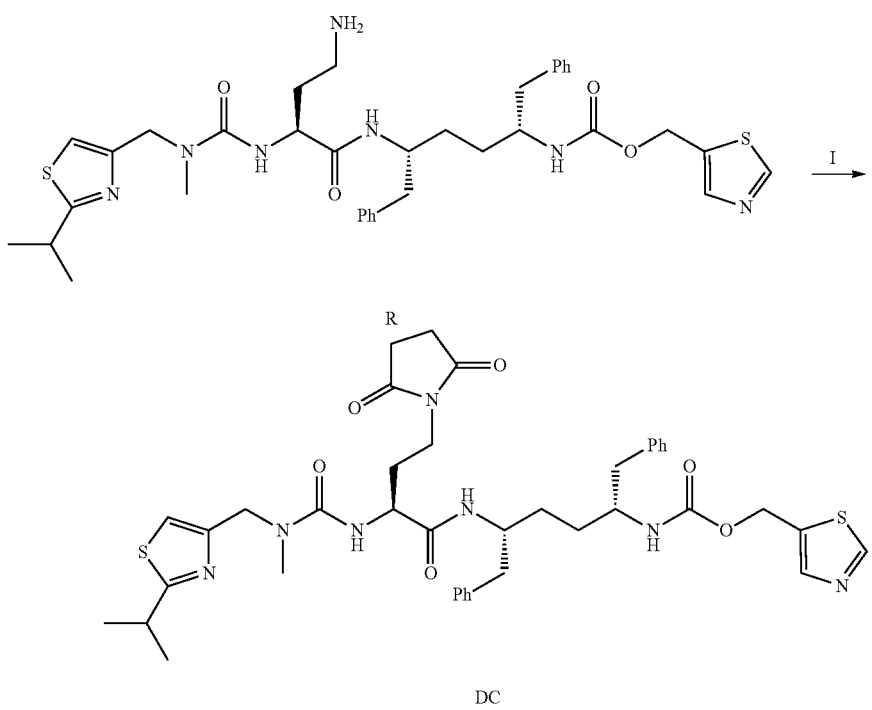

DC

I. a. succinic anhydride/CH₂Cl₂; b. Ac₂O/NaOAc.

Example DC

To a solution of Example R (220 mg, 0.34 mmol) in dichloromethane (1.5 mL) was added succinic anhydride (41 mg, 0.41 mmol). The mixture was heated at 45° C. for 12 hours. The solvent was removed and a white solid was dried under high vacuum. To this solid was added sodium acetate (10 mg, 0.12 mmol), followed by acetic anhydride (1.5 mL). The mixture was heated at 85° C. for 1 hour, and the solvent was removed under reduced pressure. The residue was diluted with EtOAc, and was washed sequentially with water, saturated NaHCO₃, water, and brine, and dried over Na₂SO₄. Concentration gave Example DC (190 mg). m/z: 788.2 (M+H)⁺. ¹H NMR (CD₃OD) δ 8.99 (s, 1H); 7.84 (s, 1H); 7.30-7.00 (m, 11H); 5.22 (s, 2H); 4.70-4.40 (m, 2H); 4.20-3.90 (m, 2H); 3.75 (m, 1H); 3.54 (m, 1H); 3.42 (m, 1H); 3.28 (m, 1H); 2.98 (s, 3H); 2.67 (m, 8H); 2.00 (m, 1H); 1.81 (m, 1H); 1.70-1.20 (m, 10H).

Preparation of Example DD

Scheme 85

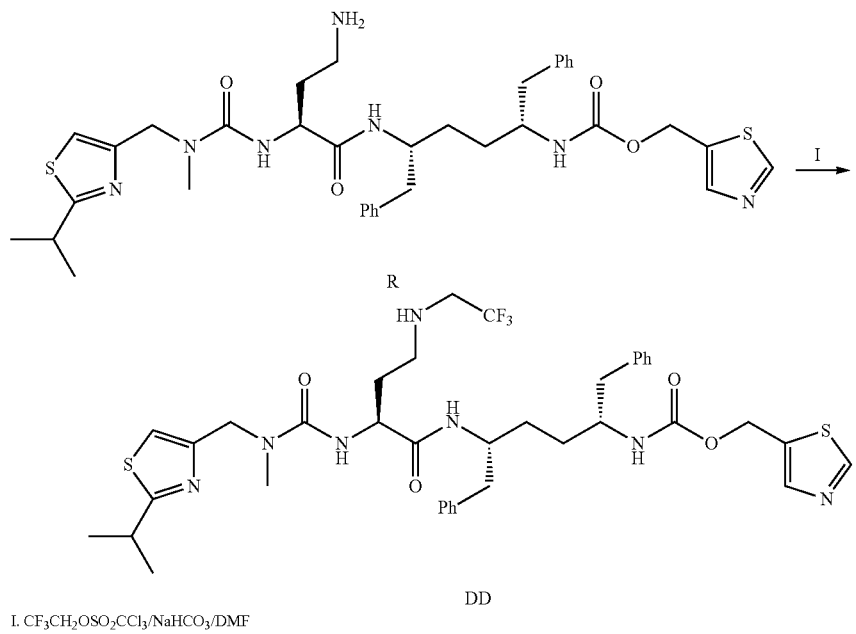

I. CF₃CH₂OSO₂CCl₃/NaHCO₃/DMF

Example DD

To a solution of Example R (220 mg, 0.34 mmol) in DMF (3 mL) was added sodium carbonate (100 mg), followed by 2,2,2-trifluoroethyl trichloromethanesulfonate (112 •l, 0.68 mmol). The mixture was stirred for 3 days and the solvent was removed under reduced pressure. The residue was diluted with EtOAc. The organic layer was sequentially washed twice with saturated sodium carbonate solution, once with water, and once with brine, and dried over Na₂SO₄. Concentration and purification by flash column chromatography (9% MeOH in dichloromethane) gave Example DD (109 mg). m/z: 788.2 (M+H)⁺. ¹H NMR (CD₃OD) δ 8.98 (s, 1H); 7.82 (s, 1H); 7.62 (d, 1H, J=9 Hz); 7.30-7.00 (m, 11H); 6.85 (d, 1H, J=9 Hz); 5.20 (m, 2H); 4.54 (s, 2H); 4.23 (m, 1H); 4.11 (m, 1H); 3.77 (m, 1H); 3.31 (m, 2H); 3.12 (q, 2H, J=10 Hz); 2.95 (m, 3H); 3.80-2.50 (m, 6H); 1.77 (m, 2H); 1.70-1.20 (m, 10H). ¹⁹F NMR (CD₃OD) •–73.28 (t, 1H, J=10 Hz).

Preparation of Example DE

Scheme 86

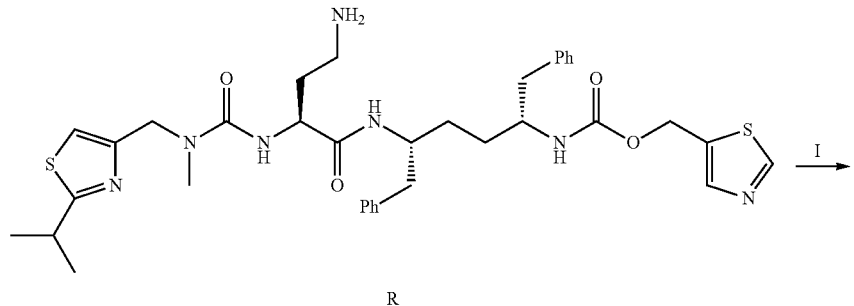

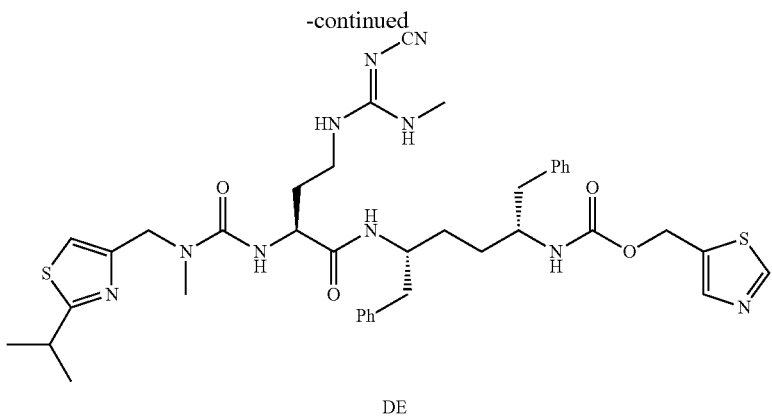

DE i.a. (MeS)₂C=NCN/EtOH; b. MeNH₂/EtOH

Example DE

To a clear solution of dimethyl N-cyanodithioiminocarbonate (50 mg, 0.34 mmol) in ethanol (0.5 mL) was added slowly a solution of Example R (220 mg, 0.34 mmol) in ethanol (2.5 mL). The mixture was stirred for 12 hours. To the above mixture was added a solution of methylamine in EtOH (1.6 mL, 33% wt). The mixture was stirred for 6 hours, and solvents were removed under reduced pressure. Purification by HPLC gave Example DE (92 mg). m/z: 787.3 (M+H)⁺. ¹H NMR (CD₃OD) δ 8.98 (s, 1H); 7.83 (s, 1H); 7.30-7.00 (m, 11H); 5.21 (s, 2H); 4.51 (s, 2H); 4.18 (m, 1H); 4.09 (m, 1H); 3.77 (m, 1H); 3.28 (m, 2H); 3.16 (m, 1H); 2.97 (s, 3H); 2.80 (s, 3H); 2.715 (m, 4H); 1.84 (m, 1H); 1.70 (m, 1H); 1.65-1.20 (m, 10H).

Preparation of Examples DF-DG

Scheme 87

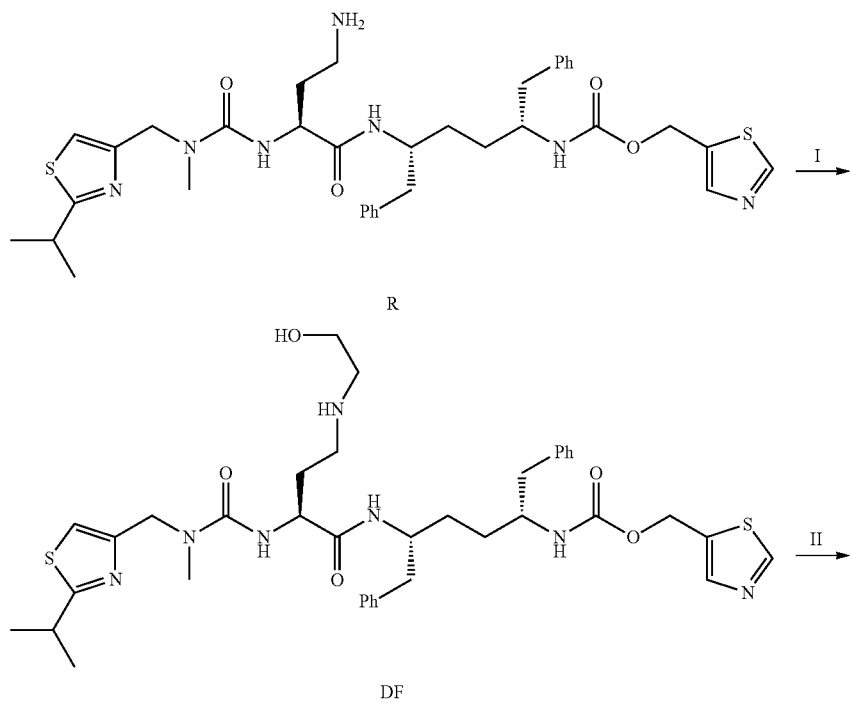

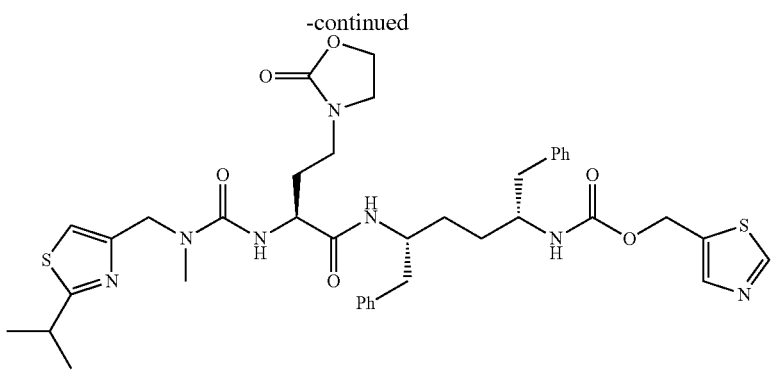

DG

I. BrCH₂CH₂OH/Na₂CO₃/DMF/70 C.; II. CDI/DMAP/THF/70 C.

Example DF

To a solution of Example R (220 mg, 0.34 mmol) in DMF (1 mL) was added sodium carbonate (72 mg, 0.68 mmol), followed by a solution of 2-bromoethanol (24 •l, 0.34 mmol) in DMF (0.4 mL). The mixture was heated at 70° C. for 12 hours. Concentration under high vacuum gave Example DF. m/z: 750.2

Example DG

To a suspension of Example DF (0.34 mmol) in THF (3.4 mL) was added carbonyldiimidazole (CDI) (83 mg, 0.51 mmol), followed by DMAP (4 mg). The mixture was heated at 70° C. for 3 hours, and the solvent was removed. The residue was diluted with EtOAc, and was washed with water and brine, and dried over Na₂SO₄. Concentration and purification with preparative TLC gave Example DG (83 mg). m/z: 776.2 (M+H)⁺. ¹H NMR (CD₃OD) δ 8.98 (s, 1H); 7.83 (s, 1H); 7.67 (m, 1H); 7.30-7.00 (m, 11H); 6.87 (m, 1H); 6.49 (m, 1H); 5.21 (s, 2H); 4.70-4.40 (m, 2H); 4.34 (t, 2H, J=8 Hz); 4.18 (m, 1H); 4.06 (m, 1H); 3.76 (m, 1H); 3.60 (t, 2H, J=8 Hz); 3.24 (m, 3H); 2.97 (s, 3H); 2.71 (m, 4H); 1.86 (m, 2H); 1.70-1.20 (m, 10H).

Preparation of Example DH

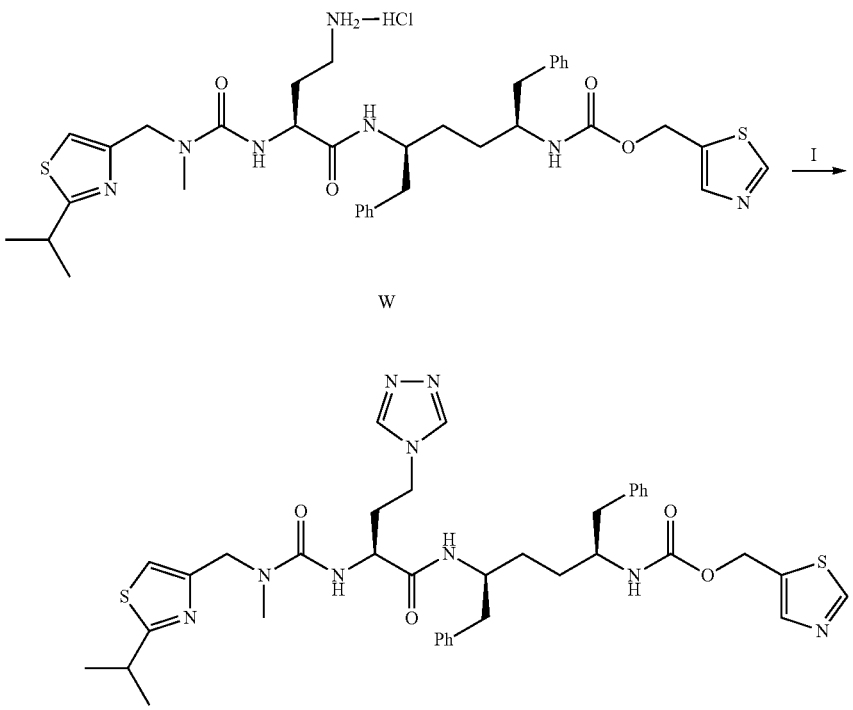

I. diformylhydrazine/pyridine/Et₃N/TMSCl/100 C.

Example W

Example W was synthesized following the procedure described in WO2008/010921 A2, and as described above in Scheme 25.

Example DH

Example DH (100 mg) was prepared following the procedure used to prepare example CY, except that Example W was used instead of Example R. $^1$H NMR (CD$_3$OD): δ 8.97 (s, 1H), 8.40 (s, 2H), 7.81 (s, 1H), 7.15 (m, 10H), 5.20 (s, 2H), 4.54 (m, 2H), 4.20 (m, 1H), 4.07 (m, 1H), 3.87 (m, 3H), 3.24 (m, 1H), 2.95 (s, 3H), 2.85 (m, 1H), 2.60 (m, 3H), 1.81 (m, 2H), 1.60-1.43 (m, 4H), 1.33 (d, J=7.2 Hz, 6H). Mass Spectrum (m/e): (M+H)$^+$ 758.2, (M−H)$^−$ 755.9.

Preparation of Example DI

Scheme 89

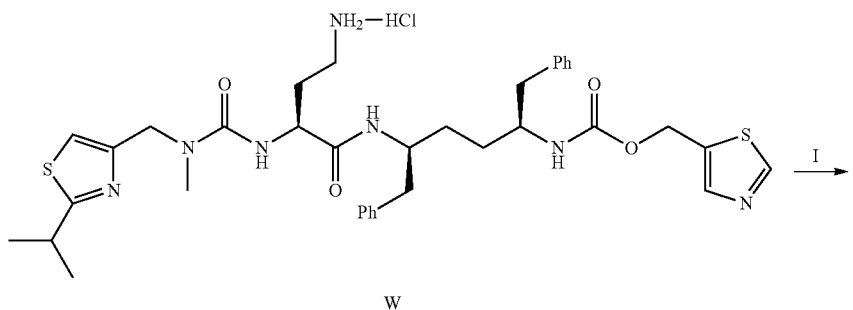

W

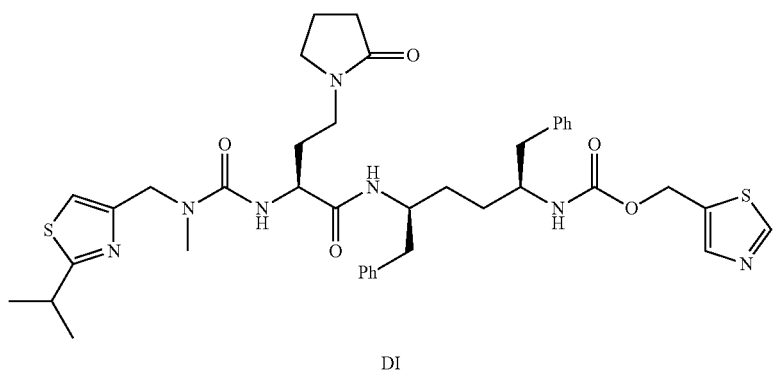

DI

I. Methyl 4-bromobutyrate/NaHCO$_3$/DMF/60 C.

Example DI

Example DI (28 mg) was prepared following the procedure used to prepare Example CZ, except that compound W (160 mg) was used instead of Example R. m/z: 774.2 (M+H)$^+$. $^1$H NMR (CD$_3$OD) δ 8.97 (1H, s), 7.81 (1H, s), 7.24-7.02 (11H, m), 5.20 (2H, s), 4.54 (2H, m), 4.18 (1H, m), 4.0 (1H, m), 3.75 (1H, m), 3.20 (4H, m), 3.01 (1H, m), 2.99 (3H, s), 2.8-2.5 (4H, m), 2.38 (2H, m), 2.04 (2H, m), 1.62-1.40 (6H, m), 1.31 (6H, m).

Preparation of Example DJ
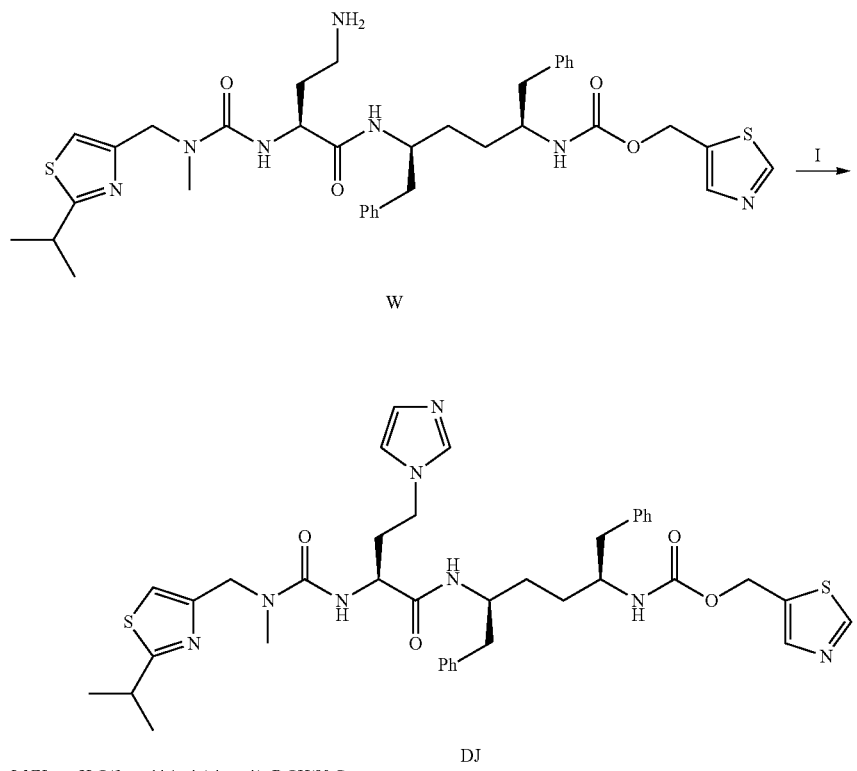
Example DJ
Example DJ (44 mg) was prepared following the procedure used to prepare Example DB, except that Example W (160 mg) was used instead of Example R. m/z: 757.3 (M+H)+. $^1$H NMR (CD$_3$OD) δ 8.97 (1H, s), 7.83 (1H, s), 7.50 (1H, s), 7.25-7.04 (11H, m), 6.99-6.96 (2H, m), 5.20 (2H, s), 4.52 (2H, m), 4.20 (1H, m), 4.03 (1H, m), 3.78 (3H, m), 3.22 (1H, m), 2.95 (3H, s), 2.9-2.4 (4H, m), 1.8 (2H, m), 1.7-1.4 (4H, m), 1.31 (6H, m).
Preparation of Examples DK-DL
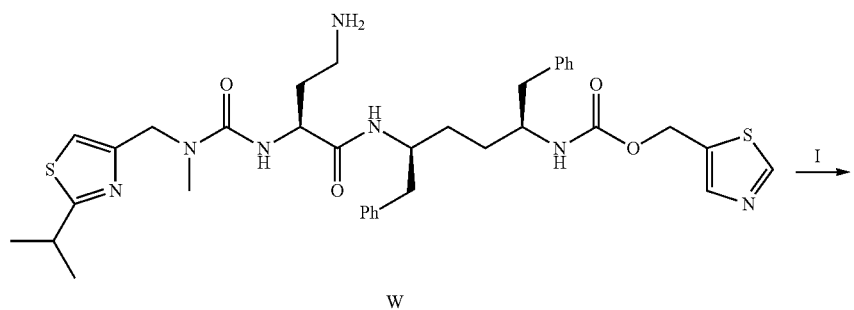

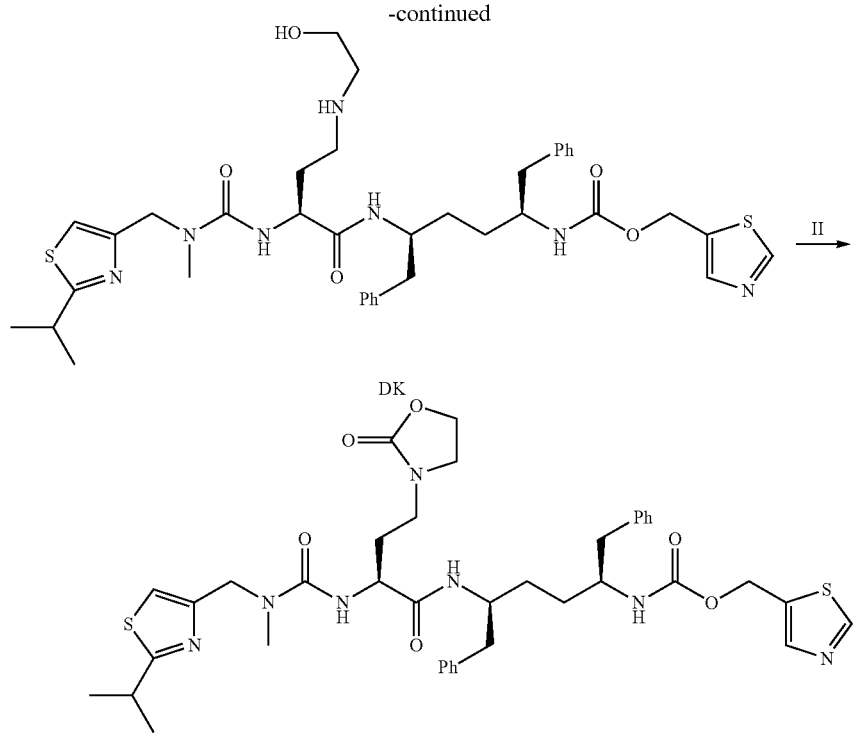

I. BrCH₂CH₂OH/Na₂CO₃/DMF/70 C.; II. CDI/DMAP/THF/70 C.

Example DK

Example DK was prepared following the procedure used to prepare Example DF, except that Example W (160 mg) was used instead of Example R.

Example DL

Example DL (28 mg) was prepared following the procedure used to prepare Example DG, except that Example DK was used instead of Example DF. m/z: 776.2 (M+H)⁺. $^1$H NMR (CD$_3$OD) δ 8.97 (1H, s), 7.81 (1H, s), 7.25-7.05 (11H, m), 5.20 (2H, s), 4.55 (2H, m), 4.31 (2H, m), 4.2-4.0 (2H, m), 3.75 (1H, m), 3.44 (2H, m), 3.3-3.0 (3H, m), 2.98 (3H, s), 2.8-2.4 (4H, m), 1.7-1.4 (6H, m), 1.32 (6H, m).

Preparation of Examples DM(a-C)

Scheme 92

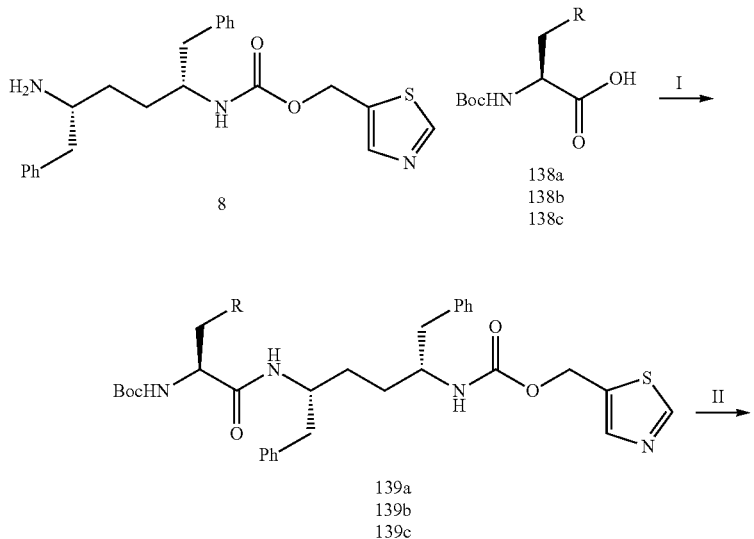

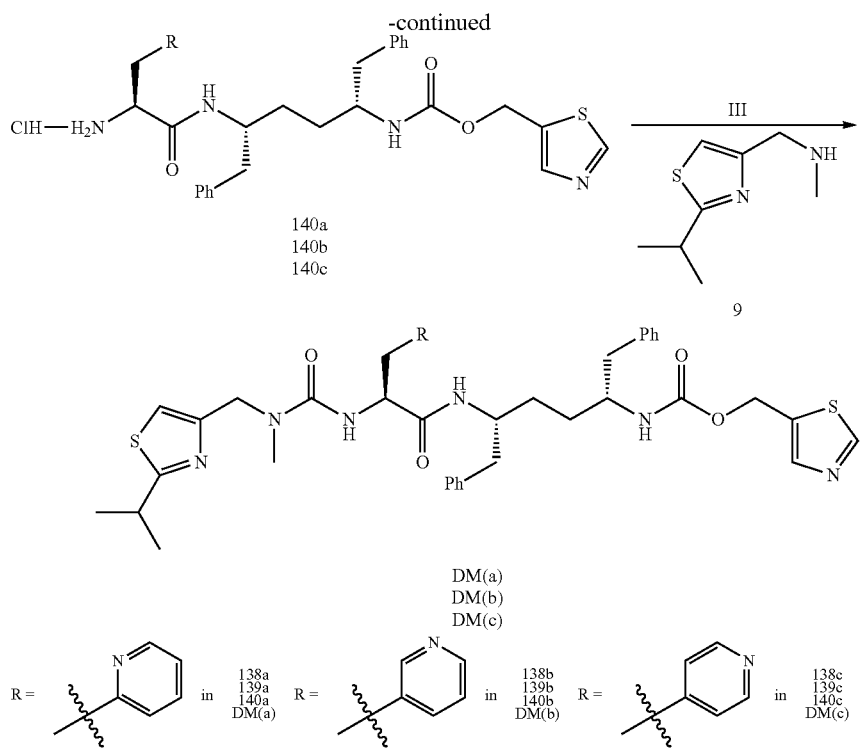

I. EDC/HOBt/DIPEA/THF; II. HCl/dioxane; III. a. CDI/DIPEA; b. cmpd 9/DIPEA

Compound 8

Compound 8 was synthesized following the procedure described in WO2008/010921 A2, and as described above.

Compounds 138a/138b/138c

Compounds 138a, 138b, and 138c were obtained from Aldrich.

Compound 139a

To a solution of acid 138a (266 mg, 1.0 mmol) and amine 8 (409 mg, 1.0 mmol) in THF (10 mL) were added HOBt (203 mg, 1.5 mmol), EDC (294 •l, 2.0 mmol), and diisopropylethylamine (0.835 mL, 4.0 mmol). The mixture was stirred for 12 hours and the solvents were removed. The residue was diluted with EtOAc. The organic phase was washed three times with saturated $Na_2CO_3$ solution, twice with water, and once with brine, and dried over $Na_2SO_4$. Concentration and purification by flash column chromatography (0%-10% MeOH in dichloromethane) gave Compound 139a (509 mg). m/z: 658.1 $(M+H)^+$.

Compound 139b

Compound 139b (543 mg) was prepared following the procedure used to prepare Compound 139a, except that Compound 138b was used instead of Compound 138a. m/z: 658.1 $(M+H)^+$.

Compound 139c

Compound 139c (587 mg) was prepared following the procedure used to prepare Compound 139a, except that Compound 138c was used instead of Compound 138a. m/z: 658.2 $(M+H)^+$.

Compound 140a

To Compound 139a (500 mg) was added 10 mL of HCl/dioxane solution (4N, 40 mmol). The mixture was stirred for 1 hour, and the solvents were removed. The residue was diluted with diethyl ether, and stirred for 1 hour. The diethyl ether layer was decanted. The solid was washed with diethyl ether (2×) and dried under vacuum. The resulting Compound 140a was a brown powder (520 mg). m/z: 558.3 $(M+H)^+$.

Compound 140b

Compound 140b (476 mg) was prepared following the procedure used to prepare Compound 140a, except that Compound 139b was used instead of Compound 139a. m/z: 558.2 $(M+H)^+$.

Compound 140c

Compound 140c (536 mg) was prepared following the procedure used to prepare Compound 140a, except that Compound 139c was used instead of Compound 139a. m/z: 558.3 $(M+H)^+$.

Compound 9

Compound 9 was synthesized following the procedure described in WO2008/010921 A2.

Example DM(a)

To the stirred solution of Compound 140a (520 mg, 0.75 mmol) and diisopropylethylamine (0.52 mL, 3.0 mmol) in dichloromethane (6 mL) was added CDI (122 mg, 0.75 mmol). The mixture was stirred for 12 hours. To this mixture was added a solution of Compound 9 (128 mg, 0.75 mmol) in dichloromethane (2 mL), and the mixture was stirred for 5 additional hours. The solvents were removed, and the residue was diluted with EtOAc. The organic layer was washed twice with water and once with brine, and dried over $Na_2SO_4$. Concentration and purification by HPLC gave Example DM(a) (270 mg). m/z: 754.3 $(M+H)^+$. $^1H$ NMR $(CD_3OD)$ δ 8.97 (s, 1H); 8.41 (m, 1H); 7.82 (s, 1H); 7.70 (m, 2H); 7.30-7.00 (m, 11H); 6.99 (s, 1H); 5.21 (s, 2H); 4.56 (m, 1H); 4.48 (s, 2H); 4.02 (m, 1H); 3.72 (m, 1H); 3.28 (m, 1H); 3.15-2.90 (m, 2H); 2.93 (s, 3H); 2.68 (m, 4H); 1.60-1.30 (m, 10H).

Example DM(b)

Example DM(b) (36 mg) was prepared following the procedure used to prepare Example DM(a), except that Compound 140b was used instead of Compound 140a. m/z: 754.3 (M+H)+. 1H NMR (CD3OD) δ 8.97 (s, 1H); 8.38 (m, 2H); 7.83 (s, 1H); 7.68 (m, 1H); 7.33 (m, 1H); 7.30-7.00 (m, 10H); 6.96 (s, 1H); 5.21 (s, 2H); 4.45 (m, 3H); 4.01 (m, 1H); 3.72 (m, 1H); 3.28 (m, 1H); 3.15-2.90 (m, 2H); 2.90 (s, 3H); 2.68 (m, 4H); 1.60-1.30 (m, 10H).

Example DM(c)

Example DM(c) (283 mg) was prepared following the procedure used to prepare Example DM(a), except that Compound 140c was used instead of Compound 140a. m/z: 754.3 (M+H)+. 1H NMR (CD3OD) δ 8.97 (s, 1H); 8.39 (d, 2H, J=6 Hz); 7.82 (s, 1H); 7.27 (d, 2H, J=6 Hz); 7.30-7.00 (m, 10H); 6.94 (s, 1H); 5.21 (s, 2H); 4.53 (m, 1H); 4.45 (s, 2H); 4.03 (m, 1H); 3.74 (m, 1H); 3.32 (m, 1H); 3.10-2.90 (m, 2H); 2.90 (s, 3H); 2.72 (m, 4H); 1.60-1.30 (m, 10H).

Preparation of Example DN

Scheme 93

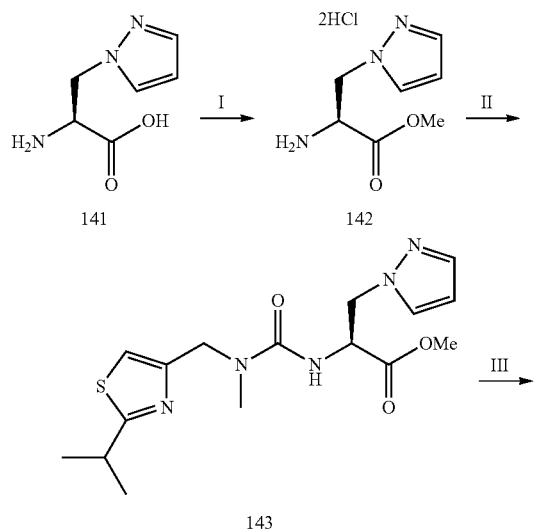

DN
I. SOCl2/MeOH; II. a. CDI/iPr2NEt; b. cmpd 9; III. a. NaOH/THF/H2O; b. HCl;
IV. cmpd 8/EDC/HOBt;

Compound 141

Compound 141 was obtained from TCI.

Compound 142

To a solution of Compound 141 (1.0 g, 6.4 mmol) in methanol (20 mL) at 0° C. was added thionyl chloride (1.0 mL, 14.2 mmol) dropwise. The mixture was stirred at 0° C. for 30 minutes and brought to reflux for 3 hours. Concentration gave Compound 142 as a white solid.

Compound 143

Compound 143 (1.68 g) was prepared following the procedure used to prepare Example DM(a), except that Compound 142 was used instead of Compound 140a. m/z: 366.0 (M+H)+.

Compound 144

To a solution of Compound 143 (1.68 g, 4.8 mmol) in MeOH/H2O (20 mL/20 mL) at 0° C. was added sodium hydroxide (229 mg, 5.74 mmol). The mixture was stirred for 1 hour and the solvents were removed under reduced pressure. Hydrochloric acid in dioxane (1.5 mL, 4 N, 6 mmol) was added, and the mixture was evaporated and dried under high vacuum. Compound 144 was obtained as a white solid (1.8 g).

Example DN

Example DN (260 mg) was prepared following the procedure used to prepare Compound 139a, except that Compound 144 was used instead of Compound 138a. m/z: 743.2 (M+H)+. 1H NMR (CDCl3) δ 8.78 (1H, s), 7.81 (1H, s), 7.44 (1H, s), 7.39 (1H, s), 7.3-7.0 (10H, m), 6.95 (2H, m), 6.7 (1H, br), 6.2 (1H, m), 5.3 (1H, m), 5.2 (2H, m), 4.5-4.2 (5H, m), 4.1 (1H, m), 3.70 (1H, m), 3.22 (1H, m), 2.96 (3H, s), 2.8-2.5 (4H, m), 1.5-1.2 (10H, m).

Preparation of Example DO

Scheme 94

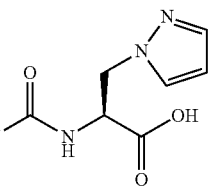

144

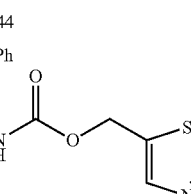

46

-continued

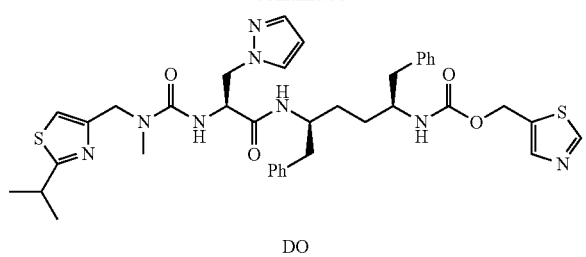

DO

I. EDC/HOBt;

Compound 46

Compound 46 was synthesized following the procedure described in WO2008/010921 A2.

Example DO

Example DO (215 mg) was prepared following the procedure used to prepare Compound 139a, except that Compounds 144 and 46 were used instead of Compounds 8 and 138a. m/z: 743.2 (M+H)+. $^1$H NMR (CD$_3$OD) δ 8.97 (s, 1H); 7.82 (s, 1H); 7.45 (s, 1H); 7.30-7.00 (m, 13H); 6.19 (s, 1H); 5.20 (s, 2H); 4.60-4.40 (m, 2H); 4.21 (m, 2H); 4.09 (m, 1H); 3.25 (m, 1H); 2.93 (s, 3H); 2.90-2.50 (m, 5H); 1.70-1.20 (m, 10H).

Preparation of Examples DP-DT

Scheme 95

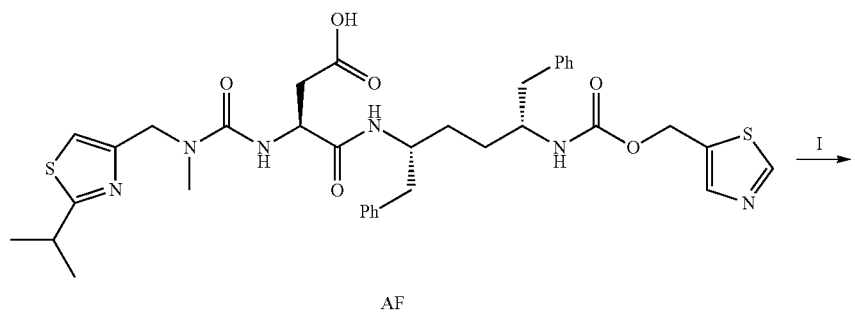

AF

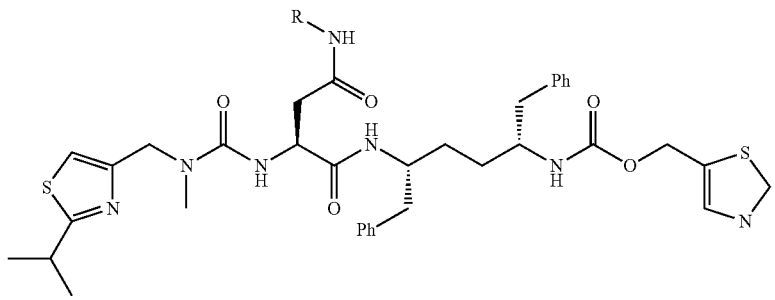

R =

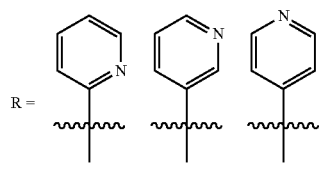

DP   DQ   DR

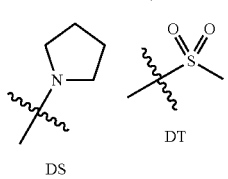

DS   DT

I. RNH$_2$/EDC/HOBt;

Example AF

Example AF was synthesized following the procedure described in WO2008/010921 A2, and as described above in Scheme 27.

Example DP

Example DP (23 mg) was prepared following the procedure used to prepare Compound 139a, except that Example AF and 2-aminopyridine were used instead of Compounds 8 and 138a. m/z: 797.2 (M+H)$^+$. $^1$H NMR (DMSO-d$_6$) δ 10.45 (1H, s), 9.06 (1H, s), 8.31 (1H, m), 8.04 (1H, m), 7.85 (1H, m), 7.75 (1H, m), 7.55 (1H, m); 7.2-7.0 (13H, m), 6.54 (1H, m), 5.12 (2H, s), 4.52 (1H, m), 4.43 (2H, s), 3.93 (1H, m), 3.58 (1H, m), 3.17 (1H, m), 2.85 (3H, s), 2.8-2.4 (6H, m), 1.36 (4H, m), 1.25 (6H, m).

Example DQ

Example DQ (32 mg) was prepared following the procedure used to prepare Compound 139a, except that Example AF and 3-aminopyridine were used instead of Compounds 8 and 138a. m/z: 797.2 (M+H)$^+$. $^1$H NMR (DMSO-d6) δ 10.39 (1H, s), 9.06 (1H, s), 8.88 (1H, s), 8.36 (1H, m), 8.18 (1H, m), 7.85 (1H, s), 7.54 (2H, m), 7.2-7.0 (12H, m), 6.60 (1H, m), 5.14 (2H, s), 4.55 (1H, m), 4.45 (2H, s), 4.0-3.5 (2H, m), 3.19 (1H, m), 2.86 (3H, s), 2.8-2.4 (6H, m), 1.37 (4H, m), 1.26 (6H, m).

Example DR

Example DR (30 mg) was prepared following the procedure used to prepare Compound 139a, except that Example AF and 4-aminopyridine were used instead of Compounds 8 and 138a. m/z: 797.3 (M+H)$^+$. $^1$H NMR (DMSO-d6) δ 11.24 (1H, s), 9.05 (1H, s), 8.61 (2H, d, J=6.3 Hz), 7.96 (2H, d, J=6.3 Hz), 7.84 (1H, s), 7.58 (1H, m), 7.2-7.0 (12H, m), 6.65 (1H, m), 5.14 (2H, s), 4.6 (1H, m), 4.46 (2H, s), 3.9 (1H, m), 3.4 (1H, m), 3.20 (1H, m), 2.87 (3H, s), 2.7-2.4 (6H, m), 1.37 (4H, m), 1.25 (6H, m).

Example DS

Example DS (50 mg) was prepared following the procedure used to prepare Compound 139a, except that Example AF and 1-aminopyrrolidine were used instead of Compounds 8 and 138a. m/z: 789.2 (M+H)$^+$. $^1$H NMR (DMSO-d6) δ 9.06 (1H, s), 8.63 (1H, s), 8.26 (1H, s), 7.85 (1H, s), 7.55 (1H, m), 7.35 (1H, m), 7.2-7.0 (10H, m); 6.40 (1H, m), 5.15 (2H, s), 4.55-4.30 (3H, m), 3.85 (1H, m), 3.63 (1H, m), 3.4-3.1 (5H, m), 2.86 (3H, s), 2.8-2.4 (6H, m), 1.66 (4H, m), 1.4-1.2 (10H, m).

Example DT

Example DT (50 mg) was prepared following the procedure used to prepare Compound 139a, except that Example AF and methanesulfonamide were used instead of Compounds 8 and 138a. m/z: 798.2 (M+H)$^+$. $^1$H NMR (DMSO-d$_6$) δ 11.65 (1H, s), 9.10 (1H, s), 7.88 (1H, s), 7.50 (1H, m), 7.2-7.0 (12H, m), 6.6 (1H, m), 5.15 (2H, s), 4.5-4.4 (3H, m), 4.0-3.4 (2H, m), 3.20 (1H, m), 3.15 (3H, s), 2.85 (3H, s), 2.7-2.4 (6H, m), 1.4-1.2 (10H, m).

Preparation of Examples DU(a-c)

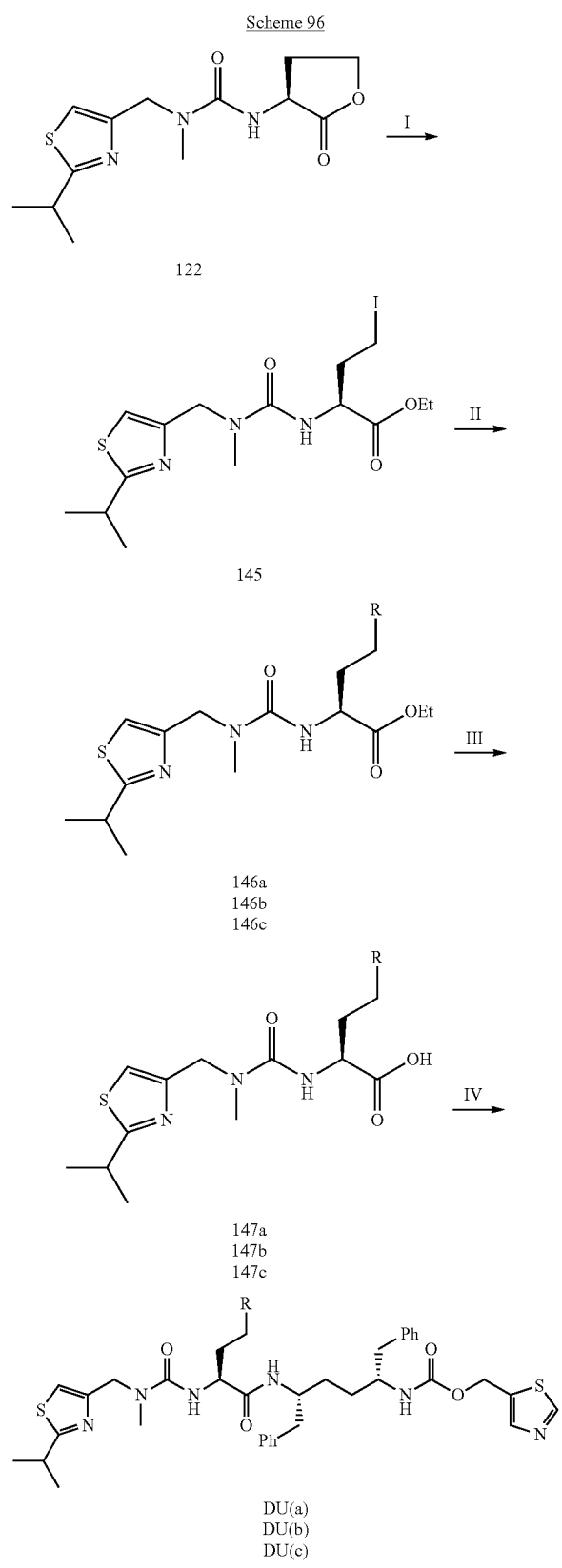

Scheme 96

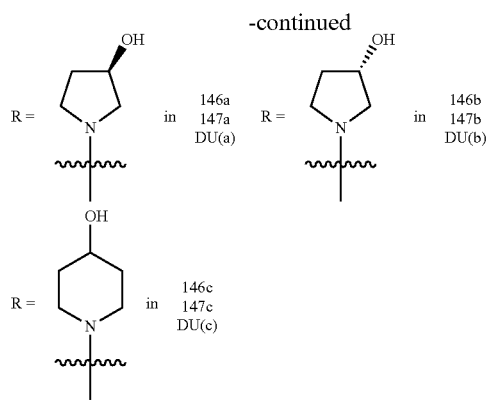

I. TMSI/EtOH/DCM; II. amino alcohol/DCM; III. a. NaOH/THF/H₂O; b. HCl;
IV. cmpd 8/EDC/HOBt/DIPEA/DMF Compound 122

Compound 122 was synthesized following the procedure described in WO2008/010921 A2, and as described above in Scheme 69.

Compound 145

To a solution of Compound 122 (1.0 g, 4 mmol) in dichloromethane (5 mL) was added ethyl alcohol (1.5 mL, 25.6 mmol), followed by iodotrimethylsilane (2 mL, 14.3 mmol). The mixture was stirred for 6 hours and the mixture was used directly for the next step. m/z: 453.9 (M+H)⁺.

Compound 146a

To a solution of Compound 145 (1 mmol) in dichloromethane (2 mL) was added a solution of (R)-3-hydroxypyrrolidine (435 mg, 5 mmol) in dichloromethane (1 mL). The mixture was stirred for 12 hours and the solvents were removed under reduced pressure. Purification by flash column chromatography (0-20% MeOH in dichloromethane) gave Compound 146a (230 mg). m/z: 413.1 (M+H)⁺.

Compound 146b

Compound 146b (200 mg) was prepared following the procedure used to prepare Compound 146a, except that compound (S)-3-hydroxypyrrolidine was used instead of compound (R)-3-hydroxypyrrolidine. m/z: 413.1 (M+H)⁺.

Compound 146c

Compound 146c (380 mg) was prepared following the procedure used to prepare Compound 146a, except that compound 4-hydroxypiperidine was used instead of compound (R)-3-hydroxypyrrolidine. m/z: 427.1 (M+H)⁺.

Compound 147a Compound 147a (250 mg) was prepared following the procedure used to prepare Compound 144, except that Compound 146a was used instead of Compound 143.

Compound 147b

Compound 147b (210 mg) was prepared following the procedure used to prepare Compound 144, except that Compound 146b was used instead of Compound 143.

Compound 147c

Compound 147c (400 mg) was prepared following the procedure used to prepare Compound 144, except that Compound 146c was used instead of Compound 143.

Example DU(a)

Example DU(a) (250 mg) was prepared following the procedure used to prepare Compound 139a, except that Compound 147a was used instead of Compound 138a. m/z: 776.3 (M+H)⁺. ¹H NMR (CD₃OD) δ 8.97 (1H, s), 7.81 (1H, s), 7.25-7.05 (11H, m), 5.19 (2H, m), 4.54 (2H, m), 4.25 (1H, m), 4.2-4.1 (2H, m), 3.75 (1H, m), 3.22 (1H, m), 2.94 (3H, s), 2.8-2.7 (6H, m), 2.5-2.3 (4H, m), 2.1-1.8 (2H, m), 1.7-1.4 (6H, m), 1.37 (6H, m).

Example DU(b)

Example DU(b) (253 mg) was prepared following the procedure used to prepare Compound 139a, except that compound 147b was used instead of Compound 138a. m/z: 776.3 (M+H)¹. ¹H NMR (CD₃OD) δ 8.97 (1H, s), 7.81 (1H, s), 7.22-7.05 (11H, m), 5.18 (2H, m), 4.5 (2H, m), 4.25 (1H, m), 4.2-4.1 (2H, m), 3.78 (1H, m), 3.25 (1H, m), 2.95 (3H, s), 2.8-2.6 (6H, m), 2.6-2.3 (4H, m), 2.1-1.8 (2H, m), 1.8-1.4 (6H, m), 1.37 (6H, m).

Example DU(c)

Example DU(c) (450 mg) was prepared following the procedure used to prepare Compound 139a, except that Compound 147c was used instead of Compound 138a. m/z: 790.3 (M+H)⁺. ¹H NMR (CD₃OD) δ 8.97 (1H, s), 7.81 (1H, s), 7.25-7.05 (11H, m), 5.20 (2H, m), 4.54 (2H, m), 4.2-4.0 (2H, m), 3.75 (1H, m), 3.58 (1H, m), 3.25 (1H, m), 2.97 (3H, s), 2.8-2.6 (6H, m), 2.25 (2H, m), 2.08 (2H, m), 1.9-1.6 (4H, m), 1.6-1.4 (6H, m), 1.38 (6H, m).

Preparation of Example DV

Scheme 97

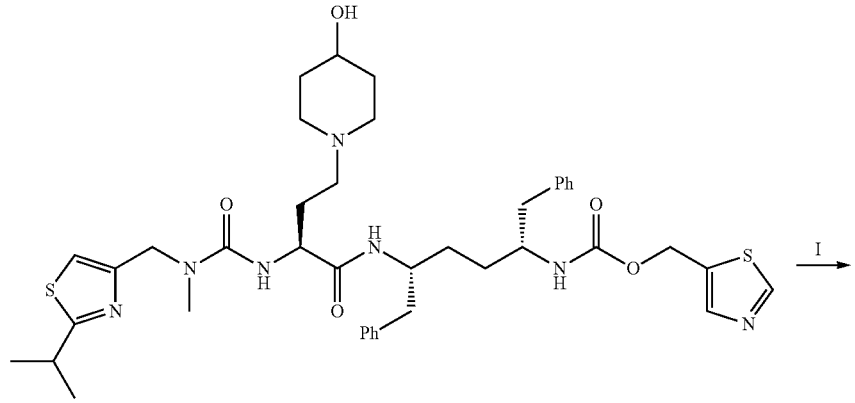

DU(c)

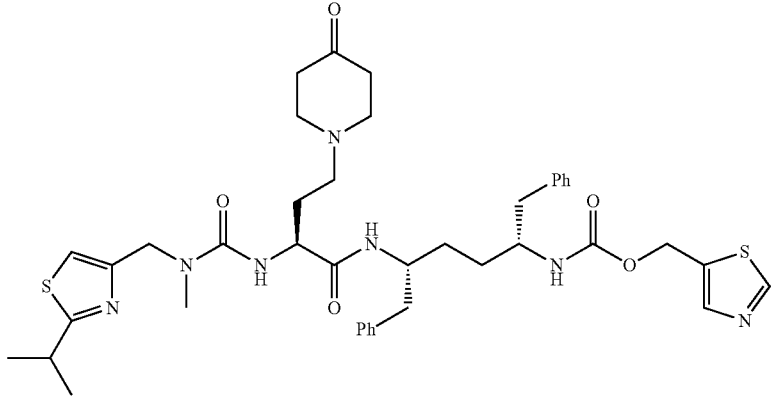

Example DV

A mixture of Example DU(c) (230 mg, 0.29 mmol) and triethylamine (0.14 mL) in DMSO (1 mL) was stirred at 25° C. for 30 minutes, and then was cooled to 5-10° C. Sulfur trioxide pyridine complex (0.17 g) was added to above reaction mixture and the mixture was stirred for 1 hour at 5-10° C. The mixture was poured into ice water, and stirred for 20 minutes, and was extracted with EtOAc. The organic phase was washed twice with water, twice with saturated NaHCO$_3$ solution, twice with water, and once with brine, and dried over Na$_2$SO$_4$. Concentration and purification by flash column chromatography (0-20% MeOH in dichloromethane) gave Example DV (67 mg). m/z: 788.3 (M+H)$^+$.
$^1$H NMR (CDCl$_3$) δ 8.78 (1H, s), 7.81 (1H, s), 7.3-7.1 (10H, m), 6.90 (1H, s), 6.5 (1H, br), 5.35 (1H, m), 5.22 (2H, s), 4.4-4.0 (4H, m), 3.78 (1H, m), 3.23 (1H, m), 2.93 (3H, s), 2.8-2.5 (8H, m), 2.4-2.2 (6H, m), 2.0-1.4 (6H, m), 1.32 (6H, m).

Preparation of Example DW

Example DW

Example DW (78 mg) was prepared following the procedure used to prepare Example DV, except that Example DU(a) was used instead of Example DU(c). m/z: 774.3 (M+H)[1]. $^1$H NMR (CDCl$_3$) δ 8.78 (1H, s), 7.82 (1H, s), 7.3-7.0 (10H, m), 6.89 (1H, s), 6.55 (1H, br), 5.40 (1H, m), 5.21 (2H, s), 4.5-4.2 (3H, m), 4.15 (1H, m), 3.78 (1H, m), 3.23 (1H, m), 3.1-2.9 (4H, m), 2.9 (3H, s), 2.8-2.5 (6H, m), 2.40 (2H, m), 1.90 (2H, m), 1.55 (2H, m), 1.38 (8H, m).

Preparation of Examples DX(a-f)

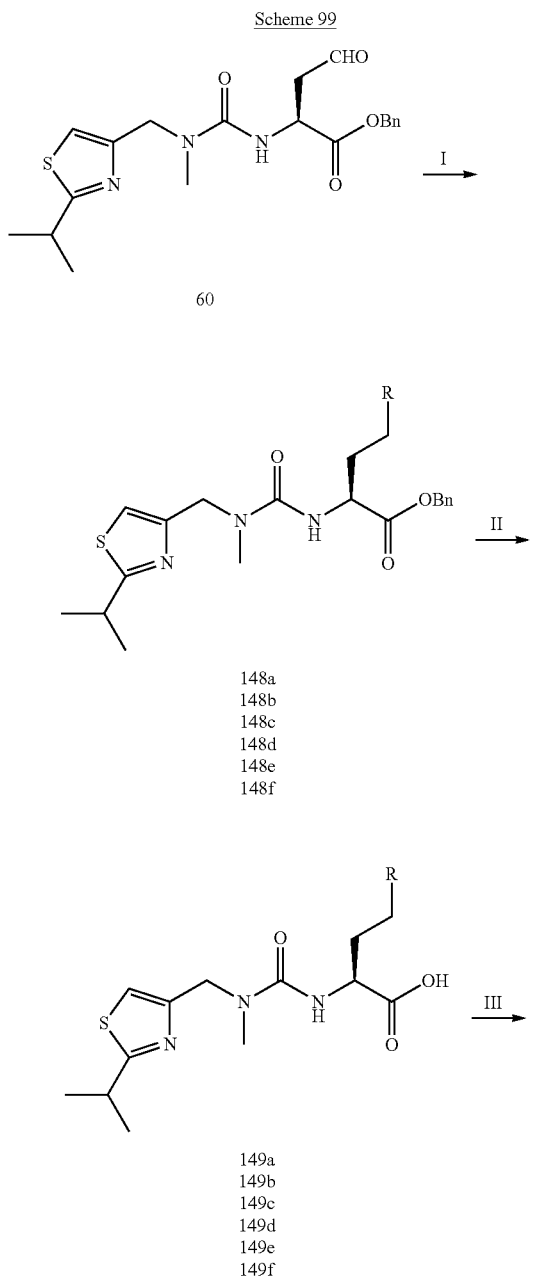

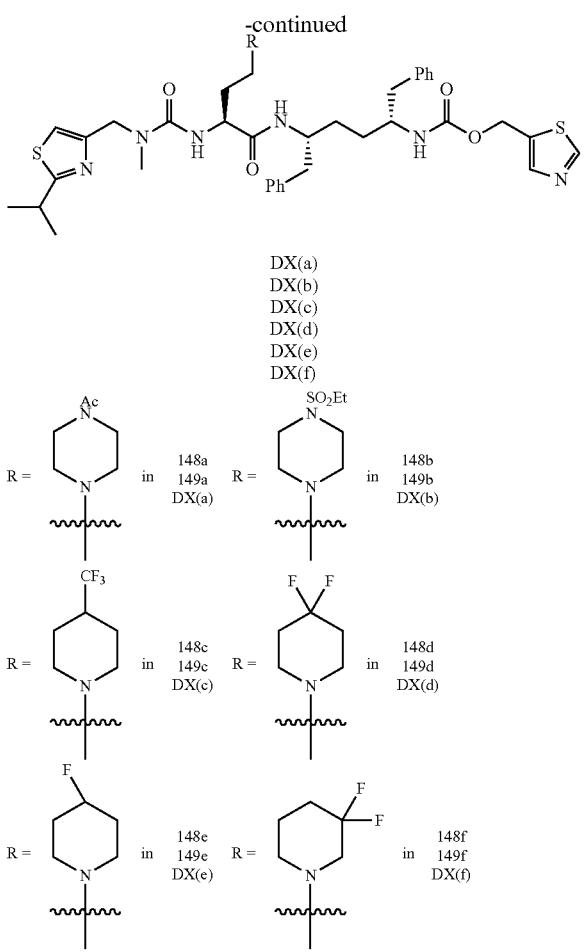

I. amine/NaBH(OAc)$_3$/AcOH/CH$_3$CN; II. a. NaOH/EtOH/H$_2$O; b. HCl; III. compound 8/EDC/HOBt/DIPEA

Compound 60

Compound 60 was synthesized following the procedure described in WO2008/010921 A2, and as described above in Scheme 23.

Compound 148a

To a solution of Compound 60 (800 mg, 2 mmol) in CH$_3$CN (8 mL) was added a solution of 1-acetylpiperazine (512 mg, 4 mmol) in CH$_3$CN (1 mL), followed by HOAc (240 ul, 4 mmol) and NaBH(OAc)$_3$ (1.33 g, 6 mmol). The mixture was stirred for 12 hours and was diluted with EtOAc. The organic phase was washed with saturated Na$_2$CO$_3$ solution, water, and brine, and dried over Na$_2$SO$_4$. Concentration and purification by flash column chromatography (0-12% iPrOH in dichloromethane) gave Compound 148a (250 mg). m/z: 516.1 (M+H)$^+$.

Compound 148b

Compound 148b (530 mg) was prepared following the procedure used to prepare Compound 148a, except that 1-ethylsulfonylpiperazine was used instead of 1-acetylpiperazine. m/z: 566.1 (M+H)$^+$.

Compound 148c

Compound 148c (384 mg) was prepared following the procedure used to prepare Compound 148a, except that 4-trifluoromethylpiperidine was used instead of 1-acetylpiperazine. m/z: 541.2 (M+H)$^+$.

Compound 148d

Compound 148d (342 mg) was prepared following the procedure used to prepare Compound 148a, except that 4,4-difluoropiperidine was used instead of 1-acetylpiperazine. m/z: 509.1 (M+H)+.

Compound 148e

Compound 148e (320 mg) was prepared following the procedure used to prepare Compound 148a, except that 4-fluoropiperidine was used instead of 1-acetylpiperazine. m/z: 491.1 (M+H)+.

Compound 148f

Compound 148f (389 mg) was prepared following the procedure used to prepare Compound 148a, except that 3,3-difluoropiperidine was used instead of 1-acetylpiperazine. m/z: 509.1 (M+H)+.

Example 149a

To a solution of Compound 148a (250 mg, 0.48 mmol) in ethyl alcohol (3 mL) was added 1.0 N sodium hydroxide solution (0.53 mL, 0.53 mmol). The mixture was stirred for 1 hour and the solvents were removed under reduced pressure. 4.0 N Hydrochloric acid in dioxane (0.13 mL, 0.52 mmol) was added, and the mixture was evaporated. Coevaporation with DMF (2×100 mL) gave Compound 149a, which was used without further purification in the next step.

Example 149b

Compound 149b was prepared following the procedure used to prepare Compound 149a, except that Compound 148b was used instead of Compound 148a.

Example 149c

Compound 149c was prepared following the procedure used to prepare Compound 149a, except that Compound 148c was used instead of Compound 148a.

Example 149d

Compound 149d was prepared following the procedure used to prepare Compound 149a, except that Compound 148d was used instead of Compound 148a.

Example 149e

Compound 149e was prepared following the procedure used to prepare Compound 149a, except that Compound 148e was used instead of Compound 148a.

Example 149f

Compound 149f was prepared following the procedure used to prepare Compound 149a, except that Compound 148f was used instead of Compound 148a.

Example DX(a)

Example DX(a) (90 mg) was prepared following the procedure used to prepare Compound 139a, except that Compound 149a was used instead of Compound 138a. m/z: 817.3 (M+H)+. $^1$H NMR (CDCl$_3$) •8.78 (1H, s), 7.81 (1H, s), 7.3-7.0 (10H, m), 6.90 (1H, s), 6.40 (1H, m), 5.40 (1H, m), 5.22 (2H, s), 4.6-4.3 (2H, m), 4.3-4.1 (2H, m), 3.78 (1H, m), 3.5-3.2 (5H, m), 2.92 (3H, s), 2.9-2.6 (4H, m), 2.4-2.2 (6H, m), 2.07 (3H, s), 1.9 (2H, m), 1.6-1.3 (10H, m).

Example DX(b)

Example DX(b) (150 mg) was prepared following the procedure used to prepare Compound 139a, except that Compound 149b was used instead of Compound 138a. m/z: 867.3 (M+H)+. $^1$H NMR (CDCl$_3$) •8.78 (1H, s), 7.81 (1H, s), 7.3-7.0 (10H, m), 6.92 (1H, s), 6.4 (1H, br), 5.35 (1H, br), 5.2 (2H, s), 4.6-4.0 (4H, m), 3.78 (1H, m), 3.3-3.1 (5H, m), 2.92 (5H, m), 2.8-2.6 (4H, m), 2.5-2.2 (6H, m), 1.90 (2H, m), 1.6-1.3 (13H, m).

Example DX(c)

Example DX(c) (427 mg) was prepared following the procedure used to prepare Compound 139a, except that Compound 149c was used instead of Compound 138a. m/z: 842.2 (M+H)+. $^1$H NMR (CDCl$_3$) •8.77 (1H, s), 7.80 (1H, s), 7.3-7.0 (10H, m), 6.88 (1H, s), 6.40 (1H, br), 5.50 (1H, br), 5.20 (2H, m), 4.7-4.3 (2H, m), 4.18 (2H, m), 3.75 (1H, m), 3.23 (1H, m), 3.05-2.8 (4H, m), 2.8-2.6 (4H, m), 2.25 (2H, m), 2.0-1.65 (6H, m), 1.6-1.2 (14H, m).

Example DX(d)

Example DX(d) (390 mg) was prepared following the procedure used to prepare Compound 139a, except that Compound 149d was used instead of Compound 138a. m/z: 810.2 (M+H)+. $^1$H NMR (CDCl$_2$) •8.78 (1H, s), 7.81 (1H, s), 7.4-7.0 (10H, m), 6.89 (1H, s), 6.40 (1H, br), 5.40 (1H, br), 5.22 (2H, m), 4.6-4.3 (2H, m), 4.22 (2H, m), 3.78 (1H, m), 3.24 (1H, m), 3.0-2.6 (7H, m), 2.5-2.2 (6H, m), 2.0-1.7 (6H, m), 1.6-1.2 (10H, m).

Example DX(e)

Example DX(e) (160 mg) was prepared following the procedure used to prepare Compound 139a, except that Compound 149e was used instead of Compound 138a. m/z: 792.3 (M+H)+. (CDCl$_3$) •8.77 (1H, s), 7.81 (1H, s), 7.3-7.0 (10H, m), 6.87 (1H, s), 6.45 (1H, br), 5.55 (1H, br), 5.20 (2H, m), 4.9-4.3 (3H, m), 4.3-4.1 (2H, m), 3.75 (1H, m), 3.25 (1H, m), 3.1-2.8 (5H, 2.8-2.6 (4H, m), 2.6-2.1 (6H, m), 2.0-1.4 (8H, m), 1.37 (6H, m).

Example DX(f)

Example DX(f) (480 mg) was prepared following the procedure used to prepare Compound 139a, except that Compound 149f was used instead of Compound 138a. m/z: 810.2 (M+H)+. $^1$H NMR (CDCl$_3$) •8.77 (1H, s), 7.80 (1H, s), 7.3-7.0 (10H, m), 6.93 (1H, br), 6.84 (1H, s), 6.40 (1H, br), 5.50 (1H, br), 5.20 (2H, m), 4.5-4.3 (2H, m), 4.3-4.1 (2H, m), 3.75 (1H, m), 3.24 (1H, m), 3.05-2.8 (5H, m), 2.8-2.6 (4H, m), 2.5-2.2 (6H, m), 2.0-1.75 (4H, m), 1.7-1.37 (10H, m).

Preparation of Example DY

Scheme 100

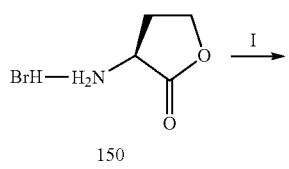

150

-continued

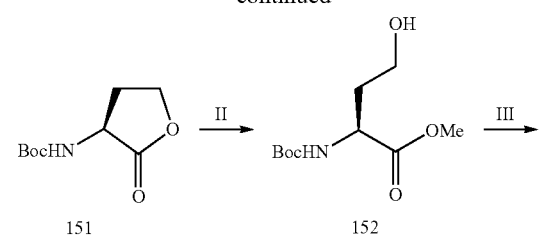

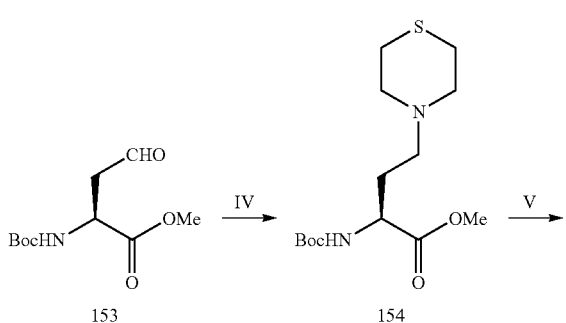

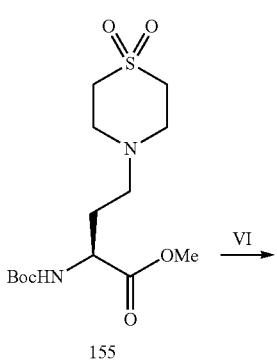

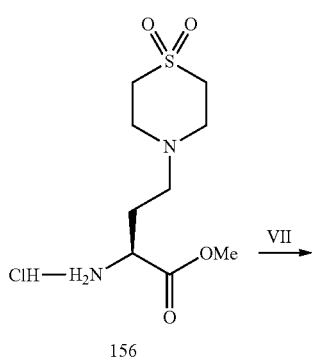

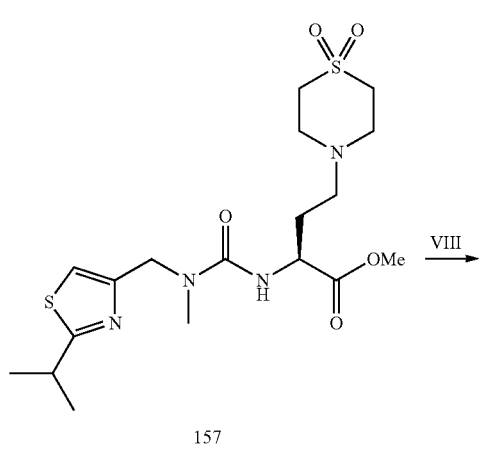

-continued

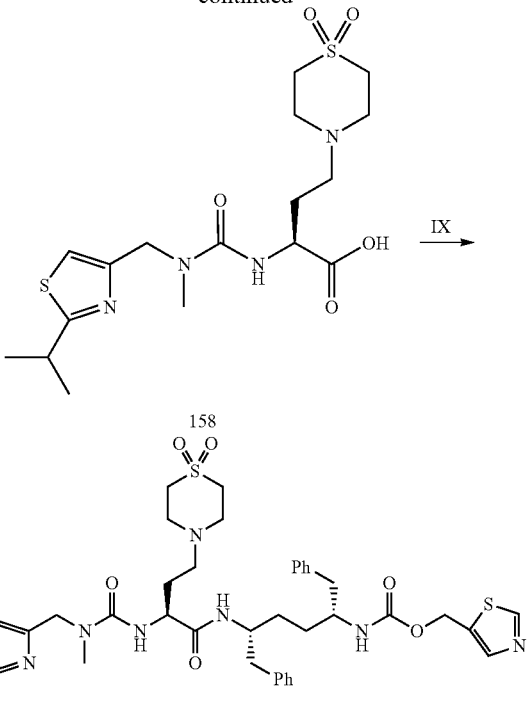

1. Boc₂O/THF; II. NaOMe/MeOH; III. SO₃-pyridine/DMSO/Et₃N;
IV. thiomorpholine/NaBH(OAc)₃/HOAc; V. 4-methylmorpholine N-oxide/OsO₄;
VI. HCl; VII. a. CDI; b. cmpd 9; VIII. a. NaOH; b. HCl;
IX. EDC/HOBt/cmpd 8

Compound 150
  Compound 150 was obtained from Aldrich.
Compound 151
  To a suspension of Compound 150 (25 g, 137 mmol) in THF (400 mL) was added triethylamine (21 mL, 151 mmol), followed by Boc₂O (31.5 g, 144 mmol). The mixture was stirred for 48 hours, and the solvents were removed. The residue was diluted with EtOAc, and washed twice with saturated sodium carbonate solution, once with water, and once with brine, and dried over Na₂SO₄. Concentration gave Compound 151 (25 g).
Compound 152
  To a solution of Compound 151 (2.0 g, 10 mmol) in MeOH (20 mL) at 0° C. was added 4.4 N sodium methoxide solution in methanol (0.46 mL, 2 mmol). The mixture was stirred for 45 minutes, and quenched with saturated NH₄Cl solution. The solvent was evaporated, and the residue was diluted with EtOAc. The organic phase was washed with saturated NH₄Cl solution, water, and brine, and dried over Na₂SO₄. Concentration gave Compound 152 (2.6 g).
Compound 153
  Compound 153 (1.9 g) was prepared following the procedure used to prepare Example DV, except that Compound 152 was used instead of Example DU(c).
Compound 154
  Compound 154 (1.65 g) was prepared following the procedure used to prepare Compound 148a, except that Compound 153 and 4-thiomorpholine were used instead of Compound 60 and 1-acetylpiperazine.
Compound 155
  To a solution of Compound 154 (1.55 g, 4.86 mmol) in acetone/water (270 mL/70 mL) was added 4-methylmorpholine N-oxide (1.25 g, 10 mmol), followed by OsO$_4$/tBuOH solution (6.8 mL, 2.5%). The mixture was stirred for 12 hours and the solvents were removed under reduced pressure. Purification by flash column chromatography (60-100% EtAOc in hexanes) gave Compound 155 (1.44 g).

Compound 156

Compound 156 was prepared following the procedure used to prepare Compound 140a, except that Compound 155 was used instead of Compound 139a.

Compound 157

Compound 157 (660 mg) was prepared following the procedure used to prepare Example DM(a), except that Compound 156 was used instead of Compound 140a. m/z: 447.0 (M+H)$^+$.

Compound 158

Compound 158 was prepared following the procedure used to prepare Compound 144, except that Compound 157 was used instead of Compound 143. m/z: 433.1 (M+H)$^+$.

Example DY

Example DY (350 mg) was prepared following the procedure used to prepare Compound 139a, except that Compound 158 was used instead of Compound 138a. m/z: 824.2 (M+H)$^+$. $^1$H NMR (CDCl$_3$) •8.80 (1H, s), 7.82 (1H, s), 7.2-7.0 (10H, m), 6.96 (1H, s), 6.71 (1H, br), 6.4 (1H, br), 5.21 (2H, m), 5.15 (1H, br), 4.5-4.1 (4H, m), 3.80 (1H, m), 3.22 (1H, m), 3.0-2.8 (11H, m), 2.8-2.6 (4H, m), 2.47 (2H, m), 2.0-1.7 (2H, m), 1.6-1.3 (10H, m).

Preparation of Examples DZ-EA

Scheme 101

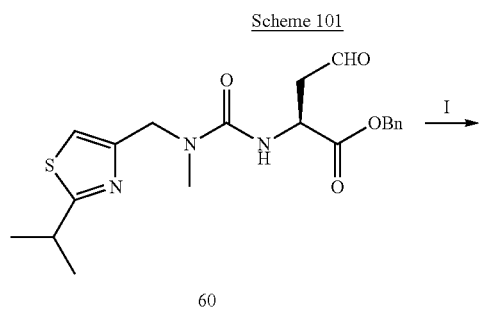

60

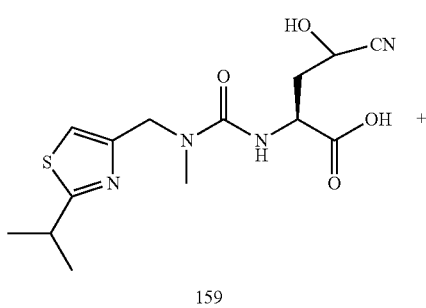

159

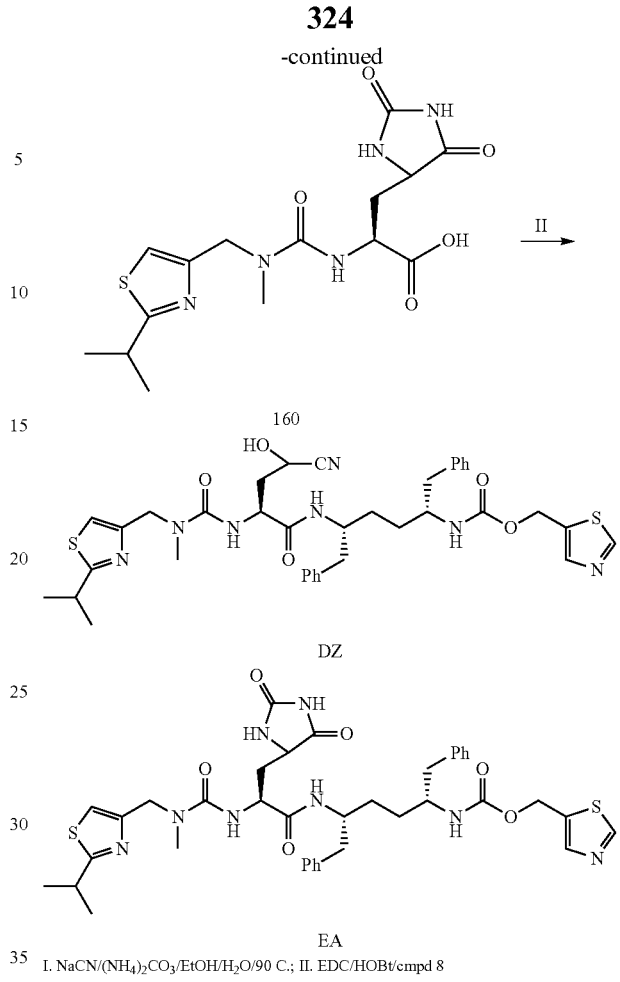

I. NaCN/(NH$_4$)$_2$CO$_3$/EtOH/H$_2$O/90 C.; II. EDC/HOBt/cmpd 8

Compounds 159/160

To a solution of Compound 60 (1.6 mmol) in EtOH/H$_2$O (1.6 mL/1.6 mL) was added ammonium carbonate (600 mg, 6.4 mmol), followed by sodium cyanide (158 mg). The mixture was heated at 90° C. for 16 hours and cooled to 25° C. 1 N hydrochloric acid was added until pH=3-4. The residue was diluted with EtOAc, and washed with water and brine. The organic phase was dried over Na$_2$SO$_4$ and concentrated to give Compounds 159 and 160, which were used without further purification in the next step.

Examples DZ/EA

Examples DZ (80 mg) and EA (60 mg) were prepared following the procedure used to prepare Compound 139a, except that Compounds 159 and 160 were used instead of Compound 138a. Example DZ: m/z: 732.3 (M+H)$^+$. $^1$H NMR (CDCl$_3$) • 8.75 (1H, m), 7.80 (1H, m), 7.3-7.0 (10H, m), 6.95 (1H, m), 6.8 (1H, br), 6.40 (1H, br), 5.8 (1H, br), 5.20 (2H, m), 4.40 (2H, m), 4.2-3.8 (3H, m), 3.78 (1H, m), 3.23 (1H, m), 2.95 (3H, m), 2.8-2.3 (6H, m), 1.6-1.3 (10H, m). Example EA: m/z: 775.2 (M+H)$^+$. $^1$H NMR (CDCl$_3$) •8.81 (1H, s), 8.02 (1H, br), 7.9 (1H, s), 7.85 (1H, br), 7.3-7.0 (11H, m), 6.3 (1H, br), 5.4-5.1 (3H, m), 4.6-4.3 (2H, m), 4.2-3.8 (2H, m), 3.8-3.4 (1H, m), 3.3 (1H, m), 3.1-2.9 (3H, m), 2.8-2.4 (4H, m), 2.15 (2H, m), 1.7-1.2 (10H, m).

Preparation of Example Eb

Scheme 102

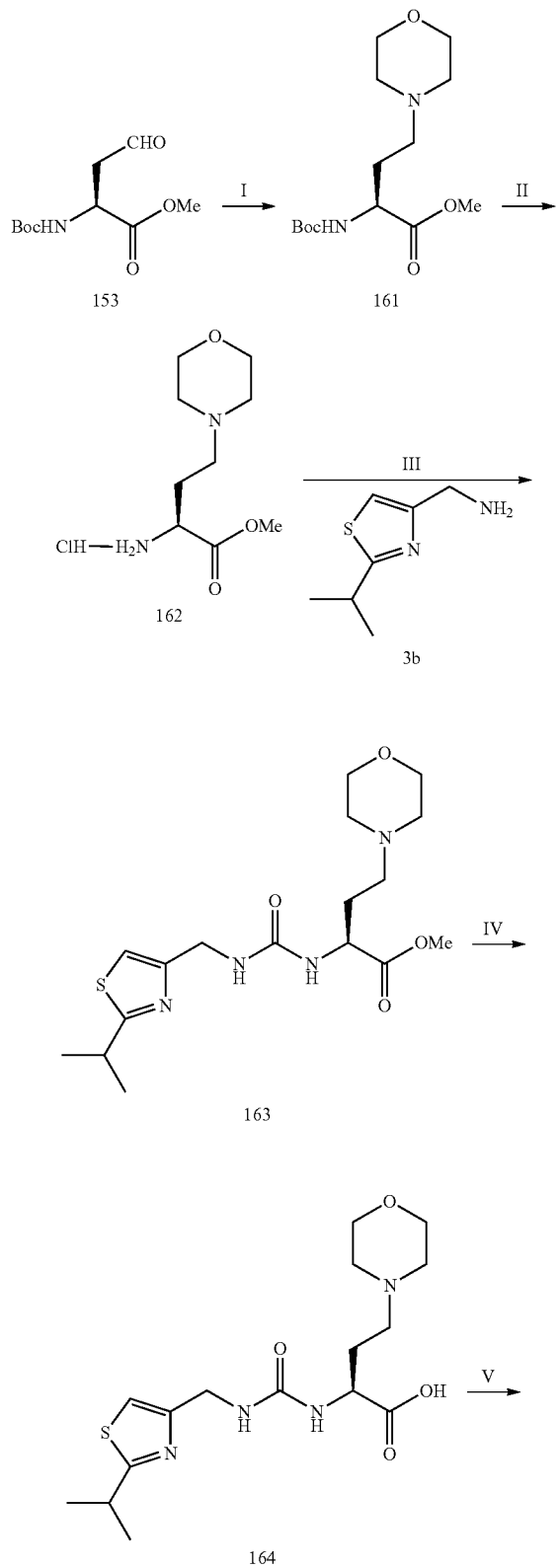

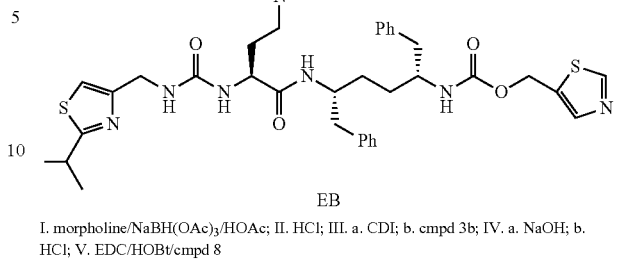

EB

I. morpholine/NaBH(OAc)₃/HOAc; II. HCl; III. a. CDI; b. cmpd 3b; IV. a. NaOH; b. HCl; V. EDC/HOBt/cmpd 8

Compound 161

Compound 161 (11 g) was prepared following the procedure used to prepare Compound 148a, except that Compounds 153 and morpholine were used instead of Compounds 60 and 1-acetylpiperazine. m/z: 303.0 (M+H)⁺.

Compound 162

Compound 162 (10.4 g) was prepared following the procedure used to prepare Compound 140a, except that Compound 161 was used instead of Compound 139a. m/z: 203.1 (M+H)⁺.

Example 3b

Compound 3b was synthesized following the procedure described in WO2008/010921 A2, and as described above in Scheme 10.

Example 163

Compound 163 (540 mg) was prepared following the procedure used to prepare Example DM(a), except that Compounds 162 and 36 were used instead of Compounds 140a and 9. m/z: 385.1 (M+H)⁺.

Example 164

Compound 164 (780 mg) was prepared following the procedure used to prepare Compound 144, except that Compound 163 was used instead of Compound 143. m/z: 371.0 (M+H)⁺.

Example EB

Example EB (210 mg) was prepared following the procedure used to prepare Compound 139a, except that Compound 164 was used instead of Compound 138a. m/z: 762.2 (M+H)⁺. ¹H NMR (DMSO-d₆) •9.06 (1H, s), 7.85 (1H, s), 7.7 (1H, br), 7.2-7.0 (12H, m), 6.55 (1H, br), 6.20 (1H, br), 5.18 (2H, s), 4.23 (2H, m), 4.15-3.8 (2H, m), 3.65 (1H, m), 3.55 (4H, m), 3.2 (1H, m), 2.7-2.4 (6H, m), 2.3-2.0 (6H, m), 1.5-1.2 (10H, m).

Preparation of Compound 166

Scheme 103

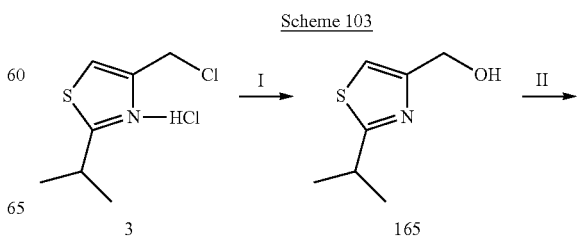

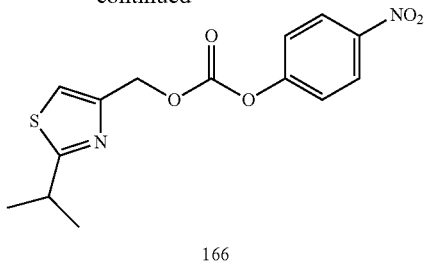

166

I. NaOH/H₂O; II. bis(4-nitrophenyl) carbonate/Et₃N

Compound 3

Compound 3 was synthesized following the procedure described in WO2008/010921 A2.

Compound 165

To a suspension of Compound 3 (2.65 g, 12.5 mmol) in water (10 mL) was added sodium hydroxide (1.5 g, 38 mmol). The mixture was heated at 90° C. for 12 hours and cooled to 25° C. The mixture was extracted with EtOAc. The organic layer was washed with brine and dried over Na₂SO₄. Purification by flash column chromatography (50% EtOAc in hexanes) gave Compound 165 (810 mg).

Compound 166

To a solution of Compound 165 (810 mg, 5.2 mmol) in DCM (12 mL) was added bis(4-nitrophenyl) carbonate (1.73 g, 5.7 mmol), followed by triethylamine (1.1 mL, 7.8 mmol). The mixture was stirred for 14 hours, and the solvents were removed. The residue was diluted with EtOAc, and washed twice with saturated sodium carbonate, followed by water, and then brine, and was dried over Na₂SO₄. Concentration and purification by flash column chromatography (20% EtOAc in hexanes) gave Compound 166 (1.4 g).

Preparation of Example EC

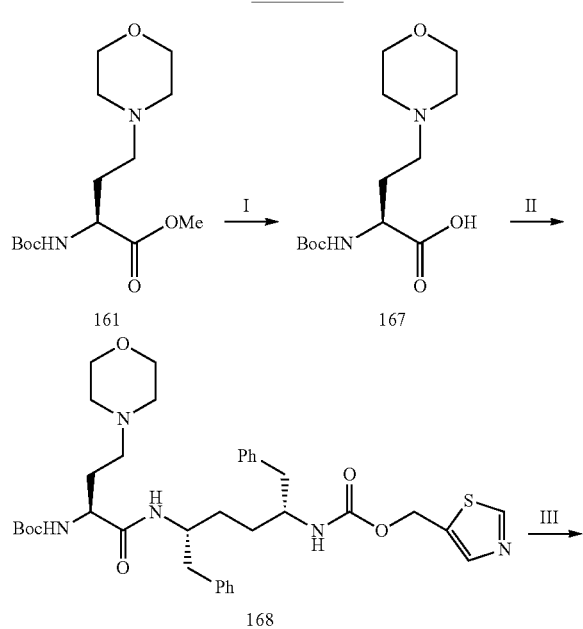

Scheme 104

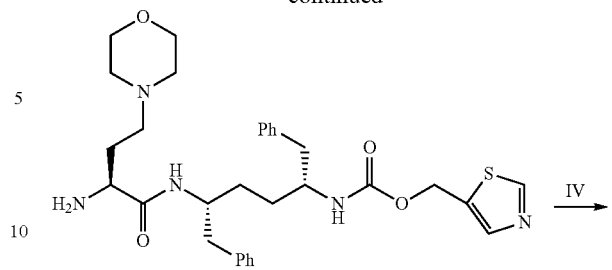

169

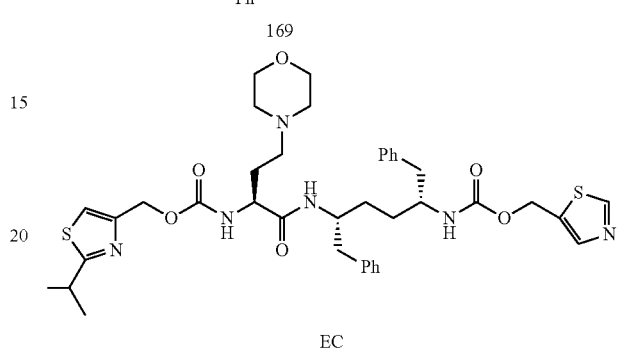

EC

I. a. NaOH; b. HCl; V. EDC/HOBt/cmpd 8; III. a. HCl; b. NaOH; IV. cmpd 166/iPr₂NEt Compound 167

Compound 167 was prepared following the procedure used to prepare Compound 144, except that Compound 161 was used instead of Compound 143.

Compound 168

Compound 168 (1.2 g) was prepared following the procedure used to prepare Compound 139a, except that Compound 167 was used instead of Compound 138a. m/z: 680.3 (M+H)⁺.

Compound 169

To a solution of Compound 168 (1.2 g, 1.8 mmol) in MeOH (10 mL) was added 4 N hydrochloric acid (4.4 mL, 17.6 mmol). The mixture was stirred for 6 hours, and the solvents were removed. The residue was basified with 2 N sodium hydroxide solution (pH=11), and extracted with EtOAc. The organic layer was washed with brine and dried over Na₂SO₄. Concentration gave Compound 169 (1.0 g)

Example EC

To a solution of Compound 169 (116 mg, 0.2 mmol) in CH₃CN (2 mL) was added Compound 166 (71 mg, 0.22 mmol), followed by triethylamine (71 •L, 0.4 mmol). The mixture was stirred for 48 hours, and was diluted with EtOAc. The organic layer was washed with saturated sodium carbonate solution, water, and brine, was dried over Na₂SO₄. Purification by flash column chromatography (0-15% iPrOH in DCM) gave compound 1073 (130 mg). m/z: 763.3 (M+H)⁺. ¹H NMR (CDCl₃) •8.75 (1H, s), 7.78 (1H, s), 7.67 (1H, br), 7.3-7.0 (11H, m), 6.22 (1H, m), 5.24 (2H, s), 5.16 (2H, s), 5.10 (1H, br), 4.28-4.10 (2H, m), 3.8 (1H, m), 3.6 (4H, m), 3.32 (1H, m), 2.9-2.6 (4H, m), 2.4-2.1 (6H, m), 1.8 (2H, m), 1.6 (2H, m), 1.4 (8H, m).

Preparation of Compound 173

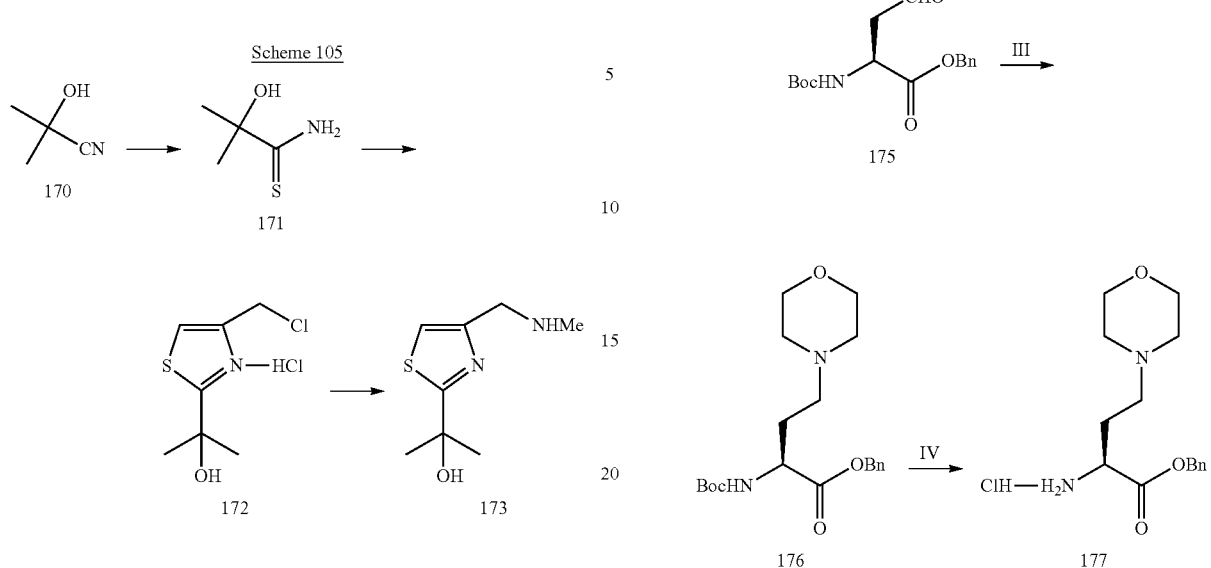

Compound 170

Compound 170 was obtained from Aldrich.

Compound 171

Hydrogen sulfide gas was passed through a solution of Compound 170 (1.8 mL, 20 mmol) in pyridine (100 mL) and triethylamine (4.4 mL) for 5 hours. The solution was purged with nitrogen for 10 minutes, and the solvents were removed. The residue was coevaporated three times with 10 mL of ethyl alcohol. Purification by flash column chromatography (10% iPrOH in DCM) gave Compound 171 (2.0 g).

Compound 172

To a solution of Compound 171 (2 g, 17 mmol) in acetone (30 mL) was added 1,3-dichloroacetone (2.1 g, 17 mmol), followed by MOO, (2.0 g, 17 mmol). The mixture was refluxed for 12 hours and cooled to 25° C. The mixture was filtered. Concentration gave Compound 172. m/z: 191.9 (M+H)$^+$.

Compound 173

To a solution of 40% methylamine in water (36 mL) was added a solution of Compound 172 (17 mmol) in water (10 mL). The mixture was stirred for 1 hour, and concentrated under reduced pressure. Purification by flash column chromatography (10% MeOH in DCM) gave Compound 173. m/z: 187.0 (M+H)$^+$.

Preparation of Compound 177

Scheme 106

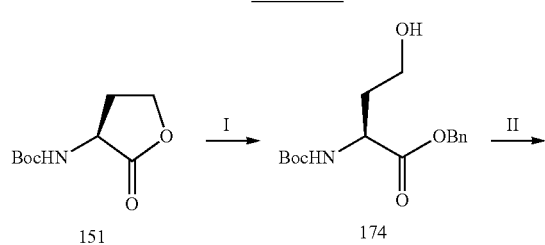

I. a. NaOH/EtOH/H$_2$O; b. BnBr/DMF; II. SO$_3$-pyridine; III. morpholine/NaBH(Oac)$_3$/HOAc; IV. HCl Compound 174

To a solution of Compound 151 (10.5 g, 50 mmol) in ethyl alcohol (160 mL) was added sodium hydroxide solution (2.1 g, 52.5 mmol, 30 mL). The mixture was stirred for 1 hour, and the solvent was removed under reduced pressure. The residue was coevaporated three times with 200 mL of ethyl alcohol. The white solid was dried at 60° C. for 2 hours under high vacuum. To this solid was added DMF (80 mL), followed by benzyl bromide (7.3 mL, 61 mmol). The mixture was stirred for 12 hours in darkness and diluted with EtOAc. The organic phase was washed five times with water followed once with brine, and was then dried over Na$_2$SO$_4$. Concentration gave Compound 174 (15 g).

Compound 175

Compound 175 was prepared following the procedure used to prepare Example DV, except that Compound 174 was used instead of Example DU(c).

Compound 176

Compound 176 was prepared following the procedure used to prepare Compound 148a, except that Compound 175 and morpholine were used instead of Compound 60 and 1-acetylpiperazine.

Compound 177

Compound 177 (3.4 g) was prepared following the procedure used to prepare example 140a, except that Compound 176 was used instead of Compound 139a. m/z: 279.1 (M+H)$^+$.

Preparation of Example ED

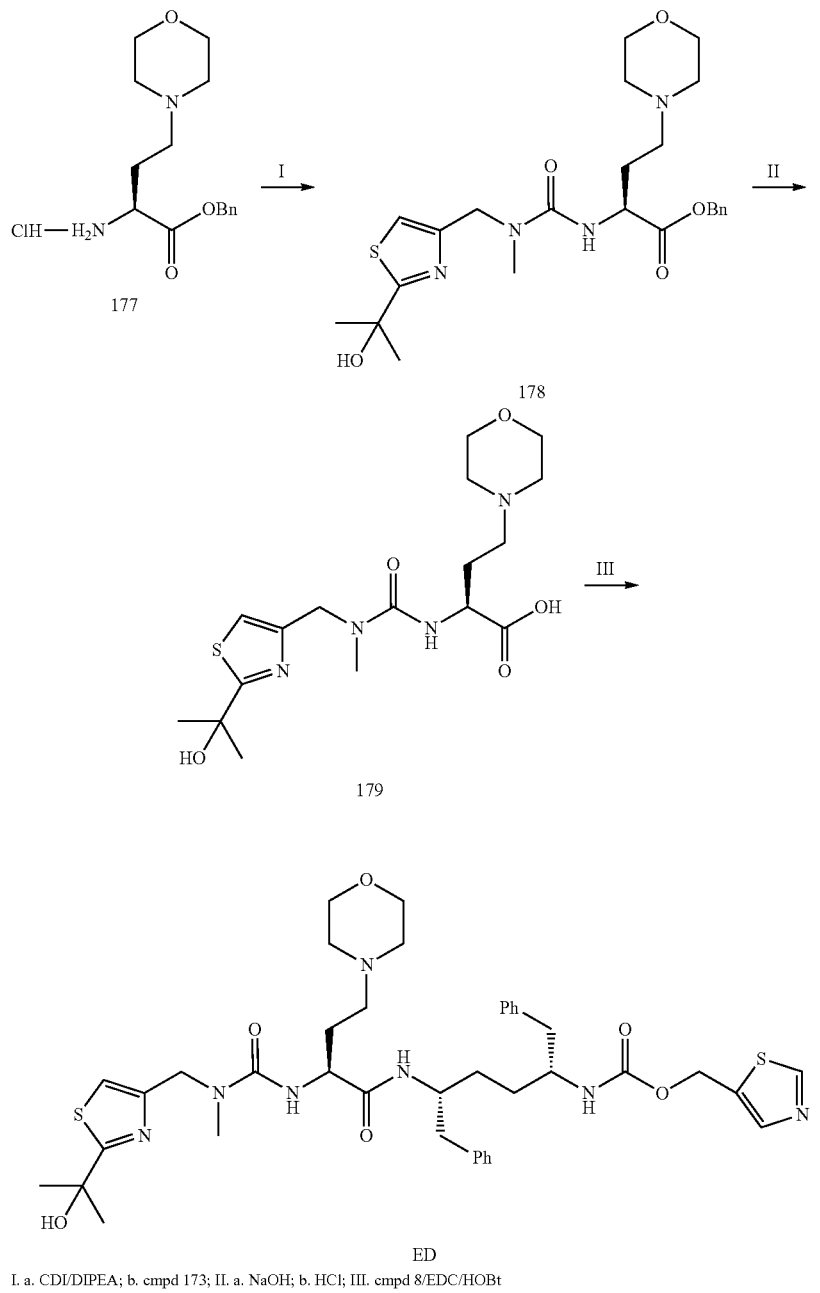

Scheme 107

I. a. CDI/DIPEA; b. cmpd 173; II. a. NaOH; b. HCl; III. cmpd 8/EDC/HOBt

Compound 178

Compound 178 (300 mg) was prepared following the procedure used to prepare Example DM(a), except that Compounds 173 and 177 were used instead of Compounds 140a and 9. m/z: 491.3 (M+H)$^+$.

Compound 179

Compound 179 was prepared following the procedure used to prepare Compound 149a, except that Compound 178 was used instead of Compound 148a.

Example ED

Example ED (370 mg) was prepared following the procedure used to prepare Compound 139a, except that Compound 179 was used instead of Compound 138a. m/z: 792.3 (M+H)$^+$. $^1$H NMR (CD$_3$OD) •8.98 (1H, s), 7.83 (1H, s), 7.20-7.08 (11H, m), 5.20 (2H, m), 4.55 (2H, m), 4.3-4.0 (4H, m), 3.75 (3H, m), 3.4 (2H, m), 3.2-3.0 (4H, m), 2.99 (3H, s), 2.70 (4H, m), 2.1-1.8 (2H, m), 1.7-1.4 (10H, m).

Preparation of Example EE

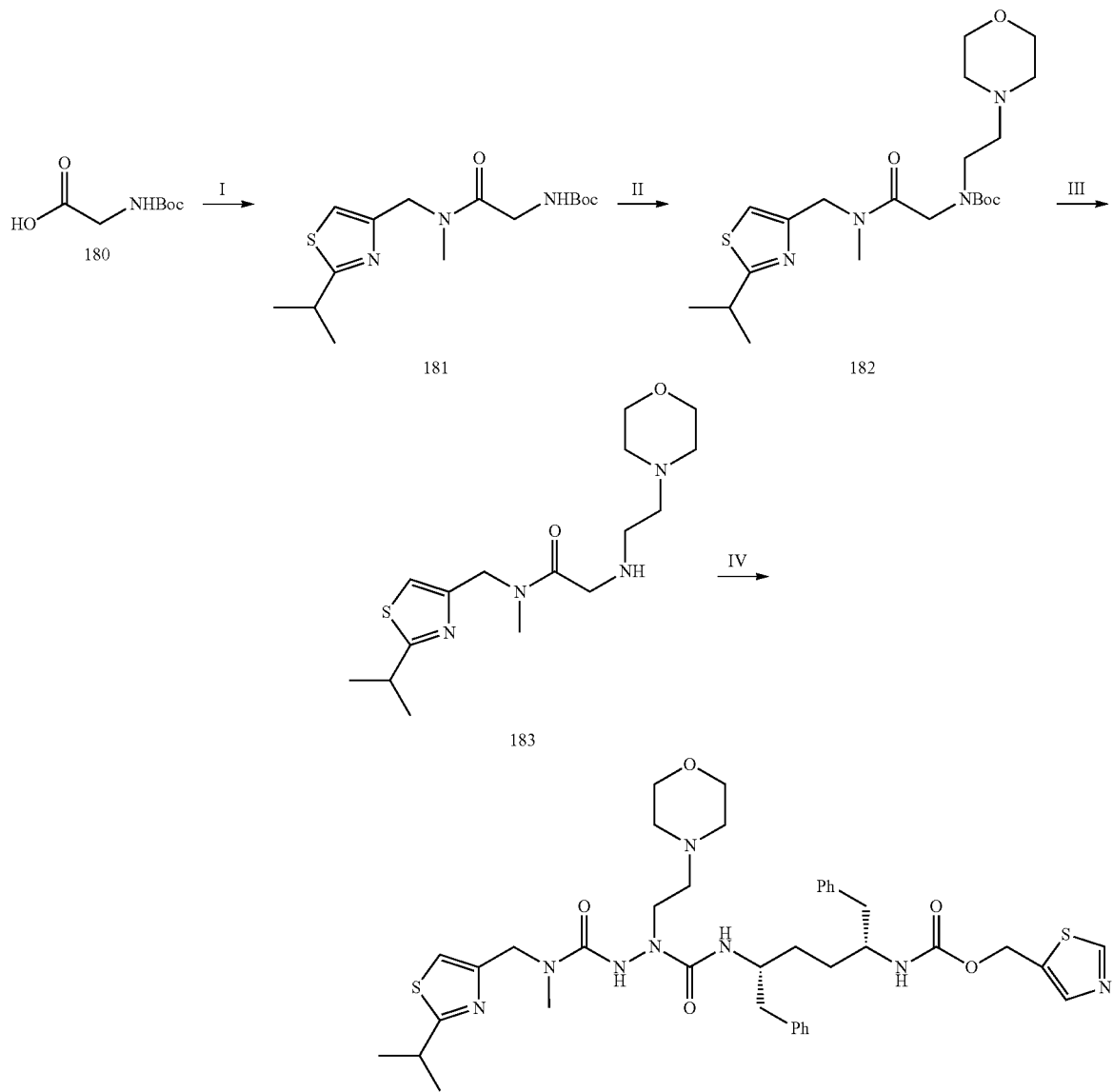

I. cmpd 9/EDC/HOBt; II. a. NaH/DMF; b. 2-morpholineethylbromide; III. a. TFA/DCM; b. NaOH; IV. a. triphosgene/DIPEA; b. cmpd 8/DIPEA Compound 180

Compound 180 was obtained from Aldrich.

Compound 181

Compound 181 (1.6 g) was prepared following the procedure used to prepare Compound 139a, except that Compounds 180 and 9 were used instead of Compounds 8 and 138a. m/z: 327.9 (M+H)$^+$.

Compound 182

To a suspension of sodium hydride (52 mg, 60%, 1.3 mmol) in DMF (4 mL) was added a solution of Compound 181 (327 mg, 1 mmol) in DMF (1 mL). The mixture was stirred for 90 minutes, and a solution of 2-morpholineethyl bromide (212 mg, 1.1 mmol) in DMF (1 mL) was added dropwise. The mixture was stirred for 12 hours, and quenched with water. The aqueous phase was extracted three times with EtOAc. The combined organic phases were washed five times with water and once with brine, and dried over Na$_2$SO$_4$. The dried organic phases were concentrated and purified by flash column chromatography (0-10% MeOH in DCM) to give Compound 182 (267 mg). m/z: 441.1 (M+H)$^+$.

Compound 183

Compound 183 (175 mg) was prepared following the procedure used to prepare Compound 169, except that Compound 182 was used instead of Compound 168. m/z: 341.2 (M+H)$^+$.

Example EE

To a solution of triphosgene (56 mg, 0.19 mmol) in DCM (1 mL) at 0° C. was added a solution of Compound 8 (210 mg, 0.51 mmol) and DIPEA (194 •l) in DCM (1.8 mL). The mixture was stirred for 30 minutes, and a solution of Compound 183 (175 mg, 0.51 mmol) and DIPEA (194 •l) in DCM (1 mL) was added. The mixture was warmed to 25° C. and stirred for 12 hours. The mixture was diluted with EtOAc, and washed twice with saturated sodium carbonate, once with water, and once with brine, and was dried over Na$_2$SO$_4$. The dried organic phases were concentrated and purified by flash column chromatography (15% iPrOH in DCM) gave Example EE (150 mg). m/z: 776.3 (M+H)$^+$. $^1$H NMR (CD$_3$OD) •8.97 (1H, s), 7.82 (1H, s), 7.25-7.05 (11H, m), 5.21 (2H, s), 4.6 (2H, m), 4.3-4.1 (2H, m), 3.95 (1H, m), 3.75 (1H, s), 3.47 (4H, m), 3.3 (5H, m), 3.06/2.94 (3H, s), 2.7 (4H, m), 2.30 (4H, m), 1.6-1.2 (10H, m).

Preparation of Examples EF-EH

Scheme 109

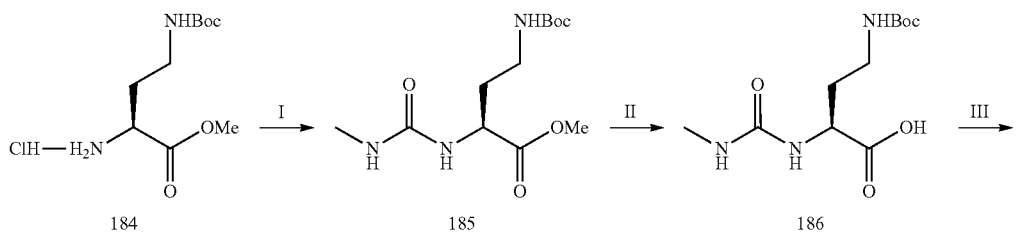

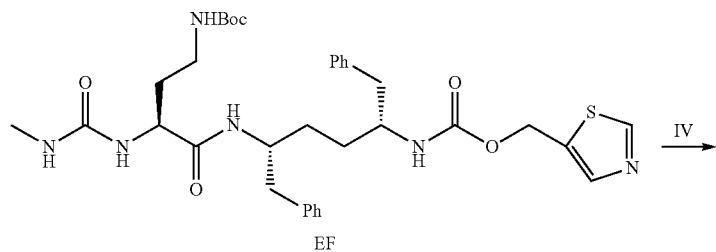

EF

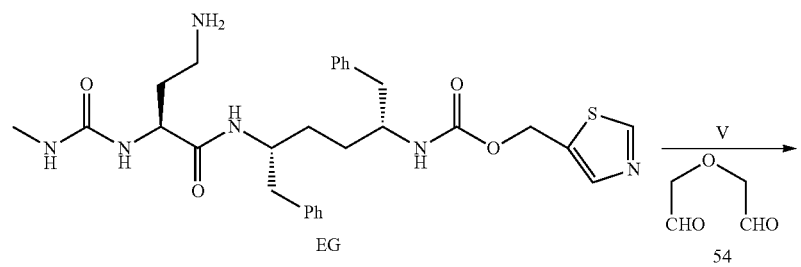

EG

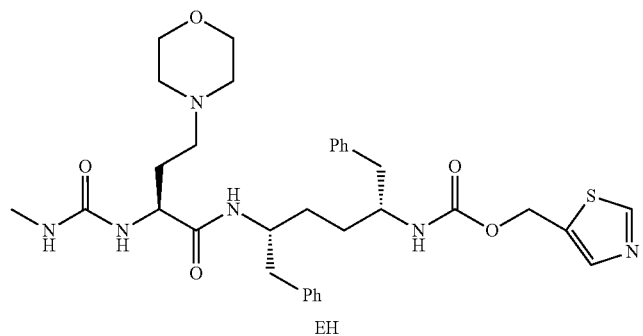

EH

I. a. CDI/DIPEA; b. MeNH$_2$; II. a. NaOH/THF/H$_2$O; b. HCl; III. cmpd 8/EDC/HOBt/DIPEA; IV. a. TFA/DCM; b. NaOH; V. NaBH(OAc)$_3$/HOAc Compound 184

Compound 184 was obtained from Aldrich.

Compound 185

Compound 185 (291 mg) was prepared following the procedure used to prepare Example DM(a), except that Compound 184 and methylamine were used instead of Compounds 140a and 9. m/z: 289.9 (M+H)$^+$.

Compound 186

Compound 186 was prepared following the procedure used to prepare Compound 144, except that Compound 185 was used instead of Compound 143. m/z: 275.9 (M+H)$^+$.

Example EF

Example EF (102 mg) was prepared following the procedure used to prepare Compound 139a, except that Compound 186 was used instead of Compound 138a. m/z: 667.1 (M+H)$^+$.

Example EG

Example EG (144 mg) was prepared following the procedure used to prepare Compound 169, except that Example EF was used instead of Compound 168 m/z: 567.2 (M+H)$^+$.

Compound 54

Compound 54 was synthesized following the procedure described in WO2008/010921 A2.

Example EH

Example EH (25 mg) was prepared following the procedure used to prepare Compound 148a, except that Example EG and Compound 54 were used instead of Compound 60 and 1-acetylpiperazine. m/z: 637.3 (M+H)$^+$. $^1$H NMR (CDCl$_3$) •9.00 (br s, 1H); 7.94 (br s, 1H); 7.72 (br s, 1H); 7.40-7.00 (m, 10H); 5.49 (m, 1H); 5.25 (s, 2H); 4.47 (m, 1H); 4.30 (m, 1H); 4.02 (br s, 1H); 3.65 (m, 2H); 3.41 (m, 2H); 2.76 (m, 9H); 2.25-1.70 (m, 4H); 1.70-1.40 (m, 6H).

Preparation of Example EI-EJ

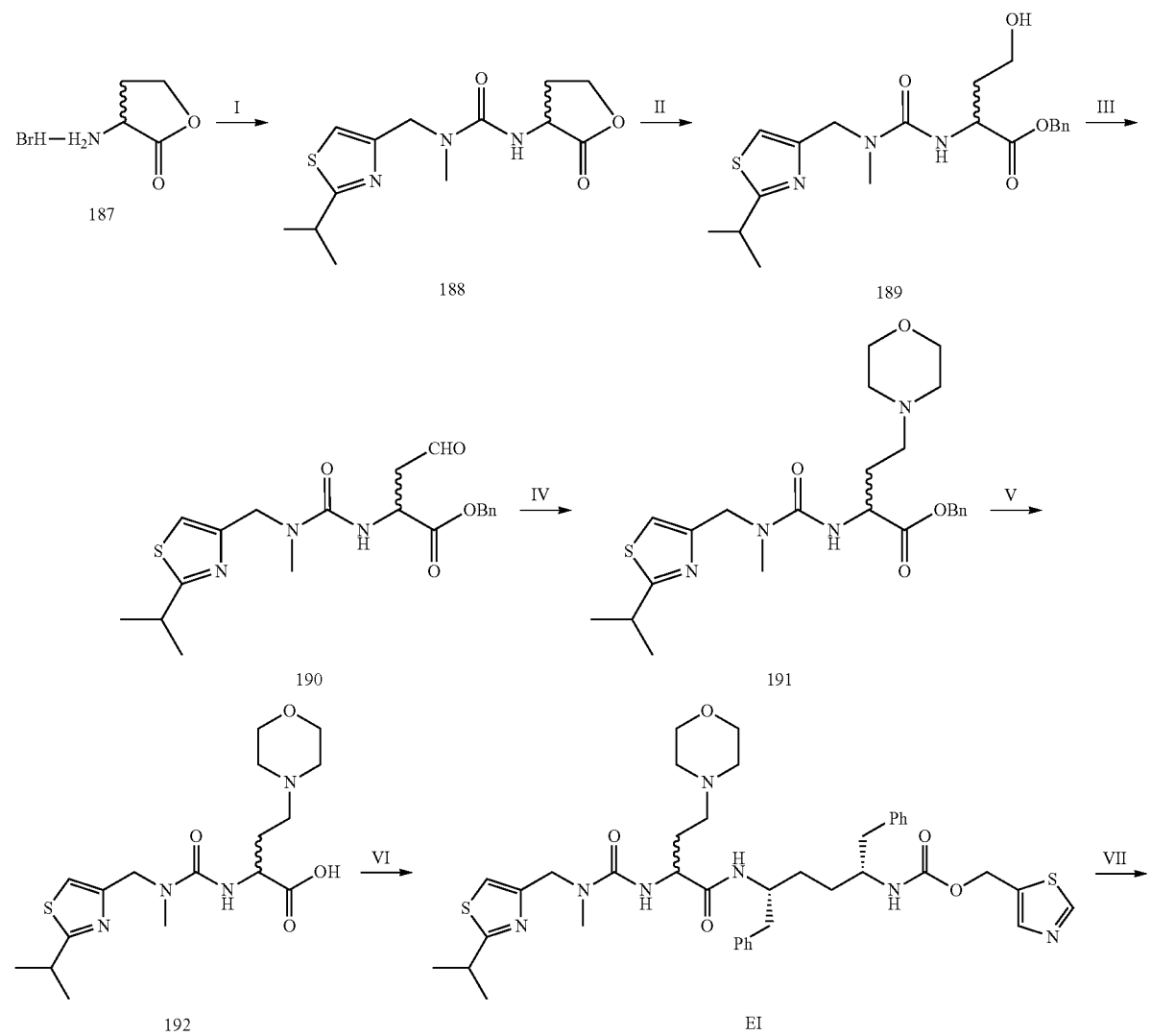

Scheme 110

-continued

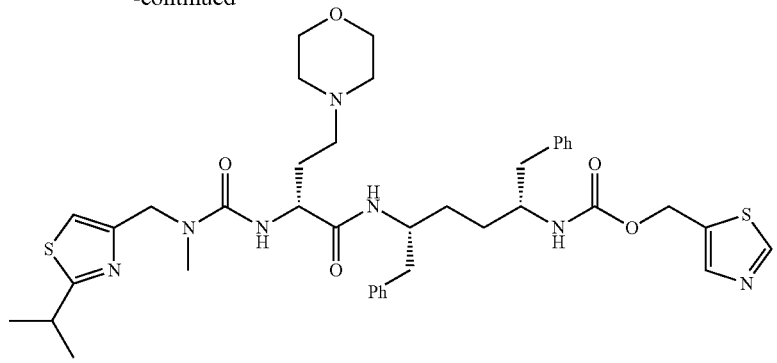

EJ

I. a. CDI/DIPEA; b. cmpd 9; II. a. NaOH/EtOH; b. BnBr/DMF; III. SO3-pyridine/Et3N; IV. morpholine/NaBH(OAc)3/AcOH/CH3CN; V. a. NaOH/EtOH/H2O; b. HCl; IV. cmpd 8/EDC/HOBt/DIPEA; VII. chiral column separation Compound 187

Compound 187 was obtained from Aldrich.

Compound 188

Compound 188 (897 mg) was prepared following the procedure used to prepare Example DM(a), except that Compound 187 was used instead of Compound 140a. m/z: 298.0 (M+H)$^+$.

Compound 189

Compound 189 (1.24 g) was prepared following the procedure used to prepare Compound 174, except that Compound 188 was used instead of Compound 151. m/z: 406.1 (M+H)$^+$.

Compound 190

Compound 190 (712 mg) was prepared following the procedure used to prepare Example DV, except that Compound 189 was used instead of Example DU(c). m/z: 40.4.0 (M+H)$^+$.

Compound 191

Compound 191 (384 mg) was prepared following the procedure used to prepare Compound 148a, except that Compound 190 and morpholine were used instead of Compound 60 and 1-acetylpiperazine. m/z: 475.1 (M+H)$^+$.

Compound 192

Compound 192 (900 mg) was prepared following the procedure used to prepare Compound 149a, except that Compound 191 was used instead of Compound 148a. m/z: 385.0 (M+H)$^+$.

Example EI

Example EI (151 mg) was prepared following the procedure used to prepare Compound 139a, except that Compound 192 was used instead of Compound 138a. m/z: 776.2 (M+H)$^+$. $^1$H NMR (CD$_3$OD) •8.97 (1H, s), 7.82 (1H, s), 7.3-7.1 (11H, m), 5.2 (2H, s), 4.5 (2H, m), 4.18 (2H, m), 3.78 (1H, m), 3.59 (4H, m), 3.23 (1H, m), 2.97 (3H, s), 2.8-2.5 (4H, m), 2.5-2.1 (6H, m), 1.9-1.6 (2H, m), 1.6-1.3 (10H, m).

Example EI

Example E1 was purified with HPLC (chiral cel OD-H column by Chiral Technologies Inc, heptane/iPrOH=70/30) to give Example EJ. m/z: 776.2 (M+H)$^+$. $^1$H NMR (CDCl$_3$) •8.98 (s, 1H); 7.90 (s, 1H); 7.75 (m, 1H); 7.40-7.00 (m, 15H), 6.55 (br s, 1H); 5.92 (br s, 1H); 7.75 (d, 1H); 5.28, 5.19 (d$_{AB}$, J=14 Hz, 2H); 4.70-4.37 (m, 3H); 3.99 (m, 5H); 3.76 (br s, 1H); 3.65-3.30 (m, 3H); 2.97 (m, 5H); 2.90-2.60 (m, 7H); 2.28 (br s, 2H); 1.91 (br s, 2H); 1.6-1.3 (m, 12H).

Preparation of Example EK

Scheme 111

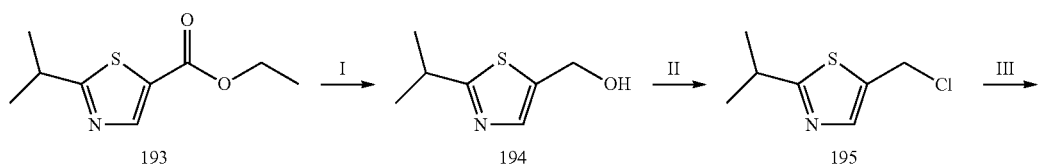

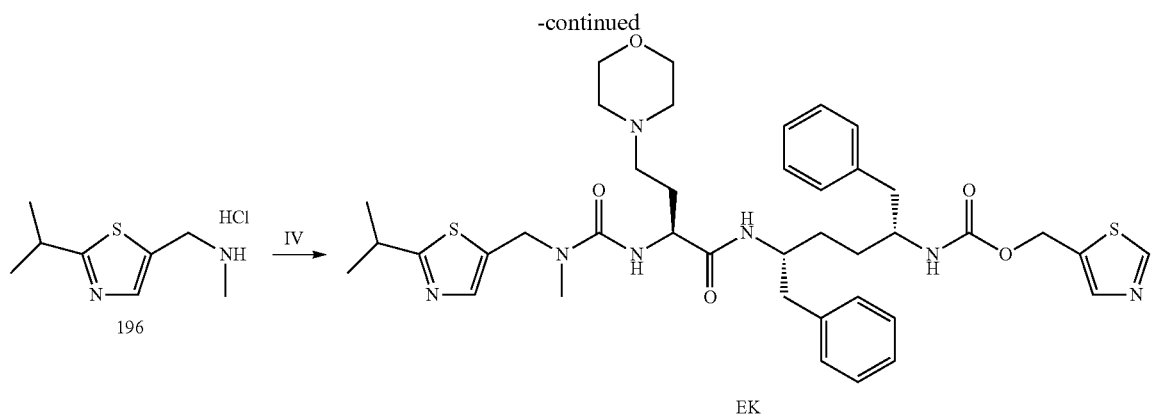

I. LiAlH4, THF; II. PCl5, toluene; III. MeNH2 in MeOH; IV. a. CDI/DIPEA; b. cmpd 169

Compound 193

Compound 193 was synthesized following the procedure from J. Med. Chem., 41(4), 1998, 602-617 (herein incorporated by reference in its entirety for all purposes).

Compound 194

Compound 193 (1.4 g, 7 mmol) was dissolved in anhydrous THF (7 mL) and added dropwise over 1 hour into a 1 M LiAlH$_4$ solution in THF stirring at 0° C. under nitrogen gas. The reaction mixture was then allowed to warm to room temperature and stirred for 1 hour, at which time HPLC showed that reaction was complete. The reaction mixture was cooled in an ice bath and methanol was slowly added. Aqueous potassium sodium tartarate solution was then added. The organic solution was extracted with ethyl acetate and then dried over anhydrous sodium sulfate and concentrated under reduced pressure to give Compound 194 (1 g, 91%), which was used in the next reaction without further purification.

Compound 195

Compound 194 (1 g, 6.37 mmol) was dissolved in anhydrous toluene (6 mL). To the resulting solution was added PCl$_5$ (1.3 g, 6.37 mmol). After the reaction mixture was stirred for 1 hour, the reaction was complete. Solid sodium bicarbonate was added to the reaction mixture, which was then diluted with ethyl acetate and washed with saturated aqueous sodium bicarbonate solution, followed by saturated aqueous sodium chloride solution. The organic layer was dried over anhydrous sodium sulfate and concentrated under reduced pressure to yield Compound 195 (0.91 g, 81%).

Compound 196

Compound 195 (0.91 g, 5.2 mmol) was dissolved in 2 M methylamine in methanol (15 mL). The reaction mixture was stirred for 15 hours, then concentrated under reduced pressure. The resulting oil was dissolved in dilute aqueous HCl solution to give a solution with a pH of 2. The solution was then washed with ethyl acetate. The aqueous layer was concentrated under reduced pressure. The residue was purified by preparative HPLC to give Compound 196 (0.6 g, 56%).

Example EK

Example EK (14 mg) was prepared following the procedure used to prepare Example DM(a), except that Compounds 169 and 196 were used instead of Compounds 140a and 9. $^1$H NMR (CD$_3$OD): •8.98 (s, 1H), 7.82 (s, 1H), 7.55 (s, 1H), 7.19 (m, 10H), 5.21 (m, 2H), 4.68 (m, 2H), 4.20 (m, 1H), 4.15 (m, 1H), 3.79 (m, 1H), 3.64 (m, 4H), 3.25 (m, 1H), 2.98 (s, 3H), 2.73 (m, 4H), 2.23-2.40 (m, 6H), 1.90-1.70 (m, 2H), 1.51 (m, 4H), 1.36 (d, J=6.9 Hz, 6H). Mass Spectrum (m/e): (M+H)$^+$ 776.3, (M−H)$^−$ 773.9.

Preparation of Example EI

Scheme 112

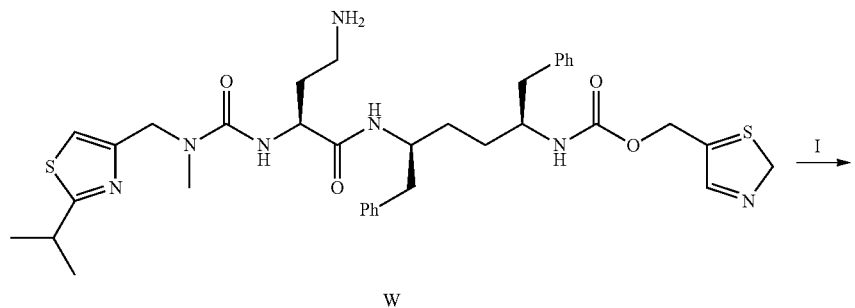

W

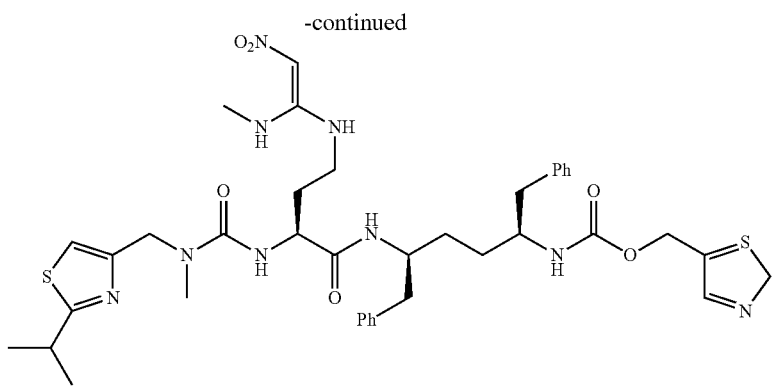

EL

I. a. 1,1-bis(methylthio)-2-nitroethylene/DMF; b. MeNH₂/MeOH

Example EL

Example W (71 mg, 0.1 mmol) and 1,1-bis(methylthio)-2-nitroethylene (17 mg, 0.1 mmol) was dissolved in anhydrous DMF (2 mL). The resulting mixture was stirred at room temperature for 90 minutes, followed by another 16 hours at 40° C. An additional 10% of 1,1-bis(methylthio)-2-nitroethylene was added and the mixture was stirred at 60° C. for 8 hours. A solution of 2 M methylamine in methanol (1.2 mL, 2.4 mmol) was added and the mixture was stirred for 3 hours at room temperature. The mixture was diluted with ethyl acetate and washed with saturated aqueous sodium bicarbonate solution and saturated aqueous sodium chloride solution. The organic layer was dried over anhydrous sodium sulfate and concentrated under reduced pressure. The crude product obtained was purified by flash silica gel column chromatography (3-10% MeOH in DCM). Final purification with $C_{18}$ reverse phase prep HPLC gave Example EL (55 mg, 68%). $^1$H NMR (CD₃OD): •8.97 (s, 1H), 7.81 (s, 1H), 7.16 (m, 10H), 6.66 (s, 1H), 5.20 (s, 2H), 4.54 (m, 2H), 4.17 (m, 2H), 3.80 (m, 1H), 3.35 (s, 3H), 3.23 (m, 1H), 3.00-2.80 (m, 9H), 2.63 (m, 3H), 1.60-1.43 (m, 6H), 1.33 (d, J=7.2 Hz, 6H). Mass Spectrum (m/e): (M+H)⁺ 806.3, (M−H)⁻ 804.1.

Preparation of Examples EM-EN

Scheme 113

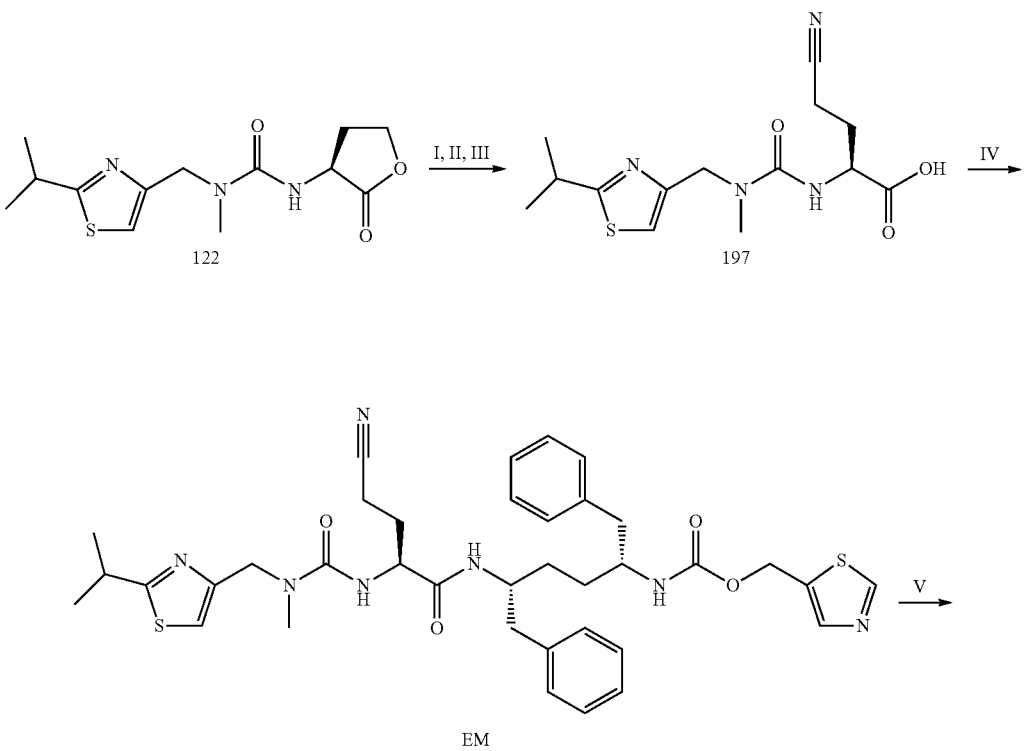

EM

-continued

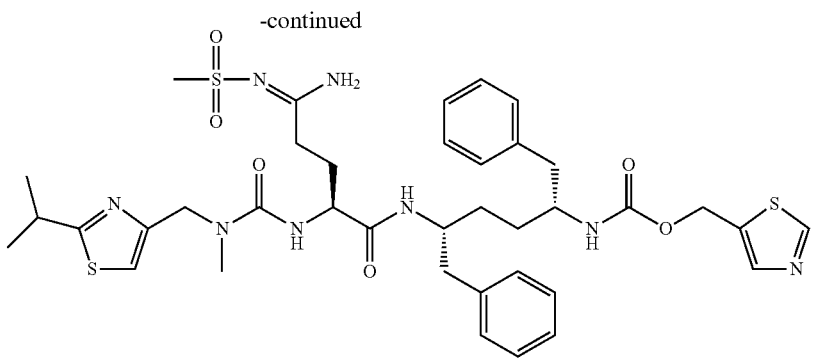

EN

I. TMS-I/EtOH; II. KCN/DMSO; III. NaOH/H₂O/EtOH; IV. EDC/HOBt/TEA/THF; V. a. HCl/MeOH; b. H₂NSO₂NH₂

Compound 197

Compound 122 (460 mg, 1.5 mmol) was dissolved in anhydrous DCM. To the resulting solution was added EtOH (540 •L, 9.28 mmol), followed by TMS-I (663 •L, 4.6 mmol) dropwise. The mixture was stirred for 2 hours at room temperature. Additional TMS-I (200 •L) was added and the mixture was stirred for 1 hour. The reaction mixture was concentrated under reduced pressure. The residue was dissolved in EtOH and concentrated under reduced pressure. The residue was again dissolved in another portion of EtOH. The resulting oil was dissolved in anhydrous DMSO (5 mL). KCN was added, and the resulting mixture was stirred at room temperature for 16 hours. The mixture was diluted with ethyl acetate and washed sequentially with saturated aqueous sodium bicarbonate solution and saturated aqueous sodium chloride solution. The organic layer was dried over anhydrous sodium sulfate and concentrated under reduced pressure. The residue was purified with flash silica gel column chromatography (EtOAc). The product (260 mg, 0.74 mmol) was dissolved in EtOH and stirred in an ice bath. NaOH (33 mg, 0.82 mmol) was dissolved in water and added to the EtOH solution in portions. The reaction mixture was acidified with 10% citric acid to a pH of 2-3 and extracted with EtOAc. The organic layer was dried over anhydrous sodium sulfate and concentrated under reduced pressure. The resulting Compound 197 (228 mg, 47%) was used in the next step without further purification.

Example EM

Compound 197 (228 mg, 0.7 mmol) was dissolved in anhydrous THF (5 mL). EDC (202 mg, 1.05 mmol) and HOBt (162 mg, 1.05 mmol) were added to the solution and the resulting mixture was stirred for 30 minutes. Compound 8 (214 mg, 0.7 mmol) was added to the reaction mixture along with anhydrous DMF (3 mL) and TEA (294 •L, 2.11 mmol). The mixture was stirred for 90 minutes, then diluted with EtOAc and washed sequentially with saturated aqueous sodium bicarbonate solution and saturated aqueous sodium chloride solution. The organic layer was dried over anhydrous sodium sulfate and concentrated under reduced pressure. The residue was purified with flash silica gel column chromatography (0-10% MeOH in DCM). Final purification with $C_{16}$-reverse phase prep HPLC gave Example EM (291 mg, 58%). ¹H NMR (CD₃OD): •8.97 (s, 1H), 7.83 (s, 1H), 7.17 (m, 10H), 5.22 (s, 2H), 4.53 (s, 2H), 4.23 (m, 1H), 4.06 (m, 1H), 3.77 (m, 1H), 3.27 (m, 1H), 2.96 (s, 3H), 2.72 (m, 4H), 2.37 (m, 2H), 1.88 (m, 2H), 1.52 (m, 4H), 1.38 (d, J=7.2 Hz, 6H). Mass Spectrum (m/e): (M+H)⁺ 716.2, (M–H)⁻ 713.9.

Example EN

Example EM (120 mg, 0.168 mmol) was dissolved in anhydrous MeOH (5 mL) and concentrated under reduced pressure. This process was repeated twice with fresh portions of MeOH. The residue was dissolved in MeOH (5 mL) and stirred in an ice bath under nitrogen gas. HCl gas was bubbled into the MeOH solution for 5-10 minutes to saturate the solution. The reaction vessel was sealed and the reaction mixture was stirred at 0° C. for 8 hours. The reaction mixture was then concentrated under reduced pressure at room temperature. The residue was dissolved in EtOAc and washed twice with 10% aqueous sodium carbonate solution, followed by saturated aqueous sodium chloride solution. The organic layer was dried over anhydrous sodium sulfate and concentrated under reduced pressure. The residue was dissolved in 2-methoxy ethanol (5 mL). Sulfamide (161 mg, 1.68 mmol) was added to the solution, which was stirred at 80° C. for 8 hours and then at room temperature for 16 hours. The reaction mixture was concentrated under reduced pressure. The residue was dissolved in EtOAc and washed with saturated aqueous sodium bicarbonate solution, followed by saturated aqueous sodium chloride solution. The organic layer was dried over anhydrous sodium sulfate and concentrated under reduced pressure. The crude material was purified with flash silica gel column chromatography (0-10% MeOH in DCM). Final purification with $C_{18}$ reverse phase prep HPLC gave Example EN (16 mg, 12%). ¹H NMR (CD₃OD): •8.98 (s, 1H), 7.83 (s, 1H), 7.67 (m, 1H), 7.16 (m, 10H), 6.82 (m, 1H), 5.21 (s, 2H), 4.53 (m, 2H), 4.15 (m, 2H), 3.77 (m, 1H), 3.28 (m, 1H), 2.96 (s, 3H), 2.68 (m, 4H), 2.21 (m, 2H), 1.88 (m, 2H), 1.45 (m, 4H), 1.35 (d, J=7.2 Hz, 6H). Mass Spectrum (m/e): (M+H)⁺ 812.1, (M–H)⁻ 810.0.

Preparation of Example EO

Scheme 114

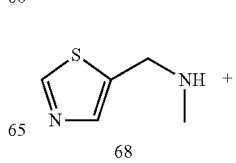

68

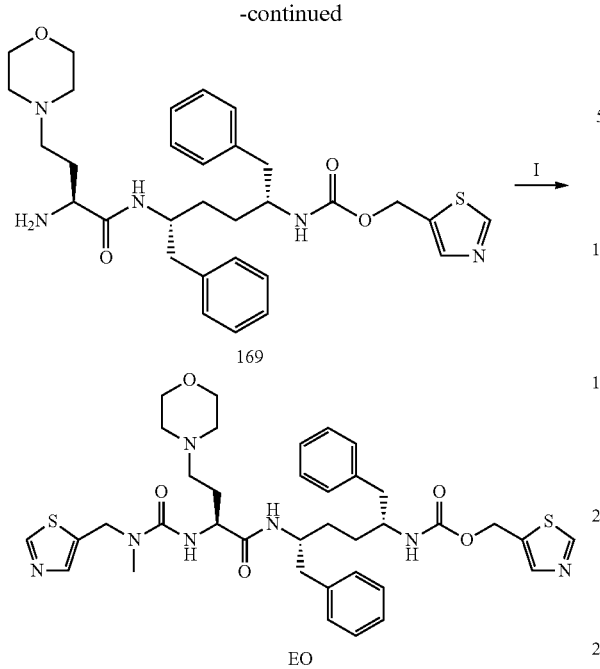

I. a. cmpd 169/CDI/DIPEA; b. cmpd 68

Compound 68

Compound 68 was synthesized following the procedure described in WO2008/010921 A2.

Example EO

Example EO (39 mg) was prepared following the procedure used to prepare Example DM(a), except that Compounds 68 and 169 were used instead of Compounds 140a and 9. $^1$H NMR (CD$_3$OD): •8.98 (s, 1H), 8.93 (s, 1H), 7.82 (s, 2H), 7.19 (m, 10H), 5.21 (s, 2H), 4.60 (m, 2H), 4.20 (m, 1H), 4.10 (m, 1H), 3.77 (m, 1H), 3.64 (m, 4H), 2.93 (s, 3H), 2.74 (m, 4H), 2.38-2.28 (m, 6H), 1.84-1.70 (m, 2H), 1.50 (m, 4H). Mass Spectrum (m/e): (M+H)$^+$ 734.3, (M−H)$^−$ 731.9.

Preparation of Example EP-EO

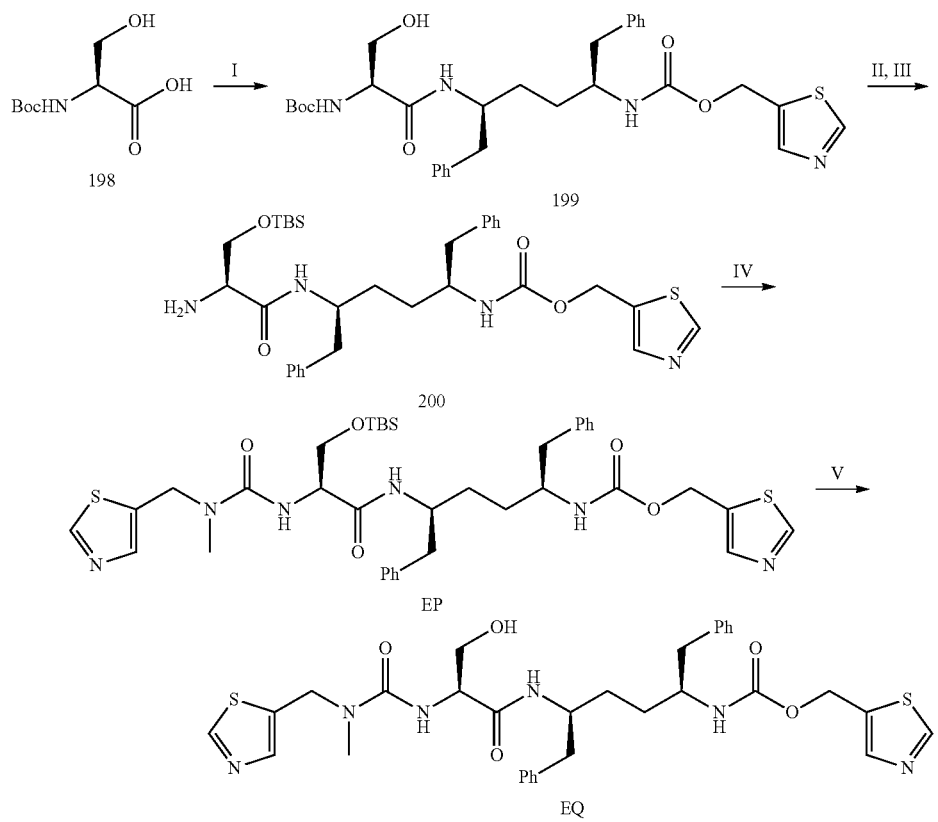

I. cmpd 46/EDC/HOBt/DIPEA; II. HCl/dioxane; III. TBSCl/pyridine; IV. a. CDI/DIPEA; b. cmpd 68; V. HCl/dioxane Compound 198

Compound 198 was obtained from Aldrich.

Compound 199

Compound 198 (205 mg, 1 mmol) was mixed with Compound 46 (446 mg, 1 mmol) and HOBt (230 mg, 1.5 mmol) in anhydrous DMF (5 mL). EDC (230 mg, 1.2 mmol) was then added. The resulting mixture was stirred for 30 minutes. DIPEA (348 mL, 2 mmol) was added. The mixture was stirred for 2 hours, then diluted with EtOAc, washed sequentially with saturated aqueous sodium bicarbonate solution and saturated aqueous sodium chloride solution. The organic layer was dried over anhydrous sodium sulfate and concentrated under reduced pressure. The crude material was purified with flash silica gel column chromatography (0-100% EtOAc in DCM) to give Compound 199 (345 mg, 58%).

Compound 200

Compound 199 (345 mg, 0.58 mmol) was dissolved in a small amount of MeOH. A solution of 4 N HCl in dioxane (5 mL) was added. The resulting mixture was stirred for 1 hour and concentrated under reduced pressure. The residue was dissolved in EtOAc and washed sequentially with saturated aqueous sodium bicarbonate solution and saturated aqueous sodium chloride solution. The organic layer was dried over anhydrous sodium sulfate and concentrated under reduced pressure. The residue was dissolved in anhydrous DCM (10 mL). Pyridine (163 •L, 2 mmol) and t-butyldimethylsilyl chloride (166 mg, 1.1 mmol) were added. The resulting mixture was stirred for 15 hours. More pyridine (163 •L) and TBS-Cl (60 mg) were added. The resulting mixture was stirred for another 24 hours. The mixture was concentrated under reduced pressure. The residue was dissolved in EtOAc and washed sequentially with saturated aqueous sodium bicarbonate solution and saturated aqueous sodium chloride solution. The organic layer was dried over anhydrous sodium sulfate and concentrated under reduced pressure. The crude material was purified by flash silica gel column chromatography (0-5% MeOH in DCM) to give Compound 200 (248 mg, 69%).

Example EP

Example EP was prepared following the procedure used to prepare Example DM(a), except that Compounds 200 and 68 were used instead of Compounds 140a and 9.

Example EO

To Example EP was added 4 N HCl in dioxane (4 mL). The mixture was stirred for 1 hour and the solvent was evaporated. The residue was diluted with EtOAc, and washed sequentially with saturated aqueous sodium carbonate, water, and brine. The organic layer was dried over $Na_2SO_4$, then concentrated. The residue was purified by flash column chromatography (10% iPrOH in DCM) to give Example EQ (35 mg). $^1$H NMR ($CD_3OD$): δ 8.97 (s, 1H), 8.89 (s, 1H), 7.81 (s, 2H), 7.70 (m, 1H), 7.19 (m, 10H), 6.92 (m, 1H), 5.20 (s, 2H), 4.73 (m, 2H), 4.22 (m, 1H), 4.13 (m, 1H), 3.78 (m, 1H), 3.56 (d, J=5.4 Hz, 2H), 3.31 (m, 1H), 2.94 (s, 3H), 2.67 (m, 4H), 1.45 (m, 4H). Mass Spectrum (m/e): $(M+H)^+$ 651.2, $(M-H)^-$ 648.8.

$IC_{50}$ Determinations for Human Liver Cytochrome P450

Materials and General Methods

Pooled (n≥15 donors) human hepatic microsomal fraction was obtained from BD-Gentest (Woburn, Mass.) who also supplied hydroxy-terfenadine, 4'-hydroxydiclofenac and NADPH regenerating system. Ritonavir was prepared from commercial Norvir® oral solution (Abbott Laboratories, Abbott Park, Ill.). Other reagents were from. Sigma-Aldrich (St. Louis, Mo.) and included terfenadine, fexofenadine, BRL 15572, diclofenac and mefenamic acid.

Incubations were performed in duplicate in 50 mM potassium phosphate buffer, pH 7.4 with NADPH regenerating system used as described by the manufacturer. The final microsomal protein concentrations had previously been determined to be within the linear range for activity and resulted in less than 20% consumption of substrate over the course of the incubation. The final substrate concentrations used were equal to the apparent Km values for the activities determined under the same conditions. Inhibitors were dissolved in DMSO, and the final concentration of DMSO, from both substrate and inhibitor vehicles, was 1% (v/v). Incubations were performed at 37° C. with shaking and were initiated by addition of substrate. Aliquots were then removed at 0, 7 and 15 minutes. Samples were quenched by treatment with an acetonitrile, formic acid, water (94.8%/0.2%/5%, v/v/v) mixture containing internal standard. Precipitated protein was removed by centrifugation at 3000 rpm for 10 min and aliquots of the supernatant were then subjected to LC-MS analysis.

The LC-MS system consisted of a Waters Acquity HPLC, with a binary solvent manager and a refrigerated (8° C.) sample organizer and sample manager, interfaced to a Micromass Quattro Premier tandem mass spectrometer operating in electrospray ionization mode. The column was a Waters Acquity HPLC BEH $C_{18}$ 2.1×50 mm, 1.7 µm pore size. Mobile phases consisted of mixtures of acetonitrile, formic acid and water, the composition for mobile phase A being 1%/0.2%/98.8% (v/v/v) and that for mobile phase B being 94.8%/0.2%/5% (v/v/v). The injection volumes were 5 µL and the flow rate was 0.8 mL/min. Concentrations of metabolites were determined by reference to standard curves generated with authentic analytes under the same conditions as the incubations.

$IC_{50}$ values (the concentration of inhibitor reducing CYP3A activity by 50%) were calculated by non-linear regression using GraphPad Prism 4.0 software and a sigmoidal model.

CYP3A Inhibition Assay

The potencies of the compounds as inhibitors of human hepatic cytochromes P450 of the CYP3A subfamily (particularly CYP3A4) were assessed using terfenadine oxidase, a well-characterized CYP3A-selective activity described in Ling, K.-H. J., et al *Drug Metab. Dispos.* 23, 631-636, (1995) and Jurima-Romet, et al *Drug Metab. Dispos.* 22, 849-857, (1994). The final concentrations of microsomal protein and terfenadine substrate were 0.25 mg/mL and 3 µM, respectively. Metabolic reactions were terminated by treatment with seven volumes of quench solution containing 0.1 µM BRL 15572 as internal standard. A further 8 volumes of water were added before centrifugation and aliquots of the supernatant were removed for analysis.

For LC-MS analysis chromatographic elution was achieved by a series of linear gradients starting at 20% B and holding for 0.1 minutes, then increasing to 80% B over 1.5 minutes, holding for 0.4 minutes and then returning to the starting conditions for 0.05 min. The system was allowed to re-equilibrate for at least 0.25 minutes prior to the next injection. The mass spectrometer was operated in positive ion mode and the following precursor ($[M+H]^+$)/product ion pairs were monitored and quantified using MassLynx 4.0 (SP4, 525) software: hydroxy-terfenadine 488.7/452.4, fexofenadine 502.7/466.4 and BRL 15572 407.5/209.1. Terfenadine oxidase activity was determined from the sum of hydroxy-terfenadine and carboxy-terfenadine (fexofenadine) metabolites.

CYP2C9 Inhibition Assay

The potencies of the compounds as inhibitors of human hepatic CYP2C9 were assessed using diclofenac 4'-hydroxylase, an activity specific for this enzyme, as described in Leeman, T., et al *Life Sci.* 52, 29-34, (1992). The final concentrations of microsomal protein and diclofenac substrate were 0.08 mg/mL and 4 µM, respectively. Metabolic reactions were terminated by treatment with three volumes of quench solution containing 1 µM mefenamic acid as internal standard. After centrifugation a further 4 volumes of water were added. Aliquots of the supernatant were then subjected to LC-MS analysis.

For LC-MS analysis chromatographic elution was achieved by a series of linear gradients starting at 20% B and holding for 0.3 minutes, then increasing to 99% B over 1.2 minutes, holding for 0.5 minutes and then returning to the starting conditions for 0.25 min. The system was allowed to re-equilibrate for at least 0.25 minutes prior to the next injection. The mass spectrometer was operated in negative ion mode and the following precursor ([M−H]$^-$)/product ion pairs were monitored and quantified: 4'-hydroxy-diclofenac 312.4/294.2 and mefenamic acid 242.4/224.2.

Biological Assays Used for the Characterization of HIV Protease Inhibitors

HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, *Int. J. Peptide Protein Res.* 36, 544 (1990) (herein incorporated by reference in its entirety for all purposes).

The assay employed (2-aminobenzoyl)Thr-Ile-Nle-(p-nitro)Phe-Gln-Arg as the substrate and recombinant HIV-1 protease expressed in *E. coli* as the enzyme. Both of the reagents were supplied by Bachem California, Inc. (Torrance, Calif.; Cat. no. H-2992). The buffer for this reaction was 100 mM ammonium acetate, pH 5.3, 1 M sodium chloride, 1 mM ethylendiaminetetraacetic acid, 1 mM dithiothreitol, and 10% dimethylsulfoxide.

To determine the inhibition constant $K_i$, a series of solutions were prepared containing identical amount of the enzyme (1 to 2.5 nM) and the inhibitor to be tested at different concentrations in the reaction buffer. The solutions were subsequently transferred into a white 96-well plate (190 µl each) and preincubated for 15 min at 37° C. The substrate was solublized in 100% dimethylsulfoxide at a concentration of 800 µM and 10 µl of 800 µM substrate was added into each well to reach a final substrate concentration of 40 µM. The real-time reaction kinetics was measured at 37° C. using a Gemini 96-well plate fluorimeter (Molecular Devices, Sunnyvale, Calif.) at λ(Ex)=330 nm and λ(Em)=420 nm. Initial velocities of the reactions with different inhibitor concentrations were determined and the $K_i$ value (in picomolar concentration units) was calculated by using EnzFitter program (Biosoft, Cambridge, U.K.) according to an algorithm for tight-binding competitive inhibition described by Ermolieff J., Lin X., and Tang J., *Biochemistry* 36, 12364 (1997).

HIV-1 Protease Enzyme Assay (IC50)

As for the $K_i$ assay, above, the 1050 assay is based on the fluorimetric detection of synthetic hexapeptide substrate cleavage by HIV-1 protease in a defined reaction buffer as initially described by M. V. Toth and G. R. Marshall, *Int. J. Peptide Protein Res.* 36, 544 (1990).

The assay employed (2-aminobenzoyl)Thr-Ile-Nle-(p-nitro)Phe-Gln-Arg as the substrate and recombinant HIV-1 protease expressed in *E. coli* as the enzyme. Both of the reagents were supplied by Bachem California, Inc. (Torrance, Calif.; Cat. nos. H-2992 and H-9040, respectively). The buffer for this reaction was 100 mM ammonium acetate, pH 5.5, 1 M sodium chloride, 1 mM ethylendiaminetetraacetic acid, and 1 mM dithiothreitol, and 10% dimethylsulfoxide.

To determine the IC50 value, 170 µL of reaction buffer was transferred into the wells of a white 96-well microtiter plate. A series of 3-fold dilutions in DMSO of the inhibitor to be tested was prepared, and 10 µL of the resulting dilutions was transferred into the wells of the microtiter plate. 10 µL of a 20-50 nM enzyme stock solution in reaction buffer was added to each well of the 96-well plate to provide a final enzyme concentration of 1-2.5 nM. The plates were then preincubated for 10 minutes at 37° C. The substrate was solublized in 100% dimethylsulfoxide at a concentration of 400 and 10 µl of the 400 µM substrate was added into each well to reach a final substrate concentration of 20 µM. The real-time reaction kinetics were measured using a Gemini 96-well plate fluorimeter (Molecular Devices, Sunnyvale, Calif.) at λ(Ex)=330 nm and λ(Em)=420 nm. Initial velocities of the reactions with different inhibitor concentrations were determined and the 1050 value (in nanomolar concentration units) was calculated by using GraphPad Prism™ software to fit nonlinear regression curves.

Anti-HIV-1 Cell Culture Assay (EC50)

The assay is based on quantification of the HIV-1-associated cytopathic effect by a calorimetric detection of the viability of virus-infected cells in the presence or absence of tested inhibitors. HIV-1-induced cell death was determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R, *J. Natl. Cancer Inst.* 81, 577 (1989) (herein incorporated by reference in its entirety for all purposes).

MT2 cells (NIH AIDS reagent program, Cat #237) maintained in RPMI-1640 medium supplemented with 5% fetal bovine serum and antibiotics were infected with the wild-type HIV-1 strain IIIB (Advanced Biotechnologies, Columbia, Md.) for 3 hours at 37° C. using the virus inoculum corresponding to a multiplicity of infection equal to 0.01. The infected cells in culture media were distributed into a 96-well plate (20,000 cells in 100 µl/well), and incubated in the presence of a set of solutions containing 5-fold serial dilutions of the tested inhibitor (100 µl/well) for 5 days at 37° C. Samples with untreated infected and untreated mock-infected control cells were also distributed to the 96-well plate and incubated under the same conditions.

To determine the antiviral activity of the tested inhibitors, a substrate XTT solution (6 mL per assay plate) at a concentration of 2 mg/mL in a phosphate-buffered saline pH 7.4 was heated in water-bath for 5 min at 55° C. before 50 µl of N-methylphenazonium methasulfate (5 µg/mL) was added per 6 mL of XTT solution. After removing 100 µl media from each well on the assay plate, 100 µl of the XTT substrate solution was added to each well. The cells and the XTT solution were incubated at 37° C. for 45 to 60 min in a $CO_2$ incubator. To inactivate the virus, 20 µl of 2% Triton X-100 was added to each well. Viability, as determined by the amount of XTT metabolites produced, was quantified spectrophotometrically by the absorbance at 450 nm (with subtraction of the background absorbance at 650 nm). Data from the assay was expressed as the percentage absorbance relative to untreated control and the fifty percent effective concentration ($EC_{50}$) was calculated as the concentration of compound that effected an increase in the percentage of XTT metabolite production in infected, compound treated cells to 50% of that produced by uninfected, compound-free cells.
Anti-HIV-1 Cell Culture Assay ($EC_{50}$) in presence of 40% Human Serum or Human Serum Proteins This assay is almost identical to the Anti-HIV-1 Cell Culture Assay described above, except that the infection was made in the presence or absence of 40% human serum (Type AB Male Cambrex 14-498E) or human serum proteins (Human α-acid Glycoprotein, Sigma G-9885; Human Serum Albumin, Sigma A1653, 96-99%) at physiological concentration. The HIV-1-induced cell death was determined as described above, except that the infected cells distributed in the 96-well plate were incubated in 80% Human Serum (2× concentration) or in 2 mg/mL Human α-acid Glycoprotein+70 mg/mL HSA (2× concentration) rather than in culture media.
Cytotoxicity Cell Culture Assay ($CC_{50}$)

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, *J. Natl. Cancer Inst.* 81, 577 (1989). This assay is almost identical to the previous assay described (Anti-HIV-1 Cell Culture Assay), except that the cells were not infected. The compound induced cell death (or growth reduction) was determined as previously described.

MT-2 cells maintained in RPMI-1640 medium supplemented with 5% fetal bovine serum and antibiotics were distributed into a 96-well plate (20,000 cells in 100 µl/well) and incubated in the presence or absence of 5-fold serial dilutions of the tested inhibitor (100 µl/well) for 5 days at 37° C. Controls included untreated infected cells and infected cells protected by 1 µM of P4405 (Podophyllotoxin, Sigma Cat # P4405).

To determine cytotoxicity, an XTT solution (6 mL per assay plate) at a concentration of 2 mg/mL in phosphate-buffered saline pH 7.4 was heated in the dark in a water-bath for 5 min at 55° C. before 50 µl of N-methylphenazonium methasulfate (5 µg/mL) was added per 6 mL of XTT solution. After removing 100 µL media from each well on the assay plate, 100 µL of the XTT substrate solution was added to each well. The cells and the XTT solution were incubated at 37° C. for 45 to 60 min in a $CO_2$ incubator. To inactivate the virus, 20 µl of 2% Triton X-100 was added to each well. Viability, as determined by the amount of XTT metabolites produced, is quantified spectrophotometrically by the absorbance at 450 nm (with subtraction of the background absorbance at 650 nm). Data from the assay is expressed as the percentage absorbance relative to untreated control, and the fifty percent cytotoxicity concentration ($EC_{50}$) was calculated as the concentration of compound that effected an increase in the percentage of cell growth in compound treated cells to 50% of the cell growth provided by uninfected, compound-free cells.

Experimental data based on representative Examples A-EQ demonstrate that the compounds of Formula (IV) of the present invention can have a CYP450 3A4 inhibition activity in a range represented by an $IC_{50}$ from about 100 nM to about 4700 nM, and a CYP450 2C9 inhibition activity in a range represented by an $IC_{50}$ from about 100 nM to about 10,000 nM.

Experimental data based on representative Examples A-EQ demonstrate that the compounds of Formula (IV) of the present invention can have a protease inhibition activity in a range represented by HIV $EC_{50}$ from about 140 nM to greater than about 30000 nM.

Experimental data based on representative Examples P, S, and T have a CYP450 3A4 inhibition activity in a range represented by an $IC_{50}$ from about 80-150 nM, a CYP450 2C9 inhibition activity in a range represented by an $IC_{50}$ from about 1000-10,000 nM, and a protease inhibition activity in a range represented by HIV $EC_{50}$ greater than about 30,000 nM.

What is claimed:

1. A pharmaceutical composition comprising:

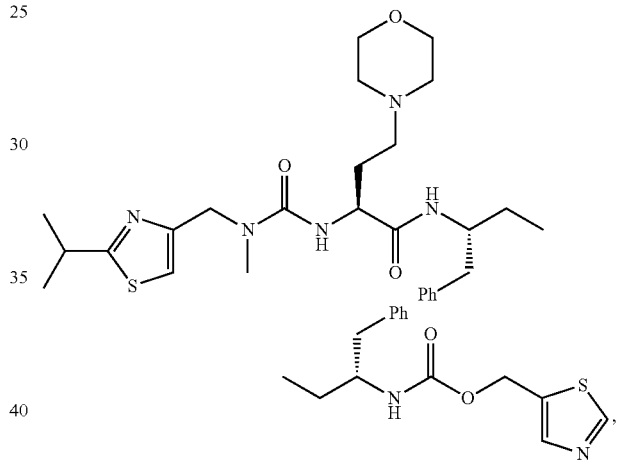

emtricitabine, elvitegravir, and a pharmaceutically acceptable carrier or excipient.

2. The pharmaceutical composition of claim 1, wherein the pharmaceutical composition further comprises tenofovir disoproxil fumarate.

3. A method of treating an HIV infection comprising administering to a patient in need thereof a therapeutically effective amount of the pharmaceutical composition of claim 1.

4. A method of treating an HIV infection comprising administering to a patient in need thereof a therapeutically effective amount of the pharmaceutical composition of claim 2.

* * * * *

UNITED STATES PATENT AND TRADEMARK OFFICE
CERTIFICATE OF CORRECTION

PATENT NO.         : 9,891,239 B2                                    Page 1 of 1
APPLICATION NO.    : 12/528185
DATED              : February 13, 2018
INVENTOR(S)        : Manoj C. Desai et al.

It is certified that error appears in the above-identified patent and that said Letters Patent is hereby corrected as shown below:

In the Claims

Column 354, Claim 1, Line 24, delete:

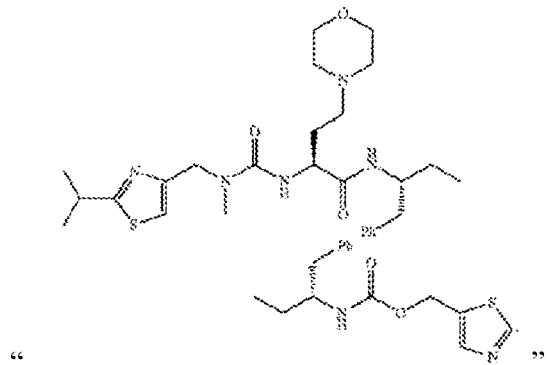

" "

And insert:

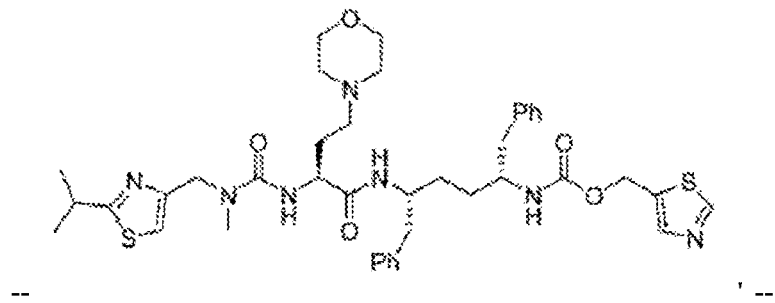

-- ' --

Signed and Sealed this
Third Day of April, 2018

Andrei Iancu
*Director of the United States Patent and Trademark Office*